US00RE48461E

(19) United States
(12) Reissued Patent
Macleod et al.

(10) Patent Number: US RE48,461 E
(45) Date of Reissued Patent: Mar. 9, 2021

(54) MODULATION OF ANDROGEN RECEPTOR EXPRESSION

(71) Applicant: Ionis Pharmaceuticals, Inc., Carlsbad, CA (US)

(72) Inventors: Robert A. Macleod, Carlsbad, CA (US); Youngsoo Kim, Carlsbad, CA (US); Tianyuan Zhou, Carlsbad, CA (US); Susan M. Freier, Carlsbad, CA (US); Punit Seth, Carlsbad, CA (US); Eric Swayze, Carlsbad, CA (US); Brett Monia, Carlsbad, CA (US)

(73) Assignee: Ionis Pharmaceuticals, Inc., Carlsbad, CA (US)

(21) Appl. No.: 16/275,198

(22) Filed: Feb. 13, 2019

Related U.S. Patent Documents

Reissue of:
(64) Patent No.: 9,567,588
Issued: Feb. 14, 2017
Appl. No.: 14/854,281
Filed: Sep. 15, 2015

U.S. Applications:
(63) Continuation of application No. 14/050,574, filed on Oct. 10, 2013, now Pat. No. 9,175,291.

(60) Provisional application No. 61/712,756, filed on Oct. 11, 2012, provisional application No. 61/712,780, filed on Oct. 11, 2012, provisional application No. 61/723,701, filed on Nov. 7, 2012, provisional application No. 61/777,813, filed on Mar. 12, 2013, provisional application No. 61/777,851, filed on Mar. 12, 2013, provisional application No. 61/777,895, filed on Mar. 12, 2013.

(51) Int. Cl.

| | |
|---|---|
| ***C12N 15/11*** | (2006.01) |
| ***C12N 15/113*** | (2010.01) |
| ***A61K 31/7088*** | (2006.01) |
| ***A61K 31/4166*** | (2006.01) |

(52) U.S. Cl.
CPC ..... *C12N 15/1138* (2013.01); *A61K 31/4166* (2013.01); *A61K 31/7088* (2013.01); *C12N 2310/11* (2013.01); *C12N 2310/315* (2013.01); *C12N 2310/321* (2013.01); *C12N 2310/3231* (2013.01); *C12N 2310/3341* (2013.01); *C12N 2310/341* (2013.01); *C12N 2310/346* (2013.01); *C12N 2320/30* (2013.01)

(58) Field of Classification Search
CPC ..... C12N 15/1138; C12N 2310/11
See application file for complete search history.

(56) References Cited

U.S. PATENT DOCUMENTS 8,927,515 B2 * 1/2015 Brown ..... A61P 43/00 514/44 A
2005/0246794 A1 * 11/2005 Khvorova et al. ... A61K 31/713 800/286

FOREIGN PATENT DOCUMENTS

| | | | |
|---|---|---|---|
| WO | WO 2002/000716 | 1/2002 | |
| WO | WO 2011/005765 | 1/2011 | |
| WO | WO 2012/012467 | 1/2012 | |
| WO | WO 2012006241 A2 * | 1/2012 | ..... C12N 15/1138 |
| WO | WO 2012/087983 | 6/2012 | |
| WO | WO 2012/120374 | 9/2012 | |
| WO | WO 2014/059238 | 4/2014 | |

OTHER PUBLICATIONS

N Souleimanian et al. Antisense 2'-Deoxy, 2'-Fluoroarabino Nucleic Acid (2'F-ANA) Oligonucleotides: In Vitro Gymnotic Silencers of Gene Expression Whose Potency Is Enhanced by Fatty Acids Molecular Therapy—Nucleic Acids (2012) 1, e43; (Year: 2012).*
I.E. Eder et al. Inhibition of LNCaP prostate cancer cells by means of androgen receptor antisense oligonucleotides Cancer Gene Therapy, vol. 7, No. 7, 2000: pp. 997-1007 (Year: 2000).*
J. K. Watts et al. Gene silencing by siRNAs and antisense oligonucleotides in the laboratory and the clinic Pathol. Jan. 2012 ; 226(2): 365-379 (Year: 2012).*
GenBank Accession No. AL158016 (2009).
Zhang et al., "Reduced Expression of the Androgen Receptor by Third Generation of Antisense Shows Antitumor Activity in Models of Prostate Cancer" Molecular Cancer Therapeutics (2011) 10(12): 2309-2319.
Aartsma-Rus A "Overview on AON design" Methods Mol Biol. (2012) 867:117-29.
Chan et al., "Antisense oligonucleotides: from design to therapeutic application" Clin Exp Pharmacol Physiol. (2006) 33(5-6):533-40.
Hamy et al., "Specific block of androgen receptor activity by antisense oligonucleotides" Prostate Cancer Prostatic Dis. (2003) 6(1):27-33.

* cited by examiner

*Primary Examiner* — Bruce R Campell
(74) *Attorney, Agent, or Firm* — Knobbe, Martens, Olson & Bear, LLC

(57) ABSTRACT

Certain embodiments are directed to compounds and compositions targeted to human androgen receptor (AR) for inhibiting androgen receptor levels in a cell, which can be useful for methods of treating cancer and inhibiting cancer cell growth or proliferation.

50 Claims, No Drawings

Specification includes a Sequence Listing.

MODULATION OF ANDROGEN RECEPTOR EXPRESSION

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED PATENT APPLICATIONS

This application is a continuation of U.S. patent application Ser. No. 14/050,574, filed Oct. 10, 2013, which claims the benefit of priority to U.S. Provisional Patent Application No. 61/712,780 filed Oct. 11, 2012; U.S. Provisional Patent Application No. 61/712,756 filed Oct. 11, 2012; U.S. Provisional Patent Application No. 61/723,701 filed Nov. 7, 2012; U.S. Provisional Patent Application No. 61/777,813 filed Mar. 12, 2103; U.S. Provisional Patent Application No. 61/777,851 filed Mar. 12, 2103 and U.S. Provisional Patent Application No. 61/777,895 filed Mar. 12, 2103. The entire text of the above-referenced patent applications is incorporated herein by reference in their entirety.

SEQUENCE LISTING

The present application is being filed along with a Sequence Listing in electronic format. The Sequence Listing is provided as a file entitled BIOL0212WOSEQ.txt created Sep. 17, 2013, which is approximately 556 KB in size. The information in the electronic format of the sequence listing is incorporated herein by reference in its entirety.

FIELD

Certain embodiments are directed to compounds and compositions targeted to human androgen receptor (AR) for inhibiting androgen receptor levels in a cell, which can be useful for methods of treating cancer and inhibiting cancer cell growth or proliferation.

BACKGROUND

Androgen receptor (AR) belongs to the superfamily of nuclear receptors and is activated by binding to its hormone ligands: androgen, testosterone, or DHT. Upon binding hormone ligand in the cytoplasm, androgen receptor translocates to the nucleus where it binds DNA and functions as a transcription factor to regulate expression of a number of target genes, such as prostate specific antigen (PSA) and TMPRSS2. Knudsen et al. (Trends Endocrinol Metab 21: 315-24, 2010) Bennett et al. (Int J Biochem Cell Biol. 42:813-827, 201).

Androgen receptor (AR) signaling is a critical survival pathway for prostate cancer cells, and androgen-deprivation therapy (ADT), also known as "chemical castration", is a first-line treatment strategy against hormone-sensitive, androgen-dependent prostate cancer that reduces circulating androgen levels and thereby inhibits AR activity. Although a majority of patients initially respond to ADT, most will eventually develop castrate resistance in which the disease progresses despite castrate levels of testosterone. This type of cancer is known as castrate-resistant prostate cancer (CRPC). There are a number of mechanisms underlying the development of castrate (castration) resistance including an increase in the expression of AR protein which can sensitize cells to low levels of androgen, AR mutations that can alter transactivation or sensitize AR to alternative ligands and the emergence of alternatively spliced forms of AR, which lack the ligand binding domain but can nevertheless act to promote tumour growth in the absence of ligand stimulation. Additionally prostate tumors may also synthesize their own androgens thereby increasing the local intra-tumoral testosterone levels available to activate the AR.

Androgen receptor (AR) signaling is a critical survival pathway for prostate cancer cells, and androgen-deprivation therapy (ADT) remains the principal treatment for patients with locally advanced and metastatic disease. Although a majority of patients initially respond to ADT, most will eventually develop castrate resistance in which the disease progresses despite castrate levels of testosterone. This type of cancer is known as castrate-resistant prostate cancer (CRPC) (Karantos et al., Oncogene advance online: 1-13, 2013). There are a number of mechanisms underlying the development of castration resistance including an increase in the expression of AR protein which can sensitize cells to low levels of androgen (Gregory et al., Cancer Res 61: 2892-2898, 2001; Linja et al., Cancer Res 61: 3550-3555, 2001), AR mutations that can alter transactivation or sensitize AR to alternative ligands (Scher et al., J Clin Oncol 23: 8253-8261, 2005) and the emergence of alternatively spliced forms of AR, which lack the ligand binding domain but can nevertheless act to promote tumour growth in the absence of ligand stimulation (Yingming et al., Cancer Res 73:483-489, 2013). Additionally prostate tumors may also synthesize their own androgens thereby increasing the local intratumoral testosterone levels available to activate the AR (Attard et al., Cancer Cell 16:458-462, 2009).

The fact that the androgen receptor remains active in castrate resistant prostate cancer has led to the development of new agents that inhibit the production of androgen ligands or block the actions of these ligands on the AR. These new agents include abiraterone acetate which inhibits 17-α-hydroxylase/17,20-lyase (CYP17) activity resulting in a reduction in residual androgens synthesized by the adrenals and in the prostate tumour itself deBono et al. (N Engl J Med 364: 1995-2006, 2011) and enzalutamide which prevents androgen ligand from binding to AR, translocating to the nucleus, and binding to DNA (Scher et al., N Engl J Med 367:1187-1197, 2012). A number of other androgen synthesis inhibitors or androgen receptor blockers are under development either pre-clinically or clinically and include for example, ARN509, ODM201, TOK001, VT464.

Although the activity of agents such as enzalutamide and abiraterone in CRPC is very encouraging, neither works in all patients and both are associated with the development of additional resistance through re-activation of the AR by the mechanisms described above (Yingming et al., Cancer Res 73:483-489, 2013). Thus, there is a continued need to identify alternative therapies for the treatment of CRPC, and in particular those that can either remove and/or inhibit the activity of all forms of AR including for example, wildtype, mutated and splice variant ARs.

The present invention provides antisense oligonclueotides which by virtue of their design and mode of action (base-pair with the AR RNA target and mediate its destruction by RNase H, an enzyme that destroys the RNA in a DNA/RNA duplex) are aimed at inhibiting the major forms of AR By targeting an appropriate region of the AR mRNA the antisense oligonucleotide will result in inhibition of the major forms (full length, splice variant and mutated forms) of androgen receptor proteins and therefore be suitable for the treatment of patients with CRPC.

Aside from prostate cancer, AR is also implicated as a factor in the progression of other tumours such as breast cancer. In breast cancer AR is expressed in 70-80% of tumours which are also ER positive and in 12% cases which are known as triple negative (no expression of ER, PR and HER2) (Hickey et al., Molecular Endocrinology 26: 1252-1267, 2012). In pre-clinical studies, the androgen receptor antagonist bicalutamide induces anti-proliferative responses in vitro in breast cancer cells and this is potentiated by addition of a Pi3K/mTOR inhibitor (Ni et al., Cancer Cell 20: 119-131, 2011). The 2nd generation anti-androgen, enzalutamide inhibits dihydrotestosterone (DHT) mediated proliferation in ER+/AR+ breast cancer cells and is as effective as tamoxifen at inhibiting estrogen-stimulated breast cancer tumour growth in pre-clinical models in vivo (Cochrane et al., Cancer Res 72(24 Supplement): P2-14-02, 2012). Enzalutamide also inhibits proliferation in HER2 + and triple-negative breast cancer cells. It appears that in situations where estrogen action is reduced (eg. long-term estrogen deprivation or absence of ER) AR levels increase and can become oncogenic. This would suggest that AR antagonists may be best positioned in triple negative or hormone resistant breast cancer settings (Hickey et al., Molecular Endocrinology 26: 1252-1267, 2012). AR targeted therapies are currently under investigation in clinical trials for breast cancer (NCT00468715, NCT01597193, NCT01381874, NCT00755886).

AR is also expressed in a variety of other tumours, including, but not limited to bladder, ovarian, gastric, lung and liver. Pre-clinical data support a similar role as in breast cancer, to promote tumour cell proliferation survival; thus blocking AR in these tumours could have therapeutic clinical benefit (Chang et al., Oncogene advance online: 1-10, 2013).

SUMMARY

Several embodiments provided herein relate to the discovery of compounds and compositions for inhibiting androgen receptor levels in a cell, which can be useful for methods of treating cancer and inhibiting proliferation or growth of cancer cells, such as prostate, breast, ovarian, gastric or bladder cancer or cancer cells.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O$(CH_2)_2$—$OCH_3$) refers to an O-methoxy-ethyl modification at the 2' position of a sugar ring, e.g. a furanose ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" means a nucleoside comprising a substituent at the 2'-position of the furanosyl ring other than H or OH. In certain embodiments, 2' substituted nucleosides include nucleosides with bicyclic sugar modifications.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5' position. A 5-methylcytosine is a modified nucleobase.

"About" means within ±7% of a value. For example, if it is stated, "the compounds affected at least about 70% inhibition of Androgen Receptor", it is implied that Androgen Receptor levels are inhibited within a range of 63% and 77%.

"Administration" or "administering" refers to routes of introducing an antisense compound provided herein to a subject to perform its intended function. An example of a route of administration that can be used includes, but is not limited to parenteral administration, such as subcutaneous, intravenous, or intramuscular injection or infusion.

"Androgen-receptor positive" with respect to breast cancer or a breast cancer cell refers to a breast cancer or a breast cancer cell that expresses androgen receptor.

"Animal" refers to a human or non-human animal, including, but not limited to, mice, rats, rabbits, dogs, cats, pigs, and non-human primates, including, but not limited to, monkeys and chimpanzees.

"Anti-androgenic agent" refers to a therapeutic compound or drug which is an androgen synthesis inhibitor or an androgen receptor blocker.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Antisense oligonucleotide" means a single-stranded oligonucleotide having a nucleobase sequence that permits hybridization to a corresponding region or segment of a target nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases.

"Bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

Also included within the definition of LNA according to the invention are LNAs in which the 2'-hydroxyl group of the ribosyl sugar ring is connected to the 4' carbon atom of the sugar ring, thereby forming a methyleneoxy (4-$CH_2$—O-2') bridge to form the bicyclic sugar moiety. The bridge can also be a methylene (—$CH_2$—) group connecting the 2' oxygen atom and the 4' carbon atom, for which the term methyleneoxy (4-$CH_2$—O-2') LNA is used. Furthermore; in the case of the bicylic sugar moiety having an ethylene bridging group in this position, the term ethyleneoxy (4'-$CH_2CH_2$—O-2') LNA is used. α-L-methyleneoxy (4-$CH_2$—O-2'), an isomer of methyleneoxy (4-$CH_2$—O-2') LNA is also encompassed within the definition of LNA, as used herein.

"Cap structure" or "terminal cap moiety" means chemical modifications, which have been incorporated at either terminus of an antisense compound.

"Castrate-resistant prostate cancer" or "Castration-resistant prostate cancer" and prostate cancer cells refer to the reduction of sensitivity of prostate cancer and prostate cancer cells to androgen deprivation therapy or an anti-androgenic agent.

"cEt" or "constrained ethyl" means a bicyclic sugar moiety comprising a bridge connecting the 4'-carbon and the 2'-carbon, wherein the bridge has the formula: 4-CH($CH_3$)—O-2'.

"Constrained ethyl nucleoside" (also cEt nucleoside) means a nucleoside comprising a bicyclic sugar moiety comprising a 4'-CH($CH_3$)—O-2' bridge.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Complementarity" means the capacity for pairing between nucleobases of a first nucleic acid and a second nucleic acid.

"Comprise," "comprises" and "comprising" will be understood to imply the inclusion of a stated step or element or group of steps or elements but not the exclusion of any other step or element or group of steps or elements.

"Contiguous nucleobases" means nucleobases immediately adjacent to each other.

"Deoxyribonucleotide" means a nucleotide having a hydrogen at the 2' position of the sugar portion of the nucleotide. Deoxyribonucleotides may be modified with any of a variety of substituents.

"Designing" or "Designed to" refer to the process of designing an oligomeric compound that specifically hybridizes with a selected nucleic acid molecule.

"Downstream" refers to the relative direction toward the 3' end or C-terminal end of a nucleic acid.

"Efficacy" means the ability to produce a desired effect.

"Estrogen-receptor (ER) positive" with respect to breast cancer or a breast cancer cell refers to breast cancer or a breast cancer cell that expresses estrogen receptor (ER).

"Estrogen-receptor (ER) negative" with respect to breast cancer or a breast cancer cell refers to breast cancer or a breast cancer cell that does not express estrogen receptor (ER).

"Expression" includes all the functions by which a gene's coded information is converted into structures present and operating in a cell. Such structures include, but are not limited to the products of transcription and translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Her2/neu negative" with respect to breast cancer or a breast cancer cell refers to breast cancer or a breast cancer cell that does not express Her2/neu.

"Hybridization" means the annealing of complementary nucleic acid molecules. In certain embodiments, complementary nucleic acid molecules include, but are not limited to, an antisense compound and a nucleic acid target. In certain embodiments, complementary nucleic acid molecules include, but are not limited to, an antisense oligonucleotide and a nucleic acid target.

"Immediately adjacent" means there are no intervening elements between the immediately adjacent elements.

"Individual" means a human or non-human animal selected for treatment or therapy.

"Induce", "inhibit", "potentiate", "elevate", "increase", "decrease", upregulate", "downregulate", or the like, generally denote quantitative differences between two states.

"Inhibiting the expression or activity" refers to a reduction, blockade of the expression or activity and does not necessarily indicate a total elimination of expression or activity.

"Internucleoside linkage" refers to the chemical bond between nucleosides.

"Lengthened" antisense oligonucleotides are those that have one or more additional nucleosides relative to an antisense oligonucleotide disclosed herein.

"Linked deoxynucleoside" means a nucleic acid base (A, G, C, T, U) substituted by deoxyribose linked by a phosphate ester to form a nucleotide.

"Linked nucleosides" means adjacent nucleosides linked together by an internucleoside linkage.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C) and uracil (U).

"Modified nucleoside" means a nucleoside having, independently, a modified sugar moiety and/or modified nucleobase.

"Modified nucleotide" means a nucleotide having, independently, a modified sugar moiety, modified internucleoside linkage, or modified nucleobase.

"Modified oligonucleotide" means an oligonucleotide comprising at least one modified internucleoside linkage, a modified sugar, and/or a modified nucleobase.

"Modified sugar" means substitution and/or any change from a natural sugar moiety.

"Monomer" refers to a single unit of an oligomer. Monomers include, but are not limited to, nucleosides and nucleotides, whether naturally occuring or modified.

"Motif" means the pattern of unmodified and modified nucleosides in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, and double-stranded nucleic acids.

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(═O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Oligomeric compound" means a polymer of linked monomeric subunits which is capable of hybridizing to at least a region of a nucleic acid molecule.

"Oligonucleoside" means an oligonucleotide in which the internucleoside linkages do not contain a phosphorus atom.

"Oligonucleotide" means a polymer of linked nucleosides each of which can be modified or unmodified, independent one from another.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound "Progesterone receptor (PR) negative" with respect to breast cancer or a breast cancer cell refers to breast cancer or a breast cancer cell that does not express progesterone receptor (PR).

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Segments" are defined as smaller or sub-portions of regions within a target nucleic acid.

"Sites," as used herein, are defined as unique nucleobase positions within a target nucleic acid.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments. "Stringent hybridization conditions" or "stringent conditions" refer to conditions under which an oligomeric compound will hybridize to its target sequence, but to a minimal number of other sequences.

"Subject" means a human or non-human animal selected for treatment or therapy.

"Synergy" or "synergize" refers to an effect of a combination that is greater than additive of the effects of each component alone.

"Target" refers to a protein, the modulation of which is desired.

"Target gene" refers to a gene encoding a target.

"Targeting" means the process of design and selection of an antisense compound that will specifically hybridize to a target nucleic acid and induce a desired effect.

"Target nucleic acid," "target RNA," "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Treating cancer" refers to performing actions that lead to amelioration of cancer or of the symptoms accompanied therewith. The combination of said actions is encompassed by the term "treatment." Amelioration of cancer includes, but is not limited to, reducing the number of cancer cells in a subject or reducing the number of cancer cells in the subject. Said treatment as used herein also includes an entire restoration of the health with respect to cancer. It is to be understood that treatment as used in accordance with embodiments provided herein may not be effective in all subjects to be treated. However, a population of subjects suffering from cancer referred to herein can be successfully treated. In certain embodiments, "treating cancer" can be described by a number of different parameters including, but not limited to, reduction in the size of a tumor in a subject having cancer, reduction in the growth or proliferation of a tumor in a subject having cancer, preventing metastasis or reducing the extent of metastasis, and/or extending the survival of a subject having cancer compared to control. The cancer referred to in this definition can be any cancer including one selected from prostate cancer, breast cancer, ovarian cancer, gastric cancer and bladder cancer.

"Unmodified" nucleobases mean the purine bases adenine (A) and guanine (G), and the pyrimidine bases thymine (T), cytosine (C) and uracil (U).

"Unmodified nucleotide" means a nucleotide composed of naturally occuring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Upstream" refers to the relative direction toward the 5' end or N-terminal end of a nucleic acid.

Certain Embodiments

Certain embodiments provide methods, compounds, and compositions for inhibiting androgen receptor (AR) mRNA expression.

Certain embodiments provide antisense compounds or compositions targeted to an androgen receptor nucleic acid. In certain embodiments, the androgen receptor nucleic acid is the sequences set forth in GENBANK Accession No. NT_011669.17_TRUNC_5079000_5270000 (incorporated herein as SEQ ID NO: 1), GENBANK Accession No. NM_000044.3 (incorporated herein as SEQ ID NO: 2), GENBANK Accession No. NM_001011645.2 (incorporated herein as SEQ ID NO: 3), GENBANK Accession No. FJ235916.1 (incorporated herein as SEQ ID NO: 4), GENBANK Accession No. FJ235917.1 (incorporated herein as SEQ ID NO: 5), GENBANK Accession No. FJ235918.1 (incorporated herein as SEQ ID NO: 6), GENBANK Accession No. FJ235919.1 (incorporated herein as SEQ ID NO: 7), or GENBANK Accession No. FJ235920.1 (incorporated herein as SEQ ID NO: 8).

In certain embodiments, the compounds or compositions comprise a modified oligonucleotide 10 to 30 linked nucleosides in length targeted to AR. The AR target can have a sequence recited in any one of SEQ ID NOs: 1-8 or a portion thereof or a variant thereof. In certain embodiments, the AR target can have a sequence of known AR splicing variants including, but are not limited to, AR-V1, AR-V2, AR-V3, AR-V4, AR-V5, AR-V6, and AR-V7 (also referred to as AR3), which contain exons 1-3 but lack exons 4-8. AR-V1, AR-V2, AR-V3, AR-V4, AR-V5, AR-V6, AR-V7, and additional splicing variants targetable by compounds provided herein are described in Hu et al., Cancer Res 2009; 69:16-22 and US Patent Application Publication No. US 2010/0068802, each of which is incorporated herein by reference in its entirety.

In certain embodiments, the compounds or compositions comprise a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, one or more modified nucleosides in the wing segment have a modified sugar. In certain embodiments, the modified sugar is a bicyclic sugar. In certain embodiments, the modified nucleoside is an LNA nucleoside. In certain embodiments, the modified nucleoside is a 2'-substituted nucleoside. In certain embodiments, 2' substituted nucleosides include nucleosides with bicyclic sugar modifications. In certain embodiments, the modified nucleoside is a 2'-MOE nucleoside. In certain embodiments, the modified nucleoside is a constrained ethyl (cEt) nucleoside.

In certain embodiments, the compounds or compositions comprise a modified oligonucleotide consisting of 10 to 30 linked nucleosides and having a nucleobase sequence consisting of a nucleobase sequence of any of SEQ ID NOs: 12-179. In certain embodiments, one or more modified nucleosides in the wing segment have a modified sugar. In certain embodiments, the modified sugar is a bicyclic sugar. In certain embodiments, the modified nucleoside is an LNA nucleoside. In certain embodiments, the modified nucleoside is a 2'-substituted nucleoside. In certain embodiments, 2' substituted nucleosides include nucleosides with bicyclic sugar modifications. In certain embodiments, the modified nucleoside is a 2'-MOE nucleoside. In certain embodiments, the modified nucleoside is a constrained ethyl (cEt) nucleoside.

In certain embodiments, the compounds or compositions targeted to androgen receptor comprise a single-stranded modified oligonucleotide consisting of 16 linked nucleosides having a nucleobase sequence consisting of the sequence of SEQ ID NO: 35, 39, 43, 124, 150, 155, 169, or 175, or a pharmaceutically acceptable salt thereof. In certain embodiments, the antisense compound targeted to human AR is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

In certain embodiments, the modified oligonucleotide comprises: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar.

In certain embodiments, the modified oligonucleotide consists of 20 linked nucleosides, the gap segment consisting of 10 linked deoxynucleosides, the 5' wing segment consisting of five linked nucleosides, the 3' wing segment consisting of five linked nucleosides, each nucleoside of each wing segment comprises a 2'-O-methoxyethyl sugar, each internucleoside linkage is a phosphorothioate linkage and each cytosine is a 5-methylcytosine.

In certain embodiments, the modified oligonucleotide consists of 16 linked nucleosides, a gap segment consisting of 10 linked deoxynucleosides, a 5' wing segment consisting of three linked nucleosides, a 3' wing segment consisting of three linked nucleosides, each nucleoside of each wing segment comprises a constrained ethyl (cEt) sugar, each internucleoside linkage is a phosphorothioate linkage and each cytosine is a 5-methylcytosine.

In certain embodiments, the modified oligonucleotide consists of 16 linked nucleosides, a gap segment consisting of 9 linked deoxynucleosides, a 5' wing segment consisting of three linked nucleosides, a 3' wing segment consisting of four linked nucleosides; the three linked nucleosides of the 5' wing segment are each a constrained ethyl (cEt) sugar; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

In certain embodiments, the modified oligonucleotide consists of 16 linked nucleosides, a gap segment consisting of 8 linked deoxynucleosides, a 5' wing segment consisting of five linked nucleosides, a 3' wing segment consisting of three linked nucleosides; the five linked nucleosides of the 5' wing segment are each a constrained ethyl (cEt) sugar; the three linked nucleosides of the 3' wing segment are each a constrained ethyl (cEt) sugar; each internucleoside linkage is a phosphorothioate linkage; and each cytosine is a 5-methylcytosine.

In certain embodiments, the modified oligonucleotide consists of 16 linked nucleosides, a gap segment consisting of 8 linked deoxynucleosides, a 5' wing segment consisting of four linked nucleosides, a 3' wing segment consisting of four linked nucleosides; the four linked nucleosides of the 5' wing segment are a 2'-O-methoxyethyl sugar, a constrained ethyl (cEt) sugar, a constrained ethyl (cEt) sugar, and a constrained ethyl (cEt) sugar in the 5' to 3' direction; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

In certain embodiments, the modified oligonucleotide consists of 16 linked nucleosides, a gap segment consisting of 8 linked deoxynucleosides, a 5' wing segment consisting of five linked nucleosides, a 3' wing segment consisting of three linked nucleosides; the five linked nucleosides of the 5' wing segment are a 2'-O-methoxyethyl sugar, a 2'-O-methoxyethyl sugar, a constrained ethyl (cEt) sugar, a constrained ethyl (cEt) sugar, and a constrained ethyl (cEt) sugar in the 5' to 3' direction; the three linked nucleosides of the 3' wing segment are each a constrained ethyl (cEt) sugar; each internucleoside linkage is a phosphorothioate linkage; and each cytosine is a 5-methylcytosine.

In certain embodiments, the modified oligonucleotide consists of 16 linked nucleosides, a gap segment consisting of 7 linked deoxynucleosides, a 5' wing segment consisting of seven linked nucleosides, a 3' wing segment consisting of two linked nucleosides; the seven linked nucleosides of the 5' wing segment are a 2'-O-methoxyethyl sugar, a constrained ethyl (cEt) sugar, a constrained ethyl (cEt) sugar, a 2'-O-methoxyethyl sugar, a 2'-O-methoxyethyl sugar, a constrained ethyl (cEt) sugar, and a constrained ethyl (cEt) sugar in the 5' to 3' direction; the two linked nucleosides of the 3' wing segment are each a constrained ethyl (cEt) sugar; each internucleoside linkage is a phosphorothioate linkage; and each cytosine is a 5-methylcytosine.

In certain embodiments, the modified oligonucleotide consists of 16 linked nucleosides, a gap segment consisting of 7 linked deoxynucleosides, a 5' wing segment consisting of six linked nucleosides, a 3' wing segment consisting of three linked nucleosides; the six linked nucleosides of the 5' wing segment are a 2'-O-methoxyethyl sugar, a constrained ethyl (cEt) sugar, a constrained ethyl (cEt) sugar, a 2'-O-methoxyethyl sugar, a constrained ethyl (cEt) sugar, and a constrained ethyl (cEt) sugar in the 5' to 3' direction; the three linked nucleosides of the 3' wing segment are each a constrained ethyl (cEt) sugar; each internucleoside linkage is a phosphorothioate linkage; and each cytosine is a 5-methylcytosine.

In certain embodiments, the modified oligonucleotide consists of 16 linked nucleosides, a gap segment consisting of 7 linked deoxynucleosides, a 5' wing segment consisting of five linked nucleosides, a 3' wing segment consisting of four linked nucleosides; the five linked nucleosides of the 5' wing segment are a 2'-O-methoxyethyl sugar, a 2'-O-methoxyethyl sugar, a constrained ethyl (cEt) sugar, a constrained ethyl (cEt) sugar, and a constrained ethyl (cEt) sugar in the 5' to 3' direction; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

In certain embodiments, the modified oligonucleotide consists of 16 linked nucleosides, a gap segment consisting of 7 linked deoxynucleosides, a 5' wing segment consisting of four linked nucleosides, a 3' wing segment consisting of five linked nucleosides; the four linked nucleosides of the 5' wing segment are a 2'-O-methoxyethyl sugar, a constrained ethyl (cEt) sugar, a constrained ethyl (cEt) sugar, and a constrained ethyl (cEt) sugar in the 5' to 3' direction; the five linked nucleosides of the 3' wing segment are a constrained ethyl (cEt) sugar, a constrained ethyl (cEt) sugar, a constrained ethyl (cEt) sugar, a 2'-O-methoxyethyl sugar, and a 2'-O-methoxyethyl sugar in the 5' to 3' direction; each internucleoside linkage is a phosphorothioate linkage; and each cytosine is a 5-methylcytosine.

In certain embodiments, the compounds or compositions targeted to androgen receptor comprise a single-stranded modified oligonucleotide consisting of 16 linked nucleosides having a nucleobase sequence consisting of the sequence of SEQ ID NO: 35, 39, 43, 124, 150, 155, 169, or 175, or a pharmaceutically acceptable salt thereof, wherein the modified oligonucleotide comprises a gap segment consisting of deoxynucleosides; a 5' wing segment; and a 3' wing segment, wherein the gap segment is positioned between the 5' wing segment and the 3' wing segment and each nucleoside of each wing segment comprises a modified sugar. In certain embodiments, each internucleoside linkage of the modified oligonucleotide is a phosphorothioate linkage. In certain embodiments, each cytosine of the modified oligonucleotide is a 5'-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 35, or a pharmaceutically acceptable salt thereof, wherein the modified oligonucleotide comprises:

a gap segment consisting of 9 linked deoxynucleosides;

a 5' wing segment consisting of three linked nucleosides; and a 3' wing segment consisting of four linked nucleosides;

wherein the gap segment is positioned between the 5' wing segment and the 3' wing segment; the three linked nucleosides of the 5' wing segment are each a constrained ethyl (cEt) sugar; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 39, or a pharmaceutically acceptable salt thereof, wherein the modified oligonucleotide comprises:

a gap segment consisting of 9 linked deoxynucleosides;

a 5' wing segment consisting of three linked nucleosides; and a 3' wing segment consisting of four linked nucleosides;

wherein the gap segment is positioned between the 5' wing segment and the 3' wing segment; the three linked nucleosides of the 5' wing segment are each a constrained ethyl (cEt) sugar; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 39, or a pharmaceutically acceptable salt thereof, wherein the modified oligonucleotide comprises:

a gap segment consisting of 8 linked deoxynucleosides;

a 5' wing segment consisting of four linked nucleosides; and a 3' wing segment consisting of four linked nucleosides;

wherein the gap segment is positioned between the 5' wing segment and the 3' wing segment; the four linked nucleosides of the 5' wing segment are a 2'-O-methoxyethyl sugar, a constrained ethyl (cEt) sugar, a constrained ethyl (cEt) sugar, and a constrained ethyl (cEt) sugar in the 5' to 3' direction; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 39, or a pharmaceutically acceptable salt thereof, wherein the modified oligonucleotide comprises:

a gap segment consisting of 8 linked deoxynucleosides;

a 5' wing segment consisting of five linked nucleosides; and a 3' wing segment consisting of three linked nucleosides;

wherein the gap segment is positioned between the 5' wing segment and the 3' wing segment; the five linked nucleosides of the 5' wing segment are a 2'-O-methoxyethyl sugar, a 2'-O-methoxyethyl sugar, a constrained ethyl (cEt) sugar, a constrained ethyl (cEt) sugar, and a constrained ethyl (cEt) sugar in the 5' to 3' direction; the three linked nucleosides of the 3' wing segment are each a constrained ethyl (cEt) sugar; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 39, or a pharmaceutically acceptable salt thereof, wherein the modified oligonucleotide comprises:

a gap segment consisting of 7 linked deoxynucleosides;

a 5' wing segment consisting of four linked nucleosides; and a 3' wing segment consisting of five linked nucleosides;

wherein the gap segment is positioned between the 5' wing segment and the 3' wing segment; the four linked nucleosides of the 5' wing segment are a 2'-O-methoxyethyl sugar, a constrained ethyl (cEt) sugar, a constrained ethyl (cEt) sugar, and a constrained ethyl (cEt) sugar in the 5' to 3' direction; the five linked nucleosides of the 3' wing segment are a constrained ethyl (cEt) sugar, a constrained ethyl (cEt) sugar, a constrained ethyl (cEt) sugar, a 2'-O-methoxyethyl sugar, and a 2'-O-methoxyethyl sugar in the 5' to 3' direction; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 35, or a pharmaceutically acceptable salt thereof, wherein the modified oligonucleotide comprises:

a gap segment consisting of 7 linked deoxynucleosides;

a 5' wing segment consisting of six linked nucleosides; and a 3' wing segment consisting of three linked nucleosides;

wherein the gap segment is positioned between the 5' wing segment and the 3' wing segment; the six linked nucleosides of the 5' wing segment are a 2'-O-methoxyethyl sugar, a constrained ethyl (cEt) sugar, a constrained ethyl (cEt) sugar, a 2'-O-methoxyethyl sugar, a constrained ethyl (cEt) sugar, and a constrained ethyl (cEt) sugar in the 5' to 3' direction; the three linked nucleosides of the 3' wing segment are each a constrained ethyl (cEt) sugar; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 43, or a pharmaceutically acceptable salt thereof, wherein the modified oligonucleotide comprises:

a gap segment consisting of 10 linked deoxynucleosides;

a 5' wing segment consisting of three linked nucleosides; and a 3' wing segment consisting of three linked nucleosides;

wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 124, or a pharmaceutically acceptable salt thereof, wherein the modified oligonucleotide comprises:

a gap segment consisting of 10 linked deoxynucleosides;

a 5' wing segment consisting of three linked nucleosides; and a 3' wing segment consisting of three linked nucleosides;

wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 150, or a pharmaceutically acceptable salt thereof, wherein the modified oligonucleotide comprises:

a gap segment consisting of 10 linked deoxynucleosides;

a 5' wing segment consisting of three linked nucleosides; and a 3' wing segment consisting of three linked nucleosides;

wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 155, or a pharmaceutically acceptable salt thereof, wherein the modified oligonucleotide comprises:

a gap segment consisting of 10 linked deoxynucleosides;

a 5' wing segment consisting of three linked nucleosides; and a 3' wing segment consisting of three linked nucleosides;

wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 169, or a pharmaceutically acceptable salt thereof, wherein the modified oligonucleotide comprises:

a gap segment consisting of 10 linked deoxynucleosides;

a 5' wing segment consisting of three linked nucleosides; and a 3' wing segment consisting of three linked nucleosides;

wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 175, or a pharmaceutically acceptable salt thereof, wherein the modified oligonucleotide comprises:

a gap segment consisting of 10 linked deoxynucleosides;

a 5' wing segment consisting of three linked nucleosides; and a 3' wing segment consisting of three linked nucleosides;

wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

In certain embodiments, an antisense compound or antisense oligonucleotide targeted to an androgen receptor nucleic acid is complementary within the following nucleotide regions of SEQ ID NO: 1: 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5052-5067, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, 5521-5536, 5666-5681, 6222-6237, 6701-6716, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58739, 58720-58735, 58721-58736, 58722-58737, 58723-58738, 58724-58739, 58724-58739, 58725-58740, 58725-58740, 58725-58740, 58750-58769, 58750-58765, 58751-58766, 58752-58767, 58753-58768, 58754-58769, 58755-58770, 60902-60917, 67454-67469, 102156-102171, 114874-114889, 115272-115287, 115365-115380, 134971-134986, 139682-139697, 139762-139777, 139782-139797, 144856-144871, 144938-144953, 148406-148421, 148443-148458, 148520-148535, 181695-181710, 182958-182973, or 183049-183064.

In certain embodiments, an antisense compound or antisense oligonucleotide targeted to an androgen receptor nucleic acid target the following nucleotide regions of SEQ ID NO: 1: 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5052-5067, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, 5521-5536, 5666-5681, 6222-6237, 6701-6716, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58739, 58720-58735, 58721-58736, 58722-58737, 58723-58738, 58724-58739, 58724-58739, 58725-58740, 58725-58740, 58725-58740, 58750-58769, 58750-58765, 58751-58766, 58752-58767, 58753-58768, 58754-58769, 58755-58770, 60902-60917, 67454-67469, 102156-102171, 114874-114889, 115272-115287, 115365-115380, 134971-134986, 139682-139697, 139762-139777, 139782-139797, 144856-144871, 144938-144953, 148406-148421, 148443-148458, 148520-148535, 181695-181710, 182958-182973, or 183049-183064.

In certain embodiments, antisense compounds or antisense oligonucleotides target a region of an androgen receptor nucleic acid. In certain embodiments, such compounds or oligonucleotides targeted to a region of an androgen receptor nucleic acid have a contiguous nucleobase portion that is complementary to an equal length nucleobase portion of the region. For example, the portion can be at least an 8, 9, 10, 11, 12, 13, 14, 15, or 16 contiguous nucleobases portion complementary to an equal length portion of a region recited herein. In certain embodiments, such compounds or oligonucleotide target the following nucleotide regions of SEQ ID NO: 1: 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5052-5067, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, 5521-5536, 5666-5681, 6222-6237, 6701-6716, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58739, 58720-58735, 58721-58736, 58722-58737, 58723-58738, 58724-58739, 58724-58739, 58725-58740, 58725-58740, 58725-58740, 58750-58769, 58750-58765, 58751-58766, 58752-58767, 58753-58768, 58754-58769, 58755-58770, 60902-60917, 67454-67469, 102156-102171, 114874-114889, 115272-115287, 115365-115380, 134971-134986, 139682-139697, 139762-139777, 139782-139797, 144856-144871, 144938-144953, 148406-148421, 148443-148458, 148520-148535, 181695-181710, 182958-182973, or 183049-183064.

In certain embodiments, an antisense compound or antisense oligonucleotide provided herein targets AR within exon 1, for example within nucleotide regions 2863-5593 (exon 1) or 27672-27853 (exon 1B) of SEQ ID NO: 1. In certain embodiments, an antisense compound provided herein targeted to exon 1 of AR is complementary within any of the following nucleotide regions of SEQ ID NO: 1: 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4047-4062, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5052-5067, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, or 5521-5536.

In certain embodiments, an antisense compound or antisense oligonucleotide provided herein targets AR within exon 2, for example within nucleotide regions 102087-102238 (exon 2) or 139551-139834 (exon 2c) of SEQ ID NO: 1. In certain embodiments, an antisense compound provided herein targeted to exon 2 of AR is complementary within any of the following nucleotide regions of SEQ ID NO: 1: 102155-102170, 102156-102171, 139682-139697, 139762-139777, or 139782-139797.

In certain embodiments, an antisense compound or antisense oligonucleotide provided herein targets AR within exon 3, for example within nucleotide regions 144841-144957 (exon 3), 148380-148594 (exon 3b), or 153504-154908 (exon 3d) of SEQ ID NO: 1. In certain embodiments, an antisense compound provided herein targeted to exon 3 of AR is complementary within any of the following nucleotide regions of SEQ ID NO: 1: 144856-144871, 144938-144953, 148406-148421, 148443-148458, or 148520-148535.

In certain embodiments, an antisense compound or antisense oligonucleotide provided herein targets AR within exon 7, for example within nucleotide region 181658-181815 of SEQ ID NO: 1. In certain embodiments, an antisense compound provided herein targeted to exon 7 of AR is complementary within nucleotide region 181695-181710 of SEQ ID NO: 1.

In certain embodiments, an antisense compound or antisense oligonucleotide provided herein targets AR within exon 8, for example within nucleotide region 182517-189455 of SEQ ID NO: 1. In certain embodiments, an antisense compound provided herein targeted to exon 8 of AR is complementary within nucleotide regions 182958-182973 or 183049-183064 of SEQ ID NO: 1.

In certain embodiments, an antisense compound or antisense oligonucleotide provided herein targets AR within intron 1, for example within nucleotide regions 5594-27671 or 27854-102086 of SEQ ID NO: 1. In certain embodiments, an antisense compound provided herein targeted to intron 1 of AR is complementary within any of the following nucleotide regions of SEQ ID NO: 1: 5666-5681, 6222-6237, 6701-6716, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58739, 58720-58735, 58721-58736, 58722-58737, 58723-58738, 58724-58739, 58724-58739, 58725-58740, 58725-58740, 58725-58740, 58750-58769, 58750-58765, 58751-58766, 58752-58767, 58753-58768, 58754-58769, 58755-58770, 60902-60917, or 67454-67469.

In certain embodiments, an antisense compound or antisense oligonucleotide provided herein targets AR within intron 2, for example within nucleotide regions 102239-139550 or 139835-144840 of SEQ ID NO: 1. In certain embodiments, an antisense compound provided herein targeted to intron 2 of AR is complementary within any of the following nucleotide regions of SEQ ID NO: 1: 114874-114889, 115272-115287, 115365-115380, or 134971-134986.

In certain embodiments, the following nucleotide regions of SEQ ID NO: 1, when targeted by antisense compounds or antisense oligonucleotides, display at least 50% inhibition: 3099-3114, 3120-3135, 3351-3366, 3353-3368, 3361-3376, 3513-3528, 3519-3534, 3768-3783, 3799-3814, 3851-3866, 3888-3903, 4059-4074, 4534-4549, 4555-4570, 4571-4586, 4578-4593, 4655-4670, 4699-4714, 4750-4765, 4755-4770, 4865-4880, 5054-5069, 5060-5075, 5061-5076, 5062-5077, 5155-5170, 5265-5280, 5392-5407, 5448-5463, 5483-5498, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58735, 58720-58739, 58721-58736, 58722-58737, 58723-58738, 58724-58739, 58725-58740, 58750-58765, 58750-58769, 58751-58766, 58752-58767, 58753-58768, 58754-58769, 58755-58770, 60902-60917, 67454-67469, 102156-102171, 114874-114889, 114874-114889, 115272-115287, 115365-115380, 134971-134986, 144856-144871, 181695-181710, 182958-182973, and 183049-183064.

In certain embodiments, the following nucleotide regions of SEQ ID NO: 1, when targeted by antisense compounds or antisense oligonucleotides, display at least 60% inhibition: 3799-3814, 3851-3866, 3888-3903, 4059-4074, 4534-4549, 4555-4570, 4571-4586, 4578-4593, 4655-4670, 4699-4714, 4755-4770, 4865-4880, 5060-5075, 5061-5076, 5062-5077, 5155-5170, 5265-5280, 5392-5407, 5448-5463, 5483-5498, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 42017-42032, 56050-56065, 58719-58734, 58720-58735, 58720-58739, 58721-58736, 58722-58737, 58723-58738, 58724-58739, 58725-58740, 58750-58765, 58750-58769, 58751-58766, 58752-58767, 58753-58768, 58754-58769, 58755-58770, 67454-67469, 102156-102171, 115272-115287, 115365-115380, 144856-144871, 181695-181710, 182958-182973, and 183049-183064.

In certain embodiments, the following nucleotide regions of SEQ ID NO: 1, when targeted by antisense compounds or antisense oligonucleotides, display at least 70% inhibition: 3799-3814, 3851-3866, 3888-3903, 4059-4074, 4534-4549, 4655-4670, 4699-4714, 4755-4770, 4865-4880, 5060-5075, 5062-5077, 5155-5170, 5265-5280, 5392-5407, 5448-5463, 5483-5498, 7543-7558, 8471-8486, 8638-8653, 9464-9479, 10865-10880, 11197-11212, 11855-11870, 13189-13204, 13321-13336, 13346-13361, 16555-16570, 16793-16808, 16968-16983, 17206-17221, 18865-18880, 33315-33330, 42017-42032, 58719-58734, 58720-58739, 58720-58735, 58721-58736, 58722-58737, 58723-58738, 58724-58739, 58725-58740, 58750-58769, 58750-58765, 58751-58766, 58752-58767, 58753-58768, 58754-58769, 58755-58770, 102156-102171, 115365-115380, 144856-144871, 181695-181710, 182958-182973, and 183049-183064.

In certain embodiments, the following nucleotide regions of SEQ ID NO: 1, when targeted by antisense compounds or antisense oligonucleotides, display at least 80% inhibition: 3799-3814, 3851-3866, 3888-3903, 4059-4074, 4534-4549, 4655-4670, 4699-4714, 4755-4770, 4865-4880, 5060-5075, 5062-5077, 5155-5170, 5265-5280, 5392-5407, 5448-5463, 5483-5498, 8471-8486, 8638-8653, 9464-9479, 10865-10880, 11197-11212, 13189-13204, 16793-16808, 58719-58734, 58720-58735, 58721-58736, 58722-58737, 58723-58738, 58724-58739, 58725-58740, 58750-58765, 58751-58766, 58752-58767, 58753-58768, 58754-58769, 58755-58770, 102156-102171, 144856-144871, 181695-181710, 182958-182973, and 183049-183064.

In certain embodiments, the following nucleotide regions of SEQ ID NO: 1, when targeted by antisense compounds or antisense oligonucleotides, display at least 90% inhibition: 4534-4549, 5060-5075, 5062-5077, 5155-5170, 5265-5280, 5448-5463, 58720-58735, 58721-58736, 58722-58737, 58723-58738, 58724-58739, 58725-58740, 58750-58765, 58751-58766, 58752-58767, 58753-58768, 58754-58769, 58755-58770, 182958-182973, and 183049-183064.

In certain embodiments, the following antisense compounds or antisense oligonucleotides target a region of an androgen receptor nucleic acid and effect at least a 50% inhibition of an androgen receptor mRNA, ISIS IDs: 549332, 549334, 549338, 549347, 549358, 549360, 549361, 549362, 549366, 549371, 549372, 549374, 549377, 549379, 549380, 549381, 549387, 549390, 549414, 549432, 549434, 549457, 549458, 549459, 560071, 560098, 560099, 560100, 560131, 560132, 560133, 560137, 569213, 569215, 569216, 569220, 569222, 569223, 569227, 569228, 569229, 569236, 569238, 583559, 583567, 583608, 583609, 583613, 583635, 583638, 583662, 583795, 583796, 583799, 583834, 583919, 584145, 584148, 584149, 584152, 584157, 584158, 584162, 584163, 584165, 584166, 584167, 584168, 584179, 584180, 584183, 584184, 584192, 584233, 584242, 584245, 584263, 584269, 584274, 584312, 584329, 584361, 584465, 584465, 584468, 584469, 584469, 584495, 584495, 585233, 585259, 585262, 585263, 585264, 585265, 585268, 585269, 585271, 585274, 586124, 586224, 586224, 586225, 586225, 586227, and 586227.

In certain embodiments, the following antisense compounds or antisense oligonucleotides target a region of an androgen receptor nucleic acid and effect at least a 50% inhibition of an androgen receptor mRNA, SEQ ID NOs: 12, 13, 14, 15, 16, 17, 18, 19, 20, 21, 22, 23, 24, 25, 26, 27, 29, 31, 32, 33, 34, 35, 36, 37, 38, 39, 40, 41, 42, 43, 46, 49, 53, 54, 55, 57, 59, 63, 92, 93, 95, 101, 125, 148, 149, 150, 151, 152, 153, 154, 155, 156, 157, 158, 159, 160, 161, 162, 163, 164, 165, 166, 167, 168, 169, 170, 171, 172, 173, 174, 175, 176, and 177.

In certain embodiments, the following antisense compounds or antisense oligonucleotides target a region of an androgen receptor nucleic acid and effect at least a 60% inhibition of an androgen receptor mRNA, ISIS IDs: 549332, 549334, 549338, 549347, 549358, 549360, 549361, 549362, 549366, 549371, 549372, 549374, 549377, 549379, 549380, 549381, 549387, 549390, 549414, 549432, 549434, 549457, 549458, 549459, 560071, 560098, 560099, 560100, 560131, 560137, 569213, 569216, 569222, 569228, 569236, 583795, 583796, 583799, 584145, 584148, 584149, 584152, 584157, 584158, 584162, 584163, 584165, 584166, 584167, 584168, 584179, 584180, 584183, 584184, 584192, 584233, 584242, 584245, 584274, 584312, 584361, 584468, 584469, 585233, 585259, 585262, 585263, 585264, 585265, 585268, 585269, 585274, 586124, 586224, 586225, and 586227.

In certain embodiments, the following antisense compounds or antisense oligonucleotides target a region of an androgen receptor nucleic acid and effect at least a 60% inhibition of an androgen receptor mRNA, SEQ ID NOs: 12, 13, 14, 15, 16, 17, 18, 19, 20, 21, 22, 23, 24, 25, 26, 27, 29, 31, 32, 33, 34, 35, 36, 37, 38, 38, 39, 40, 41, 42, 43, 92, 93, 95, 148, 149, 150, 151, 152, 153, 154, 155, 156, 157, 158, 159, 160, 161, 162, 163, 164, 165, 166, 167, 170, 171, 173, 175, and 176.

In certain embodiments, the following antisense compounds or antisense oligonucleotides target a region of an androgen receptor nucleic acid and effect at least a 70% inhibition of an androgen receptor mRNA, ISIS IDs: 549332, 549334, 549338, 549347, 549358, 549360, 549361, 549362, 549366, 549371, 549372, 549374, 549377, 549379, 549380, 549381, 549387, 549390, 549414, 549432, 549434, 549457, 549458, 549459, 560071, 560098, 560099, 560100, 560131, 560137, 569222, 584145, 584148, 584149, 584152, 584162, 584163, 584165, 584166, 584167, 584168, 584179, 584180, 584183, 584184, 584192, 584245, 584274, 584469, 585259, 585262, 585268, 585269, 586124, 586224, 586225, and 586227.

In certain embodiments, the following antisense compounds or antisense oligonucleotides target a region of an androgen receptor nucleic acid and effect at least a 70% inhibition of an androgen receptor mRNA, SEQ ID NOs: 12, 13, 14, 15, 16, 17, 18, 19, 20, 21, 22, 23, 24, 25, 26, 27, 29, 31, 32, 33, 34, 35, 36, 37, 38, 39, 40, 41, 43, 148, 149, 150, 151, 154, 155, 156, 157, 158, 159, 160, 161, 162, 163, 164, 167, 170, and 176.

In certain embodiments, the following antisense compounds or antisense oligonucleotides target a region of an androgen receptor nucleic acid and effect at least a 80% inhibition of an androgen receptor mRNA, ISIS IDs: 549332, 549334, 549338, 549347, 549358, 549360, 549361, 549362, 549366, 549371, 549372, 549374, 549377, 549379, 549380, 549381, 549387, 549390, 549414, 549432, 549434, 549457, 549458, 549459, 560098, 560099, 560100, 560137, 584148, 584149, 584152, 584162, 584163, 584166, 584180, 586124, 586224, 586225, and 586227.

In certain embodiments, the following antisense compounds or antisense oligonucleotides target a region of an androgen receptor nucleic acid and effect at least a 80% inhibition of an androgen receptor mRNA, SEQ ID NOs: 12, 13, 14, 15, 16, 17, 18, 19, 20, 21, 22, 23, 24, 25, 26, 27, 29, 31, 32, 33, 34, 35, 36, 37, 39, 40, 41, 43, 149, 150, 151, 154, 155, 157, and 161.

In certain embodiments, the following antisense compounds or antisense oligonucleotides target a region of an androgen receptor nucleic acid and effect at least a 90% inhibition of an androgen receptor mRNA, ISIS IDs: 549358, 549371, 549372, 549374, 549377, 549380, 549432, 549434, 549457, 549458, 549459, 560098, 560099, 560100, 560137, and 586224.

In certain embodiments, the following antisense compounds or antisense oligonucleotides target a region of an androgen receptor nucleic acid and effect at least a 90% inhibition of an androgen receptor mRNA, SEQ ID NOs: 16, 21, 22, 23, 24, 26, 33, 34, 35, 36, 37, 39, 40, and 41.

Percent inhibition of androgen receptor mRNA can be determined using standard methods known to those of skill in the art, such as described in Example 1.

It is understood that the sequence set forth in each SEQ ID NO in the examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by ISIS number (ISIS #) indicate a combination of nucleobase sequence, chemical modification, and motif.

In certain embodiments, the compounds or compositions as described herein are efficacious by virtue of having at least one of an in vitro $IC_{50}$ of less than 250 nM, less than 200 nM, less than 150 nM, less than 100 nM, less than 90 nM, less than 80 nM, less than 70 nM, less than 65 nM, less than 60 nM, less than 55 nM, less than 50 nM, less than 45 nM, less than 40 nM, less than 35 nM, less than 30 nM, less than 25 nM, or less than 20 nM when delivered to HuVEC cells. In certain embodiments inhibition is measured with primer probe set RTS3559, as described herein.

In certain embodiments, the compounds or compositions as described herein are highly tolerable as demonstrated by having at least one of an increase an ALT or AST value of no more than 4 fold, 3 fold, or 2 fold over saline treated animals or an increase in liver, spleen, or kidney weight of no more than 30%, 20%, 15%, 12%, 10%, 5%, or 2%. In certain embodiments, the compounds or compositions as described herein are highly tolerable as demonstrated by having no increase of ALT or AST over saline treated animals. In certain embodiments, the compounds or compositions as described herein are highly tolerable as demonstrated by having no increase in liver, spleen, or kidney weight over saline treated animals.

In certain embodiments, an antisense compound provided herein targets an AR splicing variant that includes exon 1 encoding the N-terminal domain and exons 2 and 3 encoding the DNA binding domain, but does not include at least a portion of exon 4 encoding the short hinge region or at least a portion of exons 4-8 encoding the ligand binding domain. An example of such an AR splicing variant includes, but is not limited to, AR-V7, which contains exons 1-3 but lacks exons 4-8. Additional examples of such AR splicing variants include, for example, AR3, AR4, AR4b, AR5, and AR6 (SEQ ID NOs: 4-8, respectively). In certain embodiments, an antisense compound targeted to AR upstream of the 3' end of exon 3 and/or upstream of the ligand binding domain is capable of inhibiting androgen receptor levels to a greater extent than an antisense compound targeted to the ligand binding domain, such as EZN-4176, which is targeted to exon 4 and corresponds to SEQ ID NO: 58 described in U.S. Pat. No. 7,737,125.

In certain embodiments, an antisense compound targets an AR splicing variant that has a functional DNA binding domain, but not a functional ligand binding domain. It will be understood that in certain embodiments an antisense compound can target an AR splicing variant that includes the entire or at least a functional portion of exon 1 encoding the N-terminal domain and the entire or at least a functional portion of exons 2 and 3 encoding the DNA binding domain, but does not include at least a functional portion of exon 4 encoding the short hinge region or at least a functional portion of exons 4-8 encoding the ligand binding domain. It is contemplated that certain AR splicing variants targeted by the antisense compounds provided herein substantially consisting of exons 1-3 may also include a non-functional portion of nucleic acid sequence from a genomic region or exons 4-8. It is contemplated that the splicing process may give rise to such AR splicing variants that retain DNA binding function but not ligand binding function. In certain embodiments, an antisense compound targeted to an AR splicing variant that has a functional DNA binding domain, but not a functional ligand binding domain, is capable of inhibiting growth or proliferation of prostate cancer cells that are castrate-resistant. In certain embodiments, an antisense compound targeted to an AR splicing variant that has a functional DNA binding domain, but not a functional ligand binding domain, is capable of inhibiting growth or proliferation of a prostate cancer cell resistant to a diarylhydantoin AR inhibitor of Formula XI to a greater extent than an antisense compound targeted to the ligand binding domain, such as EZN-4176, which is targeted to exon 4 and corresponds to SEQ ID NO: 58 described in U.S. Pat. No. 7,737,125. In certain embodiments, an antisense compound provided herein targets AR within exon 1, which is upstream of the 3' end of exon 3 and/or upstream of the ligand binding domain. In certain embodiments, an antisense compound provided herein targets AR within exon 2, which is upstream of the 3' end of exon 3 and/or upstream of the ligand binding domain. In certain embodiments, an antisense compound provided herein targets AR within intron 1, which is upstream of the 3' end of exon 3 and/or upstream of the ligand binding domain.

In certain embodiments, an antisense compound provided herein is capable of reducing expression of both full-length AR and an AR splicing variant that includes exon 1 encoding the N-terminal domain and exons 2 and 3 encoding the DNA binding domain, but does not include at least a portion of exon 4 encoding the short hinge region or at least a portion of any one of exons 4-8 encoding the ligand binding domain. In certain embodiments, such an antisense compound targets human androgen receptor upstream of the ligand binding domain. In certain embodiments, such antisense compounds target human androgen receptor upstream of the 3' end of exon 3. In certain embodiments, an antisense compound provided herein targets AR within exon 1, which is upstream of the 3' end of exon 3 and/or upstream of the ligand binding domain. In certain embodiments, an antisense compound provided herein targets AR within exon 2, which is upstream of the 3' end of exon 3 and/or upstream of the ligand binding domain. In certain embodiments, an antisense compound provided herein targets AR within intron 1, which is upstream of the 3' end of exon 3 and/or upstream of the ligand binding domain.

In certain embodiments, an antisense compound provided herein targets an AR splicing variant that includes exon 1 encoding the N-terminal domain and exons 2 and 3 encoding the DNA binding domain, but does not include at least a portion of exon 4 encoding the short hinge region or at least a portion of exons 4-8 encoding the ligand binding domain. An example of such an AR splicing variant includes, but is not limited to, AR-V7, which contains exons 1-3 but lacks exons 4-8.

Certain embodiments are drawn to an antisense compound targeted to human androgen receptor (AR) upstream of the ligand binding domain that is capable of inhibiting growth or proliferation of the resistant prostate cancer cell to a greater extent than an antisense compound targeted to the ligand binding domain, such as EZN-4176, which is targeted to exon 4 and corresponds to SEQ ID NO: 58 described in U.S. Pat. No. 7,737,125. In certain embodiments, an antisense compound targeted to human androgen receptor (AR) upstream of the ligand binding domain is targeted to a region of AR upstream of the 3' end of exon 3. In certain embodiments, an antisense compound provided herein targets AR within exon 1, which is upstream of the 3' end of exon 3 and/or upstream of the ligand binding domain. In certain embodiments, an antisense compound provided herein targets AR within exon 2, which is upstream of the 3' end of exon 3 and/or upstream of the ligand binding domain. In certain embodiments, an antisense compound provided herein targets AR within intron 1, which is upstream of the 3' end of exon 3 and/or upstream of the ligand binding domain.

In certain embodiments, the nucleobase sequence of a modified oligonucleotide provided herein is at least 70%, 75%, 80%, 85%, 90%, 95% or 100% complementary to any one of SEQ ID NOs: 1-8, as measured over the entirety of the modified oligonucleotide.

In certain embodiments, an antisense compound is a modified oligonucleotide consisting of 12 to 30 linked nucleosides and having a nucleobase sequence at least 90% complementary to any of SEQ ID NOs: 1-8 as measured over the entirety of said modified oligonucleotide.

In certain embodiments, an antisense compound is a modified oligonucleotide consisting of 12 to 30 linked nucleosides and having a nucleobase sequence 100% complementary to any of SEQ ID NOs: 1-8 as measured over the entirety of said modified oligonucleotide. In certain embodiments, a compound or modified oligonucleotide provided herein is single-stranded.

In certain embodiments, a modified oligonucleotide provided herein consists of 8, 9, 10, 11, 12, 13, 14, 15, 16, 17, 18, 19, 20, 21, 22, 23, 24, 25, 26, 27, 28, 29 or 30 linked nucleosides. In certain embodiments, the modified oligonucleotide consists of 20 linked nucleosides. In certain embodiments, the modified oligonucleotide consists of 16 linked nucleosides.

In certain embodiments, at least one internucleoside linkage of a modified oligonucleotide provided herein is a modified internucleoside linkage. In certain embodiments, each internucleoside linkage is a phosphorothioate internucleoside linkage.

In certain embodiments, at least one nucleoside of the modified oligonucleotide comprises a modified sugar. In certain embodiments, at least one modified sugar comprises a 2'-O-methoxyethyl group (2'-O$(CH_2)_2$—$OCH_3$). In certain embodiments, the modified sugar comprises a 2'-O—$CH_3$ group.

In certain embodiments, at least one modified sugar is a bicyclic sugar. In certain embodiments, the bicyclic sugar comprises a 4'-$(CH_2)_n$—O-2' bridge, wherein n is 1 or 2. In certain embodiments, the bicyclic sugar comprises a 4'-$CH_2$—O-2' bridge. In certain embodiments, the bicyclic sugar comprises a 4-CH$(CH_3)$—O-2' bridge.

In certain embodiments, at least one nucleoside of a modified oligonucleotide provided herein comprises a modified nucleobase. In certain embodiments, the modified nucleobase is a 5-methylcytosine.

In certain embodiments, a modified oligonucleotide provided herein consists of a single-stranded modified oligonucleotide.

In certain embodiments, compounds or compositions provided herein comprise a salt of the modified oligonucleotide.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to an androgen receptor nucleic acid can be utilized in pharmaceutical compositions by combining the antisense compound with a suitable pharmaceutically acceptable diluent or carrier. In certain embodiments, a pharmaceutically acceptable diluent is water, such as sterile water suitable for injection. Accordingly, in one embodiment, employed in the methods described herein is a pharmaceutical composition comprising an antisense compound targeted to an androgen receptor nucleic acid and a pharmaceutically acceptable diluent. In certain embodiments, the pharmaceutically acceptable diluent is water. In certain embodiments, the antisense compound is an antisense oligonucleotide provided herein.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

In certain embodiments, the compounds or compositions further comprise a pharmaceutically acceptable carrier or diluent.

Certain Indications

Certain aspects of the invention are directed to methods of treating cancer which comprises administering an antisense compound targeted to androgen receptor as provided herein. In certain embodiments, the cancer is AR positive. In certain embodiments, the cancer is prostate cancer, breast cancer, ovarian cancer, bladder cancer or gastric cancer. In certain embodiments, the antisense compound targeted to androgen receptor comprises a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, the antisense compound targeted to androgen receptor comprises a modified oligonucleotide consisting of 10 to 30 linked nucleosides and having a nucleobase sequence comprising any of SEQ ID NOs: 12-179. In certain embodiments, the antisense compound targeted to androgen receptor comprises a modified oligonucleotide consisting of the nucleobase sequence of any of SEQ ID NOs: 12-179. In certain embodiments, the antisense compound targeted to androgen receptor comprises a modified oligonucleotide consisting of 16 linked nucleosides and having a nucleobase sequence consisting of SEQ ID NO: 35, 39, 43, 124, 150, 155, 169, or 175. In certain embodiments, the antisense compound is single-stranded. In certain embodiments, the antisense compound targeted to androgen receptor is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

Certain aspects are directed to an antisense compound targeted to androgen receptor provided herein for use in treating cancer. In certain embodiments, the cancer is AR positive. In certain embodiments, the cancer is prostate cancer, breast cancer, ovarian cancer, bladder cancer or gastric cancer. In certain embodiments, the antisense compound targeted to androgen receptor comprises a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, the antisense compound targeted to androgen receptor comprises a modified oligonucleotide consisting of 10 to 30 linked nucleosides and having a nucleobase sequence comprising any of SEQ ID NOs: 12-179. In certain embodiments, the antisense compound targeted to androgen receptor comprises a modified oligonucleotide consisting of the nucleobase sequence of any of SEQ ID NOs: 12-179. In certain embodiments, the antisense compound targeted to androgen receptor comprises a modified oligonucleotide consisting of 16 linked nucleosides and having a nucleobase sequence consisting of SEQ ID NO: 35, 39, 43, 124, 150, 155, 169, or 175. In certain embodiments, the antisense compound is single-stranded. In certain embodiments, the antisense compound targeted to androgen receptor is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

Certain aspects are directed to use of an antisense compound targeted to androgen receptor provided herein for the manufacture of a medicament for treating cancer. In certain embodiments, the cancer is AR positive. In certain embodiments, the cancer is prostate cancer, breast cancer, ovarian cancer, bladder cancer or gastric cancer. In certain embodiments, the antisense compound targeted to androgen receptor comprises a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, the antisense compound targeted to androgen receptor comprises a modified oligonucleotide consisting of 10 to 30 linked nucleosides and having a nucleobase sequence comprising any of SEQ ID NOs: 12-179. In certain embodiments, the antisense compound targeted to androgen receptor comprises a modified oligonucleotide consisting of the nucleobase sequence of any of SEQ ID NOs: 12-179. In certain embodiments, the antisense compound targeted to androgen receptor comprises a modified oligonucleotide consisting of 16 linked nucleosides and having a nucleobase sequence consisting of SEQ ID NO: 35, 39, 43, 124, 150, 155, 169, or 175. In certain embodiments, the antisense compound is single-stranded. In certain embodiments, the antisense compound targeted to androgen receptor is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

Certain aspects of the invention are directed to the use of an antisense compound targeted to human androgen receptor (AR) as described herein, for treating a cancer patient whose cancer has become resistant to treatment with an anti-androgenic agent (e.g. compound or drug). In certain embodiments, said cancer is prostate cancer. In certain embodiments, said patient is one that has, or whose cancer has, developed resistance to treatment with an agent selected from: MDV3100, ARN-059, ODM-201, abiraterone acetate, TOK001, TAK700 and VT464. In certain embodiments, the antisense compound targeted to androgen receptor comprises a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, the antisense compound targeted to androgen receptor comprises a modified oligonucleotide consisting of 10 to 30 linked nucleosides and having a nucleobase sequence comprising any of SEQ ID NOs: 12-179. In certain embodiments, the antisense compound targeted to androgen receptor comprises a modified oligonucleotide consisting of the nucleobase sequence of any of SEQ ID NOs: 12-179. In certain embodiments, the antisense compound targeted to androgen receptor comprises a modified oligonucleotide consisting of 16 linked nucleosides and having a nucleobase sequence consisting of SEQ ID NO: 35, 39, 43, 124, 150, 155, 169, or 175. In certain embodiments, the antisense compound targets AR within exon 1, for example within nucleotide regions 2863-5593 (exon 1) or 27672-27853 (exon 1B) of SEQ ID NO: 1. In certain embodiments, an antisense compound provided herein targeted to exon 1 of AR is complementary within any of the following nucleotide regions of SEQ ID NO: 1: 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5052-5067, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, or 5521-5536. In certain embodiments, an antisense compound provided herein targets AR within exon 2, for example within nucleotide regions 102087-102238 (exon 2) or 139551-139834 (exon 2c) of SEQ ID NO: 1. In certain embodiments, an antisense compound provided herein targeted to exon 2 of AR is complementary within any of the following nucleotide regions of SEQ ID NO: 1: 102155-102170, 102156-102171, 139682-139697, 139762-139777, or 139782-139797. In certain embodiments, an antisense compound provided herein targets AR within exon 3, for example within nucleotide regions 144841-144957 (exon 3), 148380-148594 (exon 3b), or 153504-154908 (exon 3d) of SEQ ID NO: 1. In certain embodiments, an antisense compound provided herein targeted to exon 3 of AR is complementary within any of the following nucleotide regions of SEQ ID NO: 1: 144856-144871, 144938-144953, 148406-148421, 148443-148458, or 148520-148535. In certain embodiments, an antisense compound provided herein targets AR within intron 1, for example within nucleotide regions 5594-27671 or 27854-102086 of SEQ ID NO: 1. In certain embodiments, an antisense compound provided herein targeted to intron 1 of AR is complementary within any of the following nucleotide regions of SEQ ID NO: 1: 5666-5681, 6222-6237, 6701-6716, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58739, 58720-58735, 58721-58736, 58722-58737, 58723-58738, 58724-58739, 58724-58739, 58725-58740, 58725-58740, 58725-58740, 58750-58769, 58750-58765, 58751-58766, 58752-58767, 58753-58768, 58754-58769, 58755-58770, 60902-60917, or 67454-67469. In certain embodiments, an antisense compound provided herein targets AR within intron 2, for example within nucleotide regions 102239-139550 or 139835-144840 of SEQ ID NO: 1. In certain embodiments, an antisense compound provided herein targeted to intron 2 of AR is complementary within any of the following nucleotide regions of SEQ ID NO: 1: 114874-114889, 115272-115287, 115365-115380, or 134971-134986. In certain embodiments, the antisense compound is single-stranded. In certain embodiments, the antisense compound targeted to androgen receptor is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

By resistant to treatment with a particular agent (e.g. compound or drug) is meant that the agent is less or no longer effective in halting the growth or spread of the cancer and so the patient, or their cancer, has become less responsive or sensitive to it over time. Typically such patient would be classed as resistant to said agent and would no longer be treated with such agent. A subject having prostate cancer resistant to an agent selected from: MDV3100, ARN-059, ODM-201, abiraterone acetate, TOK001, TAK700 and VT464 can include, for example, a patient who previously received said agent but whose prostate cancer has become less sensitive or responsive to a agent. For example, prostate cancer resistant to an anti-androgenic agent selected from: MDV3100, ARN-059, ODM-201, abiraterone acetate, TOK001, TAK700 and VT464, can include prostate cancer that has increased in tumor volume, metastasis, or progression despite treatment with the agent. In certain embodiments, prostate cancer resistant to an anti-androgenic agent selected from: MDV3100, ARN-059, ODM-201, abiraterone acetate, TOK001, TAK700 and VT464, can include prostate cancer that is refractory to the agent and is not decreasing in tumor volume, metastasis, or progression despite treatment. Several embodiments relate to a method of treating prostate cancer resistant to an anti-androgenic agent selected from: MDV3100, ARN-059, ODM-201, abiraterone acetate, TOK001, TAK700 and VT464, in a subject comprising identifying the subject as having prostate cancer resistant to the agent and administering to the subject an antisense compound targeted to human androgen receptor (AR) upstream of the 3' end of exon 3 and/or upstream of the ligand binding domain, as described herein. Several embodiments relate to a method of treating prostate cancer resistant to an anti-androgenic agent selected from: MDV3100, ARN-059, ODM-201, abiraterone acetate, TOK001, TAK700 and VT464, in a subject comprising administering to a subject identified or diagnosed as having prostate cancer resistant to said anti-androgenic agent an antisense compound targeted to human androgen receptor (AR) upstream of the 3' end of exon 3 and/or upstream of the ligand binding domain, as described herein. In certain embodiments, prostate cancer cells resistant to an anti-androgenic agent selected from: MDV3100, ARN-059, ODM-201, abiraterone acetate, TOK001, TAK700 and VT464, preferentially expresses an AR splicing variant over full-length AR.

Certain aspects of the invention are directed to a method of treating a patient suffering from prostate cancer wherein the patient has, or their cancer has, developed or become resistant to treatment with an anti-androgenic agent (compound or drug) comprising administering to said patient an antisense compound targeted to human androgen receptor (AR) as described herein. In certain embodiments, said patient is one that has developed resistance to treatment with an agent selected from: MDV3100, ARN-059, ODM-201, abiraterone acetate, TOK001, TAK700 and VT464. In certain embodiments, the antisense compound targeted to androgen receptor comprises a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, the antisense compound targeted to androgen receptor comprises a modified oligonucleotide consisting of 10 to 30 linked nucleosides and having a nucleobase sequence comprising any of SEQ ID NOs: 12-179. In certain embodiments, the antisense compound targeted to androgen receptor comprises a modified oligonucleotide consisting of the nucleobase sequence of any of SEQ ID NOs: 12-179. In certain embodiments, the antisense compound targeted to androgen receptor comprises a modified oligonucleotide consisting of 16 linked nucleosides and having a nucleobase sequence consisting of SEQ ID NO: 35, 39, 43, 124, 150, 155, 169, or 175. In certain embodiments, the antisense compound is single-stranded. In certain embodiments, the antisense compound targeted to androgen receptor is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

A prostate cancer that has developed or become resistant to treatment with an anti-androgenic agent is referred to as castrate-resistant prostate cancer (CRPC). Thus, in several embodiments, a prostate cancer cell resistant to an anti-androgenic agent, such as MDV3100, was previously exposed to the inhibitor and has become less responsive or sensitive to it over time. For example, MDV3100 might initially inhibit prostate cancer cell growth or proliferation in the patient, but over time such inhibitory effect may be diminished when the cells become resistant to the inhibitor.

Certain aspects of the invention are directed to the use of an antisense compound targeted to androgen receptor provided herein for the manufacture of a medicament for treating cancer in a patient whose cancer has become become resistant to treatment with an anti-androgenic agent (compound or drug). In certain embodiments the cancer is prostate cancer. In certain embodiments, said patient is one that has, or whose cancer has, developed resistance to treatment with an agent selected from: MDV3100, ARN-059, ODM-201, abiraterone acetate, TOK001, TAK700 and VT464. In certain embodiments, the antisense compound targeted to androgen receptor comprises a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, the antisense compound targeted to androgen receptor comprises a modified oligonucleotide consisting of 10 to 30 linked nucleosides and having a nucleobase sequence comprising any of SEQ ID NOs: 12-179. In certain embodiments, the antisense compound targeted to androgen receptor comprises a modified oligonucleotide consisting of the nucleobase sequence of any of SEQ ID NOs: 12-179. In certain embodiments, the antisense compound targeted to androgen receptor comprises a modified oligonucleotide consisting of 16 linked nucleosides and having a nucleobase sequence consisting of SEQ ID NO: 35, 39, 43, 124, 150, 155, 169, or 175. In certain embodiments, the antisense compound is single-stranded. In certain embodiments, the antisense compound targeted to androgen receptor is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

Enzalutamide:

MDV3100, also known as enzalutamide (Xtandi™) and by the IUPAC name 4-(3-(4-cyano-3-(trifluoromethyl)phenyl)-5,5-dimethyl-4-oxo-2-thioxoimidazolidin-1-yl)-2-fluoro-N-methylbenzamide, is an androgen receptor ligand binding inhibitor belonging to the diarylhydantoin class of androgen receptor inhibitors represented by Formula XI. MDV3100 has the following chemical formula:

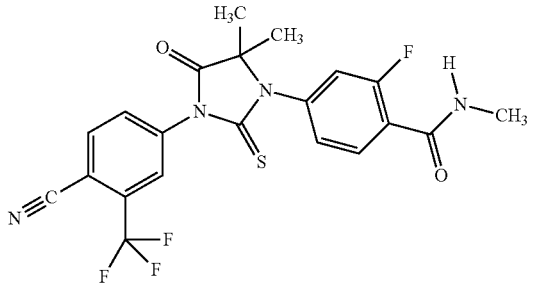

MDV3100 and additional diarylhydantoin androgen receptor inhibitors suitable for use in certain embodiments provided herein are described in U.S. Pat. No. 7,709,517, US Patent Application Publication No. US20100172975 and US Patent Application Publication No. US20100210665, which are incorporated herein by reference in their entireties.

ARN-509:

(XII)

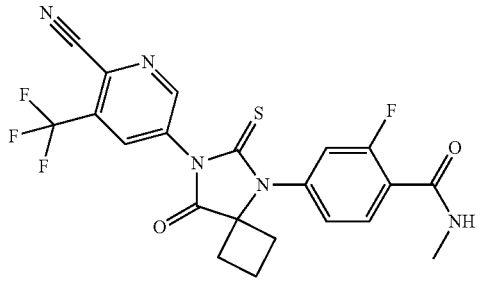

The compound of Formula XII, also known as ARN-509 and by the IUPAC name 4-(7-(6-Cyano-5-(trifluoromethyl) pyridin-3-yl)-6,8-dioxo-5,7-diazaspiro[3.4]octan-5-yl)-2-fluoro-N-methylbenzamide, is an androgen receptor ligand binding inhibitor. ARN-509 and additional androgen receptor inhibitors suitable for use in certain embodiments provided herein are described in WO 2007126765, WO 2008119015 and US Patent Application Publication No. 2013/0116258, which are incorporated herein by reference in their entirety.

Abiraterone Acetate

The compound of Formula XIII, which is also known as Abiraterone acetate and ZYTIG-A® and by the IUPAC name [(3S,8R,9S,10R,13S,14S)-10,13-dimethyl-17-(3-pyridyl)-2,3,4,7,8,9,11,12,14,15-decahydro-1H-cyclopenta[a]phenanthren-3-yl]acetate, is an androgen biosynthesis inhibitor and has the following chemical formula:

(XIII)

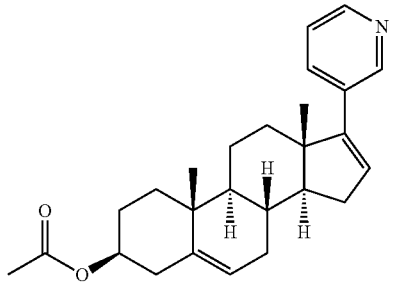

The structure and synthesis of Abiraterone acetate is described in Potter et al., Journal of Medicinal Chemistry (38(13), 2463-71, 1995), which is incorporated herein by reference in its entirety.

Galeterone:

The compound of Formula XIV, which is also known as TOK-001 and Galeterone, and by the IUPAC name (3S,10R,13S)-17-(1H-benzo[d]imidazol-1-yl)-10,13-dimethyl-2,3,4,7,8,9,10,11,12,13,14,15-dodecahydro-1H-cyclopenta[a]phenanthren-3-ol, has the following chemical formula:

(XIV)

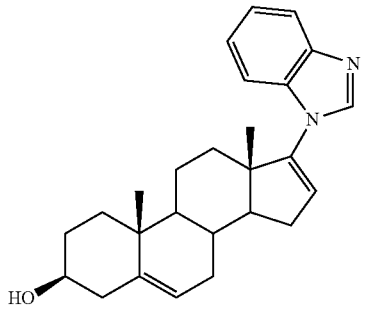

The structure and synthesis of TOK-001 is described in Handratta et al., (Journal of Medicinal Chemistry (2005), 48(8), 2972-84, 2005), which is incorporated herein by reference in its entirety:

Orteronel:

The compound of Formula XV, which is also known as TAK-700 and Orteronel and by the IUPAC name 6-[7(S)-hydroxy-6,7-dihydro-5H-pyrrolo[1,2-c]imidazol-7-yl]-N-methylnaphthalene-2-carboxamide, is an androgen biosynthesis inhibitor and has the following chemical formula:

(XV)

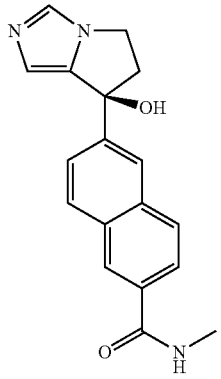

The structure and synthesis of TAK-700 is described in Kaku et al., Bioorganic and Medicinal Chemistry (19(21), 6383-99, 2011).

Yin et al., (Int. J. Mol. Sci., 14(7):13958-13978, 2013) discusses recent progress with various pharmaceutical therapies, including ODM-21, VT464, ARN509, TAK700 and TOK-001, for castration-resistant prostate cancer.

Certain Combinations and Combination Therapies

In certain embodiments, a first agent comprising the compound described herein is co-administered with one or more secondary agents. In certain embodiments, such second agents are designed to treat the same disease, disorder, or condition as the first agent described herein. In certain embodiments, such second agents are designed to treat a different disease, disorder, or condition as the first agent described herein. In certain embodiments, a first agent is designed to treat an undesired side effect of a second agent. In certain embodiments, second agents are co-administered with the first agent to treat an undesired effect of the first agent. In certain embodiments, such second agents are designed to treat an undesired side effect of one or more pharmaceutical compositions as described herein. In certain embodiments, second agents are co-administered with the first agent to produce a combinational effect. In certain embodiments, second agents are co-administered with the first agent to produce a synergistic effect. In certain embodiments, the co-administration of the first and second agents permits use of lower dosages than would be required to achieve a therapeutic or prophylactic effect if the agents were administered as independent therapy.

In certain embodiments, one or more compounds or compositions provided herein are co-administered with one or more anti-androgenic agents. In certain embodiments, one or more compounds or compositions provided herein and one or more anti-androgenic agents, are administered at different times. In certain embodiments, one or more compounds or compositions provided herein and one or more anti-androgenic agents, are prepared together in a single formulation. In certain embodiments, one or more compounds or compositions provided herein and one or more anti-androgenic agents, are prepared separately. In certain embodiments, an anti-androgenic agent is selected from MDV3100, ARN-059, ODM-201, abiraterone, TOK001, TAK700 and VT464.

Certain aspects of the invention are directed to the use of an antisense compound targeted to human androgen receptor (AR) as described herein in combination with an anti-androgenic agent. In particular embodiments such use is in a method of treating a patient suffering from cancer or in the manufacture of a medicament for treating cancer. In certain embodiments the cancer is selected from: prostate cancer, breast cancer, ovarian cancer, bladder cancer or gastric cancer. Particular classes of anti-androgenic agents are the second generation anti-hormonal agents such as: enzalutamide (MDV3100), ARN-059, ODM-201, abiraterone acetate, Galeterone (TOK001), orteronel (TAK700) and VT464 (see Yin et al. supra).

Certain aspects are drawn to a combination of an antisense compound targeted to human androgen receptor (AR) as described herein and an anti-androgenic agent, such as a second generation anti-hormonal agent selected from: MDV3100, ARN-059, ODM-201, abiraterone, TOK001, TAK700 and VT464.

In certain embodiments, such a combination of an antisense compound targeted to androgen receptor (AR) as described herein and an anti-androgenic agent, such as a second generation anti-hormonal agent selected from: MDV3100, ARN-059, ODM-201, abiraterone, TOK001, TAK700 and VT464, is useful for inhibiting cancer cell growth or proliferation and/or treating cancer. In certain embodiments the cancer is selected from: prostate cancer, breast cancer, ovarian cancer, bladder cancer or gastric cancer. In certain embodiments the cancer is prostate cancer. In certain embodiments the cancer is breast cancer. In certain embodiments, an antisense compound targeted to AR as described herein and an anti-androgenic agent, such as a second generation anti-hormonal agent selected from: MDV3100, ARN-059, ODM-201, abiraterone, TOK001, TAK700 and VT464, synergize in combination to inhibit growth or proliferation of a cancer cell. In several embodiments, the cancer cell is a prostate cancer cell which is or has become castration-resistant. In various embodiments, the cancer cell is a prostate cancer cell which is or has become resistant to a second generation anti-hormonal agent selected from: MDV3100, ARN-059, ODM-201, abiraterone, TOK001, TAK700 and VT464. In certain embodiments, the antisense compound targeted to androgen receptor comprises a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, the antisense compound targeted to androgen receptor comprises a modified oligonucleotide consisting of 10 to 30 linked nucleosides and having a nucleobase sequence comprising any of SEQ ID NOs: 12-179. In certain embodiments, the antisense compound targeted to androgen receptor comprises a modified oligonucleotide consisting of the nucleobase sequence of any of SEQ ID NOs: 12-179. In certain embodiments, the antisense compound targeted to androgen receptor comprises a modified oligonucleotide consisting of 16 linked nucleosides and having a nucleobase sequence consisting of SEQ ID NO: 35, 39, 43, 124, 150, 155, 169, or 175. In certain embodiments, the antisense compound targeted to androgen receptor is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

Several embodiments are drawn to a combination of an antisense compound targeted to human androgen receptor (AR) and a diarylhydantoin AR inhibitor of Formula XI, such as MDV3100. In several embodiments, a diarylhydantoin Androgen Receptor (AR) inhibitor is a compound of Formula XVI:

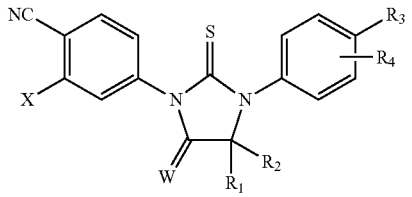

(XVI)

wherein X is selected from the group consisting of trifluoromethyl and iodo, wherein W is selected from the group consisting of O and NR5, wherein R5 is selected from the group consisting of H, methyl, and

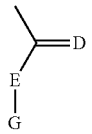

wherein D is S or O and E is N or O and G is alkyl, aryl, substituted alkyl or substituted aryl; or D is S or a and E-G together are C1-C4 lower alkyl, wherein R1 and R2 together comprise eight or fewer carbon atoms and are selected from the group consisting of alkyl, substituted alkyl including haloalkyl, and, together with the carbon to which they are linked, a cycloalkyl or substituted cycloalkyl group, wherein R3 is selected from the group consisting of hydrogen, halogen, methyl, C1-C4 alkoxy, formyl, haloacetoxy, trifluoromethyl, cyano, nitro, hydroxyl, phenyl, amino, methylcarbamoyl, methoxycarbonyl, acetamido, methanesulfonamino, methanesulfonyl, 4-methanesulfonyl-1-piperazinyl, piperazinyl, and C1-C6 alkyl or alkenyl optionally substituted with hydroxyl, methoxycarbonyl, cyano, amino, amido, nitro, carbamoyl, or substituted carbamoyl including methylcarbamoyl, dimethylcarbamoyl, and hydroxyethylcarbamoyl, wherein R4 is selected from the group consisting of hydrogen, halogen, alkyl, and haloalkyl, and wherein R3 is not methylaminomethyl or dimethylaminomethyl.

R5 may be

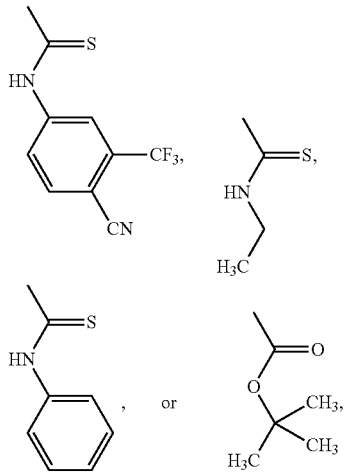

In certain embodiments, such a combination of an antisense compound targeted to androgen receptor (AR) and a diarylhydantoin AR inhibitor of Formula XVI, such as MDV3100, is useful for inhibiting prostate cancer cell growth or proliferation and/or treating prostate cancer. In certain embodiments, an antisense compound targeted to AR and a diarylhydantoin AR inhibitor of Formula XVI, such as MDV3100, synergize in combination to inhibit growth or proliferation of a prostate cancer cell. In several embodiments, the prostate cancer cell is castration-resistant. In various embodiments, the prostate cancer cell is resistant to a diarylhydantoin AR inhibitor of Formula XVI, such as MDV3100. In certain embodiments, the prostate cancer cell or castration-resistant prostate cancer cell preferentially expresses an AR splicing variant over full-length AR. In certain embodiments the antisense compound targeted to AR as described herein and the other anti-androgenic agent are used in combination treatment by administering the two agents simultaneously, separately or sequentially. In certain embodiments the two agents are formulated as a fixed dose combination product. In other embodiments the two agents are provided to the patient as separate units which can then either be taken simultaneously or serially (sequentially).

In certain embodiments, antisense compounds useful for inhibiting prostate cancer cell and/or castration-resistant prostate cancer cell growth or proliferation in combination with another anti-androgenic agent, such as a second generation anti-hormonal agent selected from: MDV3100, ARN-059, ODM-201, abiraterone, TOK001, TAK700 and VT464, target human androgen receptor upstream of the 3' end of exon 3 and/or upstream of the ligand binding domain. In certain embodiments, an antisense compound provided herein targets AR within exon 1, exon 2, exon 3, intron 1, or intron 2 as described herein.

In certain embodiments, an antisense compound provided herein targets an AR splicing variant that includes exon 1 encoding the N-terminal domain and exons 2 and 3 encoding the DNA binding domain, but does not include at least a portion of exon 4 encoding the short hinge region or at least a portion of exons 4-8 encoding the ligand binding domain. An example of such an AR splicing variant includes, but is not limited to, AR-V7, which contains exons 1-3 but lacks exons 4-8. Additional examples of such AR splicing variants include, for example, AR3, AR4, AR4b, AR5, and AR6 (SEQ ID NOs: 4-8, respectively). In certain embodiments, the prostate cancer cell, which may be castration-resistant, preferentially expresses an AR splicing variant over full-length AR. In particular embodiments the prostate cancer cell is castration-resistant to an anti-androgenic agent selected from: MDV3100, ARN-059, ODM-201, abiraterone, TOK001, TAK700 and VT464 In certain embodiments, an antisense compound targeted to AR upstream of the 3' end of exon 3 and/or upstream of the ligand binding domain is capable of inhibiting growth or proliferation of a prostate cancer cell, including a castration-resistant prostate cancer cell, in combination with an anti-androgenic agent selected from: MDV3100, ARN-059, ODM-201, abiraterone, TOK001, TAK700 and VT464, to a greater extent than an antisense compound targeted to the ligand binding domain, such as EZN-4176, which is targeted to exon 4 and corresponds to SEQ ID NO: 58 described in U.S. Pat. No. 7,737,125, in combination with the same anti-androgenic agent selected from: MDV3100, ARN-059, ODM-201, abiraterone, TOK001, TAK700 and VT464. In certain embodiments, the combination of an antisense compound as described herein and the anti-androgenic agent selected from: MDV3100, ARN-059, ODM-201, abiraterone, TOK001, TAK700 and VT464, provides a synergistic (e.g. greater-than-additive) effect in inhibiting the growth or proliferation of a prostate cancer cell, such as a castration-resistant prostate cancer cell, compared to the antisense compound alone or the anti-androgenic agent selected from: MDV3100, ARN-059, ODM-201, abiraterone, TOK001, TAK700 and VT464 alone. Accordingly, in certain embodiments the amounts of either or both of the antisense compound and/or anti-androgenic agent selected from: MDV3100, ARN-059, ODM-201, abiraterone, TOK001, TAK700 and VT464, when used in combination can be less than the corresponding amount of either the antisense compound alone or the anti-androgenic agent selected from: MDV3100, ARN-059, ODM-201, abiraterone, TOK001, TAK700 and VT464, alone necessary to achieve an equivalent level of prostate cancer cell growth or proliferation inhibition.

In certain embodiments, an antisense compound provided herein useful for inhibiting prostate cancer cell and/or castration-resistant prostate cancer cell growth or proliferation in combination with an anti-androgenic agent selected from: MDV3100, ARN-059, ODM-201, abiraterone, TOK001, TAK700 and VT464, targets an AR splicing variant that has a functional DNA binding domain, but not a functional ligand binding domain. It will be understood that in certain embodiments an antisense compound can target an AR splicing variant that includes the entire or at least a functional portion of exon 1 encoding the N-terminal domain and the entire or at least a functional portion of exons 2 and 3 encoding the DNA binding domain, but does not include at least a functional portion of exon 4 encoding the short hinge region or at least a functional portion of exons 4-8 encoding the ligand binding domain. It is contemplated that certain AR splicing variants targeted by the antisense compounds provided herein substantially consisting of exons 1-3 may also include a non-functional portion of nucleic acid sequence from a genomic region or exons 4-8. It is contemplated that the splicing process may give rise to such AR splicing variants that retain DNA binding function but not ligand binding function. In certain embodiments, the prostate cancer cell, which may be castrate-resistant, preferentially expresses an AR splicing variant over full-length AR.

In certain embodiments the prostate cancer cell is castrate-resistant to an anti-androgenic agent selected from: MDV3100, ARN-059, ODM-201, abiraterone, TOK001, TAK700 and VT464. In certain embodiments, an antisense compound provided herein targets AR within exon 1, which is upstream of the 3' end of exon 3 and/or upstream of the ligand binding domain. In certain embodiments, an antisense compound provided herein targets AR within exon 1, exon 2, exon 3, intron 1, or intron 2 as described herein.

In certain embodiments, an antisense compound targeted to an AR splicing variant that has a functional DNA binding domain, but not a functional ligand binding domain, is capable of inhibiting growth or proliferation of a prostate cancer cell, including a castration-resistant prostate cancer cell, in combination with a an anti-androgenic agent selected from: MDV3100, ARN-059, ODM-201, abiraterone, TOK001, TAK700 and VT464, to a greater extent than an antisense compound targeted to the ligand binding domain, such as EZN-4176, which is targeted to exon 4 and corresponds to SEQ ID NO: 58 described in U.S. Pat. No. 7,737,125, in combination with a the same anti-androgenic agent selected from: MDV3100, ARN-059, ODM-201, abiraterone, TOK001, TAK700 and VT464. In certain embodiments, the combination of an antisense compound and anti-androgenic agent selected from: MDV3100, ARN-059, ODM-201, abiraterone, TOK001, TAK700 and VT464, provides a synergistic (e.g. greater-than-additive) effect in inhibiting the growth or proliferation of a prostate cancer cell, such as a castration-resistant prostate cancer cell, compared to the antisense compound alone or the anti-androgenic agent alone. Accordingly, in certain embodiments the amounts of either or both of the antisense compound and/or anti-androgenic agent selected from: MDV3100, ARN-059, ODM-201, abiraterone, TOK001, TAK700 and VT464, when used in combination can be less than the corresponding amount of either the antisense compound alone or anti-androgenic agent, alone necessary to achieve an equivalent level of prostate cancer cell growth or proliferation inhibition.

In certain embodiments, an antisense compound provided herein useful for inhibiting prostate cancer cell and/or castration-resistant prostate cancer cell growth or proliferation in combination with a anti-androgenic agent selected from: MDV3100, ARN-059, ODM-201, abiraterone, TOK001, TAK700 and VT464 is capable of reducing expression of both full-length AR and an AR splicing variant that includes exon 1 encoding the N-terminal domain and exons 2 and 3 encoding the DNA binding domain, but does not include at least a portion of exon 4 encoding the short hinge region or at least a portion of any one of exons 4-8 encoding the ligand binding domain. In certain embodiments, such an antisense compound targets human androgen receptor upstream of the ligand binding domain. In certain embodiments, such antisense compounds target human androgen receptor upstream of the 3' end of exon 3. In certain embodiments, an antisense compound provided herein targets AR within exon 1, which is upstream of the 3' end of exon 3 and/or upstream of the ligand binding domain.

In certain embodiments, there is provided a combination of an antisense compound targeted to human androgen receptor (AR) as described herein and an anti-androgenic agent selected from: MDV3100, ARN-059, ODM-201, abiraterone, TOK001, TAK700 and VT464, wherein the antisense compound comprises a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, there is provided a combination of an antisense compound targeted to human androgen receptor (AR) and an anti-androgenic agent selected from: MDV3100, ARN-059, ODM-201, abiraterone, TOK001, TAK700 and VT464, wherein the antisense compound comprises a modified oligonucleotide consisting of 10 to 30 linked nucleosides and having a nucleobase sequence comprising any of SEQ ID NOs: 12-179. In certain embodiments, there is provided a combination of an antisense compound targeted to human androgen receptor (AR) and an anti-androgenic agent selected from: MDV3100, ARN-059, ODM-201, abiraterone, TOK001, TAK700 and VT464, wherein the antisense compound comprises a modified oligonucleotide consisting of the nucleobase sequence of any of SEQ ID NOs: 12-179. In certain embodiments, there is provided a combination of an antisense compound targeted to human androgen receptor (AR) and a diarylhydantoin AR inhibitor of Formula XI, such as MDV3100, wherein the antisense compound comprises a modified oligonucleotide consisting of 16 linked nucleosides and having a nucleobase sequence consisting of SEQ ID NO: 35, 39, 43, 124, 150, 155, 169, or 175. In certain embodiments, there is provided a combination of an antisense compound targeted to human androgen receptor (AR) and a diarylhydantoin AR inhibitor of Formula XI, such as MDV3100, wherein the antisense compound targeted to androgen receptor is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

Several embodiments are drawn to a method of inhibiting prostate cancer cell growth or proliferation comprising contacting the prostate cancer cell with an antisense compound targeted to human androgen receptor (AR) and an anti-androgenic agent selected from: MDV3100, ARN-059, ODM-201, abiraterone, TOK001, TAK700 and VT464. In certain embodiments, the antisense compound and an anti-androgenic agent selected from: MDV3100, ARN-059, ODM-201, abiraterone, TOK001, TAK700 and VT464, synergize in combination to inhibit the growth or proliferation of the prostate cancer cell. In several embodiments, the prostate cancer cell is castration-resistant. In various embodiments, the prostate cancer cell is castration-resistant by being resistant to an anti-androgenic agent selected from: MDV3100, ARN-059, ODM-201, abiraterone, TOK001, TAK700 and VT464. In certain embodiments, the prostate cancer cell or castration-resistant prostate cancer cell preferentially expresses an AR splicing variant over full-length AR.

In certain aspects of any of the foregoing embodiments, antisense compounds useful for inhibiting prostate cancer cell growth or proliferation in combination with a diarylhydantoin AR inhibitor of Formula XVI, such as MDV3100, can target (i) human androgen receptor upstream of the 3' end of exon 3 and/or upstream of the ligand binding domain or (ii) an AR splicing variant that has a functional DNA binding domain, but not a functional ligand binding domain; and/or is capable of (i) reducing expression of both full-length AR and an AR splicing variant that includes exon 1 encoding the N-terminal domain and exons 2 and 3 encoding the DNA binding domain, but does not include at least a portion of exon 4 encoding the short hinge region or at least a portion of any one of exons 4-8 encoding the ligand binding domain; with the proviso that the antisense compounds do not have a nucleobase sequence consisting of any of SEQ ID NOs: 194-215 identified in Table A below.

TABLE A

| SEQ ID NO: | Sequence |
|---|---|
| 194 | GAGAACCATCCTCACC |
| 195 | GGACCAGGTAGCCTGT |
| 196 | CCCCTGGACTCAGATG |
| 197 | GCACAAGGAGTGGGAC |
| 198 | GCTGTGAAGAGAGTGT |
| 199 | TTTGACACAAGTGGGA |
| 200 | GTGACACCCAGAAGCT |
| 201 | CATCCCTGCTTCATAA |
| 202 | TGGGGAGAACCATCCTCACCCTGC |
| 203 | TCCAGGACCAGGTAGCCTGTGGGG |
| 204 | TGTTCCCCTGGACTCAGATGCTCC |
| 205 | TGGGGCACAAGGAGTGGGACGCAC |
| 206 | TTCGGCTGTGAAGAGAGTGTGCCA |
| 207 | CGCTTTTGACACAAGTGGGACTGG |
| 208 | CATAGTGACACCCAGAAGCTTCAT |
| 209 | GAGTCATCCCTGCTTCATAACATT |
| 210 | CTGTGAAGAGAGTG |
| 211 | TGTGAAGAGAGT |
| 212 | TTGACACAAGTGGG |
| 213 | TGACACAAGTGG |
| 214 | TGACACCCAGAAGC |
| 215 | GACACCCAGAAG |

In certain aspects of any of the foregoing embodiments, antisense compounds useful for inhibiting growth or proliferation of a prostate cancer cell resistant to anti-androgenic agent selected from: MDV3100, ARN-059, ODM-201, abiraterone, TOK001, TAK700 and VT464, can target (i) human androgen receptor upstream of the 3' end of exon 3 and/or upstream of the ligand binding domain or (ii) an AR splicing variant that has a functional DNA binding domain, but not a functional ligand binding domain; and/or is capable of (i) reducing expression of both full-length AR and an AR splicing variant that includes exon 1 encoding the N-terminal domain and exons 2 and 3 encoding the DNA binding domain, but does not include at least a portion of exon 4 encoding the short hinge region or at least a portion of any one of exons 4-8 encoding the ligand binding domain; or (ii) inhibiting growth or proliferation of the resistant prostate cancer cell to a greater extent than an antisense compound targeted to the ligand binding domain, such as EZN-4176; with the proviso that the antisense compounds do not have a nucleobase sequence consisting of any of SEQ ID NOs: 194-215 described in U.S. Pat. No. 7,737,125 as SEQ ID NOs: 2-9, 49-50, 52-53, 55-56, and 86-93 (herein incorporated by reference), and identified in Table A.

Certain aspects are directed to methods of treating breast cancer and methods of inhibiting breast cancer cell growth or proliferation with an antisense oligonucleotide targeted to human androgen receptor (AR) as described herein. In certain embodiments, the breast cancer has one or more of the following characteristics: Androgen Receptor positive, dependent on androgen for growth, Estrogen Receptor (ER) negative, independent of estrogen for growth, Progesterone Receptor (PR) negative, independent of progesterone for growth, or Her2/neu negative. In certain embodiments, the breast cancer or breast cancer cell is apocrine.

Certain embodiments are drawn to a method of treating breast cancer in a subject comprising administering to the subject an antisense compound targeted to human androgen receptor (AR). Certain embodiments are drawn to a method of treating breast cancer in a subject comprising identifying a subject having breast cancer and administering to the subject an antisense compound targeted to human androgen receptor (AR), thereby treating the subject's breast cancer. Certain embodiments are directed to a method of inhibiting growth or proliferation of a breast cancer cell comprising contacting the breast cancer cell with an antisense compound targeted to human androgen receptor (AR). Certain embodiments relate to a method of inhibiting AR expression in a subject having or at risk of having breast cancer comprising identifying a subject breast cancer, and administering to the subject an antisense compound targeted to human AR, wherein the antisense compound inhibits AR expression in the subject.

In certain embodiments, the breast cancer or breast cancer cell has one or more of the following characteristics: Androgen Receptor positive, dependent on androgen for growth, Estrogen Receptor (ER) negative, independent of estrogen for growth, Progesterone Receptor (PR) negative, independent of progesterone for growth, or Her2/neu negative. In certain embodiments, the breast cancer or breast cancer cell is ER, PR, and HER2 triple negative and AR positive (ER−, PR−, HER2−, AR+). In certain embodiments, the breast cancer or breast cancer cell is ER negative and AR positive (ER−, AR+). In certain embodiments, the breast cancer or breast cancer cell is ER positive and AR positive (ER+, AR+).

In certain embodiments, the breast cancer or breast cancer cell is apocrine. Apocrine breast cancers are often "triple negative", meaning that the cells do not express ER, PR, or HER2 receptors, and usually, but not necessarily, AR positive. In certain embodiments, an apocrine breast cancer or breast cancer cell is ER, PR, and HER2 triple negative and AR positive (ER−, PR−, HER2−, AR+). In certain embodiments, an apocrine breast cancer or breast cancer cell is ER negative and AR positive (ER−, AR+). In certain embodiments, an apocrine breast cancer or breast cancer cell originates from the sweat gland of the breast. In certain embodiments, an apocrine breast cancer or breast cancer cell is a ductal cancer or cancer cell of the breast. In certain embodiments, an apocrine breast cancer can have any one or more of the following features: a large amount of eosinophilic granular cytoplasm, well-defined margins, large vesicular nuclei, a nuclear to cytoplasmic ratio of about 1:2, and/or accumulations of secreted granules in the apical cytoplasm known as apical snouts.

In certain embodiments, the breast cancer or breast cancer cell is an ER negative and AR positive (ER−, AR+) molecular apocrine breast cancer or breast cancer cell. In certain aspects, an ER negative and AR positive (ER−, AR+) molecular apocrine breast cancer or breast cancer cell can further be PR positive, PR negative, HER2 negative, or HER2 positive.

Breast cancer can be identified as positive or negative with respect to hormone receptors, such as ER, PR, or HER2 by standard histological techniques. For example, histological breast cancer samples can be classified as "triple negative" (ER−, PR−, HER2−) when less than 1% of cells demonstrate nuclear staining for estrogen and progesterone receptors, and immunohistochemical staining for HER2 shows a 0, 1-fold, or a 2-fold positive score and a FISH ratio (HER2 gene signals to chromosome 17 signals) of less than 1.8 according to the relevant ASCO and CAP guidelines. (Meyer, P. et al., PLoS ONE 7(5): e38361 (2012)).

In certain embodiments, an antisense compound useful for treating breast cancer or inhibiting growth or proliferation of a breast cancer cell target provided herein targets AR within exon 1, which is upstream of the 3' end of exon 3 and/or upstream of the ligand binding domain. In certain embodiments, an antisense compound provided herein targets AR within exon 1, for example within nucleotide regions 2863-5593 (exon 1) or 27672-27853 (exon 1B) of SEQ ID NO: 1. In certain embodiments, an antisense compound provided herein targeted to exon 1 of AR is complementary within any of the following nucleotide regions of SEQ ID NO: 1: 3353-3368, 3361-3376, 3519-3534, 3735-3750, 3768-3783, 3798-3813, 3799-3814, 3851-3866, 3870-3885, 3874-3889, 3888-3903, 4047-4062, 4062-4077, 4109-4124, 4534-4549, 4537-4552, 4555-4570, 4571-4586, 4573-4588, 4578-4593, 4655-4670, 4750-4765, 4752-4767, 4833-4848, 4837-4852, 4839-4854, 4865-4880, 4872-4887, 4874-4889, 4876-4891, 4916-4931, 4918-4933, 5052-5067, 5054-5069, 5060-5075, 5061-5076, 5061-5076, 5062-5077, 5155-5170, 5265-5280, 5293-5308, 5392-5407, 5448-5463, 5483-5498, 5486-5501, or 5494-5509.

In certain embodiments, an antisense compound provided herein targets AR within exon 2, which is upstream of the 3' end of exon 3 and/or upstream of the ligand binding domain. In certain embodiments, an antisense compound useful for treating breast cancer or inhibiting growth or proliferation of a breast cancer cell target provided herein targets AR within exon 2, for example within nucleotide regions 102087-102238 (exon 2) or 139551-139834 (exon 2c) of SEQ ID NO: 1. In certain embodiments, an antisense compound provided herein targeted to exon 2 of AR is complementary within any of the following nucleotide regions of SEQ ID NO: 1: 102155-102170 or 102156-107171.

In certain aspects, an antisense compound useful for treating breast cancer or inhibiting growth or proliferation of a breast cancer cell provided herein targets AR within intron 1, which is upstream of the 3' end of exon 3 and/or upstream of the ligand binding domain. In certain embodiments, an antisense compound provided herein targets AR within intron 1, for example within nucleotide regions 5594-27671 or 27854-102086 of SEQ ID NO: 1. In certain aspects, an antisense compound provided herein targeted to intron 1 of AR is complementary within any of the following nucleotide regions of SEQ ID NO: 1: 5666-5681, 6701-6716, 7543-7558, 8471-8486, 8638-8653, 9464-9479, 10865-10880, 11197-11212, 11855-11870, 13189-13204, 13321-13336, 13346-13361, 16793-16808, 16968-16983, 17206-17221, 18865-18880, 32290-32305, 33315-33330, 39055-39070, 40615-40630, 42017-42032, 56050-56065, 58719-58734, 58720-58735, 58721-58736, 58722-58737, 58723-58738, 58725-58740, 58750-58765, 58751-58766, 58752-58767, 58753-58768, 58754-58769, or 58755-58770.

In certain aspects of any of the foregoing embodiments, antisense compounds useful for treating breast cancer or inhibiting growth or proliferation of a breast cancer cell target human androgen receptor upstream of the 3' end of exon 3 and/or upstream of the ligand binding domain. In certain embodiments, antisense compounds provided herein, including but not limited to those that target human androgen receptor upstream of the 3' end of exon 3 and/or upstream of the ligand binding domain, can treat breast cancer or inhibiting growth or proliferation of a breast cancer cell to a greater extent than an antisense compound targeted to the ligand binding domain, such as EZN-4176; with the proviso that the antisense compounds do not have a nucleobase sequence consisting of any of SEQ ID NOs: 194-215 described in U.S. Pat. No. 7,737,125 as SEQ ID NOs: 2-9, 49-50, 52-53, 55-56, and 86-93 (herein incorporated by reference), and identified in Table A.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound is 10-30 subunits in length. In certain embodiments, an antisense compound is 12 to 30 subunits in length. In certain embodiments, an antisense compound is 12 to 22 subunits in length. In certain embodiments, an antisense compound is 14 to 30 subunits in length. In certain embodiments, an antisense compound is 14 to 20 subunits in length. In certain embodiments, an antisense compound is 15 to 30 subunits in length. In certain embodiments, an antisense compound is 15 to 20 subunits in length. In certain embodiments, an antisense compound is 16 to 30 subunits in length. In certain embodiments, an antisense compound is 16 to 20 subunits in length. In certain embodiments, an antisense compound is 17 to 30 subunits in length. In certain embodiments, an antisense compound is 17 to 20 subunits in length. In certain embodiments, an antisense compound is 18 to 30 subunits in length. In certain embodiments, an antisense compound is 18 to 21 subunits in length. In certain embodiments, an antisense compound is 18 to 20 subunits in length. In certain embodiments, an antisense compound is 20 to 30 subunits in length. In other words, such antisense compounds are from 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits, respectively. In certain embodiments, an antisense compound is 14 subunits in length. In certain embodiments, an antisense compound is 16 subunits in length. In certain embodiments, an antisense compound is 17 subunits in length. In certain embodiments, an antisense compound is 18 subunits in length. In certain embodiments, an antisense compound is 20 subunits in length. In other embodiments, the antisense compound is 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleotides.

In certain embodiments antisense oligonucleotides may be shortened or truncated. For example, a single subunit may be deleted from the 5' end (5' truncation), or alternatively from the 3' end (3' truncation). A shortened or truncated antisense compound targeted to an Androgen Receptor nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al. (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Certain Antisense Compound Motifs and Mechanisms

In certain embodiments, antisense compounds have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may confer another desired property e.g., serve as a substrate for the cellular endonuclease RNase H, which cleaves the RNA strand of an RNA:DNA duplex.

Antisense activity may result from any mechanism involving the hybridization of the antisense compound (e.g., oligonucleotide) with a target nucleic acid, wherein the hybridization ultimately results in a biological effect. In certain embodiments, the amount and/or activity of the target nucleic acid is modulated. In certain embodiments, the amount and/or activity of the target nucleic acid is reduced. In certain embodiments, hybridization of the antisense compound to the target nucleic acid ultimately results in target nucleic acid degradation. In certain embodiments, hybridization of the antisense compound to the target nucleic acid does not result in target nucleic acid degradation. In certain such embodiments, the presence of the antisense compound hybridized with the target nucleic acid (occupancy) results in a modulation of antisense activity. In certain embodiments, antisense compounds having a particular chemical motif or pattern of chemical modifications are particularly suited to exploit one or more mechanisms. In certain embodiments, antisense compounds function through more than one mechanism and/or through mechanisms that have not been elucidated. Accordingly, the antisense compounds described herein are not limited by particular mechanism.

Antisense mechanisms include, without limitation, RNase H mediated antisense; RNAi mechanisms, which utilize the RISC pathway and include, without limitation, siRNA, ssRNA and microRNA mechanisms; and occupancy based mechanisms. Certain antisense compounds may act through more than one such mechanism and/or through additional mechanisms.

RNase H-Mediated Antisense

In certain embodiments, antisense activity results at least in part from degradation of target RNA by RNase H. RNase H is a cellular endonuclease that cleaves the RNA strand of an RNA:DNA duplex. It is known in the art that single-stranded antisense compounds which are "DNA-like" elicit RNase H activity in mammalian cells. Accordingly, antisense compounds comprising at least a portion of DNA or DNA-like nucleosides may activate RNase H, resulting in cleavage of the target nucleic acid. In certain embodiments, antisense compounds that utilize RNase H comprise one or more modified nucleosides. In certain embodiments, such antisense compounds comprise at least one block of 1-8 modified nucleosides. In certain such embodiments, the modified nucleosides do not support RNase H activity. In certain embodiments, such antisense compounds are gapmers, as described herein. In certain such embodiments, the gap of the gapmer comprises DNA nucleosides. In certain such embodiments, the gap of the gapmer comprises DNA-like nucleosides. In certain such embodiments, the gap of the gapmer comprises DNA nucleosides and DNA-like nucleosides.

Certain antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE and 2'-O—$CH_3$, among others), and bicyclic sugar modified nucleosides (such bicyclic sugar modified nucleosides may include those having a constrained ethyl). In certain embodiments, nucleosides in the wings may include several modified sugar moieties, including, for example 2'-MOE and bicyclic sugar moieties such as constrained ethyl or LNA. In certain embodiments, wings may include several modified and unmodified sugar moieties. In certain embodiments, wings may include various combinations of 2'-MOE nucleosides, bicyclic sugar moieties such as constrained ethyl nucleosides or LNA nucleosides, and 2'-deoxynucleosides.

Each distinct region may comprise uniform sugar moieties, variant, or alternating sugar moieties. The wing-gap-wing motif is frequently described as "X-Y-Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X-Y-Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same; in other embodiments they are different. In certain embodiments, "Y" is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30 or more nucleosides.

In certain embodiments, the antisense compound targeted to an Androgen Receptor nucleic acid has a gapmer motif in which the gap consists of 6, 7, 8, 9, 10, 11, 12, 13, 14, 15, or 16 linked nucleosides.

In certain embodiments, the antisense oligonucleotide has a sugar motif described by Formula A as follows: $(J)_m$-$(B)_n$-$(J)_p$-$(B)_r$-$(A)_t$-$(D)_g$-$(A)_v$-$(B)_w$-$(J)_x$-$(B)_y$-$(J)_z$ wherein:

each A is independently a 2'-substituted nucleoside;

each B is independently a bicyclic nucleoside;

each J is independently either a 2'-substituted nucleoside or a 2'-deoxynucleoside; each D is a 2'-deoxynucleoside;

m is 0-4; n is 0-2; p is 0-2; r is 0-2; t is 0-2; v is 0-2; w is 0-4; x is 0-2; y is 0-2; z is 0-4; g is 6-14; provided that:

at least one of m, n, and r is other than 0;

at least one of w and y is other than 0;

the sum of m, n, p, r, and t is from 2 to 5; and the sum of v, w, x, y, and z is from 2 to 5.

RNAi Compounds

In certain embodiments, antisense compounds are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). In certain embodiments, antisense compounds comprise modifications that make them particularly suited for such mechanisms.

i. ssRNA Compounds

In certain embodiments, antisense compounds including those particularly suited for use as single-stranded RNAi compounds (ssRNA) comprise a modified 5'-terminal end. In certain such embodiments, the 5'-terminal end comprises a modified phosphate moiety. In certain embodiments, such modified phosphate is stabilized (e.g., resistant to degradation/cleavage compared to unmodified 5'-phosphate). In certain embodiments, such 5'-terminal nucleosides stabilize the 5'-phosphorous moiety. Certain modified 5'-terminal nucleosides may be found in the art, for example in WO/2011/139702.

In certain embodiments, the 5'-nucleoside of an ssRNA compound has Formula IIc:

IIc

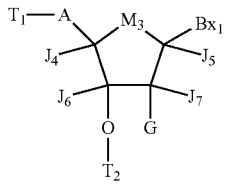

wherein:

$T_1$ is an optionally protected phosphorus moiety;

$T_2$ is an internucleoside linking group linking the compound of Formula IIc to the oligomeric compound;

A has one of the formulas:

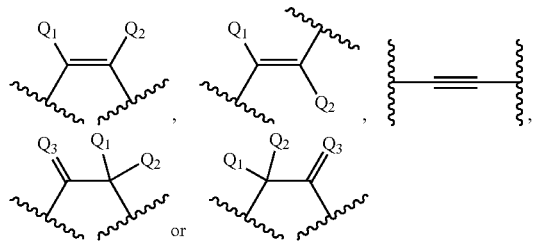

$Q_1$ and $Q_2$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or $N(R_3)(R_4)$;

$Q_3$ is O, S, $N(R_5)$ or $C(R_6)(R_7)$;

each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;

$M_3$ is O, S, $NR_{14}$, $C(R_{15})(R_{16})$, $C(R_{15})(R_{16})C(R_{17})(R_{18})$, $C(R_{15})$═$C(R_{17})$, $OC(R_{15})(R_{16})$ or $OC(R_{15})(Bx_2)$;

$R_{14}$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$R_{15}$, $R_{16}$, $R_{17}$ and $R_{18}$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$Bx_1$ is a heterocyclic base moiety;

or if $Bx_2$ is present then $Bx_2$ is a heterocyclic base moiety and $Bx_1$ is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

or $J_4$ forms a bridge with one of $J_5$ or $J_7$ wherein said bridge comprises from 1 to 3 linked biradical groups selected from O, S, $NR_{19}$, $C(R_{20})(R_{21})$, $C(R_{20})=C(R_{21})$, $C[=C(R_{20})(R_{21})]$ and C(=O) and the other two of $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

G is H, OH, halogen or $O—[C(R_8)(R_6)]_n—[(C=O)_m—X_1]_j—Z$;

each $R_8$ and $R_9$ is, independently, H, halogen, $C_1$-$C_6$ alkyl or substituted $C_1$-$C_6$ alkyl;

$X_1$ is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=X_2)N(J_1)(J_2)$;

$X_2$ is O, S or $NJ_3$;

each $J_1$, $J_2$ and $J_3$ is, independently, H or $C_1$-$C_6$ alkyl;

when j is 1 then Z is other than halogen or $N(E_2)(E_3)$; and wherein said oligomeric compound comprises from 8 to 40 monomeric subunits and is hybridizable to at least a portion of a target nucleic acid.

In certain embodiments, $M_3$ is O, CH=CH, $OCH_2$ or $OC(H)(Bx_2)$. In certain embodiments, $M_3$ is O.

In certain embodiments, $J_4$, $J_5$, $J_6$ and $J_7$ are each H. In certain embodiments, $J_4$ forms a bridge with one of $J_5$ or $J_7$.

In certain embodiments, A has one of the formulas:

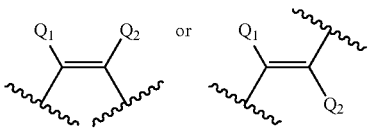

wherein:

$Q_1$ and $Q_2$ are each, independently, H, halogen, $C_1$-$C_6$ alkyl, substituted $C_1$-$C_6$ alkyl, $C_1$-$C_6$ alkoxy or substituted $C_1$-$C_6$ alkoxy. In certain embodiments, $Q_1$ and $Q_2$ are each H. In certain embodiments, $Q_1$ and $Q_2$ are each, independently, H or halogen. In certain embodiments, $Q_1$ and $Q_2$ is H and the other of $Q_1$ and $Q_2$ is F, $CH_3$ or $OCH_3$.

In certain embodiments, $T_1$ has the formula:

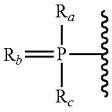

wherein:

$R_a$ and $R_c$ are each, independently, protected hydroxyl, protected thiol, $C_1$-$C_6$ alkyl, substituted $C_1$-$C_6$ alkyl, $C_1$-$C_6$ alkoxy, substituted $C_1$-$C_6$ alkoxy, protected amino or substituted amino; and $R_b$ is O or S. In certain embodiments, $R_b$ is O and $R_a$ and $R_c$ are each, independently, $OCH_3$, $OCH_2CH_3$ or $CH(CH_3)_2$.

In certain embodiments, G is halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2—CH=CH_2$, $O(CH_2)_2—OCH_3$, $O(CH_2)_2—SCH_3$, $O(CH_2)_2—OCF_3$, $O(CH_2)_3—N(R_{10})(R_{11})$, $O(CH_2)_2—ON(R_{10})(R_{11})$, $O(CH_2)_2—O(CH_2)_2—N(R_{10})(R_{11})$, $OCH_2C(=O)—N(R_{10})(R_{11})$, $OCH_2C(=O)—N(R_{12})—(CH_2)_2—N(R_{10})(R_{11})$ or $O(CH_2)_2—N(R_{12})—C(=NR_{13})[N(R_{10})(R_{11})]$ wherein $R_{10}$, $R_{11}$, $R_{12}$ and $R_{13}$ are each, independently, H or $C_1$-$C_6$ alkyl. In certain embodiments, G is halogen, $OCH_3$, $OCF_3$, $OCH_2CH_3$, $OCH_2CF_3$, $OCH_2—CH=CH_2$, $O(CH_2)_2—OCH_3$, $O(CH_2)_2—O(CH_2)_2—N(CH_3)_2$, $OCH_2C(=O)—N(H)CH_3$, $OCH_2C(=O)—N(H)—(CH_2)_2—N(CH_3)_2$ or $OCH_2—N(H)—C(=NH)NH_2$. In certain embodiments, G is F, $OCH_3$ or $O(CH_2)_2—OCH_3$. In certain embodiments, G is $O(CH_2)_2—OCH_3$.

In certain embodiments, the 5'-terminal nucleoside has Formula IIe:

IIc

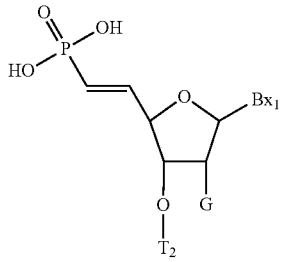

In certain embodiments, antisense compounds, including those particularly suitable for ssRNA comprise one or more type of modified sugar moieties and/or naturally occurring sugar moieties arranged along an oligonucleotide or region thereof in a defined pattern or sugar modification motif Such motifs may include any of the sugar modifications discussed herein and/or other known sugar modifications.

In certain embodiments, the oligonucleotides comprise or consist of a region having uniform sugar modifications. In certain such embodiments, each nucleoside of the region comprises the same RNA-like sugar modification. In certain embodiments, each nucleoside of the region is a 2'-F nucleoside. In certain embodiments, each nucleoside of the region is a 2'-OMe nucleoside. In certain embodiments, each nucleoside of the region is a 2'-MOE nucleoside. In certain embodiments, each nucleoside of the region is a cEt nucleoside. In certain embodiments, each nucleoside of the region is an LNA nucleoside. In certain embodiments, the uniform region constitutes all or essentially all of the oligonucleotide. In certain embodiments, the region constitutes the entire oligonucleotide except for 1-4 terminal nucleosides.

In certain embodiments, oligonucleotides comprise one or more regions of alternating sugar modifications, wherein the nucleosides alternate between nucleotides having a sugar modification of a first type and nucleotides having a sugar modification of a second type. In certain embodiments, nucleosides of both types are RNA-like nucleosides. In certain embodiments the alternating nucleosides are selected from: 2'-OMe, 2'-F, 2'-MOE, LNA, and cEt. In certain embodiments, the alternating modificatios are 2'-F and 2'-OMe. Such regions may be contiguous or may be interupted by differently modified nucleosides or conjugated nucleosides.

In certain embodiments, the alternating region of alternating modifications each consist of a single nucleoside (i.e., the patern is $(AB)_xA_y$ wheren A is a nucleoside having a sugar modification of a first type and B is a nucleoside having a sugar modification of a second type; x is 1-20 and y is 0 or 1). In certain embodiments, one or more alternating regions in an alternating motif includes more than a single nucleoside of a type. For example, oligonucleotides may include one or more regions of any of the following nucleoside motifs:

```
AABBAA;

ABBABB;

AABAAB;

ABBABAABB;

ABABAA;

AABABAB;

ABABAA;

ABBAABBABABAA;

BABBAABBABABAA;
or

ABABBAABBABABAA;
```

wherein A is a nucleoside of a first type and B is a nucleoside of a second type. In certain embodiments, A and B are each selected from 2'-F, 2'-OMe, BNA, and MOE.

In certain embodiments, oligonucleotides having such an alternating motif also comprise a modified 5' terminal nucleoside, such as those of formula IIc or IIe.

In certain embodiments, oligonucleotides comprise a region having a 2-2-3 motif Such regions comprises the following motif:

$$-(A)_2-(B)_x-(A)_2-(C)_y-(A)_3-$$

wherein: A is a first type of modifed nucleosde;

B and C, are nucleosides that are differently modified than A, however, B and C may have the same or different modifications as one another;

x and y are from 1 to 15.

In certain embodiments, A is a 2'-OMe modified nucleoside. In certain embodiments, B and C are both 2'-F modified nucleosides. In certain embodiments, A is a 2'-OMe modified nucleoside and B and C are both 2'-F modified nucleosides.

In certain embodiments, oligonucleosides have the following sugar motif:

$$5'-(Q)-(AB)_xA_y-(D)_z$$

wherein:

Q is a nucleoside comprising a stabilized phosphate moiety. In certain embodiments, Q is a nucleoside having Formula IIc or IIe;

A is a first type of modifed nucleoside;

B is a second type of modified nucleoside;

D is a modified nucleoside comprising a modification different from the nucleoside adjacent to it. Thus, if y is 0, then D must be differently modified than B and if y is 1, then D must be differently modified than A. In certain embodiments, D differs from both A and B.

X is 5-15;

Y is 0 or 1;

Z is 0-4.

In certain embodiments, oligonucleosides have the following sugar motif:

$$5'-(Q)-(A)_x-(D)_z$$

wherein:

Q is a nucleoside comprising a stabilized phosphate moiety. In certain embodiments, Q is a nucleoside having Formula IIc or IIe;

A is a first type of modifed nucleoside;

D is a modified nucleoside comprising a modification different from A.

X is 11-30;

Z is 0-4.

In certain embodiments A, B, C, and D in the above motifs are selected from: 2'-OMe, 2'-F, 2'-MOE, LNA, and cEt. In certain embodiments, D represents terminal nucleosides. In certain embodiments, such terminal nucleosides are not designed to hybridize to the target nucleic acid (though one or more might hybridize by chance). In certain embodiments, the nucleobase of each D nucleoside is adenine, regardless of the identity of the nucleobase at the corresponding position of the target nucleic acid. In certain embodiments the nucleobase of each D nucleoside is thymine.

In certain embodiments, antisense compounds, including those particularly suited for use as ssRNA comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphoro-thioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least one block of at least 12 consecutive phosphoro-thioate internucleoside linkages. In certain such embodiments, at least one such block is located at the 3' end of the oligonucleotide. In certain such embodiments, at least one such block is located within 3 nucleosides of the 3' end of the oligonucleotide.

Oligonucleotides having any of the various sugar motifs described herein, may have any linkage motif. For example, the oligonucleotides, including but not limited to those described above, may have a linkage motif selected from non-limiting the table below:

| 5' most linkage | Central region | 3'-region |
|---|---|---|
| PS | Alternating PO/PS | 6 PS |
| PS | Alternating PO/PS | 7 PS |
| PS | Alternating PO/PS | 8 PS |

ii. siRNA Compounds

In certain embodiments, antisense compounds are double-stranded RNAi compounds (siRNA). In such embodiments, one or both strands may comprise any modification motif described above for ssRNA. In certain embodiments, ssRNA compounds may be unmodified RNA. In certain embodiments, siRNA compounds may comprise unmodified RNA nucleosides, but modified internucleoside linkages.

Several embodiments relate to double-stranded compositions wherein each strand comprises a motif defined by the location of one or more modified or unmodified nucleosides. In certain embodiments, compositions are provided comprising a first and a second oligomeric compound that are fully or at least partially hybridized to form a duplex region and further comprising a region that is complementary to and hybridizes to a nucleic acid target. It is suitable that such a composition comprise a first oligomeric compound that is an antisense strand having full or partial complementarity to a nucleic acid target and a second oligomeric compound that is a sense strand having one or more regions of complementarity to and forming at least one duplex region with the first oligomeric compound.

The compositions of several embodiments modulate gene expression by hybridizing to a nucleic acid target resulting in loss of its normal function. In some embodiments, the target nucleic acid is Androgen Receptor. In certain embodiment, the degradation of the targeted Androgen Receptor is facilitated by an activated RISC complex that is formed with compositions of the invention.

Several embodiments are directed to double-stranded compositions wherein one of the strands is useful in, for example, influencing the preferential loading of the opposite strand into the RISC (or cleavage) complex. The compositions are useful for targeting selected nucleic acid molecules and modulating the expression of one or more genes. In some embodiments, the compositions of the present invention hybridize to a portion of a target RNA resulting in loss of normal function of the target RNA.

Certain embodiments are drawn to double-stranded compositions wherein both the strands comprises a hemimer motif, a fully modified motif, a positionally modified motif or an alternating motif Each strand of the compositions of the present invention can be modified to fulfil a particular role in for example the siRNA pathway. Using a different motif in each strand or the same motif with different chemical modifications in each strand permits targeting the antisense strand for the RISC complex while inhibiting the incorporation of the sense strand. Within this model, each strand can be independently modified such that it is enhanced for its particular role. The antisense strand can be modified at the 5'-end to enhance its role in one region of the RISC while the 3'-end can be modified differentially to enhance its role in a different region of the RISC.

The double-stranded oligonucleotide molecules can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The double-stranded oligonucleotide molecules can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double-stranded structure, for example wherein the double-stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the double-stranded oligonucleotide molecule are complementary to the target nucleic acid or a portion thereof). Alternatively, the double-stranded oligonucleotide is assembled from a single oligonucleotide, where the self-complementary sense and antisense regions of the siRNA are linked by means of a nucleic acid based or non-nucleic acid-based linker(s).

The double-stranded oligonucleotide can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The double-stranded oligonucleotide can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNAi.

In certain embodiments, the double-stranded oligonucleotide comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the double-stranded oligonucleotide comprises nucleotide sequence that is complementary to nucleotide sequence of a target gene. In another embodiment, the double-stranded oligonucleotide interacts with nucleotide sequence of a target gene in a manner that causes inhibition of expression of the target gene.

As used herein, double-stranded oligonucleotides need not be limited to those molecules containing only RNA, but further encompasses chemically modified nucleotides and non-nucleotides. In certain embodiments, the short interfering nucleic acid molecules lack 2'-hydroxy (2'-OH) containing nucleotides. In certain embodiments short interfering nucleic acids optionally do not include any ribonucleotides (e.g., nucleotides having a 2'-OH group). Such double-stranded oligonucleotides that do not require the presence of ribonucleotides within the molecule to support RNAi can however have an attached linker or linkers or other attached or associated groups, moieties, or chains containing one or more nucleotides with 2'-OH groups. Optionally, double-stranded oligonucleotides can comprise ribonucleotides at about 5, 10, 20, 30, 40, or 50% of the nucleotide positions. As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, double-stranded oligonucleotides can be used to epigenetically silence genes at both the post-transcriptional level and the pre-transcriptional level. In a non-limiting example, epigenetic regulation of gene expression by siRNA molecules of the invention can result from siRNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

It is contemplated that compounds and compositions of several embodiments provided herein can target Androgen Receptor by a dsRNA-mediated gene silencing or RNAi mechanism, including, e.g., "hairpin" or stem-loop double-stranded RNA effector molecules in which a single RNA strand with self-complementary sequences is capable of assuming a double-stranded conformation, or duplex dsRNA effector molecules comprising two separate strands of RNA. In various embodiments, the dsRNA consists entirely of ribonucleotides or consists of a mixture of ribonucleotides and deoxynucleotides, such as the RNA/DNA hybrids disclosed, for example, by WO 00/63364, filed Apr. 19, 2000, or U.S. Ser. No. 60/130,377, filed Apr. 21, 1999. The dsRNA or dsRNA effector molecule may be a single molecule with a region of self-complementarity such that nucleotides in one segment of the molecule base pair with nucleotides in another segment of the molecule. In various embodiments, a dsRNA that consists of a single molecule consists entirely of ribonucleotides or includes a region of ribonucleotides that is complementary to a region of deoxyribonucleotides. Alternatively, the dsRNA may include two different strands that have a region of complementarity to each other.

In various embodiments, both strands consist entirely of ribonucleotides, one strand consists entirely of ribonucleotides and one strand consists entirely of deoxyribonucleotides, or one or both strands contain a mixture of ribonucleotides and deoxyribonucleotides. In certain embodiments, the regions of complementarity are at least 70, 80, 90, 95, 98, or 100% complementary to each other and to a target nucleic acid sequence. In certain embodiments, the region of the dsRNA that is present in a double-stranded conformation includes at least 19, 20, 21, 22, 23, 24, 25, 26, 27, 28, 29, 30, 50, 75, 100, 200, 500, 1000, 2000 or 5000 nucleotides or includes all of the nucleotides in a cDNA or other target nucleic acid sequence being represented in the dsRNA. In some embodiments, the dsRNA does not contain any single stranded regions, such as single stranded ends, or the dsRNA is a hairpin. In other embodiments, the dsRNA has one or more single stranded regions or overhangs. In certain embodiments, RNA/DNA hybrids include a DNA strand or region that is an antisense strand or region (e.g, has at least 70, 80, 90, 95, 98, or 100% complementarity to a target nucleic acid) and an RNA strand or region that is a sense strand or region (e.g, has at least 70, 80, 90, 95, 98, or 100% identity to a target nucleic acid), and vice versa.

In various embodiments, the RNA/DNA hybrid is made in vitro using enzymatic or chemical synthetic methods such as those described herein or those described in WO 00/63364, filed Apr. 19, 2000, or U.S. Ser. No. 60/130,377, filed Apr. 21, 1999. In other embodiments, a DNA strand synthesized in vitro is complexed with an RNA strand made in vivo or in vitro before, after, or concurrent with the transformation of the DNA strand into the cell. In yet other embodiments, the dsRNA is a single circular nucleic acid containing a sense and an antisense region, or the dsRNA includes a circular nucleic acid and either a second circular nucleic acid or a linear nucleic acid (see, for example, WO 00/63364, filed Apr. 19, 2000, or U.S. Ser. No. 60/130,377, filed Apr. 21, 1999.) Exemplary circular nucleic acids include lariat structures in which the free 5' phosphoryl group of a nucleotide becomes linked to the 2' hydroxyl group of another nucleotide in a loop back fashion.

In other embodiments, the dsRNA includes one or more modified nucleotides in which the 2' position in the sugar contains a halogen (such as fluorine group) or contains an alkoxy group (such as a methoxy group) which increases the half-life of the dsRNA in vitro or in vivo compared to the corresponding dsRNA in which the corresponding 2' position contains a hydrogen or an hydroxyl group. In yet other embodiments, the dsRNA includes one or more linkages between adjacent nucleotides other than a naturally-occurring phosphodiester linkage. Examples of such linkages include phosphoramide, phosphorothioate, and phosphorodithioate linkages. The dsRNAs may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000, or U.S. Ser. No. 60/130,377, filed Apr. 21, 1999.

In other embodiments, the dsRNA can be any of the at least partially dsRNA molecules disclosed in WO 00/63364, as well as any of the dsRNA molecules described in U.S. Provisional Application 60/399,998; and U.S. Provisional Application 60/419,532, and PCT/US2003/033466, the teaching of which is hereby incorporated by reference. Any of the dsRNAs may be expressed in vitro or in vivo using the methods described herein or standard methods, such as those described in WO 00/63364.

Occupancy

In certain embodiments, antisense compounds are not expected to result in cleavage or the target nucleic acid via RNase H or to result in cleavage or sequestration through the RISC pathway. In certain such embodiments, antisense activity may result from occupancy, wherein the presence of the hybridized antisense compound disrupts the activity of the target nucleic acid. In certain such embodiments, the antisense compound may be uniformly modified or may comprise a mix of modifications and/or modified and unmodified nucleosides.

Target Nucleic Acids, Target Regions and Nucleotide Sequences

Nucleotide sequences that encode human Androgen Receptor include, without limitation, the following: GENBANK Accession No. NT_011669.17_TRUNC_5079000_5270000 (incorporated herein as SEQ ID NO: 1), GENBANK Accession No. NM_000044.3 (incorporated herein as SEQ ID NO: 2), GENBANK Accession No. NM_001011645.2 (incorporated herein as SEQ ID NO: 3), GENBANK Accession No. FJ235916.1 (incorporated herein as SEQ ID NO: 4), GENBANK Accession No. FJ235917.1 (incorporated herein as SEQ ID NO: 5), GENBANK Accession No. FJ235918.1 (incorporated herein as SEQ ID NO: 6), GENBANK Accession No. FJ235919.1 (incorporated herein as SEQ ID NO: 7), and GENBANK Accession No. FJ235920.1 (incorporated herein as SEQ ID NO: 8).

Androgen Receptor mRNA encodes several functional domains. In certain embodiments, full-length Androgen Receptor mRNA includes exon 1 encoding the N-terminal domain, exons 2 and 3 encoding the DNA binding domain, exon 4 encoding the short hinge region, and exons 4-8 encoding the ligand binding domain.

In certain embodiments, Androgen Receptor splicing variants targetable by the antisense compounds provided herein include exon 1 encoding the N-terminal domain and exons 2 and 3 encoding the DNA binding domain, or functional portions thereof, but does not include at least a portion of exon 4 encoding the short hinge region or at least a portion of exons 4-8 encoding the ligand binding domain. Examples of such AR splicing variants include, but are not limited to, AR-V1, AR-V2, AR-V3, AR-V4, AR-V5, AR-V6, and AR-V7 (also referred to as AR3), which contain exons 1-3 but lack exons 4-8. AR-V1, AR-V2, AR-V3, AR-V4, AR-V5, AR-V6, AR-V7, and additional splicing variants targetable by the antisense compounds provided herein are described in Hu et al., Cancer Res 2009; 69:16-22 and US Patent Application Publication No. US 2010/0068802, each of which is incorporated herein by reference in its entirety. Further examples of such AR splicing variants targetable by the antisense compounds provided herein include, but are not limited to, AR3, AR4, AR4b, AR5, and AR6 (SEQ ID NOs: 4-8, respectively) as described in Guo et al., Cancer Res. 2009; 69: 2305-13, which is incorporated herein by reference in its entirety.

Hybridization

In some embodiments, hybridization occurs between an antisense compound disclosed herein and an Androgen Receptor. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with Androgen Receptor.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an Androgen Receptor nucleic acid).

Non-complementary nucleobases between an antisense compound and an Androgen Receptor nucleic acid may be tolerated provided that the antisense compound remains able to specifically hybridize to a target nucleic acid. Moreover, an antisense compound may hybridize over one or more segments of an Androgen Receptor nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to an Androgen Receptor nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having four noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, an antisense compound may be fully complementary to an Androgen Receptor nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an Androgen Receptor nucleic acid, or specified portion thereof.

In certain embodiments, antisense compounds that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an Androgen Receptor nucleic acid, or specified portion thereof.

The antisense compounds provided also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds are complementary to at least an 11 nucleobase portion of a target segment. In certain embodiments, the antisense compounds are complementary to at least a 12 nucleobase portion of a target segment. In certain embodiments, the antisense compounds are complementary to at least a 13 nucleobase portion of a target segment. In certain embodiments, the antisense compounds are complementary to at least a 14 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occuring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an Androgen Receptor nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein 4'-$(CH_2)$—O-2' (LNA) is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$, 2'-$OCH_2CH_3$, 2'-$OCH_2CH_2F$ and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—$N(R_m)(R_n)$, O—$CH_2$—C(═O)—$N(R_m)(R_n)$, and O—$CH_2$—C(═O)—$N(R_1)$—$(CH_2)_2$—$N(R_m)(R_n)$, where each $R_1$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-$(CH_2)$—O-2' (LNA); 4'-$(CH_2)$—S-2; 4'-$(CH_2)_2$—O-2' (ENA); 4-$CH(CH_3)$—O-2' (also referred to as constrained ethyl or cEt) and 4'-$CH(CH_2OCH_3)$—O-2' (and analogs thereof see U.S. Pat. No. 7,399,845, issued on Jul. 15, 2008); 4'-$C(CH_3)(CH_3)$—O-2' (and analogs thereof see published International Application WO/2009/006478, published Jan. 8, 2009); 4-$CH_2$—$N(OCH_3)$-2' (and analogs thereof see published International Application WO/2008/150729, published Dec. 11, 2008); 4-$CH_2$—O—$N(CH_3)$-2' (see published U.S. Patent Application US2004-0171570, published Sep. 2, 2004); 4-$CH_2$—N(R)—O-2', wherein R is H, $C_1$-$C_{12}$ alkyl, or a protecting group (see U.S. Pat. No. 7,427,672, issued on Sep. 23, 2008); 4-$CH_2$—C—$(H)(CH_3)$-2' (see Chattopadhyaya et al., J. Org. Chem., 2009, 74, 118-134); and 4-$CH_2$—C(═$CH_2$)-2' (and analogs thereof see published International Application WO 2008/154401, published on Dec. 8, 2008).

Further reports related to bicyclic nucleosides can also be found in published literature (see for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A, 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 2007, 129(26) 8362-8379; Elayadi et al., Curr. Opinion Invest. Drugs, 2001, 2, 558-561; Braasch et al., Chem. Biol., 2001, 8, 1-7; and Orum et al., Curr. Opinion Mol. Ther., 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —$[C(R_a)(R_b)]_n$—, —$C(R_a)$═$C(R_b)$—, —$C(R_a)$═N—, —C(═O)—, —C(═$NR_a$)—, —C(═S)—, —O—, —$Si(R_a)_2$—, —$S(═O)_x$—, and —$N(R_a)$—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(═O)—H), substituted acyl, CN, sulfonyl $(S(═O)_2$-$J_1)$, or sulfoxyl (S(═O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(═O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is —$[C(R_a)(R_b)]_n$—, —$[C(R_a)(R_b)]_n$—O—, —$C(R_aR_b)$—N(R)—O— or —$C(R_aR_b)$—O—N(R)—. In certain embodiments, the bridge is 4-$CH_2$-2', 4'-$(CH_2)_2$-2', 4'-$(CH_2)_3$-2', 4-$CH_2$—O-2', 4'-$(CH_2)_2$—O-2', 4-$CH_2$—O—

N(R)-2' and 4-$CH_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4-$CH_2$—O-2') BNA's have been incorporated into antisense oligonucleotides that showed antisense activity (Frieden et al., Nucleic Acids Research, 2003, 21, 6365-6372).

In certain embodiments, bicyclic nucleosides include, but are not limited to, (A) α-L-methyleneoxy (4'-$CH_2$—O-2') BNA, (B) β-D-methyleneoxy (4'-$CH_2$—O-2') BNA, (C) ethyleneoxy (4'-$(CH_2)_2$—O-2') BNA, (D) aminooxy (4'-$CH_2$—O—N(R)-2') BNA, (E) oxyamino (4'-$CH_2$—N(R)—O-2') BNA, and (F) methyl(methyleneoxy) (4'-$CH(CH_3)$—O-2') BNA, (G) methylene-thio (4'-$CH_2$—S-2') BNA, (H) methylene-amino (4'-$CH_2$—N(R)-2') BNA, (I) methyl carbocyclic (4'-$CH_2$—$CH(CH_3)$-2') BNA, (J) propylene carbocyclic (4'-$(CH_2)_3$-2') BNA and (K) vinyl BNA as depicted below:

(A)

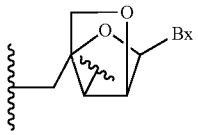

(B)

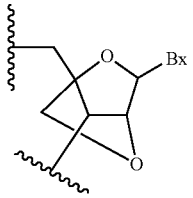

(C)

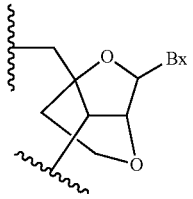

(D)

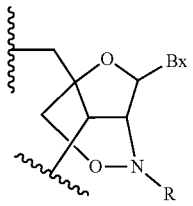

(E)

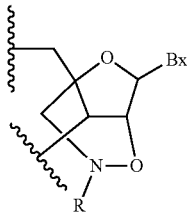

-continued (F)

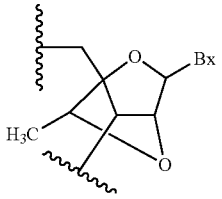

(G)

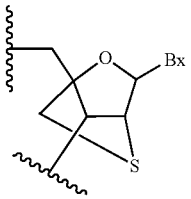

(H)

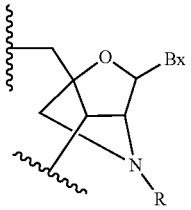

(I)

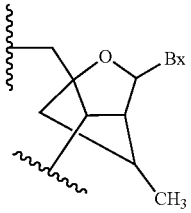

(J)

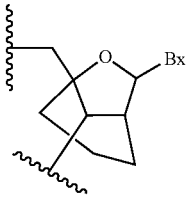

(K)

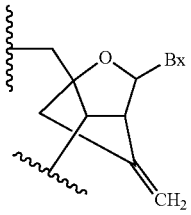

wherein Bx is the base moiety and R is independently H, a protecting group, $C_1$-$C_{12}$ alkyl or $C_1$-$C_{12}$ alkoxy.

In certain embodiments, bicyclic nucleosides are provided having Formula I:

I

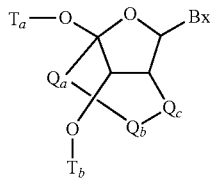

wherein:

Bx is a heterocyclic base moiety;

$-Q_a-Q_b-Q_c-$ is $—CH_2—N(R_c)—CH_2—$, $—C(=O)—N(R_c)—CH_2—$, $—CH_2—O—N(R_c)—$, $—CH_2—N(R_c)—O—$ or $—N(R_c)—O—CH_2$;

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

II

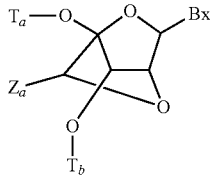

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_cC(=X)NJ_cJ_d$, wherein each $J_c$, $J_d$ and $J_c$ is, independently, H, $C_1$-$C_6$ alkyl, or substituted $C_1$-$C_6$ alkyl and X is O or $NJ_c$.

In certain embodiments, bicyclic nucleosides are provided having Formula III:

III

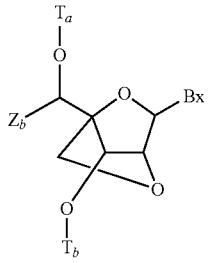

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

IV

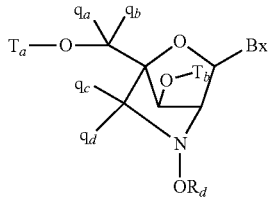

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

V

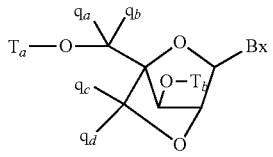

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O—C(=O)—NJ_jJ_k$, $N(H)C(=NH)NJ_jJ_k$, $N(H)C(=O)NJ_jJ_k$ or $N(H)C(=S)NJ_jJ_k$;

or $q_e$ and $q_f$ together are $=C(q_g)(q_h)$;

$q_g$ and $q_h$ are each, independently, H, halogen, $C_1$-$C_{12}$ alkyl or substituted $C_1$-$C_{12}$ alkyl.

The synthesis and preparation of the methyleneoxy (4-$CH_2$—O-2') BNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). Bicyclic nucleic acids (BNAs) and preparation thereof are also described in WO 98/39352 and WO 99/14226.

Analogs of methyleneoxy (4-$CH_2$—O-2') BNA and 2'-thio-BNAs, have also been prepared (Kumar et al., Bioorg. Med. Chem. Lett., 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., J. Org. Chem., 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

VI

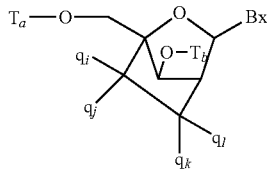

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $N_3$, CN, $C(=O)OJ_j$, $C(=O)NJ_jJ_k$, $C(=O)J_j$, O—$C(=O)NJ_jJ_k$, $N(H)C(=NH)NJ_jJ_k$, $N(H)C(=O)NJ_jJ_k$ or $N(H)C(=S)NJ_jJ_k$; and $q_i$ and $q_j$ or $q_l$ and $q_k$ together are $=C(q_g)(q_h)$, wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-$(CH_2)_3$-2' bridge and the alkenyl analog bridge 4'-CH=CH—$CH_2$-2' have been described (Freier et al., Nucleic Acids Research, 1997, 25(22), 4429-4443 and Albaek et al., J. Org. Chem., 2006, 71, 7731-7740). The synthesis and preparation of carbocyclic bicyclic nucleosides along with their oligomerization and biochemical studies have also been described (Srivastava et al., J. Am. Chem. Soc., 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nF$, $O(CH_2)_nONH_2$, $OCH_2C(=O)N(H)CH_3$, and $O(CH_2)_nON[(CH_2)_nCH_3]_2$, where n and m are from 1 to about 10. Other 2'- substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modifed nucleosides comprise a 2'-MOE side chain (Baker et al., J. Biol. Chem., 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, Helv. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, Bioorg. Med. Chem., 2002, 10, 841-854) or fluoro HNA (F-HNA) having a tetrahydropyran ring system as illustrated below:

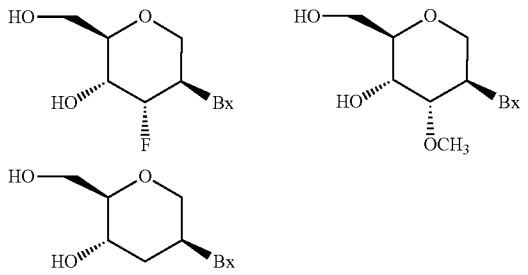

In certain embodiments, sugar surrogates are selected having Formula VII:

VII

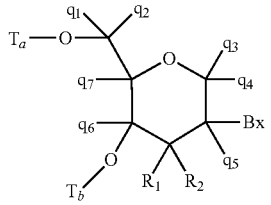

wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, subsitituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is methoxyethoxy and $R_2$ is H.

In certain embodiments, sugar surrogates comprise rings having more than 5 atoms and more than one heteroatom. For example nucleosides comprising morpholino sugar moieties and their use in oligomeric compounds has been reported (see for example: Braasch et al., Biochemistry, 2002, 41, 4503-4510; and U.S. Pat. Nos. 5,698,685; 5,166,315; 5,185,444; and 5,034,506). As used here, the term "morpholino" means a sugar surrogate having the following formula:

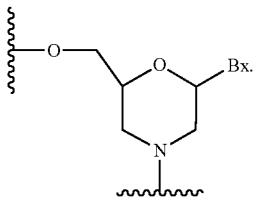

In certain embodiments, morpholinos may be modified, for example by adding or altering various substituent groups from the above morpholino structure. Such sugar surrogates are referred to herein as "modifed morpholinos."

Combinations of modifications are also provided without limitation, such as 2'-F-5'-methyl substituted nucleosides (see PCT International Application WO 2008/101157 published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., J. Am. Chem. Soc. 2007, 129(26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., J. Am. Chem. Soc., 2008, 130(6), 1979-1984; Horváth et al., Tetrahedron Letters, 2007, 48, 3621-3623; Nauwelaerts et al., J. Am. Chem. Soc., 2007, 129(30), 9340-9348; Gu et al., Nucleosides, Nucleotides & Nucleic Acids, 2005, 24(5-7), 993-998; Nauwelaerts et al., Nucleic Acids Research, 2005, 33(8), 2452-2463; Robeyns et al., Acta Crystallographica, Section F: Structural Biology and Crystallization Communications, 2005, F61(6), 585-586; Gu et al., Tetrahedron, 2004, 60(9), 2111-2123; Gu et al., Oligonucleotides, 2003, 13(6), 479-489; Wang et al., J. Org. Chem., 2003, 68, 4499-4505; Verbeure et al., Nucleic Acids Research, 2001, 29(24), 4941-4947; Wang et al., J. Org. Chem., 2001, 66, 8478-82; Wang et al., Nucleosides, Nucleotides & Nucleic Acids, 2001, 20(4-7), 785-788; Wang et al., J. Am. Chem., 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

X

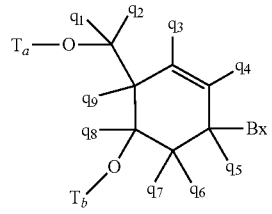

wherein independently for each of said at least one cyclohexenyl nucleoside analog of Formula X:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2'substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—N($R_m$)($R_n$) or O—$CH_2$—C(═O)—N($R_m$)($R_n$), where each $R_m$ and $R_n$ is, independently, H or substituted or unsubstituted $C_1$-$C_{10}$ alkyl. 2'-modifed nucleosides may further comprise other modifications, for example at other positions of the sugar and/or at the nucleobase.

As used herein, "2'-F" refers to a nucleoside comprising a sugar comprising a fluoro group at the 2' position of the sugar ring.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, Bioorg. Med. Chem., 2002, 10, 841-854). Such ring systems can undergo various additional substitutions to enhance activity.

Methods for the preparations of modified sugars are well known to those skilled in the art. Some representative U.S. patents that teach the preparation of such modified sugars include without limitation, U.S.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005, and each of which is herein incorporated by reference in its entirety.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH($CH_3$)—O-2') bridging group. In certain embodiments, the (4-CH($CH_3$)—O-2') modified nucleosides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties can also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and 0-6 substituted purines, including 2 aminopropyladenine, 5-propynyluracil and 5-propynylcytosine.

In certain embodiments, antisense compounds targeted to an androgen receptor nucleic acid comprise one or more modified nucleobases. In certain embodiments, shortened or gap-widened antisense oligonucleotides targeted to an androgen receptor nucleic acid comprise one or more modified nucleobases. In certain embodiments, the modified nucleobase is 5-methylcytosine. In certain embodiments, each cytosine is a 5-methylcytosine.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

In certain embodiments, antisense compounds, including, but not limited to those particularly suited for use as ssRNA, are modified by attachment of one or more conjugate groups. In general, conjugate groups modify one or more properties of the attached oligonucleotide, including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

For additional conjugates including those useful for ssRNA and their placement within antisense compounds, see e.g., PCT Publication No.; WO2013/033230.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to an androgen receptor nucleic acid can be utilized in pharmaceutical compositions by combining the antisense compound with a suitable pharmaceutically acceptable diluent or carrier. In certain embodiments, a pharmaceutically acceptable diluent is water, such as sterile water suitable for injection. Accordingly, in one embodiment, employed in the methods described herein is a pharmaceutical composition comprising an antisense compound targeted to an androgen receptor nucleic acid and a pharmaceutically acceptable diluent. In certain embodiments, the pharmaceutically acceptable diluent is water. In certain embodiments, the antisense compound is an antisense oligonucleotide provided herein.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

In Vitro Testing of Antisense Oligonucleotides

Described herein are methods for treatment of cells with antisense oligonucleotides, which can be modified appropriately for treatment with other antisense compounds.

Cells may be treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides may be mixed with LIPOFECTIN in OPTI-MEM 1 (Invitrogen, Carlsbad, Calif.) to achieve the desired final concentration of antisense oligonucleotide and a LIPOFECTIN concentration that may range from 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that may range from 2 to 12 ug/mL per 100 nM antisense oligonucleotide.

Another technique used to introduce antisense oligonucleotides into cultured cells includes electroporation.

Yet another technique used to introduce antisense oligonucleotides into cultured cells includes free uptake of the oligonucleotides by the cells.

Cells are treated with antisense oligonucleotides by routine methods. Cells may be harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

EMBODIMENTS

E1. A compound comprising a modified oligonucleotide consisting of 10 to 30 linked nucleosides and having a nucleobase sequence comprising at least 8 contiguous nucleobases of any of the nucleobase sequences of SEQ ID NOs: 12-179.

E2. A compound comprising a modified oligonucleotide consisting of 16 to 30 linked nucleosides and having a nucleobase sequence comprising the nucleobase sequence of any one of SEQ ID NOs: 12-179.

E 3. A compound comprising a modified oligonucleotide consisting of the nucleobase sequence of any one of SEQ ID NOs: 12-179.

E 4. A compound comprising a modified oligonucleotide consisting of 10 to 30 linked nucleosides and having a nucleobase sequence comprising at least 8 contiguous nucleobases of any of the nucleobase sequences of SEQ ID NO: 35, 39, 43, 124, 150, 155, 169, or 175.

E 5. A compound comprising a modified oligonucleotide consisting of 16 to 30 linked nucleosides and having a nucleobase sequence comprising the nucleobase sequence of SEQ ID NO: 35, 39, 43, 124, 150, 155, 169, or 175.

E6. A compound comprising a modified oligonucleotide consisting of 16 linked nucleosides and having a nucleobase sequence consisting of the nucleobase sequence of SEQ ID NO: 35, 39, 43, 124, 150, 155, 169, or 175.

E7. A compound comprising a modified oligonucleotide consisting of 10 to 30 linked nucleosides complementary within nucleotides 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5052-5067, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, 5521-5536, 5666-5681, 6222-6237, 6701-6716, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58739, 58721-58736, 58722-58737, 58723-58738, 58724-58739, 58725-58740, 58750-58769, 58751-58766, 58752-58767, 58753-58768, 58754-58769, 58755-58770, 60902-60917, 67454-67469, 114874-114889, 115272-115287, 115365-115380, 134971-134986, 102156-102171, 139682-139697, 139762-139777, 139782-139797, 144856-144871, 144938-144953, 148406-148421, 148443-148458, 148520-148535, 181695-181710, 182958-182973, or 183049-183064 of SEQ ID NO: 1, wherein said modified oligonucleotide is at least 90% complementary to SEQ ID NO: 1.

E8. A compound comprising a modified oligonucleotide consisting of 10 to 30 linked nucleosides having a nucleobase sequence comprising a portion of at least 8 contiguous nucleobases 100% complementary to an equal length portion of nucleobases 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5052-5067, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, 5521-5536, 5666-5681, 6222-6237, 6701-6716, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58739, 58721-58736, 58722-58737, 58723-58738, 58724-58739, 58725-58740, 58750-58769, 58751-58766, 58752-58767, 58753-58768, 58754-58769, 58755-58770, 60902-60917, 67454-67469, 114874-114889, 115272-115287, 115365-115380, 134971-134986, 102156-102171, 139682-139697, 139762-139777, 139782-139797, 144856-144871, 144938-144953, 148406-148421, 148443-148458, 148520-148535, 181695-181710, 182958-182973, or 183049-183064 of SEQ ID NO: 1, wherein the nucleobase sequence of the modified oligonucleotide is complementary to SEQ ID NO: 1.

E9. The compound of any one of E1, E7, or E8, wherein the compound comprises a modified oligonucleotide consisting of 10 to 30 linked nucleosides complementary within exon 1 nucleotides 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5052-5067, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, or 5521-5536 of SEQ ID NO:1.

E10. The compound of E9, wherein the compound comprises a modified oligonucleotide consisting of 10 to 30 linked nucleosides complementary within exon 1 nucleotides 5052-5067 of SEQ ID NO:1.

E11. The compound of any one of E1, E7, or E8, wherein the compound comprises a modified oligonucleotide consisting of 10 to 30 linked nucleosides complementary within intron 1 nucleotides 5666-5681, 6222-6237, 6701-6716, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58739, 58721-58736, 58722-58737, 58723-58738, 58724-58739, 58725-58740, 58750-58769, 58751-58766, 58752-58767, 58753-58768, 58754-58769, 58755-58770, 60902-60917, 67454-67469, 114874-114889, 115272-115287, 115365-115380, or 134971-134986 of SEQ ID NO:1.

E12. The compound of E11, wherein the compound comprises a modified oligonucleotide consisting of 10 to 30 linked nucleosides complementary within intron 1 nucleotides 8638-8653, 11197-11212, 40615-40630, 58719-58734, 58720-58735, or 58721-58736 of SEQ ID NO:1.

E13. The compound of any one of E1-12, wherein the modified oligonucleotide comprises at least one modified sugar.

E14. The compound of E13, wherein at least one modified sugar comprises a 2'-O-methoxyethyl group.

E15. The compound of E13, wherein the at least one modified sugar is a bicyclic sugar.

E16. The compound of E15, wherein the bicyclic sugar comprises a 4'-$CH(CH_3)$—O-2' group.

E17. The compound of E15, wherein the bicyclic sugar comprises a 4'-$CH_2$—O-2' or 4'-$(CH_2)_2$—O-2'group.

E18. The compound of any one of E1-17, wherein the modified oligonucleotide comprises at least one modified internucleoside linkage.

E19. The compound of E18, wherein each internucleoside linkage of the antisense oligonucleotide is a phosphorothioate internucleoside linkage.

E20. The compound of any one of E1-19, wherein the modified oligonucleotide comprises at least one modified nucleobase.

E21. The compound of E20, wherein the modified nucleobase is a 5-methylcytosine.

E22. The compound of any one of E1-21, wherein the modified oligonucleotide comprises:

a gap segment consisting of linked deoxynucleosides;

a 5' wing segment consisting of linked nucleosides; and a 3' wing segment consisting of linked nucleosides;

wherein the gap segment is positioned between the 5' wing segment and the 3' wing segment and wherein each nucleoside of each wing segment comprises a modified sugar.

E23. The compound of E22, wherein the modified oligonucleotide comprises:

a gap segment consisting of ten linked deoxynucleosides;

a 5' wing segment consisting of 3 linked nucleosides; and a 3' wing segment consisting of 3 linked nucleosides;

wherein the gap segment is positioned between the 5' wing segment and the 3' wing segment, wherein each nucleoside of each wing segment comprises a 2'-O-methoxyethyl sugar or a constrained ethyl sugar; and wherein each internucleoside linkage is a phosphorothioate linkage.

E24. A compound comprising a single-stranded modified oligonucleotide consisting of 16 linked nucleosides having a nucleobase sequence consisting of the sequence of SEQ ID NO: 35, or a pharmaceutically acceptable salt thereof, wherein the modified oligonucleotide comprises:

a gap segment consisting of 9 linked deoxynucleosides;

a 5' wing segment consisting of three linked nucleosides; and a 3' wing segment consisting of four linked nucleosides;

wherein the gap segment is positioned between the 5' wing segment and the 3' wing segment; the three linked nucleosides of the 5' wing segment are each a constrained ethyl (cEt) sugar; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

E25. A compound comprising a single-stranded modified oligonucleotide consisting of 16 linked nucleosides having a nucleobase sequence consisting of the sequence of SEQ ID NO: 39, or a pharmaceutically acceptable salt thereof, wherein the modified oligonucleotide comprises:

a gap segment consisting of 9 linked deoxynucleosides;

a 5' wing segment consisting of three linked nucleosides; and a 3' wing segment consisting of four linked nucleosides;

wherein the gap segment is positioned between the 5' wing segment and the 3' wing segment; the three linked nucleosides of the 5' wing segment are each a constrained ethyl (cEt) sugar; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

E26. A compound comprising a single-stranded modified oligonucleotide consisting of 16 linked nucleosides having a nucleobase sequence consisting of the sequence of SEQ ID NO: 39, or a pharmaceutically acceptable salt thereof, wherein the modified oligonucleotide comprises:

a gap segment consisting of 8 linked deoxynucleosides;

a 5' wing segment consisting of four linked nucleosides; and a 3' wing segment consisting of four linked nucleosides;

wherein the gap segment is positioned between the 5' wing segment and the 3' wing segment; the four linked nucleosides of the 5' wing segment are a 2'-O-methoxyethyl sugar, a constrained ethyl (cEt) sugar, a constrained ethyl (cEt) sugar, and a constrained ethyl (cEt) sugar in the 5' to 3' direction; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

E27. A compound comprising a single-stranded modified oligonucleotide consisting of 16 linked nucleosides having a nucleobase sequence consisting of the sequence of SEQ ID NO: 39, or a pharmaceutically acceptable salt thereof, wherein the modified oligonucleotide comprises:

a gap segment consisting of 8 linked deoxynucleosides;

a 5' wing segment consisting of five linked nucleosides; and a 3' wing segment consisting of three linked nucleosides; wherein the gap segment is positioned between the 5' wing segment and the 3' wing segment; the five linked nucleosides of the 5' wing segment are a 2'-O-methoxyethyl sugar, a 2'-O-methoxyethyl sugar, a constrained ethyl (cEt) sugar, a constrained ethyl (cEt) sugar, and a constrained ethyl (cEt) sugar in the 5' to 3' direction; the three linked nucleosides of the 3' wing segment are each a constrained ethyl (cEt) sugar; each internucleoside linkage is a phosphorothioate linkage; and each cytosine is a 5-methylcytosine.

E28. A compound comprising a single-stranded modified oligonucleotide consisting of 16 linked nucleosides having a nucleobase sequence consisting of the sequence of SEQ ID NO: 39, or a pharmaceutically acceptable salt thereof, wherein the modified oligonucleotide comprises:

a gap segment consisting of 7 linked deoxynucleosides;

a 5' wing segment consisting of four linked nucleosides; and a 3' wing segment consisting of five linked nucleosides; wherein the gap segment is positioned between the 5' wing segment and the 3' wing segment; the four linked nucleosides of the 5' wing segment are a 2'-O-methoxyethyl sugar, a constrained ethyl (cEt) sugar, a constrained ethyl (cEt) sugar, and a constrained ethyl (cEt) sugar in the 5' to 3' direction; the five linked nucleosides of the 3' wing segment are a constrained ethyl (cEt) sugar, a constrained ethyl (cEt) sugar, a constrained ethyl (cEt) sugar, a 2'-O-methoxyethyl sugar, and a 2'-O-methoxyethyl sugar in the 5' to 3' direction; each internucleoside linkage is a phosphorothioate linkage; and each cytosine is a 5-methylcytosine.

E29. A compound comprising a single-stranded modified oligonucleotide consisting of 16 linked nucleosides having a nucleobase sequence consisting of the sequence of SEQ ID NO: 35, or a pharmaceutically acceptable salt thereof, wherein the modified oligonucleotide comprises:

a gap segment consisting of 7 linked deoxynucleosides;

a 5' wing segment consisting of six linked nucleosides; and a 3' wing segment consisting of three linked nucleosides; wherein the gap segment is positioned between the 5' wing segment and the 3' wing segment; the six linked nucleosides of the 5' wing segment are a 2'-O-methoxyethyl sugar, a constrained ethyl (cEt) sugar, a constrained ethyl (cEt) sugar, a 2'-O-methoxyethyl sugar, a constrained ethyl (cEt) sugar, and a constrained ethyl (cEt) sugar in the 5' to 3' direction; the three linked nucleosides of the 3' wing segment are each a constrained ethyl (cEt) sugar; each internucleoside linkage is a phosphorothioate linkage; and each cytosine is a 5-methylcytosine.

E30. A compound comprising a single-stranded modified oligonucleotide consisting of 16 linked nucleosides having a nucleobase sequence consisting of the sequence of SEQ ID NO: 43, or a pharmaceutically acceptable salt thereof, wherein the modified oligonucleotide comprises:

a gap segment consisting of 10 linked deoxynucleosides;

a 5' wing segment consisting of three linked nucleosides; and a 3' wing segment consisting of three linked nucleosides; wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

E31. A compound comprising a single-stranded modified oligonucleotide consisting of 16 linked nucleosides having a nucleobase sequence consisting of the sequence of SEQ ID NO: 124, or a pharmaceutically acceptable salt thereof, wherein the modified oligonucleotide comprises:

a gap segment consisting of 10 linked deoxynucleosides;

a 5' wing segment consisting of three linked nucleosides; and a 3' wing segment consisting of three linked nucleosides; wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

E32. A compound comprising a single-stranded modified oligonucleotide consisting of 16 linked nucleosides having a nucleobase sequence consisting of the sequence of SEQ ID NO: 150, or a pharmaceutically acceptable salt thereof, wherein the modified oligonucleotide comprises:

a gap segment consisting of 10 linked deoxynucleosides;

a 5' wing segment consisting of three linked nucleosides; and a 3' wing segment consisting of three linked nucleosides; wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

E33. A compound comprising a single-stranded modified oligonucleotide consisting of 16 linked nucleosides having a nucleobase sequence consisting of the sequence of SEQ ID NO: 155, or a pharmaceutically acceptable salt thereof, wherein the modified oligonucleotide comprises:

a gap segment consisting of 10 linked deoxynucleosides;

a 5' wing segment consisting of three linked nucleosides; and a 3' wing segment consisting of three linked nucleosides; wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

E34. A compound comprising a single-stranded modified oligonucleotide consisting of 16 linked nucleosides having a nucleobase sequence consisting of the sequence of SEQ ID NO: 169, or a pharmaceutically acceptable salt thereof, wherein the modified oligonucleotide comprises:

a gap segment consisting of 10 linked deoxynucleosides;

a 5' wing segment consisting of three linked nucleosides; and a 3' wing segment consisting of three linked nucleosides; wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

E35. A compound comprising a single-stranded modified oligonucleotide consisting of 16 linked nucleosides having a nucleobase sequence consisting of the sequence of SEQ ID NO: 175, or a pharmaceutically acceptable salt thereof, wherein the modified oligonucleotide comprises:

a gap segment consisting of 10 linked deoxynucleosides;

a 5' wing segment consisting of three linked nucleosides; and a 3' wing segment consisting of three linked nucleosides; wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

E36. The compound of any one of E1-35, wherein the modified oligonucleotide is at least 90% complementary to a nucleic acid encoding androgen receptor.

E37. The compound of any one of E1-36, wherein the antisense oligonucleotide is 100% complementary to a nucleic acid encoding androgen receptor.

E38. The compound of E37, wherein the nucleic acid encoding androgen receptor comprises the nucleotide sequence of any one of SEQ ID NOs: 1-8.

E39. A composition comprising the compound of any one of E1-38, or pharmaceutically acceptable salt thereof, and a pharmaceutically acceptable diluent or carrier.

E40. A composition comprising the compound of any one of E1-38 and a diarylhydantoin Androgen Receptor (AR) inhibitor of Formula XVI:

(XVI)

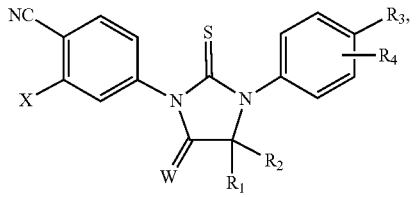

wherein X is selected from the group consisting of trifluoromethyl and iodo, wherein W is selected from the group consisting of O and NR5, wherein R5 is selected from the group consisting of H, methyl, and

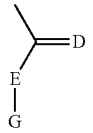

wherein D is S or O and E is N or O and G is alkyl, aryl, substituted alkyl or substituted aryl; or D is S or O and E-G together are C1-C4 lower alkyl, wherein R1 and R2 together comprise eight or fewer carbon atoms and are selected from the group consisting of alkyl, substituted alkyl including haloalkyl, and, together with the carbon to which they are linked, a cycloalkyl or substituted cycloalkyl group, wherein R3 is selected from the group consisting of hydrogen, halogen, methyl, C1-C4 alkoxy, formyl, haloacetoxy, trifluoromethyl, cyano, nitro, hydroxyl, phenyl, amino, methylcarbamoyl, methoxycarbonyl, acetamido, methanesulfonamino, methanesulfonyl, 4-methanesulfonyl-1-piperazinyl, piperazinyl, and C1-C6 alkyl or alkenyl optionally substituted with hydroxyl, methoxycarbonyl, cyano, amino, amido, nitro, carbamoyl, or substituted carbamoyl including methylcarbamoyl, dimethylcarbamoyl, and hydroxyethylcarbamoyl, wherein R4 is selected from the group consisting of hydrogen, halogen, alkyl, and haloalkyl, and wherein R3 is not methylaminomethyl or dimethylaminomethyl.

R5 may be

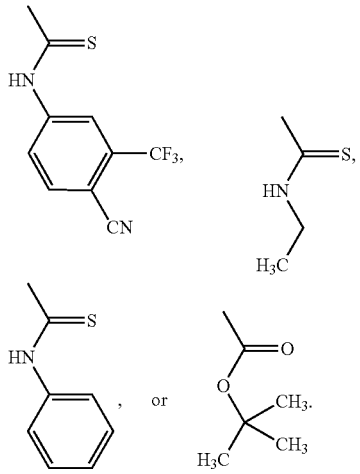

E41. The composition of E40, wherein the diarylhydantoin Androgen Receptor (AR) inhibitor is MDV3100.

E42. A composition comprising the compound of any one of E1-38 and an anti-androgenic agent selected from: MDV3100, ARN-059, ODM-201, abiraterone, TOK001, TAK700 and VT464.

E43. A method of treating cancer comprising administering to a subject having cancer the compound of any one of E1-38 or composition of any one of E39-42, thereby treating cancer in the subject.

E44. An antisense compound of any one of E1-38 or composition of any one of E39-42 for use in treating cancer E45. The compound or composition of E44, wherein the cancer is prostate cancer, breast cancer, ovarian cancer, gastric cancer or bladder cancer.

E46. The compound or composition of E45, wherein the cancer is castrate-resistant prostate cancer.

E47. The compound or composition of E46, wherein the castrate-resistant prostate cancer is resistant to an anti-androgenic agent selected from: MDV3100, ARN-059, ODM-201, abiraterone, TOK001, TAK700 and VT464.

E48. The method of E43, wherein the cancer is prostate cancer, breast cancer, ovarian cancer, gastric cancer or bladder cancer.

E49. The method of E48, wherein the cancer is castrate-resistant prostate cancer.

E50. The method of E49, wherein the castrate-resistant prostate cancer is resistant to an anti-androgenic agent selected from: MDV3100, ARN-059, ODM-201, abiraterone, TOK001, TAK700 and VT464.

E51. The compound of E44-47 or the method of E49 or E50, wherein the antisense compound targets an AR splicing variant.

E52. The compound or method of E51, wherein the AR splicing variant lacks a functional ligand binding domain.

E53. The compound of E44-47 or the method of any one of E49-52, wherein the antisense compound is capable of reducing expression of full-length AR and an AR splicing variant lacking any one of exons 4-8.

E54. The compound or method of E51, wherein the AR splicing variant consists of exons 1-3.

E55. The compound of E44-47 or the method of any one of E49-52, wherein the antisense compound is targeted to AR upstream of the 3' end of exon 3 and is capable of inhibiting growth or proliferation of the prostate cancer cell to a greater extent than an antisense compound targeted to a region of AR downstream of the 3' end of exon 3.

E56. The compound or method of E55, wherein the antisense compound targeted to a region of AR downstream of the 3' end of exon 3 is capable of reducing levels of full-length AR but not an AR splicing variant consisting of exons 1-3.

E57. The compound or method of E56, wherein the region downstream of the 3' end of exon 3 comprises exon 4.

E58. The compound of E44-47 or the method of any one of E49-52, wherein the prostate cancer cell preferentially expresses an AR splicing variant over full-length AR.

E59. The compound or method of E58, wherein the AR splicing variant lacks a functional ligand binding domain.

E60. A method of treating prostate cancer resistant to a anti-androgenic agent selected from: MDV3100, ARN-059, ODM-201, abiraterone, TOK001, TAK700 and VT464 in a subject comprising administering to the subject an antisense compound targeted to human androgen receptor (AR) upstream of the 3' end of exon 3, thereby treating the prostate cancer.

E61. The method of E60, wherein the subject is diagnosed as having prostate cancer resistant to the anti-androgenic agent selected from: MDV3100, ARN-059, ODM-201, abiraterone, TOK001, TAK700 and VT464.

E62. The method of E60 or E61, wherein the antisense compound targets an AR splicing variant.

E63. The method of E62, wherein the AR splicing variant lacks a functional ligand binding domain.

E64. The method of any one of E60-63, wherein the antisense compound is capable of reducing expression of full-length AR and an AR splicing variant lacking any one of exons 4-8.

E65. The method of E64, wherein the AR splicing variant consists of exons 1-3.

E66. The method of any one of E60-65, wherein the antisense compound is targeted to AR upstream of the 3' end of exon 3 and is capable of inhibiting growth or proliferation of a prostate cancer cell resistant to the diarylhydantoin Androgen Receptor (AR) inhibitor to a greater extent than an antisense compound targeted to a region of AR downstream of the 3' end exon 3.

E67. The method of E66, wherein the antisense compound targeted to a region of AR downstream of the 3' end of exon 3 is capable of reducing levels of full-length AR but not an AR splicing variant lacking any one of exons 4-8.

E68. The method of E67, wherein the AR splicing variant consists of exons 1-3.

E69. The method of E68, wherein the region downstream of the 3' end of exon 3 comprises exon 4.

E70. The method of any one of E60-69, wherein the prostate cancer is castration-resistant.

E71. The method of any one of E60-70, wherein the prostate cancer comprises cells that preferentially express an AR splicing variant over full-length AR.

E72. The method of E71, wherein the AR splicing variant lacks any one of exons 4-8.

E73. The method of E72, wherein the AR splicing variant consists of exons 1-3.

E74. The method of E72, wherein the AR splicing variant lacks a functional ligand binding domain.

E75. A method of inhibiting prostate cancer cell growth or proliferation comprising contacting the prostate cancer cell with an antisense compound targeted to human androgen receptor (AR) and anti-androgenic agent selected from: MDV3100, ARN-059, ODM-201, abiraterone, TOK001, TAK700 and VT464, wherein the antisense compound and the anti-androgenic agent synergize in combination to inhibit the growth or proliferation of the prostate cancer cell.

E76. The method of E75, wherein the antisense compound is targeted to AR upstream of the 3' end of exon 3.

E77. The method of E75 or E76, wherein the prostate cancer cell is contacted with an amount of the antisense compound and an amount of anti-androgenic agent that are each or both less in combination than the amount of either the antisense compound or anti-androgenic agent alone effective in inhibiting the growth or proliferation of said prostate cancer cell.

E78. The method of any one of E75-77, wherein the antisense compound and anti-androgenic agent provide a greater-than-additive effect compared to the antisense compound alone or anti-androgenic agent alone in inhibiting the growth or proliferation of said prostate cancer cell.

E79. The method of any one of E75-78, wherein the antisense compound targets an AR splicing variant.

E80. The method of E79, wherein the AR splicing variant lacks a functional ligand binding domain.

E81. The method of any one of E75-80, wherein the antisense compound is capable of reducing expression of full-length AR and an AR splicing variant consisting of exons 1-3.

E82. A method of inhibiting growth or proliferation of an androgen receptor (AR)-positive breast cancer cell comprising contacting the breast cancer cell with an antisense compound targeted to human androgen receptor (AR) wherein the growth or proliferation of the breast cancer cell is inhibited.

E83. A method of inhibiting AR expression in a subject having or at risk of having an androgen receptor (AR)-positive breast cancer comprising:

identifying a subject having or at risk of having AR-positive breast cancer, and administering to the subject an antisense compound targeted to human AR, wherein the antisense compound inhibits AR expression in the subject.

E84. A method of treating AR-positive breast cancer in a subject comprising administering to the subject an antisense compound targeted to human androgen receptor (AR), thereby treating the breast cancer in the subject.

E85. The method of any one of E82-84, wherein the AR-positive breast cancer or breast cancer cell is dependent on androgen expression for growth.

E86. The method of any one of E82-85, wherein the breast cancer or breast cancer cell is estrogen receptor (ER)-negative, progesterone receptor (PR)-negative, or Her2/neu-negative.

E87. The method of any one of E82-85, wherein the breast cancer or breast cancer cell is ER-positive and AR-positive.

E88. The method of any one of E82-85, wherein the breast cancer or breast cancer cell is ER-negative and AR-positive.

E89. The method of any one of E82-88, wherein the breast cancer or breast cancer cell is an apocrine breast cancer or breast cancer cell.

E90. The method of any one of E60-88, wherein the antisense compound is the compound of any one of E1-38, or pharmaceutically acceptable salt thereof.

E91. The method of any one of E60-88, wherein the antisense compound is the compound of any one of E24-35, or pharmaceutically acceptable salt thereof.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1

Antisense Inhibition of Human AR in HuVEC Cells

Antisense oligonucleotides were designed targeting an AR nucleic acid and were tested for their effects on AR mRNA in vitro. The antisense oligonucleotides were tested in a series of experiments that had similar culture conditions. The results for each experiment are presented in separate tables shown below. Cultured HuVEC cells at a density of 20,000 cells per well were transfected using electroporation with 500 nM antisense oligonucleotide. After a treatment period of approximately 24 hours, RNA was isolated from the cells and AR mRNA levels were measured by quantitative real-time PCR. Human primer probe set RTS3559 (forward sequence TCCTTCACCAATGTCAACTCC, designated herein as SEQ ID NO: 9; reverse sequence GAGCCATCCAAACTCTTGAGA, designated herein as SEQ ID NO: 10; probe sequence AGTACCGCATGCACAAGTCCCG, designated herein as SEQ ID NO: 11) was used to measure mRNA levels. AR mRNA levels were adjusted according to total RNA content, as measured by RIBOGREEN®. Results are presented as percent inhibition of AR, relative to untreated control cells. A total of 155 oligonucleotides were tested. Only those oligonucleotides which were selected for further study are shown in Tables 1 and 2.

The newly designed chimeric antisense oligonucleotides in Tables 1 and 2 were designed as 3-10-3 (S)-cET gapmers. The gapmers are 16 nucleosides in length, wherein the central gap segment comprises of ten 2'-deoxynucleosides and is flanked by wing segments on both the 5' direction and on the 3' direction comprising three nucleosides. Each nucleoside in the 5' wing segment and each nucleoside in the 3' wing segment has an (S)-cEt modification. The internucleoside linkages throughout each gapmer are phosphorothioate linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in Tables 1 and 2 is targeted to either the human AR genomic sequence, designated herein as SEQ ID NO: 1 (GENBANK Accession No. NT_011669.17 truncated from nucleotides 5079000 to 5270000) or the human AR mRNA sequence, designated herein as SEQ ID NO: 2 (GENBANK Accession No. NM_000044.3), or both. 'n/a.' indicates that the oligonucleotide does not target that particular gene sequence.

TABLE 1

| Target Start Site for SEQ ID NO: 1 | Target Start Site for SEQ ID NO: 2 | ISIS No | Sequence | % inhibition | SEQ ID NO |
|---|---|---|---|---|---|
| 3799 | 937 | 549332 | GCGCTCTGACAGCCTC | 84 | 12 |
| 3851 | 989 | 549334 | CACCTGCGGGAAGCTC | 83 | 13 |
| 3888 | 1026 | 549338 | GGCTGTGATGATGCGG | 83 | 14 |
| 4047 | 1185 | 549345 | TCTGGAACAGATTCTG | 82 | 191 |
| 4059 | 1197 | 549347 | CTTCGCGCACGCTCTG | 84 | 15 |
| 4534 | 1672 | 549358 | ATGGTGCTGGCCTCGC | 91 | 16 |
| 4655 | 1793 | 549360 | GGTCGAAGTGCCCCCT | 89 | 17 |
| 4699 | 1837 | 549361 | GACACCGACACTGCCT | 84 | 18 |
| 4755 | 1893 | 549362 | CCCGAAGCTGTTCCCC | 85 | 19 |
| 4865 | 2003 | 549366 | CTTGCCTGCGCTGTCG | 84 | 20 |
| 5060 | 2198 | 549371 | GTTGTAGTAGTCGCGA | 93 | 21 |
| 5062 | 2200 | 549372 | AAGTTGTAGTAGTCGC | 92 | 22 |
| 5155 | 2293 | 549374 | GCGCTGCCGTAGTCCA | 93 | 23 |
| 5265 | 2403 | 549377 | AGGATGAGGAAGCGGC | 90 | 24 |
| 5392 | 2530 | 549379 | GCTCCCGCCTCGCCGC | 86 | 25 |
| 5448 | 2586 | 549380 | CGCTTTCCTGGCCCGC | 94 | 26 |
| 5483 | 2621 | 549381 | GCCGCCAGGGTACCAC | 89 | 27 |

TABLE 1-continued

| Target Start Site for SEQ ID NO: 1 | Target Start Site for SEQ ID NO: 2 | ISIS No | Sequence | % inhibition | SEQ ID NO |
|---|---|---|---|---|---|
| n/a | 2721 | 549383 | CCAAACGCATGTCCCC | 88 | 28 |
| 102155 | 2800 | 549386 | GCTTCATCTCCACAGA | 77 | 192 |
| 102156 | 2801 | 549387 | AGCTTCATCTCCACAG | 84 | 29 |
| n/a | 2871 | 549388 | TCCCTTCAGCGGCTCT | 88 | 30 |
| 144856 | 2801 | 549390 | TTTCTGCTGGCGCACA | 89 | 31 |

TABLE 2

| Target Start Site for SEQ ID NO: 1 | Target Start Site for SEQ ID NO: 2 | ISIS No | Sequence | % inhibition | SEQ ID NO |
|---|---|---|---|---|---|
| 181695 | 3602 | 549414 | GTTCATTCGAAGTTCA | 81 | 32 |
| 182958 | 4164 | 549432 | GAGGATCATCACAGAT | 90 | 33 |
| 183049 | 4255 | 549434 | CTAAACTTCCCGTGGC | 96 | 34 |
| 58721<br>58751 | n/a | 549457 | TTGATTTAATGGTTGC | 98 | 35 |
| 58722<br>58752 | n/a | 549458 | GTTGATTTAATGGTTG | 95 | 36 |
| 58725<br>58755 | n/a | 549459 | ATGGTTGATTTAATGG | 96 | 37 |

Example 2

Dose-Dependent Antisense Inhibition of Human AR in HuVEC Cells

Gapmers from the study described above exhibiting significant in vitro inhibition of AR mRNA were selected and tested at various doses in HuVEC cells. Cells were plated at a density of 20,000 cells per well and transfected using electroporation with 18.5 nM, 55.6 nM, 166.7 nM, 500.0 nM and 1500.0 nM concentrations of antisense oligonucleotide, as specified in Tables 3 and 4. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells. The antisense oligonucleotides were tested in a series of experiments that had similar culture conditions. The results for each experiment are presented in separate tables shown below.

The half maximal inhibitory concentration ($IC_{50}$) of each oligonucleotide is also presented in Tables 3 and 4. As illustrated, AR mRNA levels were reduced in a dose-dependent manner in the antisense oligonucleotide treated cells.

TABLE 3

| ISIS No | 18.5 nM | 55.6 nM | 166.7 nM | 500.0 nM | 1500.0 nM | $IC_{50}$ (nM) |
|---|---|---|---|---|---|---|
| 549358 | 0 | 29 | 63 | 85 | 95 | 141 |
| 549360 | 2 | 44 | 58 | 79 | 83 | 116 |
| 549361 | 0 | 12 | 30 | 52 | 66 | 525 |
| 549362 | 0 | 10 | 23 | 57 | 74 | 447 |
| 549371 | 0 | 30 | 52 | 83 | 88 | 148 |
| 549372 | 0 | 22 | 51 | 85 | 89 | 150 |
| 549374 | 15 | 40 | 59 | 83 | 92 | 108 |
| 549377 | 0 | 13 | 52 | 72 | 93 | 216 |
| 549379 | 9 | 11 | 51 | 68 | 88 | 237 |
| 549380 | 14 | 50 | 87 | 94 | 98 | 62 |
| 549381 | 4 | 14 | 33 | 71 | 91 | 261 |
| 549383 | 2 | 10 | 34 | 75 | 88 | 270 |
| 549388 | 0 | 15 | 42 | 36 | 86 | 428 |
| 549390 | 12 | 0 | 35 | 55 | 91 | 369 |

TABLE 4

| ISIS No | 18.5 nM | 55.6 nM | 166.7 nM | 500.0 nM | 1500.0 nM | $IC_{50}$ (nM) |
|---|---|---|---|---|---|---|
| 549332 | 24 | 35 | 57 | 79 | 79 | 104 |
| 549334 | 9 | 29 | 46 | 63 | 72 | 253 |
| 549338 | 30 | 32 | 47 | 67 | 78 | 154 |
| 549347 | 5 | 15 | 37 | 62 | 71 | 357 |
| 549366 | 8 | 44 | 58 | 72 | 91 | 129 |
| 549387 | 2 | 9 | 41 | 68 | 92 | 261 |

TABLE 4-continued

| ISIS No | 18.5 nM | 55.6 nM | 166.7 nM | 500.0 nM | 1500.0 nM | $IC_{50}$ (nM) |
|---|---|---|---|---|---|---|
| 549414 | 0 | 21 | 35 | 53 | 76 | 366 |
| 549432 | 10 | 15 | 46 | 80 | 92 | 179 |
| 549434 | 27 | 38 | 60 | 86 | 96 | 85 |
| 549457 | 50 | 70 | 95 | 99 | 99 | 18 |
| 549458 | 22 | 48 | 84 | 97 | 98 | 57 |
| 549459 | 51 | 61 | 90 | 94 | 97 | 18 |

Example 3

Antisense Inhibition of Human AR in HuVEC Cells

Additional antisense oligonucleotides were designed targeting an AR nucleic acid and were tested for their effects on AR mRNA in vitro. Cultured HuVEC cells at a density of 20,000 cells per well were transfected using electroporation with 500 nM antisense oligonucleotide. After a treatment period of approximately 24 hours, RNA was isolated from the cells and AR mRNA levels were measured by quantitative real-time PCR. Human primer probe set RTS3559 was used to measure mRNA levels. AR mRNA levels were adjusted according to total RNA content, as measured by RIBOGREEN®. Results are presented as percent inhibition of AR, relative to untreated control cells. A total of 82 oligonucleotides were tested. Only those oligonucleotides which were selected for further study are shown in Table 5.

The newly designed chimeric antisense oligonucleotides in Table 5 were designed as 3-10-3 (S)-cET gapmers or 5-10-5 MOE gapmers. The 3-10-3 (S)-cEt gapmers are 16 nucleosides in length, wherein the central gap segment comprises of ten 2'-deoxynucleosides and is flanked by wing segments on both the 5' direction and on the 3' direction comprising three nucleosides. Each nucleoside in the 5' wing segment and each nucleoside in the 3' wing segment has an (S)-cEt modification. The 5-10-5 MOE gapmer is 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in Table 5 is targeted to the human AR genomic sequence, designated herein as SEQ ID NO: 1 (GENBANK Accession No. NT_011669.17 truncated from nucleotides 5079000 to 5270000)

TABLE 5

| Target Start Site | Target Stop Site | ISIS No | ISIS No | Motif | % inhibition | SEQ ID NO |
|---|---|---|---|---|---|---|
| 58721<br>58751 | 58736<br>58766 | 549457 | TTGATTTAATGGTTGC | 3-10-3 | 98 | 35 |
| 58722<br>58752 | 58737<br>58767 | 549458 | GTTGATTTAATGGTTG | 3-10-3 | 94 | 36 |
| 58725<br>58755 | 58740<br>58770 | 549459 | ATGGTTGATTTAATGG | 3-10-3 | 92 | 37 |
| 58720<br>58750 | 58739<br>58769 | 560071 | TGGTTGATTTAATGGTTGCA | 5-10-5 | 73 | 38 |
| 58720<br>58750 | 58735<br>58765 | 560098 | TGATTTAATGGTTGCA | 3-10-3 | 99 | 39 |
| 58723<br>58753 | 58738<br>58768 | 560099 | GGTTGATTTAATGGTT | 3-10-3 | 95 | 40 |
| 58724<br>58754 | 58739<br>58769 | 560100 | TGGTTGATTTAATGGT | 3-10-3 | 91 | 41 |
| 58721<br>58751 | 58736<br>58766 | 560137 | TTGATTTAATGGTTGC | 3-10-3 | 95 | 35 |

Example 4

Dose-Dependent Antisense Inhibition of Human AR in HuVEC Cells

Gapmers from the studies described above exhibiting significant in vitro inhibition of AR mRNA were selected and tested at various doses in HuVEC cells. Cells were plated at a density of 20,000 cells per well and transfected using electroporation with 31.3 nM, 62.5 nM, 125.0 nM, 250.0 nM, 500.0 nM, and 1000.0 nM concentrations of antisense oligonucleotide, as specified in Table 6. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells. The antisense oligonucleotides were tested in a series of experiments that had similar culture conditions. The results for each experiment are presented in separate tables shown below.

The half maximal inhibitory concentration ($IC_{50}$) of each oligonucleotide is also presented in Table 6. As illustrated, AR mRNA levels were reduced in a dose-dependent manner in the antisense oligonucleotide treated cells.

TABLE 6

| ISIS No | 31.25 nM | 62.5 nM | 125.0 nM | 250.0 nM | 500.0 nM | 1000.0 nM | $IC_{50}$ (μM) |
|---|---|---|---|---|---|---|---|
| 549457 | 40 | 57 | 78 | 89 | 96 | 96 | 0.03 |
| 549458 | 15 | 25 | 47 | 70 | 88 | 93 | 0.1 |
| 549459 | 16 | 23 | 50 | 71 | 85 | 92 | 0.1 |
| 560071 | 7 | 0 | 19 | 40 | 57 | 76 | 0.4 |
| 560098 | 20 | 41 | 64 | 83 | 94 | 94 | 0.1 |
| 560099 | 13 | 29 | 58 | 72 | 89 | 94 | 0.1 |
| 560100 | 16 | 24 | 53 | 69 | 81 | 93 | 0.1 |
| 560137 | 27 | 49 | 61 | 82 | 91 | 96 | 0.1 |

Example 5

Antisense Inhibition of Human AR in HuVEC Cells

Additional antisense oligonucleotides were designed targeting an AR nucleic acid and were tested for their effects on AR mRNA in vitro. Cultured HuVEC cells at a density of 20,000 cells per well were transfected using electroporation with 250 nM antisense oligonucleotide. After a treatment period of approximately 24 hours, RNA was isolated from the cells and AR mRNA levels were measured by quantitative real-time PCR. Human primer probe set RTS3559 was used to measure mRNA levels. AR mRNA levels were adjusted according to total RNA content, as measured by RIBOGREEN®. Results are presented as percent inhibition of AR, relative to untreated control cells. A total of 40 oligonucleotides were tested. Only those oligonucleotides which were selected for further study are shown in Table 7.

The newly designed chimeric antisense oligonucleotides in Table 7 were designed as 3-10-3 (S)-cET gapmers or deoxy, MOE and (S)-cEt oligonucleotides. The 3-10-3 (S)-cEt gapmers are 16 nucleosides in length, wherein the central gap segment comprises of ten 2'-deoxynucleosides and is flanked by wing segments on both the 5' direction and on the 3' direction comprising three nucleosides. Each nucleoside in the 5' wing segment and each nucleoside in the 3' wing segment has an (S)-cEt modification. The deoxy, MOE and (S)-cEt oligonucleotides are 16 nucleosides in length wherein the nucleoside have either a MOE sugar modification, an (S)-cEt sugar modification, or a deoxy modification. The 'Chemistry' column describes the sugar modifications of each oligonucleotide. 'k' indicates an (S)-cEt sugar modification; the number indicates the number of deoxynucleosides; and 'e' indicates a MOE modification. The internucleoside linkages throughout each gapmer are phosphorothioate linkages. All cytosine residues throughout each gapmer are 5-methylcytosines. The SEQ ID NO listed in the table refers to the oligonucleotide sequence. "Start site" indicates the 5'-most nucleoside to which the gapmer is targeted in the human gene sequence. "Stop site" indicates the 3'-most nucleoside to which the gapmer is targeted human gene sequence. Each gapmer listed in Table 7 is targeted to the human AR genomic sequence, designated herein as SEQ ID NO: 1 (GENBANK Accession No. NT_011669.17 truncated from nucleotides 5079000 to 5270000).

TABLE 7

| Target Start Site | Target Stop Site | Sequence | ISIS No | Chemistry | % inhibi-tion | SEQ ID NO |
|---|---|---|---|---|---|---|
| 58721<br>58751 | 58736<br>58766 | TTGATTTAATGGTTGC | 549457 | kkk-10-kkk | 67 | 35 |
| 58722<br>58752 | 58737<br>58767 | GTTGATTTAATGGTTG | 549458 | kkk-10-kkk | 71 | 36 |
| 58720<br>58750 | 58735<br>58765 | TGATTTAATGGTTGCA | 560098 | kkk-10-kkk | 69 | 39 |
| 58721<br>58751 | 58736<br>58766 | TTGATTTAATGGTTGC | 560131 | kkk-9-kkke | 74 | 35 |
| 58721<br>58751 | 58736<br>58766 | TTGATTTAATGGTTGC | 560137 | ekkk-8-kkke | 66 | 35 |
| 58720<br>58750 | 58735<br>58765 | TGATTTAATGGTTGCA | 569213 | kkk-9-kkke | 69 | 39 |
| 58720<br>58750 | 58735<br>58765 | TGATTTAATGGTTGCA | 569216 | ekkk-8-kkke | 68 | 39 |
| 58721<br>58751 | 58736<br>58766 | TTGATTTAATGGTTGC | 569222 | eekkk-8-kkk | 74 | 35 |
| 58721<br>58751 | 58736<br>58766 | TTGATTTAATGGTTGC | 569228 | eekkk-7-kkke | 67 | 35 |
| 58720<br>58750 | 58735<br>58765 | TGATTTAATGGTTGCA | 569236 | ekkk-7-kkkee | 66 | 39 |

Example 6

Dose-Dependent Antisense Inhibition of Human AR in HuVEC Cells

Gapmers from the studies described above exhibiting significant in vitro inhibition of AR mRNA were selected and tested at various doses in HuVEC cells. Cells were plated at a density of 20,000 cells per well and transfected using electroporation with 31.3 nM, 62.5 nM, 125.0 nM, 250.0 nM, 500.0 nM, and 1000.0 nM concentrations of antisense oligonucleotide, as specified in Table 8. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells. The antisense oligonucleotides were tested in a series of experiments that had similar culture conditions. The results for each experiment are presented in separate tables shown below.

The half maximal inhibitory concentration ($IC_{50}$) of each oligonucleotide is also presented in Table 8. As illustrated, AR mRNA levels were reduced in a dose-dependent manner in the antisense oligonucleotide treated cells.

TABLE 8

| ISIS No | 31.25 nM | 62.5 nM | 125.0 nM | 250.0 nM | 500.0 nM | 1000.0 nM | $IC_{50}$ (μM) |
|---|---|---|---|---|---|---|---|
| 549457 | 34 | 44 | 75 | 82 | 93 | 96 | 0.06 |
| 549458 | 30 | 36 | 54 | 70 | 85 | 90 | 0.10 |
| 560098 | 30 | 54 | 65 | 78 | 89 | 97 | 0.07 |
| 560131 | 16 | 48 | 65 | 82 | 89 | 97 | 0.09 |

TABLE 8-continued

| ISIS No | 31.25 nM | 62.5 nM | 125.0 nM | 250.0 nM | 500.0 nM | 1000.0 nM | $IC_{50}$ (μM) |
|---|---|---|---|---|---|---|---|
| 560137 | 35 | 39 | 64 | 73 | 89 | 94 | 0.08 |
| 569213 | 35 | 53 | 65 | 83 | 94 | 96 | 0.06 |
| 569216 | 38 | 51 | 68 | 83 | 91 | 96 | 0.05 |
| 569222 | 36 | 48 | 67 | 83 | 91 | 98 | 0.06 |
| 569228 | 26 | 43 | 62 | 78 | 88 | 92 | 0.09 |
| 569236 | 17 | 39 | 54 | 79 | 84 | 92 | 0.11 |

Example 7

Dose-Dependent Antisense Inhibition of Human AR in HuVEC Cells

Additional antisense oligonucleotides were designed as deoxy, MOE and (S)-cEt oligonucleotides targeting AR gene sequences and were tested at various doses in HuVEC cells. The oligonucleotides are 16 nucleosides in length wherein the nucleoside have either a MOE sugar modification, an (S)-cEt sugar modification, or a deoxy modification. The 'Chemistry' column describes the sugar modifications of each oligonucleotide. 'k' indicates an (S)-cEt sugar modification; the number indicates the number of deoxynucleosides; otherwise 'd' indicates deoxyribose; and 'e' indicates a MOE modification. The internucleoside linkages throughout each gapmer are phosphorothioate linkages. All cytosine residues throughout each gapmer are 5-methylcytosines. The SEQ ID NO listed in the table refers to the oligonucleotide sequence. "Start site" indicates the 5'-most nucleoside to which the gapmer is targeted in the human gene sequence. "Stop site" indicates the 3'-most nucleoside to which the gapmer is targeted human gene sequence. Each gapmer listed in Table 9 is targeted to the human AR genomic sequence, designated herein as SEQ ID NO: 1 (GENBANK Accession No. NT_011669.17 truncated from nucleotides 5079000 to 5270000)

TABLE 9

| Target Start Site | Target Stop Site | Sequence | ISIS No | Chemistry | SEQ ID NO |
|---|---|---|---|---|---|
| 58720<br>58750 | 58735<br>58765 | TGATTTAATGGTTGCA | 569221 | eekkk-8-kkk | 39 |
| 58720<br>58750 | 58735<br>58765 | TGATTTAATGGTTGCA | 569227 | eekkk-7-kkke | 39 |
| 58720<br>58750 | 58735<br>58765 | TGATTTAATGGTTGCA | 569236 | ekkk-7-kkkee | 39 |
| 58720<br>58750 | 58735<br>58765 | TGATTTAATGGTTGCA | 579666 | ekkeekk-7-kk | 39 |
| 58721<br>58751 | 58736<br>58766 | TTGATTTAATGGTTGC | 579667 | ekkeekk-7-kk | 35 |
| 58720<br>58750 | 58735<br>58765 | TGATTTAATGGTTGCA | 579670 | ekkekk-7-kkk | 39 |
| 58721<br>58751 | 58736<br>58766 | TTGATTTAATGGTTGC | 579671 | ekkekk-7-kkk | 35 |
| 58721<br>58751 | 58736<br>58766 | TTGATTTAATGGTTGC | 569228 | eekkk-7-kkke | 35 |
| 58723<br>58753 | 58738<br>58768 | GGTTGATTTAATGGTT | 579669 | ekkeekk-7-kk | 40 |
| 58722<br>58752 | 58737<br>58767 | GTTGATTTAATGGTTG | 579672 | ekkekk-7-kkk | 36 |

TABLE 9-continued

| Target Start Site | Target Stop Site | Sequence | ISIS No | Chemistry | SEQ ID NO |
|---|---|---|---|---|---|
| 58722<br>58752 | 58737<br>58767 | GTTGATTTAATGGTTG | 569217 | ekkk-8-kkke | 36 |
| 58723<br>58753 | 58738<br>58768 | GGTTGATTTAATGGTT | 569214 | kkk-9-kkke | 40 |
| 58723<br>58753 | 58738<br>58768 | GGTTGATTTAATGGTT | 560099 | kkk-10-kkk | 40 |

Cells were plated at a density of 20,000 cells per well and transfected using electroporation with 62.5 nM, 125.0 nM, 250.0 nM, 500.0 nM, and 1000.0 nM concentrations of antisense oligonucleotide, as specified in Tables 10-12. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells. The antisense oligonucleotides were tested in a series of experiments that had similar culture conditions. The results for each experiment are presented in separate tables shown below.

The half maximal inhibitory concentration ($IC_{50}$) of each oligonucleotide is also presented in Tables 10-12. As illustrated, AR mRNA levels were reduced in a dose-dependent manner in some of the antisense oligonucleotide treated cells.

TABLE 10

| ISIS No | 62.5 nM | 125.0 nM | 250.0 nM | 500.0 nM | 1000.0 nM | $IC_{50}$ (nM) |
|---|---|---|---|---|---|---|
| 549458 | 25 | 46 | 55 | 64 | 78 | 203 |
| 569227 | 8 | 40 | 33 | 51 | 73 | 388 |
| 569228 | 29 | 44 | 63 | 77 | 87 | 158 |
| 569236 | 4 | 35 | 54 | 68 | 88 | 252 |
| 579666 | 33 | 34 | 47 | 64 | 80 | 229 |
| 579667 | 30 | 29 | 44 | 36 | 76 | 411 |

TABLE 11

| ISIS No | 62.5 nM | 125.0 nM | 250.0 nM | 500.0 nM | 1000.0 nM | $IC_{50}$ (nM) |
|---|---|---|---|---|---|---|
| 549458 | 16 | 22 | 44 | 64 | 74 | 324 |
| 579669 | 24 | 39 | 45 | 74 | 91 | 207 |
| 579670 | 27 | 28 | 55 | 75 | 70 | 236 |
| 579671 | 6 | 40 | 54 | 57 | 77 | 288 |
| 579672 | 9 | 30 | 50 | 72 | 86 | 258 |

TABLE 12

| ISIS No | 62.5 nM | 125.0 nM | 250.0 nM | 500.0 nM | 1000.0 nM | $IC_{50}$ (nM) |
|---|---|---|---|---|---|---|
| 549458 | 19 | 22 | 45 | 38 | 71 | 470 |
| 569214 | 20 | 26 | 61 | 62 | 76 | 265 |
| 569217 | 34 | 39 | 49 | 64 | 64 | 247 |
| 569221 | 12 | 32 | 59 | 57 | 73 | 294 |

Example 8

Antisense Inhibition of Human AR in HuVEC Cells

Additional antisense oligonucleotides were designed targeting an AR nucleic acid and were tested for their effects on AR mRNA in vitro. Cultured HuVEC cells at a density of 20,000 cells per well were transfected using electroporation with 1,000 nM antisense oligonucleotide. After a treatment period of approximately 24 hours, RNA was isolated from the cells and AR mRNA levels were measured by quantitative real-time PCR. Human primer probe set RTS3559 was used to measure mRNA levels. AR mRNA levels were adjusted according to total RNA content, as measured by RIBOGREEN®. Results are presented as percent inhibition of AR, relative to untreated control cells. A total of 75 oligonucleotides were tested. Only those oligonucleotides which were selected for further study are shown in Table 13.

The newly designed chimeric antisense oligonucleotides in Table 13 were designed as 3-10-3 (S)-cET gapmers, 3-9-4 (S)-cEt gapmers, 4-8-4 (S)-cEt gapmers, 4-9-3 (S)-cEt gapmers, 5-7-4 (S)-cEt gapmers, 5-8-3 (S)-cEt gapmers, 6-7-3 (S)-cEt gapmers, or deoxy, MOE and (S)-cEt oligonucleotides. The 3-10-3 (S)-cEt gapmers are 16 nucleosides in length, wherein the central gap segment comprises of ten 2'-deoxynucleosides and is flanked by wing segments on both the 5' direction and on the 3' direction comprising three nucleosides. The 3-9-4 (S)-cEt gapmers are 16 nucleosides in length, wherein the central gap segment comprises of nine 2'-deoxynucleosides and is flanked by a wing segment on the 5' direction comprising three nucleotides and on the 3' direction comprising four nucleosides. The 4-8-4 (S)-cEt gapmers are 16 nucleosides in length, wherein the central gap segment comprises of eight 2'-deoxynucleosides and is flanked by wing segments on both the 5' direction and on the 3' direction comprising four nucleosides. The 4-9-3 (S)-cEt gapmers are 16 nucleosides in length, wherein the central gap segment comprises of nine 2'-deoxynucleosides and is flanked by a wing segment on the 5' direction comprising four nucleotides and on the 3' direction comprising three nucleosides. The 5-7-4 (S)-cEt gapmers are 16 nucleosides in length, wherein the central gap segment comprises of seven 2'-deoxynucleosides and is flanked by a wing segment on the 5' direction comprising five nucleotides and on the 3' direction comprising four nucleotides. The 5-8-3 (S)-cEt gapmers are 16 nucleosides in length, wherein the central gap segment comprises of eight 2'-deoxynucleosides and is flanked by a wing segment on the 5' direction comprising five nucleotides and on the 3' direction comprising three nucleosides. The 6-7-3 (S)-cEt gapmers are 16 nucleosides in length, wherein the central gap segment comprises of seven 2'-deoxynucleosides and is flanked by a wing segment on the 5' direction comprising six nucleotides and on the 3' direction comprising three nucleosides. Each nucleoside in the 5' wing segment and each nucleoside in the 3' wing segment has an (S)-cEt modification. The deoxy, MOE and (S)-cEt oligonucleotides are 16 nucleosides in length wherein the nucleoside have either a MOE sugar modification, an (S)-cEt sugar modification, or a deoxy modification. The 'Chemistry' column describes the sugar modifications of each oligonucleotide. 'k' indicates an (S)-cEt sugar modification; the number indicates the number of deoxynucleosides; otherwise 'd' indicates deoxyribose; and 'e' indicates a MOE modification. The internucleoside linkages throughout each gapmer are phosphorothioate linkages. All cytosine residues throughout each gapmer are 5-methylcytosines.

The SEQ ID NO listed in the table refers to the oligonucleotide sequence. "Start site" indicates the 5'-most nucleoside to which the gapmer is targeted in the human gene sequence. "Stop site" indicates the 3'-most nucleoside to which the gapmer is targeted human gene sequence. Each gapmer listed in Table 13 is targeted to the human AR genomic sequence, designated herein as SEQ ID NO: 1 (GENBANK Accession No. NT_011669.17 truncated from nucleotides 5079000 to 5270000).

TABLE 13

| Target Start Site | Target Stop Site | Sequence | ISIS No | Chemistry | % inhibition | SEQ ID NO |
|---|---|---|---|---|---|---|
| 5062 | 5077 | AAGTTGTAGTAGTCGC | 549372 | kkk-10-kkk | 64 | 22 |
| 5061 | 5076 | AGTTGTAGTAGTCGCG | 585233 | kkk-8-keeee | 69 | 42 |
| 5062 | 5077 | AAGTTGTAGTAGTCGC | 585259 | ekkk-9-kkk | 71 | 22 |
| 5062 | 5077 | AAGTTGTAGTAGTCGC | 585262 | kkk-9-kkke | 77 | 22 |
| 5062 | 5077 | AAGTTGTAGTAGTCGC | 585263 | kkk-8-kkkee | 69 | 22 |
| 5062 | 5077 | AAGTTGTAGTAGTCGC | 585264 | kkk-7-kkkeee | 62 | 22 |
| 5062 | 5077 | AAGTTGTAGTAGTCGC | 585265 | eekk-8-kkee | 69 | 22 |
| 5062 | 5077 | AAGTTGTAGTAGTCGC | 585268 | keke-8-ekek | 72 | 22 |
| 5062 | 5077 | AAGTTGTAGTAGTCGC | 585269 | ekek-8-ekek | 73 | 22 |
| 5062 | 5077 | AAGTTGTAGTAGTCGC | 585271 | ekk-10-kke | 57 | 22 |
| 5062 | 5077 | AAGTTGTAGTAGTCGC | 585274 | kkk-10-kke | 65 | 22 |
| 58719 | 58734 | GATTTAATGGTTGCAA | 586124 | kkk-10-kkk | 82 | 43 |
| 58720<br>58750 | 58735<br>58765 | TGATTTAATGGTTGCA | 569227 | eekkk-7-kkke | 51 | 39 |
| 58722<br>58752 | 58737<br>58767 | GTTGATTTAATGGTTG | 560132 | kkk-9-kkke | 58 | 36 |
| 58722<br>58752 | 58737<br>58767 | GTTGATTTAATGGTTG | 569229 | eekkk-7-kkke | 57 | 36 |
| 58722<br>58752 | 58737<br>58767 | GTTGATTTAATGGTTG | 569238 | ekkk-7-kkkee | 51 | 36 |
| 58722<br>58752 | 58737<br>58767 | GTTGATTTAATGGTTG | 549458 | kkk-10-kkk | 87 | 36 |
| 58722<br>58752 | 58737<br>58767 | GTTGATTTAATGGTTG | 569223 | eekkk-8-kkk | 59 | 36 |
| 58724<br>58754 | 58739<br>58769 | TGGTTGATTTAATGGT | 569215 | kkk-9-kkke | 59 | 41 |
| 58725<br>58755 | 58740<br>58770 | ATGGTTGATTTAATGG | 560133 | kkk-9-kkke | 53 | 37 |
| 58725<br>58755 | 58740<br>58770 | ATGGTTGATTTAATGG | 569220 | ekkk-8-kkke | 58 | 37 |
| 58721<br>58751 | 58736<br>58766 | TTGATTTAATGGTTGC | 586224 | kkkkk-8-kkk | 90 | 35 |
| 58722<br>58752 | 58737<br>58767 | GTTGATTTAATGGTTG | 586225 | kkkkk-8-kkk | 88 | 36 |
| 58720<br>58750 | 58735<br>58765 | TGATTTAATGGTTGCA | 586227 | kkkkk-8-kkk | 87 | 39 |

Example 9

Dose-Dependent Antisense Inhibition of Human AR in HuVEC Cells

Antisense oligonucleotides from the studies described above exhibiting significant in vitro inhibition of AR mRNA were selected and tested at various doses in HuVEC cells. Cells were plated at a density of 20,000 cells per well and transfected using electroporation with 31.25 nM, 62.5 nM, 125.0 nM, 250.0 nM, 500.0 nM, and 1000.0 nM concentrations of antisense oligonucleotide, as specified in Table 14. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells. The antisense oligonucleotides were tested in a series of experiments that had similar culture conditions. The results for each experiment are presented in separate tables shown below.

The half maximal inhibitory concentration ($IC_{50}$) of each oligonucleotide is also presented in Table 14. As illustrated, AR mRNA levels were reduced in a dose-dependent manner in the antisense oligonucleotide treated cells.

TABLE 14

| ISIS No | 31.25 nM | 62.5 nM | 125.0 nM | 250.0 nM | 500.0 nM | 1000.0 nM | $IC_{50}$ nM |
|---|---|---|---|---|---|---|---|
| 549372 | 2 | 17 | 31 | 51 | 61 | 80 | 271 |
| 549458 | 0 | 19 | 40 | 63 | 74 | 90 | 196 |
| 560132 | 8 | 19 | 21 | 53 | 65 | 85 | 252 |
| 560133 | 17 | 15 | 24 | 35 | 58 | 79 | 336 |
| 569215 | 12 | 2 | 26 | 55 | 71 | 90 | 234 |
| 569220 | 11 | 29 | 34 | 43 | 59 | 78 | 275 |
| 569223 | 21 | 20 | 30 | 59 | 73 | 87 | 191 |
| 569227 | 13 | 22 | 45 | 46 | 61 | 74 | 255 |
| 569229 | 16 | 14 | 36 | 47 | 74 | 84 | 220 |
| 569238 | 4 | 32 | 33 | 54 | 71 | 88 | 202 |

Example 10

Dose-Dependent Antisense Inhibition of Human AR in HuVEC Cells

Gapmers from Example 8 exhibiting significant in vitro inhibition of AR mRNA were selected and tested at various doses in HuVEC cells. Cells were plated at a density of 20,000 cells per well and transfected using electroporation with 46.9 nM, 187.5 nM, 750.0 nM, and 3000.0 nM concentrations of antisense oligonucleotide, as specified in Table 15. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells.

The half maximal inhibitory concentration ($IC_{50}$) of each oligonucleotide is also presented in Table 15. As illustrated, AR mRNA levels were reduced in a dose-dependent manner in antisense oligonucleotide treated cells.

TABLE 15

| ISIS No | 46.9 nM | 187.5 nM | 750.0 nM | 3000.0 nM | $IC_{50}$ (μM) |
|---|---|---|---|---|---|
| 549372 | 9 | 41 | 66 | 87 | 0.29 |
| 549458 | 15 | 50 | 85 | 96 | 0.19 |
| 586124 | 28 | 47 | 84 | 94 | 0.13 |
| 586224 | 39 | 75 | 93 | 98 | 0.05 |
| 586225 | 17 | 61 | 89 | 97 | 0.13 |
| 586227 | 20 | 60 | 88 | 96 | 0.13 |

Example 11

Antisense Inhibition of Human AR in HuVEC Cells

Additional antisense oligonucleotides were designed targeting an AR nucleic acid and were tested for their effects on AR mRNA in vitro. Cultured HuVEC cells at a density of 20,000 cells per well were transfected using electroporation with 500 nM antisense oligonucleotide. After a treatment period of approximately 24 hours, RNA was isolated from the cells and AR mRNA levels were measured by quantitative real-time PCR. Human primer probe set RTS3559 was used to measure mRNA levels. AR mRNA levels were adjusted according to total RNA content, as measured by RIBOGREEN®. Results are presented as percent inhibition of AR, relative to untreated control cells. A total of 616 oligonucleotides were tested. Only those oligonucleotides which were selected for further study are shown in Tables 16-23.

The newly designed chimeric antisense oligonucleotides in Tables 16-23 were designed as 3-10-3 (S)-cET gapmers. The gapmers are 16 nucleosides in length, wherein the central gap segment comprises of ten 2'-deoxynucleosides and is flanked by wing segments on both the 5' direction and on the 3' direction comprising three nucleosides. Each nucleoside in the 5' wing segment and each nucleoside in the 3' wing segment has an (S)-cEt modification. The internucleoside linkages throughout each gapmer are phosphorothioate linkages. All cytosine residues throughout each gapmer are 5-methylcytosines.

The SEQ ID NO listed in the table refers to the oligonucleotide sequence. "Start site" indicates the 5'-most nucleoside to which the gapmer is targeted in the human gene sequence. "Stop site" indicates the 3'-most nucleoside to which the gapmer is targeted human gene sequence. Each gapmer listed in Tables 16-23 is targeted to either the human AR genomic sequence, designated herein as SEQ ID NO: 1 (GENBANK Accession No. NT_011669.17 truncated from nucleotides 5079000 to 5270000) or the human AR mRNA sequence, designated herein as SEQ ID NO: 2 (GENBANK Accession No. NM_000044.3), or both. 'n/a.' indicates that the oligonucleotide does not target that particular gene sequence.

TABLE 16

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 47 | 22 |
| 58722<br>58752 | 58737<br>58767 | GTTGATTTAATGGTTG | 549458 | 60 | 36 |
| 2957 | 2972 | ACAGCACTGGAGCGGC | 583542 | 45 | 44 |
| 3079 | 3094 | AACTTCACCGAAGAGG | 583556 | 43 | 45 |
| 3099 | 3114 | AGTCTTTAGCAGCTTT | 583559 | 52 | 46 |
| 3109 | 3124 | GCTTCCTCCGAGTCTT | 583564 | 45 | 47 |
| 3113 | 3128 | CCTTGCTTCCTCCGAG | 583566 | 47 | 48 |
| 3120 | 3135 | GCACTTTCCTTGCTTC | 583567 | 52 | 49 |
| 3133 | 3148 | TCAGTCCTACCAGGCA | 583571 | 43 | 50 |
| 3224 | 3239 | GACTGAGGCAGCTGCG | 583583 | 45 | 51 |
| 3226 | 3241 | CCGACTGAGGCAGCTG | 583584 | 44 | 52 |

TABLE 17

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 40 | 22 |
| 58722<br>58752 | 58737<br>58767 | GTTGATTTAATGGTTG | 549458 | 46 | 36 |
| 3351 | 3366 | GCTAGCTCGCCCGCTC | 583608 | 51 | 53 |
| 3353 | 3368 | CAGCTAGCTCGCCCGC | 583609 | 51 | 54 |
| 3361 | 3376 | GCAATGTGCAGCTAGC | 583613 | 51 | 55 |
| 3388 | 3403 | GTCGCCTGGCTCCTAA | 583620 | 41 | 56 |
| 3513 | 3528 | CTGGCTCCGCACTCGG | 583635 | 50 | 57 |
| 3517 | 3532 | ATCTCTGGCTCCGCAC | 583637 | 43 | 58 |
| 3519 | 3534 | TGATCTCTGGCTCCGC | 583638 | 51 | 59 |
| 3641 | 3656 | AGTGTCCACTGAAGTA | 583642 | 42 | 60 |
| 3735 | 3750 | AGGCTCACAGTCTGTC | 583649 | 46 | 61 |
| 3764 | 3779 | GACACACGGTGGACAA | 583660 | 44 | 62 |
| 3768 | 3783 | AGAAGACACACGGTGG | 583662 | 51 | 63 |
| 3798 | 3813 | CGCTCTGACAGCCTCA | 583667 | 42 | 64 |

TABLE 18

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 26 | 22 |
| 58722<br>58752 | 58737<br>58767 | GTTGATTTAATGGTTG | 549458 | 48 | 36 |
| 3870 | 3885 | GTCGCTGCAGCTAGCT | 583685 | 47 | 65 |

TABLE 18-continued

| Target Start Site | Target Stop Site | Sequence | ISIS No | % inhibition | SEQ ID NO |
|---|---|---|---|---|---|
| 3874 | 3889 | GGTAGTCGCTGCAGCT | 583687 | 41 | 66 |
| 3876 | 3891 | GCGGTAGTCGCTGCAG | 583688 | 38 | 67 |
| 3878 | 3893 | ATGCGGTAGTCGCTGC | 583689 | 39 | 68 |
| 3884 | 3899 | GTGATGATGCGGTAGT | 583692 | 41 | 69 |
| 3886 | 3901 | CTGTGATGATGCGGTA | 583693 | 36 | 70 |
| 3901 | 3916 | GAAGAGTTCAACAGGC | 583700 | 36 | 71 |
| 3956 | 3971 | GCTTGGCTGAATCTTC | 583709 | 39 | 72 |
| 3962 | 3977 | CCTTGAGCTTGGCTGA | 583712 | 37 | 73 |
| 3964 | 3979 | ATCCTTGAGCTTGGCT | 583713 | 36 | 74 |
| 3967 | 3982 | TCCATCCTTGAGCTTG | 583714 | 36 | 75 |
| 4019 | 4034 | GTAGGTCTTGGACGGC | 583719 | 36 | 76 |
| 4038 | 4053 | GATTCTGGAAAGCTCC | 583727 | 40 | 77 |
| 4049 | 4064 | GCTCTGGAACAGATTC | 583728 | 45 | 78 |
| 4056 | 4071 | CGCGCACGCTCTGGAA | 583731 | 34 | 79 |
| 4062 | 4077 | TCACTTCGCGCACGCT | 583734 | 46 | 80 |
| 4066 | 4081 | TGGATCACTTCGCGCA | 583736 | 47 | 81 |
| 4070 | 4085 | GTTCTGGATCACTTCG | 583738 | 36 | 82 |
| 4101 | 4116 | CGCTCGCGGCCTCTGG | 583745 | 40 | 83 |
| 4103 | 4118 | TGCGCTCGCGGCCTCT | 583746 | 32 | 84 |
| 4105 | 4120 | GCTGCGCTCGCGGCCT | 583747 | 35 | 85 |

TABLE 19

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 39 | 22 |
| 58722<br>58752 | 58737<br>58767 | GTTGATTTAATGGTTG | 549458 | 50 | 36 |
| 4109 | 4124 | AGGTGCTGCGCTCGCG | 583749 | 36 | 86 |
| 4305 | 4320 | GCTGTTCCTCATCCAG | 583759 | 38 | 87 |
| 4405 | 4420 | TGCTGCGGCAGCCCCT | 583771 | 40 | 88 |
| 4532 | 4547 | GGTGCTGGCCTCGCTC | 583787 | 37 | 89 |
| 4537 | 4552 | TGCATGGTGCTGGCCT | 583789 | 39 | 90 |
| 4539 | 4554 | GTTGCATGGTGCTGGC | 583790 | 39 | 91 |
| 4555 | 4570 | TGCTGTTGCTGAAGGA | 583795 | 63 | 92 |
| 4571 | 4586 | GGATACTGCTTCCTGC | 583796 | 65 | 93 |
| 4573 | 4588 | TCGGATACTGCTTCCT | 583797 | 35 | 94 |
| 4578 | 4593 | TGCCTTCGGATACTGC | 583799 | 65 | 95 |
| 4597 | 4612 | CTCGCTCTCCCGCTGC | 583802 | 37 | 96 |

TABLE 19-continued

| Target Start Site | Target Stop Site | Sequence | ISIS No | % inhibition | SEQ ID NO |
|---|---|---|---|---|---|
| 4632 | 4647 | TGTCCTTGGAGGAAGT | 583809 | 45 | 97 |
| 4656 | 4671 | TGGTCGAAGTGCCCCC | 583818 | 42 | 98 |
| 4662 | 4677 | CAGAAATGGTCGAAGT | 583821 | 42 | 99 |

TABLE 20

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 23 | 22 |
| 58722<br>58752 | 58737<br>58767 | GTTGATTTAATGGTTG | 549458 | 54 | 36 |
| 4747 | 4762 | TGTTCCCCTGGACTCA | 583833 | 37 | 100 |
| 4750 | 4765 | AGCTGTTCCCCTGGAC | 583834 | 52 | 101 |
| 4752 | 4767 | GAAGCTGTTCCCCTGG | 583835 | 44 | 102 |
| 4754 | 4769 | CCGAAGCTGTTCCCCT | 583836 | 37 | 103 |
| 4769 | 4784 | GTACATGCAATCCCCC | 583843 | 35 | 104 |
| 4798 | 4813 | ACAGCGGGTGGAACTC | 583847 | 34 | 105 |
| 4804 | 4819 | GGACGCACAGCGGGTG | 583850 | 38 | 106 |
| 4807 | 4822 | GTGGGACGCACAGCGG | 583851 | 33 | 107 |
| 4833 | 4848 | TGCATTCGGCCAATGG | 583853 | 33 | 108 |
| 4837 | 4852 | CCTTTGCATTCGGCCA | 583855 | 44 | 109 |
| 4839 | 4854 | AACCTTTGCATTCGGC | 583856 | 45 | 110 |
| 4868 | 4883 | GCTCTTGCCTGCGCTG | 583862 | 32 | 111 |
| 4872 | 4887 | CAGTGCTCTTGCCTGC | 583864 | 46 | 112 |
| 4874 | 4889 | TTCAGTGCTCTTGCCT | 583865 | 45 | 113 |
| 4876 | 4891 | TCTTCAGTGCTCTTGC | 583866 | 32 | 114 |
| 4887 | 4902 | ACTCAGCAGTATCTTC | 583868 | 34 | 115 |
| 4889 | 4904 | ATACTCAGCAGTATCT | 583871 | 47 | 116 |
| 4916 | 4931 | TTTGGTGTAACCTCCC | 583880 | 39 | 117 |
| 4918 | 4933 | CCTTTGGTGTAACCTC | 583881 | 47 | 118 |
| 4938 | 4953 | CTAGGCTCTCGCCTTC | 583890 | 32 | 119 |
| 4942 | 4957 | CAGCCTAGGCTCTCGC | 583892 | 35 | 120 |
| 4944 | 4959 | AGCAGCCTAGGCTCTC | 583893 | 34 | 121 |
| 4951 | 4966 | CTGCCAGAGCAGCCTA | 583896 | 37 | 122 |

TABLE 21

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 37 | 22 |
| 58722<br>58752 | 58737<br>58767 | GTTGATTTAATGGTTG | 549458 | 47 | 36 |
| 5050 | 5065 | TCGCGACTCTGGTACG | 583917 | 37 | 123 |
| 5052 | 5067 | AGTCGCGACTCTGGTA | 583918 | 47 | 124 |
| 5054 | 5069 | GTAGTCGCGACTCTGG | 583919 | 55 | 125 |
| 5056 | 5071 | TAGTAGTCGCGACTCT | 583920 | 42 | 126 |
| 5061 | 5076 | AGTTGTAGTAGTCGCG | 583922 | 37 | 42 |
| 5133 | 5148 | TCTCCAGCTTGATGCG | 583932 | 39 | 127 |
| 5141 | 5156 | CAGCGGGTTCTCCAGC | 583933 | 38 | 128 |
| 5293 | 5308 | CCTTCTTCGGCTGTGA | 583969 | 44 | 129 |
| 5308 | 5323 | GGTCCATACAACTGGC | 583975 | 42 | 130 |

TABLE 22

| Target Start Site on SEQ ID NO: 1 | Target Start Site on SEQ ID NO: 2 | Sequence | ISIS No | % inhibition | SEQ ID NO |
|---|---|---|---|---|---|
| 5062 | 2200 | AAGTTGTAGTAGTCGC | 549372 | 46 | 22 |
| 58722<br>58752 | n/a<br>n/a | GTTGATTTAATGGTTG | 549458 | 39 | 36 |
| 5469 | 2607 | ACACATCAGGTGCGGT | 583990 | 30 | 131 |
| 5481 | 2619 | CGCCAGGGTACCACAC | 583996 | 33 | 132 |
| 5486 | 2624 | CATGCCGCCAGGGTAC | 583998 | 45 | 133 |
| 5488 | 2626 | ACCATGCCGCCAGGGT | 583999 | 29 | 134 |
| 5494 | 2632 | CTGCTCACCATGCCGC | 584002 | 30 | 135 |
| 5521 | 2659 | ACACAAGTGGGACTGG | 584006 | 33 | 136 |
| n/a | 2870 | CCCTTCAGCGGCTCTT | 584044 | 29 | 137 |

TABLE 23

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 25 | 22 |
| 58722<br>58752 | 58737<br>58767 | GTTGATTTAATGGTTG | 549458 | 51 | 36 |
| 144938 | 144953 | CAGAGTCATCCCTGCT | 584069 | 36 | 138 |
| 148406 | 148421 | CACCCTCAAGATTCTT | 584100 | 36 | 139 |
| 148443 | 148458 | AAGGTAGTCTTTAAGG | 584106 | 30 | 140 |
| 148520 | 148535 | GTTTTCAAATGCAGCC | 584111 | 33 | 141 |
| 139682 | 139697 | GCCATGAGACAGCTTT | 584125 | 35 | 142 |

TABLE 23-continued

| Target Start Site | Target Stop Site | Sequence | ISIS No | % inhibition | SEQ ID NO |
|---|---|---|---|---|---|
| 139762 | 139777 | ATTCTTGACTGTCTGA | 584128 | 38 | 143 |
| 139782 | 139797 | GCATGCCAGCTGGCTC | 584130 | 29 | 144 |
| 5666 | 5681 | CGCGCAGGTAGGAGCC | 584138 | 35 | 145 |
| 6222 | 6237 | TCTAAACATGACGGTT | 584139 | 37 | 146 |
| 6701 | 6716 | ATGCAATTGCCTGCCA | 584141 | 39 | 147 |

Example 12

Antisense Inhibition of Human AR in HuVEC Cells

Additional antisense oligonucleotides were designed targeting an AR nucleic acid and were tested for their effects on AR mRNA in vitro. Cultured HuVEC cells at a density of 20,000 cells per well were transfected using electroporation with 1,000 nM antisense oligonucleotide. After a treatment period of approximately 24 hours, RNA was isolated from the cells and AR mRNA levels were measured by quantitative real-time PCR. Human primer probe set RTS3559 was used to measure mRNA levels. AR mRNA levels were adjusted according to total RNA content, as measured by RIBOGREEN®. Results are presented as percent inhibition of AR, relative to untreated control cells. A total of 385 oligonucleotides were tested. Only those oligonucleotides which were selected for further study are shown in Tables 24-28.

The newly designed chimeric antisense oligonucleotides in Tables 24-28 were designed as 3-10-3 (S)-cET gapmers. The gapmers are 16 nucleosides in length, wherein the central gap segment comprises of ten 2'-deoxynucleosides and is flanked by wing segments on both the 5' direction and on the 3' direction comprising three nucleosides. Each nucleoside in the 5' wing segment and each nucleoside in the 3' wing segment has an (S)-cEt modification. The internucleoside linkages throughout each gapmer are phosphorothioate linkages. All cytosine residues throughout each gapmer are 5-methylcytosines.

The SEQ ID NO listed in the table refers to the oligonucleotide sequence. "Start site" indicates the 5'-most nucleoside to which the gapmer is targeted in the human gene sequence. "Stop site" indicates the 3'-most nucleoside to which the gapmer is targeted human gene sequence. Each gapmer listed in Tables 24-28 is targeted to the human AR genomic sequence, designated herein as SEQ ID NO: 1 (GENBANK Accession No. NT_011669.17 truncated from nucleotides 5079000 to 5270000)

TABLE 24

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 63 | 22 |
| 58722<br>58752 | 58737<br>58767 | GTTGATTTAATGGTTG | 549458 | 88 | 36 |
| 7543 | 7558 | ATGGGAGTAACTTTTG | 584145 | 76 | 148 |
| 8471 | 8486 | CATATTATTGTGCTGC | 584148 | 85 | 149 |
| 8638 | 8653 | GTCAATATCAAAGCAC | 584149 | 85 | 150 |
| 9464 | 9479 | GAGTTGTGATTTCAGG | 584152 | 88 | 151 |
| 10217 | 10232 | TTGATGGAATGCTGAT | 584157 | 69 | 152 |
| 10250 | 10265 | GGTTAACTTTCTCTGA | 584158 | 69 | 153 |
| 10865 | 10880 | TGGATTGTAAATTACG | 584162 | 82 | 154 |
| 11197 | 11212 | GAACATTATTAGGCTA | 584163 | 81 | 155 |
| 11855 | 11870 | TCAATCTAGATACCAT | 584165 | 70 | 156 |
| 13189 | 13204 | CACATCAGAAGGAGTA | 584166 | 89 | 157 |
| 13321 | 13336 | GAGTGTTAATGAAGAC | 584167 | 78 | 158 |
| 13346 | 13361 | CTGATTAGCTATGACC | 584168 | 70 | 159 |
| 16555 | 16570 | ATGAGTCCTCAGAATC | 584179 | 74 | 160 |
| 16793 | 16808 | GTAGATTCTAGCTTTG | 584180 | 81 | 161 |

TABLE 24-continued

| Target Start Site | Target Stop Site | Sequence | ISIS No | % inhibition | SEQ ID NO |
|---|---|---|---|---|---|
| 16968 | 16983 | ACAGGCTCTGACTAGG | 584183 | 76 | 162 |
| 17206 | 17221 | TGTGTGACCCTTGGAC | 584184 | 78 | 163 |
| 18865 | 18880 | AAGTATGAGCATGGTT | 584192 | 73 | 164 |

TABLE 25

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 59 | 22 |
| 58722<br>58752 | 58737<br>58767 | GTTGATTTAATGGTTG | 549458 | 76 | 36 |
| 29329 | 29344 | GGATTCTCTACACACA | 584233 | 62 | 165 |
| 32290 | 32305 | CCATTTGTGCCAAACC | 584242 | 62 | 166 |
| 33315 | 33330 | AGGTTAGGGAGTAGGC | 584245 | 70 | 167 |
| 39055 | 39070 | TAGGGTTTGGTCAGAA | 584263 | 56 | 168 |
| 40615 | 40630 | CCTTATGGATGCTGCT | 584269 | 57 | 169 |
| 42017 | 42032 | GTTATCTTACTCTCCC | 584274 | 70 | 170 |

TABLE 26

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 58 | 22 |
| 58722<br>58752 | 58737<br>58767 | GTTGATTTAATGGTTG | 549458 | 79 | 36 |
| 56050 | 56065 | GATTGTGTATAGCTGC | 584312 | 65 | 171 |
| 60902 | 60917 | GGTTATGGTTCTGTCT | 584329 | 58 | 172 |
| 67454 | 67469 | CTTCATTGCAGGTCTG | 584361 | 61 | 173 |

TABLE 27

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 70 | 22 |
| 58722<br>58752 | 58737<br>58767 | GTTGATTTAATGGTTG | 549458 | 76 | 36 |
| 114874 | 114889 | TAGCCAACTTTCTTTA | 584465 | 58 | 174 |
| 115272 | 115287 | CATTGTACTATGCCAG | 584468 | 64 | 175 |
| 115365 | 115380 | TTTGGTAACATTAGGC | 584469 | 74 | 176 |
| 134971 | 134986 | ATGGTTGTCCTGTACA | 584495 | 58 | 177 |

TABLE 28

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 54 | 22 |
| 58722<br>58752 | 58737<br>58767 | GTTGATTTAATGGTTG | 549458 | 65 | 36 |
| 114874 | 114889 | TAGCCAACTTTCTTTA | 584465 | 54 | 174 |
| 115365 | 115380 | TTTGGTAACATTAGGC | 584469 | 63 | 176 |
| 134971 | 134986 | ATGGTTGTCCTGTACA | 584495 | 53 | 177 |

Example 13

Dose-Dependent Antisense Inhibition of Human AR in HuVEC Cells

Gapmers from the studies described above exhibiting significant in vitro inhibition of AR mRNA were selected and tested at various doses in HuVEC cells. Cells were plated at a density of 20,000 cells per well and transfected using electroporation with 46.9 nM, 187.5 nM, 750.0 nM, and 3000.0 nM concentrations of antisense oligonucleotide, as specified in Tables 29-37. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells.

The half maximal inhibitory concentration ($IC_{50}$) of each oligonucleotide is also presented in Tables 29-37. As illustrated, AR mRNA levels were reduced in a dose-dependent manner in some of the antisense oligonucleotide treated cells.

TABLE 29

| ISIS No | 46.9 nM | 187.5 nM | 750.0 nM | 3000.0 nM | $IC_{50}$ (μM) |
|---|---|---|---|---|---|
| 549372 | 7 | 41 | 70 | 91 | 0.32 |
| 549458 | 21 | 72 | 91 | 97 | 0.11 |
| 583542 | 9 | 28 | 47 | 66 | 0.90 |
| 583556 | 19 | 47 | 68 | 66 | 0.34 |
| 583559 | 30 | 49 | 63 | 80 | 0.22 |
| 583564 | 16 | 33 | 55 | 74 | 0.52 |
| 583566 | 0 | 28 | 50 | 74 | 0.73 |
| 583567 | 17 | 34 | 60 | 79 | 0.43 |
| 583571 | 18 | 36 | 53 | 59 | 0.80 |
| 583583 | 21 | 31 | 49 | 64 | 0.79 |
| 583584 | 24 | 44 | 52 | 73 | 0.41 |
| 583608 | 12 | 46 | 67 | 76 | 0.35 |
| 583609 | 16 | 48 | 63 | 73 | 0.36 |
| 583613 | 24 | 60 | 70 | 75 | 0.19 |
| 583635 | 35 | 56 | 69 | 78 | 0.13 |
| 583638 | 33 | 64 | 79 | 85 | 0.11 |
| 583649 | 28 | 50 | 68 | 84 | 0.20 |
| 583660 | 21 | 39 | 61 | 72 | 0.42 |
| 583662 | 27 | 59 | 75 | 75 | 0.15 |

TABLE 30

| ISIS No | 46.9 nM | 187.5 nM | 750.0 nM | 3000.0 nM | $IC_{50}$ (μM) |
|---|---|---|---|---|---|
| 549372 | 13 | 29 | 69 | 90 | 0.37 |
| 549458 | 22 | 62 | 92 | 97 | 0.13 |
| 583620 | 0 | 17 | 44 | 54 | 1.85 |
| 583637 | 22 | 32 | 59 | 75 | 0.45 |
| 583642 | 18 | 35 | 67 | 74 | 0.46 |
| 583667 | 35 | 55 | 73 | 82 | 0.14 |
| 583685 | 32 | 53 | 73 | 81 | 0.16 |
| 583687 | 34 | 67 | 83 | 81 | 0.08 |
| 583688 | 3 | 26 | 50 | 60 | 1.05 |
| 583689 | 20 | 34 | 62 | 74 | 0.44 |
| 583692 | 8 | 47 | 61 | 71 | 0.44 |
| 583709 | 8 | 50 | 70 | 84 | 0.29 |
| 583712 | 15 | 47 | 72 | 78 | 0.29 |
| 583727 | 18 | 49 | 70 | 76 | 0.29 |
| 583728 | 9 | 48 | 67 | 70 | 0.40 |
| 583734 | 29 | 60 | 74 | 75 | 0.12 |
| 583736 | 21 | 38 | 60 | 63 | 0.51 |
| 583738 | 16 | 40 | 56 | 71 | 0.51 |
| 583745 | 19 | 51 | 68 | 77 | 0.27 |

TABLE 31

| ISIS No | 46.9 nM | 187.5 nM | 750.0 nM | 3000.0 nM | $IC_{50}$ (μM) |
|---|---|---|---|---|---|
| 549372 | 5 | 36 | 69 | 88 | 0.36 |
| 549458 | 24 | 59 | 92 | 98 | 0.13 |
| 583693 | 12 | 39 | 64 | 80 | 0.38 |
| 583700 | 14 | 34 | 57 | 71 | 0.55 |
| 583713 | 29 | 51 | 67 | 74 | 0.22 |
| 583714 | 22 | 34 | 59 | 79 | 0.40 |
| 583719 | 22 | 46 | 65 | 72 | 0.32 |
| 583731 | 18 | 24 | 47 | 58 | 1.31 |
| 583746 | 24 | 44 | 65 | 67 | 0.35 |
| 583747 | 13 | 38 | 50 | 69 | 0.64 |
| 583771 | 17 | 27 | 47 | 69 | 0.77 |
| 583789 | 30 | 49 | 71 | 85 | 0.19 |
| 583790 | 17 | 42 | 65 | 81 | 0.32 |
| 583795 | 37 | 61 | 83 | 90 | 0.09 |
| 583796 | 38 | 69 | 83 | 90 | 0.07 |
| 583799 | 29 | 60 | 76 | 85 | 0.14 |
| 583809 | 13 | 37 | 68 | 81 | 0.36 |
| 583818 | 9 | 46 | 71 | 84 | 0.31 |
| 583821 | 11 | 35 | 61 | 77 | 0.46 |

TABLE 32

| ISIS No | 46.9 nM | 187.5 nM | 750.0 nM | 3000.0 nM | $IC_{50}$ (μM) |
|---|---|---|---|---|---|
| 549372 | 15 | 39 | 70 | 86 | 0.30 |
| 549458 | 19 | 58 | 89 | 96 | 0.15 |
| 583749 | 34 | 40 | 75 | 87 | 0.17 |

TABLE 32-continued

| ISIS No | 46.9 nM | 187.5 nM | 750.0 nM | 3000.0 nM | $IC_{50}$ (μM) |
|---|---|---|---|---|---|
| 583759 | 5 | 28 | 61 | 67 | 0.63 |
| 583787 | 15 | 31 | 66 | 74 | 0.43 |
| 583797 | 21 | 50 | 74 | 82 | 0.22 |
| 583802 | 17 | 25 | 47 | 60 | 1.07 |
| 583834 | 34 | 54 | 73 | 84 | 0.13 |
| 583835 | 20 | 55 | 74 | 88 | 0.19 |
| 583836 | 11 | 27 | 67 | 86 | 0.39 |
| 583850 | 9 | 21 | 54 | 78 | 0.60 |
| 583855 | 22 | 50 | 81 | 91 | 0.18 |
| 583856 | 31 | 55 | 74 | 89 | 0.14 |
| 583864 | 30 | 49 | 72 | 85 | 0.17 |
| 583864 | 0 | 47 | 62 | 85 | 0.37 |
| 583865 | 33 | 42 | 68 | 85 | 0.19 |
| 583871 | 28 | 30 | 68 | 87 | 0.28 |
| 583880 | 13 | 52 | 78 | 92 | 0.22 |
| 583881 | 28 | 50 | 85 | 91 | 0.15 |

TABLE 33

| ISIS No | 46.9 nM | 187.5 nM | 750.0 nM | 3000.0 nM | $IC_{50}$ (μM) |
|---|---|---|---|---|---|
| 549372 | 14 | 33 | 64 | 90 | 0.34 |
| 549458 | 21 | 61 | 90 | 96 | 0.13 |
| 583833 | 26 | 43 | 70 | 74 | 0.26 |
| 583843 | 22 | 40 | 67 | 85 | 0.30 |
| 583847 | 8 | 30 | 60 | 84 | 0.46 |
| 583851 | 8 | 24 | 54 | 76 | 0.61 |
| 583853 | 24 | 51 | 70 | 80 | 0.21 |
| 583862 | 15 | 37 | 64 | 79 | 0.41 |
| 583866 | 17 | 48 | 71 | 91 | 0.24 |
| 583868 | 19 | 31 | 59 | 81 | 0.41 |
| 583890 | 0 | 0 | 17 | 33 | >30 |
| 583892 | 22 | 38 | 68 | 83 | 0.27 |
| 583893 | 15 | 35 | 62 | 79 | 0.42 |
| 583896 | 13 | 17 | 49 | 69 | 0.86 |
| 583918 | 16 | 47 | 68 | 86 | 0.30 |
| 583919 | 27 | 60 | 85 | 91 | 0.14 |
| 583920 | 11 | 16 | 50 | 72 | 0.76 |
| 583969 | 12 | 26 | 66 | 86 | 0.44 |
| 583975 | 19 | 49 | 55 | 88 | 0.36 |

TABLE 34

| ISIS No | 46.9 nM | 187.5 nM | 750.0 nM | 3000.0 nM | $IC_{50}$ (μM) |
|---|---|---|---|---|---|
| 549372 | 14 | 36 | 64 | 88 | 0.32 |
| 549458 | 14 | 53 | 84 | 95 | 0.18 |
| 583917 | 6 | 30 | 50 | 70 | 0.64 |
| 583922 | 16 | 43 | 76 | 92 | 0.23 |
| 583932 | 9 | 35 | 64 | 81 | 0.38 |
| 583933 | 22 | 25 | 56 | 81 | 0.41 |
| 583990 | 0 | 9 | 33 | 56 | 1.92 |
| 583996 | 26 | 12 | 50 | 70 | 0.71 |
| 583998 | 4 | 25 | 38 | 70 | 0.89 |
| 583999 | 13 | 12 | 30 | 64 | 1.53 |
| 584002 | 12 | 46 | 70 | 92 | 0.25 |
| 584006 | 21 | 26 | 59 | 88 | 0.35 |
| 584044 | 23 | 30 | 51 | 78 | 0.44 |
| 584069 | 18 | 40 | 63 | 82 | 0.30 |
| 584100 | 6 | 5 | 20 | 44 | 7.79 |
| 584125 | 12 | 12 | 47 | 76 | 0.72 |
| 584128 | 20 | 22 | 41 | 72 | 0.74 |
| 584139 | 13 | 33 | 56 | 85 | 0.4 |
| 584141 | 22 | 37 | 61 | 85 | 0.29 |

TABLE 35

| ISIS No | 46.9 nM | 187.5 nM | 750.0 nM | 3000.0 nM | $IC_{50}$ (μM) |
|---|---|---|---|---|---|
| 549372 | 0 | 28 | 64 | 88 | 0.42 |
| 549458 | 13 | 49 | 84 | 91 | 0.19 |
| 584106 | 3 | 13 | 12 | 32 | >30 |
| 584111 | 22 | 30 | 59 | 84 | 0.33 |
| 584130 | 0 | 10 | 11 | 37 | >30 |
| 584138 | 2 | 40 | 62 | 89 | 0.37 |
| 584145 | 6 | 32 | 63 | 88 | 0.36 |
| 584148 | 16 | 48 | 79 | 95 | 0.20 |
| 584149 | 11 | 37 | 68 | 89 | 0.31 |
| 584152 | 28 | 59 | 87 | 95 | 0.11 |
| 584162 | 24 | 45 | 80 | 92 | 0.18 |
| 584163 | 19 | 37 | 74 | 90 | 0.25 |
| 584166 | 34 | 52 | 84 | 92 | 0.10 |
| 584167 | 13 | 45 | 76 | 93 | 0.21 |
| 584179 | 1 | 25 | 62 | 87 | 0.44 |
| 584180 | 26 | 56 | 84 | 96 | 0.12 |
| 584183 | 3 | 41 | 64 | 87 | 0.31 |
| 584184 | 9 | 42 | 76 | 93 | 0.23 |
| 584192 | 1 | 34 | 73 | 95 | 0.30 |

TABLE 36

| ISIS No | 46.9 nM | 187.5 nM | 750.0 nM | 3000.0 nM | $IC_{50}$ (μM) |
|---|---|---|---|---|---|
| 549372 | 2 | 26 | 61 | 85 | 0.42 |
| 549458 | 1 | 51 | 83 | 96 | 0.23 |
| 584157 | 6 | 6 | 52 | 82 | 0.59 |
| 584158 | 14 | 37 | 70 | 89 | 0.26 |
| 584165 | 12 | 34 | 66 | 89 | 0.30 |
| 584168 | 5 | 32 | 70 | 91 | 0.32 |
| 584233 | 0 | 30 | 66 | 86 | 0.39 |
| 584242 | 12 | 38 | 66 | 93 | 0.27 |
| 584245 | 4 | 33 | 69 | 90 | 0.32 |
| 584263 | 9 | 24 | 67 | 90 | 0.34 |
| 584269 | 6 | 26 | 69 | 92 | 0.34 |
| 584274 | 17 | 36 | 74 | 93 | 0.23 |
| 584312 | 17 | 37 | 65 | 93 | 0.26 |
| 584329 | 0 | 17 | 67 | 86 | 0.46 |
| 584361 | 0 | 18 | 71 | 87 | 0.41 |
| 584465 | 0 | 0 | 32 | 51 | 2.5 |
| 584468 | 9 | 26 | 60 | 90 | 0.37 |
| 584469 | 13 | 46 | 73 | 89 | 0.22 |
| 584495 | 0 | 14 | 55 | 74 | 0.65 |

TABLE 37

| ISIS No | 46.9 nM | 187.5 nM | 750.0 nM | 3000.0 nM | $IC_{50}$ (μM) |
|---|---|---|---|---|---|
| 549372 | 9 | 41 | 66 | 87 | 0.29 |
| 549458 | 15 | 50 | 85 | 96 | 0.19 |
| 586124 | 28 | 47 | 84 | 94 | 0.13 |
| 586195 | 41 | 62 | 90 | 95 | 0.07 |
| 586197 | 27 | 47 | 77 | 94 | 0.14 |
| 586198 | 39 | 62 | 89 | 96 | 0.07 |
| 586199 | 25 | 56 | 89 | 97 | 0.13 |
| 586200 | 23 | 44 | 85 | 95 | 0.15 |
| 586205 | 34 | 67 | 89 | 95 | 0.07 |
| 586207 | 0 | 39 | 79 | 93 | 0.3 |
| 586208 | 32 | 70 | 88 | 93 | 0.08 |
| 586212 | 20 | 60 | 86 | 94 | 0.13 |
| 586221 | 39 | 72 | 94 | 98 | 0.04 |
| 586224 | 39 | 75 | 93 | 98 | 0.05 |
| 586225 | 17 | 61 | 89 | 97 | 0.13 |
| 586227 | 20 | 60 | 88 | 96 | 0.13 |
| 586232 | 24 | 45 | 82 | 91 | 0.17 |
| 586240 | 14 | 49 | 83 | 93 | 0.18 |
| 586570 | 16 | 44 | 81 | 91 | 0.21 |

Example 14

Selection of Antisense Oligonucleotides Targeting Human Androgen Receptor (AR) mRNA for Assays with Prostate Cancer Cell Lines Antisense oligonucleotides from those presented in the studies above, targeting different regions of the human AR genomic sequence, were selected for further studies in prostate cancer cell lines. AR-V7 and AR-V567es are major AR splice variants detected in cancer patients as described in Hornberg, E. et al., PLoS One 2011. Vol. 6.

The following ISIS oligonucleotides were selected for further studies: ISIS 549372, which targets the human AR genomic sequence at exon 1; ISIS 549434, which targets the human AR genomic sequence at the 3'-end of exon 8 beyond the stop codon of AR; ISIS 560131, which targets the human AR genomic sequence at intron 1; and ISIS 569236, which targets the human AR genomic sequence at intron 1. Another antisense oligonucleotide, ISIS 554221 (ACCAAGTTTCTTCAGC, designated herein as SEQ ID NO: 178), was designed as a 3-10-3 LNA gapmer with phosphorothioate backbone targeted to exon 4, (i.e. the ligand binding domain) of AR identical to an antisense oligonucleotide designated as SEQ ID NO: 58 of U.S. Pat. No. 7,737,125 for use as a benchmark.

Example 15

Effect of Antisense Inhibition of Human Androgen Receptor (AR) mRNA on Androgen Receptor Protein Levels in MDV3100-Resistant C4-2B Cells C4-2B cells are androgen-independent human prostate adenocarcinoma cells commonly used in the field of oncology and have been established as clinically relevant cultured cells (Thalmann, G. N. et al., Cancer Res. 1994. 54: 2577). MDV3100 or Enzalutamide is an experimental androgen receptor antagonist drug developed by Medivation for the treatment of castration-resistant prostate cancer. ISIS 549372, ISIS 554221, and ISIS 549434 were tested in MDV3100-resistant (MR) C4-2B cells.

The cells were cultured in the presence of 5 μM concentration of MDV3100 over the course of 2 months to induce MDV3100 resistance. ISIS 549372, ISIS 549434, and ISIS 554221 at 1 μM concentration of antisense oligonucleotide were each added to the culture media at 1 μM concentration for free uptake by the cells. After a treatment period of 2 days, cells were harvested in RIPA buffer containing protease inhibitors. The presence of bands for full-length AR, as well as the variant form, AR-V7, was detected by western blot using AR antibody (N-20, Santa Cruz). Treatment of the cells with ISIS 549372 reduced full-length AR and AR-V7 more extensively than treatment with either ISIS 554221 or ISIS 549434.

Example 16

Effect of Antisense Inhibition of Human Androgen Receptor (AR) mRNA on AR-Target Genes in MDV3100-Resistant C4-2B Cells The effect of antisense inhibition of AR on AR target genes was analyzed. ISIS 549372, ISIS 549458, ISIS 554221, and ISIS 549434 were tested in C4-2B MR cells.

Cells were plated at a density of 40,000 cells per well in 96-well plates and cultured in RPMI1640 medium with 10% fetal bovine serum. The cells were cultured in the presence of 5 μM concentration of MDV3100 over the course of 2 months to induce MDV3100 resistance. ISIS 549372, ISIS 549458, ISIS 549434, and ISIS 554221 were each added at 0.04 μM, 0.20 μM, 1.00 μM, and 5.00 μM concentrations of antisense oligonucleotide to culture media for free uptake by the cells. A control oligonucleotide, ISIS 347526 (sequence TCTTATGTTTCCGAACCGTT (SEQ ID NO: 179) 5-10-5 MOE gapmer) with no known target region in human gene sequences, was included as a negative control. After a treatment period of 24 hrs, total AR mRNA levels were measured by quantitative real-time PCR using primer probe set RTS3559. Human AR primer probe set hAR_LTS00943 (forward sequence GCCCCTGGATGGATAGCTACT, designated herein as SEQ ID NO: 180; reverse sequence CCACAGATCAGGCAGGTCTTC, designated herein as SEQ ID NO: 181; probe sequence ACTGCCAGGGACCATGTTTTGCCC, designated herein as SEQ ID NO: 182) was used to measure AR-V7 mRNA levels. AR mRNA levels were adjusted to human actin mRNA levels. Results are presented in Table 38 as percent inhibition of total AR, relative to untreated control cells. Treatment of the cells with ISIS 549372, ISIS 549458, and ISIS 549434 reduced total AR transcript levels in a dose dependent manner more extensively than treatment with ISIS 554221.

Western analysis of full-length AR, as well as the AR-V7 variant, was also conducted in a manner similar to the assay described above. The assay demonstrated that treatment with ISIS 549372 and ISSI 549458 reduced levels of full-length AR and AR-V7. Treatment with ISIS 549434 reduced levels of full-length AR but not that of AR-V7. Treatment with ISIS 554221 reduced levels of full-length AR less extensively compared to ISIS 549372, and did not reduce levels of AR-V7. The control oligonucleotide ISIS 347526 did not reduce protein levels, as expected.

The mRNA level of the AR target gene, KLK2 was measured using the primer probe set hKLK2_LTS00963 (forward sequence CTTGCGCCCCAGGAGTCT, designated herein as SEQ ID NO: 183; reverse sequence CTCAGAGTAAGCTCTAGCACACATGTC, designated herein as SEQ ID NO: 184; probe sequence AGTGTGTGAGCCTCCATCTCCTGTCCAA, designated herein as SEQ ID NO: 185). The mRNA level of the AR target gene, KLK3 was measured using the primer probe set RTS1072 (forward sequence GCCAAGGAGGGAGGGTCTT, designated herein as SEQ ID NO: 186; reverse sequence CCCCCCATAGTGAATCAGCTT, designated herein as SEQ ID NO: 187; probe sequence ATGAAGTAAGGAGAGGGACTGGACCCCC, designated herein as SEQ ID NO: 188). As presented in Tables 39 and 40, treatment with I ISIS 549372, ISIS 549458, and ISIS 549434 reduced target gene levels in a dose dependent manner more extensively than treatment with ISIS 554221.

TABLE 38

Percent inhibition of full-length AR mRNA in C4-2B MR cells

| ISIS No | 0.04 μM | 0.20 μM | 1.00 μM | 5.00 μM |
|---|---|---|---|---|
| 549372 | 35 | 47 | 88 | 91 |
| 549434 | 9 | 36 | 66 | 88 |
| 549458 | 41 | 78 | 94 | 97 |
| 554221 | 0 | 0 | 0 | 23 |
| 347526 | 28 | 35 | 31 | 17 |

TABLE 39

| Percent inhibition of KLK3 mRNA in C4-2B MR cells | | | | |
|---|---|---|---|---|
| ISIS No | 0.04 μM | 0.20 μM | 1.00 μM | 5.00 μM |
| 549372 | 17 | 35 | 68 | 80 |
| 549434 | 10 | 47 | 42 | 64 |
| 549458 | 0 | 42 | 81 | 92 |
| 554221 | 0 | 0 | 47 | 56 |
| 347526 | 5 | 38 | 42 | 16 |

TABLE 40

| Percent inhibition of KLK2 mRNA in C4-2B MR cells | | | | |
|---|---|---|---|---|
| ISIS No | 0.04 μM | 0.20 μM | 1.00 μM | 5.00 μM |
| 549372 | 14 | 16 | 57 | 87 |
| 549434 | 5 | 27 | 49 | 68 |
| 549458 | 35 | 47 | 87 | 93 |
| 554221 | 24 | 25 | 56 | 66 |
| 347526 | 28 | 29 | 23 | 22 |

Example 17

Effect of Antisense Inhibition of Human Androgen Receptor (AR) mRNA on the Proliferative Ability of MDV3100-Resistant C4-2B Cells The effect of antisense inhibition of AR on the proliferative ability of cancer cells was analyzed. ISIS 549372, ISIS 549458, ISIS 554221, and ISIS 549434 were tested in C4-2B MR cells.

ISIS 549372, ISIS 549434, ISIS 549458, and ISIS 554221 were each added to the culture media at 0.04 μM, 0.20 μM, 1.00 μM, and 5.00 μM concentration of antisense oligonucleotide. ISIS 347526 was included as a negative control. After a treatment period of 6 days, the proliferative capacity of the cancer cells was measured with using CellTiter 96® AQueous One Solution Cell Proliferation kit (Promega), following the manufacturer's instructions. Results are presented in Table 41 as percent inhibition of proliferation, relative to non-treated cells. Treatment of the cells with ISIS 549372, ISIS 549434, and ISIS 549458 reduced proliferation of the cells in a dose dependent manner more extensively than treatment with ISIS 554221.

TABLE 41

| Percent inhibition of C4-2B MR cell proliferation | | | | |
|---|---|---|---|---|
| ISIS No | 0.04 μM | 0.20 μM | 1.00 μM | 5.00 μM |
| 549372 | 0 | 4 | 25 | 43 |
| 549434 | 0 | 0 | 21 | 22 |
| 549458 | 8 | 16 | 41 | 56 |
| 554221 | 11 | 12 | 0 | 24 |
| 347526 | 11 | 22 | 7 | 16 |

Example 18

Effect of Antisense Inhibition of Human Androgen Receptor (AR) mRNA on MDV3100-Resistant LMR20 Cells An MDV3100-resistant cell line, designated as LMR20, was created. The effect of antisense inhibition of AR on the proliferative ability and AR mRNA levels of LMR20 cells was analyzed. ISIS 560131, ISIS 549458, and ISIS 569236 were tested along with the LNA gapmer, ISIS 554221.

LnCaP cells were incubated with increasing concentrations of MDV3100 for approximately 6 months. A single clone was selected after extensive culturing in the presence of 20 μM MDV3100. The clone, LMR20, maintained the ability to allow free uptake of antisense oligonucleotides without lipid-mediated transfection, while demonstrating an approximately ten-fold increase in $IC_{50}$ when treated with MDV3100, compared to parental LnCaP cells.

Study 1

LMR20 cells were plated at 1,500 cells per well in phenol red-free medium with charcoal-stripped fetal bovine serum (CSS), to remove any androgens from the medium (Life Technologies). ISIS 560131, ISIS 549458, ISIS 569236, and ISIS 554221 were individually added to the culture media at 0.04 μM, 0.2 μM, 1.0 μM, or 5.0 μM concentration. ISIS 549148, which has no known human target sequence, was included as a control. The synthetic androgen agonist, R1881, (Takeda, A. N. et al., Mol. Pharmacol. 2007. 71: 473-82) was added on day 1 at 1 nM dose to a set of cells also treated with each of the antisense oligonucleotides. DHT was added on day 1 at a dose of 10 nM to another set of cells also treated with each of the antisense oligonucleotides. MDV3100 was added on day 1 at a dose of 10 nM to another set of cells untreated with antisense oligonucleotide, which served as a control. After a treatment period of 5 days, the proliferative ability of the cancer cells was measured by the standard MTT assay. Results are presented in Table 42 as percent inhibition of proliferation, relative to non-treated cells.

As presented in Table 42, in the presence of androgen agonists R1881 or DHT, ISIS 560131, ISIS 549458, and ISIS 569236 significantly inhibited MDV3100-resistant prostate cancer cell proliferation in a dose dependent manner more extensively than ISIS 554221 Inhibition of proliferation by the antisense oligonucleotides was also either comparable or more potent than with treatment with MDV3100.

TABLE 42

| Percent inhibition of LMR20 cell proliferation | | | | | | |
|---|---|---|---|---|---|---|
| Treatment | ASO (μM) | ISIS 560131 | ISIS 569236 | ISIS 549458 | ISIS 554221 | MDV3100 |
| CSS | 0.04 | 0 | 0 | 0 | 0 | 0 |
| | 0.20 | 0 | 10 | 0 | 1 | 5 |
| | 1.0 | 9 | 0 | 0 | 2 | 0 |
| | 5.0 | 16 | 12 | 5 | 16 | 11 |
| CSS + R1881 | 0.04 | 0 | 0 | 0 | 1 | 0 |
| | 0.20 | 13 | 2 | 22 | 10 | 5 |
| | 1.0 | 55 | 34 | 59 | 19 | 31 |
| | 5.0 | 70 | 61 | 74 | 54 | 67 |
| CSS + DHT | 0.04 | 0 | 0 | 0 | 0 | 0 |
| | 0.20 | 13 | 10 | 25 | 0 | 1 |
| | 1.0 | 57 | 32 | 60 | 10 | 13 |
| | 5.0 | 71 | 57 | 70 | 36 | 41 |

Study 2

LMR20 cells were plated at 1,500 cells per well in phenol red-free medium with CSS. ISIS 560131, ISIS 549458, ISIS 569236, and the LNA gapmer ISIS 554221 were individually added to the culture media at 0.04 μM, 0.2 μM, 1.0 μM, or 5.0 μM concentration. ISIS 549148, which has no known human target sequence, was included as a control. MDV3100 was added on day 1 at a dose of 10 nM to a set of cells, and served as a control. DHT was added on day 1 at a dose of 10 nM for 72 hrs to one set of cells also treated with each of the antisense oligonucleotides or MDV3100. R1881 was added on day 1 at a dose of 10 nM for 72 hrs to another set of cells also treated with each of the antisense oligonucleotides or MDV3100. mRNA levels of AR, prostate-specific antigen (PSA) and TMPRSS2, an androgen-regulated gene (Lin, B., et al., Cancer Res. 1999. 59: 4180), were measured. Results are presented in Tables 43-45 as mRNA levels expressed as a percentage of the baseline values. mRNA levels may be lowered or increased after treatment.

As presented in Tables 43-45, ISIS 560131, ISIS 549458, and ISIS 569236 reduced AR mRNA levels in LMR20 cells, treated with or without either AR agonist, in a dose dependent manner relative to the baseline. Treatment with the LNA gapmer ISIS 554221 did not alter AR mRNA levels. ISIS 560131, ISIS 549458, and ISIS 569236 reduced PSA levels and TMPRSS2 more extensively than the LNA gapmer ISIS 554221 or MDV3100. Treatment with MDV3100 increased the levels of AR mRNA in cells treated with AR agonist, and did not reduce either PSA or TMPRSS2 mRNA levels.

TABLE 43 mRNA levels (% baseline value) of cells without AR agonist treatment

| Gene | ASO (μM) | 560131 | 569236 | 549458 | 554221 | MDV3100 |
|---|---|---|---|---|---|---|
| AR | 0.04 | 107 | 104 | 101 | 124 | 106 |
| | 0.20 | 74 | 87 | 75 | 140 | 101 |
| | 1.0 | 29 | 42 | 30 | 132 | 99 |
| | 5.0 | 17 | 27 | 25 | 98 | 92 |
| PSA | 0.04 | 113 | 122 | 135 | 106 | 98 |
| | 0.20 | 83 | 90 | 85 | 118 | 93 |
| | 1.0 | 75 | 78 | 50 | 58 | 90 |
| | 5.0 | 71 | 73 | 72 | 87 | 113 |
| TMPRSS2 | 0.04 | 92 | 96 | 110 | 95 | 101 |
| | 0.20 | 67 | 81 | 85 | 117 | 119 |
| | 1.0 | 52 | 59 | 54 | 77 | 119 |
| | 5.0 | 45 | 48 | 62 | 73 | 141 |

TABLE 44 mRNA levels (% baseline value) after treatment with DHT

| Gene | ASO (μM) | 560131 | 569236 | 549458 | 554221 | MDV3100 |
|---|---|---|---|---|---|---|
| AR | 0.04 | 89 | 94 | 91 | 137 | 105 |
| | 0.20 | 55 | 77 | 66 | 135 | 124 |
| | 1.0 | 25 | 44 | 34 | 136 | 110 |
| | 5.0 | 20 | 34 | 31 | 100 | 143 |
| PSA | 0.04 | 74 | 108 | 93 | 97 | 124 |
| | 0.20 | 61 | 79 | 71 | 86 | 108 |
| | 1.0 | 35 | 46 | 47 | 64 | 95 |
| | 5.0 | 35 | 46 | 47 | 64 | 95 |
| TMPRSS2 | 0.04 | 112 | 113 | 127 | 121 | 134 |
| | 0.20 | 108 | 123 | 119 | 118 | 144 |
| | 1.0 | 93 | 111 | 106 | 122 | 132 |
| | 5.0 | 71 | 110 | 91 | 114 | 124 |

TABLE 45 mRNA levels (% baseline value) after treatment with R1881

| Gene | ASO (μM) | 560131 | 569236 | 549458 | 554221 | MDV3100 |
|---|---|---|---|---|---|---|
| AR | 0.04 | 87 | 89 | 88 | 131 | 94 |
| | 0.20 | 65 | 80 | 56 | 133 | 107 |

TABLE 45-continued mRNA levels (% baseline value) after treatment with R1881

| Gene | ASO (μM) | 560131 | 569236 | 549458 | 554221 | MDV3100 |
|---|---|---|---|---|---|---|
| | 1.0 | 30 | 44 | 25 | 124 | 115 |
| | 5.0 | 26 | 37 | 32 | 99 | 136 |
| PSA | 0.04 | 92 | 90 | 93 | 100 | 84 |
| | 0.20 | 77 | 90 | 67 | 93 | 101 |
| | 1.0 | 44 | 57 | 50 | 80 | 92 |
| | 5.0 | 35 | 41 | 44 | 57 | 87 |
| TMPRSS2 | 0.04 | 132 | 126 | 137 | 136 | 114 |
| | 0.20 | 117 | 131 | 119 | 134 | 125 |
| | 1.0 | 88 | 98 | 96 | 125 | 133 |
| | 5.0 | 76 | 95 | 96 | 122 | 139 |

Example 19

Effect of Antisense Inhibition of Human Androgen Receptor (AR) mRNA in Combination with MDV3100 on the Proliferative Ability of C4-2B Cells The effect of antisense inhibition of AR in combination with different doses of MDV3100 on the proliferative ability of cancer cells was analyzed. ISIS 549372, ISIS 549434, ISIS 549458, and ISIS 554221 were tested in C4-2B cells.

C4-2B cells were plated at 1,500 cells per well. ISIS 549372, ISIS 549434, ISIS 549458, or ISIS 554221 were individually added to the culture media at 0.1 μM concentration. ISIS 347526 was included as a negative control. MDV3100 was also added on day 1 at doses of 0.25 μM or 1.00 μM. After a treatment period of 6 days, the proliferative capacity of the cancer cells was measured with CellTiter 96® AQueous One Solution Cell Proliferation kit (Promega), following the manufacturer's instructions. Results are presented in Table 46 as percent inhibition of proliferation, relative to non-treated cells. Treatment of the cells with ISIS 549372 or ISIS 549458 reduced proliferation of the cells more extensively than treatment with ISIS 554221. For instance, as presented in Table 46, treatment with ISIS 549372 alone reduced cell proliferation by 59% and treatment with ISIS 549458 reduced cell proliferation by 74% compared to ISIS 554221 alone, which reduced cell proliferation by 23%.

As presented in Tables 46 and 47, ISIS 549372 or ISIS 549458 in combination with MDV3100 inhibited prostate cancer cell proliferation to a greater extent than an equal molar concentration of ISIS 554221 in combination of MDV3100.

To find out whether treatment of the cells with ISIS 549372 or ISIS 549458 was synergistic with MDV3100, the assay was repeated at 0.1 μM ASO. As presented in Table 46, treatment with ISIS 549372 or ISIS 549458 was synergistic with MDV3100. For instance, MDV3100 alone at 0.25 μM inhibited proliferation by 4%; ISIS 549372 alone at 0.1 μM inhibited cell proliferation by 23%; in combination, cell proliferation was inhibited by 66%. Similarly, ISIS 549458 alone at 0.1 μM inhibited cell proliferation by 39%; in combination, cell proliferation was inhibited by 75%. Hence, the combination of ISIS 549372 or ISIS 549458 and MDV3100 was synergistic (i.e. greater than additive) in terms of inhibition of prostate cancer cell proliferation.

TABLE 46

Percent inhibition of C4-2B cell proliferation with 0.1 μM ASO

| | MDV3100 | | |
|---|---|---|---|
| | 0 μM | 0.25 μM | 1 μM |
| PBS | 0 | 9 | 38 |
| ISIS 549372 | 23 | 44 | 66 |
| ISIS 549458 | 39 | 59 | 75 |
| ISIS 554221 | 9 | 29 | 59 |
| ISIS 141923 | 0 | 4 | 38 |

TABLE 47

Percent inhibition of C4-2B cell proliferation with 0.2 μM ASO

| | MDV3100 | | |
|---|---|---|---|
| | 0 μM | 0.25 μM | 1 μM |
| PBS | 0 | 20 | 46 |
| ISIS 549372 | 59 | 69 | 77 |
| ISIS 549458 | 74 | 75 | 79 |
| ISIS 554221 | 23 | 45 | 67 |
| ISIS 141923 | 0 | 5 | 50 |

Example 20

Effect of Antisense Inhibition of Human Androgen Receptor (AR) mRNA in Combination with MDV3100 on the Proliferative Ability of LNCaP Cells The effect of antisense inhibition of AR in combination with different doses of MDV3100 on the proliferative ability of cancer cells was analyzed. ISIS 560131 and ISIS 569236 were tested in LNCaP cells.

LNCaP cells were plated at 1,000 cells per well. ISIS 560131 or ISIS 569236 was individually added to the culture media at 0.08 μM, 0.04 μM, 0.2 μM, or 1.0 μM concentration. ISIS 549148 was included as a negative control. MDV3100 was added to the ISIS oligonucleotide-treated cells on day 2 at doses of 0.016 μM, 0.08 μM, 0.4 μM, or 2.0 μM. After a treatment period of 5 days, the proliferative capacity of the cancer cells was measured with CellTiter 96® AQueous One or CellTiter-Glo® Solution Cell Proliferation kit (Promega), following the manufacturer's instructions. Results are presented in Tables 48-52 as percent inhibition of proliferation, relative to non-treated cells.

As presented in the Tables, treatment with ISIS 560131 or ISIS 569236 was synergistic with MDV3100. For instance, MDV3100 with control oligonucleotide, ISIS 549148, at 0.08 μM inhibited proliferation by an average of 7%; ISIS 560131 alone at 0.04 μM inhibited cell proliferation by 24%; in combination, cell proliferation was inhibited by 41%. Similarly, ISIS 569236 alone at 0.04 μM inhibited cell proliferation by 9%; in combination, cell proliferation was inhibited by 26%. Hence, the combination of ISIS 560131 or ISIS 569236 and MDV3100 was synergistic (i.e. greater than additive) in terms of inhibition of prostate cancer cell proliferation.

TABLE 48

Proliferation (% untreated control) in LNCaP without MDV-3100

| | ASO Dose | | | |
|---|---|---|---|---|
| | 0.08 μM | 0.04 μM | 0.2 μM | 1.0 μM |
| ISIS 560131 | 106 | 76 | 50 | 26 |
| ISIS 569236 | 106 | 91 | 60 | 35 |
| ISIS 549148 | 104 | 101 | 91 | 82 |

TABLE 49

Proliferation (% untreated control) in LNCaP with 0.016 μM MDV-3100

| | ASO Dose | | | |
|---|---|---|---|---|
| | 0.08 μM | 0.04 μM | 0.2 μM | 1.0 μM |
| ISIS 560131 | 103 | 71 | 49 | 25 |
| ISIS 569236 | 104 | 92 | 58 | 29 |
| ISIS 549148 | 106 | 86 | 83 | 59 |

TABLE 50

Proliferation (% untreated control) in LNCaP with 0.08 μM MDV-3100

| | ASO Dose | | | |
|---|---|---|---|---|
| | 0.08 μM | 0.04 μM | 0.2 μM | 1.0 μM |
| ISIS 560131 | 99 | 59 | 48 | 27 |
| ISIS 569236 | 98 | 74 | 51 | 31 |
| ISIS 549148 | 93 | 101 | 89 | 90 |

TABLE 51

Proliferation (% untreated control) in LNCaP with 0.4 μM MDV-3100

| | ASO Dose | | | |
|---|---|---|---|---|
| | 0.08 μM | 0.04 μM | 0.2 μM | 1.0 μM |
| ISIS 560131 | 68 | 50 | 40 | 26 |
| ISIS 569236 | 61 | 48 | 41 | 27 |
| ISIS 549148 | 65 | 57 | 50 | 48 |

TABLE 52

Proliferation (% untreated control) in LNCaP with 2.0 μM MDV-3100

| | ASO Dose | | | |
|---|---|---|---|---|
| | 0.08 μM | 0.04 μM | 0.2 μM | 1.0 μM |
| ISIS 560131 | 45 | 42 | 38 | 23 |
| ISIS 569236 | 44 | 41 | 35 | 23 |
| ISIS 549148 | 39 | 42 | 41 | 32 |

Example 21

Effect of Antisense Inhibition of Human Androgen Receptor (AR) mRNA in Combination with MDV3100 on the Proliferative Ability of C4-2B Cells The effect of antisense inhibition of AR in combination with different doses of MDV3100 on the proliferative ability of cancer cells was analyzed. ISIS 560131 and ISIS 569236 were tested in C4-2B cells.

C4-2B cells were plated at 1,000 cells per well. ISIS 560131 or ISIS 569236 was individually added to the culture media at 0.08 μM, 0.04 μM, 0.2 μM, or 1.0 μM concentration. ISIS 549148 was included as a negative control. MDV3100 was added to the ISIS oligonucleotide-treated cells on day 2 at doses of 0.016 μM, 0.08 μM, 0.4 μM, or 2.0 μM. After a treatment period of 5 days, the proliferative capacity of the cancer cells was measured with CellTiter 96® AQueous One Solution Cell Proliferation kit (Promega), following the manufacturer's instructions. Results are presented in Tables 53-57 as percent inhibition of proliferation, relative to non-treated cells.

As presented in the Tables, treatment with ISIS 560131 or ISIS 569236 was synergistic with MDV3100. For instance, MDV3100 with control oligonucleotide, ISIS 549148, at 0.4 μM inhibited proliferation by an average of 6%; ISIS 560131 alone at 0.08 μM inhibited cell proliferation by 16%; in combination, cell proliferation was inhibited by 31%. Similarly, MDV3100 with control oligonucleotide, ISIS 549148, at 0.08 μM did not inhibit proliferation (0%); ISIS 569236 alone at 0.2 μM inhibited cell proliferation by 37%; in combination, cell proliferation was inhibited by 52%. Hence, the combination of ISIS 560131 or ISIS 569236 and MDV3100 was synergistic (i.e. greater than additive) in terms of inhibition of prostate cancer cell proliferation.

TABLE 53

Proliferation (% untreated control) in C4-2B without MDV-3100

| | ASO Dose | | | |
|---|---|---|---|---|
| | 0.08 μM | 0.04 μM | 0.2 μM | 1.0 μM |
| ISIS 560131 | 84 | 59 | 47 | 41 |
| ISIS 569236 | 100 | 72 | 63 | 51 |
| ISIS 549148 | 111 | 117 | 118 | 126 |

TABLE 54

Proliferation (% untreated control) in C4-2B with 0.016 μM MDV-3100

| | ASO Dose | | | |
|---|---|---|---|---|
| | 0.08 μM | 0.04 μM | 0.2 μM | 1.0 μM |
| ISIS 560131 | 104 | 71 | 53 | 39 |
| ISIS 569236 | 107 | 74 | 65 | 55 |
| ISIS 549148 | 110 | 107 | 124 | 103 |

TABLE 55

Proliferation (% untreated control) in C4-2B with 0.08 μM MDV-3100

| | ASO Dose | | | |
|---|---|---|---|---|
| | 0.08 μM | 0.04 μM | 0.2 μM | 1.0 μM |
| ISIS 560131 | 66 | 73 | 56 | 42 |
| ISIS 569236 | 89 | 79 | 51 | 43 |
| ISIS 549148 | 84 | 125 | 123 | 114 |

TABLE 56

Proliferation (% untreated control) in C4-2B with 0.4 μM MDV-3100

| | ASO Dose | | | |
|---|---|---|---|---|
| | 0.08 μM | 0.04 μM | 0.2 μM | 1.0 μM |
| ISIS 560131 | 69 | 69 | 48 | 48 |
| ISIS 569236 | 90 | 63 | 48 | 39 |
| ISIS 549148 | 89 | 110 | 88 | 88 |

TABLE 57

Proliferation (% untreated control) in C4-2B with 2.0 μM MDV-3100

| | ASO Dose | | | |
|---|---|---|---|---|
| | 0.08 μM | 0.04 μM | 0.2 μM | 1.0 μM |
| ISIS 560131 | 37 | 42 | 49 | 43 |
| ISIS 569236 | 44 | 45 | 48 | 46 |
| ISIS 549148 | 47 | 40 | 52 | 59 |

Example 22

Effect of Antisense Inhibition of Human Androgen Receptor (AR) mRNA in Combination with MDV3100 on the Proliferative Ability of 22RV1 Cells The effect of antisense inhibition of AR in combination with different doses of MDV3100 on the proliferative ability of cancer cells was analyzed. ISIS 560131 and ISIS 569236 were tested in 22RV1 cells.

22RV1 cells were plated at 2,000 cells per well in 5% CSS medium for 48 hours. Cells were transfected using RNAiMAX reagent with ISIS 560131 or ISIS 569236 at 0.4 nM, 1.34 nM, 4 nM, or 13.4 nM concentrations. ISIS 549148 was included as a negative control. DHT at 1 nM and/or MDV3100 at doses of 0.04 μM, 0.2 μM, 1.0 μM, or 5.0 μM were added after 4 hours. After a treatment period of 3 days, the proliferative capacity of the cancer cells was measured with CellTiter 96® AQueous One Solution Cell Proliferation kit (Promega), following the manufacturer's instructions. Results are presented in Tables 58-62 as percent inhibition of proliferation, relative to non-treated cells.

As presented in the Tables, treatment with ISIS 560131 or ISIS 569236 was synergistic with MDV3100. For instance, MDV3100 with control oligonucleotide, ISIS 549148, at 1.0 μM inhibited proliferation by an average of 5%; ISIS 560131 alone at 1.34 nM inhibited cell proliferation by 3%; in combination, cell proliferation was inhibited by 23%. Similarly, MDV3100 with control oligonucleotide, ISIS 549148, at 1.0 μM inhibited proliferation by 5%; ISIS 569236 alone at 1.0 μM inhibited cell proliferation by 17%; in combination, cell proliferation was inhibited by 30%. Hence, the combination of ISIS 560131 or ISIS 569236 and MDV3100 was synergistic (i.e. greater than additive) in terms of inhibition of prostate cancer cell proliferation.

TABLE 58

Proliferation (% untreated control) in 22RV1 without MDV-3100

| | ASO Dose | | | |
|---|---|---|---|---|
| | 0.4 nM | 1.34 nM | 4.0 nM | 13.4 nM |
| ISIS 560131 | 103 | 97 | 77 | 57 |
| ISIS 569236 | 97 | 83 | 69 | 37 |
| ISIS 549148 | 109 | 109 | 109 | 99 |

TABLE 59

Proliferation (% untreated control) in 22RV1 cells with 0.04 μM MDV-3100

| | ASO Dose | | | |
|---|---|---|---|---|
| | 0.4 nM | 1.34 nM | 4.0 nM | 13.4 nM |
| ISIS 560131 | 96 | 80 | 65 | 39 |
| ISIS 569236 | 83 | 70 | 61 | 24 |
| ISIS 549148 | 106 | 106 | 100 | 85 |

TABLE 60

Proliferation (% untreated control) in 22RV1 cells with 0.2 μM MDV-3100

| | ASO Dose | | | |
|---|---|---|---|---|
| | 0.4 nM | 1.34 nM | 4.0 nM | 13.4 nM |
| ISIS 560131 | 95 | 90 | 76 | 51 |
| ISIS 569236 | 93 | 77 | 60 | 20 |
| ISIS 549148 | 101 | 115 | 110 | 96 |

TABLE 61

Proliferation (% untreated control) in 22RV1 cells with 1.0 μM MDV-3100

| | ASO Dose | | | |
|---|---|---|---|---|
| | 0.4 nM | 1.34 nM | 4.0 nM | 13.4 nM |
| ISIS 560131 | 96 | 77 | 63 | 40 |
| ISIS 569236 | 79 | 70 | 52 | 18 |
| ISIS 549148 | 106 | 95 | 98 | 82 |

TABLE 62

Proliferation (% untreated control) in 22RV1 cells with 5.0 μM MDV-3100

| | ASO Dose | | | |
|---|---|---|---|---|
| | 0.4 nM | 1.34 nM | 4.0 nM | 13.4 nM |
| ISIS 560131 | 91 | 76 | 63 | 41 |
| ISIS 569236 | 82 | 72 | 52 | 24 |
| ISIS 549148 | 96 | 102 | 98 | 85 |

Example 23

Effect of Antisense Inhibition of Human Androgen Receptor (AR) mRNA on CWR22-RV1 Cells The effect of antisense inhibition of AR on the proliferative ability of cancer cells was analyzed. ISIS 549372, ISIS 549434, ISIS 549458, and ISIS 554221 were tested in CWR22-RV1 cells.

CWR22-RV1 cells were plated and transfected using RNAiMax reagent (Life Technologies) with ISIS oligonucleotides at 1.7 nM, 5.0 nM, 16.7 nM, or 50 nM concentrations. ISIS 347526 was included as a negative control. After a treatment period of 6 days, the target reduction and proliferative capacity of the cancer cells was measured.

Antisense inhibition of AR full-length mRNA was measured with the RTS3559 primer probe set. The results are presented in Table 63 as percent inhibition relative to non-treated cells. The reduction in V7 splice variant of the AR mRNA was also measured by RT-PCR using SYBR Green staining (Hu, R. et al., Cancer Res. 2009. 69: 16-22). The results are presented in Table 64, as percent reduction, relative to non-treated cells. Cell proliferation was measured with CellTiter 96® AQueous One Solution Cell Proliferation kit (Promega), following the manufacturer's instructions. Results are presented in Table 65 as percent inhibition of proliferation, relative to non-treated cells.

TABLE 63

Percent inhibition of AR full-length mRNA

| Dose (nM) | ISIS 549372 | ISIS 549434 | ISIS 549458 | ISIS 554221 | ISIS 347526 |
|---|---|---|---|---|---|
| 1.7 | 24 | 27 | 28 | 24 | 0 |
| 5.0 | 53 | 46 | 41 | 41 | 3 |
| 16.7 | 64 | 69 | 61 | 67 | 4 |
| 50.0 | 78 | 86 | 78 | 72 | 0 |

TABLE 64

Percent inhibition of AR splice variant, V7

| Dose (nM) | ISIS 549372 | ISIS 549434 | ISIS 549458 | ISIS 554221 | ISIS 347526 |
|---|---|---|---|---|---|
| 1.7 | 23 | 0 | 18 | 25 | 17 |
| 5.0 | 35 | 20 | 34 | 1 | 0 |
| 16.7 | 56 | 4 | 58 | 7 | 0 |
| 50.0 | 82 | 23 | 82 | 35 | 10 |

TABLE 65

Percent inhibition of cell proliferation

| Dose (nM) | ISIS 549372 | ISIS 549434 | ISIS 549458 | ISIS 554221 | ISIS 347526 |
|---|---|---|---|---|---|
| 1.7 | 0 | 8 | 0 | 17 | 0 |
| 5.0 | 0 | 15 | 0 | 11 | 0 |
| 16.7 | 25 | 13 | 17 | 27 | 0 |
| 50.0 | 53 | 38 | 40 | 47 | 0 |

Example 24

Effect of Antisense Inhibition of Human Androgen Receptor (AR) mRNA by Free Uptake of Antisense Oligonucleotide by C4-2B Cells The effect of free uptake of antisense oligonucleotides on AR mRNA levels was investigated. ISIS 549372, ISIS 549434, ISIS 549458, and ISIS 554221 were tested.

Cells were plated at a concentration of 1,000 cells/well in 96-well plates to measure cell proliferation, and at 4,000 cells/well to measure target reduction. ISIS 549458, ISIS 549372, ISIS 549434, and ISIS 554221 were added individually at 0.04 μM, 0.20 μM, 1.00 μM, or 5.00 μM. After an incubation period of 24 hrs, mRNA levels were measured using hAR_LTS00943. The data is presented in Table 66. The results indicate that ISIS 549458, ISIS 549372, and ISIS 549434 inhibited AR mRNA expression more potently than ISIS 554221.

On day 6, cells plated for measuring proliferation were incubated with MTT reagent until the development of color. Color intensity was measured using a spectrophotometer at 490 nm. The data is presented in Table 67.

TABLE 66

| Percent inhibition of AR full-length mRNA | | | | |
|---|---|---|---|---|
| Dose (μM) | ISIS 549372 | ISIS 549434 | ISIS 549458 | ISIS 554221 |
| 0.04 | 10 | 10 | 16 | 0 |
| 0.20 | 36 | 35 | 48 | 0 |
| 1.00 | 73 | 52 | 80 | 0 |
| 5.00 | 80 | 55 | 86 | 0 |

TABLE 67

| Percent inhibition of cell proliferation | | | | |
|---|---|---|---|---|
| Dose (μM) | ISIS 549372 | ISIS 549434 | ISIS 549458 | ISIS 554221 |
| 0.04 | 8 | 0 | 7 | 0 |
| 0.20 | 34 | 14 | 31 | 10 |
| 1.00 | 44 | 35 | 45 | 21 |
| 5.00 | 45 | 37 | 41 | 30 |

Example 25

Effect of Antisense Inhibition of Human Androgen Receptor (AR) mRNA by Free Uptake of Antisense Oligonucleotide by LnCaP Cells The effect of free uptake of antisense oligonucleotides on AR mRNA levels was investigated.

Cells were plated at a concentration of 4,000 cells/well in 96-well plates. ISIS oligonucleotides, specified in Table 68, were added individually at 0.02 μM, 0.10 μM, 0.50 μM, 2.50 μM, or 10.00 μM. After an incubation period of 24 hrs, mRNA levels were measured using primer probe set hAR_LTS00943. The data is presented in Table 68. The results indicate that most of the ISIS oligonucleotides inhibited AR mRNA expression more potently than ISIS 554221 at each concentration.

TABLE 68

| Percent inhibition of AR mRNA | | | | | |
|---|---|---|---|---|---|
| ISIS No | 0.02 μM | 0.1 μM | 0.5 μM | 2.5 μM | 10 μM |
| 554221 | 0 | 0 | 0 | 0 | 17 |
| 549372 | 0 | 0 | 21 | 63 | 78 |
| 549458 | 4 | 14 | 67 | 86 | 89 |
| 560131 | 0 | 0 | 13 | 31 | 57 |
| 569213 | 3 | 0 | 31 | 59 | 78 |
| 569216 | 15 | 17 | 49 | 66 | 82 |
| 569221 | 18 | 31 | 49 | 78 | 91 |
| 569227 | 0 | 0 | 4 | 33 | 55 |
| 569236 | 3 | 2 | 21 | 43 | 70 |
| 579666 | 0 | 8 | 30 | 49 | 68 |
| 579667 | 0 | 0 | 8 | 12 | 40 |
| 579671 | 15 | 0 | 19 | 54 | 71 |
| 583918 | 8 | 0 | 0 | 0 | 13 |
| 584149 | 0 | 0 | 0 | 14 | 39 |
| 584163 | 0 | 0 | 19 | 41 | 70 |
| 584269 | 0 | 0 | 0 | 12 | 23 |
| 584468 | 0 | 0 | 10 | 44 | 73 |
| 586124 | 0 | 0 | 19 | 64 | 82 |
| 586227 | 0 | 0 | 14 | 44 | 59 |

Example 26

Effect of Antisense Inhibition of Human Androgen Receptor (AR) mRNA in the Presence of DHT on the Proliferative Ability of 22RV1 Cells Dihydrotestosterone (DHT) is an androgen hormone and AR activator. The effect of antisense inhibition of AR on the proliferative ability of cancer cells treated with DHT was analyzed. ISIS 560131 and ISIS 569236 were tested in the human prostate carcinoma cell line, 22RV1.

22RV1cells were plated at 1,500 cells per well. ISIS 560131 and ISIS 569236 were individually transfected into the cells using RNAiMAX™ reagent (Life Technologies) at 1.34 nM, 4.00 nM, 13.4 nM, or 40.0 nM concentration. ISIS 549148, which has no known human target sequence, was included as a control. Separate sets of cells, also treated with each of the antisense oligonucleotides, were treated with DHT added on day 1 at a final concentration of 1 nM. After a treatment period of 5 days, the proliferative ability of the cancer cells was measured using the standard MTT assay. Results are presented in Table 69 as percent inhibition of proliferation, relative to non-treated cells.

As presented in Table 69, both ISIS 560131 and ISIS 569236 significantly inhibited prostate cancer cell proliferation even in the presence of AR activator, DHT, compared to the control. The control oligonucleotide did not show any effect on proliferation, as expected.

TABLE 69

| Percent inhibition of 22RV1 cell proliferation | | | | |
|---|---|---|---|---|
| | ASO (nM) | ISIS 560131 | ISIS 569236 | ISIS 549148 |
| −DHT | 1.34 | 0 | 0 | 0 |
| | 4.0 | 2 | 18 | 0 |
| | 13.4 | 29 | 47 | 4 |
| | 40.0 | 54 | 64 | 0 |
| +DHT | 1.34 | 0 | 0 | 0 |
| | 4.0 | 1 | 6 | 0 |
| | 13.4 | 13 | 32 | 3 |
| | 40.0 | 34 | 56 | 0 |

Example 27

Time-Course Study of Treatment C4-2B Cells with ISIS Oligonucleotides Targeting AR The effect of antisense inhibition of on C4-2B cancer cells on gene expression was analyzed. ISIS 560131 and ISIS 569236 were tested.

AR mRNA Analysis

C4-2B cells were plated at 1,000 cells per well in complete medium. ISIS 560131 or ISIS 569236 was individually added to the culture media to the final concentrations of 0.04 μM, 0.2 μM, 1.0 μM, or 5.0 μM concentrations without using transfection reagent. ISIS 549148 was included as a negative control. MDV3100 was added at dose of 0.04 μM, 0.2 μM, 1.0 μM, or 5.0 μM in a separate set of cells. After a treatment period of 8 hours, 24 hours, and 48 hours, AR expression was measured with primer probe set hAR-LTS00943. Results are presented in Tables 70-72 as percent expression of AR, relative to non-treated cells. Treatment of the cells with ISIS 560131 or ISIS 569236 reduced AR expression in the cells relative to the control set. Treatment with MDV-3100 increased AR expression at the 48 hour time-point.

TABLE 70

Percent expression of AR compared to the control group in 8 hours

| | 0.04 μM | 0.2 μM | 1 μM | 5.0 μM |
|---|---|---|---|---|
| ISIS 560131 | 110 | 85 | 68 | 45 |
| ISIS 569236 | 100 | 87 | 84 | 58 |
| ISIS 549148 | 116 | 105 | 111 | 110 |
| MDV-3100 | 99 | 100 | 92 | 103 |

TABLE 71

Percent expression of AR compared to the control group in 24 hours

| | 0.04 μM | 0.2 μM | 1 μM | 5.0 μM |
|---|---|---|---|---|
| ISIS 560131 | 47 | 18 | 5 | 4 |
| ISIS 569236 | 103 | 35 | 15 | 5 |
| ISIS 549148 | 87 | 85 | 87 | 107 |
| MDV-3100 | 88 | 99 | 96 | 84 |

TABLE 72

Percent expression of AR compared to the control group in 48 hours

| | 0.04 μM | 0.2 μM | 1 μM | 5.0 μM |
|---|---|---|---|---|
| ISIS 560131 | 33 | 5 | 6 | 4 |
| ISIS 569236 | 80 | 19 | 7 | 2 |
| ISIS 549148 | 98 | 90 | 87 | 99 |
| MDV-3100 | 94 | 94 | 113 | 126 |

AR Protein Analysis

Protein levels in the cells were also analyzed. The cells were harvested in RIPA buffer containing protease inhibitors. The presence of bands for full-length AR was detected by western blot using AR antibody (N-20, SC-816, Santa Cruz Biotechnology). Full-length AR was significantly reduced in cells treated with ISIS 560131 or ISIS 569236 for 24 hours and 48 hours, normalized to the levels of the house-keeping gene, GAPDH.

mRNA Expression Analysis of Downstream Genes

Expression analysis of prostate-specific antigen (PSA) and TMPRSS2 were also analyzed. Results are presented in Tables 73-75 as percent inhibition of PSA expression and Tables 76-78 as percent inhibition of TMPRSS2 expression, relative to non-treated cells. Treatment of the cells with ISIS 560131 or ISIS 569236 reduced PSA and TMPRSS2 expression in the cells relative to the control set at the 24 hr and 48 hr time points. Treatment with MDV-3100 also reduced downstream gene expressions but not as potently as that with the ISIS oligonucleotides.

TABLE 73

Percent inhibition of PSA expression compared to the control group in 8 hours

| | 0.04 μM | 0.2 μM | 1 μM | 5.0 μM |
|---|---|---|---|---|
| ISIS 560131 | 12 | 0 | 3 | 1 |
| ISIS 569236 | 18 | 3 | 0 | 0 |
| ISIS 549148 | 1 | 8 | 8 | 0 |
| MDV-3100 | 0 | 3 | 23 | 33 |

TABLE 74

Percent inhibition of PSA expression compared to the control group in 24 hours

| | 0.04 μM | 0.2 μM | 1 μM | 5.0 μM |
|---|---|---|---|---|
| ISIS 560131 | 27 | 46 | 56 | 60 |
| ISIS 569236 | 10 | 34 | 44 | 54 |
| ISIS 549148 | 22 | 13 | 16 | 6 |
| MDV-3100 | 24 | 24 | 53 | 65 |

TABLE 75

Percent inhibition of PSA expression compared to the control group in 48 hours

| | 0.04 μM | 0.2 μM | 1 μM | 5.0 μM |
|---|---|---|---|---|
| ISIS 560131 | 20 | 61 | 71 | 80 |
| ISIS 569236 | 4 | 45 | 68 | 76 |
| ISIS 549148 | 2 | 0 | 18 | 10 |
| MDV-3100 | 5 | 5 | 32 | 63 |

TABLE 76

Percent inhibition of TMPRSS2 expression compared to the control group in 8 hours

| | 0.04 μM | 0.2 μM | 1 μM | 5.0 μM |
|---|---|---|---|---|
| ISIS 560131 | 0 | 0 | 6 | 0 |
| ISIS 569236 | 0 | 0 | 0 | 0 |
| ISIS 549148 | 5 | 0 | 0 | 0 |
| MDV-3100 | 0 | 6 | 45 | 52 |

TABLE 77

Percent inhibition of TMPRSS2 expression compared to the control group in 24 hours

| | 0.04 μM | 0.2 μM | 1 μM | 5.0 μM |
|---|---|---|---|---|
| ISIS 560131 | 35 | 57 | 66 | 67 |
| ISIS 569236 | 10 | 32 | 57 | 66 |
| ISIS 549148 | 29 | 10 | 29 | 10 |
| MDV-3100 | 23 | 31 | 63 | 72 |

TABLE 78

| Percent inhibition of TMPRSS2 expression compared to the control group in 48 hours | | | | |
|---|---|---|---|---|
| | 0.04 μM | 0.2 μM | 1 μM | 5.0 μM |
| ISIS 560131 | 46 | 71 | 77 | 76 |
| ISIS 569236 | 22 | 57 | 70 | 75 |
| ISIS 549148 | 0 | 4 | 0 | 0 |
| MDV-3100 | 5 | 16 | 46 | 59 |

Example 28

Antisense Inhibition of AR mRNA in LNCaP Cells Cultured in Complete Media and CSS Media The effect of antisense inhibition of AR in LNCaP cells cultured in complete medium, as well as CSS medium with DHT, was investigated.

Gene Expression in Complete Medium

Cells were plated at 1,000 cells per well. ISIS 560131 or ISIS 569236 was added individually at 0.04 μM, 0.2 μM, 1.0 μM, or 5.0 μM. ISIS 549148 was included as a negative control. MDV3100 was added a dose of 0.04 μM, 0.2 μM, 1.0 μM, or 5.0 μM. μM in a separate set of cells. After an incubation period of 48 hours, RNA levels of AR, PSA and TMPRSS2 were measured. The data is presented in Tables 79-81.

Protein analysis of full-length AR also demonstrated a dose-dependent decrease of expression, normalized to levels of the house-keeping gene, GAPDH.

TABLE 79

| Percent expression of AR in LNCaP cells cultured in complete medium | | | | |
|---|---|---|---|---|
| | 0.04 μM | 0.2 μM | 1 μM | 5.0 μM |
| ISIS 560131 | 101 | 53 | 17 | 7 |
| ISIS 569236 | 98 | 90 | 47 | 20 |
| ISIS 549148 | 102 | 111 | 109 | 109 |
| MDV-3100 | 111 | 133 | 121 | 139 |

TABLE 80

| Percent inhibition of PSA expression in LNCaP cells cultured in complete medium | | | | |
|---|---|---|---|---|
| | 0.04 μM | 0.2 μM | 1 μM | 5.0 μM |
| ISIS 560131 | 0 | 60 | 87 | 90 |
| ISIS 569236 | 0 | 19 | 63 | 81 |
| ISIS 549148 | 0 | 0 | 0 | 0 |
| MDV-3100 | 0 | 35 | 84 | 87 |

TABLE 81

| Percent inhibition of TMPRSS2 expression in LNCaP cells cultured in complete medium | | | | |
|---|---|---|---|---|
| | 0.04 μM | 0.2 μM | 1 μM | 5.0 μM |
| ISIS 560131 | 0 | 25 | 50 | 51 |
| ISIS 569236 | 0 | 5 | 40 | 48 |
| ISIS 549148 | 0 | 0 | 0 | 0 |
| MDV-3100 | 0 | 0 | 34 | 39 |

Gene Expression in CSS Medium and CSS+DHT Media

Cells were plated at 2,000 cells per well and cultured in phenol red-free RPMI supplemented with 5% charcoal stripped serum (Gibco) media for 16 hours. ISIS 560131 or ISIS 569236 was added individually at 0.04 μM, 0.2 μM, 1.0 μM, or 5.0 μM to each cell set. ISIS 549148 was included as a negative control. MDV3100 was added at 0.04 μM, 0.2 μM, 1.0 μM, or 5.0 μM in a separate set of cells. After an incubation period of 4 hrs, DHT was added to the medium to a final concentration of 1 nM as indicated. RNAs were collected 48 hrs later and levels of AR, PSA and TMPRSS2 were measured. The data is presented in Table 82-85. In the absence of DHT, AR expression in LNCaP cells was 95%, PSA expression was 7% and TMPRSS2 expression was 24% compared to the untreated control.

TABLE 82

| Percent expression of AR in LNCaP cells cultured in CSS medium | | | | |
|---|---|---|---|---|
| | 0.04 μM | 0.2 μM | 1 μM | 5.0 μM |
| ISIS 560131 | 81 | 46 | 16 | 5 |
| ISIS 569236 | 94 | 66 | 35 | 13 |
| ISIS 549148 | 106 | 97 | 96 | 104 |
| MDV-3100 | 91 | 67 | 64 | 77 |

TABLE 83

| Percent expression of AR in LNCaP cells cultured in CSS + DHT medium | | | | |
|---|---|---|---|---|
| | 0.04 μM | 0.2 μM | 1 μM | 5.0 μM |
| ISIS 560131 | 101 | 71 | 27 | 10 |
| ISIS 569236 | 104 | 86 | 55 | 21 |
| ISIS 549148 | 98 | 102 | 96 | 111 |
| MDV-3100 | 107 | 121 | 110 | 113 |

TABLE 84

| Percent inhibition of PSA expression in LNCaP cells cultured in CSS + DHT medium | | | | |
|---|---|---|---|---|
| | 0.04 μM | 0.2 μM | 1 μM | 5.0 μM |
| ISIS 560131 | 10 | 21 | 21 | 72 |
| ISIS 569236 | 4 | 11 | 45 | 59 |
| ISIS 549148 | 0 | 8 | 0 | 9 |
| MDV-3100 | 15 | 38 | 81 | 82 |

TABLE 85

| Percent inhibition of TMPRSS2 expression in LNCaP cells cultured in CSS + DHT medium | | | | |
|---|---|---|---|---|
| | 0.04 μM | 0.2 μM | 1 μM | 5.0 μM |
| ISIS 560131 | 6 | 11 | 26 | 64 |
| ISIS 569236 | 6 | 8 | 40 | 50 |
| ISIS 549148 | 0 | 0 | 1 | 10 |
| MDV-3100 | 8 | 24 | 60 | 69 |

Effect on Proliferation in CSS Medium and CSS+DHT Media

After a treatment period of 5 days in complete medium or CSS+1 nM DHT medium, the proliferative capacity of the cancer cells was measured with using CellTiter 96® AQueous One Solution or CellTiter-Glo® solution Cell Proliferation kit (Promega), following the manufacturer's instructions. Results are presented in Tables 86 and 87 as percent inhibition of proliferation, relative to non-treated cells. Treatment of the cells with ISIS 560131, ISIS 569236, and MDV-3100 reduced proliferation of the cells in a dose dependent compared to the control. Treatment with ISIS oligonucleotides in CSS+DHT medium reduced the proliferative capacity to a greater extent than treatment with MVD-3100. The proliferative capacity of cells cultured in CSS medium without DHT is 17% of untreated control levels.

TABLE 86

| Proliferation (% untreated control) in LNCaP cells cultured in complete medium | | | | |
|---|---|---|---|---|
| | 0.04 μM | 0.2 μM | 1 μM | 5.0 μM |
| ISIS 560131 | 96 | 70 | 48 | 45 |
| ISIS 569236 | 100 | 85 | 68 | 54 |
| ISIS 549148 | 101 | 95 | 94 | 110 |
| MDV-3100 | 107 | 88 | 65 | 45 |

TABLE 87

| Proliferation (% untreated control) in LNCaP cells cultured in CSS + DHT medium | | | | |
|---|---|---|---|---|
| | 0.04 μM | 0.2 μM | 1 μM | 5.0 μM |
| ISIS 560131 | 97 | 81 | 46 | 8 |
| ISIS 569236 | 95 | 99 | 54 | 17 |
| ISIS 549148 | 112 | 96 | 95 | 89 |
| MDV-3100 | 112 | 95 | 74 | 33 |

Example 29

Antisense Inhibition of AR mRNA in C4-2 Cells Cultured in Complete Media and CSS Media The effect of antisense inhibition of AR mRNA levels in C4-2 cells cultured in complete medium, as well as CSS medium with DHT, was investigated.

Gene Expression in Complete Medium

Cells were plated at 1,000 cells per well. ISIS 560131 or ISIS 569236 was added individually at 0.04 μM, 0.2 μM, 1.0 μM, or 5.0 μM. ISIS 549148 was included as a negative control. MDV3100 was added at 0.04 μM, 0.2 μM, 1.0 μM, or 5.0 μM in a separate set of cells. After an incubation period of 48 hrs, RNA levels of AR, PSA and TMPRSS2 were measured. The data is presented in Tables 88-90. Treatment with ISIS oligonucleotide inhibited AR expression, whereas treatment with MDV-3100 increased AR expression in the cells.

Protein analysis of full-length AR and PSA also demonstrated a dose-dependent decrease of expression, normalized to levels of the house-keeping gene, GAPDH.

TABLE 88

| Percent expression of AR in C4-2 cells cultured in complete medium | | | | |
|---|---|---|---|---|
| | 0.04 μM | 0.2 μM | 1 μM | 5.0 μM |
| ISIS 560131 | 48 | 13 | 8 | 8 |
| ISIS 569236 | 72 | 27 | 11 | 9 |
| ISIS 549148 | 89 | 90 | 84 | 86 |
| MDV-3100 | 95 | 99 | 132 | 137 |

TABLE 89

| Percent inhibition of PSA expression in C4-2 cells cultured in complete medium | | | | |
|---|---|---|---|---|
| | 0.04 μM | 0.2 μM | 1 μM | 5.0 μM |
| ISIS 560131 | 48 | 78 | 88 | 89 |
| ISIS 569236 | 35 | 62 | 83 | 88 |
| ISIS 549148 | 15 | 24 | 24 | 23 |
| MDV-3100 | 28 | 40 | 72 | 89 |

TABLE 90

| Percent inhibition of TMPRSS2 expression in C4-2 cells cultured in complete medium | | | | |
|---|---|---|---|---|
| | 0.04 μM | 0.2 μM | 1 μM | 5.0 μM |
| ISIS 560131 | 29 | 62 | 76 | 71 |
| ISIS 569236 | 17 | 54 | 67 | 67 |
| ISIS 549148 | 2 | 7 | 10 | 0 |
| MDV-3100 | 10 | 20 | 44 | 67 |

Gene Expression in CSS+DHT Media

Cells were plated at 2,000 cells per well and cultured in CSS media with 1 nM DHT. ISIS 560131 or ISIS 569236 was added individually at 0.04 μM, 0.2 μM, 1.0 μM, or 5.0 μM to each cell set. ISIS 549148 was included as a negative control. MDV3100 was added at 0.04 μM, 0.2 μM, 1.0 μM, or 5.0 μM in a separate set of cells. After an incubation period of 48 hrs, RNA levels of AR, PSA and TMPRSS2 were measured. The data is presented in Table 91-93. In the absence of DHT, AR expression in C4-2 cells was 153%, PSA expression was 42% and TMPRSS2 expression was 23% compared to the untreated control. Treatment with ISIS oligonucleotide inhibited AR expression, whereas treatment with MDV-3100 increased AR expression in the cells.

TABLE 91

| Percent expression of AR in C4-2 cells cultured in CSS + DHT medium | | | | |
|---|---|---|---|---|
| | 0.04 μM | 0.2 μM | 1 μM | 5.0 μM |
| ISIS 560131 | 88 | 57 | 20 | 15 |
| ISIS 569236 | 89 | 82 | 52 | 23 |
| ISIS 549148 | 101 | 101 | 118 | 111 |
| MDV-3100 | 101 | 109 | 156 | 148 |

TABLE 92

| Percent inhibition of PSA expression in C4-2 cells cultured in CSS + DHT medium | | | | |
|---|---|---|---|---|
| | 0.04 μM | 0.2 μM | 1 μM | 5.0 μM |
| ISIS 560131 | 10 | 24 | 49 | 74 |
| ISIS 569236 | 0 | 4 | 57 | 64 |
| ISIS 549148 | 0 | 8 | 21 | 22 |
| MDV-3100 | 9 | 8 | 51 | 73 |

TABLE 93

| Percent inhibition of TMPRSS2 expression in C4-2 cells cultured in CSS + DHT medium | | | | |
|---|---|---|---|---|
| | 0.04 μM | 0.2 μM | 1 μM | 5.0 μM |
| ISIS 560131 | 10 | 17 | 51 | 78 |
| ISIS 569236 | 0 | 11 | 61 | 67 |
| ISIS 549148 | 3 | 0 | 22 | 28 |
| MDV-3100 | 9 | 0 | 44 | 78 |

Effect on Proliferation in CSS Medium and CSS+DHT Media

After a treatment period of 5 days in complete medium or CSS+1 nM DHT medium, the proliferative capacity of the cancer cells was measured with using CellTiter 96® AQueous One Solution or CellTiter-Glo® Cell Proliferation kit (Promega), following the manufacturer's instructions. Results are presented in Tables 94 and 95 as percent inhibition of proliferation, relative to non-treated cells. Treatment of the cells with ISIS 560131, ISIS 569236, and MDV-3100 reduced proliferation of the cells in a dose dependent manner compared to the control. The proliferative capacity of cells cultured in CSS medium without DHT is 17% of untreated control levels.

TABLE 94

| Proliferation (% untreated control) in C4-2 cells cultured in complete medium | | | | |
|---|---|---|---|---|
| | 0.04 μM | 0.2 μM | 1 μM | 5.0 μM |
| ISIS 560131 | 104 | 82 | 70 | 51 |
| ISIS 569236 | 103 | 81 | 57 | 58 |
| ISIS 549148 | 106 | 112 | 91 | 94 |
| MDV-3100 | 105 | 108 | 71 | 67 |

TABLE 95

| Proliferation (% untreated control) in C4-2 cells cultured in CSS + DHT medium | | | | |
|---|---|---|---|---|
| | 0.04 μM | 0.2 μM | 1 μM | 5.0 μM |
| ISIS 560131 | 106 | 94 | 47 | 31 |
| ISIS 569236 | 99 | 99 | 88 | 51 |
| ISIS 549148 | 102 | 82 | 82 | 91 |
| MDV-3100 | 122 | 124 | 87 | 22 |

Example 30

Antisense Inhibition of AR mRNA in C4-2B Cells Cultured in Complete Media and CSS Media The effect of antisense inhibition of AR mRNA levels in C4-2B cells cultured in complete medium, as well as CSS medium with DHT, was investigated.

Gene Expression in Complete Medium

Cells were plated at 1,000 cells per well. ISIS 560131 or ISIS 569236 was added individually at 0.04 μM, 0.2 μM, 1.0 μM, or 5.0 μM. ISIS 549148 was included as a negative control. MDV3100 was added at 0.04 μM, 0.2 μM, 1.0 μM, or 5.0 μM in a separate set of cells. After an incubation period of 48 hrs, RNA levels of AR, PSA and TMPRSS2 were measured. The data is presented in Tables 96-98. Treatment with ISIS oligonucleotide inhibited AR expression, whereas treatment with MDV-3100 increased AR expression in the cells.

Protein analysis of full-length AR also demonstrated a dose-dependent decrease of expression, normalized to levels of the house-keeping gene, GAPDH.

TABLE 96

| Percent expression of AR in C4-2B cells cultured in complete medium | | | | |
|---|---|---|---|---|
| | 0.04 μM | 0.2 μM | 1 μM | 5.0 μM |
| ISIS 560131 | 34 | 15 | 14 | 14 |
| ISIS 569236 | 61 | 23 | 20 | 16 |
| ISIS 549148 | 101 | 91 | 88 | 87 |
| MDV-3100 | 108 | 121 | 157 | 182 |

TABLE 97

| Percent inhibition of PSA expression in C4-2B cells cultured in complete medium | | | | |
|---|---|---|---|---|
| | 0.04 μM | 0.2 μM | 1 μM | 5.0 μM |
| ISIS 560131 | 56 | 84 | 89 | 92 |
| ISIS 569236 | 30 | 72 | 81 | 89 |
| ISIS 549148 | 3 | 11 | 18 | 14 |
| MDV-3100 | 8 | 27 | 73 | 88 |

TABLE 98

| Percent inhibition of TMPRSS2 expression in C4-2B cells cultured in complete medium | | | | |
|---|---|---|---|---|
| | 0.04 μM | 0.2 μM | 1 μM | 5.0 μM |
| ISIS 560131 | 46 | 71 | 72 | 75 |
| ISIS 569236 | 33 | 59 | 69 | 73 |
| ISIS 549148 | 0 | 2 | 4 | 0 |
| MDV-3100 | 3 | 24 | 55 | 71 |

Gene Expression in CSS+DHT Media

Cells were plated at 2,000 cells per well and cultured in CSS media with 1 nM DHT. ISIS 560131 or ISIS 569236 was added individually at 0.04 μM, 0.2 μM, 1.0 μM, or 5.0 μM to each cell set. ISIS 549148 was included as a negative control. MDV3100 was added at 0.04 μM, 0.2 μM, 1.0 μM, or 5.0 μM in a separate set of cells. After an incubation period of 48 hrs, RNA levels of AR, PSA and TMPRSS2 were measured. The data is presented in Tables 99-101. In the absence of DHT, AR expression in C4-2 cells was 188%, PSA expression was 43% and TMPRSS2 expression was 27% compared to the untreated control. Treatment with ISIS oligonucleotide inhibited AR expression, whereas treatment with MDV-3100 increased AR expression in the cells.

TABLE 99

| Percent expression of AR in C4-2B cells cultured in CSS + DHT medium | | | | |
|---|---|---|---|---|
| | 0.04 μM | 0.2 μM | 1 μM | 5.0 μM |
| ISIS 560131 | 55 | 31 | 15 | 13 |
| ISIS 569236 | 67 | 49 | 24 | 19 |
| ISIS 549148 | 91 | 104 | 101 | 95 |
| MDV-3100 | 112 | 144 | 165 | 173 |

TABLE 100

| Percent inhibition of PSA expression in C4-2B cells cultured in CSS + DHT medium | | | | |
|---|---|---|---|---|
| | 0.04 μM | 0.2 μM | 1 μM | 5.0 μM |
| ISIS 560131 | 0 | 17 | 50 | 61 |
| ISIS 569236 | 0 | 5 | 33 | 46 |
| ISIS 549148 | 0 | 0 | 0 | 0 |
| MDV-3100 | 0 | 0 | 37 | 45 |

TABLE 101

| Percent inhibition of TMPRSS2 expression in C4-2B cells cultured in CSS + DHT medium | | | | |
|---|---|---|---|---|
| | 0.04 μM | 0.2 μM | 1 μM | 5.0 μM |
| ISIS 560131 | 0 | 34 | 60 | 76 |
| ISIS 569236 | 0 | 6 | 43 | 59 |
| ISIS 549148 | 0 | 0 | 0 | 3 |
| MDV-3100 | 0 | 11 | 48 | 66 |

Effect on Proliferation in CSS Medium and CSS+DHT Media

After a treatment period of 5 days in complete medium or CSS+1 nM DHT medium, the proliferative capacity of the cancer cells was measured with using CellTiter 96® AQueous One or CellTiter-Glo® Solution Cell Proliferation kit (Promega), following the manufacturer's instructions. Results are presented in Tables 102 and 103 as percent inhibition of proliferation, relative to non-treated cells. Treatment of the cells with ISIS 560131, ISIS 569236, and MDV-3100 reduced proliferation of the cells in a dose dependent compared to the control. Treatment with ISIS oligonucleotides in CSS+DHT medium reduced the proliferative capacity to a greater extent than treatment with MVD-3100. The proliferative capacity of cells cultured in CSS medium without DHT is 12% of untreated control levels.

TABLE 102

| Proliferation (% untreated control) in C4-2B cells cultured in complete medium | | | | |
|---|---|---|---|---|
| | 0.04 μM | 0.2 μM | 1 μM | 5.0 μM |
| ISIS 560131 | 93 | 50 | 50 | 41 |
| ISIS 569236 | 98 | 64 | 55 | 48 |
| ISIS 549148 | 119 | 97 | 103 | 98 |
| MDV-3100 | 131 | 105 | 72 | 60 |

TABLE 103

| Proliferation (% untreated control) in C4-2B cells cultured in CSS + DHT medium | | | | |
|---|---|---|---|---|
| | 0.04 μM | 0.2 μM | 1 μM | 5.0 μM |
| ISIS 560131 | 111 | 75 | 49 | 40 |
| ISIS 569236 | 109 | 109 | 67 | 39 |
| ISIS 549148 | 109 | 131 | 119 | 114 |
| MDV-3100 | 125 | 100 | 83 | 17 |

Example 31

Antisense Inhibition of AR mRNA in VCaP Cells Cultured in Complete Media and CSS Media The effect of antisense inhibition of AR in VCaP prostate cancer cells (Korenchuk, S. et al., In Vivo. 2001. 15: 163-168) cultured in complete medium, as well as CSS medium with DHT, was investigated. VCaP cells express both full length AR, as well as the V7 variant.

Gene Expression in Complete Medium

Cells were plated at 10,000 cells per well. ISIS 560131 or ISIS 569236 was added individually at 1.34 nM, 4 nM, 13.4 nM, or 40 nM using RNAiMax transfection reagent. ISIS 549148 was included as a negative control. After an incubation period of 48 hrs, RNA levels of full length AR, the V7 variant, PSA and TMPRSS2 were measured. The data is presented in Tables 104-107.

Protein analysis of full-length AR and the V7 variant also demonstrated a dose-dependent decrease of expression of both compared to levels of the house-keeping gene, GAPDH.

TABLE 104

| Percent inhibition of full-length AR in VCaP cells cultured in complete medium | | | | |
|---|---|---|---|---|
| | 1.34 nM | 4.0 nM | 13.4 nM | 40 nM |
| ISIS 560131 | 0 | 59 | 77 | 84 |
| ISIS 569236 | 0 | 41 | 49 | 74 |
| ISIS 549148 | 0 | 8 | 5 | 17 |

TABLE 105

| Percent inhibition of AR V7 variant in VCaP cells cultured in complete medium | | | | |
|---|---|---|---|---|
| | 1.34 nM | 4.0 nM | 13.4 nM | 40 nM |
| ISIS 560131 | 0 | 57 | 78 | 84 |
| ISIS 569236 | 0 | 40 | 53 | 80 |
| ISIS 549148 | 0 | 8 | 0 | 14 |

TABLE 106

| Percent inhibition of PSA expression in VCaP cells cultured in complete medium | | | | |
|---|---|---|---|---|
| | 1.34 nM | 4.0 nM | 13.4 nM | 40 nM |
| ISIS 560131 | 2 | 24 | 35 | 46 |
| ISIS 569236 | 7 | 19 | 40 | 52 |
| ISIS 549148 | 2 | 0 | 0 | 20 |

TABLE 107

| Percent inhibition of TMPRSS2 expression in VCaP cells cultured in complete medium | | | | |
|---|---|---|---|---|
| | 1.34 nM | 4.0 nM | 13.4 nM | 40 nM |
| ISIS 560131 | 0 | 0 | 0 | 4 |
| ISIS 569236 | 0 | 0 | 0 | 36 |
| ISIS 549148 | 0 | 0 | 0 | 0 |

A separate set of cells was treated with MDV-3100 at 0.04 μM, 0.2 μM, 1.0 μM, or 5.0 μM. After an incubation period of 48 hrs, RNA levels of full length AR, the V7 variant, PSA and TMPRSS2 were measured. The data is presented in Tables 108 expressed as percent expression of gene levels compared to the untreated control.

TABLE 108

Percent of gene expression in VCaP cells treated with MDV-3100 and cultured in complete medium

| | 0.04 μM | 0.2 μM | 1.0 μM | 5.0 μM |
|---|---|---|---|---|
| Full length AR | 136 | 135 | 160 | 178 |
| AR V7 variant | 172 | 179 | 244 | 237 |
| PSA | 105 | 76 | 75 | 61 |
| TMPRSS2 | 131 | 121 | 135 | 141 |

Gene Expression in CSS+DHT Media

Cells were plated at 15,000 cells per well and cultured in CSS media for 16 hours. Cells were then transfected using RNAiMax reagent with ISIS 560131 or ISIS 569236 at 1.34 nM, 4 nM, 13.4 nM, or 40 nM to each cell set. ISIS 549148 was included as a negative control. After 4 hrs, 1 nM DHT was added. MDV3100 was added in a separate set of cells at doses of 0.04 μM, 0.2 μM, 1.0 μM, or 5.0 μM. After an incubation period of 48 hrs, RNA levels of AR, PSA and TMPRSS2 were measured. The data is presented in Tables 109-113. In the absence of DHT, AR expression in VCaP cells was 555%, V7 variant expression was 656%, PSA expression was 11%, and TMPRSS2 expression was 22% compared to the untreated control.

TABLE 109

Percent inhibition of full-length AR in VCaP cells cultured in CSS medium

| | 1.34 nM | 4.0 nM | 13.4 nM | 40 nM |
|---|---|---|---|---|
| ISIS 560131 | 12 | 16 | 37 | 38 |
| ISIS 569236 | 23 | 21 | 38 | 35 |
| ISIS 549148 | 0 | 0 | 0 | 0 |

TABLE 110

Percent inhibition of AR V7 variant in VCaP cells cultured in CSS + DHT medium

| | 1.34 nM | 4.0 nM | 13.4 nM | 40 nM |
|---|---|---|---|---|
| ISIS 560131 | 27 | 31 | 39 | 41 |
| ISIS 569236 | 37 | 33 | 48 | 39 |
| ISIS 549148 | 12 | 0 | 0 | 5 |

TABLE 111

Percent inhibition of PSA expression in VCaP cells cultured in CSS + DHT medium

| | 1.34 nM | 4.0 nM | 13.4 nM | 40 nM |
|---|---|---|---|---|
| ISIS 560131 | 0 | 35 | 69 | 73 |
| ISIS 569236 | 8 | 25 | 62 | 74 |
| ISIS 549148 | 0 | 3 | 9 | 0 |

TABLE 112

Percent inhibition of TMPRSS2 expression in VCaP cells cultured in CSS + DHT medium

| | 1.34 nM | 4.0 nM | 13.4 nM | 40 nM |
|---|---|---|---|---|
| ISIS 560131 | 0 | 21 | 49 | 57 |
| ISIS 569236 | 6 | 19 | 40 | 54 |
| ISIS 549148 | 0 | 0 | 0 | 0 |

TABLE 113

Percent of gene expression in VCaP cells treated with MDV-3100 and cultured in CSS + DHT medium

| | 0.04 μM | 0.2 μM | 1.0 μM | 5.0 μM |
|---|---|---|---|---|
| Full length AR | 114 | 94 | 142 | 233 |
| AR V7 variant | 82 | 65 | 101 | 181 |
| PSA | 90 | 72 | 57 | 30 |
| TMPRSS2 | 115 | 96 | 70 | 42 |

Effect on Proliferation

After a treatment period of 5 days in complete medium or CSS+1 nM DHT medium, the proliferative capacity of the cancer cells was measured with using CellTiter 96® AQueous One or CellTiter-Glo® Solution Cell Proliferation kit (Promega), following the manufacturer's instructions. Results are presented in Tables 114-116 as percent inhibition of proliferation, relative to non-treated cells. Treatment of the cells with ISIS 560131, ISIS 569236, and MDV-3100 reduced proliferation of the cells in a dose dependent compared to the control. Treatment with ISIS oligonucleotides in CSS+DHT medium reduced the proliferative capacity to a greater extent than treatment with MVD-3100. The proliferative capacity of cells cultured in CSS medium without DHT is 12% of untreated control levels.

TABLE 114

Proliferation (% untreated control) in VCaP cells cultured in complete medium

| | 1.34 nM | 4.0 nM | 13.4 nM | 40 nM |
|---|---|---|---|---|
| ISIS 560131 | 98 | 66 | 53 | 48 |
| ISIS 569236 | 98 | 76 | 68 | 59 |
| ISIS 549148 | 98 | 98 | 113 | 106 |

TABLE 115

Proliferation (% untreated control) in VCaP cells cultured in CSS + DHT medium

| | 1.34 nM | 4.0 nM | 13.4 nM | 40 nM |
|---|---|---|---|---|
| ISIS 560131 | 95 | 65 | 42 | 37 |
| ISIS 569236 | 83 | 68 | 61 | 45 |
| ISIS 549148 | 114 | 123 | 104 | 92 |

TABLE 116

Proliferation (% untreated control) in VCaP cells treated with MDV-3100

| | Complete medium | CSS + DHT medium |
|---|---|---|
| 0.04 μM | 49 | 117 |
| 0.2 μM | 44 | 119 |

TABLE 116-continued

| Proliferation (% untreated control) in VCaP cells treated with MDV-3100 | | |
|---|---|---|
| | Complete medium | CSS + DHT medium |
| 1.0 μM | 27 | 71 |
| 5.0 μM | 17 | 65 |

Effect on Apoptosis

After a treatment period of 72 hours in complete medium, apoptosis of the cancer cells was measured with Caspase-Glo 3/7 assay (Promega). Results are presented in Tables 117 and 118 as percent apoptosis of the cells, relative to non-treated cells. Treatment of the cells with ISIS 560131, ISIS 569236, and MDV-3100 increased apoptosis of the cells in a dose dependent compared to the control.

Apoptosis was also measured by protein western blot analysis of cleaved PARP levels, which were shown to be increased in a dose-dependent manner in cells treated with ISIS 560131, ISIS 569236, and MDV-3100.

TABLE 117

| Apoptosis (% untreated control) in VCaP cells cultured in complete medium | | | | |
|---|---|---|---|---|
| | 1.34 nM | 4.0 nM | 13.4 nM | 40 nM |
| ISIS 560131 | 189 | 253 | 356 | 262 |
| ISIS 569236 | 176 | 293 | 402 | 581 |
| ISIS 549148 | 131 | 108 | 103 | 146 |

TABLE 118

| Apoptosis (% untreated control) in VCaP cells treated with MDV-3100 | |
|---|---|
| | % |
| 0.04 μM | 186 |
| 0.2 μM | 210 |
| 1.0 μM | 612 |
| 5.0 nM | 528 |

Example 32

Antisense Inhibition of AR mRNA in 22RV1 Cells Cultured in Complete Media and CSS Media The effect of antisense inhibition of AR in 22RV1 cells cultured in complete medium, as well as CSS medium with DHT, was investigated.

Gene Expression in Complete Medium

Cells were plated at 1,000 cells per well. ISIS 560131 or ISIS 569236 was added individually at 1.34 nM, 4 nM, 13.4 nM, or 40 nM using RNAiMax transfection reagent. ISIS 549148 was included as a negative control. After an incubation period of 48 hrs, RNA levels of full length AR, the V7 variant, PSA and TMPRSS2 were measured. The data is presented in Tables 119-122.

Protein analysis of full-length AR and the V7 variant also demonstrated a dose-dependent decrease of expression compared to levels of the house-keeping gene, GAPDH.

TABLE 119

| Percent inhibition of full-length AR in 22RV1 cells cultured in complete medium | | | | |
|---|---|---|---|---|
| | 1.34 nM | 4.0 nM | 13.4 nM | 40 nM |
| ISIS 560131 | 7 | 19 | 49 | 76 |
| ISIS 569236 | 17 | 15 | 37 | 71 |
| ISIS 549148 | 6 | 0 | 11 | 17 |

TABLE 120

| Percent inhibition of AR V7 variant in 22RV1 cells cultured in complete medium | | | | |
|---|---|---|---|---|
| | 1.34 nM | 4.0 nM | 13.4 nM | 40 nM |
| ISIS 560131 | 12 | 29 | 57 | 81 |
| ISIS 569236 | 30 | 2 | 46 | 81 |
| ISIS 549148 | 0 | 0 | 22 | 26 |

TABLE 121

| Percent inhibition of PSA expression in 22RV1 cells cultured in complete medium | | | | |
|---|---|---|---|---|
| | 1.34 nM | 4.0 nM | 13.4 nM | 40 nM |
| ISIS 560131 | 10 | 20 | 27 | 36 |
| ISIS 569236 | 0 | 17 | 25 | 7 |
| ISIS 549148 | 9 | 11 | 17 | 27 |

TABLE 122

| Percent inhibition of TMPRSS2 expression in 22RV1 cells cultured in complete medium | | | | |
|---|---|---|---|---|
| | 1.34 nM | 4.0 nM | 13.4 nM | 40 nM |
| ISIS 560131 | 7 | 3 | 19 | 32 |
| ISIS 569236 | 0 | 13 | 21 | 36 |
| ISIS 549148 | 15 | 9 | 14 | 4 |

A separate set of cells was treated with MDV-3100 at 0.04 μM, 0.2 μM, 1.0 μM, or 5.0 μM. After an incubation period of 48 hrs, RNA levels of full length AR, the V7 variant, PSA and TMPRSS2 were measured. The data is presented in Tables 123 expressed as percent expression of gene levels compared to the untreated control.

TABLE 123

| Percent of gene expressionin 22RV1 cells treated with MDV-3100 and cultured in complete medium | | | | |
|---|---|---|---|---|
| | 0.04 μM | 0.2 μM | 1.0 μM | 5.0 μM |
| Full length AR | 103 | 93 | 81 | 83 |
| AR V7 variant | 106 | 98 | 87 | 77 |
| PSA | 83 | 70 | 71 | 86 |
| TMPRSS2 | 101 | 80 | 82 | 93 |

Gene Expression in CSS+DHT Media

Cells were plated at 2,000 cells per well and cultured in CSS media for 16 hours. Cells were then transfected using RNAiMax reagent with ISIS 560131 or ISIS 569236 at 1.34 nM, 4 nM, or 13.4 nM to each cell set. ISIS 549148 was included as a negative control. After 4 hrs, 1 nM DHT was added. MDV3100 was added in a separate set of cells at doses of 0.04 μM, 0.2 μM, 1.0 μM, or 5.0 μM. After an incubation period of 48 hrs, RNA levels of AR, AR V7 variant, PSA and TMPRSS2 were measured. The data is presented in Tables 124-128. In the absence of DHT, AR expression in VCaP cells was 555%, V7 variant expression was 656%, PSA expression was 11%, and TMPRSS2 expression was 22% compared to the untreated control.

Treatment with ISIS oligonucleotides resulted in significant inhibition of full length AR and the V7 variant, as well as downstream gene expression. Treatment with ISIS oligonucleotides resulted in inhibition of gene expression to a greater extent than treatment with MVD-3100.

TABLE 124

Percent inhibition of full-length AR in 22RV1 cells cultured in CSS + DHT medium

| | 1.34 nM | 4.0 nM | 13.4 nM |
|---|---|---|---|
| ISIS 560131 | 65 | 85 | 93 |
| ISIS 569236 | 59 | 89 | 97 |
| ISIS 549148 | 2 | 13 | 22 |

TABLE 125

Percent inhibition of AR V7 variant in 22RV1 cells cultured in CSS + DHT medium

| | 1.34 nM | 4.0 nM | 13.4 nM |
|---|---|---|---|
| ISIS 560131 | 63 | 83 | 93 |
| ISIS 569236 | 54 | 88 | 97 |
| ISIS 549148 | 19 | 19 | 32 |

TABLE 126

Percent inhibition of PSA expression in 22RV1 cells cultured in CSS + DHT medium

| | 1.34 nM | 4.0 nM | 13.4 nM |
|---|---|---|---|
| ISIS 560131 | 3 | 50 | 66 |
| ISIS 569236 | 28 | 49 | 70 |
| ISIS 549148 | 8 | 23 | 29 |

TABLE 127

Percent inhibition of TMPRSS2 expression in 22RV1 cells cultured in CSS + DHT medium

| | 1.34 nM | 4.0 nM | 13.4 nM |
|---|---|---|---|
| ISIS 560131 | 39 | 50 | 59 |
| ISIS 569236 | 27 | 50 | 75 |
| ISIS 549148 | 0 | 3 | 1 |

TABLE 128

Percent of gene expression in 22RV1 cells treated with MDV-3100 and cultured in CSS + DHT medium

| | 0.04 μM | 0.2 μM | 1.0 μM | 5.0 μM |
|---|---|---|---|---|
| Full length AR | 5 | 11 | 6 | 18 |
| AR V7 variant | 16 | 17 | 19 | 12 |
| PSA | 15 | 19 | 18 | 16 |
| TMPRSS2 | 17 | 9 | 26 | 18 |

Effect on Proliferation

After a treatment period of 5 days in complete medium, the proliferative capacity of the cancer cells was measured with using CellTiter 96® AQueous One or CellTiter-Glo® Solution Cell Proliferation kit (Promega), following the manufacturer's instructions. Results are presented in Tables 129 and 130 as percent inhibition of proliferation, relative to non-treated cells. Treatment of the cells with ISIS 560131, ISIS 569236, and MDV-3100 reduced proliferation of the cells in a dose dependent compared to the control. Treatment with ISIS oligonucleotides in CSS+DHT medium reduced the proliferative capacity to a greater extent than treatment with MVD-3100. The proliferative capacity of cells cultured in CSS medium without DHT is 12% of untreated control levels.

TABLE 129

Proliferation (% untreated control) in 22RV1 cells cultured in complete medium

| | 1.34 nM | 4.0 nM | 13.4 nM | 40 nM |
|---|---|---|---|---|
| ISIS 560131 | 94 | 72 | 50 | 17 |
| ISIS 569236 | 92 | 53 | 20 | 7 |
| ISIS 549148 | 97 | 97 | 101 | 83 |

TABLE 130

Proliferation (% untreated control) in 22RV1 cells treated with MDV-3100

| | % |
|---|---|
| 0.04 μM | 87 |
| 0.2 μM | 83 |
| 1.0 μM | 81 |
| 5.0 μM | 74 |

Effect on Apoptosis

After a treatment period of 72 hours in complete medium or CSS+DHT medium, apoptosis of the cancer cells was measured with Caspase-glo 3/7 assay kit (Promega). Results are presented in Tables 131 and 132 as percent apoptosis of the cells, relative to non-treated cells. Treatment of the cells with ISIS 560131 and ISIS 569236 increased apoptosis of the cells in a dose dependent compared to the control.

TABLE 131

Apoptosis (% untreated control) in 22RV1 cells cultured in complete medium

| | 1.34 nM | 4.0 nM | 13.4 nM | 40 nM |
|---|---|---|---|---|
| ISIS 560131 | 99 | 127 | 131 | 566 |
| ISIS 569236 | 91 | 141 | 333 | 1452 |
| ISIS 549148 | 81 | 76 | 72 | 123 |

TABLE 132

Apoptosis (% untreated control) in 22RV1 cells cultured in CSS + DHT medium

| | 1.34 nM | 4.0 nM | 13.4 nM | 40 nM |
|---|---|---|---|---|
| ISIS 560131 | 121 | 113 | 172 | 518 |
| ISIS 569236 | 127 | 106 | 257 | 1136 |
| ISIS 549148 | 113 | 94 | 102 | 108 |

Example 33

Effect of ISIS Antisense Oligonucleotides Targeting Human Androgen Receptor in Cynomolgus Monkeys Cynomolgus monkeys were treated with ISIS antisense oligonucleotides selected from studies described above. Antisense oligonucleotide efficacy and tolerability were evaluated. The human antisense oligonucleotides tested are cross-reactive with the rhesus genomic sequence (GENBANK Accession No. NW_001218131.1 truncated from nucleotides 134001 to 308000 and designated herein as SEQ ID NO: 189). The target start site and target region of each oligonucleotide to SEQ ID NO: 189, as well as the details of their chemistry and sequence, is presented in Table 133.

TABLE 133

Antisense oligonucleotides complementary to SEQ ID NO: 189

| ISIS No | Target Start Site | Target Region | Sequence | Chemistry | SEQ ID NO |
|---|---|---|---|---|---|
| 560131 | 59450 | Intron | TTGATTTAATGGTTGC | Deoxy, MOE, and (S)-cEt | 35 |
| 569213 | 59449 | Intron | TGATTTAATGGTTGCA | Deoxy, MOE, and (S)-cEt | 39 |
| | 59479 | | TGATTTAATGGTTGCA | | 39 |
| 569216 | 59449 | Intron | TGATTTAATGGTTGCA | Deoxy, MOE, and (S)-cEt | 39 |
| | 59479 | | TGATTTAATGGTTGCA | | 39 |
| 569221 | 59449 | Intron | TGATTTAATGGTTGCA | Deoxy, MOE, and (S)-cEt | 39 |
| | 59479 | | TGATTTAATGGTTGCA | | 39 |
| 569236 | 59449 | Intron | TGATTTAATGGTTGCA | Deoxy, MOE, and (S)-cEt | 39 |
| | 59479 | | TGATTTAATGGTTGCA | | 39 |
| 579671 | 59450 | Intron | TTGATTTAATGGTTGC | Deoxy, MOE, and (S)-cEt | 35 |
| 586124 | 59448 | Intron | GATTTAATGGTTGCAA | 3-10-3 (S)-cEt | 43 |
| 583918 | 3754 | Exon | AGTCGCGACTCTGGTA | 3-10-3 (S)-cEt | 124 |
| 584149 | 7260 | Intron | GTCAATATCAAAGCAC | 3-10-3 (S)-cEt | 150 |
| 584163 | 9811 | Intron | GAACATTATTAGGCTA | 3-10-3 (S)-cEt | 155 |
| 584269 | 41322 | Intron | CCTTATGGATGCTGCT | 3-10-3 (S)-cEt | 169 |
| 584468 | 109552 | Intron | CATTGTACTATGCCAG | 3-10-3 (S)-cEt | 175 |

Treatment

Prior to the study, the monkeys were kept in quarantine for a 30-day period, during which the animals were observed daily for general health. The monkeys were 2-4 years old and weighed between 2 and 4 kg. Thirteen groups of four randomly assigned male cynomolgus monkeys each were injected subcutaneously with ISIS oligonucleotide or PBS. PBS solution or ISIS oligonucleotides, at a dose of 40 mg/kg, were administered with a loading regimen consisting of four doses on the first week of the study (days 1, 3, 5, and 7), followed by a maintenance regimen consisting of once weekly administration starting on Day 14 (weeks 2 to 6). Subcutaneous injections were performed in clock-wise rotations at 4 sites on the back; one site per dose. The injection sites were delineated by tattoo, while sedated using ketamine, and were separated by a minimum of 3 cm.

During the study period, the monkeys were observed a minimum of once daily for signs of illness or distress. The protocols described in the Example were approved by the Institutional Animal Care and Use Committee (IACUC).

Target Reduction

RNA Analysis

RNA was extracted from liver, heart, skeletal muscle, kidney, and prostate tissues for real-time PCR analysis of AR using primer probe set RTS3559. The results were normalized to RIBOGREEN®. Results are presented as percent inhibition of AR mRNA, relative to PBS control. As shown in Table 134, treatment with ISIS antisense oligonucleotides resulted in significant reduction of AR mRNA, relative to the PBS control. 'n/a' indicates that mRNA levels were not measured in that organ.

TABLE 134

Percent Inhibition of AR mRNA in the cynomolgus monkey relative to the PBS control

| ISIS No | Heart | Skeletal Muscle | Kidney | Liver | Prostate |
|---|---|---|---|---|---|
| 560131 | 32 | 30 | 19 | 65 | 27 |
| 569221 | 52 | 35 | 31 | 60 | n/a |
| 569236 | 42 | 47 | 42 | 33 | 32 |
| 579671 | 24 | 31 | 53 | 33 | n/a |
| 583918 | 76 | 74 | 73 | 88 | 58 |
| 584149 | 33 | 63 | 77 | 93 | 45 |
| 584163 | 53 | 73 | 90 | 98 | 58 |
| 584269 | 72 | 76 | 92 | 96 | 41 |
| 584468 | 33 | 53 | 88 | 97 | 50 |

Protein Analysis

Serum testosterone protein levels were measured in the plasma with an ELISA kit (Enzo Life Sciences), following the manufacturer's instructions. The results are presented in Table 135, expressed in ng/mL. The results indicate that some of the ISIS oligonucleotides reduced testosterone protein levels.

TABLE 135

Testosterone protein levels in the cynomolgus monkey

| | ng/mL |
|---|---|
| PBS | 12.6 |
| ISIS 560131 | 14.7 |
| ISIS 569221 | 8.8 |
| ISIS 569236 | 12.7 |
| ISIS 579671 | 7.3 |
| ISIS 584269 | 14.1 |
| ISIS 584468 | 13.6 |

Tolerability Studies

Body and Organ Weight Measurements

To evaluate the effect of ISIS oligonucleotides on the overall health of the animals, body and organ weights were measured. Body weights were measured on day 42 and are presented in Table 136. Organ weights were measured at the time of euthanasia and the data is also presented in Table 136. Specifically, treatment with ISIS 560131 was well tolerated in terms of the body and organ weights of the monkeys.

TABLE 136

Final body and organ weights in cynomolgus monkeys

| Treatment | Body Wt (kg) | Spleen (g) | Heart (g) | Kidney (g) | Mesenteric lymph nodes (g) | Liver (g) |
|---|---|---|---|---|---|---|
| PBS | 2.5 | 2.6 | 8.5 | 13 | 1.4 | 58 |
| ISIS 560131 | 2.4 | 2.5 | 9.8 | 12 | 2.0 | 58 |
| ISIS 569213 | 2.4 | 5.3 | 8.3 | 16 | 2.4 | 69 |
| ISIS 569216 | 2.6 | 4.9 | 9.3 | 15 | 2.7 | 71 |
| ISIS 569221 | 2.5 | 3.3 | 8.5 | 14 | 3.5 | 68 |
| ISIS 569236 | 2.4 | 3.2 | 8.4 | 12 | 2.4 | 56 |
| ISIS 579671 | 2.4 | 3.2 | 8.8 | 14 | 2.5 | 62 |
| ISIS 586124 | 2.5 | 3.3 | 9.4 | 14 | 2.8 | 58 |
| ISIS 583918 | 2.5 | 4.6 | 8.9 | 12 | 3.5 | 60 |
| ISIS 584149 | 2.5 | 2.2 | 9.3 | 13 | 2.1 | 60 |
| ISIS 584163 | 2.5 | 3.2 | 8.4 | 15 | 3.3 | 54 |
| ISIS 584269 | 2.5 | 4.7 | 8.7 | 13 | 3.6 | 60 |
| ISIS 584468 | 2.5 | 4.1 | 8.3 | 13 | 3.8 | 60 |

Liver Function

To evaluate the effect of ISIS oligonucleotides on hepatic function, the monkeys were fasted overnight. Approximately, 1.5 mL of blood samples were collected on day 44 from all the study groups. Blood was collected in tubes without anticoagulant for serum separation. The tubes were kept at room temperature for a minimum of 90 min and then centrifuged at 3,000 rpm for 10 min. Levels of various liver function markers were measured using a Toshiba 120FR NEO chemistry analyzer (Toshiba Co., Japan). The results are presented in Table 137. Specifically, treatment with ISIS 560131 was well tolerated in terms of the liver function markers.

TABLE 137

Liver function markers in cynomolgus monkey plasma

| Treatment | Albumin (g/dL) | AST (IU/L) | ALT (IU/L) |
|---|---|---|---|
| PBS | 4.2 | 37 | 39 |
| ISIS 560131 | 4.0 | 87 | 68 |
| ISIS 569213 | 3.7 | 80 | 47 |
| ISIS 569216 | 3.7 | 93 | 75 |
| ISIS 569221 | 4.0 | 73 | 48 |
| ISIS 569236 | 4.1 | 45 | 35 |
| ISIS 579671 | 4.0 | 53 | 56 |
| ISIS 586124 | 3.9 | 94 | 56 |
| ISIS 583918 | 4.1 | 73 | 75 |
| ISIS 584149 | 4.5 | 58 | 57 |
| ISIS 584163 | 4.2 | 68 | 50 |
| ISIS 584269 | 4.0 | 81 | 75 |
| ISIS 584468 | 4.0 | 52 | 46 |

Hematology

To evaluate any effect of ISIS oligonucleotides in cynomolgus monkeys on hematologic parameters, blood samples of approximately 0.5 mL of blood was collected day 44 from each of the available study animals in tubes containing $K_2$-EDTA. Samples were analyzed for red blood cell (RBC) count, white blood cells (WBC) count, platelet count, hemoglobin content and hematocrit, using an ADVIA2120i hematology analyzer (SIEMENS, USA). The data is presented in Table 138.

The data indicate treatment with most of the oligonucleotides did not cause any changes in hematologic parameters outside the expected range for antisense oligonucleotides at this dose. Specifically, treatment with ISIS 560131 was well tolerated in terms of the hematology of the monkeys.

TABLE 138

Hematological parameters in cynomolgus monkeys

| Treatment | RBC ($\times 10^6$ μL) | Platelets ($\times 10^3$ μL) | WBC ($\times 10^3$ μL) | Hemoglobin (g/dL) | HCT (%) |
|---|---|---|---|---|---|
| PBS | 5.3 | 426 | 13.6 | 13.2 | 43 |
| ISIS 560131 | 5.8 | 392 | 11.3 | 13.1 | 44 |
| ISIS 569213 | 5.6 | 426 | 12.9 | 12.5 | 42 |
| ISIS 569216 | 5.6 | 504 | 12.2 | 12.8 | 43 |
| ISIS 569221 | 5.6 | 406 | 11.1 | 12.9 | 45 |
| ISIS 569236 | 5.7 | 358 | 14.4 | 13.1 | 44 |
| ISIS 579671 | 5.4 | 438 | 10.0 | 12.5 | 42 |
| ISIS 586124 | 5.8 | 391 | 10.4 | 13.6 | 45 |
| ISIS 583918 | 5.8 | 435 | 12.7 | 13.3 | 46 |
| ISIS 584149 | 5.7 | 478 | 11.3 | 13.7 | 45 |
| ISIS 584163 | 5.5 | 461 | 9.1 | 12.8 | 44 |
| ISIS 584269 | 5.2 | 522 | 9.8 | 12.4 | 41 |
| ISIS 584468 | 5.9 | 408 | 11.1 | 13.5 | 45 |

Kidney Function

To evaluate the effect of ISIS oligonucleotides on kidney function, the monkeys were fasted overnight. Approximately, 1.5 mL of blood samples were collected from all the study groups on day 44. Blood was collected in tubes without anticoagulant for serum separation. The tubes were kept at room temperature for a minimum of 90 min and then centrifuged at 3,000 rpm for 10 min. Levels of BUN and creatinine were measured using a Toshiba 120FR NEO chemistry analyzer (Toshiba Co., Japan). Results are presented in Table 139, expressed in mg/dL. The plasma chemistry data indicate that most of the ISIS oligonucleotides did not have any effect on the kidney function outside the expected range for antisense oligonucleotides. Specifically, treatment with ISIS 560131 was well tolerated in terms of the kidney function of the monkeys.

Kidney function was also assessed by urinalysis. Fresh urine from all animals was collected on day 44 using a clean cage pan on wet ice. Food was removed overnight the day before fresh urine collection was done but water was supplied. The total protein and creatinine levels were measured using a Toshiba 120FR NEO automated chemistry analyzer (Toshiba Co., Japan) and the protein to creatinine ratio was calculated. The results are presented in Table 140.

TABLE 139

Plasma BUN and creatinine levels (mg/dL) in cynomolgus monkeys

| Treatment | BUN | Creatinine |
|---|---|---|
| PBS | 30.5 | 0.78 |
| ISIS 560131 | 23.7 | 0.84 |
| ISIS 569213 | 29.4 | 0.91 |
| ISIS 569216 | 28.4 | 0.81 |
| ISIS 569221 | 20.2 | 0.86 |
| ISIS 569236 | 24.9 | 0.87 |
| ISIS 579671 | 22.7 | 0.74 |
| ISIS 586124 | 23.8 | 0.87 |
| ISIS 583918 | 24.5 | 0.87 |
| ISIS 584149 | 26.4 | 0.85 |
| ISIS 584163 | 22.4 | 0.82 |
| ISIS 584269 | 21.8 | 0.89 |
| ISIS 584468 | 22.2 | 0.78 |

TABLE 140

Urine protein/creatinine ratio in cynomolgus monkeys

| Treatment | Ratio |
|---|---|
| PBS | 0.00 |
| ISIS 560131 | 0.02 |
| ISIS 569213 | 0.02 |
| ISIS 569216 | 0.08 |
| ISIS 569221 | 0.00 |
| ISIS 569236 | 0.02 |
| ISIS 579671 | 0.00 |
| ISIS 586124 | 0.01 |
| ISIS 583918 | 0.01 |
| ISIS 584149 | 0.01 |
| ISIS 584163 | 0.01 |
| ISIS 584269 | 0.00 |
| ISIS 584468 | 0.00 |

C-Reactive Protein Level Analysis

To evaluate any inflammatory effect of ISIS oligonucleotides in cynomolgus monkeys, the monkeys were fasted overnight. Approximately, 1.5 mL of blood samples were collected from all the study groups on day 44. Blood was collected in tubes without anticoagulant for serum separation. The tubes were kept at room temperature for a minimum of 90 min and then centrifuged at 3,000 rpm for 10 min. C-reactive protein (CRP), which is synthesized in the liver and which serves as a marker of inflammation, was measured on day 43 using a Toshiba 120FR NEO chemistry analyzer (Toshiba Co., Japan). Complement C3 was also measured similarly, and the data is presented as a percentage of baseline values. The results are presented in Table 141 and indicate that treatment with most of the ISIS oligonucleotides did not cause any inflammation in monkeys.

TABLE 141

C-reactive protein and C3 levels in cynomolgus monkey plasma

| Treatment | CRP (mg/dL) | C3 (% of baseline) |
|---|---|---|
| PBS | 2.5 | 118 |
| ISIS 560131 | 1.7 | 100 |
| ISIS 569213 | 2.8 | 60 |
| ISIS 569216 | 3.6 | 94 |
| ISIS 569221 | 4.9 | 91 |
| ISIS 569236 | 2.6 | 103 |
| ISIS 579671 | 4.5 | 101 |
| ISIS 586124 | 4.0 | 93 |
| ISIS 583918 | 3.5 | 89 |
| ISIS 584149 | 1.7 | 110 |
| ISIS 584163 | 1.0 | 102 |
| ISIS 584269 | 4.9 | 102 |
| ISIS 584468 | 1.3 | 111 |

Pharmacokinetics Studies

The concentrations of the full-length oligonucleotide in the kidney and the liver of select treatment groups were measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTTGCTCTTCTTCTTGCGTTTTTT, designated herein as SEQ ID NO: 190) was added prior to extraction. Tissue sample concentrations were calculated using calibration curves, with a lower limit of quantitation (LLOQ) of approximately 1.14 μg/g.

The results are presented in Table 142, expressed as μg/g tissue. The kidney to liver ratio was also calculated and is presented in Table 142.

TABLE 142

Oligonucleotide concentration of in cynomolgous monkeys

| Treatment | Liver | Kidney | K/L ratio |
|---|---|---|---|
| ISIS 560131 | 793 | 2029 | 2.6 |
| ISIS 569221 | 966 | 1372 | 1.4 |
| ISIS 569236 | 898 | 1282 | 1.4 |
| ISIS 579671 | 871 | 2576 | 3.0 |
| ISIS 584269 | 698 | 2823 | 4.0 |
| ISIS 584468 | 474 | 2441 | 5.2 |

Example 34

Effect of Antisense Inhibition of Androgen Receptor (AR) on an Androgen Receptor-Dependent Breast Cancer Orthotopic Model MDA-MB-453 cells express AR in the absence of estrogen receptors and progesterone receptor (Hall, R. E. et al., Eur. J. Cancer 1994. 30: 484-490). The effect of inhibition of AR mRNA expression with antisense oligonucleotides was examined in MDA-MB-453 tumor-bearing mice.

Study 1

ISIS 569216 (TGATTTAATGGTTGCA; SEQ ID NO: 39), which is the antisense oligonucleotide tested in the assay, was designed as a deoxy, MOE and (S)cEt oligonucleotide, and is 16 nucleosides in length. The chemistry of the oligonucleotide is 5'-Te Gk Ak Tk Td Td Ad Ad Td Gd Gd Td Tk Gk Ck A, where 'e' denotes a 2'-O-methoxyethyl ribose; 'k' denotes an (S)-cEt; 'd' denotes a 2'-deoxyribose. The internucleoside linkages throughout the oligonucleotide are phosphorothioate (P═S) linkages. All cytosine residues throughout the oligonucleotide are 5-methylcytosines. ISIS 569216 has two target start sites, 58720 and 58750, on the human AR genomic sequence (GENBANK Accession No. NT_011669.17 truncated from nucleosides 5079000 to 5270000, SEQ ID NO: 1).

Treatment

MDA-MB-453 breast carcinoma cells ($5\times10^6$), mixed with 50% Matrigel, were injected into the mammary fat pad of 10 female NSG mice. Dihydrotestosterone (DHT) pellets, the active form of the major circulating androgen, testosterone, were implanted subcutaneously at the same time. Once the tumor reached a size of 100 $mm^3$, the mice were randomly divided into two treatment groups. The first treatment group was injected with ISIS 569216 administered by subcutaneous injection at a dose of 50 mg/kg five times a week for 4 weeks. The second treatment group was injected with vehicle only, administered by subcutaneous injection five times a week for 4 weeks, and served as the control group. Tumor growth was monitored once a week and mice were sacrificed on day 32 after treatment. Tumor tissue and TB-interface samples were collected and processed for further analysis.

RNA Analysis

Tumors were excised and the tissue was processed for RNA extraction and qPCR analyses. AR mRNA expression was assessed at the TB-interface and normalized to actin mRNA expression. AR mRNA expression in mice treated with ISIS 569216 was inhibited by 48% compared to the control group.

Measurement of Tumor Volume

Tumor volumes were measured on a regular basis throughout the study period, using Vernier calipers. As shown in Table 143, tumor volumes were significantly decreased in mice treated with ISIS 569216 compared to the control group.

TABLE 143

Tumor volume on different days in the MDA_MB-453 cancer orthotopic model

| | Day 16 | Day 23 | Day 30 | Day 37 | Day 44 | Day 51 |
|---|---|---|---|---|---|---|
| ISIS 569216 | 134 | 142 | 173 | 125 | 92 | 73 |
| Control | 111 | 141 | 155 | 195 | 287 | 347 |

Study 2.

Treatment

MDA-MB-453 cells obtained from ATCC were maintained in Leibovitz's L-15 media with 10% FBS. Female NSG mice (Jackson Laboratories) were implanted in the mammary fat pad with $5\times10^6$ tumor cells in growth-factor-reduced matrigel (1:1). DHT pellets were also implanted at the same time in the mice between the shoulder blades.

After 20 days, the mice were then randomly divided into treatment groups. Groups of mice were injected with 50 mg/kg of ISIS 569236 or ISIS 560131 administered subcutaneously 5 days per week for 2 weeks. A group of mice were similarly treated with control oligonucleotide, ISIS 549148 (a 3-10-3 (S)-cEt gapmer with sequence GGCTACTACGCCGTCA, designated herein as SEQ ID NO: 193, with no known human sequence). Another control group of mice was similarly treated with PBS.

Measurement of Tumor Growth

Tumor volumes were measured on a regular basis throughout the study period, using Vernier calipers. As shown in Table 144, tumor volumes were decreased in mice treated with antisense oligonucleotides targeting AR compared to the control group.

TABLE 144

Tumor volumes in the MDA-MB-453 model

| | Day 0 | Day 8 | Day 13 | Day 20 | Day 23 | Day 27 | Day 29 |
|---|---|---|---|---|---|---|---|
| PBS | 136 | 336 | 331 | 358 | 338 | 417 | 481 |
| ISIS 549148 | 148 | 303 | 312 | 365 | 413 | 490 | 550 |
| ISIS 560131 | 144 | 261 | 243 | 204 | 232 | 233 | 258 |
| ISIS 569236 | 134 | 283 | 260 | 230 | 264 | 329 | 323 |

RNA Analysis

RNA extraction was performed using an RNA extraction kit from Qiagen. AR RNA expression was measured using primer probe set LTS00943 and normalized to human actin mRNA expression.

Human AR RNA expression was assessed in tumor tissue. AR RNA expression in mice treated with ISIS 560131 was inhibited by 35% and AR expression in mice treated with ISIS 569236 was inhibited by 19% compared to the control group.

SEQUENCE LISTING

```
<160> NUMBER OF SEQ ID NOS: 215

<210> SEQ ID NO 1
<211> LENGTH: 191001
<212> TYPE: DNA
<213> ORGANISM: Homo sapiens

<400> SEQUENCE: 1

ctgacagaaa gcagatcatt ggttgcctga ggaggaggag tataggagag gtggagggaa      60

aatgtacaaa gtggcacaat aaaaactttt ggaatcatag atatattcac tatcttgatt     120

gagtgatgat ttcatgagtg cacgcgtgtg tcaaaaatga tcaatttatg caactttaaa     180
```

```
tatgtgcagt ttattgtata tatcaattat acctcagtac ggctattaaa aagaaaccct    240
ctggctgcac aatgcagaac tgattctagg aaagagtgga gggaggatga ccatttacag    300
tgctccaggt ggaagagaac ggtgccttct ggaagtgaac taggttggca acaacagaga    360
tgaaataaat gggcagatgt gtgagatact taggaaataa aacccgatgg tcaccatttt    420
ccaaaggtca gctcatcctg gctttccaga gcaaagagct agggaagact ttattaataa    480
atccctcttg aagttgcaga ggaagcttat agcagaaact tactctcaac ctgactaatc    540
tgagagaaca cctctggttc catttgatta ctaaaaaact gcaaagaaca ggaggagaaa    600
gaagaagaaa gctggtacaa acagtgaact tatataatat taatcaataa ttgtctcttg    660
ttcttaaaag caatgggaag aaaatgagat ttgagctgga agatcagagt tcaaaatcca    720
aataaagtat atggccctaa tatgcttata gtagttaacc tttcctgata atgatataat    780
tgttgacagc accatcttta aaaataaaaa taacatagta atccttcaga tttgtagaat    840
gctttcctgt ttacaagttt gttctataca cattatgtct tttaaatgac acactagcct    900
tctgagggta acttatattg gcaacagttt tcagatgtgg aaactgtgaa gacaatgttg    960
gtgatgtgga agcaacataa actttggagt ctttcagacc caggtttgaa tgtcagactg   1020
ctttttattc agagtaactt cagagcatta tttctcacct taattttttt tcaggcctct   1080
ttgtgtctat gtgtcctctt cactcctgtc cattgttcat tcagtgattt ttgcaccttc   1140
cttcactgtt agtgtgtaga cacatagttc tcctggctct gagacctatg ttaattccat   1200
tctaccatcc tgccagccca ctcaattcct attgagcaat gctagttgaa agttgtggtg   1260
ggattaaatg ttgcaatgag tattcaaatg aggttgaagt atctacgcat tctacttaca   1320
tatggtgagg tatattcaag gaaggctgta gccattaaaa tctcaggaaa taatttttca   1380
cctcctcagg tgaaagggtc ttcaggcctt tgtgttctgg aaggttcatt tatagccatt   1440
tcccaaatga caatgcgatt gatgagtcta gagtctagct caaatagcaa tggactggaa   1500
gactagttta ggttttacta atgtggaaca tagaacaaat tatgtccttg tttcagcctg   1560
ttcatctgtg aaatagagcc tatcatatcc agtcttcctt gcctttaggt ttgagttacc   1620
ttctttggtc aaggtaagta aatgcctatg atgtttggct gtgcacaaga taaagctaca   1680
acaaagctac aacccatctt ttctctgtag aagactgcaa aaagcaaaag agacccaggc   1740
aaaaatctcg gaatgacttt tggaacagag agcctcccca gaatcagaag tcaaaggaat   1800
ttaaaacata gggaggccca gggtctctac tgacataaag gaaagatgtt ttccttatag   1860
gtttacgttt acattttctc tctctttcca ttcccacttg catctccacc tttacacagg   1920
gcttatggga cctcctccac aaaagagcag ttgcagtaac ccacatcatc ctctacgcct   1980
ggctgtccat caagaggcga aaagcagccc tatataggtt ctatccttgg atagttccag   2040
ttgtaaagtt taaaatatgc gaaggcaact tggaaaagca agcggctgca tacaaagcaa   2100
acgtttacag agctctggac aaaattgagc gcctatgtgt acatggcaag tgtttttagt   2160
gtttgtgtgt ttacctgctt gtctgggtga ttttgccttt gagagtctgg atgagaaatg   2220
catggttaaa ggcaattcca gacaggaaga aaggcagaga agagggtaga aatgacctct   2280
gattcttggg gctgagggtt cctagagcaa atggcacaat gccacgaggc ccgatctatc   2340
cctatgacgg aatctaaggt ttcagcaagt atctgctggc ttggtcatgg cttgctcctc   2400
agtttgtagg agactctccc actctcccat ctgcgcgctc ttatcagtcc tgaaaagaac   2460
ccctggcagc caggagcagg tattcctatc gtccttttcc tccctccctc gcctccaccc   2520
```

-continued

```
tgttggtttt ttagattggg ctttggaacc aaatttggtg agtgctggcc tccaggaaat   2580
ctggagccct ggcgcctaaa ccttggttta ggaaagcagg agctattcag gaagcagggg   2640
tcctccaggg ctagagctag cctctcctgc cctcgcccac gctgcgccag cacttgtttc   2700
tccaaagcca ctaggcaggc gttagcgcgc ggtgagggga ggggagaaaa ggaaagggga   2760
ggggagggaa aaggaggtgg gaaggcaagg aggccggccc ggtgggggcg ggacccgact   2820
cgcaaactgt tgcatttgct ctccacctcc cagcgccccc tccgagatcc cggggagcca   2880
gcttgctggg agagcgggac ggtccggagc aagcccagag gcagaggagg cgacagaggg   2940
aaaaagggcc gagctagccg ctccagtgct gtacaggagc cgaagggacg caccacgcca   3000
gccccagccc ggctccagcg acagccaacg cctcttgcag cgcggcggct tcgaagccgc   3060
cgcccggagc tgccctttcc tcttcggtga agtttttaaa agctgctaaa gactcggagg   3120
aagcaaggaa agtgcctggt aggactgacg gctgcctttg tcctcctcct ctccaccccg   3180
cctcccccca ccctgccttc ccccccctccc ccgtcttctc tcccgcagct gcctcagtcg   3240
gctactctca gccaaccccc ctcaccaccc ttctccccac ccgcccccccc gcccccgtcg   3300
gcccagcgct gccagcccga gtttgcagag aggtaactcc ctttggctgc gagcgggcga   3360
gctagctgca cattgcaaag aaggctctta ggagccaggc gactggggag cggcttcagc   3420
actgcagcca cgacccgcct ggttaggctg cacgcggaga gaaccctctg ttttccccca   3480
ctctctctcc acctcctcct gccttcccca ccccgagtgc ggagccagag atcaaaagat   3540
gaaaaggcag tcaggtcttc agtagccaaa aaacaaaaca aacaaaaaca aaaaagccga   3600
aataaaagaa aaagataata actcagttct tatttgcacc tacttcagtg gacactgaat   3660
ttggaaggtg gaggattttg tttttttctt ttaagatctg ggcatctttt gaatctaccc   3720
ttcaagtatt aagagacaga ctgtgagcct agcagggcag atcttgtcca ccgtgtgtct   3780
tcttctgcac gagactttga ggctgtcaga gcgctttttg cgtggttgct cccgcaagtt   3840
tccttctctg gagcttcccg caggtgggca gctagctgca gcgactaccg catcatcaca   3900
gcctgttgaa ctcttctgag caagagaagg ggaggcgggg taagggaagt aggtggaaga   3960
ttcagccaag ctcaaggatg gaagtgcagt tagggctggg aagggtctac cctcggccgc   4020
cgtccaagac ctaccgagga gctttccaga atctgttcca gagcgtgcgc gaagtgatcc   4080
agaacccggg ccccaggcac ccagaggccg cgagcgcagc acctcccggc gccagtttgc   4140
tgctgctgca gcagcagcag cagcagcagc agcagcagca gcagcagcag cagcagcagc   4200
agcagcagca gcagcaagag actagcccca ggcagcagca gcagcagcag ggtgaggatg   4260
gttctcccca agcccatcgt agaggcccca caggctacct ggtcctggat gaggaacagc   4320
aaccttcaca gccgcagtcg gccctggagt gccaccccga gagaggttgc gtcccagagc   4380
ctggagccgc cgtggccgcc agcaaggggc tgccgcagca gctgccagca cctccggacg   4440
aggatgactc agctgcccca tccacgttgt ccctgctggg ccccactttc cccggcttaa   4500
gcagctgctc cgctgacctt aaagacatcc tgagcgaggc cagcaccatg caactccttc   4560
agcaacagca gcaggaagca gtatccgaag gcagcagcag cgggagagcg agggaggcct   4620
cgggggctcc cacttcctcc aaggacaatt acttaggggg cacttcgacc atttctgaca   4680
acgccaagga gttgtgtaag gcagtgtcgg tgtccatggg cctgggtgtg gaggcgttgg   4740
agcatctgag tccaggggaa cagcttcggg gggattgcat gtacgcccca cttttgggag   4800
ttccacccgc tgtgcgtccc actccttgtg ccccattggc cgaatgcaaa ggttctctgc   4860
tagacgacag cgcaggcaag agcactgaag atactgctga gtattcccct ttcaagggag   4920
```

gttacaccaa agggctagaa ggcgagagcc taggctgctc tggcagcgct gcagcaggga 4980
gctccgggac acttgaactg ccgtctaccc tgtctctcta caagtccgga gcactggacg 5040
aggcagctgc gtaccagagt cgcgactact acaactttcc actggctctg gccggaccgc 5100
cgccccctcc gccgcctccc catccccacg ctcgcatcaa gctggagaac ccgctggact 5160
acggcagcgc ctgggcggct gcggcggcgc agtgccgcta tggggacctg gcgagcctgc 5220
atggcgcggg tgcagcggga cccggttctg ggtcaccctc agccgccgct tcctcatcct 5280
ggcacactct cttcacagcc gaagaaggcc agttgtatgg accgtgtggt ggtggtgggg 5340
gtggtggcgg cggcggcggc ggcggcggcg gcggcggcgg cggcggcggc ggcggcgagg 5400
cgggagctgt agccccctac ggctacactc ggccccctca ggggctggcg ggccaggaaa 5460
gcgacttcac cgcacctgat gtgtggtacc ctggcggcat ggtgagcaga gtgccctatc 5520
ccagtcccac ttgtgtcaaa agcgaaatgg gcccctggat ggatagctac tccggacctt 5580
acggggacat gcggtaagtt tttccttcca gaaatgtcgc ctttcggccc agggcagagt 5640
cactctgtgt tctggggtat ctagcggctc ctacctgcgc gaacactcag attgcccctg 5700
ggagagctca gcagggtaaa cctagagctc tcccgtggac tcccggcctg ccagaggttt 5760
aacctgagct ctcctaattt ctgctgcgtg ccctgggtgc tgattcctgc cctcccagat 5820
tcttcaactc ccccaaccgc cccaaattct cactacctcc tggtactcga ggtcccaaac 5880
agaaatccta ttgcacgggc caccttcaga gataaagctc ccaagccctc cactcttcct 5940
ttcctcctgt cctcaaagtc tgagaacctc aacaggaatt tgggcaattt ctcctcttca 6000
ggtctgttag gatttcactt tcagcctgcg cagattagag tcaaaaagac cggcccaata 6060
gcttctcagc gggtatcctc cagagaggta aagtgaaatt ctcggttagg gaaagaaagt 6120
ggtctctggg tgctgaggtc tgctgtgtga aagggtgaac ttctttctcc tgaagcaact 6180
ggggacttgc tccagggctg gaggtcagta gagataatcc aaaccgtcat gtttagagta 6240
ggcagagggg caactttctt ggtaaagact tcacaggatt tgcactcaca gtttctcaac 6300
gttggttgac tatgttgaaa gtagttgctt gggtcggttt tctcttgtaa agtgtttatt 6360
ttctctgtgg attataacag atccacagcc ccctacttca ggtttgcatc agatctataa 6420
agaggagaat attcttttaa tgtacaattt aattaggctt gactctgact tacaaaactg 6480
ttggaaaaca tttttttgta aagcatttcc tgctatttca gtgtgctcca aaatctccac 6540
tggggagggt ggagtgaggt tttttattat attcctttat ttttaggaca tgtttgcatt 6600
ttagaatatg tgcagttagc tctaacaaat tgagtaagaa ctcttaatga cctatgagcc 6660
gtaatcttac cccaaagttt taattagcat atgagaaaag tggcaggcaa ttgcatcgtg 6720
cttattaaaa attattcctc accgcagttg ttgagcttct tggagaccat gctgaagatt 6780
ttctccccca gcaaattaag atattagttt atctgctgag ggaggacaga ctgaattggg 6840
gaattaactc ctcaggtagg ccaggtgctg atgtccctgt ggacttttgt cttattcttt 6900
gtttctatgg ctgttttctt ttacctgtga cttctccgaa atttctttgt tagccttaac 6960
atctttgttt ggggacttaa atccagcaat ttgccttctt tcactgatgc tttccttctt 7020
acaaggtaga tagcacagtg ttagtaaaga aagaaagagg agggtaggat ttcatattat 7080
ttcgtgggct gttgaagaaa cagcttctta ccaggcttta cattccatta ggtttttaat 7140
gtttgactta caagattttc agagggttca tttgatattg tcaaagtctt ttccagttaa 7200
tttagactct tcatttttgt aatgggttta tgctatggga caaaaaaagt attcttcatt 7260

```
ttataagaac aaatttactt ggtagggtta atttttttc tagggctgtc actagacggt   7320
ggagcccctc ttctactgta aacttttctt gggggaaaat gtctaaggtg cattttgacc   7380
tgccatgata ctaaacccag acactggaac cttccatctt ctgcatgcct cccccacaac   7440
ttacttactt aacagggaaa aaactgatgg ttccacatat ttgctaaaaa atgtgtgcct   7500
tcaaagacaa aaccaaaatt tttagggaat aactatagag agcaaaagtt actcccatca   7560
agtagacaac gagcttggtg attttatttc aggtcttaat gaaaaaagct tctttatgag   7620
gaaggttatc atatcttggt gcctccttga cagtccgctt aaattaatga cataaactaa   7680
tgagaattta gcagttcctg cagaaagtac aagtttattt tttttttctg gtttgtgatt   7740
gctgcactga atatgaggag tctagttaaa gggacaactg gtgttcctgt cttgtgagtt   7800
gacgaagact ttccatttct aggatataga aaatccttaa gccggtttat tgaaaattaa   7860
tcaatttaat cagaatgcaa tcaattccaa tacaaaagtt agtattttct ttctttttat   7920
tgaaaattaa tttaatcaga atacaatcaa ttccaatcca aaagttgata ttttcttact   7980
ttctcttttt ttccctcatt ttgtagggat acaatttggt gaaaggcaag agatttctta   8040
agccaaagca agagtgtctt ccctctctgt gttgcatgca ttatgtgcca tgtttgagct   8100
aaaaatctca aaattgggca ggcttccaat gacctgttgg gtccctccct ttaccattca   8160
tgtgtgtgtt tatgtacata attttgtgga ggggtttttt taaaccttag taacatctgc   8220
actcactctg tgttcttata catttacagt gtttctgctg agaggaggga agatgcaaag   8280
gtggtctctt ttacttaatt tagcatgtgg tttgaacaga aggaaaaata aaaagtgatg   8340
gggcttgtgt gcaaccctga tgatatttta tggagctgtc tgtcttctct ctgagatcaa   8400
acaggactac aactttgtta attgaccact ggctcccttg gcaaaagtag ggcttcttat   8460
attccagcaa gcagcacaat aatatgacaa aaatttattc ttgggagttg ggttctaaga   8520
gagtgcatgc cagaattaga gtttggggtt tagagaaatt atccagatgc caaaagaaca   8580
ttttaatttt tctcttggta atttgttctg gtctccatag taggtagtat tttagtagtg   8640
ctttgatatt gacaagtctt gctccctttc tctattagat ttttcaaaat aaggcatttt   8700
attaattcct ctttccttct cctctctcct ctcagttatc aagcattttt atgactatct   8760
tacaagcaac agtttgtctt gtaaagcaga attttccttt gaaaccaaga cagattattt   8820
ctgcccatag gcttcaggaa ccaatatttt ggcaagaagc atcttttctt tgtggtcagc   8880
aaataggtgg tgagttctgt ctggatccca acaatcaaca cctgaggacc aaatagccac   8940
actgggtggc accccattcg gaagtataca caggaagtag ccctcttgct tgttcacagc   9000
tcaagtcagc caaagattaa cactggtgag agatattttc aaagaagttt gcaggcttcc   9060
aattgcaggg tcattttggg gtgctttctt gcctgtacta attttatctc atcaagcttc   9120
cattctttga gctgtaaact ttgaaataat atactggatt tgctggtacg tttaattttc   9180
tttgttaagt gttttcattc ccatagtaat ttttcatcta gtgtacatat atgcatttaa   9240
aacaaaaatt ctttggtctc cttatgcgta tatgcactgc ggcttgtaca cgtacaagct   9300
acttggtggg attatgtgaa ctggagttag aaatgtggac aattttatta tgattatttt   9360
taatggtgat atcaagatca ccagtttcat tcggaacctt gcataagcag ggagcagaat   9420
gcggactggg tgtggcaaag caagggctta ttttatagcc aaacctgaaa tcacaactct   9480
gaaaaataaa aaaaaaaaaa accaaacaaa aaaatcaagt tttgtgagct tggtcagaga   9540
aggaaaagga aatctctccc taccccccac ctccaccatt ttctctttgt ctgcagcttc   9600
ctcaagtgct gcctgtcccc gattttcttt tattccactc ctttcatgtt tttgacattg   9660
```

```
aaatacagac tcttctttcc acttctcagg gtatttttct tattacacct gtggcatgct   9720
cctaaagaat ttctttttta aaaaaaatct gtagagtagt agattagatt aaccccagta   9780
tctctccctt aagactagat gacatgaggg gattgcaaaa tgaatagctg ggtttttttt   9840
tttttttttt tttttacctt gaggttaaag cctggttcaa cagttgctga gagagttaac   9900
tagattgctt gaggacttgg caatttcata aagtattttg tcttatgctg tctctgtctc   9960
tgtcttgatc tctgtctctc tctgtctact gtaatgttgg ctactttctc tcagagcctg  10020
agagacagct ctgagacact tcccaggtct gttcggttca gacctcagta gctggatcac  10080
aagcagtacc caatatgcat atgagggtgc gtgctgcaag tgtccggctg ggctaatctg  10140
cttaagcttc ataaaaatta atcatttgaa aacaaagaaa gatattaaag aaattattct  10200
atctccgact tcccctatca gcattccatc aagttctggg atgttaaatt cagagaaagt  10260
taaccttatc ttaaacacaa agttgacttt taaacaaaat tgcttataaa gttctgtaca  10320
gttaccagca ttggttgccc tttgtcgtac ggaagagaat tatgaaatct catatttaca  10380
tagcattctt ccaaaaaaag agacggtgtt ttccagttta ttcactgcat tcgtgtaagt  10440
gtgagtaggc caggaggggt gcttagtgat tacccttttg ctaggtaaca aagtagaaag  10500
ttagattttc tatgatattt gtttaccacg taggggaacc tctctagagc aatactccca  10560
agctttttct tcttgaaatt tcccacctga cagataatac tttagattgt tgctcttaag  10620
gacttctctc agtagctgct acatagagat gattgtccgt gaattattgc ttgcacactc  10680
atgggtgatg ctactccctc tctctcatgg caattcttgc tgccaacctg caggccacac  10740
caggattgag ggcagctcat ctcgataaat ttatagcatt aaagtgctgg gtcatttgag  10800
aatgttgtca atttaggtta cttagtacct aagttttatt ctttaaataa cagctttatt  10860
gagacgtaat ttacaatcca tacaattcac tcatctaaag tgtacagttt catgcttttt  10920
agaatattca gagttgtgca accattattg caatcaattt tagaacattt taatcacccc  10980
caaaggaaac cctatgcacc tttgtgttca tccccctata ttccctcagt ccttagcaac  11040
caataatcta cttctatcta tggatgtgct tattctaaca ttttgtatga atgaaatcat  11100
gtaatatgtg gtcttttgtg actagcttct ttcacataaa atatgttttc aaggtcatcc  11160
atgttgaagc acatatcagt acttcactat tttttatagc ctaataatgt tccactatat  11220
ggatatacca cattctatct atccatttat caggtgatga gcattacggt tgtttccacc  11280
ttttggctat tatgaataat actgctgtga acattcacgt gcaagtttat tgtggacata  11340
ttcagtccac atattttgga cattttcagt tcttttggat acatacatag gattgaaatc  11400
tctgagtcat atgatacctc tgtgtttatc cttttgaaga actgtcaaac tgttttctaa  11460
agtgtctgca ctgttttaca atcccatcag caacctatgg gggtccattt cttccacatc  11520
cttgccaaca cttgttattc tctgtctttt tcattatagc tatattagtg ggtgtgaagt  11580
ggtacctcat tgtggctttt atttccattt ccctaataac aaataatgtt cagtatccat  11640
gttcttattg gccatttgta tatcttcttt tttgagaaat atctatttgg atcctttgct  11700
cagtttttag ttgggttttt tattattgag ttttaagatt tttaaaaaat atattctgga  11760
tacatgtcct ttaatagatt gtgatttgta gatatttttt cacattctgt gagttgtctt  11820
ttttactttc ctttttttc tttttacgtt cttaatggta tctagattga agcacaaaaa  11880
tgtttttaag tttgatgaag tccaattcat ctatttattt tctgttttgg cttatgattt  11940
tggcgtcgta tctaagaagt ctttgcctaa tccaagatca caaagattta catatgtttc  12000
```

```
cttctaagag ttttatagtt ttcgctattt acatttaggt ctttcatcag ttttgatgta  12060
atgtttatat atgactgagg taggggtcca acttcattct tttgcatgta gatattcagt  12120
tctcacaata ttgttgttga atctttcctc acttaactgt cttggcaccc tttgtgtaaa  12180
atcagttgac cgtaaatgtg agggtttaat tgtggactct caactatatt cagttgatct  12240
atatgtttat tcctatgccg gtaccacgtt atcttgatta ttgtaggttt ttagtgagtt  12300
ttgaaattag gaattttgaa ctcttcaact ttggtcttct ttttcaagat tgctttggct  12360
cttgtgggtc ccttgaattt tcaaatgaat tgggataagc ttgtcaattt ctacgaagaa  12420
gtcagctagg attctcacag gaactatatt aaatctgtaa accaatttgg ggagcattgt  12480
catctcaaca acgttaagtt attttcatcc ataaatatgc gatgtcttcc catttattta  12540
ggtcttcctt ttgtcaacaa tttttattgt tttcagatta taagttttgc agttcttttt  12600
aaaatttatt cctaagtgat ttattttttg atactataaa ttgaactgtc ttattgattt  12660
tattttcaga ttattcgctg ccaatgtatg gaaatataat tgttttgtat attgatcttg  12720
tatcctgcaa ccttgctgaa aatacctgag ttttgaatgc ttctgggact tatggggaag  12780
agggcttctg ctgctgcact gaaagttaaa gcttacttca tttcatcctg tatgaaggct  12840
gcatggggac attcttctca gttttactca gctataaatt cgaactggta atcccatccc  12900
ctttcgggat gaataggaga gtgtttttaa atgttcatct ctttagagaa cagcaggaaa  12960
gaagcctagt aaggtttggg tagtttataa tccctttttt agaatttgga tttgggaact  13020
attagcaagg cagtgagtaa taataataat ttctatatag aaaactaaca tgtagaggtg  13080
acaaatgaaa tcactagcta tattaggctt atgtttaggt tatcgtaagc agctaaaatc  13140
ataattttat gtttttatat gttgtccttt ggacaaagta aattccagta ctccttctga  13200
tgtgcatttc tagatgggga aaggattcat ttactctcat ataatttaag cttcttttta  13260
gggatgtact ccatagccat gaagcaaaga taaaattcat ctatacacag actgaacttt  13320
gtcttcatta acactctagg ctaagggtca tagctaatca gctacaactg taatgtcctg  13380
ataattgtga attaactgca gggcacccag caaaaggttt agttataatc taatagctgt  13440
ctgtagagat tagcctaata aagggatttt ttaaaaaaga atctggccgg gcatggtggc  13500
tcaatcctgt aatcccagca ctttgggagg ccgaggtggg tggatcacct gagatcggga  13560
gtccaagacc agcctggcca acatggtgaa accccatgtc tactaaaaat acaaaaatta  13620
tccaggcgtt ttggtgagca cccacaatcc cagctacttg tgaggctgag gcaggaggat  13680
cacttaagcc taagaggcag aggttgcagt gagccgagat catgccactg cactccaggc  13740
tccgtcaaaa aaaaaaaaaa aaaagaatct atcaatcaac cacttttcat taagcacctg  13800
ctatgtgccc agcatgtgct aggaagagat aaggtgaaag gggacacaat tcagacagaa  13860
tcttcttgag gtaactgctt acgaggagct tatagccact aaaaacaaaa acaaacaaaa  13920
accaaacaac caaaaaccaa acagaaatgc agtatcatca tgccatgatg cctgtatgag  13980
atcctggatt gtacggtatg gatttcttaa aatgtagata ttttaaaaaa aaagaggaat  14040
gaatcaatag aggctgaagt ggtcagcaat gttacctgtg gctgctttta atccttcgtg  14100
gaagtaagta ggagcatgtc taaactcaag caatagatta aagatcttga tgtatatttt  14160
aaataacaga agttagtacc actggaaaga atgaactgga ggaatgggtt gaaatctatt  14220
tctgcttatt caatagtgca ccccagtcaa gttagttgcc aatttcttct tcagtttctt  14280
tggctatatc attgcacttg gtgggtacat gtttatgatg tctttatctg aacaagtcag  14340
caataatatg agtaataaat taaaattgaa ggtgattaat ggctctgaat ttgacataag  14400
```

agttgttttc ctgccttcta agtttccatt gatcctgatg aattgcacaa accaaacaat 14460
tcggggagta agggggcaca tgatgatctt ataagagctt tgctgtatta gacaacgtaa 14520
cattctgaaa tggcctacca cctaacatgg gctctgttct ctgcaggttg agtaggttcc 14580
ttgcttgtgg aactgtagtc ccgctatttg gccgctaggg ggactgcaag tgccccgtgg 14640
caggatttcc ctgggaatgg tgagcctcca ttgatggttt caacacacag ccaaggccct 14700
atcgcaggat aacttgaacc agaactgcct agcaccagac aataaataag ctactatggt 14760
acttactgtt tcatttggga tgttgtttct cgaagtggca agcatttttt agtaatattt 14820
tgacttttta ataccttttct ttgcatatgg agcagaaaac agtgacactg gatatattca 14880
agtagcactg tccagtttat agagaagttt catattccat tattgcattt cattcttgtt 14940
tctacctttt acaagtaact agagtttgga gtattataat agtattcata ctattacagt 15000
actattattc ccattataaa aattgtgcaa agagtggtta agttacatgt ttacaatcaa 15060
acagcttcaa agtgactgat ctggaatttc agtcccattc tttcttctcc agatcatgtg 15120
ttccctgctt ttatctcaca gctcttttta ccttatagat gggaaacatg agagtcagag 15180
aggcaaaaga accacaagtg gtatcaatac tagaaattta tgaatttctt aaggcttcta 15240
ggtttgttac ccatccacca gactgatgga tttggttgtg tgagagttct gggtgccaat 15300
aaccttgcca ttctacttta cagactgcat atattcaata aatgcttatt aagcatctac 15360
tatatgccaa attctgtact aggcaccaat gatgtagtgg tgaacagaac agacaaaaat 15420
ctcttcgtgg agcagacagt ttaatgagag gagacatgta gtgtacatct gagcatgaaa 15480
agtgccatgc agaataactt cacagagtgt agggtataga gattgatggt gagagggaat 15540
attttatatt tgctggccag ggaaaacctt actggaaaag taaattttga gtagtgacct 15600
gaaggaaatt aggaaatgag ctgctatttg gacatctgga gttagaatat tccaggccca 15660
gggaaccaca ggcgcaaagg gcctgaggca ggagcacact tgctgtgatg gaggacaaag 15720
aggcccatat ggctggttta aataagtgaa ggatggtaga caatgagatc agagttaatg 15780
aggttgcatg gtaggtcttc cttaggactt tgaattttac tcctaagcag gttgtattgg 15840
acggttttga gcagggtaac atgacctgac ttacatttta acaggctccc tcctcttcat 15900
aacatctgtc actctgatat attatacgtt tgtttgttta cttactgtat gtgggggggaa 15960
gagactgtgg gagcaagggg ggaagcaggg aaacaagtac actgcagtga tctgggtgag 16020
aggtgaccgt gtctcagact aaggtggtat tggtggagaa ggtaggaagt ggctgaattc 16080
tggatgagtt ttgatggtat agccaacagc atttactgac agattggata ttcactgtga 16140
aaaaaataga gatgaggatg attgccaagt ttttggtctg agtaactgga aaaatgagat 16200
tgccatttac tgaaatggtg aagactgtat gtagagcagg tgcatgggca gggtagaaat 16260
caagagtttg atttttgact tataaagttt gaattatctg atgaacatcc tgatggcttc 16320
ttctcagtta gttctcatgc agtgccttca gctttgctgt tcttcaagaa aattaaaaag 16380
gaacttagag atcgcctagg ctgtaggtac cctctcccct ctttcctttt actttataga 16440
ggtctataga agggtaggga cttatccaag gtgaaacagt gagctggcga cagaactagg 16500
gcacaaaccc agttctcttg aattctgaat cagtagattt tctttttta gtgtgattct 16560
gaggactcat ttgggcaaga gtgagttttt tgttattgtt ttttgtttgt ttctttgccc 16620
aaacctaaaa ccaggtaatt aaactaaata gtgaataaaa ctgggaaact atacaaattg 16680
gttgctctcc ccaatcacac tgaaatatta ttatttttac tgaaccacat accaaaatat 16740

```
ttttcctgta aaaacacagt aagtgaactt ttaaaggcaa ttgagctttt aacaaagcta  16800
gaatctacag aggacctgga cagaaatggc cttaaatcct aggaaattag agttcatgga  16860
acctgggaga ccatcttgtc cagctagctc attttatggg tgaggtgcct gaggcaccaa  16920
gatggaaagg gacctggcta agctcataca gcaagctagt gcctgagcct agtcagagcc  16980
tgttttaagg gttagtcgta tgttgttttc ttgaaaaaag ttacattgga aaagtgaaaa  17040
ttctttggtc catactgaga acaaagaatt atacataatc atatataata ataatgatag  17100
cacttcctga atgtttgctg tgtaaacttt ggcaccttgc atgaattgat tcatttaatt  17160
ctcatgtcaa ctttaggaag caggcctaga gaggttaagg aacatgtcca agggtcacac  17220
agctaggaag tagcagaact tgtgtgcact cccaggaagt ctggcttcta accacaaggt  17280
tctaactact gtgcaatacc aggagcttct cagattaccc ttcaccttta ccaacccaaa  17340
tgactggtga cgtaggtgac ttcattatgc tctgccccta ttatagtcca ctgatcctca  17400
ccaaataggt gggtggccta gaggttaaag tagaggcaga gtgatggaaa ggggtggtta  17460
gaagaagttg atgactcatg atagggattg gaaaacagga ctacaggaat tattgaaaag  17520
ggcctagaga tcccaaggag gttgatctcc gactgctaca aacctgggca attcaatgcc  17580
tgcttaaata ggagagttaa gataagaaaa ataaaattgc caatttttac agtcagacat  17640
tgttttattt attttacatg tattaattca tttaatcctc aaaatactcc atgaggtagc  17700
tacaattatc atttctatgt tgtagatgaa gaaacaggca cagagcaatt aaataacatg  17760
cacaagatta gagaacaagt aagtggaagt gccaatatta gaatctaggt agttcagctc  17820
cacaacttat gttattttcc actatattta tggaatgagg taattttctt ataacagaaa  17880
gtttttaaaa tgcaaaaaca ttgtgcctga acttcaaaca ctgaacaact catatcctta  17940
atatgcacca gtttctttta agcactctta gaaggaagga tacttaacct aatgtcacat  18000
ggtgagtaag tagcagaacc ggaacttgaa tttgagactc cggactgcca gacctctttc  18060
cactctatca cttgggctcc cttctaacat tgacttgtct ccctccattc ctcctccgta  18120
ttgttctgcc cttcaccttt taattacctg tctccatcaa caagattgga cagagaattg  18180
ggagagtgag cagagtccat ttccttccag agactggaca aaaggaacaa aatgttagga  18240
aaaaatgtca gcatgtggga tttgtgggat ttacactaaa taagaaggga cacttcccag  18300
gactgacaag atgctacctc cgtccctcta ggccccaatg tgttgtgcag gatcccatag  18360
gaagtcatga atgtggttgt cagataacct ttttgttact gtggaaatgg aagcaggcta  18420
ctgcaaaaat ctgtctctcc aggttttctt ttaaagaagg tagtcttgct aaatgataac  18480
tatttcagca tttatttgaa aatgggcagt gcaggagaga aagaattttt ccaagcttgt  18540
cacattgggc cacctctctg aagcattgtc caacttctaa ttagatgagg agactgcata  18600
aaccaagagt tgagagtaaa gatggaaaca cttgatgttt ggtgtttggg tgcagaaagg  18660
attccagaac atgttttggg tctctttact ctgtccatcc ctccttccct ttcatctttg  18720
tttaaaaacc acagttagca aatgtgtagt ctgtttgcaa ttgttcatct gaaaaatttg  18780
tttgatcagc cttttgaata aaaaagacca aattagactg agatatttca gtcaccaact  18840
atctaataat agaccaaaaa ttttaaccat gctcatactt tcatatggta tgtagtttgc  18900
tttagacatt ttctgggctt cagtgaggtg ctagattgac tcaaaatatg gcaggtcaga  18960
tgtgggattg agcagggtgg actcttctct acccttccca attcagagtt ccccatcaaa  19020
gatgatctca tagtgtttga aaaaccaagc tgaaggcttt gggaattagg gtgctgaagg  19080
gatatgctgt ttcccaaagc cttctcagtc attccttctc cccccagttc agattcttaa  19140
```

```
cacctctttc caggattagt gcagtgatcc cacgtccttt ctctctagct ctctctgcta  19200
ctctctaatt cctattgtat ttgtgccacc agatctttcc aaagtttagc tccaatcttg  19260
tctgtatact gctttaaatg tctattagtc tttaagctcc ttaagggtgg gagtcctgtc  19320
ttatttttc cctattcttc gtgcttaatg caaaggaagc cttgctgtat agttgtgtaa  19380
tgcatgatta caatttcagc ttctccccat tggcttatgg gttaaagtcc aaattattta  19440
aatctggtgt tcaagtcctt ttatgatctg cttatttttc cagcctgaat tcctggagtt  19500
cccttacaaa actcttaaaa cccagccaaa aggatctagt cactgtcact ttaaaccatc  19560
ctcactctct tgtttttga acatgttatt tttcttataa tccctttgac cttgaaggct  19620
atcccaattt caatactatc cattcttcta tgacagcccc ctacaaaatg aatattctca  19680
acctcccaac ccaaggagaa gtgatctata tgacacaata tggttgaaag aatgttggct  19740
tcacttcttt atctgtaaac caggggctag aaatctctag tttataagat tttgtggaga  19800
ggggatcata tgtgattatg gatgttaggc acaagtcaag agtgcataag accttttgga  19860
tttatccctt ttttctttct ccatcaatat ggtacttagt cccttaaatc agaagtactt  19920
gtgttaatgt ctgataacgt ccttctaaat atacctctaa acatctgtct ctctttaggg  19980
caaaggttgg atatatctgc aaagattctc tttggatata agatatccac agcacataac  20040
ttaacagtgg tgtacacagt aggtattcca taagtatttc tttatgaaat gattcagagt  20100
caatagtagt aagtaactgc caaaaacaac tgatggattg taagttccat taacataaat  20160
acagtcagcc ctccatatcc atggattcca tatccacaga tttaagcaac tgcagatgga  20220
aaatatattt tagagacaca gtaaaaataa caattcgaca gtaaaaaaat acaaataaaa  20280
ttatgtaaaa caactattta cataacattg tattagctat tacaagtaat ctagatataa  20340
atgaaatata tgggggatgt atataggtta aatacaaata tgacaccatt ttatatgttt  20400
tagttaagga acatgaatat ttttggattt tggtattcat gggagtgggg gaatggaacc  20460
atgccccttc aaataccaag ggactattat atgggacaca gaataaagga gttgattgtc  20520
ttgctctgtt aaattctggt cagacacatt tgcaatgtat tgttcagccc cagtattcat  20580
ggagcatctc cttttgtaaa gcatggagga gctgtgagag agacatggag cagtgaacat  20640
aactattgtt tcaacgtacc tgaaggatta tcatggaata aagaagttag atgtttttct  20700
gtagtacccc aaagggcaaa agcaatgagg acagattaca gttcagtaaa cgaaagaggt  20760
tttttttttt tttttttttt tttttgaga tgggagtctt cactcttgtc gcccaggctg  20820
gagtgcaatg gcgcaatctt ggctcactgc aacctcgcct cccgggttca agtgattctc  20880
ctgccttagc ctctggagta gctgggatta caggtgtata ccaccactcc tgggtaattt  20940
tatttattat ttatttattt ctttatttat tttagtagag acggagattt catcatgttg  21000
gccaagctgg tctcaaactc ctgactgcag gtgatccgcc tgcctcggcc tcccaaattg  21060
ttgagattac aggcgtgaat caatgtgccc agcctgaaag atattttctt agaatagctt  21120
ctttcaccct tcatcagaag ttgtcaacat ggaccatatg agttttgttt ggtctatatg  21180
gtgtatatgt gtgtgtgtgt gtgtgtgtgt gtgtgtgtgt gtgtgtatgt gtgtgtgttt  21240
attgaattac ttgctaacat tttacttcaa aattcagatt tccaccatag ggaatgaaga  21300
tctggcaata caggactttc attcctacat ggtaatgacc agctgtaggt gaaaagcagc  21360
tgatcctctg gatgggccat gcactttgca gtttgcccag gcagcactga tccgctttat  21420
tcatttaagt tacctgcttg actcttctag tcattcgagt atgtcatccc catcagatca  21480
```

gagacctaag caaatcttgg gtcccttgct tactccaagg gctttcactc ctcgtatagg 21540
aggagctaaa gaaatgtaca agcagcacca caataggatc agacctggct ttcaattcta 21600
gcacggccac ataacatagt tggatgacct caggacagta acataacccc tctgagcctc 21660
tagatcttca ttatctgtag agcactcttc ttatagagtt attataagaa tgaaataaaa 21720
caactaggat aaagggcatg gcacttagta ggtgctgaaa tattagttcc cttcttctaa 21780
ttcaccacac catatctgtc tatctattgg ctgaatcaca taaatagtaa attcacattc 21840
actgaagaca ttcaagaaga gtctggaccc tttgggaacc atgtataggg caaaggtttg 21900
aactcatagt agatgatttt tacagtcact ttttaacaat ttaaaagcct atagatgact 21960
ccaaaatgcc catttggatg atatgaggca tactttgtgt agttaaggat tttaaataca 22020
taacagagag gctgaagggc cttcgggaaa gaagctgggg taagagtcaa agtgtagtat 22080
gttgaccgat gttcaggaat aggctttggc atctgacaga ttttgtttta aatactggct 22140
ctgggtctta ctagcttcca gttctgggct gcttcacctc tcttgagttt cagtttcttc 22200
atttctaaaa tgaagatact aatgcttcct ttgttgggtt tttgtgaata taagtgagat 22260
aataaatgta aatatctagc ccagggcctg gtgcatagta caagcttcat aaattgtacc 22320
tattattatt agtagtagta gtagtccaga caaacagagc ttgggaaaac gctagactct 22380
ggctgacata catgggcttt tccccaggcc actgctgcct ggcttcccct tccacaaagc 22440
tttgagtctc caaaatgctt tggctggaat gtaagcgtga ggtcattgca gataacaggg 22500
gagcatgatt tgcttcggta atgcaagtta ttaagttact tccctcagcc cagctgaaat 22560
ctcttattgg ttgatgtgtg cttcaaagtg tgagacagag ctagtctgag gagagaggga 22620
gagtgagaag attcctcttc ttggccagag gtcatggtct tccacaagga acagaatgac 22680
tcaatgcaaa ttatgggacc tctttgagtt tggggcccct acatttaaac tagtaactcc 22740
gttgcacata ttggcaccct tcccccaaca aaattactgg gcaggaattt tcttgaatcc 22800
ttccgtggcc tggaatgatc tcccttctca tccttgtgat ccacacagct ggcaaatggc 22860
aggcagcaga acaaaaacaa gcctcttagc atatagggag agaaagagtc acagcagtac 22920
tgaatttgct tgggaaccta atgttaacaa aggaccttcc tctcaacacc ccaaacagat 22980
taaaacattt ttttaacagc aagttgtgtc tcggagcagc tctttgcttg ggtatattta 23040
aagatctgct gagtcattta agagcaggct ggcatatcct aagaggcaag gactataccc 23100
cagtctatgg gggagtaagt tgagaggtga aatctgtttg gctttctccc atggaaacaa 23160
acaaggtgat ccacttccat ctcccacgac tctggagagc atctactaag ccttcttatt 23220
ctatcaactt tgaactcctc agtgtataat agagtaaggg tgagagggaa ggagcagtcg 23280
taccagtgtc attattggta tgttcaggag ttcaatttct tcctgattca gtcttggcgg 23340
gatgtatttg tttgggaatt tatccatttt ttctagattt ttctagtttg tgtgcataga 23400
ggtgttcata ataccttctg atagttattt ttatttctgt ggtgtcagtg gtaataaccc 23460
ctgctgtctg aaattgtaat ggccctgcta ttggtagctg agagtagcat ggaagtgtca 23520
ggttgatggg ttcatttaat tcttttcttt tcagtttcag tcacatgcat tgttaccatg 23580
gcatatgaca gttgctagaa agtgaaataa tttttttct actttattct ccactgcact 23640
tctaaattta ttagtggaga aattagcagt taccaactgt tcattatagg tacacattgg 23700
ggtttcctta gagccaattt tccccctggt tttcatcttg taaatctgta atcctaaaaa 23760
ttagcaaaac ctagagcttc tctttggtcc tggcctgttt gaaccctgtt ccacagaccc 23820
caatcttctt tcttgtttga ggcaactatc cttctctttg cccaccgcca ttttccttca 23880

```
tctacttttc ccttctctag cacctcagac tgtcttccca cagtggcaca gcctcccact  23940
ccactttcac tgtgccatct ccttgccatc aaaaccatcc tcacagaccc ttctgaaacc  24000
acttctagga agggaaatca caatggatcc atgaaggatg ctttctggat gactttaaaa  24060
gattggtatt aagatatttt atcagtggta gcaacactga cttattcagg cagccatgcc  24120
ccggatctat aagaaatcag gtaagctaaa agttgcttga gctggcagga gacctagttc  24180
tctttttcc tttccctctt gcattttgtt tatcgatggt tttcaaagga cttagaggct  24240
ggctttgtta tagttagttg gtaagagaaa tggtggagga ccggaaaatg ggagtggaac  24300
gaatgagcat gtttgagact aagttattac aattcctagg atgtataaat tgcttgaaat  24360
ctaccaagta ctttcagaca cattatcttt tttactcttc aaaatcaact tggaggtagg  24420
cacaacaggg atcaaatcct tagttcacag atgagtaaac tgagactgga ggaaattaaa  24480
ggagattcca aggtaactca gacaataagc aacagaacca ggatttggtg aatttttgg  24540
ggggtgggag gtacagagtc tcactcaggc tggagtgcag tggcaaggtc tcgtctcact  24600
gcaacctctg cctcctgagt tcaagtgatt ctcgtgcctc aacctcctga gtagctggga  24660
ttacagacat gtgctacaat gcctggctaa tttttgtatt tttagtagag atgaggtttt  24720
gtcatgttgc ccaggccggt cctgaattct tggtctcaag tgatccacct ccattggcct  24780
tccaaagtgc agggattata agcatgagcc actgctccca gccccagacc attaattttt  24840
gacagtaagt ccaacttttt tcaagttcac agctcagatt tgctattgaa tgaatgagta  24900
tatatgtcat ttgggaacat tctttccaac ttttggttga agatttgttt tatcacttgt  24960
gaaaattttt tttcattctt agcaatgtca gtttagttaa atgagcattt catttgcgaa  25020
ttcactaatt aattatttta ttcatcaata catttcctga gtaccaactt tctatcaaac  25080
cctgtgctgg attctgaggc tacaaagaga aataagatac catctcaggc ctctaaaatc  25140
tcacagactg gggactgaca tctcagtagt aaacatatga acagcaactt gtgaaacgcc  25200
attagcaaaa tctcaagtta tattcttcag tgactatggc catcctaaaa atggggtgtc  25260
ttttatttgg ggtaaatgaa gatgaagcct tatgagaaat tgcattttaa tctaatcttg  25320
tcttgctaag aacagaagtg gaatgtttca gcctctgtgt gtgtatttgt gtgtgtgaag  25380
gttgagtgtg tgatgatgga tggggctgcg agattgttaa gtaggatcta tgggggggcct  25440
taaatggtcc tggtgagtcc caactttctg gttatgtatt tgagtagagt atgggggtga  25500
caaagattgt tgtttaagag ttgattttag atttttttcca agtaaatggt cagctgactt  25560
ggagcatcat cattccactt gctttgaaaa cctgccactt aaggctcctt ccagtcatag  25620
gttaactctt tctggtcaag tattactctt tttgagcatt tacctgtcag tgacaggtac  25680
aatgttagat gttgtctctc tgttttcttg tttaatcttt actttgatcc taggtagctc  25740
ttattagttc cactttatag gtaagaaact gaatttcaga gacttgaatg acttgttcaa  25800
gatcacatag tatagtaact tggtagtttg ggacttgaat tttgattgtt cagtttttg  25860
tttgtttgtt tcctggcctc cctgctgttt tcactattcc acaccacttc agctttattt  25920
ttcatagagg ccattaaatg taccctccat cagccaaagc ctcttgcctc ccttcaacgt  25980
aactcttctc tagcgtcctc ttaataatct tctgaaaagg ttttacagcc tttctgggta  26040
ctgggaccca gagtcttaat ccaggctctt aagtgcctta tttaactgta atatggaaaa  26100
tcaaagtcac agctaattca ggaaaaatga gtttgggatg tgaatttcct aggcaacttg  26160
tcatctcttt tttacttcct tagcttcata aacttaccca caatgttccc tgaggactaa  26220
```

gagtaatgga gggtgatgag gaaaggcttt cctcccttcc tttccgagag tcctttagcc 26280
aaatgccaca cctcctcctg tttccctagt ctccgtgcag agatggaagt gggagataga 26340
catgggttcc tttcagccct gagttcatgc cagggttttc tttccctcta gctggactga 26400
ggtaggagga gaggttgaag tccaccaata agaccatgag tgaagaagac taaagtactt 26460
gaaagagcag cagacctacg cttaaaatac tagggtttgt gtccagactt tgtgggttac 26520
tatctgtata attttgggca agtcaacagt tctgagtcag agttccctta tcagcagatt 26580
ggaagataaa ttctaattat atagatgaaa cattaagtct agaagtaatt tgtaaattca 26640
gaaagggctt atagatttaa agtgtagccg ttttgattac cacaaactaa atcctatact 26700
tcagggataa aatcttctcc tgtttttct aaaagcctgt gcatgtgtgg tgtaaggggt 26760
gggttttccc ttgtaccagc aacttagcaa ttgtagtaac ggggctgagg gcagtggcat 26820
gcttcttcat tgagcaagtg tgaaaagagg gttatgcatt caggggtcag cagatggcag 26880
gcagagtagc ccctccaaat ctccctccca taccacaaag ccctcttatt tattcaaact 26940
taacattaga agctcatttc aagtaggcac gtctgtgtct gggcgtctat tttccttctt 27000
tgtatatagc aggcatttgt caacttggtg aaaagcatta ctcttctttc catttctgag 27060
gactaattgt gcttcttcgc tagacacgag ttcaaaacag tgggttgaaa gagggcaagt 27120
ttatgccaaa gaatcagaaa tagtcataat ttagagagaa ttctagaggt cagttccctt 27180
tcgtatggac tgggcaactg aaacccagac agggaaggga attagaccaa gttcacaagc 27240
acaaacactt tactggcaca ttcagattgg aaatcgaggg cttctgctcc caggtcagaa 27300
ctaaatgccc tttctagcta gggtgttctt tgatctcagt gattttgact ctttctactg 27360
cactctgggg acagtgggtt ctgcggtacc aactccaatt aaagtgggaa tatgtaccag 27420
cccctcccct tggtttttat ttttcagagg cctggcagtc agagggattc tgatctctat 27480
atgcaatatt ttcacactac tgtacttatt gaaatcacat ttgaatcttg gcaattaaca 27540
aggcagtaat tggcatcagg agggtatgtt agtttgctta tctgcgccgt ccctcctctt 27600
cccaacccac tgtgtattgc agaatgtttt atcagctctg atttgccaag ttgctctctt 27660
ctccagtagg tgctgcgagc agagagggat tcctcggagg tcatctgttc catcttcttg 27720
cctatgcaaa tgcctgcctg aagctgctgg aggctggctt tgtaccggac tttgtacagg 27780
gaaccaggga aacgaatgca gagtgctcct gacattgcct gtcacttttt cccatgatac 27840
tctggcttca caggtgggag gttcttcaat tgaaaactta gaactcagtt tctagggtag 27900
tgagtgttgt aaggtttgga ctgtgaccta atattacgca gccatgacat tatctattag 27960
gcatctagac tagcttgctt gaatatctta gcatgttgac taatttgggg cagaatatag 28020
tgtgggtggg ggattttgtg tgtgggggg ggttgggggt tgagcaattc attattatta 28080
aaatgcaaaa agcacttaat tcgctatgat aagattgcct ttttcatgca tactggccta 28140
cctgcaagac ccctagagac agtaagcagc atacatggtg tcttccagtt ttcagccttt 28200
gtgcaaggaa caactgtggg tttctgcaca tgtgttgtgg tttgatgttt gtatgtgatt 28260
gtgtaccagg gtatgtgtgt ctgttattgt gagttcattt ctgagcagtt gtgacacaca 28320
gagatccaga aacagtgtct taccctgtgt gctttgctag tgggaacgtg tcttttcttt 28380
tgtgctcgta tctctgtgta atcgagtgtc ttgctaagtc aatgtgcctc tgtctctttt 28440
taccagttct gtctttgtgt ctctgtgcct tcatgtattt tttcccctga gtttgcacgt 28500
ctctgtctat gtggatatct ctcactccag gccactgtat cactgtgtct gtattacagc 28560
tgtttatttc tgtcggtgtg tggatttcta tgtctgtttt catcttaatt tgtgtgtcta 28620 agcaagactg ttttggggtg actatttcag tttatgtcat agccattctt tgtgtgactg 28680
cttctaggta tgtctttttc tatgccccta ttgtccccat ctccatgtgt ctctgtgtgt 28740
atatgttcta atgtatctgc ctacttatct tagtttgtat ttctctgggt gtatatccct 28800
ctcttgcagt tctgggcctt tgcagttttt ggcttatgtt tttgtatata tccactagaa 28860
ttggcttctt atctttttg tgcatgtttt agtttgtatg agtgagcata tccaactctg 28920
tctttgagaa gcagaactgt ctgtgtttgc agtcagttgt gttggctgtc cctgtgtttg 28980
tccctgtgtg tgcatttcat tgtatgtgta cgcatccatg tatctttctg cttctctgtg 29040
accagatatt tctgtgtagc tgtctatgta tattggcttc tgtctgtgtc tgtgttgttg 29100
gctctacgtc tgtgcatatg cacccaccgg gttcataaaa agctcacctg ctctccaagg 29160
aatctaccag attattttgt gaaataactc acgtttcgtt tttttacttg ccagctgcta 29220
tggtacttaa aagtgtgttg gtacgtaggt gtgcataatt tattcatgta ggatgtcaaa 29280
agagtcagtt aaaaattatg cacagtgtgt ctttattaac aggacacttg tgtgtagaga 29340
atccttgaga aatgagtggt tagatgataa atcttttcat attaatttca tgatgtcagt 29400
gaagtaaatt tgcaagatat gggctgcata agaactatgt tctttttaaa actcagcata 29460
ttgatggtgg agaaagcatt tatttgtact gcaaagtctt atttctgata agacatcaca 29520
aataagaatt attgtgatga gacttatcac aaataagaat tattgtgata attcttattt 29580
gtgataagaa ttactgggtt agaaggtgtt acttttctgg ttttgtttgg gtttttgttt 29640
tgaagtgtta ctacagatgg tgtcttaggg acaaagagct ctgaggttga cttagaacac 29700
atggagtaca gataaaaagg agaatgaaaa gtaacagaga gatgggcata ttccttgttt 29760
gaatggagtc atccaggggc tcaggatgga gtgcacagga aatggagagg tgaaggtcat 29820
agagagaagt ttagcaggac cagatctttc cttgtcctgg gctgctgtga ccatataagg 29880
aaggcagtaa ggggaggggt agggatgagg aagagaccag ctctcctctt tctttctgat 29940
ggaaggttac cacctctatt taaaacttct gttcttttgg tttctctttc tttctttgat 30000
tatattattt tctggacttg ttctgccaaa gcaagaagga aattccacat gtggctcact 30060
catttattat acttgtttct ttgcacgata ttaaagacag cttgttaagt gtcactgcaa 30120
acatcataca cactgatcca ctgatatggg caggggggttc tttatgccag ttctgctctc 30180
ttcccagtgt atctgtggtg cttaatgggc gcaaccatga tttttctgat gtcagtctgt 30240
gatgtcagtt gtccagtgtg tatgcaggct gcttaagagt acatacagtt ccttcacaat 30300
tatggtagtc cctgagaagg aagtggtcat taataaaaga ctaggttcag tagaaacatg 30360
taagttgtct aggtgttgga aattaataca gtactgtgct aagggaacat atatctagaa 30420
gttaactgaa ttatgctcaa taaaaagagt acaaatgttt cataaatatt ttgacctaat 30480
cctcctgtaa gattaggaga gggatatttc cgatattcaa ataatttttt taattggcaa 30540
acaccttaga catactattt acataaaatt gacatgacaa aattaagtca ttgtgtctgt 30600
tttatgataa aacaggctct tttgatttag ttagaattat tgaatgtaaa ataatgaaaa 30660
ttaaaaaaaa aacaaggagg aggaatctat cctattttat aattcagacc gttgaattga 30720
gtttttcttt tgttgtattg atttaaatgc agagaagtct atgatgctgg attccagtca 30780
gaagataaac atttgtatgt gggctctaca ttgcagccaa ccttgataat ttcaaacctc 30840
gattttctca tctgtataat ggtaataata aagcctgtct cagtagctac caaatgattg 30900
catatgacaa acttctcact tatttaaggg aaaaaataag aaaaagaagg acaatagggt 30960

```
ggatttttca tatagtaaaa tttattcagt tagggtaata ttctgagatt gtcttctgaa  31020
gcaaaccctg caaaccctgg ccattctgtt ttgtttagga aagaattcat cagttctgat  31080
tctgcctttt ctggggaggg aggctgagta ttggattgaa gaggagtcac tacttttctg  31140
agatgatata tccgtggtaa aaattattaa tgctttgcac atgcaacata gagtgttcaa  31200
ttttgttagt caacaaatat ttaagtggca gctgttatga cctcaggggt gtagtgactt  31260
ccttattgtc ctttaattat taaaaaagaa atctatatca gaatatcagg taaactctta  31320
ttacatcaaa tattataata aagatacttt ttatattctc taaacaaagt agagatctca  31380
gatgttggtt catttatcaa tataatatta gatttgaaaa ttccagtata caaaaggaaa  31440
aggacagctt cttaaagttt atagtgattt tctatgaact atcaattccg tttttttctg  31500
ttttactggt atgatggaaa ctaaatttcg agttgtaagt agtagataat tagactgcag  31560
ggtaagcctt gagattactt cttttcaggt aggaaactct actgtgtatt tggctagttc  31620
aacctatcat gggtagtcaa aaatagttac atatacaagt cagcattttt taaattgttc  31680
agttgtgctt aagattggtc ctttccagga acaatccagc tttatcaaaa aattattgcg  31740
tacatgtaaa gtgttctgac attttaatgc tcacaatagc cgaatgacgt gggtaagaat  31800
cttcgtcttc attttataga tgaagaaatg aagacacaga gacataaatt aactgggcca  31860
gggtcctacc actagaatgt gatagatgat aatttgagct cagcacatag ttatttccct  31920
ataatatttg ttttatgatt gtatagatgt ctgctgacca accttaatct ctgctcccta  31980
agattaacca ttctacaaag cagaaactgg aggtcattca aatgaaagct ctacactttt  32040
agagggccat taacaatgct caagttaaag aaaagcaatc aaagacaact aaaatactgg  32100
taccttcaaa cagtacttat gaattattta accttagata atttggcttt gagttagaaa  32160
gatagagtaa gatggaggaa ccaattcttc cctgggttga tatttattta tcttgctctt  32220
ttgaagtcta ggccaatcat cctatttatt ctgaatggcc cgttaacgtt tatccattta  32280
gggacagcag gtttggcaca aatggattgg ttttctgagg tcttatgtag agggctgcac  32340
tgactgactt ctgaaagtcc cccctaaccc ttcaaatctc agggtcatct ggtctcaagc  32400
cttcaattat gaatacattt ctattgcctt tttgagtaac agcacaacac tgcaagctga  32460
cccactgggt ggatggaatg gggctcttgc cctaccaccc tttggcaaac aatttgaggg  32520
tggcattgtc actacctcat tgtatatagg gtctcttgag gcccagaatg gcaaaataat  32580
tttcccagtg tcacacagcg agttattgtc agagtaaata tcaattttga atttgtagac  32640
cacgtggttt tacctcatca tttctgtttg ttatgaaagt tttacaaata attagaagta  32700
gaaataatga ttaaaataaa gcataactac taaaaaatag tttattgcag caccacctaa  32760
attcatctca ccactctacc agtagcatac atttcacaat tgggttaaca ttgctctgga  32820
tcttatagct gttgaagaag acaaaattct ttccattctc cagcttatat tttccccatt  32880
tgtaaaacat aatggaagtg tacggaaaat aggagttgat aatttttaag gcccttgcca  32940
gcacattagt acataggatt cttgcaagtg gtggtttact tcacttcaac tatagaaggc  33000
ctatgcgaca ccacccatag agggtagttt gaaagaaaat gctagtgact acgtgtgttt  33060
ccttcctgac atattttata gaaggtgatg agttccagca ttttttcaga cttggatctg  33120
gctttcattc cccttctcct cccaccctct aaaacaacag aggcagcaac catttacaca  33180
ctttccagaa gtaagtaagt aagactgtat tccagaaaca ccctatatca aaatggaaat  33240
atactcaagt gccccaatga cccattgggc tagtttgaac gtgtgcagtc tctgtgctcc  33300
ccgttttagc ttaagcctac tccctaacct gtcatatgtc acccagccat ggagcctagg  33360
```

```
gcaatgactg ccatcatatc tgactttatg gcctctcagc tttcaatgac tagctttgta  33420
gcagaagttt agcctctcat ccccataact ttggaagtag tgttgagata aagaaacgtt  33480
gaattgaagg ttgtgttttc tagatttctt tcaattgctc cttaggcttt agaagataaa  33540
ttctcctaaa agagaggtgc tacaattaat ccaagcaaag ggaaagatgt cagtaaaact  33600
gcccctttc atagaggtgt ggcaactgct gggaaggaag aaattagcct gaggccatgt  33660
gattactaat aaactcaaag cggcattttt ttacttctca atatgaggtt gaaactataa  33720
gcttaaattg ctgactttct ggcagcacca aacagtaagg aaaccacaaa gataaaccca  33780
aataatagag ccaattttct ttttttccgg gggggatgac ttctaactag tgatatgagg  33840
aaggataaga aaatgtttct ttgtaggaca tatgatcttt gctaagtgca ctgaatgtat  33900
gtagaggaga caagtctgct gagggtatga gaattgggcc aagatttaac acattttcaa  33960
agctccatga agaagcctac tgagcagtgg gagtggagca ggttggggat agtgaagtat  34020
ttgtaattca tttttaaaaa ggagagggag agagaaaagg aaaaactggg ccacccatcc  34080
tttgaaaaga aaccttgaaa gaggtccaaa tatccttaga aatccttgac ttcttaaaag  34140
tgatgtttgt tttttccccc tgacaattat agaggtcaga gagtttttct tttctattac  34200
aaaacattga gagtgtgtag aaataattgt aggtagctta gccttggctg tagtcagaac  34260
ttttgtactg tgactttagg atctgtatgg aatcgtatga tatgcggata caccaaaaac  34320
tctatgggtt atcaaaatgg gatagcatta aaagaaatag tgcttttgtt tagaagaaga  34380
aatgaaatgc ttgtgtccag atgcttaaag gaaggcagtg cagactttca gaaactagac  34440
tttaagagct gtactcagat actgagaagg gctgatggct gaaggaggaa caatttaaaa  34500
gaataaccgt ctctcctctc cctgtatatt ggacataaaa gaatatccca ttcttttcag  34560
aaatgtaata caacagttta gcttgctagt aacttcacat gctatttcct ttacctctta  34620
tatttgaggt gtctatttgg agtgggctgt gtttctagct attctgttta tctggtttgt  34680
ttttgttggt gtaggaaact ggtataaatt ttatttgggt aaatatcacc tcaattttca  34740
actaaagctt tatttaagtt tcacatgaaa aagacaaatg aggcaaagga agagaaaaat  34800
gcattgtcag aatcagaatt atgagaaaaa aagtcaaaca aacatatttg aaatgtccag  34860
aaaacctgtg agtttttatg tatactatac aggaaagata ttctgtcatc tggttgccaa  34920
actatggagg gtgggagact tcgaattttt gtcaaaaagt attctttcat tagaaagata  34980
catgggtgtg cttccatgtc agcaacatga ctgcagacca ggaagtcctc acggagagct  35040
ggaatatggg tattttggac tctctggtta gatgcagctt ttacttcaca tcctcagtgg  35100
tactactgta aattttcatt ttcctgtgga ataccctatt tggttccatt gtatatagtt  35160
gacaactaga attcgttcgc tgttgcttga gcccaactat aacttcttgg cactatacct  35220
atcttctgat gtgcctgtgg aagagctacc ataatgaatg tgtacatgga caaaaaaaaa  35280
gagagagaga gagagaatta aatcatgagt ttgtgccttg ggagctacag tttaaacatt  35340
tgctgttttt ctcacttaat gaaaaattta tttgaaaata acagcacaga aaggaagaaa  35400
gacaggctgg caagcatcct cctcctaata cacttatcca cgtttggata ccttggtctc  35460
agcctcagag gtcatatttt tagtaaaatg gccaccagaa ataaaggatt ttattttcca  35520
gactttggtg tttggagctg gtgtgctgag agctagcaga gaaagcccta ctcaggtaga  35580
tgtaccagag caggatggtt gctggtggat atggtggaat accttttatg tggttatctc  35640
ctccttgtaa ctcttggctg cataaccctt attttctttt ctatttttat tctctctctt  35700
```

-continued

```
ggaaaaaaaa ttggtggtaa attttcatgt gagccatatt gtctttttaa atagttttat  35760
taatataaaa tgtacgtacc ataaagcata cccatttaaa ctgtaaatgt caatgggttt  35820
ctctctctct ctctcttttt tttttttttt ttggatgctc agagttgtgc aacaattatc  35880
aaaatcaatt ttggaacaat ttcattgccc caaaaggaaa ccctctgccc attagcagtt  35940
actccccatt tcccccaccc cctgaccctt caaccctagg caagcacaaa tgtactttct  36000
gtctctatag atttagccat tctggacatt tcatgtaaac agaatcatgc aatatgtcac  36060
cctttgtatc tggcttcttt cacttagcat gatgtttcca aggttcatct gcattgtagc  36120
atctgccaat acttcattcc ttatttatgg ctgaataata ttccattgta ttaatgtatc  36180
atatttgttt tttccaatca tcagttgatg gacatttggg ttgttttcat cctttttta  36240
gctattttaa ataatgctgc tatgaacgtt cgtgtacaag tttttgtatg aacatctgtt  36300
tttatttctc cttggtatac acctaggagt ggaattgctg ggtaatatgg tagcttaaca  36360
tttaatcttt tgaggaactg ccagattttt ccaaagcagc agaatcattt tacattttga  36420
ccagaagtat atgagagttt tagtttctcc acatcctcaa caacactcat tattgtcatt  36480
gtccttttca gctttttga taatagtaat ctcaatgggt gtgaattggg accccatcat  36540
gcttttgatt tgcatttcct tgaagagtaa ggatattgat catcttttca tgtgcttatt  36600
ggccgtttgt atattttttg atcctttgct catttccaaa ttgggttatt tgtctttgca  36660
ttattgagtt gtaagatctt acaatatatt ttggatgttt gtcattttag ggatgatact  36720
tcacagttat atgatgtttt ctagcaagca tttgcgttgt tctactggtg ttacatatct  36780
tagctgcatt agccactttg ctgggtatga atgccagcag aatctaagtg accttggctt  36840
cactactgag aatgcaaccc aagaacagaa atttgtcaga aatttagcac tgaagccccc  36900
cacttcccaa acttatctgg gacaaggaga atctacattt aaagctctat actttgtgtt  36960
gtgtttttt tactttagct tggttggatt taggatcttt tctttttgtt ttgccttatg  37020
catacctaag cagaggcaag ggaggaaagg gatatgaacc tggtagaaaa gtaagtaagc  37080
tttattcaga ttggcatatc catcttaata tggttcaatt ggctgaagaa gtatctcaac  37140
taaaactctg gaatactttg aagtaccagc aatatgtacc aaatgtactt tttatttatg  37200
tttggtctct atgtacttgt gtgtgaaaca atgagcacaa ataataccct ccttgttttt  37260
aagcaattta tattggtgat ttaaaaataa aataaactca agtgggaaat catgaaaccc  37320
catgtaaaaa caataagagc atgttttaaa atcccacaga ctttagtttc aaatagtggt  37380
tttgctattt cttagctgtg tgtcactgtg caagttactt tgtttctctg agtctttatt  37440
ggtgatatat gtaaaaaccc accttctcaa attattgtga ggacaaaatg aagtaattaa  37500
cataaagttc ctggtgtata ataagtgttc atattttgta tttgagcaca gggcaactgg  37560
gtttttgaaa ctgcacatta ctgttgcagt caaatctggc atgaaattag tgcatagaca  37620
gaatgggctg ggaaaatgaa aggactttga acatttatat tctgctttat ttaggcataa  37680
gtgcttaata attattgata gtttcttctg gttatctgac attttgaaga tactattacc  37740
tagcagaaat ttcttgtaat aataatctct tacacttata tactgttttg tgcctttaga  37800
agtacttaat gctctttatt tcactatctg ttcataaaca ttctctgaag caagcataca  37860
gtcagtatga attccatttt tcagatgaga cagctgaggc tgaaagacat agagttactt  37920
gtctcaattc acaaagtaaa gtgccagagt ttgaaccaga gcccaggtct tctctctcaa  37980
cgtagctctt tttctccttc attatatcag gcatagtagc aacgtattct tttactagct  38040
ttttatcttg aatatccttt tagcgacttg cctttggtgt tagtgtgcct ataacattgt  38100
```

cgttgaatat cttaatacat ttagtggtct tggcaagcag ttttgtcttc agaaggacac 38160
tgaaatctgt ggaaaggact gcagaagatt gggtgggcag acacctatca ctttcggggc 38220
tggtagactt tctattgaag caatttgcaa ggctactttg tattgtctaa aagcactact 38280
tcagaaaagg gttgtgatgt caaaataggc actttgagtg aagaaagggc tgtaagcatg 38340
ggtggaaaat gtggtagatg attgtcttga gttattttct ttaatgtcaa acaggcagtc 38400
cttggaatgc tacttcaaaa agtgttgtat aatgttgaag atacagttac agatttccaa 38460
cacgaaactc ataaatatgc aattccctgt cctcctaggc acatgaagga aaatttatga 38520
gcttcaggtt tctatgcagc tattaaagca tatttaatct gctttgagct caagctcact 38580
ctcgttggct ctcttcgttt cttcctctta catgagcaaa ctgcctttct ttttgtttaa 38640
aaatagtaag taggtttgtt ttcctccagg tgtcatgaat gcaaacattg taatttctca 38700
tctgttcagc ctttttgcac aacaaaatgg cagcacccag gaggttgaaa gggttaaatt 38760
gttccttctc tgagtagtac cataagttgt tagtctgcta ctctttctcc cagttggcac 38820
atgaccctaa catccaatcg ctagtggtgt ggccattttt tggtcttatt ttggcctttc 38880
ctcagccacc actcatcagt tctcatgcgt atttgtcaga tcctgctccc caactccaca 38940
gttcttagtt catcttaagc atatggctgt ctgtcttttc tctaaagatc ctcaagggaa 39000
aaaaaaaaaa gcatctccag ggggaattta ctgcctcata gccctgacag agatttctga 39060
ccaaacccta acgaaaaaat ttcttccctc catttgtctt ttattgtttt tacaggggag 39120
atatgtaaca taataacaat tatattgcac ataataatta cttctacaaa taataatctg 39180
ttgtcaaaaa tatacacagc tttggatttc cttattatgg cccttcatta agttgtggtt 39240
taagaatagc tatgattatt acttttgtga taattataat ccataatatg gaaacttata 39300
aaattacctt taaagtgtta ctattattct ggccacagga tggaaagttg ttcgctagtt 39360
actcatttat aacctgaatg tactttttac tgaatctaaa ggtatcatct ttgcttggca 39420
attcccatga cttgtctttc tgactcttca gatctcagct taaaagctct cccttcaaag 39480
aagccttccc tgaccactct ggtttttttct tctttttta cctctactcc ttttcccatt 39540
acttgctgtc atagcattct gtttgtttcc tttgaagtgc ctattccaat ttgtcattat 39600
gaatgagttt ttttgttctg ttgcttatta tccattttcc ccactagatt gtcaactctg 39660
tgagggcaga gaccatgata ctctgttcac tcctatatac attcccagca ctatcagact 39720
ttttggcaca tagaagatac tcagtaaata tttgttgaat gaataagtca taaagaagag 39780
tttatatttt aactcttagt tgaataatct aagccaagaa ttatcaacct gggttggacg 39840
tgagaatcat taatgaatct ttaaaacaat gacaaggcaa tctatttatt aattatctcc 39900
aggtctaaac tttagcacgt atatacattt taaaagccca taagtgattc ttacgtatag 39960
ccagtgctat ctgtctcttc tcctgtcctt tcccctcctc tccttactcc tctctcatag 40020
ttttaggatt agcatggccc cacaacaaat ctttaattca catggcaatt tctaggattt 40080
atcatggaaa atgagccaaa ttgccttcaa gaagttttta cgtacctctt atatagaatg 40140
tgatgtttta tatgtacctc ttatagaatg tgagctttta agaggcatat cttattgcaa 40200
gaaatttcaa tgttgaaaaa aatattgaat atttataaag tcaaaaatgc aaacttttat 40260
atgattttca aacctatgaa gttatatcat gttcaggcct tctttccagc atgtggctct 40320
cagccctggt actgtcctta accataaacc tcatctttgc cctctatagg gagaggttta 40380
tggttataat tactcatttt aaatagtgta tattagtaat gtacactatt tgtatatttg 40440

```
ttgactgcct cctatatgcc aaccactatg ctagaaattt tgtaatattc ttcacgatat  40500
tcaagatatt aacatatccg cattttataa atgaggaaac tgctctcaaa gaggttagtt  40560
tacacagcca gtaagccgct aagcctagat tggatggaag gtatgtgaga aaaaagcagc  40620
atccataagg ttttcattct cctaccctgt acgacagagg taatagaaat tattagttaa  40680
agaaataata gaattttaca agactctagg aagggagaat gtgaaggata cagttctcag  40740
ttactggaat gagtgccaga gtaccagtac atggcttgcc ttggggtttg gactacctat  40800
cttaactcct ttgctcctcc caatcttgat ctcatttgtt tgaaagatca tctgcccaac  40860
ataaaaatgc atttctaatt ctgtaattta agtcagtggc aagatcagat tcagttaaag  40920
tttactttcc tgacagcttt ttagtatcat atctattttg caaaactcta gtgataaatg  40980
tatgcacatt tacacataca gcatctcttc tgattctgac taagatatta ctgggttgtg  41040
tagaagtgat gggctcttta gaagaaaggt ttgatatact actaatctaa ggactgaatt  41100
ttctcatctt tgtctttgcc ccttttgact gatgaccaga gcaggagcac ataacattct  41160
tttgtgctaa cagtatctct gcatcacatt gatcaggaga attggcatct ccagagccct  41220
gggatggtaa cttctctgtt gattttcagg aaagattagg tgatattttc tccatgggaa  41280
gaggatgttt gatgtgtgtt ggctttagca aaaggaagct tgtggagtca actgtaagta  41340
gacagaattg cctttgactt aatctgtttc agtcgttgtt catactcagg tcctccagag  41400
gacctttaag catttttatt gactttgtgg tctattacac gaaactaaag atactgattc  41460
tcagtcatga gtctgctcca aaattgccta gggaatcaaa aataattgta ccagttccta  41520
ttcctggaca ttatgattca tttggtctgg tatgaaggcc aggaatctgt atttttaaaa  41580
ttcactcaag caattttcat atatagctat aattgaaaat ctgtggctga acttctccac  41640
tcccgtatcc atcgcaatac ttccccaagg tggcatttaa gatgggccta gagggttata  41700
taagatttca atattaaaac atggattaaa agtgaagact tttcacatgg agataatttg  41760
gaagaaaaac ttgcaaaaat gtgagagcat tgagaacttt tctttcccaa ggaaagaagt  41820
ggcagcttca tttttggtca ttgcaaacag cagtgccata catgaaagga aagtggtggt  41880
gctcatcaac tttgaataac tttgtacaga acccttgaga ctcctctctg cttataaaga  41940
aaaagtgtca actgtaaagt tgatttattt atgaaccata ggctactatg aaatctctgt  42000
tcccagctag aggcctggga gagtaagata actacttgtt tattccacgg agccacttat  42060
tagctttttc tatagcacat acctcaaatg aagcatttca ataaaagaac cacattctat  42120
tcacatgctt cattttattc tgatttatgt aaaaattccc aaactcctca agcagtgttt  42180
ctttgtaagg caataatctt cagttctgtt gcaaaggtca ggagtgatag aatgaaaatg  42240
gtactagata caacagctct ttggtatttg catggccatt acattgccat ggggctgcaa  42300
gacttgtgag tgcttgatat tttgcttgtt gatgaatgag tctgtgtttg tgctaatgga  42360
gtgatttgag aggtagttct ccactgtcag tcaagaggtt ggttttgaaa gctgattgcc  42420
aatggtcatt ctgctaacca ctctggttct cctttagata gagacttatt cagattcaag  42480
tcttcatgta ctttgtggca taaacattgt acacaccaga tgtattcaac aaccataaaa  42540
aaaaacaatt aggactcaag tagtatgtca gagtgtagtc actgatgata tataattctc  42600
cactaccaag aagatggaag cacactgttg agtagctaca tcctacatat gttggccaga  42660
atttaggaat acacatgtga tctatacatt ttgaggtatt gtctgacccc tagaaaatcc  42720
tggtgaagtt tttctggtgt cagtttggtc ttaatgttta ggaaatgccc acagactact  42780
cctgctttct gcttattcac atagtaaacg caaagcacag gactagtttg tcatctggat  42840
```

caaggagaaa tgagttagca gatataaaat aaatcagaaa ggaggtagtt ctcaaatatt 42900
tactccatga atagttgctg gatgttcatt aactctatag catttgttac tacttattgg 42960
ggatcctgga aagaaaatat attgtctata tccactgttc actgaggccc tctccctacc 43020
cagaaactcc ctgtctccat cactcactct ccacattcat tgacccaggg gaacagttca 43080
tggatgagtg aacttgagct ctatcttaaa ggatggagtt cgatttcaag gcaagaggta 43140
taagagaaag ttcagagaca acactggcta tggtctttgt gaagaaaagt gaattgaata 43200
ggctcctgtg gagatcttaa gtaagtactt ctggagataa ggttgaggaa aagtaggttt 43260
gaatcttcat ccagaggtag cccctaaatg tgttgagttt attgaaagag tacttgactt 43320
ggattcagac agatctgcat ttgactcctg ttttgccatt tataagaatt tgagtaatta 43380
ttgtttctaa ataagagttt attgagccaa gcactcagta aatgtttgaa tgggaaaatt 43440
aactgccctg tttttctatt gtcagatggt cctcttcgtt ggataacttg gtaactgttg 43500
ataacctttt ctcaggaatc agaaggtaga aaggttggga aaatataaga aacaaaaagg 43560
catattccta tttttatttt catattgtct tccaactctc ccaggcttct ttgtttgcaa 43620
ggctgacttt tataatactt tttgggtaga gcaggtcctt ctttggtttg gggttaaacc 43680
gtgagtaacc ttattttcta ggtctcagcc aactttgaag ggcatgaact cacagtagcc 43740
tcactaggat cacttcagca gtgagaattt atctttcttg tataaaagtg taagagttga 43800
tggcggccag gcgcagtggc tcacgactgt aatcccagca ctttaggagg ttgagatggg 43860
tggatcacct gaggtcagga gttcaagacc agcctgacca acatggtgaa accccatgtc 43920
tactaaaaat acaaaaatta gttgggtgtg gtggcacatg cctgtaatcc cagctactca 43980
ggaggctgag acagaagaat tgcttgaacc tggaaagcag aggttggaga ttgcagtgag 44040
ccgagattgc accactgcac tccagcctgg gtgacagagt gagactgtca aaaaaaaaaa 44100
aaaaaaagag ttgatagcaa aataactatc tgtagcataa acctcagtat tctttatcat 44160
tcagtatcaa cattattact gaaaacaata agcaatatgg actgagtttc tgtggggtgg 44220
aaatgtgaag tggatcatag catgatataa cttgtcattt ggcttccttt ataaacatta 44280
tcaactacct cagctctatc aatcacttgg cagtccgtag tgaacattat aactcaaatg 44340
actagtcagg tctgttcatt gcccatgtaa aggcatatac ctgaagtgag aagtctgagg 44400
taacttagca ataagcttgc agtacagtgt ttagtgaagc cgaggaattc aaggatttga 44460
gtcatgccag attgctccat aaccatagcc tatctttgtc acaagtaaga aggtttaaaa 44520
atcaccatac cattattggt cacaacgttt ggagataggg aagagtttgt ggatggatca 44580
tggcagtgca tggacagtga ttagcccata acacaaccag tgaacactgt tgtacccaaa 44640
gcacataaat caccacatat actattaata tatttatgga tgacaacaga cactataatt 44700
ttatgtcagt gctttctgct gtgaaaaaca aagaaagtta agggtacctt ttttatattt 44760
gcatcatatc tccagacctt ttcctttatc tccttcttgc aagttcttct ttctttcagc 44820
tgactatctg ctgttcctgc tatggctccc agtggctttt caagagggta cttgtttttt 44880
aagagaagac ccttgaagga cagagagagc ctgaatcatt caaaataatg aattactcag 44940
gatgaaattt caataatttg caagtgtgtg gagatagata ttttgaggaa gcataatttt 45000
ctatgtaccc ctcaaatcgt ggctggagat gacagcctct tccacctcca tataagacca 45060
tttcatttcc ttctactttt ttctccctcc ttcccccaaa cacacaaaca tacacatatc 45120
ctgtgcttca gtcacacaga acttcttact atttcatttc aattctctat ggctttgcat 45180 gttctgctcc ttctgcctag aatgctcctt tccttttttc acctggaaac atcccaattc 45240
aaatgtcacc tcccttattt ataccaactt tgtctgtaac tcctttatca cacttcttcc 45300
tgtgattagt caattcactt gtctgctgtt acacctctat gagagatgaa aattccttct 45360
ccatctctgg aactcatgcc cttcgcatat agtaggcaat ctgtaaatgt ttgaaggttg 45420
agtgaattaa tgaatgacct tcaacctttc aggcttccaa ttttctctct gaaaaggaca 45480
gccaaatgaa aactcataat tttagaagat gaggttagac ggttggtagg tgcatgcaga 45540
gaccagttat tatttaggta ttatggaagt ttatagttct tgtatgttga gttcagtgta 45600
agagtggccc caaacatagt taatgaccac tccagaccca gttgttatag agttggcccc 45660
agctgtattg cttctattta agactaggat aagaaatgac actttcctac tttttacctt 45720
attgaaaggg tagaggctca ctgttatcaa tctcagttca cttgttgatt gcactggctt 45780
gccaagtgag aatattagca cctctgcaca tttctatagc tctgccactt atgagatctt 45840
tccttcccat tgtcatattt aataatcagg atagccctat aaaatatgca ttctcatttc 45900
ccagatgagg atactaaggc tcaagtagga gaacttactt gtttagtaag atcatacagc 45960
taggaagtgg gagaggcaag agttgaaccc agatcttcct agctcctagt ccattgttct 46020
gtctactggg tcacactgga ccagccagga ggcaggaaaa tcagctgggg aatgtggtgc 46080
caacgtgtga tgtttgccta aatgtgtgca tccttgctgg aagccagcca tgattcatgc 46140
tgcataagta ttcattaatg ttcatttcat ttatttggct atccatatgc tttccagggc 46200
gaaggcaagc taggacaagg gcagacaagc agccttaaag tttgggtgct ttccttcgaa 46260
gttgagctgc ctgtttgaaa atcacacttt ttggtgatag aagatggttc cagtacagat 46320
tttatttatt actgcatcta catggataga cattttccaa agcatagctg aaaatatgtg 46380
taagtcccag aatattttct gatttagaca cagactttga gcatgataac cacatttagc 46440
atgttaggaa attctgtcag aatgcttctg gaaaggctac ctttccagaa tgaaatgaaa 46500
aaagaaaagg atggactttg aaactggcta gatttgggtt atacttactc atagtgtgac 46560
cctggcaaat gatttaactt ctccgaattt cacttttctt attctttgaa gtgaaatttt 46620
aaaatgccat cttgcctgat ttttgtgaga atgaaaatga gatcccacac caggaattta 46680
gaagctactc agtaaatatt gcttctctcc tttccccttc cccagtcctg tcccccgaga 46740
cattcagtag ttattcacag gcatgcattc tgaagtctgc ctactgctcc atgttgaaat 46800
gcactgctct tgcaaggact gattatctat ttttctgtct tccaaggccc cctgtgttcc 46860
actccaccct cccaattctg ggggcttcca aagtgggcag gtacagaatg ttctgtggag 46920
catcggaggc tgttactcaa tatcttggcc agcactctca actgctcttt gcacacactc 46980
catatgaagg caaactccag atcttggagc ccatgtgtgt gtcatgcatt gtactgcttc 47040
ttgtacccaa atccatctca agggtgagta gaccaggctc agacttgtcc tgggagcaga 47100
tttctcaagc tgcccatgtc cccacactgt ttgattaaaa ggaggtgctt caaactcttt 47160
ggctttatat agactagaat cagaatgatt ggtggtgcct ctgttctcaa ggtatcccaa 47220
agcactttgt aaggaaatat gacaagcgct gaggccatgc aggccagtac aacagccgcc 47280
acccagcact tcacaattag tcatgcccag cctgggatca tcaagcctgt ttttattgga 47340
agagcaagag agagagggaa tgctagctgg caatttcccc aggtaccctt tatgaaagtg 47400
cccttggctc ttccaatttc atctgaataa ccagctcagg caaattttcc tctatcaaaa 47460
agcagaatgt gatagtgaca agctgatgcc cggctgatgc cccaggacat tgactaaata 47520
gacttggcct cacaattggt ttttattctc tatctccttt cttccctttt gttctttttc 47580 tgtgtttctt tccccattgc catctgcaga gtgttctcag tcagaagtca gctgtggggt 47640
ggacagtttg tcattttaag atcatcccta ttctgtctac ctttcttatc cctcatatca 47700
ttgcttttag agcaaggaca attctggaag tgaaactaca ataacactct gggctccttt 47760
ccctctagta gtactcaaca cacttgtaat tacatgttca aatttgtctt tcttatttct 47820
acttaggttc atgaaggcaa gggacatgcc tgtgttgctt actttctctt ggcaggcaca 47880
tacagcaagt cttcaaaaaa tgcttgttaa ctacaaatta agtgtttaag aagtccactg 47940
ttaattagcc gggcgcggtg gcgggcgcct gtagtcccag ctactcggga ggctgaggca 48000
ggagaatggc gtgaacccgg gaagcggagc ttgcagtgag ccgagattgc gccactgcag 48060
tccgcagtcc ggcctgggcg acagagcgag actccgtctc aaaaaaaaaa aaaaaaaaga 48120
agtccactgt tagtatcttt tcccctgcct agtttgtaag caactggcct cttctatttg 48180
taagttacct gttttcattt ccatatgccc caaagcaaac tttagctcac ggccttacag 48240
agtgtgtatg ttagtatgtt aaaatgaaat caactttcct ctcccaggcc ttctaattga 48300
catgaatttg ggagtagact tgcattggcc tttgtcctga cagccaacag agtcctcttc 48360
tgttgtattc actgttgcct tccatgagga tcccatggag aaagtttgtc attgatatac 48420
attttgaggg cagactcaac ttgagtaaac ctgattgagc tttccccatc tgcctcccag 48480
agatcactgc ctgtgctttg ttaaaaagag aattatagga gtcctctcaa ggcagagagg 48540
cctaaaatta gacatggcag ccatgccttt ggtgtgcatg gaggttggat acaggcagcc 48600
agtttcccct ctgttttctc ccttgcttac acagccaagg agtggagcca agcctcaagg 48660
ggaggagctg tatactcgag catgccctgt ggttcctggc cctgactgag ggactatttt 48720
atatatccca atagagaagc gtggaagaca tctaggttgc cactgtcatt tgaaattgga 48780
atttttaaaa gagaaacctg aagacttgaa gaaagctttc ttttgcctcc ccttacagtt 48840
gatttttgag cttcttaaag ctacctagtc caaagtaccc acactcttat tcttttgtct 48900
ttcctactgg ttttattttt ttttcatctt cccaggtgtt tgatgatcac taagagcttc 48960
aacattgctc accctgacca ggtatgaagc caagagtttg gtttagggca taaaagaatg 49020
tcggaactca aggactaggt tgaggtgggg aagggggatg aaggcttctt tttttcttgg 49080
gttaagcaga aataacttag atctcagagt gaaagccttg aattatcaca tatatcactg 49140
gaaaagacta gttctttgct atgataacaa ttgttcatca tctctcccct gaggatttgg 49200
ggtcaaggcc tggctacacc ttttaatgat ttcagtcatg tgacttaacc tctttaaact 49260
tggattttct tcatctttac aatggaaatg atgacaataa tcactacctc acagatattg 49320
ataataatga tatctcacta ggaagagaat taagtaatat gagggataaa aaggcatttg 49380
taaatggtaa aatgagatta tgattttgaa agctattatt attttccttt cactgtctat 49440
tatctcaact cttctatttt cttgcctttt gtacagcatg gataatttag atgtgactct 49500
ggacagaggg atggatcaga tgacttctta agttatcttc cagtttagga gttcgtaaac 49560
tatactttct cctttccaga ctatcctagt aagaaaattc tcttttaaga cagagtagaa 49620
ctctggaatt catcagtttt gatgtttctt aaagtgtaat ctaagatagt gctcctgtat 49680
taagttctga tgtctgacca ttgttcaaat aaagagtaaa atgcaaatga caggaaattg 49740
gctgcgttct gaatcctatt tttatttggg ataacaataa gcctgtatgg tcactgtgac 49800
ctttgatttg ctgtttctgc aacctcacac ttgtctcagg attcttcttc cacttctgca 49860
ctttatattg ggtttcttcc aggcatcata ttaaacttta agccaggtat gtgtatatgc 49920

```
atgggctgtg ggcctgaaaa aaattagccc gagagagaaa aaaatttaag tagtgggcta  49980
gaagtaagca tgctactaga aacagaattt gggaacacag ctctgggcct agaaaagcga  50040
cctgtcaact tgttacagtt aacatcaata actataggat gggtttggtg gaaaattatg  50100
ctgaccaaca gggtgggaga gaatagggtc agaatatata tcgctgtaag gttgagaaaa  50160
aaagaagtga aaaaaaaaga aatgcataga gagaaaaagg agtttagagg taacatgtta  50220
aagtgtgaga aataaactgg agagcttgac ttctcttgaa tatattttta aataaagtac  50280
tcctttcaac tccaaatgca gcaggcttgg ttcccttctc ctacctccat tgcggatgaa  50340
agcttaatct ttaagatggg cttgggtggg tagagtacgc cccttggtga gcactgtgct  50400
ctctgcaacc ccaataaggc ccaacagggc tctccaagga ggcaaaattc tgatgataca  50460
tttctgttta gtggaaaatg ggtagggaaa attatgtctt agaatcaatt aaccaaacat  50520
aaaatcctcc aaggggcttg gtaggatgcc tagggaagag ccacgagata aaaactccag  50580
gctggaaggg cattgttgca gcactgtcat tctccagttt ctcttggagt tgtcaccacc  50640
ctctcctttg ttctcactgc tgacatcatt tgtaaaataa tttcttccct taaataaaca  50700
agacatacaa tcctctaaat gactaaagaa cagttaccta gaagaaacct tagtggaaag  50760
tattttcttc atctaacgga tgattgtctt tacagaggtg gagtaaagga tgtgcgaggg  50820
agcataatca agctaagaga tgcatgctga cttaaaaggc atgatatatg tgaaactaag  50880
ataatgtgtt caagagtgat gctttgttga tgcagaacca ctgaattcct tactattatg  50940
tttgcctgac tatcggcctc ttaataaaga acttgtggtt tgagtgttca ttgaaattag  51000
ccatattagg tttatgtggg gatgtgagga tctatgtcta ccaattgcag cctctgctgc  51060
aaattggagg cagaaatctg ggctgaacaa taggtaagag tgtcaactct acagatctct  51120
cacatgctaa gcaagcacaa tatagggcaa tccaggttta cacaaaggat taatttggga  51180
acaattatcc tcattttcac ttcctaaaaa gattttgaat aagatgtctt ttaagtaaga  51240
agctccctga atgcatttaa aatatgattt gattatgtac atttcagatt tttctacctt  51300
tctaggagta tctctgttgt ataaaaacac aaaattctgg aacttttgaa aggaagatgt  51360
gcctctcttc atacatttgt cattcttgaa cgattgtaaa atgaagtgac tgcatatcac  51420
gtcatgtgcc ctattgattt cttttcttgt tttaggaata ttcccagaaa aaaaaaaaac  51480
tttttttttt ttaaaatcta ctaagcatgc taggtaagac tgaagatgaa tctatttaag  51540
ttatgtcaat atctatttat aaagattttt gtgatattct tttcactgta gaacttcaag  51600
catatcctaa aaggaacggt tagatacctc tacaaactgt ggcaatgact tactgagtaa  51660
ttgctggcaa ctgatttttg gtgcttcttg ttttgatagt atagcagtgc gagtaggttt  51720
cagaagagca aaactaagac aatccaggga aatgccattt gagaatttct aactttaaaa  51780
aaacaagtaa aatagtgcca agaatattat ctaactaacc ccaaagtcta caatgtaact  51840
cttttatttt gataatgctg ttctaaccct atctacttca gtcctttccc acccagctgg  51900
tttaggaatc aaattcccaa tgtttcatca ctgttaacat tactgtttta ctcttcactt  51960
tagttcttaa atggcatagt gtcttaaatt ccctcagcct ctttcacatt tgatttcttt  52020
ggaaactttt tacctttca ttgaagccca tatgatcttt tccgaaacag acccttatct  52080
ttacctcctt ctttggagtc tttctcctac ttgaatttct gaacttctta aaatggccgc  52140
tttgggttgg tgtcagtaat tcagtaataa gttttctttt ctttttttt ttttcttttt  52200
ttttgagaca gagtcttgct ctgtcaccag gctgcaggct gtagtgcagt ggagtgatct  52260
tggctcactg caacctccac ctcccgggtt caagcgattc ccttgcctca gactcccaag  52320
```

tagcaagtag cagcaccatg cccagctaat gtttgtattt ttagtagagt cggggtttcg 52380
ccatgttggc caggatggtc tcgatctctt gacctcatga tctgcccgcc ttgccctccc 52440
aaagtgctgg gattacaggc gtgtgccagt atgcccagcc agtaataagt tttcttaagt 52500
gctttcttaa tattctgata tttttaaaaa agatctggac tattttgtca tacaggcaac 52560
agaatgttaa accatttcat aaaacaatga caaatataca tgaatttttc atcagttata 52620
aatgcatttc ctttataaca ttgaacatgt ttttgcaact gaaataagta cggttttcat 52680
ttttagaagg cacatgataa agttaaggca gtggttaatt aatttttca gattaatttt 52740
tcagaaaagt gactgtttct gtctattgtc ttaaccccag gcatcaaagg attttaatca 52800
gaaagaaccg aggaataatt tggttatttt agtgcctttt tttgagacaa agtcttattc 52860
tgtctcccag gctggagtac agtagtgcgc tcatggctta ctacagcctc gatctcctgg 52920
ttcaagtgat cctccaactt cactttccca gctaactggg accacaagtg ggcaccacac 52980
tctctgcaat ttattttaat ttttcataga aatggggtct cactatgttg ccctggctgg 53040
tctcagaatc ctaggttcaa gcaatccttc cacctcagcc tcctaaagtg ctgtgatttc 53100
aggcataagc cactacactc accctatttt agagctttgt caagctttgg aaagaaaacc 53160
atttataata taatagataa attatggata tttgaggcag tttttatcat agtatacatg 53220
gtaaaccaca gcccccttt ataatatttg tatttaataa aaatgaaaat attactttta 53280
tcttaaacat gttttaacaa agcaagcata tgtagattag cactaattaa aacaaaaacc 53340
tttgtaatga tagctgtttt ttatatgatt acaaaaaatt tactatacaa atttttatcc 53400
taatcagtgt gaaaaactgc aaatattagc ttatagggct agtcttcaga gtcctcttcc 53460
tacctactac tgctaataag ccaatgaaaa actctctgat gtgtgtggtg gctcaggcct 53520
gtaatcccag cactttggga ggccaaggtg ggtggatcac ttgcactcag gagtttaaga 53580
ccagcctggg caacatggtg aaaccctgtc tctactaaaa atacaaaaaa ttagctaggc 53640
gttgtggtac gcacctgtag tcccagctac tcaggaggct gaggtgggag gatcacttga 53700
gcccaggagg ttgaggttgc agtgagccaa gatcacagga ctgcactcca gcctgagcta 53760
caaagtgaaa ccttgtcaaa aagaaagaaa gaagagagag agagagagac aggctcctcc 53820
gctttttcag ttcctaaata attttccaat ctagaatgca aaagattctg aaggaagaca 53880
gttaccattt cagatcggca gaagttgtgg ctttaatcta gactcgaata tgttttacat 53940
caaagggttg cctcaacagt gctcaaacct gcctctctga aaacatgctg agcacgaagg 54000
ttacttgaag tcttagcttg agtacttaag agagtgctat ggagggattg ttgatgagag 54060
ctgtgtcaca gctaattttt ctttagtaat taaaggttta taaaaatctt acactgtata 54120
ttgacaaatt tagcaacaaa atgagcttga gaaaaaaatc aaggcctgcc atggcatctt 54180
tgctttttt tcttaaaaaa aaaacttttt agaaagatta tgcgactgta ttatctgtaa 54240
ctactgcaat ggtgtaaatc ctgatggtat aatttgcttt ttaaagctat ctttacttca 54300
gtataactta gattaaattt attttaaatt taaatgatat ttttctcttt gtttattatt 54360
ttataatgtt tcccatagaa ttcacaaaat tcattagaaa gatttttttt tacttcctta 54420
ggtcattaag attctgattt gtcaatggat ttcacataaa ccctgtcttt ccaaaaatat 54480
acaaaaaaaa aaaaaatagc caggcgtgat ggtgcgtgcc tatagtccca gctactcaga 54540
aggccgagtt gggaggattg cttgaaccca ggaagttatg gctgcagtga gctatggtca 54600
caccactgca ctccagcctg ggcaacaaag tgagacccca tctccaataa ataaataaac 54660

```
aaataagtaa ataattttca ccttgaaaag cttataaatg tatgaaatca caatgagggt  54720
cgctgatata gtttggatgt gtgtccctgc ccaaatttgg ttttgaattg taatccccag  54780
tgttggagat ggggcctgga gggaggtgat tggatcatga gggcagtttt ttcatgaatg  54840
gctcagcacc atccccttgg tgctgttgtg gtgatagtaa gttctcatga gatctggttg  54900
tatagcacct cccccttgc tctcttgttc ctgctttcac catgtgacat gcctgctccc  54960
ccttcacctt ctgccataat tttaagttgc ctgaggcctc accagaagcc gaacagatgc  55020
cggcaccatg ctttctgcac agcttgcaaa gccatgagcc aattaaacct cttttttttt  55080
tttttataaa ttacccagtc tcaagtattc tttatagcaa ggcaagaatg gacttacaca  55140
gtctcttttg tatcagggag agggtcttct tggtgactcc acttcttttc tttgtttatg  55200
tatccttcca gatgatgtat ttatttcctt tgtttttcaa ttgatattta ctcttaaatt  55260
aaactaatta tttaaaaaag cattttaaag tctcatttta gattattttg actatctgat  55320
ttttaaaatg gtttaaaaaa tctatcttgg cctccatatg caatcaaata agaaacacat  55380
tttaagcata ttatttacct tgtggattct gccttcctca gtgtgttcag tctgtgtata  55440
ttcatttctc ccacactgta agaagctagt cagatgtata attggattat catgctacat  55500
aatcttagca cactcatttt aagcatacat agactagtga gcaccactca ttacatgtca  55560
tttctctaga gaaactagtt gggccatggc tgcaggactc tcacttgaaa agacatgtgt  55620
ggtgatgttt tctcaggcag ttaagcaata aagtgtaccc tgatttgcac tgaaaataaa  55680
gattccttta aagggagcag ttctagttat ctctctcttt aggtaccata tgctgaacgt  55740
ttttctatgc actaaaacag caactaggtt ttatactctg ccttacagcc tacttcacac  55800
ccatttcaca gggagaggaa cagagaggta agtgatttgc cccaaattac ataactagga  55860
agttatttgc tcagtgtgga aacttgttca gaaggtcatt tcattgaaat gtaggaagag  55920
tttctggcac ttctcttgag caggagtcaa aaaccttttt ttgcactagc ccagatagta  55980
aacattttag gctttgtggg ccatatgatc tctgtcaaaa ctcctctact tcgttgttgt  56040
agtgcaaaag cagctataca caatcctgaa atgaatgggt gtggccgtgt tccagtacaa  56100
ccttacagaa aaggcaatag gctggatttg gctctgagac tgtagtttgc tgacctcagc  56160
tcttgaactg agctctttaa ctgacctcag ctcttgaact atggtacaag atcccatggt  56220
cctgtttggt acctccattt gccctccttt tcactctctg ggagcatagc taagttcaaa  56280
attgaattag gtacttgtag taagagcata cttataatcc tgggatcttc atgttgccag  56340
atattaacct cttgaagttt ttcaccacaa cctgggcact tttctgattt gctcacttct  56400
agccccacct ttgggcccct tcataagcaa acatgcaggt tttccagaga gctgtatgct  56460
actgaatgca gaaaatttgg ctcatactgg cctatggact atctgctcac tgccctgata  56520
actattttcc aagggagtgg gtgccctacc tttcctacat gaagtttttt gctagtcttg  56580
ccctaaaaat tctaggtatc ccttgctttt aggataaata tgtttcactg ggaccagctg  56640
gaaaacgaaa aatagaatta tccaactacc actttaaaat tggacaaaga cttttgttgt  56700
tgttgttgga gggggtggta aacatcattt tagcagacca aatatacttt tggtgaaagg  56760
cagcctgttg caaagacaca acacttggac aagattttga agccctggtt gcctttacta  56820
ctgacttaac tacagtattt gcggacttga gcaagttgct tcccttctgt gagcctcagg  56880
ttattcatct ttgaaatgag tataatacct gtgattataa ttacttatct ggattctgca  56940
gagaattgaa ggagataatg ggtgtaaaag tactttagcg cccagcactg ctccttatga  57000
aaatgaggaa ataattgaga tgagtgagcc attgaggcaa cagtacaaaa agtgctgaaa  57060
```

```
actcactgct taaataagca cctcttactg cttttgtggc actttgtagc aatgtttttt  57120
tttttttttt tgagacggag tcttgctgtc ttgcccaggc tggagttcag tggcacgatc  57180
tcggctcact gcaacctccg cctcacaggt tcaagcattc tctgacttca gcctcctgaa  57240
tagctggatt agaggtgcgt gccaccacgc ccagctaatt tttgtatttt tagtagagac  57300
ggggtttcac catgttgatc aggttggtct cgaactcctg acctcatgat ctgcccgcct  57360
tggcctccca aaatgctagg attacagatg tgagccaccg caccccacct cagcaatgtg  57420
tttttattct gactagaaaa gtaatgtttg gttttgtttg gctctttgct taatataccc  57480
ataataaggg tacctatttg cctttggacc attagttcaa atattatttt attaatatgg  57540
aattactggg ctccagaagc catagtcttc ttagctgctc cctatcccca ctctcacctc  57600
aattttttt tttcactttt gtttttcttc tcagggaaag gtttgaggca aagaatgtct  57660
tcttatgatc caaaaccaag catggtggtg atttattcac caagagattc ctaagtacct  57720
gtgtgatgga catggtagaa tctttgtcct gagggagcta tctagatcca ttccttctga  57780
tatgcagcca gtagccactt gtggtaatgg agcaatagaa acaacactag ttcaagtgga  57840
aacgtgagat gagaagtagg aggtggagag aactaaccag aagagggtac ccaaataaac  57900
cagaaatatg tatgtgttag agaaggggcc tattgagcgg gtggcagtgg catgtgtggc  57960
attacttgct cctgtattct ctgcttttta cttagttgtg gctttggtgg tatagtctca  58020
aatctaagtt acgtaggtaa tattgttatg tatcatgttt tggcaatgta gactaaatac  58080
ttgctcataa gagtacagga caatgaggat agtttggttt tgtttactgc atggaaaatg  58140
caggatgttt agtaaataga ttcatggcgt agtgagttca ctactaaaat cagactctga  58200
gaatgggttt gatttaaatg gctagtttag aagactgaat ttaggccact tgattgagaa  58260
aggccatttt gggtaattat aaaccaccaa cattgtgttt tgaatgttaa agcttatatt  58320
tgtcttccag ttaccagaat gtaagcttct tgaggaggga gagaggagtt ttcttaatct  58380
ctgaacctgc acctttcttc tgtgcctagc ccagtgcctg gcaccaaaca ggtgctcaat  58440
caatgttgat tctatgctac caacaaaaat gagtccatga tgtttactat tcaacaaatg  58500
aatacaattt tagagtaaat ttttactgct tacactacat gtagattttc tttttagaga  58560
tttcgcaatg ctgatttatt tcaaaataag cttgaagcta agcgacaaag ctgaatgatg  58620
atttgttttt tatttatttt taaatccaaa cttacaattt tacatgtcat tgccagaaaa  58680
atcattaaat aaattatgat atgcgcatat ggaatacttt gcaaccatta aatcaaccat  58740
taaatactat gcaaccatta aatcaaccat taaatatgtt ggtatatgca aatgtgcata  58800
taccaacata ttatatagtt gagtaagaaa agctagtttc aaatgagtat gttaatatca  58860
tctgactctt gcaaaaggaa aaccatacat ttgaatgtac atatatgcat atgtttatat  58920
gtgcatagaa aaagctatga ggggatatac ctcaagttgc taaaagtggc tccacctgga  58980
gagggacatg gaaaggagtt ggctaaaaac tgaggtttgt tatggtatac acccctgcac  59040
agtttgattt tttaaaaaca atgattataa attactttta ttatttataa aaatattatt  59100
taaaattttg gtactaaaaa cagagctcca tcaacaggtc aatggataaa gaaaatgtgg  59160
tacatatata caaccgagta ctattcgtca taaaaaaatg agaccctgtc atttttgcaa  59220
caaaatggat ggaactggaa attattatat taagtgaaat aaggcaggca cagaaaggca  59280
aacattgcat gttctcattt aatctgtgga atctaaaaat caaaacaatt gaactaatgg  59340
atatagaaag tagaaggatg gtaaccaaag gctagaaagg atagttggtg gggcagggga  59400
```

```
gggtgaggtg agcatgttta atgggcacaa aaaaatagaa acaatgaata agacctatta  59460
tgtgatagca caataaggtg actatagtta ataataattt aattgtacat tttaaaataa  59520
ctaaagaggt ataataggat tgattgtaac acaaagaata aatgcttgag ggatgtatac  59580
ctcattctct ataatgtgat tagtacacat tgcatgcttc tatcaaaaat tttcatatac  59640
cccataaata tatacatcca ttgtgtactc acaaaattaa aaaaaactgt gcattaaaga  59700
aaaacaaaaa taaaaaccat agttcaagtt ataaacaaaa taaaggtaat ttggaggaaa  59760
actgtcttca gttatattgg atatttgggg gacatttttg tatgttagtt agcaaagatc  59820
acttgaaaaa gaagattctt ccttctatga ttcaagggag cctagcaaaa aataaatgaa  59880
atgaaataaa ataatacaaa gagaaaagat tattccataa attctgctta cttatttctg  59940
gcaaacttgt tgacagcaca tgtgaccttt tggtaaaaag acatttttat atttttagtt  60000
aagtttcaaa tataaattgt ttgtgttttt aaaataaatt aaatggatga tttcagccag  60060
atcattatga aaacacatga gatattgggt tatgcaatga ctaacagtgt gtacctttc  60120
ttgatattta ttcataaact ggggaataaa agtacatttt ggcccattta ctccttaaat  60180
aattttatgt ctcccaagga gagttgtaag ttgcttgata gtaaatgcta tgtattttgt  60240
accttagtgt atatattatg ggatttcagc gttagaagag ctcttaaatg ccgtgttcat  60300
agtccaacct gtcttctgat gcttgaaatc cccttgcagt aggaaatgca aagtagagag  60360
cagacactca ataatgtagt tagtgaatta tttagaaaga ggcattttga gcccataatg  60420
tatgataggt acttctacat ttattatttt attctttgca gacctgcaga aaactgtaag  60480
aaaaaagttt atttcagatt catgtgttta tttgattaat ctcttcatag gtttcatttt  60540
tcagctcctg tcagaaaata cagattctta taaggttcac cttttaccca taagaataat  60600
agtataaagg ggataatgtg aaatacaatc acttcacaga ctgtttcaat taaataagag  60660
ctcgtagata attcagtcca ccacacccca ttttacagat gttgaaattg aagcccccac  60720
caaaaggaaa agacttgttc aaagtcacac agcaagtcag tggtgaacct aattaggccc  60780
cctgccttcc attttagtga gattcctgtg ctgatagtca tacccatatc aaatcctctt  60840
tggcagttat agcttgccca cagtaatgtg tcctgaaaaa tatgacaatt aattaagttg  60900
gagacagaac cataacctct ttataaaaat tttctggaaa gtttacatga cagtaagtaa  60960
tatataatta gaaaggataa ttcttatttc atatttatct ttttgtttca gaataataaa  61020
ctaagctatc tctactcagt ccattttaat acaaaaatat ttttacccgg actgagtttt  61080
tatgcttttt aggaactttg tatctgcctc acttagttaa aatcctagct gcactaatca  61140
cttactgtgg tgggcagaat tctagaatga ccctgaatac cttgtccttg tatgattcct  61200
tcctctttaa gtaaggataa aaactgtgaa tatgatatca ctcccttgat taggctttgt  61260
tatatggcac agttaacttt aagaaaggac caatcacaca agccatttga aagcagaggg  61320
tttgggtatt ttttaactgg tggcagaaag ccacgcagag atttgaacat tgaggggaat  61380
ttgaatttga tgtgccagta ctaacttgaa gatagaggag gctgcatgga aagtggcctt  61440
taggagtgat ccctggctga cagccagtaa gaaaatgagg gcctcagacc tacagccata  61500
aagaattctg tcagtgaact tgaacttgga agtggattct tcctctagaa cttccatata  61560
agagtccagc ctgattgaca ccttgatttt ggacttgtga gaccctgagc agagaatcca  61620
gttgacttct gacctaaaaa aaaagtcaga taataaatga gtattgtttt aaactgctaa  61680
ttttgtgata atttgttatg cagcaataaa aaactaatat atttaccatg caaggcaagg  61740
catttatcct ctcatgattc agtttctttt tacctgacat aatggaatta atttatactg  61800
```

```
ctgtgaagtt gtagttgaga aacatgactt ctaaagtaat agaggacatg tattattaat  61860
tttagtagta ttaatagtaa tgatactgat tctcccaggc ctatacaaat cctttgatac  61920
acaaatgaat agtaaaggaa cataaattgt ctctaggtag actttcccac aatgcaattt  61980
taggatacag aggtcatatg cctgttattc tactgtggca gagaaaatat ggagcctgga  62040
aaactgttca tttgcatcac atacatcttg ggagctcact ctgaacctgg taccataata  62100
agctctgtag acagtataaa gaggaaagga atcagacatg gtgtctgacc tcaagtgtct  62160
cataacgtag tagaagaggt aaaatatggg tcacactaac tctactgcaa agtaggaagt  62220
gcttgtcgcc ttgagattga caaaatttgg taagagttca gaggagattg tctgtgaact  62280
gggccttgaa gaatagttag gatttgaata ggagaaggtg aagaaggaag gcattccagc  62340
tagggagaag agcacaaaca aaagcataga taaccttgaa catcatcata tgggataatt  62400
caatagttca gtataatgga agtataagat gcataaaaat aagtgtagta ggaaacaagt  62460
ttaaaagtat agattggggt tagtcataca aggccttgaa tttcaggcta aggagtttag  62520
acattaacat ttgtttttga acaaaggggt gaactgatca catctgtgat ttagaaagaa  62580
aattctagca atagtgtaga taagggttga tggtaaagtt tggaaggtgg tgaggcagag  62640
gctggagaca gggagcacat ttaggataga aagatgataa agagatgatt tagaagagtt  62700
gttttggaaa aggagaagac agaaaatgtt ttagaggtgt catagagata aaattggcat  62760
ggcatggtgc aaggaggtaa agcccaatag ctttgtaagg tgctgagata gattgaaatc  62820
acagagttag gaagttttag agtcaggatt agtaccaaga cagcttggct ctagatctca  62880
tacttaacac ttacagtata attctgagag ggtgggtaac agcaatagtc agaggaaaga  62940
accctttat acatgatggt acaggaacaa cactggcttc caaccccaca gctgctcttt  63000
aacagaaggt cagaagctgg ggagaaatat gtgtgtgtgt gtgtgtgtgt gtgtgtgtgt  63060
gtgtgtgtgt gtgtgtatgt gccatttctg ggactaagga tgggaagtag attagttgag  63120
gccactgcag tggggtctgc aagttgctag cactcacccg ttccaagagg ccttaaaggt  63180
gttgatctgt tccctgggca tcaccacatt ccacaaatta atgttcctct gagagaatag  63240
ggtgattcaa tttcactgtg cccgaaggtt acttttgggg ttcatgtttg ttctaagtct  63300
atgctaatga tctgccaact gtctgtttgt cactttctct aacccttagc atgtataaac  63360
tgatctgttg ggaaatgtgt agcatttata ggatggtagg atttgtaaca tgcgatcaca  63420
ggactgttta tatagagtcc ctgggaaggg gagagaagag tatttctgtt acaaatgtgg  63480
attctttggc ccctcctcaa acttactgag gttcaagaat tgacatttat aataagcaca  63540
tatccatttt caataaacat gaaagtttca taccctcttt taatgtttga aatcctcaaa  63600
taaattagtc attggtgcca gagtatcaaa taattatggt acagaatgta tttctctgaa  63660
tgacaccttc tcccagagat tctgatatat attcctctgc actcaccctg tttgataatt  63720
accagtatat ggaccattta cctgaagaat aagagtaggg tttcctactg ttgttgaaaa  63780
tttgcttgac tcttaacaac ttgtgtgtga ctgtaacaag atcacacagg gtaaacaata  63840
ttagcttatt caaccactgg ctgaagaaat ttaggaaagt gaacacattt ttctttacat  63900
ttctctttgt tctgtgagcc ttttatgctg gaatagtttt cactgcaggc tgttattgtc  63960
tgcctccaga ggagggagtt gacctagcag tggtaactgg agagtgtttt ttgaaacctc  64020
tttccaaggt tagttgccaa tggcatcttt ggaacagtgt ccttcacttt tgtccctcag  64080
ggaccagtgt gagaatggga actttatgat ctggagctgg ttaagtgaag tccaaaaata  64140
```

```
attaagaaag tgtttccttc cctgggaatg agttcagtag gaatctcaat gtattgtaga  64200
gcactaagga ctcagcctca ggcatttgca aaggattctt ccagttgcct gtgttacaga  64260
ggacacagtt ggcatttcct tttggtgttg aggggagatg tgtacatggt tgtgagatga  64320
ctcacccttt ttgcttagat agttccactt tcattgtgga cagactcttt ggagggccag  64380
tttggcatgc acgtgtgtgt tcattccatc ctggagcatt ctttatgaga aagccatttg  64440
ttgagtggtt tgccattttg ttttacagcc actctgtggg ctatgaaatg gtcatccggc  64500
cgctttattt gtccctaaaa aaagcagttt ttccctttct tatcttcatg gctgccaagc  64560
agcagaaaga gtaactcagg gaagccatgt gatagccttt tatctgtctg ttcagaaact  64620
gatgatgtat tggatttgat aattcatcaa atctgaggtt tactggtttg tatttgcctc  64680
aaaatgggca tataatattt tgtcaggtaa cataatagac agatcattgg cattgcttta  64740
ttgaagtgaa ttaattcaat aagcctgtaa gtgcctgaca tgtgccaggc actgtgctag  64800
gcattctgtt aacagatgag acaaatctct gtcttttagg tgttttcagt cgaacagggg  64860
agacaaatat atgagcaaat tgctattttt tttaaatttc atagtgtaca tgagtataag  64920
gtgctgaata tgtgattgat tctgagggaa aagagagata agggaaagtt ctcagagaaa  64980
gtcaagctga gggaagaaaa gcaccccaga cagagggact agcatagagc tatgctagta  65040
cattgagttt aagggaatgg cacatacttc actgttgctt cagcagacag caggcctgtt  65100
aggttacaaa gggccttgga tgacatgctg aggggtttta aaattttatt taaattttaa  65160
ttgacaaaat ataattgtat atttctgtga ggtacaatgt gacgttatga tatatgtatg  65220
caatgtagaa tgattaaatc aagctaattt gtatatctac cacctcacat acttattttt  65280
tggttagaac atttaaaatt tattctctta acaactttga aatagacaac acattattat  65340
caactgtagt caccatgttg tgcagatctc aaaaacttct aacaaaaact ttttaccctt  65400
tgaagatatt gaactgtttt atgaacacaa tcttagaagg atttaaaaaa taatttgcta  65460
ttcaccaagt acttcttacg tacactgtgc atgaaatgat tattactttt tctaatatta  65520
gttttcttga ttgaggcttg gcaattatta gtttgtatgc ctttagaagg atcataagca  65580
gaggtttatc ccagtaggat ttgcatttta gaatgatgac tttgggagta aaatacagag  65640
aagtgaaacc agagatagtg ggatcattct ggagtctgtt gcctacactg aacagtagtt  65700
gagcgaaaaa ggatgggcag aatgtgttgg ttctgggtat tgcaaattca tggcacttga  65760
gtgaaaaagt ttaagccttc tattggctct ttgtgaatat cttcaacatg catgactaca  65820
aatagaacac atggttttgt tgttattgtt gttgtgtttt tgtttttttt tttatttgag  65880
atggagtttt gctcttcttg cccagactgg agtgcaatgg cacgaatttg gctcaccaca  65940
acctccgcct cccaggttca agcgattctc ctgcctcagc ctcctgagta gctgggatta  66000
gaatcatgcg ccaccacacc cggctaattt tgtattttta gtagaaacag ggtttctcca  66060
tgttggtcag gctgtcttga actcccgacc tcagatgatc ctcccacctc ggcctcccaa  66120
agtactgaga ttacgggcat gagccaccgc gcccggccca cacggtattt ttgaaagaac  66180
agtgagcttg gattagaaca ctagtgtcca ggccctgctg ctactacata agtaattatg  66240
aatccatagc catcttgttg ctcttcttct ctgagccttg gtttctttag ctataaaatg  66300
ggaagttgaa actttctagc tacttctttg agttatgagt aacaagttag gtaatacact  66360
taaaagagaa tgtgctatac aaatactggt tcttaagaca gctgttgtta atgtactgag  66420
tattatgctt acctcacagg gttattgtga gcatcaaatg ggataatgga tttgtaagca  66480
ttttgtttaa agtgtgattc aaatgttaag aattagtaaa aatagtaaaa gaacaattca  66540
```

```
ttctccatcc agatgttctg tccccactgt gacttatgtg ctcattcaga gttgtacaga  66600
aaaacctcca cttaattttc acaagctgga gttccacatg taacagaatc atatgggacc  66660
aaaaaattct ctgtattggc ttcttccctg ccgtattttg gctctgggac caacaagaca  66720
cccattttgc atgagctgcc tgccaccaac tttgcgctca catctagttc tgttgcccat  66780
gtgcaagctg aatttgggcc cgggccccca gatctaacat gaaactcaag tttccttctg  66840
ttcaaactgt ccaggcataa tagtcttaaa gtccgatgcc cagcagagcc gtagattttt  66900
cactggccaa aaatcaacat gaaaccagat gtatctgtaa atctagtttc ataacacttt  66960
gtagtcaatg gaaatacagt agcaggcaga ccagaccaga gtttactatt tgcagtggaa  67020
ttaataacca catggaaact ttgcctttgg tatctgcgag atggaagata aaggtgcgaa  67080
ttcaaagcag ttcccacctt accctctaaa ttccaacata aagaggcctt gaatgtcctt  67140
ctatcttatt gtatatttca ttaacagaag tatgttccta gctacttagt cattctatct  67200
ctattctcct ttgttttaac ttcagtggtg ccagcttaag atgctctggc tttcagcttt  67260
catggagcac gtcatgtttt taaacttatc tttagggaca gaaatgttag gaagatccta  67320
gttcctcatc tctttgctcc tgacaaggaa atttagaatt gcctaaagaa aggatgtatt  67380
ggccaaccta ataataaatc agtattagtg aatctaaagc atatttgaaa aatttgtaac  67440
atgagttgaa attcagacct gcaatgaagt gtttttaaaa gatttaaaat cgaaataata  67500
taaaagaatg ttaaaaacaa gtaaaacata tcactagtta atcactctac caaaattcat  67560
ttttatgttt gcatatttaa ccatttttat tttctatatt tgtccatgaa catgtgtttt  67620
tatatattgt ttatattaaa catggtttta atcatggctt atttctttta tgttttactt  67680
cttttccttt gacataaaat attgtatttt ttaaatttta attgcttctt ggcataccct  67740
tccaatattg gtggctatat agattgaagt taaaactaat tacaatcaga gaaaattaac  67800
aattcatccc ttcaatctca ttagtcacaa gttaaatact caatagccac atctatctag  67860
ttgctactgt tttgaatagt acagatataa gacattttca tcaacacaga aaattcactt  67920
ggaaagcatt gccctggagt aaatgtgcca gactgtacta tatcattttt ctcttgttgg  67980
acatctaagt tatttcttat tttttaaata ttttatataa cttgacggtg aatataccta  68040
tgtacatagc tatttgcttt ggctgaatta tttcttagaa tcaatttcaa aagtggagtt  68100
attaggtcaa agagcatgag aagatttttt ggaacctgca gtgtattgcc atagtcctct  68160
caaaaaagtt tatgtcaact taaagtactt ctagcagcat atgattgtac taatttcgct  68220
gcaatctcaa caacactgga cattataagt ttttattcta ccctattttc cattaaaaga  68280
tagcttatgc ttgattgact ttgcatttta ttttattatt aataatgatg tggtttcctt  68340
ttttctagat tttattttta tttaaggcat cctttgattt taacctgatt ttttttctct  68400
aaaaattatt ctaagaaaag acaaaggtga tacgaaatat atcctgagtt tttatttttt  68460
tcttgcatgg gatttgtata tttgcacctt tgcccattta tactatgatt tcttagtgtc  68520
ttccctggca attttaatga agacttcatg tatatcaatt tttccacaaa tataatcttt  68580
ctaaaaatat gtttttttcca caatataatt cagacgtatt ctccgaaatg ttggaaaaac  68640
ttaagtaggc atcaaagcat ttgaagattt gtttaaaggt tgtttttata ccagttttaa  68700
attgtaattt aagggtcata aaataggtga aaattaaatc atttttcagt aagggggcaa  68760
gaccacttaa ctcttggaaa atacaggaaa cgtagatttc tagaggccaa gaaggaggta  68820
gggattattt tgtaactgcc cccaaccttc taacctgtaa tgaaacaaac actgaaggcc  68880
```

```
cttaaacatt tttaggctta attggctgtc cttgtactta gggcacatct aaaaatcctg  68940
aggcaaccac tcaagagaac atgcttttgt taattcaaag ggagctgtcc tacgagtgtc  69000
cagaatcctc tgtagtcttg ggcctggtgc ttgagagacc caaaggaaag gtcaatggaa  69060
ttacagctta gtgttagagc tttcatgcat cacactaatt aattaatgtc ataaaggtct  69120
ctctcctgtt atgggaaaaa gcagcaaata ggaacttctg gtagggtgct taaagttggt  69180
ttgatatttt ttattagcat ttttaactaa tacaagtaat acatgcttat ggtagaatga  69240
taaaactgaa aaaaaaggta tgaaaattta gaagttctcc tactcatgac ctcacccctt  69300
ctttcactcc cagtttcact cctcagaggg taaccacagt gactagcttc ttgtgtttgg  69360
ttcctgagat tttctatgta tatatattgt tagatatatg catggtatgt tttcaaaatt  69420
cctgttacac tataattact gttctacaac ttaatttttt cacttaatta atagacctta  69480
tatatgcttt tccatatcgg tatatataga tctatataag ttttcttaaa ggttgcacaa  69540
ctttcaattg tatggctgtc ttgtaattta ctttttgttt cccttactaa tggatatttc  69600
atgtttccct aactcttttg atattaagag tagtgctgca attaacatcc ttgagaggca  69660
gtatatatgg tgtttaagat gaatggttct ggagccagac tactttggat tgaatattgg  69720
tgccaccaat tccttgctgt atgaccttag gcaagttgct taatttcttt gcctcagtgt  69780
ccttgtgtga aaaaatggag gcaataatgg tcactatcca gtagggcttt tatgaggatt  69840
tagtaagtta ataatgcact ttaagaactt agttattttt agattaagta gtgaaggact  69900
atataattgt tagtataatt gtataccttt attatcatac ttttgcatgt atagcaataa  69960
gacaaattct tagatgttta accattggac ataaggaatg tacgcatttt aagtactggt  70020
agatattacc ttttccctgc caaaaattgc aaatattgga tattaacttt ttaaatctta  70080
gtaaatctga taagtataaa taacagttta tcatcatttt aagttgccta tcttaatttt  70140
gtgtgaaaat gattatcttt tcacatgttt ttttggccat ttatgtttct ttccatgtga  70200
actaactgtt cctggccatt gcctatttgt tgttgctgtt actatatggc ttttcatctg  70260
tttcttattg gtttatggag ctctttgtat atacaggaat ttagcctcta tttatatgtg  70320
tgacaaatac tttttccaat ttatctttaa aatttgttta tgttttccta ttcatcagtc  70380
taaaattatg tagttaaatt catcattgtt ttttcttatg actttagagt ttggagatca  70440
tgcttcaaag gtctttctag gtggggatga tttaaatcat gtactggaag tatttttgcc  70500
aaaaagactc acgaattatg gatgttagag ctaaaaggga ccttagagat ttcctagttc  70560
aaccaccttt tcttcatacc tttttaattt ttctctgcag atgaaaagaa gtttagtcct  70620
aaagaaagaa aagagtctaa aggttctcca gtaagctaat ggcaaaaatg tagactggaa  70680
cttctagctc ctgatgtgta tttcagtgat cattcaattt aaccagatgg tttcacaaaa  70740
agagctttct actaaaaaat aaaatacata cttaagcaac tcagagaatt tttttttat  70800
ttttcagatt aattttcact tagagattca tcagcatatg tactatacat gtacaaatca  70860
cctgtgtgtt ttggatattt agttaaacaa atgtgcaaat attttaacca aaggagcata  70920
ttcatttgtg ttttattttc ttaatggttt tcgttatgaa tgtgaaatgt gtatttacct  70980
taacagaaat taagtatatt tttggtctga catatatgag aactgaaaag cattggcttg  71040
gctgctaact gcattctcat ctttctttct ctgctttggc aaagtctggg attaaatcta  71100
ataccttttta aactgtttgg gacttcagcc agagtgacct gtcttgaatt cagaactgcg  71160
cagatcattc cccattctaa ggccctctca tgcctcctca ttgcctgtag gatgagatcc  71220
aagtacctta gcatagctta tgcactgtag tcacttgacc tctagcacct atgcagtctt  71280
```

```
ccagtcttat ttacacattc ctttgcacat gctgtttccc cgtgtggggc aactttttc  71340
ttgcctgtct gcctgcctaa gccaacttaa ataaacatca tttctgtaac ttctgtgaag  71400
ccttttccaa tctctccact ccaagacgaa ggtgtttcta taggcatgac ttctggaatg  71460
gcagatcaag gatctggtgg accctctact cagtgaaaca accgtttaac tagtaaaaat  71520
gatcaatcaa ccatttaaaa tcttcagaaa atatcctaag ggcacatagc aaaaagagaa  71580
acatttattc aagaaaagct attaagcctc agtaaaaaca gcaagagtct atggcatttg  71640
agtcatgacc tgttcctaat ccttccctta tctccattct tcaggcaagt gcaaccaaga  71700
agatggaggc ttcctctctc tcaaaatctt actccatagt tataatttca cccacaatgg  71760
ggcagaccac aagcatctct tttttttccc ccagccctat attacagaat cactgttcta  71820
ggaaggcata gcttagagga ttggagattc cttccacacc cactttctac gtatgagggc  71880
tttgccccag ggatggtaag tcaagaatac agggatcctg cttgtgcctg cctcagctca  71940
tatataaggt aaagcttcca cactaggaaa ggcaaattaa gaggactagg gaatataccg  72000
ttatccccag ggtccacttg tagaacaggg gtgtcattct gggagaagca ggtcactgcc  72060
ccacttgtgg aacaggggag tcactcgtca ctgtccctgg ttcaaattct attgcagtga  72120
cagaggttct gtcccaggga aaggcaggtt gttaggatgg agaactccac agttctccct  72180
gaggtgactg actttatttg gaacagagca tgaagaagtt catgcctaag ggcactgtca  72240
aaaataatgg agatcttggt ggtgagcaat taagagtgga ttggtagctc catgatacta  72300
gtaacaacaa gcaaaacagc agaccagcat ggaggatacc agagaaccag acaaaggaat  72360
cactaagaag agcccttgtg gaattgcact cactgctggg tgtgtggaaa gttatgcatg  72420
tgtgctttac tgtaccctct caaaagcaac ctaaacagga tgtggggtag gctctaaagc  72480
attcctcaag ccacacatgg atccatcagt aaaatgtgga gggcttaagg ataaaaaggc  72540
ttaagtacaa tctctggccc tacattttct aaatgttatg ccaccctgac caaggggcaa  72600
ctcctacaaa gccaggcaaa ataataaaat catatttgtc tctagtggaa tggataacta  72660
tgcctaaaac tgtgcccttt gaaaagcaac tagagagata atttctgaag tgtttgtccc  72720
tacctgaatg tgtggcaaaa ttctaaactc cctgaagtgt gaaagtggtt tccaagccac  72780
atgcacatcc agtagtggta aagggtgaaa atctaactgg ctaagagggc ttcatagcaa  72840
cattaaccaa aaagtggttt atgtagtctt tgcctgcttc ataattccct aggcattcta  72900
tgctattctg tactcagaag gcttaaagtc aggttaggga aaggaggcct atgaggttac  72960
tgtgcagagg cagtgctggg aaataaatga agttaaataa atttaggcca tcgtggttta  73020
aagaatggat tgtggagata agaaggataa aggaaaccca gagtcaagaa aaataaaact  73080
tttcattggt gccatgccaa cccatatccg agcctgaggc aaaaggaaaa atgtgctccc  73140
tgatatacac ttatacaaaa tatcaactaa ttttatttgt tggactgaat agaaaaagtc  73200
aacaaaaatt aaaaataaaa aaatcatgac tatattttta ataagtggtt tatgtaaacc  73260
cagagttgac caatgggatg ccagtctcaa ccataaaaac aaacaaaaca ttgtgagtaa  73320
caacaccaga agtctcaaag tgtcagggaa accaatttca cagaagcagt tcagccaagt  73380
cactaaacaa acaaacgact aagcaaaaaa caagaatgag tctcagaaag ggtcaagtca  73440
gtatccagag ttgttacaat atagtatcta aaatattgtt ttgaactaaa aattttgagg  73500
catgcaaaga atgaggaaag tatgactcat acatggtatt atatgaaaaa atcaacaaaa  73560
aactatccat gaggaaacaa agatgttgaa attcactagg gaaagacttt aaaaaccagc  73620
```

```
tatttaaata tattcaaaga actgaaggaa ctatgtctaa aatactaaaa taaagtataa  73680
taacaatttc ttgtcaagta gagaatgcca ataaagagat agaagttata aaaaaagaaa  73740
aaaatggaaa atctggagtt gaaaattata ataactgaaa tgaaaaattc actagaaaag  73800
gtcacaagaa gatataactt ggcagaagaa acaatcagca aattagaaca tagatcaata  73860
tagattattc attttgaagg gtagaaagaa aaaaagaatg aagaaaactg aagattccca  73920
aagaaatgta ggacatctta aagacacatc attaggagaa gaaaagaagg gaaagaaaag  73980
agcagaaaga atatttttta aaaaatggat aaaatcttcc aaaatttaat gaaaaacatc  74040
aacctacaca tcaaagaaaa tttttttaaa acttcaagca ggaaaatgta acgatattga  74100
tacttagata catcatagtc aaaatattgg agtcaaatat aaagagaaaa ttttgaaatt  74160
agcaagagaa aaatgaaatg gaaccacaat aagattaaca gctgattctc atcagaaata  74220
acagagagca gaaggcagtg caatcccata ttctaaacgt tgaaagaata aaaaaactgt  74280
cagtcaagaa tcatatattc aacaaaacta tctttaaagg taaaaatgaa atgaagacat  74340
tcctaggtaa acaaaggctg agagaatttt tcattagctg acatgccttg caagaaatac  74400
taaaagcttc ctagacagta gctttaatct gcatgaaaaa aaattccaat aaagggaaat  74460
ttgtaaataa taaaaataca tcattatata ttcttttcca cttaacttat ttaaaatcaa  74520
tttcttaaag cactatctgt aaaattgtat tgttatttga caataaaatg taaaagaggg  74580
gagtgggaat taagctaaat tggagtaagg aaatggtatc acatggtaaa ttgaatttac  74640
agaaagaaat gaaaaaatta agtggcaaat atgaagagta acattaaaaa cttctataaa  74700
ttaattgtgg cctcctttct tcccttagct tctgtaaaag acataagact attaaaaatg  74760
acaataatta taaacacatt gttttattag taataaacat agacaaatta tctacaacaa  74820
ttattattat acaaggagag ggaatggagc tgtagaggag taaagttttt ataacctact  74880
ggaactaagt cagtataaat atgatgtcga ttctgttaat ttgagatata tgttagaagc  74940
cccaaagtaa tcactgagaa aatgatgcaa aaatacagtt ttaaaaagtt aaaaacatag  75000
tttagcttat gtgtgcctag tactccatta ttattttttt attatatttt aagttctggg  75060
gtacatgtgc agaatgtgca ggtttgttac ataggcatac atgtgccatg gtggtttgct  75120
gcacccatca atccgtcata tacattaggt atttctccta atactatccc tccccctgtc  75180
ccctaacccc ctcaacaggc cctggtgtgt gatgttcccc tccctgtgtc catgtgttct  75240
cattgttcaa ctcccactta tgagtgagaa catgcggtgt ttcgttttct gttcttgtgt  75300
tagtttgctg agaatgatgg tttccagctt catccatgtc cttgcagagg acatgaactc  75360
atccttttta tggctgcata gtagtccatc gtgtatatgt gccacatttt ctttctgctt  75420
gttcccagga gaaagtggct gaagattcca gagagaagct gaatgcagtt taattctttt  75480
tgccataaac acgacaaccc attttcctgc aagctgtgtt agtttgctct cttcttggtt  75540
cattcattca tttattcata gcttccataa atatttaaca aacactaatt aggggccaag  75600
ccatgtgcta ggcacagggg ataaaactgt gaacaaaaca agccccagct actcttaagg  75660
aactgataga caaatggacc agcaaacacg ctggtcctgt tttgaaggca aagcgcctgg  75720
tgctcctgat ctcatgagca cagagcattt agcctaagtc tcatcctcct aaggcctcag  75780
aaataaggcc ttattttaat aagtgcaagt cagtcatttg aagactaaat catagaatcc  75840
tagaaaacta gtaccgggag caaggcaaaa gaatgggatg agcatgaaac atatattcag  75900
aagttgtggt gtgtaggtat ataagccaag ctcttttctt cacttgcttg ctaagtcact  75960
tagcttttct gccttttttgt ttgctctgtc tggaaatgga gttaatgaaa tatatctaca  76020
```

```
tgatagggat attgagacga ttaaataaga tgctgctgtc acccagtatg cccttaccct  76080
gctgtactta gaagtatatg aaattcattt tctaaatttt tgtatgagtg tttcatgcat  76140
gcccaccacc atggaagcta ccttaagaca gtgagggact ttgtttaact tgtttgtact  76200
acatcctcag tctaatggtg tctggcttat ggtaggcacc aaatataatt ttattgacag  76260
aaaggatgat aatgaatgtg aaggcatttt taagtttatg aagtgttgtg catattgttg  76320
ttaattttaa gctgttacgt taaagaaccc ctaatccaac tctcttgagt tttatagata  76380
tcatagaaga tatatcttcc cttgacatag aagcttccct tgaaggttcc cttgactcat  76440
gtatttgcct cacagtgatt gtgcagatcc cacaagataa atttatgtga atgtgcttta  76500
tgtgcttgaa gtgctccaca aatatgggtt ttataagatg agaaaataga gtcagggaga  76560
aaggtgactg atccaaggtc atgcaaagag ttagtgtcag aatttataat ggaatttcag  76620
gctcccaact cccactccag tatactaagg cagattccag agaagaaaca gtggagagca  76680
ggcactgatg agggacaaag aaaagcaggc tccgtctggc tgcaacttgt ctcttcatgg  76740
caaaaagaaa ctaggaaagt gctatgccag agacgacatg ataactttgc agaatggaaa  76800
gagcttgttt accacattga atactttatc tgtgtttatc taacgacagt tccaccagct  76860
ctttaccact tgacttttgc ctaattcaaa aatataccaa ctatgaaaca ttttccttct  76920
cagtttttat tctagattac attttgttca actttatctt aatgtgtagt gtagaaagag  76980
taaggtaaga gtatagcaag tggttatttt ccatttctac tgaggacaga gaaataatct  77040
aagggatttg tattagagat gaagaagtgc atggccagga catgagagat actgtgatag  77100
aatggatatt gtgaagtctt tggtagtttt tgaggggaaa aaagagaagg ttttctttgt  77160
ctgatatagt ttagcaacgt cttaatttag gattcaaaag ttgttcaggg tccatcttgg  77220
ccttcaaatt aagatgccct ttgagagata acattgttgt tttcaaactc tgttctgtga  77280
cttaagaatg agaggagaag gaagaaaaga ggagaaaatt tgagggaaaa gtgcccaagc  77340
agcgtcaagg ctagacactg gaaatttatc aatgaaagcc acatggtgga tgggaatcag  77400
atatgtgcat caattatttg tgttccaatc catatagaag taccgtataa tgcaccaagc  77460
taataggtgc tttgaaagaa gaccatacaa gtggagatgt gttcctattc tatctaggga  77520
tagagtcagg aagggcttca ttgaataagt ggtagcctct tgggctgaga cctgagttat  77580
gagatgatgt ggcaaaggag acagatggct gggggcaagg tggggtcatt gaaattggag  77640
gcagtagcaa tataagcaaa gctacagggg catgaaaaag caaggttaga ttagtgaatt  77700
gcaacagggt ggtactgctg gaaggtcaca tggaaaagat tgtgaaggta ttgagataag  77760
aagctagaaa taagctttga atgccatcct agtactttga atttgcatgc tgtaagccaa  77820
gtggttttca cttggtcatt taataaaatt acagattctc aggtctcacc tgtaacttca  77880
gattcagaag agtctgctaa ctgaaggtgg aatcagtgtt ccatattgct aattagctcc  77940
tcagaggatt ctaatatatc agtgagttat gaccactgct gtaagccata ggtagttatt  78000
gaaagctgct atggagagga gccacagaag cagatgtttt agataggatt cctctggggt  78060
cctgtgtaat ttatggactg gagaggatca gacaggaagc agaaagactt gaataagaca  78120
gttgcagtta ttttggaggc aaagattctc tctctctctc tctgtgtgtg tgtgtgtgtg  78180
tgtaattgta ggaactattt aggcagtaaa attaacagat attagtcact gattgactga  78240
gtggatggca gtgataggtg gggtgcgttg agggaagtgt attacattaa gtccaggatg  78300
actcatggtt ttctaagttg agtcattggg gattgccatc caatgtgaga aactatatag  78360
```

```
tcttatcata gttgatcttg gaggtagact tgaattaaaa tcttgaagcc atcaattgct  78420
gtatgtgggt cttgggcaga acacttaagg tttctggacc tcagttattt cttctgtaaa  78480
atgaggaaaa taatgcatac ctcatgcatt tgttgtaaag actaaatgag gttaaagtat  78540
gtagagtgta gtttagtaac tgggacgtat agtggtccag taaacatcag ctgttattat  78600
tgtgctatat gttgtgatgt gtactggagt gagatggggt aggggatttt ttagtctctg  78660
ccaatgactc ctctccccat gatcaaaatc agaaaatcag tctcttatgt gttgaggagt  78720
gagacacttc tcccaagtgt ttaaggctaa taccttgcct tgttttgcct tgggccagac  78780
ctcactacac atctgtttaa gagatcaggg taagctctgt tcttggtgag tatctcaatg  78840
gggctgtttt tctagttctt gtagtttctt tgggccaaca tgaaatgtct aaccttggct  78900
tcttggttgt ggattctcgt caacatttca ctgctaccca agttgtgtct gcttacatga  78960
tgctatcttc cttcttttgg gtttctgaag ccctcagaca cttggctgaa catttttcac  79020
atttcttaag ctatatcatc tgtgttttcc ctgccacaga caaagtcaca aaaggacttt  79080
aagataggtt ttggtttttt ttttccccag ggtttttata cattttgggt aagggcaagt  79140
ggtaaatgct gcttttctgc cttaaccagt agtgtctgac agaggaggta gcatgatgat  79200
tgcagagctc actggactga aagtcagatg ctttacccgc ctagactcta gtaccaaggg  79260
gaagatggag tgagatgggg taaatgggga gaaattacca tttattttga gtgtgccagg  79320
ccttttctca tgtattgtct aatgcatttg tcacaattct ctttgggttt gaaatgtgat  79380
tttcttcatt ttatagataa ggaaacttat gggaagggag gttaggttca tcttgtgccc  79440
aactttacat ggctagtgat caataatagt gagattcaaa ctcagatttc tctgccccaa  79500
agcctttgct ttttcctctt ttgacactgt aactaatgag aagatgtatt taactctgag  79560
tctcatttgc ctcaactgta aaatggagct ctgtaactct tgctctgtat gacagtaaat  79620
ctcctcagac cagacttatg ataggggata aggatatttg tatctttggg cccctaatgt  79680
attgaaagtg cttctaagtg cctggcacat agaagggcac tcaataaata tttaccacat  79740
tttccagaaa gagggtagct ccataatggg tgagatacat tttggtggct actgtagtgt  79800
ttaatgcttt taccatctgt taaaatgatt ttggagtata gctagataac tgatgatggt  79860
tgttatatag atttttttcat aggttgcctg ttccaaattc tatgccgtgg aagaagttaa  79920
atatccagaa tttgacagga aatattattc tacaacagat ccctggcgta agaatgataa  79980
cacctgtgtt ctagtctcag acttgcctct gaataactgt ttctcctggt caattctctg  80040
tctctatcta ggcttgaaat ttcccccaaa tgatgaagga gttggactag tttagtgggg  80100
ttcagcctcg agtggccatt aaaattattt ggggatcttt gaaaaaaatt agatgcccag  80160
atttttgtcg ttgttgttgt tgtttttgtt tgtttgtttt ttaattatac tttaagttct  80220
gggatacatg tgcagaacat gcaggtttgt tacataggta tacacgtgcc atggtggttt  80280
gctgcaccca tcaacccgtc atctacatta ggtatttctc ctaatgctat ccctccctag  80340
tcccctaacc ccagacaggc cctggtgtgt gatgttcccc tccctgtgtc tatgtgctct  80400
cattgttcag ctccccctta tgagtgagaa cgtgcagtgt ttggttttct gttcctgtgt  80460
tagtttgctg agaatgatgg tttccagttt catccatgtt ctttcaaagg acatgaaccc  80520
atccttttt atggtggcct gatattccat ggtgtattga actgctcact ccagttcaat  80580
taaatcagaa tacagaatgt tgagaggagc atcagtattt taagaaggcc ccctagtgaa  80640
gttcaatgtg cagccaaggg tgagaaacac tggactagat gattgataag ggccatccaa  80700
ctttgatagt caacaagaga caatgctata gagtatggtg gacagagcat gggctttaga  80760
```

gttagccagg tatgcattca gaccctggct ctgttactta ctagttgtgt gatcttgaag 80820
aaatcaaaat ggagatacac tatgtacctg gcagtaatag ttgtggggat taagcacctt 80880
caccagagct taggacataa taagccccca gtaaatagct tctttaatat cagaagttca 80940
gatggaagat gtgagaaaaa tattggttca gtaagattta acaggtaaat taaaatcaag 81000
tatttgaaaa cattttcctg tttctttagc aatggattcc agaaacataa tgtggaaata 81060
gctctcagtc cttagatttg atgacattgc agaaagaaat ctggctagtc gtcccatggc 81120
tgattggcta tgatggctag aaagccattg gaaaaaaaaa attggctcac agaagacagc 81180
agatgtggct tgggaaatgc aaggacatga ctgtaataag gatttgtcta tccagcccca 81240
tttatgagag tgattccagg agaaaaggac agatttgtat tgtcagtggg atacgctgtt 81300
aaaaaacact tttgctacta ccactccagc tgtcttggca tgtttgttgg tgatgtaagc 81360
tacagaaaat ggaaatcacc aatagggcta tagcaacctg atgcatagtg acaagtaatt 81420
gttctattca tggttatgtg ttgtacagag cacttgctgc atgtcaggtt tgagacttga 81480
gtatgcatta gggccatgga cacccccatc ttatctttaa gtagatttca aagtaaatat 81540
ttgatgaata tgtaaaatat ttagtttggt cagtcatagg gctgagaaca tggtggcagt 81600
tacctcctag tatctgcaag caaaaaaagt tttttcttcc tatagcaatt gccatctcag 81660
ccacttttgc agcatttctt tttgctacac tttgcattaa ccatttgtgc acttgtctta 81720
gcctcaaaca ggccatgaaa gctccttgag gatagggggct atgtcttttt catctttata 81780
tatgcatcat ttagcagagc tgtcccttta taatgtacta attactgaat gaagggatgc 81840
atagatgaat aaatgaatga aaagtaggag tgacctgtct tctctctttc ttcacgatgg 81900
ggactagtgt gtgtatataa ggggataatt tttgtgtcac ataaaatata accttactta 81960
gaaggcaaga cttccagaat ggtggaatga gaaccacccc cccgccccca taaatccgcc 82020
ctttcatgaa agcagtgaaa acgctagcaa acgttgtgaa aattaacttt tccagaactc 82080
tggaaaggaa acagaggctt ccaacaatct gagaagaatg tattcaagaa aaacttcggt 82140
aagctctctg atcacagtgg aaataataaa caattagtaa tagaaggata gttgggaaat 82200
tcaccatttg tgggatataa acagtggatc aaagaagaaa tcataaggga aatgagaaaa 82260
tactttgaga ttaatgaaaa tgaaaataca ttgttccaaa acttacagga tacagccaag 82320
ctaaagcagt acttaaaggg aaatttgtaa ctgcgaaggc ctatatcaac aaagacaaat 82380
gatctcaaat caagaaccta accttccacc ttagactagg aaaggaacag caaactacaa 82440
agaaagcagg aagaaagact aataaagact aaaagggaaa taaatgaaat aatagagtag 82500
aaaaacacta gaatcaatga aattaaacat tgattctttg aagagatcaa caaaactgaa 82560
aaaaacttta gtcagattga ataagaaaaa aagagagaaa attcaaatta tcaaaatgag 82620
caatgaaaat ggggccatca ctacctacct taaaaagaat tttcaaagga ttaaaagaaa 82680
atgccattgc attagttcat tctcacacaa ctataaaaaa gctacctgag atggggtagt 82740
ttatgaagaa aagcgcttta attgactcac agttccacag tctgtacagc aggcatggat 82800
catgaggcct taggaaattt acatcaggtg aaaggctaag gggcatggaa gacatgtctt 82860
cacacggcag caggagagag agcaaagagg gaagtgccac acacttttaa accatcagct 82920
ctcatgacaa ctcactcact atcatgagaa cagcaagggg aaaatctgcc ctcatgatcc 82980
aattacttcc taccaggtcc cttccccaac actggaaatt acaattcaac gtgcgatttg 83040
gatggtgtga cacagagcaa aaccatatca accatactgt atgccaaaaa attagatgac 83100

```
ctagatgaaa tggacaaata ctcagaaaaa cacaaactat ctaaagtgac cagtgaagaa  83160
acagaaaatc tgagtagtcc tgtaacaagt cctgtaacaa aactggatta gtaattaaga  83220
aacttcccac aaagaaaagc ccaggttcag tcttcactgg tgaatactat caaatattta  83280
aggaagattt aatccttcac aaattatttc aaaacttgga agaggctgga acccttttcca  83340
actaattctg caaagtcagc attaccctga tgccaaaacc aaagatatga cacaaaaata  83400
aaactgcagg ctaatatcac atttgaatat agataacttt ctaaaaatct caacaaaatg  83460
ctagcaaaca gaattcagca acaaataaaa agggttataa agggtgacca agtaggattt  83520
atctctggaa tgtaaattaa cattcaaaaa cctaagaata ggaggaaact ttcttaactt  83580
tgtaatggac atctctgaaa aacacacagc taacatcata ctaaataggg aaagattgaa  83640
atttttcctt gtaagatcag gaacaagaca aggatgactg ttctcaccat ttcaatttac  83700
cattgtattg tagattcaag tcaaggcaat taggcaaaaa aaaaaaaaaa aaaaaaaaaa  83760
aaaaagaaag aggtaaaagg cacccatatt ggaaaggaag aggtgaaaat atctatattc  83820
acagatgaca tgatcttata caaagaaaac cttaaggaat ccatgataaa ctattaaaac  83880
gagtaaacga gttcagcaag gtttcagaat acaagattaa tgtgcaaaaa tcaattgtat  83940
ttctgtacac tagcaatgag caatctgaaa atgagattaa gaaaacagtt cactcacaat  84000
ataatcaaaa taccagaata cttaaaaata aatttaacaa aagaagcgta agacttgtat  84060
gctgcaaacc acaaaacact gtggaaagta attaaaaatc taaataaata gaaaaacatc  84120
ccttgttcat gtactagagg actcaatatt gtcaagatgg aaatactccc caaagattga  84180
aggaaatccc tatcaaaata ctggctgttt tcttagcaga aaatgaaaat ctgaccctaa  84240
aattaatatt taaatacatg gaacctagga taaccaaaat aatattgaga aagaaaaaca  84300
aagtcggcgt acccatgctt cctgattcca aaccttatta caaagcagtg gtaatcaaga  84360
gtgtatggta ttggcataag gacaaacaga tcaataaatg gaatactatt gagaatccaa  84420
aagttaactc ttacatttaa gaccaattga ctttcaaaag tgttgctaag acatttcaat  84480
gaggaaagaa tagtcttttc aataaattgt actggaaaaa ttggatatcc acatgaaaat  84540
aaaagatttt ggaccacttc aaacctgcaa aaaaaataaa atgatctcat ggtgtatcat  84600
ggatctaaat gctatagagc taagatgata aatctcagaa gaaaatatca aagtaaatct  84660
ttatgacctt gaagtaggca atggtttttt ggctataaca ccaaaagcac aagcaataag  84720
agaaaaaaaa tttttttaaa aaaacccttg attattttat taaaattttg ttgtgggtac  84780
aaagtaggtg tgtatattta tggggtatat gagatatttt gatacaggca tacaatgttc  84840
aatgatcata ttaggataaa tgaagtatcc agtacctcaa gcatttatca tttgtgttac  84900
aaacaatcca attatactct tttagttatt tttaaatgta cagtacatta ttattgtagt  84960
cattcccttg tgctatcaaa tactatatgt tattcattct atctaactat attattgtac  85020
ccattaacca tccccactcc cctgcctccc agctacactt cgtagcatct ggtaaccatg  85080
atttcctctt atctccatga gttcagtagt ttcagctcat ggagatagac agaactaatt  85140
ttattagctc ccacaaatta gctcccatgt cagaacatgt aaagtttgtc tttctgtgcc  85200
aggtttattt cacataacat aacgaactct agttccaacc atgttggtgc aaatgacagg  85260
ctctctcttt tttttttttt tttttttttt tgagatggag tctggctgtc tcccaggctg  85320
gactgcagtg gtgcaatctc agctcactgc aagctccgcc tcccaggttc atgccattct  85380
cctgcctcag cctcctgagt agctgggact acaggcaccc gccaccatgc ccgactaatt  85440
ttatatatat atatatatat atatatttat tattattata ctttaagttt tagggtacat  85500
```

gtgcacaatg tgcaggttag ttacatatgt atacatgtgc catgcaggtg cgctgcaccc 85560
actaactcat catctagcat taggtatatc tcccaatgct atccctcccc cctcccccac 85620
cccacaacat tccccagagt gtgatgttcc ccttcctctg tccatgtgtt ctcattgttc 85680
aattcccacc tatgagtgag aacatgcggt gtttggtttt ttgttcttgc gatagtttac 85740
tgagaatgat gatttccaat ttcatccatg tccctacaaa ggacatgaac tcatcctttt 85800
ttatggctgc atagtattcc atggtgtata tgtgccacat tttcttaatc cagtctatca 85860
ttgttggaca tttgggttgg ttccaagtct ttgctattgt gaataatgcc gcaatgaaca 85920
tacgtgtgca tgtgtcttta tagcagcatg atttatagtc ctttgggtat atacccagta 85980
atgggatggc tggttcaaat ggtatttcta gttctagatc cctgaggaat caccacactg 86040
acttccacaa gggttgaact agtttacagt cccaccaaca gtgtcaaagt gttcctattt 86100
ctccacatcc tctccagcac ctgttgtttc ctgacttttt aatgattgcc attctaactg 86160
gcgtgagatg atatctcatt gtggttttga tttgcatttc tctgatggcc agtgatggtg 86220
agcatttttt catgtgtttt ttgggtgcat aaatgtcttc tttttagaag tgtctgttca 86280
tatccttcgc ccactttttg atggggtcgt ttgtttttt cttgtaaatt tgtttgagtt 86340
cattgtagat tctggatatt agccctttgt cagatgagta cgttgcgaaa attttctctc 86400
attttgtagg ttgcctgttc aatctgatgg tagtttcttt tgctgtgcag aagctcttta 86460
gttgaattag atcccatttg tcaattttga cttttggtgt tttagacatg cttttggtgt 86520
tttagacatg aagtccttgc ccatgcctat gtcctgaatg gtaatgccta ggttttcttc 86580
tagggttttt atggttttag gtctaacgtt taagtcttta atccatctcg aattgatttt 86640
tgtataaggt gtaaggaagg gatccagttt cagctttcta catatggcta gccagttttt 86700
ccagcaccat ttattaaata gggaatcctt gccccattgc ttatttttgt caggtttgtc 86760
aaagatcaga tagttgtaga tatgcggcat tatttctgag ggctctgttc tgtttcattg 86820
atctatatct ctcttttggt accagtacca tgctgttttg attactgtag ccttgtagta 86880
tagttagaag tcagggagtg tgatgcctcc agctttgttc ttttggctta ggattgactt 86940
ggggatgtgg gctctttttt ggttccatat gaactttaaa gtagtttttt ccaattctgt 87000
gaagaaagtc atcagtagct tgatggggat ggcattgaat ctataaatta ccttgggcag 87060
tatggccatt ttcacgatat tgattcttcc tacccatgag catggaatgt tcttccattt 87120
gtttgtatcc tcttttattt ccttgagcag tggtttgtag ttctccttga agaggtcctt 87180
cacatccctt gaaagttgga ttcctaggta ttttattctc tttgaagcaa ttgtgaatgg 87240
gagttcactc atgatttggc tctctgtttg tctgttattg gtgtataaga atgctgtgat 87300
ttttgtacat tgattttgta tcctgagact ttgctgaagt tgcttatcag cttaaggaga 87360
ttttgggctg agacaacggg gttttctaga tatacaatca tgtcatctgc aaacagggac 87420
aatttgactt cctcttttcc taattgaata ccctttattt ccttcttctg cctaattgcc 87480
ctggccagaa cttccaacac tatgttgaat aggagtggtg agagagggca tccctgtctt 87540
gtgccagttt tcaaagagaa tgcttccagt ttttgaccat tcagtatgtt attggctgtg 87600
ggtttgtcat agatagctct tattatttta aaatacggcc catcaatacc taatttattg 87660
agagttttta gcatgaagcg ttattgaatt ttgtcaaagg ccttttctgc atctattgag 87720
ataatcatgt ggtttttgtc tttggttctg tttatatgct ggattacatt tattgatttg 87780
cgtatattga accagccttg catcccaagg atgaagccca cttgatcatg gtggataagc 87840

```
tttttgatgt gctgctggat tccgtttgcc agtattttat tgaggatttt tgcatcaatg  87900
ttcatcaagc atattggtct aaaattctct tttttggttg tgtctctgcc cgtctttggt  87960
atcaggatga tgctggcctc ataaaatgag ttagggagga ttccctcttt ttctattgat  88020
tggaatagtt tcagaaggaa tggtaccagt tcctccttgt acctctgata gaattcggct  88080
gtgaatccat ctggtcctgg actctttttg gttggtaagc tattgattat tgccacaatt  88140
tcagatcctg ttattggtct attcagagat tcaacttctt cctggtttag tcttgggagg  88200
gtgtatgtgt caaggaattt atccatttct tctagatttt ctagtttatt tgcgtagagg  88260
tgtttgtagt attctctgat ggtagtttgt atttctgtgg gatcggtggt gatatcccct  88320
ttatcatttt ttattgtgtc tatttgattc ttctctcttt ttttctttat tagtcttgct  88380
agcagtctat caattttgtt gatcctttca aaaaaccacc tcctggattc attaattttt  88440
tgaagggttt tttgtgtctc tatttccttt agttctgctc tgattttagt tatttcttgc  88500
cttctgctag cttttgaatg tgtttgctct tgcttttcta gttcttttaa ttgtgatgtt  88560
agggtgtcaa ttttggatct ttcctgcttt ctcttgcggg catttagtgc tataaatttc  88620
cctctacaca ctgctttgaa tgtgtcccag agattctggt atgttgtgtc tttgttctct  88680
ttggtttcaa agaacatctt tatttctgcc ttcatttcgt tatgtaccca gtagtcattc  88740
aggagcaggt tgttcagttt ccatgtagtt gagcggtttt gagtgagatt cttaatactg  88800
agttctagtt tgattgcacg gtggtctgag agatagtttg ttataatttc tgttctttta  88860
catttgctga ggagagcttt acttccaact atgtggtcaa ttttggaata ggtgtggtgt  88920
ggtgctgaaa aaaatgtata ttctgttgat ttggggtaga gagttctgta gatgtctatt  88980
aggtctgctt ggtgcagagc tgagttcaat tcctgggtat ccttgttaac tttctgtctc  89040
gttgatctgt ctaatgttga cagtggggtg ttaaagtctc ccattattaa tgtgtgagag  89100
tctaagtctc tttgtaggtc actaaggact tgctttatga atctgggtgc tcctgtattg  89160
ggtgcatata tatttaggat acttagctct tcttgttgaa ttgatccctt taccattatg  89220
taatggcctt ctttgtctct tttgatcttt gttggtttaa agtctgtttt atcagagact  89280
agaattgtaa cccctgcctt ttttttgttt tccatttgct tggtagatct tcctccatcc  89340
ttttattttg agcctatgtg tgtctctgca tatgagatgg gtttcctgaa tacagcacac  89400
tgatgggtct tgactcttta tccaatttgc cagtctgtgt cttttaattg gagcatttag  89460
tccatttaca tttaaagtta atattgttat gtgtgaattt tatcctgtca ttatgatttt  89520
agctggttat tttgctcgtt agttgatgca gtttcttcct agtctcgatg gtctttacat  89580
tttggcatga ttttgcagcg gctggtaccg gtcgttcctt tccatgttta gtgcttcctt  89640
caggacctct tttagggcag gcctggtggt gacaaaatct ctcggcattt gcttgtctgt  89700
aaaggatttt atttctcctt cacttatgaa gcttagtttg gctggatatg aaattctggg  89760
ttgaaaattc ttttctttat gaatgttgaa tattggcccc tactctcttc tggcttgtaa  89820
agtttctgcc gagagatctg ctgttagtct gatgggcttc cctttgaggg taacctgacc  89880
tttctctctg gctgccctta acatttttc cttcatttca actttttga atctgacaat  89940
tatgtgtctt ggagttgctc ttctcaagga gtatctttgt ggcattctct gtatttcctg  90000
aatctgaatg ttggcctgcc ttgctagact ggggaggttc tcctggataa tatcctgcag  90060
agtgttttcc aacttggttc cattctcccc gtcactttca ggtacaccaa tcagacatag  90120
atttggtctt ttcccatagt cccatatttc ttggaggctt tgctcgtttc tttttattct  90180
tttttctcta aagttccctt ctcacttcat ttcattcatt tcatcttcca tcgctgatac  90240
```

```
cctttcttcc agttgatcgc attggctcct gaggtttctg cattcttcac gtagttctcg  90300
agccttagtt ttcagctcca tcagctcctt taagcacttc tctgtattgg ttattctagt  90360
tatacattct tctaaatttt tttcaaagtt ttcaacttct ttgcctttgg tttgaatgtc  90420
ctcccatagc ttggagtaat ttgattgtct gaagccttct tctctcatct catcaaagtc  90480
attctctgtc cagctttgtt ccgttgctgg tgaggaactg cgttcctttg gaggaggaga  90540
ggcgctctgc tttttagtgt ttccagtttt tctgctctgt ttttccccat ctttgtggtt  90600
ttatctactt ttggtgtttg atgatggtga tgtacagatg ggtttttggt gtggatgtcc  90660
tttctgtttt ttagttttcc ttctaagaga caggaccctc agctgcaggt ctgttggagt  90720
acccggccgt gtgaggtgtc agtctgcccc tgctgggggg tgcctcccag ttaggctgct  90780
caggggtcag gggtcaggga cccacttgag gaggcagtct gcccattctc agatctccag  90840
ctgcgtgctg ggagaaccac tgctctcttc aaagctgtcc aacagggaca tttaagtctg  90900
cagaggttac tgctgtcttt ttgtttgtct atgccctgcc cccagaggtg aagcctatag  90960
aggcaggcag gcctccttga gctgtggtgg gctccaccca gttcgagctt cccagctgct  91020
ttgtttacct aagcaagcct gggcaatggc aggtgcccct cccccagcct cgctgccacc  91080
ttgcagtttg atctcagact gctgtgctag caataagcaa gactccatgg gcgtaggacc  91140
ctctgagcca tgtgcgggat ataatctcct ggtgcgccgt tttttaagcc cgtcagaaaa  91200
acgcagtatt tgggtgggag tgacccaatt ttccaggtgc cgtctgtcac ccctttcttt  91260
gactaggaat gggaactccc tgaccccttg cgcttcccga gtgaggcaat gcctcgccct  91320
gcttcggctc acacacggtg cgctgcaccc actgacctgc gcccactgtc tggcactccc  91380
tagtgagatg agcccgctac ctcagatgga aatgcagaaa tcacccgtct tctgcttcgc  91440
tcatgctggg agctgtagac ctgagctgtt cctattcggc catcttggct ccagaaaaaa  91500
aaattgttaa attggacttc atcaaatttg aaatttttgt gctgcaaatg ataccatcaa  91560
gaaagtgaaa atctcaccca cagaatgaga gaaagtattt gcaaatcata tatctgataa  91620
gggtattgaa tttagaatat ataaagaact cttgcaactc aatataaaaa gacaacccaa  91680
ttttaaaatg ggcaaagtat ttgaatagaa atttcttgat agaagatata caaatttaaa  91740
aatgctcaac atcattagtc attagggaaa tgcagatcaa aaccaaattg agataccggt  91800
ttacacctat taagatggct atagaataaa agaacaaata acaagtattg gctttaatgt  91860
ggaggagcca gaacccttat atattgctgg taaaatgtaa agtcatgcag ccctttgaaa  91920
tacagtctgc aagtctttaa aaaattacta tttgttattt ggtttttctt cacttttaat  91980
ttaggttcag aggtacatat gcaggtttgc tatatagcta aattgtgtgt cacaggagtt  92040
tagtgtacac attatttcat cacccaggta ataagcatgg tacccaatag gtagtttttc  92100
tatcctcacc ctcctcctac cctccaccat caagtaggcc ctggtgcctc ttgttctttt  92160
ctttgtgttc atatgtactc aatatttagc ttccacttat cagtgagaac atgtggtatt  92220
tggttttctg ttcctgcttt agtttgctta ggatactggc ctccagattc atccacgttg  92280
ctgcaaagga catgatctca ttctttttgc atagtatact atggtgtaca tgtatcaaaa  92340
atgttactgt ttgacctagt aattctattc caaggtaaat actcaagaga aatgaaaaca  92400
tgtccacaca aatacttgta cacaaatgtt cattgcagca ttatttataa tagccaaaga  92460
gtggacgaca aatgtcttcc aaatgtgggc tccaaatgtc caccaactga taaatggaaa  92520
aacaaaatgt ggtatatcca tgccatggtt tatctgtcaa taataagaaa tgaagtactc  92580
```

```
atacatgctc caacatggat gaaccttgaa aacattatgc taggtgaaaa aagcaactca  92640
caaaagacta cactgtatga ttttatttgt attaaatgtc cataaaagaa aaatatttag  92700
agatagaaag gaaattagtt tttccagggt ctgggaggag acagtatgag gagtggctgc  92760
taatgggtac aggatttctt tttggagtga tataattgct ctaaaattag tttgcagtaa  92820
tagatgtgag tatgctaaaa tgggtgaatt ttatagtatg tgaaatataa ctcagtaagc  92880
ccattaaaaa caacctaatt aaattaaaac caagctataa cagaaatatt atatggcttt  92940
ggcagtttag aatagtggga aaatatggag taagggtggg gaaatagtcc caagtataat  93000
tctggttttg tcactactag tgtatggact tggacaagtc atttgctttc tctaagtatc  93060
agtttgcata tatgcaaaat agaggtaatg atacctacct cagtggtacc ttttcaaaac  93120
cttgttcttc ctcatctctc ctctaccact ttctcataat attattacag taataaccat  93180
ttattaagca ctgtgtccgc agtggtgtgg ggctgcttta cctccacaac ttcactgaat  93240
cctcactgca gtcttgtggg atctttattt ctttgcccat tttacatgta aataaattga  93300
agtcaaatga gttgttcaag gtccttctgt tagcaagtgg cagagatgga catgaaaact  93360
agatcttcta cctatgtgtc tttccacttc aactaaagaa tttattaaag agaattgaaa  93420
agctatgaac taaatttcgg taatactttt aatagtaaac attgctgccc tcgtgaatga  93480
acacacacta aatttcaaat ctcacggtgg cagggaataa agatgctacc tatcttaagc  93540
cattacttca ccaacttctc caccaaaata ttccttgtaa ccacaaataa gtaagcacaa  93600
tagatctata aggagagaat aattgtgaac tctgatttta tcttaaaaag tcatgtaggg  93660
atgtcatgtt ccacaatgtg attaataaaa tatattttgt tactaaacac aaggaaaaat  93720
attatgttcc ataaagatgt ttggtggttg cctcgacctc ttttagtttg aaaagtaggt  93780
atgtatgaga aagatatgtg tttacatgtt tacccttgcc ttctctctgt ctcttcccct  93840
ctctctccct ccctccccaa cccctatgcc ctacaccccc gcaacccccca catgtattta  93900
cctttctcta aaagctctgc atagccaaga aaagtgctct tttttatttt taggatatta  93960
gatatttcat tttcttatgg taagacaaaa gattaaggca accaagactt acaatgtgcc  94020
taccatgtgg caggcacaga ggcaagggct tttacatgtt atttaatgta attgtaattc  94080
tcacaaaagc cgtctagagt tgaaaatatt tccaactcta aatgaggcaa atggagcaca  94140
gagagcctta attatttcac ccaaagttca gtggtagagg caggattcca acccaggtct  94200
ggtgggctcc aaatccttgt tgggttgcca ttcctcttgc taacaaataa aactggtctg  94260
tgacttttgc atttcacccc gcttccacag tcactggtgg gacttactta agttaatcag  94320
attcttcaaa gtatccccaa gtcctccttt gaaaagaaag ttgggggaca ggaggaggag  94380
cagaggagag gagataaaaa ggaaaggagt cagggagaga gagagagaga gagaaacctg  94440
gtgatctcag ctgggtgcca aggtttccta agcccaagtt ccccatggtt gagcctgtat  94500
tgtcaggcca acagcttcta gtaatccact tttatttaat taatagtgaa actgttgaag  94560
aattgcaagt ggtgttctgg ttcagaaacc ttccgttcta tggggcactg cttttgcttc  94620
agattcataa aaccaaatgc tctgcctcaa gataataagt gaacgtgtaa ccctcgggag  94680
gtaagaaaaa acacaatgtc acgtgcaaat tctgcacttg ttctcaaagc aaacctctcc  94740
tgtgtttgca attaggatgt tatctaggag catattcaaa acttttgagg tttttatttt  94800
agtttttctt tcattatgtg ctgttttagt aatatcaaag aatacatgta atatataatt  94860
tatatgtcat aacaataaaa ttaatgttga tgagcccaga ttaaagaatc aacaacatta  94920
acatcatgat tgcatcaacc ctattagaat ggaagctctg tgaaggcatg gatttttgtc  94980
```

```
cattttgttc actgctatat ccccaggacc tagaggagtg tcagccacat aataggagct  95040
tagtcaatat tttaaaaata agagcataaa tctacttata tcctctttcc tcttaccatc  95100
actcccagcc tcccctcaga ggtaaccact atcctatatt tgggctttat tattcccttg  95160
cattttgata agttttcaca tgtatattcc caaataatat attgcttgct tttgcttctt  95220
tttaaacttt atataatgga atcatattgt atgtatccta ttgtgaatta tgtcttttac  95280
acaacattag tatttgagat tcaactatgt gtagctcgat tccattcctt ttcattgctg  95340
attgtagttt attggatatg tgtgccataa attatttttc tcctgtcagt taatgtttat  95400
catttatgct ttaataaaca aaactgctat gactgttcct gcatgtgcct cctagtacat  95460
atgtgaccaa ctttctctag gatataagcc tgagagaggg actgcagttg gaatttacat  95520
ttccaaagcc caaagtttag ctcatgagtc agagctgcaa tgtgcccttt gtccacacta  95580
ggtcaggatc agtgggagtg ctacccaaaa tattttgcta gctggggagt cagggagaag  95640
cagagactga cctagtgagg ccaggaggca ctatctcagg tctctagtca aaatgggttg  95700
caattagtaa aagtccagat tctgaatccc cttcactatt tatcttcctc ttcctccttt  95760
acagttattt ttgttcaagg tgcactttat taaactcatg cctaacaaac aaaactctaa  95820
tgaatatttt gtctttcatt gattgtaaat tcaattaatt agattgcttg aaaaaatttt  95880
aactgtattt tcactttagt atggatgaaa atttcgattt ctttaaaaaa catttttaa  95940
taataacaca acataaagtc taccctcata acaaaattta agggcacaac accatattgt  96000
tttttttta ttttattatt attatacttt aagttttagg gtacatgtgc acaacgtgca  96060
ggtttgttgc atatgtatac atgtgccatg ttggtgtgct gcacccatta actcgtcatt  96120
tagcattagg tatatctcct aatgctatcc ctcccccctc cccccacccc acaacagtcc  96180
ccagtgtgtg atgttcccct tcctgtgtcc atgtgttctc aatgttcagt tcccacctat  96240
gagtgagaac atgtggtgtt tggtttttg tccttgccat agtttgctga ggatgatggt  96300
ttccagcttc atccatgtcc ctacaaagga catgaactca tccttttta tggctgcata  96360
gtattccacg gtgtatatgt gccacatttt cttaatccag tctatcattg ttggacattt  96420
gggttggttc caagtctttg ctattgtgaa tagtgccgca ataaacatac gtgtgcatga  96480
caacaccata ttgttaactg taggcacaat gttgtacagc agacgtctag aactttttct  96540
tcaggcttaa ctgaaacttt atagccattg aacagcaaca ctccatttcc gtttcttaaa  96600
ggtcctttac aaaatgagct ttctgcgtgt ttccattttg tttatctgat aactttttt  96660
tctttttta ttatacttta agttctgggg tacatgtgca gaatgtacag gtttgttaca  96720
taggtacaca catgccaggg tgtttggctg cacctatcaa cctgtcatct acattagata  96780
tttctcctaa tgctattccc tcccttgccc ctcacccctc actggcccca gtgtgtgatg  96840
ttccctagcc tgtgtccaag tgttctcatt gttcaactcc cacttttgag tgagaacatg  96900
cagtgtttga ttttcttttc ttgtgttagt ttgctgagaa tgatggtttc cagcttcatc  96960
catgtccctg caaaggacat gaactcttcc ttttatatgg ctgcacaata ttccatggtg  97020
tatatgtgcc acaatttctt tatccaatct atcattgatg ggcatttcag ttgttccaag  97080
tctttgctat tgtgaatagt gccacagtag acataagtgt gcatgtgtct ttatggtaga  97140
atgatttata atcctttgtt tatataccca gtaatagaaa tgcttggtca aatggtattt  97200
ctagttctag atccttgagg aattgccaca ctgtcttcca caatggttga actaatttac  97260
actcccacca acaatgtaaa agcgttccta tttcttcaca tcctctccag cacctgttgt  97320
```

```
ttcctgactt tttaatgatc acgattctaa ctggcgtgag atggtatttc attgtggttt  97380
tgatttgcat ttctctaatg accagtgatg atgagctttt tttcatgttt gttgaccgca  97440
taaatgtctt cttttgagaa gtgcctgttc atttccttca cccacttttt gatggggttg  97500
tttgtctttt tcttgtaaat ttgtttaagt tcattgcaca ttctggatat taattaacct  97560
ttcgtcagat ggatagactg cagaaatttt ctcccattct gtaggttgct tgttcactct  97620
gatgatcgtt tcttttgctg tgcagaagct cttgagttta attagatcac atttgtcaat  97680
cttggctctt gttgccattg cttttggtgt tttagtcatg tagtctttgc ccatgcctat  97740
gtcctgaatg gtattgccta ggttttcttc tagggttttc atggttttag gtcttacgtg  97800
actcatcttg atttaatttt tgtgtaaggt gtaaggaagg ggtccagttt cagttttctg  97860
catatggcta gctagttttc ccaacaccat ttattaaata gggaatcctt tccccattgc  97920
ttgtctttgt caggtttgtc aaagattaga tggttgtaga tgtgtggtat tatttctgag  97980
acctctgttc tgttccattg gtctatatat ctgttttggt accagtaccg tgctattttg  98040
gttactgtag ccttgtagta tagtttgaag tcaggtagca tgatgcctcc agctttgtgc  98100
ttttggctta gaattgcctt ggctatgcag gctctttatt ggttccatat gaaatttaaa  98160
gtagtttttt tataattctg cgaagaaagt cattggcagc ttgatggggt tagtattgaa  98220
tctgtaaaac actttgggca gtttggccat tttcatgata atgattcttc ctatccatga  98280
gcatggaatg gttttccatt tatttttgtc ttctcttatt tccttgagca gtggtttgta  98340
attctccttg aagaggtcct tcacatccct tgtaagttgg attcctacat attttattct  98400
gtttgtagca attgtgaatg ggagttcact catgatttgg ctctctgttt gtctgttatt  98460
ggtgtatagg aatgcttgtg attttcgcac actgattttg tatcctgaga ctttgctgaa  98520
gttgcttgtc agcttaaggt gattttgggc tgagagaatg gggttttctg aatatacatt  98580
catgtcatct gcaaacagag acaatttgac ttcctgtttt cctatttgaa tatcctttat  98640
tgctttctct ttcctgattg ccctggccag aacttccaat actatgttga ataggggtgg  98700
tgagagacgg catccttgtc ttgttctggt tttcaaaggg agtgcttcca gtttttgacc  98760
attcagtatg atattgggtg tgggtttgtc ataaatagct cttattattt tgagatatat  98820
tccatcaata cctagtttat tgagagtttg agcatgaagc agtgttgtat tttgtcgaag  98880
gccttttctg catctattga gataatcata tggttttgtc attggttctg ttgatgtgat  98940
ggattatgtt tattgatttg tgtatgttga accagccttg catcccaggg gtgaagcgga  99000
cttgatcgtg gtggataagc tttttgatgt gctgctggat tgggtttgcc agtatttttt  99060
tattgaggat ttttgcactg atgttcatca gggttattgg cctgacgttt tctttttttg  99120
ttgtgtctct gccaggtttt ggtatcagga tgatgctggc ccataaaatg agttagggag  99180
gattccttct ttttctgttg tttggaatag tttcggaagg aatggtacca gctcctcttt  99240
gtacatctgg tagaattcat ctgtgaatcc ttctggttct ggactttttt tggttggtag  99300
gctattaatt acttcctcaa tttcagaact tgttatagtt ctattcaggt atttgacttc  99360
ctgctttagg cttgggaggg tatatgcgtt caggaattta tctatttctt ctagattttc  99420
tattttattt gccccagagg tgtttatagt attctctgat ggtaatttgt atttctgtgg  99480
gatccgtggt gatatcccct ttatcatttt ttattgcatc tgtgattctt ctctcttttc  99540
ttctttagta gtctggctag tggtctatct acaaaataga ctgtttatct gatatttatt  99600
ttgtaattat ctaataataa ccatcattat catcatcagc attatcatta tcatctcctt  99660
tacccataca tacatttgtg tctttcaaat aataatccca tctttgaagt gcatcctcat  99720
```

```
ctttagcagt ctgcactctg ctttcttata tcatttatta tcttatttta taattattta  99780
tttccagtcc ttcttctcta acagatagta gtttcttagg gccaaggaaa tatctcgatc  99840
accactatat ccccagcacc taaccctgtg cctggtccat agggccagat gctaagagtt  99900
gagttgaacc attgtaccta atcttaacct tcattagcac aacatggttt gtcagtggtt  99960
aagaatctac actttggagt cagactcacc caggatggaa tcctggcatt gccacttatt 100020
attaatagat gcgtgatctt gaacaagttt acttaattgt tctgagcatc agtttcctct 100080
tctgcaatat agggatgata cacagctacc tggtaggttg ttgggaaaat taaatgggat 100140
gatatgtatg aaatggcctg gcatatagag tgcctaaata catgttcttc tgattctatt 100200
tggacagttt gtgttagtaa cagaagtcaa aaaggtggag aaaggagaaa ggtacttgtg 100260
aaaattttct atttcttctc catgtttcat tcaggactga ggaagggggc acagttttta 100320
cccaaggaaa tgacattttt agccaaaaga aatgatctta gcatttagct gaattatata 100380
ttggaagtaa gctccttcca tgtggaactt atggccttgc tagccttggt ttgttggaag 100440
tgctcttgct ggctttctag ttagggtagg gaaaggaagg cttgtgggga atgaagatag 100500
gccatgatat caagccactg ggtttgcaaa tcagtagaat tttttattgc tttctgttgt 100560
acttgggact tgaataaagg ctgatatttg tgtcttgctg gtaaagtgct tgtaaagtga 100620
gtgaaagttt tctttgctct tgtcctgaca tagctgttca cttggggttg aggggaggat 100680
aacctttcat gtttttttt tttcttcatt ctgatgactg tgctgaacat tcaaaccaaa 100740
aggccattgg tggaaagtaa aggtgagtgg tgagaagaca atagggtaat ggaaactgtg 100800
ttggacttgt aatcaaattg tcctgcactt cccctctcca agtcttaacg tttttcatct 100860
gtacagtgga tattaaaatg agaaaataag cttgtcttca cagagttttc gttaggtgtt 100920
gacacaacaa acaggctccc attagggctc attttccttc attccttagt aaggaagaag 100980
tgcttataaa atatagcagt tgtgctcttg tgaatgatag catgggcagt tgtcatctcc 101040
ctgaagcaga tgtaacccag aatgtcactt gagttttgtt taatgcttag gcataagaca 101100
taggaatgac aaaagctgac ctttgggtag tgagaacaat gttccatttt gttcaaactt 101160
gaatttttta ctataggaga ctgagaatta accttccatg aaggttttag gattggcttt 101220
ctggcccttc tccttcatat ccacctgaaa gagcttgggc gcagaagttc ttgcagaaag 101280
gcagttagac aaggtgactt ctgaagctcc agtggccaag tattttgatg gtagcctaaa 101340
agatgtccag aatcattgta catcattttt tcaacagaag cttcaggcat agggattatg 101400
cttggtactt tatgttgtgg aatggaatct ggcggatgtc catgtgatct atagaaacac 101460
ctaaggaaag tgaagaaatg agggaaaaaa aagaacaaga cttttatgat aatactaatc 101520
acgatccttg tgtatttatt ccaatggcat tttatccatt atctgattta tattaccact 101580
cacagcagca gctcaatagg atgggagata ttatctctat tttatagatg agatttgagg 101640
ctcacgaagc taaagcaagg aacatcaaat cactttgata tttggtctgg ttttgttata 101700
ggtctccctt tggatgaggt aaagttacaa acctgggttc atatcattta attagtctga 101760
aaatgttgcc tggacaccac cttcagttag atatcttaac ctcaggcttc ctgccttcat 101820
tgctcccgca tatagacata gactatgaga ttggctaatc ccagagaact tccctaatcc 101880
cttggcaaga tccaaaaagg ctcagtcaca ccctacaacc atcatcttta ggagaagtct 101940
cagaaaattc agcttcacac taactaactt gagcaatgaa taatagtcat ttatgcctgc 102000
aggttaatgc tgaagacctg agacttcact tgcctatttc tgccattcag tgacatgtgt 102060
```

```
tgcattggtt ttttgtgtct ttccagtttg gagactgcca gggaccatgt tttgcccatt 102120
gactattact ttccacccca gaagacctgc ctgatctgtg gagatgaagc ttctgggtgt 102180
cactatggag ctctcacatg tggaagctgc aaggtcttct tcaaaagagc cgctgaaggt 102240
aaagggtctt gcacatgcac ttctctttcc ctttctcctt taccttccag agagagacac 102300
taacctttca gggcccagga ttttatcatc tcagaaatag agtcattggc aaggccctat 102360
caaataactt aggagcctaa ggaagcaaat ttttgtactt gctagttccc tggtttcagc 102420
agccttgttt gtacaggcaa tttaggcagt gaaggtggtc ccagctgggg cttggggctc 102480
agtgggtcct agaaatgaaa gaaaaattaa tgatttgaaa agatttaatt tcctcccttc 102540
ttgttttcta ctctgctggc tagtaaagga aaaatttgtc cttattagag aggttagaag 102600
tggagaaacc ccaactgagt ccccagcctg ttccttggga tgaatatgag actgttcctt 102660
agcaaaggct tcctggcctc ggccccagaa agggagtgtt ctcactcttc agcagactat 102720
cagtctctgc acctgctccc tcctgttgtg gcctccttgg gacctgtctt tgcattaata 102780
gttcctaggt aggtaagaac tcagagtgaa gaaacacatt tattctcctc tccagagacc 102840
tgatctcaaa gcctgtccat tagtccctaa ccttaatcta aggtagcatc ttatatctgg 102900
ctaaattggc tcaagcccta gctccttagt tttatttagc ttagaacaac tcatgtctgc 102960
tcaacctcta gaggcgctca gcccacattc tgcagtagaa actcccattt tcaggcctct 103020
tatatacggt aatgtctcct tcctctaacc acccagggct taagcttcct gcttatccac 103080
ttcaccctgt attgagggct ttcttctcaa agagacattg atgaggagcc cctagagaga 103140
gatgctgtgc tctgggacca gaccccttgt taaacaccag tattcacctc tgccccaact 103200
ttccccaaag aggtacttcc tgccaaggcc tttctctttc ctctcactgg ctggaagtgt 103260
tgagttccac ttcagaacca gaacagagaa cctttccttc tataagagct ataaaccttg 103320
agaacagtct taaaacatag gtatgtaggc cacaccattc accacgaatg tactgatact 103380
catcagaata tggaagaagc accagagagt ttgaagcatc tagagaaaag gtagaaagag 103440
aatgcccttt aactgacctc ctcagtgata gccaatcaca atgatgagtg ttgattcatc 103500
attttggcta ggtggcagaa atatctataa aacagaagct gccatgttgt tttcttccag 103560
tcctcagggc ctacaagaag gcagctatca tttggtatta ctgaaaacat gccccatgtt 103620
cagctcatac ccccaaatta cccattgcta ctgtttatgc tgggctaata tgaagcccag 103680
ggccctaatg tctaggtcta ggcagtaagg cctagagcag tgcctaaaga gcctgagagc 103740
agtgccttcc tttcttcaga gtactcatga aaggatggct gtcagaaaag gaaatgagga 103800
tgggttccag agacttcaga ccaccccaac ttccccagtg agaccctggc acctccccat 103860
accctctcac ctagcgggcc ctgtctatag agcagagaat gaaacagagc actcatctag 103920
aggtagtgtg tcagcaagcc caggcactgc accacagtaa tagcagccat atcagatggg 103980
aaaggagttc aagtgaacaa acaagcaaat tcaatagtca gatagattag attatacttg 104040
atgcttcctc tgagttttac aaatatgggt cactaaattg ttattttcag aaaacagggg 104100
aaatgctcaa tcacattgtg aaagggaaga ttttgctgtc atatcataca tcccacatgg 104160
gagctttctg cagaagttag agctgaagga gggaggcagg cagaagggca actggcaggg 104220
ctgcctggga ggagctctgc aatgaggtgg atcctgtgcc atttgagaac agggaagaaa 104280
agaaatgagg ttttggggag ggaatcaccc aactcacaga acacacagaa atccagcaag 104340
gtttcaaaac gctctacacc ttagagtctg ttaagttagg gaaactctgt gagctcatag 104400
ggccaaatgc acttgcctgc ttgaaatatg aaaaatcagc aatggattcc ttgaaaaaca 104460
```

atgaaaaggg aaccttctga gccccttggt tattttgaca tatggaccat agatttcagt 104520
cctgagccct ttgaaggtag gagaaggtgg tttagaaaac acacacacac acgcacacaa 104580
acacacacca gaatgaagca aaaaaaaaat tactggtgtt ttctttctcc tcccatctgt 104640
gaagctgttg gattgatttt actgccatca ttatccctgt ttgaaggcag ggggctgtct 104700
tattacccaa agaggacatt tattgatttg gttttctttt tccattttta caatgcatct 104760
ttatcgccca tatggccttt ctggaggtgg ttttcagtct ggcttgttga aacatcaaat 104820
tatacctgtc ttagagaaaa tagaaacaaa aatctttctc ttccttactt gcttgttgta 104880
gtcagttaac tcggactgag tattcagagt cttgattatc acttaattca tagtttcata 104940
aatctctgga atgggcatag gtacaggact taaaagcctg gcatctcaga cagaaatatg 105000
tttttagctt tggtggttta taacagatgg gacttttagg ctgtcattgg tgcagggctc 105060
agcacagagt cagttgtaat ctggacaggt tttgttgttg aggaagagtg ggaagaggga 105120
gtcctacatt ttctccttgt cagtaatgtt ggagaattgg ggtgagggtg aggctgggca 105180
gggagggtct gcatagaaaa aagggtgcgg tgagaaaaaa taatgctact aagccatgag 105240
ggtaaaatga ccaaattctg gttgagagaa acttggtcaa agtgtgtatg gggagagaaa 105300
gttggtcaaa gtctgtgtct gagtgcttgg tgggatgaac tctgggttag aaacaggcat 105360
ggagggaaat agttggttta tggagtgggt aggatgagtg gggtggtgaa agggaaggca 105420
ttttggatgc taagagacca ggaagtcaaa gcaaggcaat acacataaac agaggtaagg 105480
gctcagagag gttttagttg tgtagacttg gataagaaat tttccctttt ggacctcagt 105540
tttccttgtt tgtaaaacaa cggacttgaa ctagatattt taaaatgtgc ttccagctta 105600
gacattttgt gaccgttcta caaattacaa acataatcat catcatttca gcaaactcac 105660
atgtatttat acctgcataa gtttttggtc ttgctttcct agaaggtgac taatcccaga 105720
tcctaatcaa ttaaagaagc aatcttcaga tggggataga gccagctgag agagtgtact 105780
atggatggag tgagttaaaa ctcaggactc agattttctc cttgtgatca ttgctgggta 105840
acttcctttc ttttctattt tctcatctgg aaaatcagga tatgaatccc catctctacc 105900
tcattatgtt tcaaagaggg ttaattaatc catcatgtgc attatgtgct caagaattta 105960
ctatttttca gacattttct agtaaaacat tgaagattat atgtccattt gttttgtaca 106020
catggagtgc tgtttggtac acatcataaa attgaaactg tagtttacat tctgaactca 106080
aagaattaca ccatcctcac tgatgtttac aataggtccc aatttagttt ctttagcaaa 106140
ttttatgtaa gtatggcttt gattctctct ctcactccag gtttttgtta gggaagaaat 106200
gcaagtgaac cctcattgaa ctctttctgt cctttaaatc cattctttcc cacctcaact 106260
catgtggaat tgaatgttgc ctctagtttg gagtctagca gagagttttt ggtgcatatc 106320
agtgtcccct tcactccctg acttttcaag taacatttcc cagaggcaaa ttaactctgc 106380
taagaggatc tgcttgcagc ttcaacagag ccttcatcag gtatctttgg ccaaggagtt 106440
gactgatcct gactttgcga gtcctagaga tcttttcaca aagctcctct catgtttctg 106500
cctctgattt tcttaaatgt cacagacaga ctttagattt aggggttggt taactttttt 106560
tgtaaagggc catgtagtaa atattttagg ctttgtagat catatggtct ctgtgtcaac 106620
tactcaactc tgcctttgta ggatgaaagc agccatagac aatactggaa ctaatgggag 106680
tagctgtgtt ccaataaaac tttatgggca ctgaaatttg aatttcactt aattttcaca 106740
tgtcgtttaa tattattttt ctttttacc atttaaaaat ttagaaatca ttcttagctc 106800

```
tttgggcctc acaaaaacag atggtagagt ggatttggtt tatgggctgc agtttgttga 106860
cctgtgcttt agctaatcac ttctgtactt ataaatctgc ataggtttta tgtttttcca 106920
tctcttggta tcttagtagg ccagtcaaag tttgaacaac ttgttagcac agaatacctg 106980
gcctagtggc ttcttggtcc tgagcttatt tactaaacaa gagaaaaaat aaataagtct 107040
agaaatgcta gaagaggata ctttttgtt ttaatgatct agtagatcac tcctccttgc 107100
aatacccaga ggagaaactg aaaatatttc aaacattttc tagacttctg tgttgtaaat 107160
ttgtggataa ctatgaacta tatatgaatg aacttttctg gatgacacat atattccaga 107220
tggtaaaaag gaagggcttt ggggactctc tggtaccaag tgtcatggaa aaactgtgtg 107280
tctcatagaa agtagatccc aggaggccag cagagttgtg gatctgccat atattacctc 107340
atgattctgt cttcgcacac tcaccggctt aattctgggc ctccccataa cacgactaga 107400
ccacaggctt gcagaagaaa taatttagct ctgtaactca ttgaagttgg tgcccaccca 107460
agtctctgtc agtgcccaat tcgggagcca tgccaagaat ttgccattgc tgcttcatgg 107520
tggccttgtg cctgcttatt tatagcctgt gcattttatg aaacagggat taataagaag 107580
ttgccatagc acttgcacca ttatgtaaat atctgtaatg cttacataac ttttgtcact 107640
tgcaagacct tttgagtcca ttgccttctg ctaccatgcc ttaccaattt cctagtccct 107700
tattattatt tttcaattca ttatatttaa cttctgtgat acacgttcag aatatgcagg 107760
tttcttatat aggtatacac gtgccgtggt ggtgtgctgc aaccaacaac ccgtcatcta 107820
cattaggtat ttctcctaat gctatccctc cactagccca ccacccccta ataagcccca 107880
gtgtgtgatg ttcccctccc tgtgtccatg tgttctcatt gttcaactcc cacttatgag 107940
tgagaacatg cagtgtttgg ttttctgttc ctgtgtttgt tttctgagaa tgatggtttc 108000
cagcttcatc cgtgtccctg caaaggacat gaactcatcc ttttttatga ctgcatagta 108060
ttccatggtg tatatgtgcc acattttctt tatccagtat atcattgatg ggcatttcgg 108120
ttggttccaa gtctgtgcta ttgtgaatag tgctgcaata aacatacgta tgcatgcgtc 108180
tttatagaag aatgacttat aatcctttgg gtatataccc agtaatggga tggctgggtc 108240
aaatggcatt tcaggttcta gatccttgag gaatctccac actgtcttcc acaatggttg 108300
aactgattta cacccccacc aacaatgtaa aagtgttcct atttctccat attctctcca 108360
gcatctgttg tttcctgact ttttaatgat cgccattcta actggcattg acatggtatc 108420
tcactgtggt tttgatttgc atttccctaa tgaccagtga tgataagctt tttttcatat 108480
gtttgttggc cgcataaatg tcttcttttg agaagtgtct gttcatatcc ttcacccact 108540
ttctggtgtg gttggttatt tttttcttgt aaatttgttt aagttccttg tagattctgg 108600
atattagccc tttgtcagat ggatagattg cgaaaatttt ctctcattct gtaggttggt 108660
tgttcactct gatgatagtt tcttttgctg tgcagaagct ctttagttta attagatttc 108720
atttgtcaat tttggctttt gttgccattg cttttggtgt tttagccatg aagactttgc 108780
ccattcacaa ttgctacaaa gagaataaaa tacctaggaa tacaactcac aagggatgtg 108840
aaggacctct tcaaggagaa ctacaaacca ctgctcaagg caataagaga ggacacaaac 108900
aaaaggagaa acattccatg ctcatggata ggaacaatca atatcgtgaa aattgccata 108960
ctgcccaaag taaattatag attcaatgct atccccatta agctaccatt gactttcttc 109020
acagaattag aaaatactac tttaaatttc atatggaacc aaaaagagcc catataccca 109080
agacaattct aagcaaaaag aataaagctg gaggtatcaa gctacctgac ttcaaactat 109140
actacaaggc tacagtaacc cttatcaatt ttttatgtgc ctctccatat tctgcagtca 109200
```

gaagcttctt cagtcctttc agggaattgc tgggtgacta tcaaactctg gtagttcatt 109260
tttgcagttg gctgctgttg tgaggataag agttagactc actttctctt cagagataga 109320
aattatgtat taattctctg ggttctagac ccacagcaag gagcatactg ctcctcaaaa 109380
taactgaatt ctgcgagaag ccatcattgt aaaacaacaa tatcttcagt tatagtagcc 109440
atgtgtgcaa cttctggaaa ctgttattca gattttcatg ttccttccct gtctcttcat 109500
agctaggcag ctgctttcag ccttgtacag atgctagtga gctttctacc tacaaacctg 109560
cagaaaattg aactgagatt tggaggtgaa agactcttga taaagggaac aaggtttaga 109620
attctcagtc cctttgctcc caggctgtgt tgtgactact gaggcactcc agtgaaatca 109680
ctattcctcc tatctagact aatgcctgtc tctgcagagc acctcataag aacaggcctg 109740
gtagtaatat cctcatgcat tcagtcagta aatatttaca gagtgcttac tacatatagg 109800
gtattgggct gacatatgca agatacaggg cctgcttcca ggaggttata gcttattgat 109860
cataaatgtg gcatttttt tttttgagac ggagtcttgc tctgtctgtc acccaggctg 109920
gagtgcagtg gcacgatctc ggctcactgc aacctccacc tcccaggttc atgtgatttt 109980
cctgcctcac cctcctgagc agctgagact acaggggctc atcaccacac ccagcttttt 110040
tttttttttc tgtattttta gtagagacag ggtttcacca tattggccag gctggtctcg 110100
aactcctgac ctcgtgatcc acccacctca gcctcccaaa gtgctgggat tacaggcgtg 110160
aaaatgtggc aatctttaaa gctcttcagt ggatgaaagg ccaccctatc tgctgtcctt 110220
ttgaacttcg caactttctt ggtacagagt gagaggttat tctcttggtt ttccatataa 110280
gtaaactgag gctttgccag ttcatcaaca ggtagtaaat aatatatttg gaatttgaac 110340
ccaagtcttc tggggtcaaa ggcagcattc actctgctct gtcacagcag ctcctcaaat 110400
aagccaacat agaaaccaag tactatgcct aggcaacaag aaaggcagca atgaagagca 110460
acagcagagt caaatatgag agaaggaagt taagaaagat gttaagtact gtggggagta 110520
actgagaaac caccaagtat cgctaacatc acagggaact tgtcttccta agaaaattcc 110580
aagcacttaa aaccgctggt agttcatcag caactctctt cattagatgt gcgagggaca 110640
tgtgggccat agtccttcta ctaacttata ttcttcaggg gaaagttctg attctgatga 110700
gacccagcat ggtagctctt aattcactgt tgtcacacga ctatagaaca ggaagcacaa 110760
cttaacacct gtgctcatga gaattttgct ccttatgacc aagctaaaga aagagcttag 110820
acaggatgtg tggctataaa tgtagattaa tggttccttg gctctttggt ttgagccttc 110880
tcagcagagc atcccacgga gtgttttcca tggggccacg agcaagagaa atccacttcc 110940
ctcctcctca atgtcagaaa atagagaata ttgtctttca ggatagaatt aaaaagtcat 111000
agaggcagca acttgttttc ctatattagg gttttaaaat tctgtttttc cttcctctcc 111060
tgggtcagat cattgtgtgg atggaccttg atttcattgt ggtatctgta tgtggaccct 111120
gaagaccatg gacttctaac aattccttaa gttacataag cacattccta caggtcacaa 111180
gctcatttac ttacaggatg gttgatttgg tcacaggtta tttcatgaaa atacttaaaa 111240
gatttgcagt gttcaaaact gcagtatctt taaacactaa aacttgaagg aagggaattt 111300
agaaatcaaa aaatctggtc aaaccatttc atggaaaagg aaagtgaggc tcagagagag 111360
gaaattactt tcctgggttt gtatagccta taaatggcag aaatgagagc ctccctgcca 111420
tttctagttt tctgtctgag agactctcct gcctaatagc taattagcag agtcacagag 111480
gtcattacct tgcaattctc aagaattatg tgaggcagca tagtaagcat ttatggccct 111540 tggttcctag aaggagctta gtccctgata gtcatctctg cctttgccat tgtgtgagac 111600 tgtcttctgt aactgtatgt cttcctccct agtaagttaa tgagtaataa aggtattcta 111660 tagtgagagg actctgtaag acatttcttg gtgtgaggat tgttccaagg ttgttttgtg 111720 tgtatgtgca tgtataaact tttttaggga gcatattcat agcttttaca tggatctcag 111780 aggctctata acccagagaa gattacagaa taccagtctt gtctttggta aggattttat 111840 agacccatcc tgactacagt gatatccaac atggctatgt aatgactggc actttcccca 111900 cataacatat atttattcca cactcagtgc ctactgtgta catgagacct ataccgggca 111960 ctgggataag agacatgaaa taacagctaa aattgtttat tgagcagtca gtatgcatta 112020 gatgctttgt agtcattttc ttattcaatc tgtataccct caatttacaa atgaggaaac 112080 tgaggcacag aagagttgag tgatttgccc aaagtcatac aaatagtcag tggctatgtg 112140 atgaatagtt accaacataa aagagtgaga ttactgctgt actaaaagta ggtacataat 112200 cccctgagca gacagtatga gagaatgatt tattttacct ggaaagttta ggaaggcttc 112260 acagaggagt taagggttga tctgggtctt gagggatgga taagagtttg ccagatacaa 112320 aaaggtagga agagaacttc aggaggaggg aacaggctga gcaaagacac ggcgatgtga 112380 aagtgggagg cttgtttggg gaacattatg gaatctggag gttattgtgg ggaatctcat 112440 cagatgcagc aagctgtttg acaggccttc agttggctct ttgtaccttg ctccctccgc 112500 atgctgagct gtccatagct gccctaggct ggtgtctggg attttcggaa gaaggttact 112560 atccaggtag tgtaacaaga tgcagtgcaa aagcaccaga ttggggctct ggctctgctg 112620 ctgacttacc acctggcctt aagcatgtct agttccctct ttgtacatta aaatctccat 112680 tggaacagta acatggttgt attaaatgat cttgaagatt ttacctgcac gttttgcaca 112740 tgtaccctaa aacttaaagt ataataaaaa aattaaaata aaaaataaaa atataacaat 112800 ataaatcttt aacaataatt ttagtagtaa atctctacaa ttttacagat aatccagatg 112860 catccattgg ccaatggttc actttgtatg cataatattt gggaaacagg cagacccaat 112920 ttcaatcctt agttgtaaga cttaatacat atgtgatctc gagcaaatca cttttgtatg 112980 cctctataag gataataata gctcacagaa ttattttaag aactaaatga tgtgtaataa 113040 agctactggt actcagtaag ttttgtatcc ttttcctaga gtgagtcttg gtcataggca 113100 tgcgtatact tgcagcgtcc ctgggtaggc cgaaagagca aataagagat ggtatctatg 113160 gtattcccca ggtaaaggag gccttgggtt ggcataagat ttcacttctc tttagagtta 113220 cttaattagg gaccagaaag gccatcagca tttgtatgag aatataacaa aggtcaatct 113280 cttcctcttt actttttacc tcccagtaca ctgtgagtaa cattccccag ccagcccagc 113340 cagcacgtgt tcattgcctc tcttgacttc cagactttgg acttgaaggt gtcagagctc 113400 tctgtgtatc tttgtcccca acaagataag tctgacctcc ccagcaaatt caagtcctaa 113460 gccactgtcc aggagaaaag ctagcaaggt cataaattat tctccatatt ttccagccat 113520 tggtttccct tgtccagcca gaggtgtgtc tcaaagtatg ctgaggccag attcaataga 113580 aacctgagcc agcacctgtg taaataattt ttaaagctcc ttttcctgaa gctggatgaa 113640 tatttttaaa aactaagctg gattgtcttt tatctagcat gccgtctcct acattcctag 113700 tgctatggac ctcttggagg aatgtggttt ggttatagtg gtattgtctt gtctgttgtg 113760 ggggagggag acatttcttt cagaagcaag gtaatacttt ggtctggtct atgactctat 113820 tttgtttaaa atgaaactat ggcagtatag tggtattcat tctgcttccc ataggttaac 113880 tttacatccc tctgtcttca cccactcttc agttctgatt cttttaaaag cagccaacca 113940 aaaccagcaa gtacatactg cttatctctg acttccacca gaatcaactt cagatcttgt 114000
ccaaagctcc atctgaagag aggggaataa cacccagcca agagccctca gggcccatca 114060
gtaagtagac atcctgtcct tgaggttcct taactctgct cagcttcaga atacagaagg 114120
ggttggttct tcatttgtgt tgtttataac taaaagcctc ctactcccca ctttttgca 114180
tagcttcttc tgccatccca cctgtgtagc ctcttcaact cccccaaaac tcctctgtag 114240
cccatgtcac ttggaaagag ttttctttgt ctcttttgca acttgacaat gactagccag 114300
caagtttaag ttcaaattat tgttccatgg gagcagagat agatatagga aacaaaaaaa 114360
agggatatgg aggtatagag tgatttccca cctacctagt gagcactact gagatattca 114420
agtactctct acccaagaat tctattgata taaaggtaaa aaacttgatc ttaggtctaa 114480
tatccgttag tagtgtgacc ttgggaaaat gataccaccc ccaaaggctt agttttctta 114540
actgtaaaat aggcatacag atgaccaccc ccagaggatt cataaggata acatgagata 114600
aggcaacttg aaatttccta gcatagtgat agactttcga aaataaaatg aatcaaacac 114660
tgataacagt acttcctagt acacaaatga gaaatcagtc cctcatcaaa ttacagcaca 114720
ttttcaatgc tccaattatg tcactgtaga aatgctaatg tggattaaat aatttgtctg 114780
ttgctattta tacggataat ttgatagtag ttatttttgg acatggatag ctttgaagcc 114840
ttacagatga gtccatcccc aagtacccaa aactaaagaa agttggctag agtgatgaca 114900
aggtggcagc acagagctcc ctgcgttctg ggccctgtcc cctagctaga gagaactcca 114960
ggctataagc atttgtattc tcatagtcca atggcaggga agaagggctg gaggtgagta 115020
gttttcactc atttattttt tcaacaagca tgtatggtat caggccttgt atgcatccag 115080
agacaaatgt gaactagccg tgtcctcaag gagattccag tctggtgggc ctgccttcca 115140
aggtcagttg cagctttagc actataaaga gcacctacct gcggcagata caatgtgatg 115200
ggacatgaca gagaaaaaat ctataagcag agcctcccca ttcccaggca ttgaaacaat 115260
cctaaccaag actggcatag tacaatgagc ctgtccctat cagcaggttt ggaagcctta 115320
acaacaacaa caaaaacaat aataatggtg atgataatca tagagcctaa tgttaccaaa 115380
cattttccat gtgttaagta ctatactaag tgcatactta atcctcacaa caatgctata 115440
agatagtaga tactcttact actaccctga ttttacaaat gtggaaactg aggcacagaa 115500
gactaagaga acaggaatac acctaattca cctcagttca acaaacatca agcatctgtt 115560
ttatgtcagg cctcgtgctg gatggcaggg agagagagat gagtaaagca tagtttcagt 115620
ccagtgggag caaatgacag cacacagtgg ggcaggtata ttgcagccct tctgcttgat 115680
gctaagaact cagtgtcagt gatgaatgaa acacagtcat tctctcaaag atcttaaagc 115740
ttagtaggag atatctgtgt ggaaacaaaa attaaatact gctgtgataa gtgtcataag 115800
agataagtgg aaaatgagag agagagatca ctgtagcaat tgattggttt aaatcaaagc 115860
ccccaaaaaa atgttattga gaattataaa acaactaatt gatttaaatc aaagcccaaa 115920
cagaagtgtt tgctaatttt atttcaattt ggttgataat ttggttgaaa tgaatttatt 115980
tcatttttta ttccatcctt acaatggaag attagtgctt gtttcccacc caaggatacc 116040
aggatatttc aggggctgta ttacaatata gttaaattat tcctttatct caaagcacat 116100
ccacactttc ccctatcctt acctttactc agggtatctc ttctgcctca ggtgcttttt 116160
ctccacattt ccatattctt aagtcctacc ttccttcagg gcctcactca aatgcctcct 116220
cctccatgaa gcattcaccc gactgaaagg taccccgccc tctcctgtac tccacatcac 116280 ttcatgggtg tctccacttc ctgctttatc tttcagtaat acacttacag ttctctttcc 116340 tccactagac tgagctcttc agaggaagac tcacttggct gaaaccatga ttttacttta 116400 aacacattga aaacctctac tggagtgcat tgtgtctggt gggcttcaac cttaattctt 116460 aagtatgtga aaacacatca cctatctgga ggtttacact ttctgctaat gactttattt 116520 ttaagcccac caccctaaca caacaaatac ttaaaacttg tcttcatttc ctttaggtct 116580 ggccctcatg catgcatata atttatagag tcactgtttt gctcggttgt cctcatgcct 116640 ctatattatt ggaggtttag attgtttcca tatactcagg ttgtattcat gtccttttt 116700 tctttttaaa tttccttagc atccatttcc accattggaa attcagggtc aaaacagggg 116760 tttgggattg gagcatgtct atcacagata accaatcatg tgttatgact taagaattta 116820 tgaaagggcc ctctacctga agatatcttg ctactgatgc tgtctcacag tgtctgaaac 116880 tcccatcata tgtggaattg ttttggaagg ctttgcctcc tgggacacat tcagccataa 116940 tcaagaaata gtattgagca ttagactgtc agtatgtcca ttagcaagac tgtggaggaa 117000 tggaatcacc aatattatat tttatagggg atacagaata caagagaagt tctgaagaga 117060 aaattcttat gtagaatagg aaggcttaga tacagcatga aagctgcagg ctttgaggag 117120 ccagaggtca aatgaaagca ttgagtattt gtttagatga aagaacagaa agggaaaaag 117180 aagcagagga agggatagta gagagaaatg tataagtttt atccatttaa cttgtaattg 117240 tgtttggcta tgggcacaat agaagcagtg agatcacttt attttatttt attctttata 117300 gacagggtct tgctatgttg cccaggctgc agtgtgcagc tcttcacaag tgtgatcata 117360 gcgtactaca ccctcaaact cctggactca agcaatcctc ccatctcagc ctcctgagta 117420 gctgggacta caagtgcaca ccaccacgcc cagtgagatc acttgaaact agggagagat 117480 gtgtgagttc tgggcaacca gtagttggct ttacatagaa ctgtaggggt caaggccaaa 117540 ggggacgtcc tgttccaagt caccttcttt ggacattaga aaaccacgag gggtttggaa 117600 atcagaaaac cagcagaggc aggaaaactc agggcagcat gggagattca gtatatacaa 117660 aaaggttcac accagtaatc aaacagaatt ttaactgctg atgtggagta gaggcagctt 117720 tgtctgctgt gtgataacca aacctttacg aatagtaggt gtatatgggg aattggaggg 117780 agataggtgg ctgtgtttag taattggttg acttcactga gatggtttgg ggattgtggc 117840 ttccagatga tcagattttc ttttttaggt agagactcca acatcattac agaactataa 117900 attacatgtg gaaaagaaag gcctcctatg ttagaataga aaataaaatg ctgtggggtt 117960 gagggacaga ggtgctgtct aggaagtcag atagcgtttt ccagttctgt ccctcagagt 118020 tccttgtcct cattgagact caatttctct tactttttt tttatacttt aagttttagg 118080 gtacatgtgc acaacatgca ggtttgttac atatgtatac atgtgccatg ttggtgtgct 118140 gcacccatta actcatcatt taacattagg tatatctcct aatgctatcc ttcccctctc 118200 ccctctcccc accacaggcc ctagtgtgtg atgttcccct tcctgtgtcc atgtgttctc 118260 attgttcaat tctcacctgt gagtgagaac atgcggtgtt tggtttttg tccttgtgat 118320 agtttgctga gaatgatggt ttccagcttc atccatgtcc ctacaaagga catgaactct 118380 tcatttttta tggctgcgta gtattccatg gtatatatgt gccacatttt cttaatccag 118440 tttatcattg atggacattt gggttggttc caaggctttg ctattgtgaa tagtgccatg 118500 ataaacatac gtgtgcatgt gtctttatag cagcatgatt tataatcctt agggtatata 118560 cccagtaatg ggatggctgg gtcaaatggt atttctagtt ctagatccct gaggaatcgc 118620 cacactgact tccacaatgg ttcaactagt ttacagtccc accaacagtg taaaagggtt 118680 cctatttctc cacgtcctct ccagcacctg ttgtttcctg actttttaat gatcaccatt 118740
ctaattggtg tgagatggta tctcgtggtt ttgatttgca tttctctgat ggccagtgat 118800
gatgagcatt ttttcatgtg tctgttggct gtgtaaatgt cttctttgag acgtgtctgt 118860
tcatatcctt tgcccacttt ttgatagggt tgtttgtttt tttcttgtaa atttgtttga 118920
gttctttgta gattctggat attacccttt gtcagatgag tagattgcaa aagttttctc 118980
ccattctgta ggttgcctgt tcactctgat ggtagtttct tttgctatgc agaagttctt 119040
tagttgaatt agatcccatt tgtcaatttt ggcttttgtt gccattgctt ttggtgtttt 119100
agacatgaag tccttgccca tgcctatgtc ctgaatggta ttgcgtaggt tttcttctag 119160
ggtttttatg gttttaggtc taacatgtaa gtctttaatc catcttgaat taattttagt 119220
ataaggtgta aggaagggat ccagtttcag ctgtctacat atggctagcc agttttccca 119280
acaccattta ttaaataggg aatcctttcc ccatttcttg tttttgtcag gtttgtcaaa 119340
gatcagatgg ttgtatatat gcggcattat ttctcagggc tctgttctgt tccattggtc 119400
tatatctctg ttttggtacc agtaccatgc tgttttggct actgtagcct tgtagtatag 119460
tttgaagtca gatagcgtga tgcctccagc tctgttcttt tggcttaggg ttgacttggc 119520
gattcaggct ctttttggt tccatatgaa ctttaaagta gtttttcca tttctgtgaa 119580
gaaagtcatg ggtagcttga tgaggatggc attgaatcta taaattacct tgggcagtat 119640
ggccattttc acaatattga ttcttcctac ccatgagcat ggaatgttct tccatttgtt 119700
tgtatcttct tttatttcat tgagcagtgg tttgtagttc tccttgaaga ggtccttcaa 119760
gtcccttgta agttggattc ctaggtattt tattctctta gaagcaattg caaatgggag 119820
ttcactcatg atttggctct ctgttttctg ttattggtgc ataagaatgc ttgtgatttt 119880
tgcacattga ttttgtatcc tgagactttg ctgaagttgc ttatcagctt aaggagattt 119940
tgggttgaga cgatggggtt ttctaggtat acaatcatgt catctgcaaa cagagacaat 120000
ttgacttcct cttttcctaa ttgaatgccc tttatttcct tctcctgcct gattgccctg 120060
gccagaactt ccaacagtat gttgaatagg agtggtgaga gagggcatcc ctgtcttgtg 120120
ccagttttca aagggaatgc ttccagtttt tgcccattca gtatgatatt ggctgtgggt 120180
ttgtcataga tagctcttat tattttgaga tacgtcccat caataactaa tttattgaga 120240
gtttttagca tgaagcgctg ttgaattttg ttaaaggcct tttctgcatc tattgagata 120300
atcatgtggt ttttgtcgtt ggttctgttt atatgctgga ttatgtttat tgatttgcgt 120360
atattgaacc agccttgcat cccagggatg aagcccactt gatcatagtg gatacgcttt 120420
ttgctggtat tttattgagg atttttgcat caatgtttat cagggatatc ggtctaaaat 120480
tctctttttt gttgtgtctc tgcctggctt tggtatcagg atgatgttgg cctcctaaaa 120540
tgagttaggg aggattccct ctttttctat ttattggaat agtttcagaa ggaagggtac 120600
cagctcctcc ttgtacctct ggtaggattc agctgtgaat ccatctggtt ctggactttt 120660
tttgattggt aagctattag ttatatcctc aatttcagag cctgttattg gtctattcag 120720
agattcaact tcttcctggt ttagtcttgg gatggtgtat gtgtcgagga atttatccat 120780
ttcttctaga ttttctagtt tatttgcata caggtgttta tagtatgctc tgatggtagt 120840
ttgtacttct gtgggatcgg tgattatatc ccctttatca ttttttattg cgtctatttg 120900
attcttctcc cttttcttct ttattagtct tgctagtggt ctatcaattt tgttgatctt 120960
ttcaaaaaac cagttcctgg attcattgat tttttgaagg gtttttaca tctctatttc 121020 cttcagttct gctctgatct tagttatttc ttgccttctg ctagcttttg aatgtgtttg 121080
cccttgcttc tctagttctt ttaattgtga tgttagggtt tcaattttgg atctttcctg 121140
ctttctcttg tgggcattta gtgctataaa tttccctctc cacactgctt tgaatgtgtc 121200
ccagagattc tggtatgttg tgtctttgtt ctcattggtt tcaaagaaca tctttatttc 121260
tgccttcatt tcattatgta cctagtagtc attaaggagt aggttgttca gtttccatgt 121320
agttgagcgg ttttgagtga gtttcttaat cctgagttct agtttgattg cactgtagtc 121380
tgagagacag tttgttataa tttctgttct tttacatttg ctgaggagtg ctttacttcc 121440
aactatgtgg tcaattttgg aataggtgtg gtgtggtgct gaaaagaatg tatattctgt 121500
tgatttgggg tggagagttc tgtagatgtc tgttaggtct gcttgacagt ggagtgttaa 121560
agtctcccat tattattgtg tgggagtcta agtctctttg taggtctcta aggacttgct 121620
ttatgaatct gggtgctcct gtattggttg catatatatt taggatagtt agctcttctt 121680
gttgaattga tccctttacc attatgtaat ggccttcttt gtctcttttg atctttgttg 121740
gtttaaagtc tgttttatct gagactagga ttgcaatccc tgccttttg tgttttccgt 121800
ttgcttgata aatcttcttc catcccttta ttttgagcct atgtgtgtct ctgcatgtta 121860
gacgggtttc ctgaatacag cacactgatg ggtcttgtct ctttatccaa tttgccagtc 121920
tgtgtctttt aattggagca tttagcccat ttacatttaa ggttaatatt gttatgtgtg 121980
aatttgatcc tgtcattatg atgttagctg gttattttgc tcgttagttg atgcagtttc 122040
ttcctagcct cgacggtctt tacaatttgg tatgtttttg cagtggctgg taccggttgt 122100
tcctttccat gtttagtgct tccttcagga gctcctgcag tgcaggcctg gtggtgacaa 122160
aatttctcag catttgcttg tctgtaaagg attttatttc tccttcacct atgaaggtta 122220
gtttggctgg atatgaaatt ctggttttaa aattcttttc tttaagaatg ttgaatattg 122280
gcccccactc tcttctggct tgtagagttt ctgctgagag atcagctctt aatctgatgg 122340
gcttcccttt gtggggaacc tgacctgttt ctctggctgc ctttaacatt ttttccttca 122400
tttcaacttt ggtgaatctg acaattatgt gtcttggagt tgctcttctc aaggagtatc 122460
tttgtggtgt tctctgtatt tcctgaattt gaatattggc ctgccttgct agattgggga 122520
agttgtcctg gataatatcc tacagagtgt tttccaactt ggttccattc tccccatcac 122580
tttcaggtac accaatcaga catagatttg gtcttttcac atagtcccat atttcttgga 122640
ggctttgttc atttcttttt attctttttc ctctgaactt ctcgcttcat ttcattcatt 122700
tgatcttcaa tcactgatac cctttcttcc agttgatcta atcggctact gaggcttgtg 122760
catttgtcac gtagttctcg tgctgtgttt ttcagctcca tcaggtcctt taaggacttc 122820
tctgcattgg ttattctagt tagccatttg tctaattttt tttcaaggtt tttaacttct 122880
ttgccatgcg ttcgaacttc ctcctttagc tcagagtagt ttgattgtct gaagccttct 122940
tctctcaact cgtcaaagtc attctccatc cagctttgtt ccattgctgg tgaggagctg 123000
cattcctttg gaggaagaaa ggcactctga tttttagagt ttccggtttt tctgctctgt 123060
tttttcccca tctttgtggt tttatctccc tttggtcttt gaagatggtg atgtacagat 123120
gagcgtttgg tgtggatgtc ctttctgttt gttagttttc cttctgtcag gaccctcagc 123180
tgcaggtctg ttggagtttg ctgcaggtcc actccagacc ctgtttgcct ggttatcagc 123240
agcagaggct gcagaacagt ggatattggt gaacagaaaa tgttgctggt tgatcattcc 123300
tctggaagtt ttgtctcaga ggaatacccg gatgtgtgag gtgtcagtct gcccctactt 123360
gggggtgcct cccagttagg ctactcgggg ttcagggaac cacttgagga ggcagtctgt 123420 ccgttctcag atctccagct gcatactggg agaaccacta ctctcttcaa agctgtcaga 123480
cagggacatt taagtctgca gaggtttctg ctgccttttg ttcggctatg ccctgccccc 123540
agaggtggag tctacagagg caggcaggcc tccttgagct gtggtgggct ccacccagtt 123600
cgagcttccc agctgctttg tttacctact caagcttcag caatggcggg cacccctccc 123660
ccagcctcgc tgctgccttg cagtttggtc tcagactgct atactagcaa tgagcgaggc 123720
tctgtgggcg taggaccctc tgagccaggc acaggatata atctcctggt gtgccgtttg 123780
tgaagaccat tgaaaaagtg cagtattatg gtgggagtga cccgattttc caggtgccat 123840
ctgtcacccc tttctttgac taggaaaggg aattctctga tcccttgtgc ttcctgggtg 123900
aggcgatgtc tcgccctgct ttggctcatg ctcggtgcgc tgcacccact gtcctgcacc 123960
caccatttga cactcccctg tgagatgaac ccggtacctc agttggaaat gcagaaatca 124020
cccatcttct gtgttgctca cgctgggagc tgtagactgg agctgttcct attcggccat 124080
cttcacaaaa atcttacttt ggtttctagt gttaccaccc actgttcttt ctcatctcaa 124140
ccctgagtat aagtacagat cacattcctt gggttcttag aaaataatag aaatgaactc 124200
tcattcatca aaatgcccat tagtaaatac tgagggagaa caaactagaa atccagtata 124260
gaaaataaaa ataggattat attccttgga atctcagaaa aaaacaatga agagctttct 124320
ttgggcatta gacactttcc cataaggtgg ctgactctct tttagtcatg tcagcttggc 124380
ccaatcttca cttggtagcc cttctttctt cttcattaat ccatctccta tgctcctatg 124440
gggtcctaga gaaatgccca tcatgtacac acacatctaa taacacaaag atcactctcg 124500
actagcaagc ccttttatga tggtgtgagc atttgacacc cttgttgcta gtaacatcag 124560
tgagtgacct gacccatttt tggaacagaa tatgatcagt atgttgcctc aaggaggccc 124620
tcactgttct aggaaatata attccagagt ttgctgactc acaccatgga atatatgcat 124680
aaaatggatc ctgcagataa gcctttctct gactagtttc agacattttt ttctgggtaa 124740
ttttaaagtt atttttatt tttgtgggta caaagtaggt gtatatatgt atgaggtacc 124800
tgaggcattt tgatacaagc atacagtgta taataatcac cagagttaat ggggtatccc 124860
tcaccacaag catttatcct ttctttgtga tacaaacaat ccaattatat tcttttagtt 124920
attttaagat gtataataaa ttattgttga ctgcagtcac cctgttgagc tatcaaatac 124980
tagatcttat tcattctaac tatacttttg tacccagtag ccatcccact tcctcccctc 125040
ccactaccct tcccagcctc tgataaccat cattccactc tctatctcta tgagctcaat 125100
tgttttaagt tttagctccc acaaatatgt gagaaaatgc caagtttgtc tttctgtgcc 125160
tggcttattt cacataatat aatgtcctct agttccatcc atgttattgc aaatgacagg 125220
atctctttct tttttatggc ttaatagtac tttattgtat gtatgtacca cattttcttc 125280
atccatttgt ctgttgatag acaagagttg cttccaaata ttgactattg tgaatagtgc 125340
tgcaataaac gtgggaatgc agatctcttt gatatactga ttttctttct ttagggtgta 125400
tacccagcag tgggattgct gggtcatatg atagctctat ttttagtatt ttgtggaacc 125460
tcaaatctat tctacataat ggttttactg acttacatat ccaccaacag tgtatgagga 125520
tactcttttc tccacatcct caccagcatt cattactgcc tgttctttgg atgaaagcca 125580
ttttaactgt ggtgaaatga gatctcattg ttgttttgat gtgcacttct ctgatgatca 125640
gtgaggttga ggaccttgtc atatatctgt ttgtcatttg tatgttttat tttgagagat 125700
gtctacccag atcttttgcc catttttaa tcagattgtt agatttttt tttcctacag 125760 agtgcttgag ctctttatat gccctagtta ctagtccctg gtcagatggg tagtttgcaa 125820 atagttgctc tcattctgtg ggttgtctct tcactttgtt gatcgaatca cttgctgtgc 125880 agaaggtttt taacttgatg tgacctcatt tgtccatttt tagttgcctg tgctggtgcg 125940 gtattactca agaaattttt gcccagatta atgttctgga gagtttcccc aatgttttct 126000 tgaagtagtt tcatggattg atgtcttaga tttaagtctt taatatgttt tgattttatt 126060 tttgtatttg ctgagagata gggctctagt ttccttctgc atatggatat ccagtttttc 126120 tagcaccttt tgttaaagag actattcatt ctctaatata cgttcttggc acctttgttg 126180 aaaataagtt cactgtagat gtatggactt gtttctgggt tctctgttct gttccattgg 126240 tctatgtgtc tgcttttatg tgaataccat gttgttttgg ttgcaaaagc tctgtagtat 126300 aatttgaaat caggtaatgt gattcttcca gttttgctct gttctttttc ctcaagatag 126360 ctttgcctat cctgggtctc ttgtggttct atataaattt taggattatt ttttctattt 126420 atgtcaagaa tgtcattgat attttgatat aaattgcgtt gaatctgtag atagcttcag 126480 gtagtgtgga cattttaaca atatcaattc ttgaaatcca cgaacatgga atatccttct 126540 attatttgga tgtcttcttc aatttcttat attaattttt ttttagtttt cattgtagag 126600 atatttcatt tatttgacta agtttattgc taggtatttt attttatttt tacctattga 126660 caatgggatt gctttcttga tttctttttt agattgttca ctgttggcat acagaaatgc 126720 tactgatttt tatgtgatga ttttgtatcc cgcaacttta ctgaatttgt ttatcagttc 126780 taataggctt ttggtgcaga ctttaggctt ttccaaatat aagatcatat tatctgcaaa 126840 caagaataat ttgacttctt tcttttcaat ttggatgcct ttcatttctt tctcttgtct 126900 gattgctcta actaggactt ccagtactct gttgaataac agtggggaaa gttaacatcc 126960 ttgttttgtt tcagatctta tagccaaggc cttcagtttt tctgaattta gtatgatact 127020 agctatgggt ctgtcatata tggcttttat tatgttgaag tatgttccct agtttttga 127080 aggtttttat attttaagga agataaaaat tgaactttat caaatgcttt tcatgcaaca 127140 attgaaatga tcaagtgctt tttgtctttc attctgttga tacgatgtat cacactgatt 127200 gacttgtgta tttagaacca tccttgcatc ccgtggtaaa tcccacttag tcatggtgaa 127260 tgaacttttt aatgtgttgt tgaattcagt ttgctagtat tttgttgggg atttttgcat 127320 cagtgtttat cagggatatt ggcctatagt tttccttttt tttatgtgtc ttttgggttt 127380 tgttatcagg gtaatactgg ccttgtagaa tgagtttgga atgattctct cctctatttt 127440 ttgaaatact ttgaatagga ttgatgttac ttctttaaat gtttggtaaa attctgcact 127500 gaagccattg ggtcctgggc tttttactgc tggggagact tttcattaca gcttcaatct 127560 tattacttgt tattggtctg ttcaggcttt agatttttt catgaatcaa tcttcacaag 127620 ttgtctgttt ctcaaaattt atcaatttct tctaggtttt ccaatgtatt gtcatccagt 127680 tgctcataat gccctctaat gatgccttga atttttgcag taaccactgt aatgtttcct 127740 tttttaatct ctgattttat ttgagctttc tctttttttc ttagtctagc taaatatttg 127800 tcaatgttgt ttgttcatcc acaaaaccaa cttttcattt cactgatctt ttgtattatt 127860 ttttcctttt aattttattt atttctattc tgatatttat catttcattt cttccagtta 127920 tttgagtttg gtttgctctt gcttttccag ttctttaaga tgcattgtta ggttatttat 127980 ttgaactttt ttgatatagg tgcatattgc tataaacttt caccataata ttgcttttgc 128040 tgtatcccat aggttttagt atgttgttta gtatgtttcc aatttggtac atttcaataa 128100 atttttaaat tttcttcttt atttattgac atagtcattc cagagtatac tgtttaattt 128160

```
ccatgtggtt tgtatagttt ccaaaattcc tcttgttatt gatttctagt tttattccat 128220
tgtggtcaga gaagaagctt gatatgaatg caattgttaa taattttttt aaaacttgtt 128280
ttgtgaccta agatatgatc tgtcattgag aatgatccat atgctgagga aagaatgtat 128340
attctgcagc cattggataa aattgtcttt aaatatctat taggtccatt taagacataa 128400
tgcagattaa agccgatgtt tcattgttca tttttctgtc tggatgatct cttcagtgct 128460
gaaagtggtg tgttaaaatc tctaaatatt attgttttgg gatctttctc ttctttcaac 128520
tctgataata tttgctttag atacctgggt gctccagtgt tgggtgcata tatacttaaa 128580
attgttgtat cctcctgatg aattgacccc tttatcatta tataatgacc ttctttttct 128640
ctttgtgtag tgtttgtctt gaaatctatt ttgtcggata ttagtattgc tgctaatttt 128700
tttggtttcc atttgcatga aatatctttt tcattccttt attttcaggc agcgtgtttc 128760
tttatattta ataggtgaaa tatgtttctt gtaaataaaa attattattt taaaatattt 128820
ttaaaataat actatttttt aataagaaca attattattt tttaaaaaat ttcattagtt 128880
ttgggggcac aagtggattt tggttaaatg ggtgagttct ttagtagtgg attttgagat 128940
tttagtgcag cagccacctg agaagtgtac attacccata tattatatat atactatata 129000
tgctttatat atatagtgtg tatatataat atatatacaa ctacatattg ggtaatgtac 129060
acttctcagg tgactgctgc actaaaatct caaaatccac tactaaagaa ctcacccatt 129120
taaccaaaat ccacttgtgc ccccaaaact aatgaaattt tttaaaaaat aataattgtt 129180
cttattaaaa aatagtatta ttttaaaaat attttaaaat aataattttt atttacaaga 129240
aacataattc acctattaaa tataaagaaa cacgctgcct gaaagtaaag gaatgaaaaa 129300
gatatttcat gcaaatggaa accaaaaaaa ttagcagcta tactaatata ttatatatat 129360
actacataaa gcatatatat agtatagtat atatataata catttataaa gcatatatat 129420
agtatgtaga taatatatgt ttatatactt taagttctgg gatacatgtg cagaacgtgc 129480
aggtttctta cataggtata ctcgtgccat ggtggtttgc tgcacccatc aacctgccat 129540
atacattaag tatttctcct aatgctatct ttcccctagc cctaccccac tccctgacag 129600
gccctggtgt atgatgttcc cctccctgtg tccatgtgtt ctcattgttc aactgccact 129660
tatgagtgag aacatgtggt gtttggtttt ctgttcttgt gttttagttt gctgaggatg 129720
atggtttcca gcttcatcca tgtccctgca aaggacatga actcatcctt tttgatggct 129780
gcatagtatt ccatggtgta tatgtgccac gttttcttta tccagtatat cattgatggg 129840
cattttggtt ggttccaagt ctttgctatt gtgaatagtg ctgcaataaa catacgtgtg 129900
catttgtctt tatagaagaa tgatttataa tcttttgggt atatacccag taatgggatt 129960
gctgagtcaa atgatatttc tggttctaga tccttaatga attgccacac tgtcttccac 130020
aatggttgaa ctaatttatg ctcccaccaa cagtgtaaaa gcgttcctat ttcttcaaat 130080
cctcaccagc atctgttgtt tcctgacttt ttaatcgcca ttctaactgg catgagatgg 130140
tatctcattg tggttttgat ttgcatttct ctaatgacca gtgatgatga gctttttttc 130200
atgtttgttg gcagcataaa tgtcttcttt tgagaagtgt ctgttcatat tcttcaccca 130260
ctttttgatg gagttatttg ttttcttctt gtaaatttgt ttaagttcct tgtcgattct 130320
ggatattagc tctttgtcag atgaatagat tgcaaaaatt ttctcccatt ctgtaagttg 130380
cctgttccct ctgctgatag tttcttctgc tgtgcagaag ctctttagtt taattagatc 130440
ccatttgtca attttggctt ttgttgccat tgcttctggt gttttagtca tgaagtctct 130500
```

acccatgcct atgtcctgga tggtattgcc ttggttttct tctacagttt ttatggtttt 130560 aggtcttgca tttaagtctt taatccatct tgagttaatt ttgtataacg tgtaaggaag 130620 aggtccactt tcagttttct gcatgaggct aacgagtttt cccaacacca tttattaaat 130680 agggaatcct ttccccattg tttgtttttg tcaagtttgt caaagatcag gtggttgtag 130740 atgtgtggtg ttatttctga ggcctctgct ctgttccacg tgtctatatc tctgttttgg 130800 taccagtacc atgctgtttt gggtactgta ccacttgatt ggtgagagag ggaatccttg 130860 tcttgcactg gttttcaaag ggaatgcttc agcttttgcc tattcagtat gaccaatatg 130920 tagtctttta ttcctcaccc tctctcaaca ccccaccccc acggagtcct caaagtccat 130980 tatatcactc tgtatgtttt tgcgttctca tagcttagct cccacttata aatgagaaaa 131040 tacagtattt ggttttccat tctttggtta cttaattagt ataatggcct ccagctccat 131100 ccaggtgtct tgtttttcat ccattcagcc agtctataac ttttgcttgg agagtttcgt 131160 ccatttagat tcagcgttat gattgataac taagggctta ctcctgccat ttggttgttt 131220 tctggttatt ctgtggtctt ctcttccttt tttccttctt tcctgtctcc cttttagtga 131280 aagtggtttt ctctggtggt gtattttatt ttcttccttt ttatttttt ttgtgtgtat 131340 ttgttgcatg ttattgattt gaggttacca tgaggcttgt acataatatt ttctaactca 131400 ttatttcaaa ctgatgacaa cactctatcg cataaaaaaa catggaaaga gaaaactaat 131460 aaaaactcta cattttaact tcatctctct gcttgttgtc actttgtcgt ttctatttac 131520 atcttattgt actgtttatg tcttgaaaag tagtttcagt tattactttt gattggttca 131580 tctcatagtc tttctactca agatatgagt agttcacaca ccacaattac agtgttacaa 131640 tattctgtgt ttttctgtgt actttcaatt acccatgagt tttgtatttt cagataattt 131700 gttattgctc actaacatcc tattctttca gattaaagag ctccctttag catttcttgt 131760 aggaaaagtc tggtgttaat gaattccttc agctcttgtt gatctgtgaa agtctttatt 131820 tttccttcat gtttcaagga tattttcact ggatagtcta ttctagggta aaagtttttt 131880 tttttttttt cttcagccct tcaggtaagt catgccactc tctcctggcc tataaggcta 131940 ccactgaaaa gtctgctgcc agacatatat gagttccatt ctatgttact tgtttatttt 132000 ctcttgttac ttttaggatc ctttctttat ctttgacctt tgggagtttg attattaaat 132060 gccttgaggt ggtctttttt ggattaaatc ttcttcgtgt tcttgtactt ggatattaat 132120 atctttctct aggtttggga agttctctgt tattatccct ttgaataaac tttctaccaa 132180 gatctctctt tctctctctg tctctctctc tctctctctc tccttcttaa ggccaataac 132240 ttttagattt gccctttttga ggctgttttc tagatctcgt aggtgtgctt cattgtttgc 132300 tattttttt tttttttgt ctcttctgac tacattttca aatagcctgt tttaaaactc 132360 actaattctt tcttttgcct ggtcaattat gctgttaaga gactctgagg cattcttcag 132420 tgtgtcagtt gcatttttca gcaccagaat gtctgcttat tttttttag attatttcca 132480 tctctttgtt aaatatatct gatagaattc tgaattcttt cttagtgtta tctttaattt 132540 ccttgaattt cctcaacaca actattttga attatctgtc tgaaaggtca catatctcta 132600 tttttccagg attgctatct ggtgctttat ttagttcatt ttgtgaggtc atgttttcct 132660 ggatggtgtt aatgctagta gatgtttttc agtgtctgag cattgaaaag ttagatgttt 132720 attgtagtct tcacagtctg ggcttgttca tacctgccct ccttgggaga ctttccaagt 132780 attcgaaggg atttggatgc tgtgatctta gtctttggtc actgcagcca tatctgcttt 132840 atggagcatc ccatgctcag taatgctgtg gctctttcag actcatagag ttactgcctg 132900

```
catgctcttg ggtaagagcc aggaaaattc cctggattac caagcagaga ctcttgttct 132960
cttctctcac tttcccccaa acaaatagag tctctctctc tctctctctt tctctctctc 133020
tctctccctc tcattctctg ccgacctgcc tgaatctggg gtagggatga cacaatcaca 133080
tttgtagtca acaccattgg gactgtgcta ggtcagaccc aaagctggca cagcactgag 133140
tctcgcccaa cgcccacaga gaccactccc tgggtaatgt ctgtgtttgc tcaaagccta 133200
agggctatac aatcagtcag tggtgaagcc agcctgtctt atgtccttcc cttcagggtg 133260
atgagttcct caagcaggtc cagggatggt gtccaggagc caaggcctcg agctgtgact 133320
gagctggcac ccaatccata agacaaagat tttttccaca ctttccttcc ttgtcctcaa 133380
gcaaaggagt ctctccctgt ggccaccacc acccccatgt tcatggcaag tattgtctgg 133440
ctaccaccaa tcttcactca aggcccaggg gttctttagt tagcttatgg tgaatgctac 133500
caaggctgag tctctccctt caaggaagtg ggctcctctc tggcccaggg caggtccgga 133560
aatactatcc aagagccaag gcctggaatc agtttcccca agagtccatt tggtgctcta 133620
cacccactgt ggcagaacca gtacccaagc tgcaagacaa agtcctcttt actcttcctt 133680
ctcctttaca gagactctcc ctatagccac cacagctggg aatatgctgg gtcactcttg 133740
aagcaagaac agctctgagt ctcactcaaa actcctggca agtactgcct ggctatcaca 133800
ctgattattc agggcccaag ggctctttag tcagcaggag atgaatcctg ccagtactga 133860
ttccttccct tcaaggcagc cggtttcttt ctggcccagt gtgtatctag aaatatcatt 133920
tgggagctag ggcctggcat ggtgacctca ggactctgcc tggtgccctg ttctactgtg 133980
gctgatgtag tatccaaatt gcaagaccaa gtcctcttta ctctcccctc tcctgtcttc 134040
aagcagaagg aatgagtccg ccctggagtt gggagctgca ttgcctggga ttggaggagg 134100
ggtggcacaa gcactctctt ggtcacccca gctggtgtct tactaggtcg catgttcccc 134160
aagtccactg gctctgaggc tagcacacca ggatttgacc aagaattgca attcttgtgg 134220
cttacactgc ctttcaagtt tatttgagat cccagagcac tttagcccac agtgacaggg 134280
cttgccagaa tttagtttct gactgctgag atggacaatt tgcgtctgat tagggctggt 134340
ctaagtgctc cttctgtggg cactggctga gttctgctcc atgttgcttt ctgctgtgac 134400
agggcaacat tgagtttcaa tgcaagtccc acagtcactg caatcttcct ctcccaagcc 134460
tgctctgaac accatgtggt tgctgctggg ggctgggggga gggatgttgt aggcaattca 134520
agaatgtctt tcctaccctt ttcggtgctt ctttccttgg tatgatatta aaaccagtta 134580
ctgtgattgc tcacctgatt tttggttctt atgaaggtgc ttttttgtgt ggatcactgt 134640
tcaatttgtg cctgcaagcg gggatggggg acaattgctg gaggcttctc tttggccatc 134700
ttgctccacc tctaccctag tattagcaat ttcaaagcag ttgggatgga ggtagaagga 134760
aagggcgctt ggaatcagaa aatccatgtc ttagctttga gccttagaaa attcatttga 134820
cccttgtaag cctcagttgc ttcatctgta aaagagaaat aatataatgg ctgaaaagat 134880
caaaggtgat aatgcttttg aaaacactat agaaaatgac aaaatatcac atgagtatta 134940
ttttctagtt tctaggagtc tccttaccat tgtacaggac aaccatgtct atttttaaat 135000
aaattattat ttgcctctga gcaaccctgc aaagagttgc ctgtaggaga aacagcttta 135060
cttgcaaatc actccactgt tttctttgtg cacagcttat taatacataa ggcacatgtc 135120
ctccagcctg cagtaacatt ggaatcatta cctctttgga gtacctacca gagcttctca 135180
aagtgaattt tgtttatcac cacaaaaaat agtctgttgc agagataacc tccaaattca 135240
```

atgacaatat ttccaatcac ttttgcatga tgcagaaata gacaaatata taattttgct 135300 tatagagaca attattgtct cccaacaagt gatcagtagt cagaaaatgg ccaagaaata 135360 ccatggggtg tgccttccca taacagctta tctttgtgtt ttagttgcaa ggttactaaa 135420 agcctgtgca gggtttatgg caaaagtaaa acttgctcca ggagcaagcc cttgtttcat 135480 tgtctaatgt tcttaatccc cagcagacag gatttggatc tggcatttgg taacagggca 135540 gtttccaaag ttgctgtacg caacttgagg aagagaggtg atattatcgg aatgaatttc 135600 tttgttgtaa gttataaatg tatgggcttt tccaatccca tcacccttaa aactttattt 135660 gttttctgca gtgagggtgt ctccgttgtc tttaatatgc ttgctttgag ttcatggatg 135720 aacattcctg cctggctgac atgtggactc tctgaaattg ttataaggtc tttttctttg 135780 tttttttctt gatgcccaag ctgccaaggg tagtactggc agtggtgggc agacaaggag 135840 gtgatagcaa actttgtcct ctggcctccc ttgacccatt ccattcatta tctaagggac 135900 tccaagccag cattccacag agtgccctca ccaaactcac taagactgaa ggcgaaccag 135960 gattccaaac agccattatg aaaggaaaga gagagagact tagggtttgc aaaataagat 136020 accctgttga ttctttttat tccatacaga tactactatt ctttaggaaa acgttaaaat 136080 cacatgatct tccaggacct gggctgcttc tttaagaagc atgttacaga aagctttatt 136140 ggccaacaac atattgaaag atagattaat caatcattca ttcaaataag gtatattcag 136200 aattgaggta tattgtagcc agacagtgag actacaaaaa aagaatgcac cgtaccctta 136260 tctcttgcac aatctaacga gggagataac cactctttca atttatagtg acctataaca 136320 tttcgtacac tgctgaatat ctttacatgg taataacaca atggaaagct tgcaaaatag 136380 acagaggcta ggggaagaag gattgagtgt gaatatagcc tcttataaat cgagaggaat 136440 ggtctgtgtc ttctgatcat acagagataa taaatatgga aatgatttca aactaacaaa 136500 gcaaatgtgc agaaaatact gagaatatag tgggcaggat acctgagttt tggttccatc 136560 tctgttattg actcattgtg taatctgagt caggtctgtt ctgctctctg gatctcaccc 136620 tttcctatct gtaaaatgag attgttggat tagatgatct ccatagaggt tctcacctat 136680 tctgacattc aaaaggactc ctaatttttc ttatataata ataatatata tgatctgtag 136740 agtgctttac actttatatg atatttttgc atctgttatc tcatgtgaga aaagcactgg 136800 actgctggac tggcaatgag gacacctgga ttcttgtctc tgttttgaca ctgattcatg 136860 gtgtgatctt caagcaaatt ctctgagttt cagtttctca atctgtaaaa tagggggta 136920 tgaagattgg actaaatcag taggtctcta aaatgttcca caaagccctg gggtgggggg 136980 ctcctacaga gtttcgctaa ggcaaaccac aacgctaagc ctgcatggaa gaggagaaaa 137040 agagtggcct gacaagagaa gttcccagtt tcctatgcca accccaggca gattacattt 137100 aattttatct gatttatata gagagtttct atgtaatgtt ttattcttaa aaatagttta 137160 ctataaaaaa ctcaactggt ttgattttta aagattgcac atataagtga gatcatgcag 137220 tcagtatttg tctttctatg cctggcttat ttcacttagc ataatgtctt ccagcatcat 137280 ctatgttgct gcaaatgaca gacttttctt ttcattaaag gctatatagt attccatcgt 137340 gtatgtacac cacattttct cttttgtaac tttcatttta ggttcagggg ttcatgtgca 137400 tgtttgatat ataggtaaac tgcatgtcag agaggtttct tgtacagatt atttcatcac 137460 ccaggtaata agcatagtat ctaatcaatt tttttctgat cctctccctt ctcccaccct 137520 acaacctcaa gtaggccctg gtgtctattg ttcccctctt tgtgtccatt acaccacatt 137580 ttctttatcc acttatccat ccatggacac ttagtttgct tccatatgtt ggctattgtg 137640 aataatgctg aaaaaagtca aactcataga agcagagagt agaatggtgg ttaccaggga 137700
ctgggaggca gttgactgag ctaggaaaag agagataata aaagggtaca atgtgtcagt 137760
tatatagaag gaataagtta tattgaacta ttgcacagca tggtgaccat agttaataat 137820
aatgtattat atgtctcagt attgctaaaa gagtaaattt aaatattcta accacaaaaa 137880
attattagta ggcaaggtga tggatatgtt aatttgcttg atttaatctt tctagaatgc 137940
atacatatat caaaacatcc cactgtaccc cataaatata tacaattatt atttgtcaat 138000
ttagaaattt aaaaacttga tttagatgag ctctaaggcc ttaagtatta aagtattaag 138060
tattaaagtg atatgtaacc aagtatattg tttggtaact tcatttttgt tattatttta 138120
acaaaccaat atattgtgaa tatacttcca agtgaaaaga aaaaagacat tgcagtcatc 138180
actaataact gcaaaacatt cctttgcaag aatatggaat aattcattta atcattcccc 138240
taatgttaga cattcaaatg tttccaactt tttctattta aataatgcta caataaactt 138300
ctattttgtg cttattgtat tattttctta caacacatcc ctagaagtgg aattcctaga 138360
agtttataca catttccaat ttttttccaa atatatggca aaatttctct ctaaagtatt 138420
tttattccta ccagaaatac ctcttcacca acacgtagta tttaatctgt accaatctgg 138480
cttaagacaa tgatatttaa tttgtatttc tgtgatttct agctaaatta aataatcttc 138540
atatgcttat tggtcatttg tacttctaac tgctttctcc tgtctgttgc ccatttttct 138600
attgtgctgt ttatttttat atatcgaata tattgaccat tggttttaca tacttgatgc 138660
taataattat tcttagttta tggtttgtct ttgagtttta taatggtgtt tatttcacat 138720
aagaaattat aaatgttttc taatgaaatt tatcaagtct gtcttcactt atgttttctt 138780
cattgtcaat aacttaaaat gaccttttct acctttaaaa attttgaaat tttcctctgt 138840
attgtctaat agtacttaca tgatttcctc ttttaaattg acatatttaa tccatttgga 138900
atttattttg attttaacta gtaatttaac tttattttct tctccaaatg attcactagt 138960
tgttctgaca ttatttagtg aataattcat cctttcttca ctgaattgga atggcatatt 139020
ccatatactg tgtctggttt tggcttttct gatctcttcc actgatcaac ctaagctgga 139080
gccagtatca aactgttgta atcattatgc ctttagatac tttaaatgta cagcagggaa 139140
tgtcttatta ctcttatttt tcacaaatat cttggcattg tctcatgttt tattccttca 139200
gataaatttt gggattattt tgtcaagatt ttgtttgagt tgttttaaat ttttagattt 139260
cattgggaaa gaactgaaat ccttgaaata ttgcttcttc ttagccagga atatggtaca 139320
actttgcatt taattcagtt ctttccttaa ataccaccat gaagtttttt gttttgttca 139380
tataggtcct gcattaacac catatatata aagtgtgaga aatactacat tcttcaggat 139440
tctctgtagg ttaacaatga agatgatgac tcaacccttt ctttgtttgc ataatgtgat 139500
gccactaata gtgggtaact tctctgcctt acctcctctg ttccaaacag gatttttcag 139560
aatgaacaaa ttaaaagaat cataatcaga cactaacccc aagccatact gcatggcagc 139620
accaatggga ctgacagaaa acaacagaaa taggaagaaa tcctacagag aaacaaactt 139680
gaaagctgtc tcatggcctt tgaatcatac ttaagtttta tgatggaagg atacgactat 139740
gaagaaagac acagagcaac atcagacagt caagaatttc agagccagct ggcatgcagt 139800
ggacctcatg ccagcccatt ttatgactat ttaggtagtc aagggtttaa gatttttcta 139860
ataagacagt tattatgcat ttcaatgagt gatttctttg cagctctaga gtgtggcctt 139920
acctacttca acatgagaag atttttgtat tttgtcagtc atttcacaat gacttttagt 139980 gagcccttca ttatagactg tggatacaac tttgctgttg gaaattaaca gtgtcaaaca 140040
actgggtata atgtttgtaa tatctgagga gggggagctg cctaggaagt tgtattccct 140100
gtgttaattt ttcagtctct taggttatag aggaccttct agaaccacct tacagcagga 140160
ttacatccca tttacacagt tctctgtcac ttgaatacag agaagggatc cacaaggcca 140220
tatgcttcct agacaaagag aaaagatttc tgccacactc agaacgcttt gtcttcagac 140280
tataatcacc cacaccatat ttcctttgga tccactttcc agatttttgt gctggcacta 140340
acaccaactt gctgtggctt ggggcatgta atttcaatac tttgtgccca ttttcataag 140400
tgaagtgtca ggcatcacat tggacatttt aagattcttt acagcccaat gattctgtgt 140460
ttctaattag gcccaatggg ttagagctaa aaggaaacag tgagtttcct ggaaggaaag 140520
gacatataac acagtccaga ggtaaaatgg gctgtattca agaaaagata ggacaatact 140580
ttgcagggat gctgcagaga ggattcaagc cttgtatgga ggaatggatg tgatacaacc 140640
aaaaagtctt taaaaattct ttccaactaa tctgagattt gtaaccttat ggactgtgat 140700
ttgcagcaaa ccaaggatgt gataaagact agtattgttt ctagaatgca aggatggttc 140760
aacatatgca aatcaatagt attaacagaa tgaaggacaa aaactatatg atcatctcaa 140820
tagatgcaga aaaataattt gacaaaattc aacatcattt tatgataaaa tctttcaaga 140880
aattgggtat tagaaggaat gtttctcaac acaataaagg ccatatcaga caagcccaca 140940
gctaacatta tattcaatga ccaggaatga gataaggatg ctcactctca ccacttctgt 141000
ttaacatagt actggaagtc ctagccaatt tcatattaat gagcctcatt ttcttcatca 141060
tagaatgaag tatataataa tccctgttat acttactttg cacagattat tattattatt 141120
taattattat tttgagacag ggtctcactc tgtcacccag gctggagtgc agtaccacaa 141180
tcacagctta cttcagccac gacctcccag gcataaagga tcctagcccc tcagcctcct 141240
gagtagctgg gagtacaggt gcacaccacc acacctagct aattttttt tttcattttt 141300
ttatagagac ggagtctcac tatgctgccc aggctggtct caaactcctg tgctcaagca 141360
atctttccac cttggccttc caaagtgctg ggattacagg agtgagccac tgcacctggc 141420
cttgcagatt attattaaac tttgtaaact aatcaaatga gagtgattat tgttactgtt 141480
aagaactctg atagcctcat ccatatattt ggagaaattg aataaataat aggaaagaaa 141540
taatagcatc ccaatgattt taccttggct ctaccatcat ttggggaagt gataattcag 141600
ataggagaag tgacttggaa gcagtcttga gagattgcct gttccatccc ctatctttgt 141660
ccttaaacca aattgtacag ataaataagg tcttattttt aggacttaca gaaaaaagat 141720
tcctttcata tccatctttg caatcctcaa ccacttctgt cactattatg tgtcatttca 141780
aacattaaat tcctcattct gctttgaagg aacacatgtg tcatgtgtac ccatttgtat 141840
gttttggtgt gttttatgct ttatgtgatc acccacatat gcacagataa ttccaaaatc 141900
cagtgtgtgg gtgttgtatt ccctgtgtta attattcagt cacactcaaa cacctatgca 141960
ctcacacata catgaataca cacatgtaca ttagcatgtt tatgcttatg ttgcatgtga 142020
ctggcaacat cagtgccttt ctaaggcaat gttaactacc ttgagttttg ggagagcttt 142080
agagaacaaa gacaagagac taaatgattc tagatgtaag agacaatgtt gcaataagtt 142140
actatcctaa aaagacagaa tacagggaca agagactatt attttggata gtttcttgct 142200
taccagtaat acttaagtcc tttacattaa aaaaaaaaaa ctctgtaaat atattgcaga 142260
agaaatccag acatccttca agattcttag agctggaaaa gattttaatg actttccagt 142320
ccaatctatc tcatgtaatc aatggggccc agagaggcaa aaggtcttgt ccaaggtcat 142380 atagtgagtt agtgataagg ctgaacaagg attcagatgt tggggcttcc agcccactgc 142440
tctttctctc atctgggatt tgtgtatttt tgttcattag agattttcct ctgtaacctc 142500
aatatccaat gcagggcctt gcacataata gattatcagt aaatgttaaa ttaatatgtc 142560
atggctttgg ttgtactggg cttttgcact tactcctgag taaattgtaa agaatatcta 142620
cgttttaggt tgccttgttt tagaccaaga ggtacccaga gaaaaggtgt gaactatgct 142680
aaggaaatta tccgagttcc aaattgaaaa aaaaaaaaaa tcatgctttt ccgctataac 142740
ctctctcatt cacagagtga ttctctttca gaagggcaat ctagaactat tatgggagcc 142800
atattccatt ggtggtgcaa ccatttcttg acaaactagg gtccaagaaa gtattttcct 142860
ggggaagatg agatttctca aagaaggcac gcactttcta acctaagctt atttcagtaa 142920
tcaatgtaac aagctggtct tgatgattgc agcagtacca atactgtggg agtgtaccag 142980
ttctagaaca gctacaacat tggaattgaa cgcactagaa ttggatacag gacctgtttt 143040
tgaggagcta acacccaaag gctgaacagc actcgtagca ccgtcctttc tgtgcacata 143100
tggtagtcct cagtttgcaa cagaaataaa gctgttagca aattatgtgt tctatttatg 143160
caaataaaat cttgtggtat gctagaaaga gcactggcct ggagacctta gttttctcat 143220
atgttaaaaa cccctaacac aggcctggtt catagtaggc acccaataaa tagtagtttt 143280
cttcctttgg gggcctccga ttcagtgtgc ttcttcaggt aagtcacttc cctggaactc 143340
ctccttggaa tgagagttgt actgttgtga tttttaacag ttccttcaag ccaagcattt 143400
tggaatcctt tcataaaggg agaaaggaag gaaagaagaa aggaaaatta aaggaaaaag 143460
aacaaataaa acgttaaaaa ggaggaaagg aaaaaggatc ctttactaca ataaaactaa 143520
tcttatgttc ttgcaagtag cactttaagt aaaagaagtt ctttgctgac ctggttacta 143580
ctgaacctac tacataaaat agcctactat aatagatgca tttatgtgcc taatcttcac 143640
tttttaggct tagtaaaggg agaggaaagc tgatgtatag ttaaatttat gtttttagtt 143700
gtttttttt ctactctcaa atatcaatca ctctttagtt tctctttctt tttccgacca 143760
caagcattct tcctctgctt aaagaagctt ccctaaaatc ccagtctatc cagtaagcca 143820
aagcacagca ataaatttga ggaaaaaata ccagggactt agagacagaa aggagtgagg 143880
ggatgcagaa gctgaagctg gagcacggtt gcaagcatga gaagttctgc gtgtttcaga 143940
gcagccaagg atgtattttt gcctattcct gctggtgact ctgtgtgtct atgcatccat 144000
ctgctatatt tacatgttta gtcagtcaat ccacgtttgc tgagagcctg ctgtgtgcca 144060
ggattgtgct agcgtaaagg agcaaagtat tgagcaaaat atgtttgagc agctgtaatt 144120
ctgaggatct ctaggtctga gcatgtgtat gtgtgtgcgc ttctatgtat ctgtgacaac 144180
tccaggtgtt catgacagtg atctttgtta ctctgttggc ttcatcgaac ttccttttac 144240
ttgctgtgat tcactacata gagtgggctt tatctctgat ttttataacc tgcaagactg 144300
ggggtatgat caccagcaat ctaaaaacag ttagaaatcc catggagtta tcttttgtag 144360
aaattttcct ctactaatat tatgaaaaat aagcatctta ttagctcgag tgtaattcta 144420
tgcatgatta caggtatcaa taggaagaaa cattgactga gttcaaatct cttctacgcc 144480
atgctaaagg ggtgacaagt tccacaatgg atcattttct catgggcatt tctgactttt 144540
ggtaaaagta gagcacctta ttttaaaaac cattgagtag tcctaatagt ggagatatca 144600
tcaggatctg aattgttcat ccctaaaaaa aacaccaatg gaaatcaaac aatatagtgc 144660
caaattaaac tgtttgaata tttaggttct gtatgatcaa attgtttggt gccatactct 144720 gtccactttt ttcatgtggt aggatataat ttcatatctt ttctgttcta gaaatacccg 144780
aagaaagaga ctctggaaac tcattatcag gtctatcaac tcttgtattt gttctcccag 144840
ggaaacagaa gtacctgtgc gccagcagaa atgattgcac tattgataaa ttccgaagga 144900
aaaattgtcc atcttgtcgt cttcggaaat gttatgaagc agggatgact ctgggaggta 144960
agatactttt ctttctcttc ctcctccttc ctctctcccc cttctccctc attttctagt 145020
ctctctttag accagatttt cttctttgat gcttccaagg ggaccagcca tgctctagac 145080
acaggctgac cctttcatag gcaacgtggc catcagccag ctggtgcctt ttttttaatc 145140
cttatctata ccaatcccca ttccggggct cagcattaga gcaggcggtg tgaagcaggg 145200
atcaggagcc aacagaaggt gagtgaggat gcatctgact gggcagggcc cccaggggac 145260
ttaatgatac tggcctgatg ttgttcagtg gtagctagga tgagagaact aagaaatcca 145320
gaacagtcag aggtgcagga tgacccaggc ataggcgcag gatgacccag gcacaggctg 145380
atcctgaaca cctgggaata tcccttagct aactgctgcc tatgttgtag ggccagccac 145440
ctcgaatgag aagctacttc tctttggagc ctgtgactag gctgccacac agagccaatt 145500
tcctatccta tctctcccaa agatgagcag gtgttttaat aatttccttt tctttgcaaa 145560
gctattgacc atttccaaaa gcattttttt tcagtagcac agtaacgtga tagatggaag 145620
atacagctct ttcaagggcg ttcctctatc ataaggctct ctgtcccaca aacctgtcta 145680
ccatgagtgt tgtcaccatt ccagaaaggc ttgacatcag ttgattgaga cttatatttt 145740
ccctctccaa actcccccat ctcttcatgt ttacatctgc ccaatgccag ggtcctcgct 145800
gctgcctgct acttccaaaa agatgtgtct ttcatgagaa aaacaagatc attaatccac 145860
ttcgatttgg aaatggaatt tgaagaaagg caagcctatt tctgagtgcc tgcaactgta 145920
gcctcatacc caattattca ttattagcct ggaaaaccca agtgcctaga atccaaccct 145980
ctcccctctc ctcttaagtc taatttagac cagttgtcta tctctggctt tctgtgaggt 146040
gttcaatacc ttgtctgcct atgtgcacat ttatagacaa caactagttc tcttatcctg 146100
gagcagggcc atgtgtggat cttcatatag ataactatat cctccccatc ctcacagggc 146160
agtagtatta tttaaacaga acaaagtacc tcacatgaat tgacccaggc tggatgagag 146220
acaatttcaa aagaatcatc tcaagtagcg tccagtactc ccaaacatca caggtagatg 146280
ttctgtgagt ggctttccaa gcatccacat caaatgagac tcagatatct gagaaaactc 146340
aaccttgttt tggtttgctt ggtgcacccc aaagaaatcc aacaattgag gtctacagtg 146400
gagaagaagt aggactgggg tcagggagta cagaggcaaa ggcaggaagg gtgacaaagt 146460
gattgacaag aaaaaatgtt ctccatatga atgttgcagc cccatgttga gggttcttat 146520
acactcaact gtcaattatt tagccttctg tgaattatgt atagtataaa agatagggac 146580
tctcaagtag ggaacctctt ggcttgccat ctggcaatat gaattgcaag tccactttga 146640
tgcaggtaaa gtttaatggt aacaaaagtc ctcataacat ttggatgcaa atcttaacat 146700
taattccatg tctcagccaa cattctccat tattaagcag cctgtgatgt gattacagtg 146760
aaccactttt gaaaaggagc ctgtgtataa cagatagttt cactatacta tataaccgtc 146820
agatgcaggc ttgtaaatta atttgttggt gacaatgttt cagtacattt tcaaattgat 146880
tcattggtat agtactcaaa tttgagtggg cttggtgaac acaatgaaga caagctgaga 146940
agtgctgtga ctggccttca tttcagttgc aggcccatga tattttgagt gtcttccatg 147000
tacaaggcac catgctaggc attagagctt gaggctggca aacttcagga agtgttcaca 147060
agataccagg attcttgatg ttgtgtaaat ggccttgcct ttagagtcag gcagatctag 147120

```
tttaaaggct cagctccttt atttactgtg tgcccctctg agcctcaatt tcctcatctc 147180
tgatttagaa ataccatcct catagagtta taatgagtat cagatgacat gatgaatgtg 147240
aacatccttg ataaatagca aaatgctaga caaatatggg ggcttaatat gacattgagg 147300
tcactagtaa tttagctgga aagtctgtaa cacagcactt cccgatggct tttaccctaa 147360
gtaacttggt atgccatata atatgtaaca gcaccaacag gcagagaatc gccagaaaac 147420
actcttgatt acctcaaacg aaaaagtacc accaggatcc tgttcagaag ctaattttag 147480
taattaaggg aatcatatgc tatgttcaaa taccatgcca gtaaaaaccc aattgtttac 147540
cttcttaaat cactgcttga agagcaaatc tttccatttt gctgaatgaa cttatctcca 147600
cgttccctgc cctactgaca caaccccctc ccaagtttat tgttaactta cacattcaat 147660
gcacagcaca cctttactca aacaatggaa aagaaagaaa gtgtcaattc aaagtggccc 147720
ttgtctattc cttaaggagt agacttccat tttcatcaga tttggattta gcatagacat 147780
attgattacc ttgaagaaga attcatataa ttttatcttc tgattcccat cactcaaatc 147840
aaaattacat aatatattcc aaaatggcaa ctaggaatgt ggccttgggc aagtcccttc 147900
tctcctctga tgcttggttt tcccatcata gaactggaat tgtggcttca ccgaggacct 147960
ttctggtgct aacattttgt gattctatgt aaaaagccac acagaaagga ttgtttttca 148020
gccctttctt agattgtctg ttccctgctc ccagaagtat agatagtgag acttgagtgc 148080
tttgatacat cgtaattgta tctacctcca ttcacaccta cttaagatat ctgtctaaaa 148140
gtagactaga cagattattc agagagtgga gggcagaagg gctgtctctg tatcttaaag 148200
aagctggcac tcttcagctg atggctgctt ggtcttgagg cctcaagatc tttaatctgg 148260
ctttctctat agtgtttcat tcactgtttg gtgatggaat ctcttcagtt cagagatact 148320
taatagatat agctttttct ttcctgcttc caggcctacc tacctgtttc ttgctttttt 148380
ttctagcagc tgttgttgtt tctgaaagaa tcttgagggt gtttggagtc tcagaatggc 148440
ttccttaaag actaccttca gactctcagc tgctcatcca caacagagat cagcctttct 148500
ttgtagatga ttcattcctg gctgcatttg aaaaccacat attgttaatt gcttgacgaa 148560
tttaaatccc ttgactactt ttcatttcag aaaacactta caaaaaaagt ccaaatgagg 148620
accttccctc cagtgaatta gctgtggctt tctcacagtc catagttagg ataaatgtaa 148680
agccatttct catttttctc cgcactttcc aagggtacac tccttgtttc caagatggaa 148740
tgagaaataa agaagtgccc ttcctgccat cttctcccct gaccctttcc tccttcccac 148800
tttcctccta ttcctcccca aacatgattt atttctgcgt tttgcaactc ttgagttctc 148860
agcatttagt aaatggtgtt ggtccctgtt gattccttcc tctcctggac catggaaggt 148920
agtaggcctt tcagaaattt caggtagcag ccaaacccca gaagaagaga aggaacacag 148980
agacctagac catgtgagaa cctgaggtgt gcagcattta cttcacagat tcgtctagca 149040
tatttgagag gtgtctttcc tactaggaga ctgaactctg catctgagaa taaaaactta 149100
acatatctac aggttttgac aacctctgtg aattatctag ttgagaggat ggctcaagga 149160
gcctattgcc atggtctgat gtcgttatgg acgctatgaa catccttgca gtttccattg 149220
ttgaagacag ccctgatgcc agctgtctca tcattcccca tgttcaagag catcccagca 149280
ttgctacctc aggatcccat gtcctgaatg caacagagtg atttcgctgc tgaattacta 149340
ttcatggcat ggctcttcac agcatttatt catccatgta tctatccatt catccttcca 149400
gccagccaag aagttcacgc tttcatcttt tcatccattt actcacctat ttattcattt 149460
```

agcaaatatt tattgagtac caactatgtg ccagacactc tgctaggcat tttggggaag 149520
cagaactgaa taagatacta ttcctttcct caaaaatttg agcaagagga gaaaggaagt 149580
aatgaggaat attccttagc cataaaggaa aaataagaaa tcacttggaa gaagttaggt 149640
gagatggaag gaaaaggaca tctaaggtaa agcgtacagt ttgaataaag gcacagagac 149700
atgaacaaaa tgcattgagg gtttgaggaa cagcaattgg tttaacatgg ccagagctgg 149760
ggaaatggta agggcaagct gaaaccacat tgaaagcaaa cttggttatt atactaggta 149820
gtttagactt caagcagttg aaaatctttg agcatgggat aggcatgatg acattgtgtt 149880
tatttgcatg tttctttaaa gaaaactggc agcagcacaa atgttttgtt gatgagggtt 149940
taaattgtag aaagtgagac aattttagga aggccagcta gagagaaatt tctagcatca 150000
aattttgcta aacacctagg atttgtagtt acctccattt gggttgttac ctgcaagtac 150060
tgaccacgta tatgaagaag tactggttta gaccaaggca attggcttgt ataagaggcc 150120
taccctcata ccaaaagcca gtttccttgg tctaggccag tgtttactgg tatgtgtcct 150180
gagaaaacta gttccatgac atgttccatg aaaaatatga tttctattgt caaataagtg 150240
agggaaactt gcatatcatg gtcctgctca ggaagattta caatccttat tagcatatca 150300
caggtcctgg tgaatactgc ggtaaagtaa ccgaggagct ttgtaactca ggattcccga 150360
agttgattca accacaggac ctcatttatt cacataacac ctgttatcct acaaaaccac 150420
tgttctctgg aatacacttt cgaaaacatg ggtatagaca aaaactctat cctataggca 150480
gagaatacct atacctctag ctcaggtcat cattttgcag atgtgtgtgt cattaagaat 150540
cagtcaataa tgcattaatg atcaaaagca gaccatcctt accacatggt gcataagatt 150600
atgctattat gctattagct actaatgcca ctaaagttaa ttatgttggg tctgcaacgt 150660
tgtcatacac aaaggatagg atgcaaaact gtcctaggcc aaagcatggt tattgcccaa 150720
gttatctaat gtctgcaggt acatattcct ggcctaagga ttgtgctaaa gaagttattt 150780
ctaagaaata tagtgacttc cagcatcatg cagaatgacc atttaatatt ttgaatatct 150840
agacattctg ctgtagaatt taatagtcct tttatacact gtctgaccaa cattttgaca 150900
tttactcaga accccatcac agtgctacca cataacctca ttgctaaagt gggaggccta 150960
gaaatcacag atttgtagaa accatccaat gattgaatcc cctctacttc ctgttcagca 151020
ggcagcagag tgtcataaag aattaacaac gtggaactca gttactggga tttcttccat 151080
tctcctttga ttctctagac tagaattcca aagaccctca ggctggtgat gcaagtggga 151140
agtctcattt ctgagaagtg ctgcttccta cccacaattc tttgatagct gagtgcttta 151200
gctgatctgc ataactgagg tgtgcaccaa ggagcagaat tactctataa attttggcat 151260
caacatgtgc aacttgtgac tcagcacttt gaaactctgg ggatttttt gtttggttgg 151320
tttttgtttt aagatgtcct gtggtatagt ggaaatagta caatagactc agatacagag 151380
aggccttgtt tctagtcttg gttctgtcac ttactatctt gatgtccttg cacaaatcac 151440
cagacctctc tgagcctcag tttctccaac cacactgtgg gaataataaa atctttttta 151500
cggcattgtt gtaagtatgt agagaaactg gtacacagta ggcacacaat caatgtcacc 151560
gtacccttca gcccttcttt tgtggatgaa aaatggtctt tgtgctccca gtcaccactg 151620
gggtctgttc tctctctctc tgctgttaca gtgtggcttt tggttcttgt ttctttgttc 151680
tttggtctgt aaattaccct tgaaacaacc cttgaaattt ccactccatg acctaaatcg 151740
tcatccctaa attggttaca tacatatttg gtgacacttt ggaggggaaa agctttatgt 151800
ctctctaact gtagttctta agggaatttg catatggaaa aaacagagac tgcgtctctt 151860 aattcctcca aaccaaatta tctgggatag cacatatatg ttgtactctg tctctgagca 151920
tttgctctta gagaactatg gttagagcga agtaaatttt tctaatcata aaaattaatg 151980
ataccgcata tctgatactt gaatgagtac ctccttgtaa aatttatact taaatccttg 152040
agtttttaaa gtgtaatagc aatagaaaga ttttattgtt gtttactttt actgtgagtg 152100
ctccaaaatc cctcagttgc tcttgaaaga gcaagatgat gccataggca atattttcca 152160
aaggtagtag gcagaaaact gagtacacag cacacaatag gccatatata caaaagcaag 152220
tattttgcaa ataataataa ttcaggaaaa aagcttcact ttcgttggta acctgtttgt 152280
ttaaaaccat tttattattt attatttaaa aagagtgtca cttgttacag attgtgggat 152340
gtgttcctta agatcacaaa aatgtaaaat attttctttt tatactgaac acatgcatag 152400
acaacttacc tgagcaagct gctttttgga gacatttgca catcttttgg gatcacgttg 152460
ttaagaagta gaactaaggg aaaaacacgc agccacccag aaatcggtag agccttcagc 152520
tcatctgtta ttaatatttc tgtgacaaca gatatctagg aagtaaacag gaaattgcat 152580
cgctatcctg catcaccttt tttggaatca ggttccattc ttctcagtcc agttcaacct 152640
tgtgatactt tttagatctc aaccaaggca tagaaatata ttttcccttg cttaataccc 152700
catggaacca atgcccctgt ggttgaagta aaaattgatt gttgagggac atttcagccc 152760
tctagcagtc aacaattaaa aacatgtaag caccgagcac ctgcagaaaa cttggactgg 152820
catttggatc taagaagaaa atctgcatct tgaccaagat gaaaagtcac cagcccaagc 152880
ttgtgcagtg aagtgtcatg ttggccacaa tgaaactgaa agagactgat gactctcctc 152940
agggtggaaa atgaggcatg gaagctttga ttagtgagct gttaggcaca cagacattaa 153000
tttcaaagca ttctcatctc cagtctgagt aataatgctt atagtattat gcaattgttt 153060
ggctgctgca agaaattcag cagactccaa caagtagtct ttcttggtct ctgagtgact 153120
gtaacttaaa ttctacctcc cttctcttct cctacatctt ctcactcccc accccacccc 153180
cacatacaca caattcttgt ccactatgtt cagagagatg cacgcacaca tatatatgta 153240
tatatatagt atatttgtca ataaagcaga aaagaagaaa aaactccaag taaacaattt 153300
tccatttccc catctcactt ctgtcttaca agtggatagg aaaagaaaaa cccccagtaa 153360
aaaatggcaa ccgcccacct ccccaacttt acatgctgct tcctatgtta gaggatctgt 153420
cttaggcatc tgattatgga gcctgctaga tacaagcccg tatttagact gctacagtca 153480
acaatgtctc tctttcatac tagaaaaatt ccgggttggc aattgcaagc atctcaaaat 153540
gaccagaccc tgaagaaagg ctgacttgcc tcattcaaaa tgagggctct agagggctct 153600
agtggatagt ctggagaaac ctggcgtctg aggcttagga gcttaggttt ttgctcctca 153660
acacagactt tgacgttggg gttgggggct actctcttga ttgctgactc cctccagcgg 153720
gaccaatagt gttttcctac ctcacaggga tgttgtgagg acgggctgta gaagtaatag 153780
tggttaccat tcatgtagtt gtgagtatca tgattattgt ttcctgtaat gtggcttggc 153840
attggcaaag tgctttttga ttgttcttga tcacatatga tgggggccag gcactgactc 153900
aggcggatgc agtgaagctc tggctcagtc gcttgctttt cgtggtgtgc tgccaggaag 153960
aaactttgct gatgggactc aaggtgtcac cttggacaag aagcaactgt gtctgtctga 154020
ggttcctgtg gccatcttta tttgtgtatt aggcaattcg tatttccccc ttaggttcta 154080
gccttctgga tcccagccag tgacctagat cttagcctca ggccctgtca ctgagctgaa 154140
ggtagtagct gatccacaga agttcagtaa acaaggacca gatttctgct tctccaggag 154200 aagaagccag ccaacccctc tcttcaaaca cactgagaga ctacagtccg actttccctc 154260 ttacatctag ccttactgta gccacactcc ttgattgctc tctcacatca catgcttctc 154320 ttcatcagtt gtaagcctct cattcttctc ccaagccaga ctcaaatatt gtattgatgt 154380 caaagaagaa tcacttagag tttggaatat cttgttctct ctctgctcca tagcttccat 154440 attgacacca gtttctttct agtggagaag tggagtctgt gaagccaggg aaacacacat 154500 gtgagagtca gaaggactct ccctgacttg cctggggcct gtctttccca ccttctccag 154560 tctgtctaaa cacacacaca cacacacaca cacacacaca cacgctctct ctctctctcc 154620 ccccccaaca cacacacact ctctctctct ctcacacaca cacacataca cacacacttc 154680 tttctctttc ccctgactca gcaacattct ggagaaaagc caaggaagga cttcaggagg 154740 ggagtttccc ccttctcagg gcagaatttt aatctccaga ccaacaagaa gttccctaat 154800 gtggattgaa aggctaatga ggtttatttt taactacttt ctatttgttt gaatgttgca 154860 tatttctact agtgaaattt tcccttaata aagccattaa tacaccaatc gtattttctt 154920 atttacaaca gactgagaga attaatgctg ttaacattgg atctttttc tttttttttt 154980 ttccttttt ttctctctcg tttgctttcc aggtcatgct gacctgttca gcttggactg 155040 tttcacattt gtttttaatg tcagtttaaa tgtaattgta aaagcatgta tgctctaaaa 155100 tcatgtagtt actttttca gtggaaaagc ctggtattcg aaagcatttc caggctctgc 155160 aatttcatat gagcaggttt ttggtaaaat cttttgtccc tcactcaggg tggtatctgg 155220 acagtgagcc cctttcttct ggctcagtag tcagagagag gagacttgga gacagtttct 155280 gctggatcct gtgctttggc aaggatgtgc agcattgcat atcattctat cattaattat 155340 gtttactcct ccatgaacta aaaaccatta gactaaatag tccaacataa accttgaaag 155400 ataaaatttg atattctttt gcctggccat ttctctgacc cagaattggg gctgggaggg 155460 gattggagac ttgggggaaa gaatcaagga gccttcttgc ctgggggaat ttggcatgca 155520 cttattaatc ccatttggtt gcactcccta ctaatccctc actccatacc tgccaaggat 155580 tggctctgct ccctgcttct catccctgtc ctagttcttc ctcacctatc tccatttccc 155640 actactgatc cttctctcca gtaagatgct attcaacccg atgaaatata aagagtagca 155700 ccaccctgga agtcaggata ccttagtttt agctcctgct ctaccattat ctagctgtgt 155760 gacctggggc atgacttaac ctttgctctt cagtctgaac agtctttaag aattggtttg 155820 gaggaggaag gaagggatag acaagatcca aggcctttga actctttttt ggaaatgggt 155880 ccttttcttc aaacaaaatt tgatgcagag tcccaaattt acctacagaa taaaatactg 155940 ctgttcttgt ttgaaaggaa gtggggtgct tggagccaca tgctcaggcc cactttgccc 156000 cctctcagga accctcgaaa aaacttatag gacttatagg actgttgggg atctgccaag 156060 tctctcttat gttacatttc agtccttgtg aaactctata tgtttcatca gttcactttt 156120 tcagaaagtt cacctgcttg gggtaaaggt catgaagtgg agaatgtggg gctcagtaac 156180 tagcaatagt aaaaaacatc attgattggc ttgcagaatt tactctgttc taagcatctt 156240 acacacatac tcatccgaaa actcacaaca accttgtgag gtagatctgt tattatctta 156300 agattctgaa acctgccagc atgactctca atctttgact tgagaccagt tgcccaacat 156360 ggaaggttat acttttcaca gtttaccacc ataagcagtc tttcagagtg atttctagct 156420 agagatccat tcttagaaaa agtcagaacc tgcccattag catacactgt cacatggtgc 156480 agagtacctt cactgggttc atctcatttc ctcctaaaaa tagtcctatg cagtagtcca 156540 gtcatatcat caccattata tagatgagaa aaactgaggt gtaggagaaa tcaagagatc 156600 tgttcaaggt cacacattcc ataagactct gaataccacc atcaagaata ataaaccttt 156660
tatgtgaaaa gcattttaga acttcagtgt cattattgca ttctgcctcc tggagttcag 156720
tgcacttttt caccatgctt taatcttgga gtcctggtgg tacagaatct gccttctact 156780
ctcagacaac accacagtgt ctttatccct cataacaaac ttatgaatta agtaatgata 156840
ttatccccat tttacaaatt agttaactga gataccaaga ggctaagtct tgcccaaagt 156900
cacacagcta gtcagtgata gagccggagt tacaaatgag gcatcctgac tccagaatat 156960
ttgctcttaa ctactactct ttatacatat gtaaggaaac taaaagcaaa agagggaaag 157020
atgtccctga ggccccacag tgagctcccc tgactcacaa tccagtattc ctctgacctt 157080
ctaatcctaa agttatacag taaggtccct tgactctaat cctagtagat ggaaagatgg 157140
ctggcatgat ttaagccaga ggccacaaac tggcttcccc agagccagaa ttcacctgca 157200
gaattctgtt tgtccagcac agtgtttgtt tagaaaattg acgtagactg cccctaggca 157260
gggcatcaat cactgtcatt gtccccagcc ctccttattt atgtttgcca ggctttttta 157320
ctcatttatg tgtctgcctg acttgtgaag gtatttgagt ttatgacttt tagatttaag 157380
cattgcaata tataagcact gcacacatgc attcacaaaa gtatagccta gtctagcttc 157440
acaaagaatt tgtagcccta caccaaacac acctttatgt ttacttagtg tttagaatta 157500
gatttaagat cagaatttag tttcacaggc attcatgtgt ggaagaacct cagttattgt 157560
tttttgtttc atactgtctc acccttgctt tccctgctgt gtctggaccc ctgtcaatcc 157620
tgctttctgc cattcttcat gcctgagtta gggcccctgc aagccattca ctggttaatc 157680
tttaggaatg aatggagagt gaaaaccagt ttggagggtt cactgtgtcc caagcatcct 157740
ctcatttagt tctcataagt gtcctaagag acaggtagca gcacattcgt tttataaatg 157800
aggaaactaa atctcagaga agctgaacaa agacctcaaa gtcattaagg tagtaattaa 157860
cggagccggg atttgaacgc aagactgttg gactccagag cctattcttt tgccctacac 157920
cacagttcct tacaaggaag atgtattcat tttctattac tgcataacac attgccacaa 157980
atttagcagc ttcaaacatt tatcagctca ctgttttgta agtcagaagt ctggcacagc 158040
atggctagat tctcagttca gggtctctga aggatgaaac tgatgtgttt accaggatgc 158100
attctaatct gaagctcagg gttctcttcc aagctcatgt aattattgca ggattcagtt 158160
atttgtggtt gtaggactaa ggctccctct tcctttctgg ctaccagcca agggccattc 158220
tcagctcttg gaggctgccc tctttcctta tcatgtggac cccaacgcct tcaaagccaa 158280
caacagagac tcttccttgt gttgaatgtt tctcactcta cggatgtctt tcctggagga 158340
tcccagtccc gtaagggctc acctgatgag gtcaggtaca tcaagaatag ccacccttca 158400
aattcaactg aattagcacc ttcattacat ctacctagcc tttttacaac agcatctagg 158460
ttagtgcttg actgaatgac tggaaactaa ggtctcagaa tctcggggac cgtcttagaa 158520
gtcagcctac tacagatgtt gattcttttc atgtgtcaaa tttcatagtg agatagggag 158580
aacagaaaca tcacatcctt gaccttaggt aaagggattc aaacttccta agactttgga 158640
aacttcacgc cactttcacc ttttccttaa tcatggttga gaaggcctat atcttggagt 158700
ggccaggagt gagactggaa cagtacctaa aggttaagga cgctaaagaa gttacagatt 158760
ggttacatct gctcctccct aggaatgatc catggaacct gatttgaaat ttttttctct 158820
ggtgctatag atagctccca caggggtcta atgccccagg gctgaaaagt tagttcccca 158880
taggatccat ccaggcatga tatcaggcca ggtgttacaa tctcctaaag aggaggtatg 158940 gactggaaag ccccttgcca atggcccttt cttgtcactg ctctgaccca agactaacag 159000 ggcagagata gtgaactcac atactattaa aactatccac ttatacttcc ccctttctct 159060 ttgctttatc actccattta agtaaaccaa tgagtctctg ccttgacaca gtggcaagct 159120 gacctgtatc ttatatgaaa gaattagatt tgactctggg gctcaggtgc agagggcagg 159180 aggggcataa ggatggcctt catggaagaa aagaagtcct tggatactga gtaacagctg 159240 agactagcaa gcctcattgt ccaggattcc aagtcgtcta gcaacatcct ggtctctgct 159300 gcagacagaa cagaggatcc cccggcagaa tgaatggagt ctgatttcaa ttacgttcag 159360 tatagtcact ctctttaggc agagaagcca gaacacctgg tgcagctagg gccactgtgg 159420 tcacagggac aagcacacta cctgggtcct ggaggcaagt gggaatgcag tttttcttcc 159480 ttaagcagat gccatatagg cctggggagg aggatgtgag aataccagcc aagttctcat 159540 tggcactata cagagaaagg ggaattattt catcttgatg gattctcccc acagtctctg 159600 cacatattga tcttacttgt aatgagtttg cttaggttca cgagtcatca tcccagggag 159660 atctgagtca ttggtgggaa agtcgaggcg acagattata tctcactgat ctcactgtca 159720 ccaattgctc tgtgtgtccc tccacctttt gaaaaagtcc atggattcat ttgtgtgtaa 159780 ttcatttgga tttatttctt ctttatcaat agctttagtg gggtattgca aatgggaaag 159840 ttgccccaga gaacagtgta cattcacagc attattcagt agaactttct gagatgatga 159900 aaatcttcta tatcttatgt tgtacaatat aatacagcca ctaactacat gtagcttttg 159960 aacactggaa atgtggcagg tgagactgag ggattatatt tttaattttt taatgttgta 160020 attaatttaa ttttttaaaa tttttgcttt ctattttata gtttaataat taaactaaac 160080 ttacgtagcc cacatgtggc tagttggcta ctatactgga cagtacaagt ctagaaggat 160140 ctcagagaga cacatgctga gatacagcag gaataagtca aaaagagagc caatgtaaca 160200 tagggaattc tggattggga attagagccc tggctctaat ctcagctctg ccactaggtg 160260 accttgccct ctctggcttc agcctcccca tctttgactt gaaaggttaa actaactaac 160320 gtcgaaagtc ccaaaatggt ggctatggac tgaattcaat tttgggatac acaagtttca 160380 ggaatttttt aaaaatctat taatgccttc taggtgtgtg tatgcacgct tgcagacatg 160440 tgcccatgca caagcatggg aaggcagtaa ggcattcatt tcaattcacc agtgtactaa 160500 ccattcacac acacacacac acacacacac acacacacac atgcacacac accctactgt 160560 attgcctatg tagagcctga agatctttta atctgtcacc attggataag ataatttcta 160620 aggacccttc ctgttttgtc atgctgaaaa tctttaagcc actatagtgt cccaaatcta 160680 ttccagtttg ggcagatgac tggagtattc tcatagcctc ctgtctattc ccttctggat 160740 ttgatactag ttatgaagtt tggagtcaag ggtgaagaag ggaggcaggg atgatataac 160800 cccagcccca ctcctcaact ctgcttttga gttagaagta gggttcaggg cttcagattc 160860 cttggggagg cagtagagag aatatgggct ttataatcag aagatgaggt tcagatgatt 160920 gggttctcac ctttttata gctgtgttac ctcagtttat tcatttgtaa aatagggata 160980 agaaatatct ttaacctcct aagatcatgt ggaattaagt gatgtaatgt gatgaagcga 161040 ggcacgcaga aggccctgaa aaaattagta gttaccctta aggggactaa atggtctggc 161100 aactcccgag ctcaaagcta gaaaggtcca gtaatgggga agatggggtc tttctgtagg 161160 aactgtagca ggggagcaga tcctgtaggc caccagtctg tggagctgtg tccaagaact 161220 catgtttgca ataagcccac caaatgacaa gttattgtgg ggttcaggcc tctaactcaa 161280 gaagatggtc ttggcccaga tcataccttg cagcctgtgc ctttggtggg atgtgggtgt 161340 tggcagtggc tatgcatatc tccttattac tggctgtgcc aaagccccgc agaaatgatt 161400
gttggacaaa gtcatcttgc actcagggct ggttttccag gcttccttgt tattttcccc 161460
tgagttcttc tgtgttcctc ttgcaacacc aaccccacta ttttcctctt ccctacccta 161520
gttgttggtc caaacatgta atccattctt gcagtgattt attgggtgac accatgactg 161580
gagtttgcat tgaaggactt ctttttctaa ttagaactaa aagtcagttc caggctgggt 161640
gtggtggctc acgcctataa tcccagcact ttgggaggcc gagatgggag gattgcttaa 161700
ggccaggagt ttgagtccag cctggacaac atagtgagat cccatctcta caaaaaatgt 161760
taaccaggag tggtagtgta caactctggt cccagctact tgggagactg aggagggaga 161820
attgcttgag cccaggaagt tgaggctaca gtgagctttg atcgtgccac tgctctccag 161880
ctgggtgaca gaggaagatc ctccttcaaa aaataaataa aaactaaaaa aaaagtcagt 161940
tccaggttgt atctttttc acaggggcca gacacagatg agagcaggtt ttgttgtatt 162000
tatccattta aattgagcaa taaaattctc tctttggttt ctacctttct tatttattat 162060
tattatgtta aagggattaa agtggttcat ggtctttctc agtgcaactg cttatgctag 162120
acctcagaat tatgaccttt tcaattattt atatttctgt ctatataaat actggaaaaa 162180
atagtacaaa gtaagcatcg gaatgcctaa ggacctctaa attgtgtgtg tgagcacatg 162240
gggaagatgg ttcttaaggt ttgagttttg gattattgtg gttgtcttaa ataatgttat 162300
ttctatcatt ctttccaatg actgtctcct agcatagttc ccattttaca gactgatggc 162360
agaggcagaa agattctctc acttctttga tactattgag gacttcagcc tttcaccgct 162420
cttctcccct ttgctaaaaa agaaaaaaat caatatgtat gttacagtgc atttttttaa 162480
atatttttta ttatacttta agttctaggg tacgtgtgca caacttgcag gtttgttaca 162540
tatgtataca tgtgccaagt tggtgtgctg cacccattaa ctccttattt acattaagta 162600
tatctcctaa tgctatccct ccacccttcc ccaaccccac aacaggcccc agtgtgtgat 162660
gttccccttc ctgtgtccag gtgttctcat tgttcaattc ccacctgtga gtgagaacat 162720
gcagtgtttg gctttttgtc cttgagatag tttgctgaga atgatggttt ccagcttcat 162780
ccatgtccct acaaaggaca tgaactcatc atttttatg gctgcatagt attccatggt 162840
gtatatatgc cacattttct taatccagtc tatcattgat ggacatttgg gttggttcca 162900
aggctttgct attgtgaata gtgccacaat aaacatatgt gtgcatgtac ctttagagca 162960
gcatgacata taatcctttg ggtatatacc caataatggg atggctgggt gcaatggtat 163020
ttctagttct agatccctga ggaatcacca cactgacttc cacaatggtt gaactagttt 163080
acagtcccac caacagtgta aaagtgttcc tatttctcca catcctttcc agcacctgtt 163140
gtttcctgac tttttaatga tcgccattct aactggtgtg agatggtatc tcattgtggt 163200
tttgatttgc atttctctga tggccagtga tgatgagcat tttttcatgt gtctgttggc 163260
tgcataaatg tctttttttg agaagtatct gttaatatcc tctgcccact ttttgatggg 163320
gttgtttgtt tttttcttgt aaatttgttt gagttctttg tagattctgg gtatttgccc 163380
tttgtcagat gagtagatgg aaaaaatttt ctcccattct gtaggttgcc tgttcactct 163440
gatggtagtt tcttttgctg tgtagaagct ctttagttta attagatccc atttgtcaat 163500
tttggctttt gttgccattg cttttggtgt tttagacatg aagtccttgc cggtgcctat 163560
gtcatgaatg gtattgccta ggttttcttc tagggtttta tggttttagg tctaacattt 163620
aagtcttgaa tccatcttga attaattttt ctataaggtg taaggaaggg atccagtttc 163680 agctttctac atatggctaa ccagttttca cagcaccatt tgttaaatag ggaatctttt 163740
cccaatttct tgtttttgtc aggtttgtca aagatcagat ggttgtagat acgcagcatt 163800
atttctgagg gctctgttct gttccattga tctatatctc tgttttggta ccagtatcat 163860
gctgttttgg ttactgtagc cttgtagtat agtttgaagt caggtagcgt gatacctcca 163920
gctttgttct tttggcttag gattgtcttg gcaatgcagg ctctttttg gttccatatg 163980
aactttaaag tagttttctc caattctgtg gagaaagtca ttgatagctt gatggggatg 164040
gcattgaatc tatgaattac cttgggcagt atggccattt tcacgatatt gattcttcct 164100
acccatgagc atggaatgtt cttccatttc tttgtatcct cttttatttc attgagcagt 164160
ggtttgtagt tctccttgaa gaggtccttc acgtcccttg taagttggat tcctaggtat 164220
tttattctct tagaagcagt tgtgaatggg agttcactca tgatttggct tctgtttgtg 164280
tgttattggt gtataagaat gcttgtgatt tttgcacatt gattttgtat cctgagactt 164340
tgctgaagtt gcttatcagc ttaaggagat tttgggctga gacaatgggg ttttctagat 164400
atacaatcat gtcatcggca aacagggaca atttgacttc ctcttttcct aattgaatac 164460
cctttatttc tttctgctgc ctgattgtcc tagccagaac ttccaacact atgttgaata 164520
ggaatggtga gagagggcat ccctgtcttg tgccagtttt caaagggagt gcttccagtt 164580
tttgcctatt cagtatgata ttggctgtgg gtttgtcata aatagctctt attattttga 164640
gatacgtccc atcaatacct aatttattga gagtttttag catgaagggc tgttgaattt 164700
tgtcaaaggc cttttctgca tctattgaga taatcatgtg gtttttgtct ttggttctgt 164760
ttgtatgctc aattacattt attgatttgc atatgtggaa ccagtcttgc atcccaggga 164820
tgaagcccac ttgatcatgg tggataagct ttttgatgtg ctgctggatt cagtttgcca 164880
gtattgtatt gaggtttttt gcatcgatat tcatcaggga tattggtgta aaattctctt 164940
tttttgttgt gtctctgcca ggctttggta tcaggatgat gctggcctca taaaatgagt 165000
tagggaggat tccctctttt tctagtgatt ggaatggttt cagaaggaat ggtaccagct 165060
cctccttgta cctctggtag aattcagctg tgaaatccat ctagtcctgg actttttttg 165120
gctggtaagc tattaattat tgcctcaatt tcagaacctg ttattggtct attaagagat 165180
tcaacttcct cctagtttag tcttgggagg gtgtatgtgt cgaggaattt atccatttct 165240
tctagatttt ctagtttatt tgcatagagg tatttatagt attctctgat ggtagtttgt 165300
atttctgtgg gatcggtggt gatctcccct ttatcatttt ttattgcatc tatttgattt 165360
ttctctcttt tcttctttat tagtcttgcc agcagtctat caattttgtt gatcttttca 165420
aaaaaccagc tcctggattc attgattttt tgaagggttt cccatgtctc tatctccttc 165480
agttcttctc tgatcttggt tatttcttgc cttctgctag cttttgaatg tgtttgctct 165540
tccttctcta gttcttttaa ttgtgatgtt agggtgtcaa ttttagatct ttcctgcttt 165600
ctcttgtggg aatttggtgc tataaatttc cctctacaca ctactttaaa tgtgtcccag 165660
agattctggt atgttgtgtc tttgttctca ttggtttcaa ggaacatctt tatttctgcc 165720
ttcatttcat tatgtaccca gtagtcattc aggagcaggt tgttcagttt ccatgtagta 165780
gagtggtttt gagtgagttt cttaatcctg agttccagtt tgattgcact gtggtctgag 165840
agacagtttg ttataatttc tgttctttta catttgctga ggagtgtttt acttccaact 165900
cagtggtcaa ttttggaata ggtgtggtgt ggtgctgaga agaatgtata ttctgttgat 165960
ttggggtgga gagttctgta taagtctatt aggtccactt ggtacagagc tgagttcaat 166020
tcctggatat cctttgtgtc ttgttgatct gtctaatgtt gacagtgggg tgttaaagtc 166080

```
tcccttgatt attgtgtggg agtctaagtc tctttgtagg tctctaagta atcactttat 166140
gaatctggtt gttcctgtat tggtgcatat atatttagga tagttagttc ttcttgttga 166200
actgatccct ttaccattat gtaatggcct tctttgtctc ttttgatctt tgttggttta 166260
aagtctgttt tatcagagac tagcattgca atccctgcct cttttggttt tccatttgct 166320
tggtagatct tcctccatcc ctttgttttg agcctatatg tgtctctgca catgagatgg 166380
gtttcctgaa tacagcacac tgatgggtct tgactcttta tccaatttgc cagtctgtgt 166440
cttttaattg gagcatttag gttaatattt acgtttaagg ttaatattgt tatatgtgaa 166500
tttgatcctg tcattgtgat gttagctggt tcttttgctc gttggttgat gcagtttctt 166560
cctagcctcg atggtcttta caatttggca tgtttttgca gtggctggta ccggttgttc 166620
ctttccatgt ttagtgcttc cttcaggagc tcctgtagtg caggcctggt ggtgacaaaa 166680
tctctcagca tttgcttgtt tttaaagtat tttatttctc cttcacttat gaagcttagt 166740
ttggctggat atgaaattct gggttgaaaa ttcttttctt taagaatgat gaatattggc 166800
ccccactctc ttctggcttg tagagtttct gccaagaaat ccactgttag tctgatggct 166860
tccctttgtg ggtaacccga cctttctctc tggctgccct taacattgta tccttcattt 166920
caactttggc gaatctgata attatgtgtc ttggagttgc tcttctcgag gagtatcttt 166980
gtggcgttct ctgtatttcc tgaatgtgaa tgttggcctg tcttgctagg ttgggtaagt 167040
tctcctgggg aatatcctgc agagtgtttt ccaacttggt tccattctcc ctgtcacttt 167100
caggtacacc aatcagatgt agatttggtc ttttcacata gtcccatatt tcttggaggc 167160
tttgttcgtt tctttttact cttttttct ctaaacttct cttctcgctt catttcattc 167220
atttgatctt caatcactga tacccttttt tccagttgat cgaatcagct actgaagctt 167280
gtgcattcgt catatagttc tcgtgccatg gttttcagct ccatcaggtc atttaaggcc 167340
gtctctacat tgattattct agttagccat tcgtctaatc ttttttcaag gtttttaact 167400
tctttgcgat gggttcaaac ttcctccttt agcttggaga aatttggtca tctgaagcct 167460
tctctcaact catcaaagtc attctccgtc caggtttgtt ctgttgctgg tgaggagctg 167520
tgttcctttg gaggagaaga ggggctctga tttttagaat gtttcagttt ttctgctctg 167580
ttttttcccc atctttgtgg ttttatctac ctttggtctt tgatgatggt gacatacaga 167640
tgggattttg gtgtggatgt cctttctgtt tgttagtttt ccttctaaca gtcaggaccc 167700
tcagctgcag gtctgttgga gtttgctgga ggtccactct agaccctgtt tgcctgggtg 167760
tcggcagcag aggctcagaa cagcgaatat tgctgaacag caaatgttgc tgcctactca 167820
ttcttctgga agtttcgtct cagaggggta cctagccatg tgaggtatca gtctgcccct 167880
actggtgggt gtctcccagt taggctactc gggggtcagg gagccacttg aggaggcagt 167940
ctgtccgttc tcagatctcc agctgtgtgc tgggagaacc actactctct tcaaagctgt 168000
cagacaggga catttaagtc tgcagaggtt tctgctgcct tttgttcggc tatgccctgc 168060
ccccagaggt ggagtctaca gaggcatgca ggcctccttg agttgcggta ggctccaccc 168120
agttcgagct tcccagctgc tttgtttacc tactcaagcc tcagcaatgg cgggtgcccc 168180
tcccccagcc tcactgctgc cttgcagttc gatttcagac tgctctgcta gcagtgagcg 168240
atgctccatg ggcgtgggac cctccgagcc aggtgtggga tataatctcc tggtgtgccg 168300
tttgctaaga ccattggaaa agtgcagtat tagggtggga gtgacccaat tttccaggtg 168360
ccatctgtca cagctttgct tggctaggaa agggaatttc ctgacccttt gcacttcccg 168420
```

ggtgaggcga tgcctctccc tgctttggct cacacttggt gcactgcacc cactgtcctg 168480 tacccactgt ccaacaagcc ccagtgagat gaacccggta cctcagtcgg aaatgcagaa 168540 atcactcatc ttctgcgtca ctcacgctgg gagctgtaga ctggagctgt tcctattcgg 168600 ccatcttatg aatcatgcat gttcaactat gagcaactat gtgtattcaa tgggaaatgg 168660 aataccataa aattgtcata tgttgagccc aaaatgatag gatagaattt gatagtctga 168720 ggatggaaag gaccttcaag gccactttta aaaaccccat tcccatatga tgcttgaatt 168780 cttaaccact gtgtgtctag tattttctca tttccagtga tatgtgtgcc tgccaacctt 168840 tccgtctcca agagctttaa ctatcaaaat gtatgtgtgt gtgtttttgt gtgtgcatgt 168900 gtgtgtgagt gtgcgtgtgt gtgtgtgtgt gtttagagag agagagagag acagaaagag 168960 aaggagagac taaaatccaa ttcactgttc tttctgggac ccaaagaaca agtctagtca 169020 ttctccattt ctagtctctt tccctagcaa tcggctagac atgctagaca tagacacatg 169080 tacatcactc ctttgaatta caacattcag tatttgtcta tcacttatat gataaaatac 169140 aaacttagct tttattttta tttttttaga gacagtgttt tactatgtca cccaggctag 169200 agcatcagtg gcacaatcat agcccactgc agcctggaac ccctgggctc aaggaatcct 169260 tccacctctg cctcctgagt agcagagact acagatgtgc accaccagac ccagctaatt 169320 tggtttttta ctatttttg tggagatggt gtattgtctt gtggtgttgc tcaggctgat 169380 cttgagctcc tggcctcaag cactcctccc atctcagcct cccaaaatgc tgggattaca 169440 ggcatgaacc accttaccca gccaaatttc ttaatatgat atacatgctc ctttaaaatc 169500 aagcaccatc tttgctttca acctcattat taaccacttt cccatatatg caacatatgt 169560 ttcagccata ctagtgtcta gtttttccct gaacactcct tggtgctttt gtttatgccc 169620 tttctgccca cctttgcctg gtgaaatcct catcaatctt caaattctat caaatactat 169680 cttccatata aagcattttc taaacccacc tatgtaaaaa gattagtgtt ttcctatttt 169740 gttgatgcct ccattgcagc attttccagt ccaacgtttt ctagaattga ttgtggccag 169800 gctaccagac tgggccaggg cctgtgtctt ttctgtcacc cagaagcaaa ggtctaacaa 169860 tggatatctg ctgaatgaat gaacgaaaat gaatcattaa tatattagta aatacgttaa 169920 ttaaagttcc aggtatgaat actgaaggct gcattcaggc agagctggat ccaaggatat 169980 gctaggttgg tctagcacaa gaatcagagt tttcctctgc aagctatgaa aaatttgggt 170040 ttagcaggta tttgggatga tgaattatac atttaaccag tgttgaatga gcacttgtcc 170100 ttaaggagtt tagagtctgt gaccagggag aatggtgatt ttcttagcta gggcagtttt 170160 tctaaaaagg tagttgcatt gtgtgttttt gaccactgat gataaattca agtctctctt 170220 ccttcccaat agcccggaag ctgaagaaac ttggtaatct gaaactacag gaggaaggag 170280 aggcttccag caccaccagc cccactgagg agacaaccca gaagctgaca gtgtcacaca 170340 ttgaaggcta tgaatgtcag cccatctttc tgaatgtcct ggaagccatt gagccaggtg 170400 tagtgtgtgc tggacacgac aacaaccagc ccgactcctt tgcagccttg ctctctagcc 170460 tcaatgaact gggagagaga cagcttgtac acgtggtcaa gtgggccaag gccttgcctg 170520 gtaaggaaaa gggaagtggg agcatgagat aagggggatc atatttagtg aacgctccta 170580 tggaccagcc accatgtctg gtgcttttct gcccattaac tcaggcagtc ttcatcataa 170640 ccctgtggga gagggattgt tacaagtctc aatttaaaca tacagggatc gaaactcaga 170700 aagcaaagag aaagatagta ttatcgggtg tcttatgtgg cccacattga tgcacagcag 170760 tcatgctttc atattcaact cacaaaaatg gtcagcaaat tttccattaa tcacaaatca 170820

```
catagacata cccatatatg ccttaggatg ctcttctata tttgcacaca caggctcacc 170880
ccaaagataa tctctagttt gactgacatt ctgtcttcaa tgtcatcttt aggagctata 170940
tcatgggaac tctcataata tggtatggtg gaaagaacat gaggttggga atcagaacac 171000
ttcgggtctg ctcttagctc tgctagtaac ttattgtgtg atcccttccc cttctgggtc 171060
tcaatttctc tatctgtata atgtataaag cgtggtttgt atcaaattga tggtttccag 171120
tttttgaaaa aaggaacgct ttttgcacct taaactacct aaggaatcat aatgagagga 171180
aagattaggt aatagtgaaa gaattaccaa gtgttggtct aacagaagtt ggataacaga 171240
agttcctcag tgatggggaa ctcacttctt tcttatgtca tctgttgttt aaacaagtct 171300
ggttattaaa atattacagc ttaaggaatt cttagagatc ctctatccaa tgattcacaa 171360
actttccttt agcagccaag tgctttattt ctcaaaagaa ttgtacacag atacaagtgg 171420
agctagttta tttaaagcca gagcctgtag cttgggcctc accagttcag cctctttctc 171480
tctatcccag ggaagcccta ggtcactctt gcaaaatctt agggctccaa ggaacacagt 171540
ttgaaaacca gtgaagtata tgccctttaa aggttctcct aatcctgcaa ttatgattca 171600
aagattcttt tgaaataaca acaaccaaac cttctcttgt ggagtcaaag attaacctgc 171660
ctttcaataa taactgccat tcaggtagaa atttatagtg aacagagcaa ttttgtatgt 171720
attacctgaa ttgattctta taggaatcct ataacatgag attctttctc ttattttaca 171780
gaccaaatag ggaagctgtg agaatgatgt gattggccta tagttacata gtcagaaaat 171840
agcaggacca gaacttgagc ccaggttctc tcctgattcc aaattctctc tattccactc 171900
cacctgtagg ctgtagcacc actgcagttc tgtagctctg ggctttacag tgaggggcca 171960
aggcttcatt gaaggccact tgggtcatag tatgggcttg ttgcatttga agacatttca 172020
tgttggctgt caagtcttag atttgtattt ccaactcaca gggcctggtc acagccctaa 172080
ccatctctta taccttctca gcttgggaag ctgaggtcga ctagccaata agaacactgg 172140
gaaggaaacc caaggactct gactggatat gctctgtgcc aaaacagagg gttcactcag 172200
agaggaaaaa tataaaaaag aaaaaggaga aggttgcttt aattcttatc actttttcat 172260
ctggatattt tgatatcatg tgtttgacag agattcaaag tttaatcttc ccaagcagtt 172320
tccaaacact tatctcattt tataggctac agagcttttt catatatatg atcccactta 172380
atctttacaa caattctatg aatcatagag actattattt ccatttcaca tgccaaggct 172440
caaagaggtt aactaacttg ctccatttgg tcacttaaca catggaacca gaacttgacc 172500
tagaccttcg ggtttctaaa ttggttatct tgacaataac ctagtgcaaa acactatagc 172560
agaatttgta tgacttggga tcactggggc tttccttggc ccaaccacca agatggaaag 172620
ccccctcccc ttacattaac aaatctgcaa gccaatatca gttcaccatc tagcttgcca 172680
gactaaatga tttctgaccc caagtctttt aaaagaatag cttcaaaaga aagccaatta 172740
ccacattcac aagaactgtt cttcatatta tctataatta cctacaagta caagtaattt 172800
gctaattcaa tagattgagt tcttgacctg taagatgaac tgtgctaggc ccctaataag 172860
ataaattttg ttttaagttt tctgtgacag taaagatgta tgaaaattgc ctagtagagt 172920
acctggcaca ttaataaatg ataactgtta atttggagtg ggtgagtaga ctgggtgtgc 172980
acagtatatt tagaatcaaa tttatctggt ttggaatcct agctatggac tagttctgtg 173040
accttgagca aatcacatgt cttctctgtg cttctgtgtc ctcatttgta agatgataga 173100
ataatcacta cctttcaaat tgttgtcaac aaaaagatta tgtataaaga gcacctagta 173160
```

acgtagcctg aaacatagtc aatgctctgt aaatggtggt ttattattat gagacttgaa 173220 tgctaagcca ctgctttcac gaaactcaat tttagctacc acttgccttg cctagaagct 173280 catgcatgga ccccaaggtg aaattgtgtt ctctgaagac ctcggctggc agatgtacta 173340 cagcagcaaa gatttccaaa ctggcctttc tttgagccca ttctcccaga ctagacagga 173400 gactacaagt ttctgctgca catgaaaaaa atatgatgtc aatcggattc tagtgagaaa 173460 acagagtctc aaagaaactg cttctgctcc ctagcgtgtt taatgtgttt cagaacctga 173520 gaatgactcc tctctgtttc tccagaacag cctaacacag tggcaaatgg gtgttgagtg 173580 aatgcatact taaggaaatc tgtagggttg cagctactct ttcctcaagt aatcccttga 173640 tagtcatgta ggctacttca gagattgggc attagagaac agagtcaggt attataatca 173700 gattagactc tagggaggtt agccagccat attgctgata tgtgcacagt tactgggttt 173760 gagtgctaag cagctctcat taaggacggt taattaatat tatggccaaa ttaagctttc 173820 ccttttctct cctctttgtt agttcggtgg cattttaggg agaaaaaaat aagcatcagt 173880 atggacaatt tgcttgatac ctgtacaatt taattctcat ccttccatgt gccttcacat 173940 tcacacattc caccagaaga ccaaggttca ccagccaaaa gcttttcttg ctccccactg 174000 cctcctaccc aagatattca gggtcaacct cccaggcctc ttctctaaga gatccttggt 174060 tgctacatgc ttagaccctg cttcttattt cctgctgaga agggtcagtc caaggcattc 174120 tgtgctacag aagggttcca agcaggaact actctgggat ctgaggctcc agccggtctg 174180 tcagcgtgtc attacagtga aggtgggaag cacaggcctg ggagctaaga ctgctaagat 174240 gagggactct agaatccctg atacctggaa ggcctaggat ctaaaagaaa agaacaggga 174300 aatggggcta tatgagtgga cagggaccaa ccaagcagaa caatgtgtct ggataatgta 174360 gacttcagac ctgatcctat ggctgacaaa agctggtgac cttggtagtt cctgagctgt 174420 aaccttcatt agtggagtag aaaaaacact ggagaagaga atcagaacac ctgggttcta 174480 gtattagttc agccacatat aaaccatatg accttgggta agtcagttta tttctctggc 174540 cctcatgttc cttgttggta aaataagtgc cacatcacct aacctctggg attattgtga 174600 gagttaaatt aggtcatcaa caggaaagtg agaagtttga tctaaatttg gggaagcatt 174660 cctaatgagg tatgatgaca aaatttcaga taattctgga tttgttggtg agaagagaga 174720 gtgttggtag ggacgagctc tgaggtgatg cctttataac tttaagcatc caactgtttc 174780 aaaaactcca ggagaacatg gccatgtctg ttctacctgt gtattattgt agacgtagct 174840 tctgggagcc tctgctctct gagcttaagg gaggtaattt ggagatcatt taattctcat 174900 tttacaaaag gaaaaaaaat tgagggtctt taggccattt gtttaggtaa tatttcttaa 174960 gtgcccactc aaatacgtgg actgtactaa gtactaggga ggtaaagata aataagaaga 175020 tatggtccct gtcttcaaga agctccaagt cttgtggggg agacagacat gtatatacat 175080 agacttcaat gctgtgtaat gactgctata attgggtgag gctacacaag gtgcaatgag 175140 aatgtaaaag aagaatcttt aagccttctt cttggatgag ttgggaaagc cttcacagaa 175200 gaggtagcct ttgagtgaag acttgaaaga tgagtagtgt ttaccggatg aaaggcctga 175260 gaaggaggaa tgcattctag gcaaaagtaa ctgcctgtgc agagataaca gagatataga 175320 ggcatgtgag agcgcaagtg gcaagagatc agtctaggta ggcaggtcat aaagggccta 175380 ttcatgtata atgatggcag taagatgagg atggcagtag ggtgggaaat tagtagggcc 175440 agggtaccta ttgagtagaa aagaatggag aggaaatgcc aggcagaaag aggatggacg 175500 caagagaggg aacatgaaag tggtgaacag gtggcagtgg ctgtcaagac atctctccat 175560 accctgtaca ctgtatgtaa tatccatctc ccagggttgt tagaagggtc aaaccagatc 175620
gtagctggaa aacagctttg tgaagtgaaa actgctgttt atgtggggga aatgattgtt 175680
aaactgcatc tttggaaagg tgaagtgatc aagagcacag accttggaat ctgactgctt 175740
tgctttgtaa cttggtctgc caattactag ctgtatgatc ttggacaagt tccttaacct 175800
ctctctgact cacttgtact ggttcacaga atggagataa taatagtact taccttactc 175860
attgttgtga atgttaaatg agataatata agtaaagtgc ttagaaaaga gttaaatgta 175920
ccccataaat acatacaact atcatgtacc caaaattatt tttaattttt ttaaaaaaga 175980
gcaatccaat agcaaaagaa aaaaagagtt cactcatata agcagtcaat aagtgttaga 176040
ttatttttct cttacaactg acaatgccct ttttgtctcc atcatcatct catttgagca 176100
gctcagggaa gtagggagga taaggaatat tatcctcacc atatagtttg tgcttttccc 176160
caccacccct taatggccag cctggatggt ccctggggat ccttagggga tgcccgaata 176220
ccagagcatc tctgcccaac agggactcag acttagctca acccgtcagt acccagactg 176280
accactgcct ctgcctcttc ttctccaggc ttccgcaact tacacgtgga cgaccagatg 176340
gctgtcattc agtactcctg gatggggctc atggtgtttg ccatgggctg gcgatccttc 176400
accaatgtca actccaggat gctctacttc gcccctgatc tggttttcaa tgagtaagtg 176460
ctcctggggc ccagacctca ctaaaataca gcagcttggc cagacctggt tggtggtgat 176520
ggtgatgggg tgacagtgaa gcttagctca tttgatctgc agttgtcgca gcggatgccc 176580
cagccagcca atccagtatg aggcggcttt gccctggctt tcagccaact ggcaggagcc 176640
caggaggatg gtgctgagac cacccctttc acacccaaga accaatccta gtcatatttc 176700
tggtctgctt tgcagcttat ctcaaaacca catggaaaga ttcctcccct tcacatataa 176760
aagaggcaga aagactctgg ctttaagggc tggagtttct tgggttcttt tgctaccacc 176820
aaaggctact tctagtcacc atttgctgag caactagttt gtgccaagac tatgctagat 176880
actttctaaa tcctagctca ttgagtcctc atggtgacct gacctcacct ttttatagat 176940
aacactattt ttttatggat ggggaaaatc aggctcagca aaataaagtg actcacccaa 177000
agtcacagag ctagtgcctg ttggagacaa gattcaaacg tatgtccctg tcgatctcag 177060
ctcttctgcg tcatggtggt aactgatggg aaggagtacc tctaccgctc tctggctgtg 177120
tgaccttggt actgccattt tccttccctt aaacagcttt aattaatacc tgccctgcca 177180
ccagctccat ataacatcat gaatttggcc agtggctcag attttggaat tacatttttc 177240
tccactaaaa tctcagttct actattttct tagtcagcat ctttgggaaa gacctttaac 177300
ttttccgacc ctcaatttct tcatccatta atgataacag aaccttcata agtaatttct 177360
tatgataact aaatgggaat tgacagatgt ggaatgtctg gcccatagta ggcaagaagg 177420
aaaaaaaaag tccctttctg attcaccctt tccctaatag tgatacattt tttttccccg 177480
agatggggtt ttgctctgcc acccaggctg gagggcagtg gcgcaatgat ctcagcccag 177540
tgcaacctcc acctccctgg ttcaagcaat tctcctgcct cagcttcccg agtagctggg 177600
attatagatg cccgccaccg tgtccatcta atttttgtat ttttggtaga gacgggattt 177660
caccatgtta gccaggctgg tctcaaactc ctgacctcat gatctgcccg cctcagccgg 177720
gcatgataat cttttctatg tctgctgtat gaggtccctc gatggcattg tgaatggagc 177780
tggccagaga aatcttccca aggaccttga gctagtctca ccacagagaa tccttccagt 177840
caggacagga attgaccttc ccccctcttc agccctctaa cccagaagag tcttaaaata 177900 aaatctacag gccaatggtt ccttccagta cagcactgca atgcgaggga gagtgagcgt 177960 ccccagctgc cctctcccaa ccctgccagc ctggtagcca aaagctaaga ataaccacta 178020 ggcttttggc acaaactgct ttgtggtttt cagatctccg caaagttgcc tatgatgcca 178080 tcttctgggg caggccttga aaagcccccct aactgttcat ctcccatcct taaacccctg 178140 ctgcccttaa gcagttgaat caactccatg agcacctgct ctaccttccc cagagccctg 178200 agacctttgg agctttgaaa agtgataatt ggttgttctc taaatcctca tttccttctc 178260 tgcctctaag taagcatgtg gcatcccacc tcggcttcct ggtccagtct tgttcatctt 178320 ataaaaaggc ctccctacgg ggtcagaggc ctagacccat caaacccagg gctcctgaaa 178380 caataggacc cctattcctc ctgtaggaag ccactgtgtt agagctctca gggtgtctac 178440 aaacatctag ataagtgttt ctcaacatgg attctgttga catattggga aaaataattt 178500 tgtcattatg tagaatatgg ttaacatacc tggcaccagc ctactctata ccaaatagga 178560 ttccagtcat tctgacagcc caaactgctc ccacacattt ctgacaccca ctgaagaggc 178620 agtactctcc agttgagtgc aactaatccc tgccagcctt cctaaggtgc taatggggag 178680 cctcagaccc aaagagagag agaagaactt gtccaatgta ggtcaaccca tttgctgatc 178740 tcttcaacac caagctctat tatcagccct gtttttttct ttctttctct ctttgtagag 178800 atcacatgtt gtgaggataa tgagcttgaa ccttagctgt gtgaccttgg gcaaattact 178860 gaacttctat gtgccgcaaa ttttatctgg agactgctga agagtattat aatagcacct 178920 ttctatatgt catttattga acacctgcta tgtgtcaggc actgtgctca gtgttttcca 178980 atcttcattt ctcctcttat tttctctctt gcactcccac caaccttgtt ctcttcctaa 179040 attccattcc tgcctcattt ttctaccctc cattctcctc tctcttcctt cctttaactg 179100 tctccctagt atttttcccc ttttcccccct ttcttttccc cttcccccat gaatttcttc 179160 tctttccttt ccccttctct ttcctccatt ccccactttt tctgcccctg aggcctgcag 179220 caatgttaaa ggaatcctca ttccagcatt gtgatttcaa tggtaaaaag attgcagcat 179280 tgtcatcaac agaggtggga aagtacattg gagactggag cagagccaga cctcagggtc 179340 agccaatctt actaaaaaat tctctacagt gaaagagctt ggagcaacac tgttctgctc 179400 aattgatttg tgataccatc taaacacttc ctctttctag ttgggcttca gcctgagttg 179460 aataattcta caccatctgc cctcttctct ctttctccag gacagccaag atctctctga 179520 gataggatgc tgagcttcca cccagacaat accaggcctg ctcatcctat ggagtaggct 179580 agtggcttgg aaaccaaaat gtcaaaccat agcctttagg ctccatctgg gaggtctttg 179640 tcctcaccac ttaagtgggt gtcaaatttc cttccctttc tgcacacgct gcacaatcaa 179700 tttctgtctt acacacacac acacacacac acacacacac gatttttgaa gtgctgaaaa 179760 ctggaaggcc tactagcatg aggatgctgt gtcttctctt agaggtatgc catggtcagc 179820 catggaaccg agaggttgct cttccttgaa aagctggcca agcattggcc acttccccat 179880 ataatttata ggtgataatg tggtgatctg ttcagaagtg actataataa atgcaactca 179940 catatgtcta cagtttccaa actgtggtaa ggagcagcca gcatatgagg gaatgggctc 180000 cccttcagca ggggacattt aaactagaca ttcaaaaaca ctccctggca gatttaacat 180060 tggaactcgt tttgaaagaa caatgtggaa tctccttcac tgggagtttt tgaataagta 180120 tgaaatttct agtattccag gccagaggca aaggggtcaa caggatgacc aaacacttcg 180180 ggtcatttgc aaatcttgat gtcctgatgt taagagctga ctactggggc ttctcctaaa 180240 aatccttcat gttgagctgc ctggaaggca ggttctcatt ctggctgtag ctgagatgtt 180300 agaactgtag tcagggagac catgtgcctc ccccattgtg ttcatttggt taggctttcc 180360
tgtccctgac tcagaaaaca gaaggggcac agagacctgg aaattccatg tgctaaccca 180420
tatcctggcc agagaagatg agtagttatc agggtgtcag gattttggaa aacagagaga 180480
gaaaaaaaac aaacaaacag acaaacaaac aaaaaaacct tttcctggtc cctggagcac 180540
cagcaggaga aacagcaagc tcttcttgga aaacctggcg agggatggca atcagagaca 180600
ttccctctgg gcttattgta aacttcccct cattcctttt tcctctgtgt atctccttcc 180660
caggtaccgc atgcacaagt cccggatgta cagccagtgt gtccgaatga ggcacctctc 180720
tcaagagttt ggatggctcc aaatcacccc ccaggaattc ctgtgcatga aagcactgct 180780
actcttcagc attagtaagt gcctagaagt gcagggaatg ccccctgagg gcacagagat 180840
tcagagagga ccacttttgc cattaaaaca ttattaggga aaagccagct cctggacatt 180900
tcccttcttc attccccctc cccatcccca ctctactctc tctcagcatc attttcctaa 180960
caagaaacaa tttcatgact agaagccaat ttatttgcta gaagtcaacc tccatcagat 181020
tccccaccta tccccagtct gtctttggga caaggccttt ttgactggtt acagcaggtc 181080
tctgaatttt tccatagctt ctgctataga aacagacatg ggccaccttg tattctttgc 181140
agggcagtag agcaggaggc atttcctcct ggaaagattt cctcttctgc caacaggagg 181200
agatctatgt aagcaactca gataggattt gtatggcagc caaggaactt ttctttaata 181260
tcttttctaa gagccctctc ttagccccta cggagggaga agggcaaaat ttgatattca 181320
aagctatgtg ttttggttat ctaaatcagg gttttactgt gaatgacata aaagcttagg 181380
tcctaaaaaa tgagtatctg agaagagtag aaaaagaaaa ggttcaggaa atttgattta 181440
cttgactcct ttcagatcgg atccagctat cctttcccct gagatctccc tgacagactg 181500
aaggccccaa gcacacagac ttcaactaac aggaagccaa gtagatggtt ccctgtgggg 181560
gtgggggtca agtctgtggt cagaaaactt ggtgctttgt ctaatgctcc ttcgtgggca 181620
tgcttcccct ccccattctg tcttcatccc acatcagttc cagtggatgg gctgaaaaat 181680
caaaaattct ttgatgaact tcgaatgaac tacatcaagg aactcgatcg tatcattgca 181740
tgcaaaagaa aaaatcccac atcctgctca agacgcttct accagctcac caagctcctg 181800
gactccgtgc agcctgtaag caaacgatgg agggtgcttt atcagggaga acagcctgat 181860
agagccaatg ataatatgct tctctagagt ctggcaccac ctgttgggag gtgcttccat 181920
tcccctctgg ctttgagtgt ggtccaggaa gaaaatgtgg tgaagaaaag aacacgggtc 181980
acagtgtccc agctggatat tgtgaaaggg gtggaggagt tgagaacaga gcagttggga 182040
ctcagggaag ggacttgcag cagatgaatt ctctaggcag acaaaacaga cctggatgtt 182100
tttcccctct tctttgagtc atgttcatgt gagtttgtct gtctgtgtgt gtgtgtgtgt 182160
gtgtgtgtgt gtgtgtgtgt gtgtcagaga gagagagaga gagagagaga tggagtgcgg 182220
aggcttgggt gagagcacaa gctggagaag tcttgagtca gagagcttac aatggtataa 182280
gacatctctt gggagccctc agtgactcca tggagaccat ttctttctct ctctctcgct 182340
gtctctctct aacacacaca cacacacaca cgacctcatg ggggaggacc aaggaagtac 182400
ggggaagggg gaggaaacaa aaggctgaaa gaccaaaaat cagaggttgg ggaagaggct 182460
agcagaggcc acctccttgt caaccctgtt tttctccctc ttattgttcc ctacagattg 182520
cgagagagct gcatcagttc acttttgacc tgctaatcaa gtcacacatg gtgagcgtgg 182580
actttccgga aatgatggca gagatcatct ctgtgcaagt gcccaagatc ctttctggga 182640 aagtcaagcc catctatttc cacacccagt gaagcattgg aaaccctatt tccccacccc 182700 agctcatgcc ccctttcaga tgtcttctgc ctgttataac tctgcactac tcctctgcag 182760 tgccttgggg aatttcctct attgatgtac agtctgtcat gaacatgttc ctgaattcta 182820 tttgctgggc tttttttttc tctttctctc ctttcttttt cttcttccct ccctatctaa 182880 ccctcccatg gcaccttcag actttgcttc ccattgtggc tcctatctgt gttttgaatg 182940 gtgttgtatg cctttaaatc tgtgatgatc ctcatatggc ccagtgtcaa gttgtgcttg 183000 tttacagcac tactctgtgc cagccacaca aacgtttact tatcttatgc cacgggaagt 183060 ttagagagct aagattatct ggggaaatca aaacaaaaac aagcaaacaa aaaaaaaaag 183120 caaaaacaaa acaaaaaata agccaaaaaa ccttgctagt gtttttttcct caaaaataaa 183180 taaataaata aataaatacg tacatacata cacacataca tacaaacata tagaaatccc 183240 caaagaggcc aatagtgacg agaaggtgaa aattgcaggc ccatggggag ttactgattt 183300 tttcatctcc tccctccacg ggagacttta ttttctgcca atggctattg ccattagagg 183360 gcagagtgac cccagagctg agttgggcag gggggtggac agagaggaga ggacaaggag 183420 ggcaatggag catcagtacc tgcccacagc cttggtccct gggggctaga ctgctcaact 183480 gtggagcaat tcattatact gaaaatgtgc ttgttgttga aaatttgtct gcatgttaat 183540 gcctcacccc caaacccttt tctctctcac tctctgcctc caacttcaga ttgactttca 183600 atagtttttc taagaccttt gaactgaatg ttctcttcag ccaaaacttg gcgacttcca 183660 cagaaaagtc tgaccactga gaagaaggag agcagagatt taaccctttg taaggcccca 183720 tttggatcca ggtctgcttt ctcatgtgtg agtcagggag gagctggagc cagaggagaa 183780 gaaaatgata gcttggctgt tctcctgctt aggacactga ctgaatagtt aaactctcac 183840 tgccactacc ttttccccac ctttaaaaga cctgaatgaa gttttctgcc aaactccgtg 183900 aagccacaag caccttatgt cctcccttca gtgttttgtg ggcctgaatt tcatcacact 183960 gcatttcagc catggtcatc aagcctgttt gcttcttttg ggcatgttca cagattctct 184020 gttaagagcc cccaccacca agaaggttag caggccaaca gctctgacat ctatctgtag 184080 atgccagtag tcacaaagat ttcttaccaa ctctcagatc gctggagccc ttagacaaac 184140 tggaaagaag gcatcaaagg gatcaggcaa gctgggcgtc ttgcccttgt cccccagaga 184200 tgataccctc ccagcaagtg gagaagttct cacttccttc tttagagcag ctaaaggggc 184260 tacccagatc agggttgaag agaaaactca attaccaggg tgggaagaat gaaggcacta 184320 gaaccagaaa ccctgcaaat gctcttcttg tcacccagca tatccacctg cagaagtcat 184380 gagaagagag aaggaacaaa gaggagactc tgactactga attaaaatct tcagcggcaa 184440 agcctaaagc cagatggaca ccatctggtg agtttactca tcatcctcct ctgctgctga 184500 ttctgggctc tgacattgcc catactcact cagattcccc acctttgttg ctgcctctta 184560 gtcagaggga ggccaaacca ttgagacttt ctacagaacc atggcttctt tcggaaaggt 184620 ctggttggtg tggctccaat actttgccac ccatgaactc agggtgtgcc ctgggacact 184680 ggttttatat agtcttttgg cacacctgtg ttctgttgac ttcgttcttc aagcccaagt 184740 gcaagggaaa atgtccacct actttctcat cttggcctct gcctccttac ttagctctta 184800 atctcatctg ttgaactcaa gaaatcaagg gccagtcatc aagctgccca ttttaattga 184860 ttcactctgt ttgttgagag gatagtttct gagtgacatg atatgatcca caagggtttc 184920 cttccctgat ttctgcattg atattaatag ccaaacgaac ttcaaaacag ctttaaataa 184980 caagggagag gggaacctaa gatgagtaat atgccaatcc aagactgctg gagaaaacta 185040 aagctgacag gttccctttt tggggtggga tagacatgtt ctggttttct ttattattac 185100 acaatctggc tcatgtacag gatcactttt agctgtttta aacagaaaaa aatatccacc 185160 actcttttca gttacactag gttacatttt aataggtcct ttacatctgt tttggaatga 185220 ttttcatctt ttgtgataca cagattgaat tatatcattt tcatatctct ccttgtaaat 185280 actagaagct ctcctttaca tttctctatc aaatttttca tctttatggg tttcccaatt 185340 gtgactcttg tcttcatgaa tatatgtttt tcatttgcaa aagccaaaaa tcagtgaaac 185400 agcagtgtaa ttaaaagcaa caactggatt actccaaatt tccaaatgac aaaactaggg 185460 aaaaatagcc tacacaagcc tttaggccta ctctttctgt gcttgggttt gagtgaacaa 185520 aggagatttt agcttggctc tgttctccca tggatgaaag gaggaggatt tttttttct 185580 tttggccatt gatgttctag ccaatgtaat tgacagaagt ctcattttgc atgcgctctg 185640 ctctacaaac agagttggta tggttggtat actgtactca cctgtgaggg actggccact 185700 cagacccact tagctggtga gctagaagat gaggatcact cactggaaaa gtcacaagga 185760 ccatctccaa acaagttggc agtgctcgat gtggacgaag agtgaggaag agaaaaagaa 185820 ggagcaccag ggagaaggct ccgtctgtgc tgggcagcag acagctgcca ggatcacgaa 185880 ctctgtagtc aaagaaaaga gtcgtgtggc agtttcagct ctcgttcatt gggcagctcg 185940 cctaggccca gcctctgagc tgacatggga gttgttggat tctttgtttc atagcttttt 186000 ctatgccata ggcaatattg ttgttcttgg aaagtttatt atttttttaa ctcccttact 186060 ctgagaaagg gatattttga aggactgtca tatatctttg aaaaaagaaa atctgtaata 186120 catatatttt tatgtatgtt cactggcact aaaaaatata gagagcttca ttctgtcctt 186180 tgggtagttg ctgaggtaat tgtccaggtt gaaaaataat gtgctgatgc tagagtccct 186240 ctctgtccat actctacttc taaatacata taggcataca tagcaagttt tatttgactt 186300 gtactttaag agaaaatatg tccaccatcc acatgatgca caaatgagct aacattgagc 186360 ttcaagtagc ttctaagtgt ttgtttcatt aggcacagca cagatgtggc ctttcccccc 186420 ttctctccct tgatatctgg cagggcataa aggcccaggc cacttcctct gccccttccc 186480 agccctgcac caaagctgca tttcaggaga ctctctccag acagcccagt aactacccga 186540 gcatggcccc tgcatagccc tggaaaaata agaggctgac tgtctacgaa ttatcttgtg 186600 ccagttgccc aggtgagagg gcactgggcc aagggagtgg ttttcatgtt tgacccacta 186660 caaggggtca tgggaatcag gaatgccaaa gcaccagatc aaatccaaaa cttaaagtca 186720 aaataagcca ttcagcatgt tcagtttctt ggaaaaggaa gtttctaccc ctgatgcctt 186780 tgtaggcaga tctgttctca ccattaatct ttttgaaaat cttttaaagc agtttttaaa 186840 aagagagatg aaagcatcac attatataac caaagattac attgtacctg ctaagatacc 186900 aaaattcata agggcagggg gggagcaagc attagtgcct ctttgataag ctgtccaaag 186960 acagactaaa ggactctgct ggtgactgac ttataagagc tttgtgggtt tttttttccc 187020 taataatata catgtttaga agaattgaaa ataatttcgg gaaaatggga ttatgggtcc 187080 ttcactaagt gattttataa gcagaactgg ctttcctttt ctctagtagt tgctgagcaa 187140 attgttgaag ctccatcatt gcatggttgg aaatggagct gttcttagcc actgtgtttg 187200 ctagtgccca tgttagctta tctgaagatg tgaaaccctt gctgataagg gagcatttaa 187260 agtactagat tttgcactag agggacagca ggcagaaatc cttatttctg cccactttgg 187320 atggcacaaa aagttatctg cagttgaagg cagaaagttg aaatacattg taaatgaata 187380

```
tttgtatcca tgtttcaaaa ttgaaatata tatatatata tatatatata tatatatata 187440
tatatagtgt gtgtgtgtgt tctgatagct ttaactttct ctgcatcttt atatttggtt 187500
ccagatcaca cctgatgcca tgtacttgtg agagaggatg cagttttgtt ttggaagctc 187560
tctcagaaca aacaagacac ctggattgat cagttaacta aaagttttct cccctattgg 187620
gtttgaccca caggtcctgt gaaggagcag agggataaaa agagtagagg acatgataca 187680
ttgtacttta ctagttcaag acagatgaat gtggaaagca taaaaactca atggaactga 187740
ctgagattta ccacagggaa ggcccaaact tggggccaaa agcctaccca agtgattgac 187800
cagtggcccc ctaatgggac ctgagctgtt ggaagaagag aactgttcct tggtcttcac 187860
catccttgtg agagaagggc agtttcctgc attggaacct ggagcaagcg ctctatcttt 187920
cacacaaatt ccctcacctg agattgaggt gctcttgtta ctgggtgtct gtgtgctgta 187980
attctggttt tggatatgtt ctgtaaagat tttgacaaat gaaaatgtgt ttttctctgt 188040
taaaacttgt cagagtacta gaagttgtat ctctgtaggt gcaggtccat ttctgcccac 188100
aggtagggtg tttttctttg attaagagat tgacacttct gttgcctagg acctcccaac 188160
tcaaccattt ctaggtgaag gcagaaaaat ccacattagt tactcctctt cagacatttc 188220
agctgagata acaaatcttt tggaattttt tcacccatag aaagagtggt agatatttga 188280
atttagcagg tggagtttca tagtaaaaac agcttttgac tcagctttga tttatcctca 188340
tttgatttgg ccagaaagta ggtaatatgc attgattggc ttctgattcc aattcagtat 188400
agcaaggtgc taggtttttt cctttcccca cctgtctctt agcctgggga attaaatgag 188460
aagccttaga atgggtggcc cttgtgacct gaaacacttc ccacataagc tacttaacaa 188520
gattgtcatg gagctgcaga ttccattgcc caccaaagac tagaacacac acatatccat 188580
acaccaaagg aaagacaatt ctgaaatgct gtttctctgg tggttccctc tctggctgct 188640
gcctcacagt atgggaacct gtactctgca gaggtgacag gccagatttg cattatctca 188700
caaccttagc ccttggtgct aactgtccta cagtgaagtg cctgggggt tgtcctatcc 188760
cataagccac ttggatgctg acagcagcca ccatcagaat gacccacgca aaaaaaagaa 188820
aaaaaaaatt aaaaagtccc ctcacaaccc agtgacacct ttctgctttc ctctagactg 188880
gaacattgat tagggagtgc ctcagacatg acattcttgt gctgtccttg gaattaatct 188940
ggcagcagga gggagcagac tatgtaaaca gagataaaaa ttaattttca atattgaagg 189000
aaaaaagaaa taagaagaga gagagaaaga aagcatcaca caaagatttt cttaaaagaa 189060
acaattttgc ttgaaatctc tttagatggg gctcatttct cacggtggca cttggcctcc 189120
actgggcagc aggaccagct ccaagcgcta gtgttctgtt ctctttttgt aatcttggaa 189180
tcttttgttg ctctaaatac aattaaaaat ggcagaaact tgtttgttgg actacatgtg 189240
tgactttggg tctgtctctg cctctgcttt cagaaatgtc atccattgtg taaaatattg 189300
gcttactggt ctgccagcta aaacttggcc acatcccctg ttatggctgc aggatcgagt 189360
tattgttaac aaagagaccc aagaaaagct gctaatgtcc tcttatcatt gttgttaatt 189420
tgttaaaaca taaagaaatc taaaatttca gatgaatgtc atcagagttc ttttaattag 189480
ctctttttat tggctgtttt tattgaagtc aagagttggt atcatgcccg gttgcgtttt 189540
atgctatttt gattttcata tatttttaaa agtctttgca caagggttac aaatttgccc 189600
tgtggtggcc ttagcataag ctgacctggg accaccaaaa taacaaggaa tttgggctag 189660
aaagcacaga tggacactgg tgacccatca caacttctct tgaaaaaccc caaacttgtc 189720
agctggggaa aagccacaca aagcccagct gcccaccttc acatccttat ccttgtagga 189780
```

gcataaaatg gtgtcatcac tgcccagttc taaccaagct tcagttaaag aatgggtacc 189840 ttcacatctt cactattttt caggggcctt accgtccttg accacccaag taaaatctaa 189900 atcagccttc ttttgggttc ttcagttcaa gcaaggcctc ttcttgtggc ctctcagtat 189960 taatatttat gaggttgcag attgaatttt tgggcctgag atacaagcca tcaatgaggt 190020 gtgacaaagc atgtcaatga ataataagaa aattatctat tcttccatat cctcccctgt 190080 aataagggtt gtcagaatgc cttctttctg ggctgggttg aggattcagt gagaacatat 190140 gtgacacagc tggtgggcta ttaagctctg gctttgctcc ctgttaaaat gccagaaccc 190200 ttgagaggga tcccacattg agccatgttt atcactgacc accttagaat ggatggattt 190260 ctcagatttt tcctgagatc aatgcttgat ggagaggaga ggagaacaat agattcttgg 190320 gatgtgtgtt atgcatgtgt ttaagtaaga gacagagagt atgtttattt gcaggttgtg 190380 tgtgtaaagt cagagcctgc ctccagagga tcttctctaa ccaccattgc ttaggtcctg 190440 ttcgtttgca tctacagcga atgaccttac agccatctga cttggcttca ctcaccactc 190500 agctcctgcc taaacagacg aggtggttag catccaccat aagttttcca aggagtagca 190560 aagcacaaag gacacctatt gggttgaaaa gagcctagag gcatgagtcc tgtgtgtgac 190620 ttgttcatag tcatgcagct agtgtatagc taggattctc ccctgctgat ttactatgtg 190680 acactaggca gcaatctgcc cttgctggac ctcggttttc taatctgtaa aatgtgtgga 190740 gtaaaactac atgagatggg aagtcccttc tagtgcagat gccatggtta ttgaaaactg 190800 cagcaacatc tttcttaatc gtaaggggaa agaaaaagac catttactac tcctagaaca 190860 gttttggagc tagaatattc acatttgcac tcaataatta tttacaaaac aactagtgtg 190920 gagagggtca aaacaacagc tgagtcctgt gtaatagata ttgtcaaccc cttgatggat 190980 gaggaagggg ctcaaaggga a 191001

<210> SEQ ID NO 2
<211> LENGTH: 10661
<212> TYPE: DNA
<213> ORGANISM: Homo sapiens
<220> FEATURE:
<221> NAME/KEY: CDS
<222> LOCATION: (1116)...(3878)

<400> SEQUENCE: 2 cgagatcccg gggagccagc ttgctgggag agcgggacgg tccggagcaa gcccagaggc 60 agaggaggcg acagagggaa aaagggccga gctagccgct ccagtgctgt acaggagccg 120 aagggacgca ccacgccagc cccagcccgg ctccagcgac agccaacgcc tcttgcagcg 180 cggcggcttc gaagccgccg cccggagctg ccctttcctc ttcggtgaag tttttaaaag 240 ctgctaaaga ctcggaggaa gcaaggaaag tgcctggtag gactgacggc tgcctttgtc 300 ctcctcctct ccaccccgcc tccccccacc ctgccttccc cccctccccc gtcttctctc 360 ccgcagctgc ctcagtcggc tactctcagc caaccccccct caccaccctt ctccccaccc 420 gcccccccgc ccccgtcggc ccagcgctgc cagcccgagt ttgcagagag gtaactccct 480 ttggctgcga gcgggcgagc tagctgcaca ttgcaaagaa ggctcttagg agccaggcga 540 ctggggagcg gcttcagcac tgcagccacg acccgcctgg ttaggctgca cgcggagaga 600 accctctgtt ttcccccact ctctctccac ctcctcctgc cttccccacc ccgagtgcgg 660 agccagagat caaaagatga aaaggcagtc aggtcttcag tagccaaaaa acaaaacaaa 720 caaaaacaaa aaagccgaaa taaaagaaaa agataataac tcagttctta tttgcaccta 780

```
cttcagtgga cactgaattt ggaaggtgga ggattttgtt tttttctttt aagatctggg    840

catcttttga atctaccctt caagtattaa gagacagact gtgagcctag cagggcagat    900

cttgtccacc gtgtgtcttc ttctgcacga gactttgagg ctgtcagagc gctttttgcg    960

tggttgctcc cgcaagtttc cttctctgga gcttcccgca ggtgggcagc tagctgcagc   1020

gactaccgca tcatcacagc ctgttgaact cttctgagca agagaagggg aggcggggta   1080

agggaagtag gtggaagatt cagccaagct caagg atg gaa gtg cag tta ggg      1133
                                       Met Glu Val Gln Leu Gly
                                        1               5

ctg gga agg gtc tac cct cgg ccg ccg tcc aag acc tac cga gga gct     1181
Leu Gly Arg Val Tyr Pro Arg Pro Pro Ser Lys Thr Tyr Arg Gly Ala
            10                  15                  20

ttc cag aat ctg ttc cag agc gtg cgc gaa gtg atc cag aac ccg ggc     1229
Phe Gln Asn Leu Phe Gln Ser Val Arg Glu Val Ile Gln Asn Pro Gly
        25                  30                  35

ccc agg cac cca gag gcc gcg agc gca gca cct ccc ggc gcc agt ttg     1277
Pro Arg His Pro Glu Ala Ala Ser Ala Ala Pro Pro Gly Ala Ser Leu
    40                  45                  50

ctg ctg ctg cag cag cag cag cag cag cag cag cag cag cag cag cag     1325
Leu Leu Leu Gln Gln Gln Gln Gln Gln Gln Gln Gln Gln Gln Gln Gln
55                  60                  65                  70

cag cag cag cag cag cag cag cag cag caa gag act agc ccc agg cag     1373
Gln Gln Gln Gln Gln Gln Gln Gln Gln Glu Thr Ser Pro Arg Gln
                75                  80                  85

cag cag cag cag cag ggt gag gat ggt tct ccc caa gcc cat cgt aga     1421
Gln Gln Gln Gln Gln Gly Glu Asp Gly Ser Pro Gln Ala His Arg Arg
            90                  95                  100

ggc ccc aca ggc tac ctg gtc ctg gat gag gaa cag caa cct tca cag     1469
Gly Pro Thr Gly Tyr Leu Val Leu Asp Glu Glu Gln Gln Pro Ser Gln
        105                 110                 115

ccg cag tcg gcc ctg gag tgc cac ccc gag aga ggt tgc gtc cca gag     1517
Pro Gln Ser Ala Leu Glu Cys His Pro Glu Arg Gly Cys Val Pro Glu
    120                 125                 130

cct gga gcc gcc gtg gcc gcc agc aag ggg ctg ccg cag cag ctg cca     1565
Pro Gly Ala Ala Val Ala Ala Ser Lys Gly Leu Pro Gln Gln Leu Pro
135                 140                 145                 150

gca cct ccg gac gag gat gac tca gct gcc cca tcc acg ttg tcc ctg     1613
Ala Pro Pro Asp Glu Asp Asp Ser Ala Ala Pro Ser Thr Leu Ser Leu
                155                 160                 165

ctg ggc ccc act ttc ccc ggc tta agc agc tgc tcc gct gac ctt aaa     1661
Leu Gly Pro Thr Phe Pro Gly Leu Ser Ser Cys Ser Ala Asp Leu Lys
            170                 175                 180

gac atc ctg agc gag gcc agc acc atg caa ctc ctt cag caa cag cag     1709
Asp Ile Leu Ser Glu Ala Ser Thr Met Gln Leu Leu Gln Gln Gln Gln
        185                 190                 195

cag gaa gca gta tcc gaa ggc agc agc agc ggg aga gcg agg gag gcc     1757
Gln Glu Ala Val Ser Glu Gly Ser Ser Ser Gly Arg Ala Arg Glu Ala
    200                 205                 210

tcg ggg gct ccc act tcc tcc aag gac aat tac tta ggg ggc act tcg     1805
Ser Gly Ala Pro Thr Ser Ser Lys Asp Asn Tyr Leu Gly Gly Thr Ser
215                 220                 225                 230

acc att tct gac aac gcc aag gag ttg tgt aag gca gtg tcg gtg tcc     1853
Thr Ile Ser Asp Asn Ala Lys Glu Leu Cys Lys Ala Val Ser Val Ser
                235                 240                 245

atg ggc ctg ggt gtg gag gcg ttg gag cat ctg agt cca ggg gaa cag     1901
Met Gly Leu Gly Val Glu Ala Leu Glu His Leu Ser Pro Gly Glu Gln
            250                 255                 260
```

```
ctt cgg ggg gat tgc atg tac gcc cca ctt ttg gga gtt cca ccc gct     1949
Leu Arg Gly Asp Cys Met Tyr Ala Pro Leu Leu Gly Val Pro Pro Ala
        265                 270                 275

gtg cgt ccc act cct tgt gcc cca ttg gcc gaa tgc aaa ggt tct ctg     1997
Val Arg Pro Thr Pro Cys Ala Pro Leu Ala Glu Cys Lys Gly Ser Leu
    280                 285                 290

cta gac gac agc gca ggc aag agc act gaa gat act gct gag tat tcc     2045
Leu Asp Asp Ser Ala Gly Lys Ser Thr Glu Asp Thr Ala Glu Tyr Ser
295                 300                 305                 310

cct ttc aag gga ggt tac acc aaa ggg cta gaa ggc gag agc cta ggc     2093
Pro Phe Lys Gly Gly Tyr Thr Lys Gly Leu Glu Gly Glu Ser Leu Gly
                315                 320                 325

tgc tct ggc agc gct gca gca ggg agc tcc ggg aca ctt gaa ctg ccg     2141
Cys Ser Gly Ser Ala Ala Ala Gly Ser Ser Gly Thr Leu Glu Leu Pro
            330                 335                 340

tct acc ctg tct ctc tac aag tcc gga gca ctg gac gag gca gct gcg     2189
Ser Thr Leu Ser Leu Tyr Lys Ser Gly Ala Leu Asp Glu Ala Ala Ala
        345                 350                 355

tac cag agt cgc gac tac tac aac ttt cca ctg gct ctg gcc gga ccg     2237
Tyr Gln Ser Arg Asp Tyr Tyr Asn Phe Pro Leu Ala Leu Ala Gly Pro
    360                 365                 370

ccg ccc cct ccg ccg cct ccc cat ccc cac gct cgc atc aag ctg gag     2285
Pro Pro Pro Pro Pro Pro Pro His Pro His Ala Arg Ile Lys Leu Glu
375                 380                 385                 390

aac ccg ctg gac tac ggc agc gcc tgg gcg gct gcg gcg gcg cag tgc     2333
Asn Pro Leu Asp Tyr Gly Ser Ala Trp Ala Ala Ala Ala Ala Gln Cys
                395                 400                 405

cgc tat ggg gac ctg gcg agc ctg cat ggc gcg ggt gca gcg gga ccc     2381
Arg Tyr Gly Asp Leu Ala Ser Leu His Gly Ala Gly Ala Ala Gly Pro
            410                 415                 420

ggt tct ggg tca ccc tca gcc gcc gct tcc tca tcc tgg cac act ctc     2429
Gly Ser Gly Ser Pro Ser Ala Ala Ala Ser Ser Ser Trp His Thr Leu
        425                 430                 435

ttc aca gcc gaa gaa ggc cag ttg tat gga ccg tgt ggt ggt ggt ggg     2477
Phe Thr Ala Glu Glu Gly Gln Leu Tyr Gly Pro Cys Gly Gly Gly Gly
    440                 445                 450

ggt ggt ggc ggc ggc ggc ggc ggc ggc ggc ggc ggc ggc ggc ggc ggc     2525
Gly Gly Gly Gly Gly Gly Gly Gly Gly Gly Gly Gly Gly Gly Gly Gly
455                 460                 465                 470

ggc ggc ggc gag gcg gga gct gta gcc ccc tac ggc tac act cgg ccc     2573
Gly Gly Gly Glu Ala Gly Ala Val Ala Pro Tyr Gly Tyr Thr Arg Pro
                475                 480                 485

cct cag ggg ctg gcg ggc cag gaa agc gac ttc acc gca cct gat gtg     2621
Pro Gln Gly Leu Ala Gly Gln Glu Ser Asp Phe Thr Ala Pro Asp Val
            490                 495                 500

tgg tac cct ggc ggc atg gtg agc aga gtg ccc tat ccc agt ccc act     2669
Trp Tyr Pro Gly Gly Met Val Ser Arg Val Pro Tyr Pro Ser Pro Thr
        505                 510                 515

tgt gtc aaa agc gaa atg ggc ccc tgg atg gat agc tac tcc gga cct     2717
Cys Val Lys Ser Glu Met Gly Pro Trp Met Asp Ser Tyr Ser Gly Pro
    520                 525                 530

tac ggg gac atg cgt ttg gag act gcc agg gac cat gtt ttg ccc att     2765
Tyr Gly Asp Met Arg Leu Glu Thr Ala Arg Asp His Val Leu Pro Ile
535                 540                 545                 550

gac tat tac ttt cca ccc cag aag acc tgc ctg atc tgt gga gat gaa     2813
Asp Tyr Tyr Phe Pro Pro Gln Lys Thr Cys Leu Ile Cys Gly Asp Glu
                555                 560                 565

gct tct ggg tgt cac tat gga gct ctc aca tgt gga agc tgc aag gtc     2861
Ala Ser Gly Cys His Tyr Gly Ala Leu Thr Cys Gly Ser Cys Lys Val
            570                 575                 580
```

```
ttc ttc aaa aga gcc gct gaa ggg aaa cag aag tac ctg tgc gcc agc     2909
Phe Phe Lys Arg Ala Ala Glu Gly Lys Gln Lys Tyr Leu Cys Ala Ser
        585                 590                 595

aga aat gat tgc act att gat aaa ttc cga agg aaa aat tgt cca tct     2957
Arg Asn Asp Cys Thr Ile Asp Lys Phe Arg Arg Lys Asn Cys Pro Ser
    600                 605                 610

tgt cgt ctt cgg aaa tgt tat gaa gca ggg atg act ctg gga gcc cgg     3005
Cys Arg Leu Arg Lys Cys Tyr Glu Ala Gly Met Thr Leu Gly Ala Arg
615                 620                 625                 630

aag ctg aag aaa ctt ggt aat ctg aaa cta cag gag gaa gga gag gct     3053
Lys Leu Lys Lys Leu Gly Asn Leu Lys Leu Gln Glu Glu Gly Glu Ala
                635                 640                 645

tcc agc acc acc agc ccc act gag gag aca acc cag aag ctg aca gtg     3101
Ser Ser Thr Thr Ser Pro Thr Glu Glu Thr Thr Gln Lys Leu Thr Val
            650                 655                 660

tca cac att gaa ggc tat gaa tgt cag ccc atc ttt ctg aat gtc ctg     3149
Ser His Ile Glu Gly Tyr Glu Cys Gln Pro Ile Phe Leu Asn Val Leu
        665                 670                 675

gaa gcc att gag cca ggt gta gtg tgt gct gga cac gac aac aac cag     3197
Glu Ala Ile Glu Pro Gly Val Val Cys Ala Gly His Asp Asn Asn Gln
    680                 685                 690

ccc gac tcc ttt gca gcc ttg ctc tct agc ctc aat gaa ctg gga gag     3245
Pro Asp Ser Phe Ala Ala Leu Leu Ser Ser Leu Asn Glu Leu Gly Glu
695                 700                 705                 710

aga cag ctt gta cac gtg gtc aag tgg gcc aag gcc ttg cct ggc ttc     3293
Arg Gln Leu Val His Val Val Lys Trp Ala Lys Ala Leu Pro Gly Phe
                715                 720                 725

cgc aac tta cac gtg gac gac cag atg gct gtc att cag tac tcc tgg     3341
Arg Asn Leu His Val Asp Asp Gln Met Ala Val Ile Gln Tyr Ser Trp
            730                 735                 740

atg ggg ctc atg gtg ttt gcc atg ggc tgg cga tcc ttc acc aat gtc     3389
Met Gly Leu Met Val Phe Ala Met Gly Trp Arg Ser Phe Thr Asn Val
        745                 750                 755

aac tcc agg atg ctc tac ttc gcc cct gat ctg gtt ttc aat gag tac     3437
Asn Ser Arg Met Leu Tyr Phe Ala Pro Asp Leu Val Phe Asn Glu Tyr
    760                 765                 770

cgc atg cac aag tcc cgg atg tac agc cag tgt gtc cga atg agg cac     3485
Arg Met His Lys Ser Arg Met Tyr Ser Gln Cys Val Arg Met Arg His
775                 780                 785                 790

ctc tct caa gag ttt gga tgg ctc caa atc acc ccc cag gaa ttc ctg     3533
Leu Ser Gln Glu Phe Gly Trp Leu Gln Ile Thr Pro Gln Glu Phe Leu
                795                 800                 805

tgc atg aaa gca ctg cta ctc ttc agc att att cca gtg gat ggg ctg     3581
Cys Met Lys Ala Leu Leu Leu Phe Ser Ile Ile Pro Val Asp Gly Leu
            810                 815                 820

aaa aat caa aaa ttc ttt gat gaa ctt cga atg aac tac atc aag gaa     3629
Lys Asn Gln Lys Phe Phe Asp Glu Leu Arg Met Asn Tyr Ile Lys Glu
        825                 830                 835

ctc gat cgt atc att gca tgc aaa aga aaa aat ccc aca tcc tgc tca     3677
Leu Asp Arg Ile Ile Ala Cys Lys Arg Lys Asn Pro Thr Ser Cys Ser
    840                 845                 850

aga cgc ttc tac cag ctc acc aag ctc ctg gac tcc gtg cag cct att     3725
Arg Arg Phe Tyr Gln Leu Thr Lys Leu Leu Asp Ser Val Gln Pro Ile
855                 860                 865                 870

gcg aga gag ctg cat cag ttc act ttt gac ctg cta atc aag tca cac     3773
Ala Arg Glu Leu His Gln Phe Thr Phe Asp Leu Leu Ile Lys Ser His
                875                 880                 885

atg gtg agc gtg gac ttt ccg gaa atg atg gca gag atc atc tct gtg     3821
Met Val Ser Val Asp Phe Pro Glu Met Met Ala Glu Ile Ile Ser Val
```

```
            890                 895                 900

caa gtg ccc aag atc ctt tct ggg aaa gtc aag ccc atc tat ttc cac     3869
Gln Val Pro Lys Ile Leu Ser Gly Lys Val Lys Pro Ile Tyr Phe His
        905                 910                 915

acc cag tga agcattggaa accctatttc cccaccccag ctcatgcccc             3918
Thr Gln
    920

ctttcagatg tcttctgcct gttataactc tgcactactc ctctgcagtg ccttggggaa   3978

tttcctctat tgatgtacag tctgtcatga acatgttcct gaattctatt tgctgggctt   4038

tttttttctc tttctctcct ttctttttct tcttccctcc ctatctaacc ctcccatggc   4098

accttcagac tttgcttccc attgtggctc ctatctgtgt tttgaatggt gttgtatgcc   4158

tttaaatctg tgatgatcct catatggccc agtgtcaagt tgtgcttgtt tacagcacta   4218

ctctgtgcca gccacacaaa cgtttactta tcttatgcca cgggaagttt agagagctaa   4278

gattatctgg ggaaatcaaa acaaaaacaa gcaaacaaaa aaaaaaagca aaaacaaaac   4338

aaaaaataag ccaaaaaacc ttgctagtgt tttttcctca aaaataaata aataaataaa   4398

taaatacgta catacataca cacatacata caaacatata gaaatcccca aagaggccaa   4458

tagtgacgag aaggtgaaaa ttgcaggccc atggggagtt actgattttt tcatctcctc   4518

cctccacggg agactttatt ttctgccaat ggctattgcc attagagggc agagtgaccc   4578

cagagctgag ttgggcaggg gggtggacag agaggagagg acaaggaggg caatggagca   4638

tcagtacctg cccacagcct tggtccctgg gggctagact gctcaactgt ggagcaattc   4698

attatactga aaatgtgctt gttgttgaaa atttgtctgc atgttaatgc ctcacccccca   4758

aaccctttc tctctcactc tctgcctcca acttcagatt gactttcaat agtttttcta   4818

agacctttga actgaatgtt ctcttcagcc aaaacttggc gacttccaca gaaaagtctg   4878

accactgaga agaaggagag cagagattta acccttttgta aggccccatt tggatccagg   4938

tctgctttct catgtgtgag tcagggagga gctggagcca gaggagaaga aaatgatagc   4998

ttggctgttc tcctgcttag gacactgact gaatagttaa actctcactg ccactacctt   5058

ttccccacct ttaaaagacc tgaatgaagt tttctgccaa actccgtgaa gccacaagca   5118

ccttatgtcc tcccttcagt gttttgtggg cctgaatttc atcacactgc atttcagcca   5178

tggtcatcaa gcctgtttgc ttcttttggg catgttcaca gattctctgt taagagcccc   5238

caccaccaag aaggttagca ggccaacagc tctgacatct atctgtagat gccagtagtc   5298

acaaagattt cttaccaact ctcagatcgc tggagccctt agacaaactg gaaagaaggc   5358

atcaaaggga tcaggcaagc tgggcgtctt gcccttgtcc cccagagatg ataccctccc   5418

agcaagtgga gaagttctca cttccttctt tagagcagct aaaggggcta cccagatcag   5478

ggttgaagag aaaactcaat taccagggtg ggaagaatga aggcactaga accagaaacc   5538

ctgcaaatgc tcttcttgtc acccagcata tccacctgca gaagtcatga gaagagagaa   5598

ggaacaaaga ggagactctg actactgaat taaaatcttc agcggcaaag cctaaagcca   5658

gatggacacc atctggtgag tttactcatc atcctcctct gctgctgatt ctgggctctg   5718

acattgccca tactcactca gattccccac ctttgttgct gcctcttagt cagagggagg   5778

ccaaaccatt gagactttct acagaaccat ggcttctttc ggaaaggtct ggttggtgtg   5838

gctccaatac tttgccaccc atgaactcag ggtgtgccct gggacactgg ttttatatag   5898

tcttttggca cacctgtgtt ctgttgactt cgttcttcaa gcccaagtgc aagggaaaat   5958

gtccacctac tttctcatct tggcctctgc ctccttactt agctcttaat ctcatctgtt   6018
```

gaactcaaga aatcaagggc cagtcatcaa gctgcccatt ttaattgatt cactctgttt 6078
gttgagagga tagtttctga gtgacatgat atgatccaca agggtttcct tccctgattt 6138
ctgcattgat attaatagcc aaacgaactt caaaacagct ttaaataaca agggagaggg 6198
gaacctaaga tgagtaatat gccaatccaa gactgctgga gaaaactaaa gctgacaggt 6258
tccctttttg gggtgggata gacatgttct ggttttcttt attattacac aatctggctc 6318
atgtacagga tcacttttag ctgttttaaa cagaaaaaaa tatccaccac tcttttcagt 6378
tacactaggt tacattttaa taggtccttt acatctgttt tggaatgatt ttcatctttt 6438
gtgatacaca gattgaatta tatcattttc atatctctcc ttgtaaatac tagaagctct 6498
cctttacatt tctctatcaa atttttcatc tttatgggtt tcccaattgt gactcttgtc 6558
ttcatgaata tatgtttttc atttgcaaaa gccaaaaatc agtgaaacag cagtgtaatt 6618
aaaagcaaca actggattac tccaaatttc caaatgacaa aactagggaa aaatagccta 6678
cacaagcctt taggcctact ctttctgtgc ttgggtttga gtgaacaaag gagattttag 6738
cttggctctg ttctcccatg gatgaaagga ggaggatttt ttttttcttt tggccattga 6798
tgttctagcc aatgtaattg acagaagtct cattttgcat gcgctctgct ctacaaacag 6858
agttggtatg gttggtatac tgtactcacc tgtgagggac tggccactca gacccactta 6918
gctggtgagc tagaagatga ggatcactca ctggaaaagt cacaaggacc atctccaaac 6978
aagttggcag tgctcgatgt ggacgaagag tgaggaagag aaaaagaagg agcaccaggg 7038
agaaggctcc gtctgtgctg ggcagcagac agctgccagg atcacgaact ctgtagtcaa 7098
agaaaagagt cgtgtggcag tttcagctct cgttcattgg gcagctcgcc taggcccagc 7158
ctctgagctg acatgggagt tgttggattc tttgtttcat agctttttct atgccatagg 7218
caatattgtt gttcttggaa agtttattat ttttttaact cccttactct gagaaaggga 7278
tattttgaag gactgtcata tatctttgaa aaaagaaaat ctgtaataca tatattttta 7338
tgtatgttca ctggcactaa aaaatataga gagcttcatt ctgtcctttg ggtagttgct 7398
gaggtaattg tccaggttga aaaataatgt gctgatgcta gagtccctct ctgtccatac 7458
tctacttcta aatacatata ggcatacata gcaagtttta tttgacttgt actttaagag 7518
aaaatatgtc caccatccac atgatgcaca aatgagctaa cattgagctt caagtagctt 7578
ctaagtgttt gtttcattag gcacagcaca gatgtggcct ttcccccctt ctctcccttg 7638
atatctggca gggcataaag gcccaggcca cttcctctgc cccttcccag ccctgcacca 7698
aagctgcatt tcaggagact ctctccagac agcccagtaa ctacccgagc atggcccctg 7758
catagccctg gaaaaataag aggctgactg tctacgaatt atcttgtgcc agttgcccag 7818
gtgagagggc actgggccaa gggagtggtt ttcatgtttg acccactaca aggggtcatg 7878
ggaatcagga atgccaaagc accagatcaa atccaaaact taaagtcaaa ataagccatt 7938
cagcatgttc agtttcttgg aaaaggaagt ttctacccct gatgcctttg taggcagatc 7998
tgttctcacc attaatcttt ttgaaaatct tttaaagcag tttttaaaaa gagagatgaa 8058
agcatcacat tatataacca aagattacat tgtacctgct aagataccaa aattcataag 8118
ggcagggggg gagcaagcat tagtgcctct ttgataagct gtccaaagac agactaaagg 8178
actctgctgg tgactgactt ataagagctt tgtgggtttt tttttcccta ataatataca 8238
tgtttagaag aattgaaaat aatttcggga aaatgggatt atgggtcctt cactaagtga 8298
ttttataagc agaactggct ttccttttct ctagtagttg ctgagcaaat tgttgaagct 8358

-continued

```
ccatcattgc atggttggaa atggagctgt tcttagccac tgtgtttgct agtgcccatg   8418
ttagcttatc tgaagatgtg aaacccttgc tgataaggga gcatttaaag tactagattt   8478
tgcactagag ggacagcagg cagaaatcct tatttctgcc cactttggat ggcacaaaaa   8538
gttatctgca gttgaaggca gaaagttgaa atacattgta aatgaatatt tgtatccatg   8598
tttcaaaatt gaaatatata tatatatata tatatatata tatatatata tatagtgtgt   8658
gtgtgtgttc tgatagcttt aactttctct gcatctttat atttggttcc agatcacacc   8718
tgatgccatg tacttgtgag agaggatgca gttttgtttt ggaagctctc tcagaacaaa   8778
caagacacct ggattgatca gttaactaaa agttttctcc cctattgggt ttgacccaca   8838
ggtcctgtga aggagcagag ggataaaaag agtagaggac atgatacatt gtactttact   8898
agttcaagac agatgaatgt ggaaagcata aaaactcaat ggaactgact gagatttacc   8958
acagggaagg cccaaacttg gggccaaaag cctacccaag tgattgacca gtggccccct   9018
aatgggacct gagctgttgg aagaagagaa ctgttccttg gtcttcacca tccttgtgag   9078
agaagggcag tttcctgcat tggaacctgg agcaagcgct ctatctttca cacaaattcc   9138
ctcacctgag attgaggtgc tcttgttact gggtgtctgt gtgctgtaat tctggttttg   9198
gatatgttct gtaaagattt tgacaaatga aaatgtgttt ttctctgtta aaacttgtca   9258
gagtactaga agttgtatct ctgtaggtgc aggtccattt ctgcccacag gtagggtgtt   9318
tttctttgat taagagattg acacttctgt tgcctaggac ctcccaactc aaccatttct   9378
aggtgaaggc agaaaaatcc acattagtta ctcctcttca gacatttcag ctgagataac   9438
aaatcttttg gaatttttc acccatagaa agagtggtag atatttgaat ttagcaggtg   9498
gagtttcata gtaaaaacag cttttgactc agctttgatt tatcctcatt tgatttggcc   9558
agaaagtagg taatatgcat tgattggctt ctgattccaa ttcagtatag caaggtgcta   9618
ggtttttcc tttccccacc tgtctcttag cctggggaat taaatgagaa gccttagaat   9678
gggtggccct tgtgacctga aacacttccc acataagcta cttaacaaga ttgtcatgga   9738
gctgcagatt ccattgccca ccaaagacta gaacacacac atatccatac accaaaggaa   9798
agacaattct gaaatgctgt ttctctggtg gttccctctc tggctgctgc ctcacagtat   9858
gggaacctgt actctgcaga ggtgacaggc cagatttgca ttatctcaca accttagccc   9918
ttggtgctaa ctgtcctaca gtgaagtgcc tgggggggttg tcctatccca taagccactt   9978
ggatgctgac agcagccacc atcagaatga cccacgcaaa aaaaagaaaa aaaaaattaa  10038
aaagtcccct cacaacccag tgacaccttt ctgctttcct ctagactgga acattgatta  10098
gggagtgcct cagacatgac attcttgtgc tgtccttgga attaatctgg cagcaggagg  10158
gagcagacta tgtaaacaga gataaaaatt aattttcaat attgaaggaa aaaagaaata  10218
agaagagaga gagaaagaaa gcatcacaca aagattttct taaaagaaac aattttgctt  10278
gaaatctctt tagatggggc tcatttctca cggtggcact tggcctccac tgggcagcag  10338
gaccagctcc aagcgctagt gttctgttct ctttttgtaa tcttggaatc ttttgttgct  10398
ctaaatacaa ttaaaaatgg cagaaacttg tttgttggac tacatgtgtg actttgggtc  10458
tgtctctgcc tctgctttca gaaatgtcat ccattgtgta aaatattggc ttactggtct  10518
gccagctaaa acttggccac atcccctgtt atggctgcag gatcgagtta ttgttaacaa  10578
agagacccaa gaaaagctgc taatgtcctc ttatcattgt tgttaatttg ttaaaacata  10638
aagaaatcta aaatttcaaa aaa                                          10661
```

```
<210> SEQ ID NO 3
<211> LENGTH: 8112
<212> TYPE: DNA
<213> ORGANISM: Homo sapiens
<220> FEATURE:
<221> NAME/KEY: CDS
<222> LOCATION: (163)...(1329)

<400> SEQUENCE: 3

gctgcgagca gagagggatt cctcggaggt catctgttcc atcttcttgc ctatgcaaat     60

gcctgcctga agctgctgga ggctggcttt gtaccggact ttgtacaggg aaccagggaa    120

acgaatgcag agtgctcctg acattgcctg tcactttttc cc atg ata ctc tgg       174
                                               Met Ile Leu Trp
                                                1

ctt cac agt ttg gag act gcc agg gac cat gtt ttg ccc att gac tat      222
Leu His Ser Leu Glu Thr Ala Arg Asp His Val Leu Pro Ile Asp Tyr
 5                  10                  15                  20

tac ttt cca ccc cag aag acc tgc ctg atc tgt gga gat gaa gct tct      270
Tyr Phe Pro Pro Gln Lys Thr Cys Leu Ile Cys Gly Asp Glu Ala Ser
                 25                  30                  35

ggg tgt cac tat gga gct ctc aca tgt gga agc tgc aag gtc ttc ttc      318
Gly Cys His Tyr Gly Ala Leu Thr Cys Gly Ser Cys Lys Val Phe Phe
             40                  45                  50

aaa aga gcc gct gaa ggg aaa cag aag tac ctg tgc gcc agc aga aat      366
Lys Arg Ala Ala Glu Gly Lys Gln Lys Tyr Leu Cys Ala Ser Arg Asn
         55                  60                  65

gat tgc act att gat aaa ttc cga agg aaa aat tgt cca tct tgt cgt      414
Asp Cys Thr Ile Asp Lys Phe Arg Arg Lys Asn Cys Pro Ser Cys Arg
     70                  75                  80

ctt cgg aaa tgt tat gaa gca ggg atg act ctg gga gcc cgg aag ctg      462
Leu Arg Lys Cys Tyr Glu Ala Gly Met Thr Leu Gly Ala Arg Lys Leu
 85                  90                  95                 100

aag aaa ctt ggt aat ctg aaa cta cag gag gaa gga gag gct tcc agc      510
Lys Lys Leu Gly Asn Leu Lys Leu Gln Glu Glu Gly Glu Ala Ser Ser
                105                 110                 115

acc acc agc ccc act gag gag aca acc cag aag ctg aca gtg tca cac      558
Thr Thr Ser Pro Thr Glu Glu Thr Thr Gln Lys Leu Thr Val Ser His
            120                 125                 130

att gaa ggc tat gaa tgt cag ccc atc ttt ctg aat gtc ctg gaa gcc      606
Ile Glu Gly Tyr Glu Cys Gln Pro Ile Phe Leu Asn Val Leu Glu Ala
        135                 140                 145

att gag cca ggt gta gtg tgt gct gga cac gac aac aac cag ccc gac      654
Ile Glu Pro Gly Val Val Cys Ala Gly His Asp Asn Asn Gln Pro Asp
    150                 155                 160

tcc ttt gca gcc ttg ctc tct agc ctc aat gaa ctg gga gag aga cag      702
Ser Phe Ala Ala Leu Leu Ser Ser Leu Asn Glu Leu Gly Glu Arg Gln
165                 170                 175                 180

ctt gta cac gtg gtc aag tgg gcc aag gcc ttg cct ggc ttc cgc aac      750
Leu Val His Val Val Lys Trp Ala Lys Ala Leu Pro Gly Phe Arg Asn
                185                 190                 195

tta cac gtg gac gac cag atg gct gtc att cag tac tcc tgg atg ggg      798
Leu His Val Asp Asp Gln Met Ala Val Ile Gln Tyr Ser Trp Met Gly
            200                 205                 210

ctc atg gtg ttt gcc atg ggc tgg cga tcc ttc acc aat gtc aac tcc      846
Leu Met Val Phe Ala Met Gly Trp Arg Ser Phe Thr Asn Val Asn Ser
        215                 220                 225

agg atg ctc tac ttc gcc cct gat ctg gtt ttc aat gag tac cgc atg      894
Arg Met Leu Tyr Phe Ala Pro Asp Leu Val Phe Asn Glu Tyr Arg Met
    230                 235                 240

cac aag tcc cgg atg tac agc cag tgt gtc cga atg agg cac ctc tct      942
```

```
His Lys Ser Arg Met Tyr Ser Gln Cys Val Arg Met Arg His Leu Ser
245                 250                 255                 260

caa gag ttt gga tgg ctc caa atc acc ccc cag gaa ttc ctg tgc atg      990
Gln Glu Phe Gly Trp Leu Gln Ile Thr Pro Gln Glu Phe Leu Cys Met
                265                 270                 275

aaa gca ctg cta ctc ttc agc att att cca gtg gat ggg ctg aaa aat     1038
Lys Ala Leu Leu Leu Phe Ser Ile Ile Pro Val Asp Gly Leu Lys Asn
            280                 285                 290

caa aaa ttc ttt gat gaa ctt cga atg aac tac atc aag gaa ctc gat     1086
Gln Lys Phe Phe Asp Glu Leu Arg Met Asn Tyr Ile Lys Glu Leu Asp
        295                 300                 305

cgt atc att gca tgc aaa aga aaa aat ccc aca tcc tgc tca aga cgc     1134
Arg Ile Ile Ala Cys Lys Arg Lys Asn Pro Thr Ser Cys Ser Arg Arg
    310                 315                 320

ttc tac cag ctc acc aag ctc ctg gac tcc gtg cag cct att gcg aga     1182
Phe Tyr Gln Leu Thr Lys Leu Leu Asp Ser Val Gln Pro Ile Ala Arg
325                 330                 335                 340

gag ctg cat cag ttc act ttt gac ctg cta atc aag tca cac atg gtg     1230
Glu Leu His Gln Phe Thr Phe Asp Leu Leu Ile Lys Ser His Met Val
                345                 350                 355

agc gtg gac ttt ccg gaa atg atg gca gag atc atc tct gtg caa gtg     1278
Ser Val Asp Phe Pro Glu Met Met Ala Glu Ile Ile Ser Val Gln Val
            360                 365                 370

ccc aag atc ctt tct ggg aaa gtc aag ccc atc tat ttc cac acc cag     1326
Pro Lys Ile Leu Ser Gly Lys Val Lys Pro Ile Tyr Phe His Thr Gln
        375                 380                 385

tga agcattggaa accctatttc cccaccccag ctcatgcccc ctttcagatg          1379

tcttctgcct gttataactc tgcactactc ctctgcagtg ccttggggaa tttcctctat   1439

tgatgtacag tctgtcatga acatgttcct gaattctatt tgctgggctt tttttttctc   1499

tttctctcct ttctttttct tcttccctcc ctatctaacc ctcccatggc accttcagac   1559

tttgcttccc attgtggctc ctatctgtgt tttgaatggt gttgtatgcc tttaaatctg   1619

tgatgatcct catatggccc agtgtcaagt tgtgcttgtt tacagcacta ctctgtgcca   1679

gccacacaaa cgtttactta tcttatgcca cgggaagttt agagagctaa gattatctgg   1739

ggaaatcaaa acaaaaacaa gcaaacaaaa aaaaaaagca aaaacaaaac aaaaaataag   1799

ccaaaaaacc ttgctagtgt tttttcctca aaaataaata aataaataaa taaatacgta   1859

catacataca cacatacata caaacatata gaaatcccca aagaggccaa tagtgacgag   1919

aaggtgaaaa ttgcaggccc atggggagtt actgattttt tcatctcctc cctccacggg   1979

agactttatt ttctgccaat ggctattgcc attagagggc agagtgaccc cagagctgag   2039

ttgggcaggg gggtggacag agaggagagg acaaggaggg caatggagca tcagtacctg   2099

cccacagcct tggtccctgg gggctagact gctcaactgt ggagcaattc attatactga   2159

aaatgtgctt gttgttgaaa atttgtctgc atgttaatgc ctcacccccca aaccctttc   2219

tctctcactc tctgcctcca acttcagatt gactttcaat agtttttcta agacctttga   2279

actgaatgtt ctcttcagcc aaaacttggc gacttccaca gaaaagtctg accactgaga   2339

agaaggagag cagagattta acccttttgta aggccccatt tggatccagg tctgctttct   2399

catgtgtgag tcagggagga gctggagcca gaggagaaga aaatgatagc ttggctgttc   2459

tcctgcttag gacactgact gaatagttaa actctcactg ccactacctt ttccccacct   2519

ttaaaagacc tgaatgaagt tttctgccaa actccgtgaa gccacaagca ccttatgtcc   2579

tcccttcagt gttttgtggg cctgaatttc atcacactgc atttcagcca tggtcatcaa   2639
```

```
gcctgtttgc ttcttttggg catgttcaca gattctctgt taagagcccc caccaccaag   2699
aaggttagca ggccaacagc tctgacatct atctgtagat gccagtagtc acaaagattt   2759
cttaccaact ctcagatcgc tggagccctt agacaaactg gaaagaaggc atcaaaggga   2819
tcaggcaagc tgggcgtctt gcccttgtcc cccagagatg ataccctccc agcaagtgga   2879
gaagttctca cttccttctt tagagcagct aaaggggcta cccagatcag ggttgaagag   2939
aaaactcaat taccagggtg ggaagaatga aggcactaga accagaaacc ctgcaaatgc   2999
tcttcttgtc acccagcata tccacctgca gaagtcatga gaagagagaa ggaacaaaga   3059
ggagactctg actactgaat taaaatcttc agcggcaaag cctaaagcca gatggacacc   3119
atctggtgag tttactcatc atcctcctct gctgctgatt ctgggctctg acattgccca   3179
tactcactca gattccccac ctttgttgct gcctcttagt cagagggagg ccaaaccatt   3239
gagactttct acagaaccat ggcttctttc ggaaaggtct ggttggtgtg gctccaatac   3299
tttgccaccc atgaactcag ggtgtgccct gggacactgg ttttatatag tcttttggca   3359
cacctgtgtt ctgttgactt cgttcttcaa gcccaagtgc aagggaaaat gtccacctac   3419
tttctcatct tggcctctgc ctccttactt agctcttaat ctcatctgtt gaactcaaga   3479
aatcaagggc cagtcatcaa gctgcccatt ttaattgatt cactctgttt gttgagagga   3539
tagtttctga gtgacatgat atgatccaca agggtttcct tccctgattt ctgcattgat   3599
attaatagcc aaacgaactt caaaacagct ttaaataaca agggagaggg gaacctaaga   3659
tgagtaatat gccaatccaa gactgctgga gaaaactaaa gctgacaggt tccctttttg   3719
gggtgggata gacatgttct ggttttcttt attattacac aatctggctc atgtacagga   3779
tcacttttag ctgttttaaa cagaaaaaaa tatccaccac tcttttcagt tacactaggt   3839
tacattttaa taggtccttt acatctgttt tggaatgatt ttcatctttt gtgatacaca   3899
gattgaatta tatcattttc atatctctcc ttgtaaatac tagaagctct cctttacatt   3959
tctctatcaa atttttcatc tttatgggtt tcccaattgt gactcttgtc ttcatgaata   4019
tatgtttttc atttgcaaaa gccaaaaatc agtgaaacag cagtgtaatt aaaagcaaca   4079
actggattac tccaaatttc caaatgacaa aactagggaa aaatagccta cacaagcctt   4139
taggcctact ctttctgtgc ttgggtttga gtgaacaaag gagattttag cttggctctg   4199
ttctcccatg gatgaaagga ggaggatttt ttttttcttt tggccattga tgttctagcc   4259
aatgtaattg acagaagtct cattttgcat gcgctctgct ctacaaacag agttggtatg   4319
gttggtatac tgtactcacc tgtgagggac tggccactca gacccactta gctggtgagc   4379
tagaagatga ggatcactca ctggaaaagt cacaaggacc atctccaaac aagttggcag   4439
tgctcgatgt ggacgaagag tgaggaagag aaaaagaagg agcaccaggg agaaggctcc   4499
gtctgtgctg ggcagcagac agctgccagg atcacgaact ctgtagtcaa agaaaagagt   4559
cgtgtggcag tttcagctct cgttcattgg gcagctcgcc taggcccagc ctctgagctg   4619
acatgggagt tgttggattc tttgtttcat agctttttct atgccatagg caatattgtt   4679
gttcttggaa agtttattat ttttttaact cccttactct gagaaaggga tattttgaag   4739
gactgtcata tatctttgaa aaaagaaaat ctgtaataca tatattttta tgtatgttca   4799
ctggcactaa aaaatataga gagcttcatt ctgtcctttg ggtagttgct gaggtaattg   4859
tccaggttga aaaataatgt gctgatgcta gagtccctct ctgtccatac tctacttcta   4919
aatacatata ggcatacata gcaagtttta tttgacttgt actttaagag aaaatatgtc   4979
caccatccac atgatgcaca aatgagctaa cattgagctt caagtagctt ctaagtgttt   5039
```

gtttcattag gcacagcaca gatgtggcct ttcccccctt ctctcccttg atatctggca 5099
gggcataaag gcccaggcca cttcctctgc cccttcccag ccctgcacca aagctgcatt 5159
tcaggagact ctctccagac agcccagtaa ctacccgagc atggcccctg catagccctg 5219
gaaaaataag aggctgactg tctacgaatt atcttgtgcc agttgcccag gtgagagggc 5279
actgggccaa gggagtggtt ttcatgtttg acccactaca aggggtcatg ggaatcagga 5339
atgccaaagc accagatcaa atccaaaact taaagtcaaa ataagccatt cagcatgttc 5399
agtttcttgg aaaaggaagt ttctacccct gatgcctttg taggcagatc tgttctcacc 5459
attaatcttt ttgaaaatct tttaaagcag tttttaaaaa gagagatgaa agcatcacat 5519
tatataacca aagattacat tgtacctgct aagataccaa aattcataag ggcagggggg 5579
gagcaagcat tagtgcctct ttgataagct gtccaaagac agactaaagg actctgctgg 5639
tgactgactt ataagagctt tgtgggtttt tttttcccta ataatataca tgtttagaag 5699
aattgaaaat aatttcggga aaatgggatt atgggtcctt cactaagtga ttttataagc 5759
agaactggct ttccttttct ctagtagttg ctgagcaaat tgttgaagct ccatcattgc 5819
atggttggaa atggagctgt tcttagccac tgtgtttgct agtgcccatg ttagcttatc 5879
tgaagatgtg aaacccttgc tgataaggga gcatttaaag tactagattt tgcactagag 5939
ggacagcagg cagaaatcct tatttctgcc cactttggat ggcacaaaaa gttatctgca 5999
gttgaaggca gaaagttgaa atacattgta aatgaatatt tgtatccatg tttcaaaatt 6059
gaaatatata tatatatata tatatatata tatatatata tatagtgtgt gtgtgtgttc 6119
tgatagcttt aactttctct gcatctttat atttggttcc agatcacacc tgatgccatg 6179
tacttgtgag agaggatgca gttttgtttt ggaagctctc tcagaacaaa caagacacct 6239
ggattgatca gttaactaaa agttttctcc cctattgggt ttgacccaca ggtcctgtga 6299
aggagcagag ggataaaaag agtagaggac atgatacatt gtactttact agttcaagac 6359
agatgaatgt ggaaagcata aaaactcaat ggaactgact gagatttacc acagggaagg 6419
cccaaacttg gggccaaaag cctacccaag tgattgacca gtggcccccct aatgggacct 6479
gagctgttgg aagaagagaa ctgttccttg gtcttcacca tccttgtgag agaagggcag 6539
tttcctgcat tggaacctgg agcaagcgct ctatctttca cacaaattcc ctcacctgag 6599
attgaggtgc tcttgttact gggtgtctgt gtgctgtaat tctggttttg gatatgttct 6659
gtaaagattt tgacaaatga aaatgtgttt ttctctgtta aaacttgtca gagtactaga 6719
agttgtatct ctgtaggtgc aggtccattt ctgcccacag gtagggtgtt tttctttgat 6779
taagagattg acacttctgt tgcctaggac ctcccaactc aaccatttct aggtgaaggc 6839
agaaaaatcc acattagtta ctcctcttca gacatttcag ctgagataac aaatcttttg 6899
gaatttttc acccatagaa agagtggtag atatttgaat ttagcaggtg gagtttcata 6959
gtaaaaacag cttttgactc agctttgatt tatcctcatt tgatttggcc agaaagtagg 7019
taatatgcat tgattggctt ctgattccaa ttcagtatag caaggtgcta ggtttttcc 7079
tttccccacc tgtctcttag cctggggaat taaatgagaa gccttagaat gggtggccct 7139
tgtgacctga aacacttccc acataagcta cttaacaaga ttgtcatgga gctgcagatt 7199
ccattgccca ccaaagacta gaacacacac atatccatac accaaaggaa agacaattct 7259
gaaatgctgt ttctctggtg gttccctctc tggctgctgc ctcacagtat gggaacctgt 7319
actctgcaga ggtgacaggc cagatttgca ttatctcaca accttagccc ttggtgctaa 7379

```
ctgtcctaca gtgaagtgcc tgggggggttg tcctatccca taagccactt ggatgctgac   7439

agcagccacc atcagaatga cccacgcaaa aaaaagaaaa aaaaaattaa aaagtcccct   7499

cacaacccag tgacaccttt ctgctttcct ctagactgga acattgatta gggagtgcct   7559

cagacatgac attcttgtgc tgtccttgga attaatctgg cagcaggagg gagcagacta   7619

tgtaaacaga gataaaaatt aattttcaat attgaaggaa aaaagaaata agaagagaga   7679

gagaaagaaa gcatcacaca aagattttct taaaagaaac aattttgctt gaaatctctt   7739

tagatggggc tcatttctca cggtggcact tggcctccac tgggcagcag gaccagctcc   7799

aagcgctagt gttctgttct ctttttgtaa tcttggaatc ttttgttgct ctaaatacaa   7859

ttaaaaatgg cagaaacttg tttgttggac tacatgtgtg actttgggtc tgtctctgcc   7919

tctgctttca gaaatgtcat ccattgtgta aaatattggc ttactggtct gccagctaaa   7979

acttggccac atcccctgtt atggctgcag gatcgagtta ttgttaacaa agagacccaa   8039

gaaaagctgc taatgtcctc ttatcattgt tgttaatttg ttaaaacata aagaaatcta   8099

aaatttcaaa aaa                                                      8112


<210> SEQ ID NO 4
<211> LENGTH: 3641
<212> TYPE: DNA
<213> ORGANISM: Homo sapiens
<220> FEATURE:
<221> NAME/KEY: CDS
<222> LOCATION: (328)...(2265)

<400> SEQUENCE: 4

gacactgaat ttggaaggtg gaggattttg tttttttctt ttaagatctg ggcatctttt     60

gaatctaccc ttcaagtatt aagagacaga ctgtgagcct agcagggcag atcttgtcca    120

ccgtgtgtct tcttctgcac gagactttga ggctgtcaga gcgctttttg cgtggttgct    180

cccgcaagtt tccttctctg gagcttcccg caggtgggca gctagctgca gcgactaccg    240

catcatcaca gcctgttgaa ctcttctgag caagagaagg ggaggcgggg taagggaagt    300

aggtggaaga ttcagccaag ctcaagg atg gaa gtg cag tta ggg ctg gga agg    354
                              Met Glu Val Gln Leu Gly Leu Gly Arg
                               1               5

gtc tac cct cgg ccg ccg tcc aag acc tac cga gga gct ttc cag aat      402
Val Tyr Pro Arg Pro Pro Ser Lys Thr Tyr Arg Gly Ala Phe Gln Asn
 10                  15                  20                  25

ctg ttc cag agc gtg cgc gaa gtg atc cag aac ccg ggc ccc agg cac      450
Leu Phe Gln Ser Val Arg Glu Val Ile Gln Asn Pro Gly Pro Arg His
                 30                  35                  40

cca gag gcc gcg agc gca gca cct ccc ggc gcc agt ttg ctg ctg cag      498
Pro Glu Ala Ala Ser Ala Ala Pro Pro Gly Ala Ser Leu Leu Leu Gln
             45                  50                  55

cag cag cag cag cag cag cag cag cag cag cag cag cag cag cag cag cag   546
Gln Gln Gln Gln Gln Gln Gln Gln Gln Gln Gln Gln Gln Gln Gln Gln Gln
         60                  65                  70

cag cag cag cag cag cag cag cag cag cag cag caa gag act agc ccc      594
Gln Gln Gln Gln Gln Gln Gln Gln Gln Gln Gln Glu Thr Ser Pro
     75                  80                  85

agg cag cag cag cag cag cag ggt gag gat ggt tct ccc caa gcc cat      642
Arg Gln Gln Gln Gln Gln Gln Gly Glu Asp Gly Ser Pro Gln Ala His
 90                  95                 100                 105

cgt aga ggc ccc aca ggc tac ctg gtc ctg gat gag gaa cag caa cct      690
Arg Arg Gly Pro Thr Gly Tyr Leu Val Leu Asp Glu Glu Gln Gln Pro
                110                 115                 120
```

```
tca cag ccg cag tcg gcc ctg gag tgc cac ccc gag aga ggt tgc gtc      738
Ser Gln Pro Gln Ser Ala Leu Glu Cys His Pro Glu Arg Gly Cys Val
            125                 130                 135

cca gag cct gga gcc gcc gtg gcc gcc agc aag ggg ctg ccg cag cag      786
Pro Glu Pro Gly Ala Ala Val Ala Ala Ser Lys Gly Leu Pro Gln Gln
        140                 145                 150

ctg cca gca cct ccg gac gag gat gac tca gct gcc cca tcc acg ttg      834
Leu Pro Ala Pro Pro Asp Glu Asp Asp Ser Ala Ala Pro Ser Thr Leu
    155                 160                 165

tcc ctg ctg ggc ccc act ttc ccc ggc tta agc agc tgc tcc gct gac      882
Ser Leu Leu Gly Pro Thr Phe Pro Gly Leu Ser Ser Cys Ser Ala Asp
170                 175                 180                 185

ctt aaa gac atc ctg agc gag gcc agc acc atg caa ctc ctt cag caa      930
Leu Lys Asp Ile Leu Ser Glu Ala Ser Thr Met Gln Leu Leu Gln Gln
                190                 195                 200

cag cag cag gaa gca gta tcc gaa ggc agc agc agc ggg aga gcg agg      978
Gln Gln Gln Glu Ala Val Ser Glu Gly Ser Ser Ser Gly Arg Ala Arg
            205                 210                 215

gag gcc tcg ggg gct ccc act tcc tcc aag gac aat tac tta ggg ggc     1026
Glu Ala Ser Gly Ala Pro Thr Ser Ser Lys Asp Asn Tyr Leu Gly Gly
        220                 225                 230

act tcg acc att tct gac aac gcc aag gag ttg tgt aag gca gtg tcg     1074
Thr Ser Thr Ile Ser Asp Asn Ala Lys Glu Leu Cys Lys Ala Val Ser
    235                 240                 245

gtg tcc atg ggc ctg ggt gtg gag gcg ttg gag cat ctg agt cca ggg     1122
Val Ser Met Gly Leu Gly Val Glu Ala Leu Glu His Leu Ser Pro Gly
250                 255                 260                 265

gaa cag ctt cgg ggg gat tgc atg tac gcc cca ctt ttg gga gtt cca     1170
Glu Gln Leu Arg Gly Asp Cys Met Tyr Ala Pro Leu Leu Gly Val Pro
                270                 275                 280

ccc gct gtg cgt ccc act cct tgt gcc cca ttg gcc gaa tgc aaa ggt     1218
Pro Ala Val Arg Pro Thr Pro Cys Ala Pro Leu Ala Glu Cys Lys Gly
            285                 290                 295

tct ctg cta gac gac agc gca ggc aag agc act gaa gat act gct gag     1266
Ser Leu Leu Asp Asp Ser Ala Gly Lys Ser Thr Glu Asp Thr Ala Glu
        300                 305                 310

tat tcc cct ttc aag gga ggt tac acc aaa ggg cta gaa ggc gag agc     1314
Tyr Ser Pro Phe Lys Gly Gly Tyr Thr Lys Gly Leu Glu Gly Glu Ser
    315                 320                 325

cta ggc tgc tct ggc agc gct gca gca ggg agc tcc ggg aca ctt gaa     1362
Leu Gly Cys Ser Gly Ser Ala Ala Ala Gly Ser Ser Gly Thr Leu Glu
330                 335                 340                 345

ctg ccg tct acc ctg tct ctc tac aag tcc gga gca ctg gac gag gca     1410
Leu Pro Ser Thr Leu Ser Leu Tyr Lys Ser Gly Ala Leu Asp Glu Ala
                350                 355                 360

gct gcg tac cag agt cgc gac tac tac aac ttt cca ctg gct ctg gcc     1458
Ala Ala Tyr Gln Ser Arg Asp Tyr Tyr Asn Phe Pro Leu Ala Leu Ala
            365                 370                 375

gga ccg ccg ccc cct ccg ccg cct ccc cat ccc cac gct cgc atc aag     1506
Gly Pro Pro Pro Pro Pro Pro Pro Pro His Pro His Ala Arg Ile Lys
        380                 385                 390

ctg gag aac ccg ctg gac tac ggc agc gcc tgg gcg gct gcg gcg gcg     1554
Leu Glu Asn Pro Leu Asp Tyr Gly Ser Ala Trp Ala Ala Ala Ala Ala
    395                 400                 405

cag tgc cgc tat ggg gac ctg gcg agc ctg cat ggc gcg ggt gca gcg     1602
Gln Cys Arg Tyr Gly Asp Leu Ala Ser Leu His Gly Ala Gly Ala Ala
410                 415                 420                 425

gga ccc ggt tct ggg tca ccc tca gcc gcc gct tcc tca tcc tgg cac     1650
Gly Pro Gly Ser Gly Ser Pro Ser Ala Ala Ala Ser Ser Ser Trp His
                430                 435                 440
```

```
act ctc ttc aca gcc gaa gaa ggc cag ttg tat gga ccg tgt ggt ggt     1698
Thr Leu Phe Thr Ala Glu Glu Gly Gln Leu Tyr Gly Pro Cys Gly Gly
            445                 450                 455

ggt ggg ggt ggt ggc ggc ggc ggc ggc ggc ggc ggc ggc ggc ggc ggc     1746
Gly Gly Gly Gly Gly Gly Gly Gly Gly Gly Gly Gly Gly Gly Gly Gly
        460                 465                 470

ggc gag gcg gga gct gta gcc ccc tac ggc tac act cgg ccc cct cag     1794
Gly Glu Ala Gly Ala Val Ala Pro Tyr Gly Tyr Thr Arg Pro Pro Gln
    475                 480                 485

ggg ctg gcg ggc cag gaa agc gac ttc acc gca cct gat gtg tgg tac     1842
Gly Leu Ala Gly Gln Glu Ser Asp Phe Thr Ala Pro Asp Val Trp Tyr
490                 495                 500                 505

cct ggc ggc atg gtg agc aga gtg ccc tat ccc agt ccc act tgt gtc     1890
Pro Gly Gly Met Val Ser Arg Val Pro Tyr Pro Ser Pro Thr Cys Val
                510                 515                 520

aaa agc gaa atg ggc ccc tgg atg gat agc tac tcc gga cct tac ggg     1938
Lys Ser Glu Met Gly Pro Trp Met Asp Ser Tyr Ser Gly Pro Tyr Gly
            525                 530                 535

gac atg cgt ttg gag act gcc agg gac cat gtt ttg ccc att gac tat     1986
Asp Met Arg Leu Glu Thr Ala Arg Asp His Val Leu Pro Ile Asp Tyr
        540                 545                 550

tac ttt cca ccc cag aag acc tgc ctg atc tgt gga gat gaa gct tct     2034
Tyr Phe Pro Pro Gln Lys Thr Cys Leu Ile Cys Gly Asp Glu Ala Ser
    555                 560                 565

ggg tgt cac tat gga gct ctc aca tgt gga agc tgc aag gtc ttc ttc     2082
Gly Cys His Tyr Gly Ala Leu Thr Cys Gly Ser Cys Lys Val Phe Phe
570                 575                 580                 585

aaa aga gcc gct gaa ggg aaa cag aag tac ctg tgc gcc agc aga aat     2130
Lys Arg Ala Ala Glu Gly Lys Gln Lys Tyr Leu Cys Ala Ser Arg Asn
                590                 595                 600

gat tgc act att gat aaa ttc cga agg aaa aat tgt cca tct tgt cgt     2178
Asp Cys Thr Ile Asp Lys Phe Arg Arg Lys Asn Cys Pro Ser Cys Arg
            605                 610                 615

ctt cgg aaa tgt tat gaa gca ggg atg act ctg gga gaa aaa ttc cgg     2226
Leu Arg Lys Cys Tyr Glu Ala Gly Met Thr Leu Gly Glu Lys Phe Arg
        620                 625                 630

gtt ggc aat tgc aag cat ctc aaa atg acc aga ccc tga agaaaggctg      2275
Val Gly Asn Cys Lys His Leu Lys Met Thr Arg Pro
    635                 640                 645

acttgcctca ttcaaaatga gggctctaga gggctctagt ggatagtctg gagaaacctg   2335

gcgtctgagg cttaggagct taggtttttg ctcctcaaca cagactttga cgttggggtt   2395

gggggctact ctcttgattg ctgactccct ccagcgggac caatagtgtt ttcctacctc   2455

acagggatgt tgtgaggacg ggctgtagaa gtaatagtgg ttaccactca tgtagttgtg   2515

agtatcatga ttattgtttc ctgtaatgtg gcttggcatt ggcaaagtgc tttttgattg   2575

ttcttgatca catatgatgg gggccaggca ctgactcagg cggatgcagt gaagctctgg   2635

ctcagtcgct tgcttttcgt ggtgtgctgc caggaagaaa ctttgctgat gggactcaag   2695

gtgtcacctt ggacaagaag caactgtgtc tgtctgaggt tcctgtggcc atctttattt   2755

gtgtattagg caattcgtat ttccccctta ggttctagcc ttctggatcc cagccagtga   2815

cctagatctt agcctcaggc cctgtcactg agctgaaggt agtagctgat ccacagaagt   2875

tcagtaaaca aggaccagat ttctgcttct ccaggagaag aagccagcca acccctctct   2935

tcaaacacac tgagagacta cagtccgact ttccctctta catctagcct tactgtagcc   2995

acactccttg attgctctct cacatcacat gcttctcttc atcagttgta agcctctcat   3055
```

```
tcttctccca agccagactc aaatattgta ttgatgtcaa agaagaatca cttagagttt   3115

ggaatatctt gttctctctc tgctccatag cttccatatt gacaccagtt tctttctagt   3175

ggagaagtgg agtctgtgaa gccagggaaa cacacatgtg agagtcagaa ggactctccc   3235

tgacttgcct ggggcctgtc tttcccacct tctccagtct gtctaaacac acacacacac   3295

acacacacac acacacacac acacacacac gctctctctc tctctccccc cccaacacac   3355

acacactctc tctctcacac acacacacat acacacacac ttctttctct ttcccctgac   3415

tcagcaacat tctggagaaa agccaaggaa ggacttcagg aggggagttt ccccttctc   3475

agggcagaat tttaatctcc agaccaacaa gaagttccct aatgtggatt gaaaggctaa   3535

tgaggtttat ttttaactac tttctatttg tttgaatgtt gcatatttct actagtgaaa   3595

ttttccctta ataaagccat taatacaccc aaaaaaaaaa aaaaaa                  3641


<210> SEQ ID NO 5
<211> LENGTH: 2430
<212> TYPE: DNA
<213> ORGANISM: Homo sapiens
<220> FEATURE:
<221> NAME/KEY: CDS
<222> LOCATION: (328)...(2274)

<400> SEQUENCE: 5

gacactgaat ttggaaggtg gaggattttg tttttttctt ttaagatctg ggcatctttt     60

gaatctaccc ttcaagtatt aagagacaga ctgtgagcct agcagggcag atcttgtcca    120

ccgtgtgtct tcttctgcac gagactttga ggctgtcaga gcgctttttg cgtggttgct    180

cccgcaagtt tccttctctg gagcttcccg caggtgggca gctagctgca gcgactaccg    240

catcatcaca gcctgttgaa ctcttctgag caagagaagg ggaggcgggg taagggaagt    300

aggtggaaga ttcagccaag ctcaagg atg gaa gtg cag tta ggg ctg gga agg    354
                              Met Glu Val Gln Leu Gly Leu Gly Arg
                               1               5

gtc tac cct cgg ccg ccg tcc aag acc tac cga gga gct ttc cag aat      402
Val Tyr Pro Arg Pro Pro Ser Lys Thr Tyr Arg Gly Ala Phe Gln Asn
 10                  15                  20                  25

ctg ttc cag agc gtg cgc gaa gtg atc cag aac ccg ggc ccc agg cac      450
Leu Phe Gln Ser Val Arg Glu Val Ile Gln Asn Pro Gly Pro Arg His
                 30                  35                  40

cca gag gcc gcg agc gca gca cct ccc ggc gcc agt ttg ctg ctg cag      498
Pro Glu Ala Ala Ser Ala Ala Pro Pro Gly Ala Ser Leu Leu Leu Gln
             45                  50                  55

cag cag cag cag cag cag cag cag cag cag cag cag cag cag cag cag      546
Gln Gln Gln Gln Gln Gln Gln Gln Gln Gln Gln Gln Gln Gln Gln Gln
         60                  65                  70

cag cag cag cag cag cag cag cag cag cag caa gag act agc ccc agg      594
Gln Gln Gln Gln Gln Gln Gln Gln Gln Gln Glu Thr Ser Pro Arg
     75                  80                  85

cag cag cag cag cag cag ggt gag gat ggt tct ccc caa gcc cat cgt      642
Gln Gln Gln Gln Gln Gln Gly Glu Asp Gly Ser Pro Gln Ala His Arg
 90                  95                 100                 105

aga ggc ccc aca ggc tac ctg gtc ctg gat gag gaa cag caa cct tca      690
Arg Gly Pro Thr Gly Tyr Leu Val Leu Asp Glu Glu Gln Gln Pro Ser
                110                 115                 120

cag ccg cag tcg gcc ctg gag tgc cac ccc gag aga ggt tgc gtc cca      738
Gln Pro Gln Ser Ala Leu Glu Cys His Pro Glu Arg Gly Cys Val Pro
            125                 130                 135

gag cct gga gcc gcc gtg gcc gcc agc aag ggg ctg ccg cag cag ctg      786
Glu Pro Gly Ala Ala Val Ala Ala Ser Lys Gly Leu Pro Gln Gln Leu
```

```
        140                 145                 150

cca gca cct ccg gac gag gat gac tca gct gcc cca tcc acg ttg tcc      834
Pro Ala Pro Pro Asp Glu Asp Asp Ser Ala Ala Pro Ser Thr Leu Ser
    155                 160                 165

ctg ctg ggc ccc act ttc ccc ggc tta agc agc tgc tcc gct gac ctt      882
Leu Leu Gly Pro Thr Phe Pro Gly Leu Ser Ser Cys Ser Ala Asp Leu
170                 175                 180                 185

aaa gac atc ctg agc gag gcc agc acc atg caa ctc ctt cag caa cag      930
Lys Asp Ile Leu Ser Glu Ala Ser Thr Met Gln Leu Leu Gln Gln Gln
                190                 195                 200

cag cag gaa gca gta tcc gaa ggc agc agc agc ggg aga gcg agg gag      978
Gln Gln Glu Ala Val Ser Glu Gly Ser Ser Ser Gly Arg Ala Arg Glu
            205                 210                 215

gcc tcg ggg gct ccc act tcc tcc aag gac aat tac tta ggg ggc act     1026
Ala Ser Gly Ala Pro Thr Ser Ser Lys Asp Asn Tyr Leu Gly Gly Thr
        220                 225                 230

tcg acc att tct gac aac gcc aag gag ttg tgt aag gca gtg tcg gtg     1074
Ser Thr Ile Ser Asp Asn Ala Lys Glu Leu Cys Lys Ala Val Ser Val
    235                 240                 245

tcc atg ggc ctg ggt gtg gag gcg ttg gag cat ctg agt cca ggg gaa     1122
Ser Met Gly Leu Gly Val Glu Ala Leu Glu His Leu Ser Pro Gly Glu
250                 255                 260                 265

cag ctt cgg ggg gat tgc atg tac gcc cca ctt ttg gga gtt cca ccc     1170
Gln Leu Arg Gly Asp Cys Met Tyr Ala Pro Leu Leu Gly Val Pro Pro
                270                 275                 280

gct gtg cgt ccc act cct tgt gcc cca ttg gcc gaa tgc aaa ggt tct     1218
Ala Val Arg Pro Thr Pro Cys Ala Pro Leu Ala Glu Cys Lys Gly Ser
            285                 290                 295

ctg cta gac gac agc gca ggc aag agc act gaa gat act gct gag tat     1266
Leu Leu Asp Asp Ser Ala Gly Lys Ser Thr Glu Asp Thr Ala Glu Tyr
        300                 305                 310

tcc cct ttc aag gga ggt tac acc aaa ggg cta gaa ggc gag agc cta     1314
Ser Pro Phe Lys Gly Gly Tyr Thr Lys Gly Leu Glu Gly Glu Ser Leu
    315                 320                 325

ggc tgc tct ggc agc gct gca gca ggg agc tcc ggg aca ctt gaa ctg     1362
Gly Cys Ser Gly Ser Ala Ala Ala Gly Ser Ser Gly Thr Leu Glu Leu
330                 335                 340                 345

ccg tct acc ctg tct ctc tac aag tcc gga gca ctg gac gag gca gct     1410
Pro Ser Thr Leu Ser Leu Tyr Lys Ser Gly Ala Leu Asp Glu Ala Ala
                350                 355                 360

gcg tac cag agt cgc gac tac tac aac ttt cca ctg gct ctg gcc gga     1458
Ala Tyr Gln Ser Arg Asp Tyr Tyr Asn Phe Pro Leu Ala Leu Ala Gly
            365                 370                 375

ccg ccg ccc cct ccg ccg cct ccc cat ccc cac gct cgc atc aag ctg     1506
Pro Pro Pro Pro Pro Pro Pro Pro His Pro His Ala Arg Ile Lys Leu
        380                 385                 390

gag aac ccg ctg gac tac ggc agc gcc tgg gcg gct gcg gcg gcg cag     1554
Glu Asn Pro Leu Asp Tyr Gly Ser Ala Trp Ala Ala Ala Ala Ala Gln
    395                 400                 405

tgc cgc tat ggg gac ctg gcg agc ctg cat ggc gcg ggt gca gcg gga     1602
Cys Arg Tyr Gly Asp Leu Ala Ser Leu His Gly Ala Gly Ala Ala Gly
410                 415                 420                 425

ccc ggt tct ggg tca ccc tca gcc gcc gct tcc tca tcc tgg cac act     1650
Pro Gly Ser Gly Ser Pro Ser Ala Ala Ala Ser Ser Ser Trp His Thr
                430                 435                 440

ctc ttc aca gcc gaa gaa ggc cag ttg tat gga ccg tgt ggt ggt ggt     1698
Leu Phe Thr Ala Glu Glu Gly Gln Leu Tyr Gly Pro Cys Gly Gly Gly
            445                 450                 455

ggg ggt ggt ggc ggc ggc ggc ggc ggc ggc ggc ggc ggc ggc ggc ggc     1746
```

```
Gly Gly Gly Gly Gly Gly Gly Gly Gly Gly Gly Gly Gly Gly Gly
        460                 465                 470

gag gcg gga gct gta gcc ccc tac ggc tac act cgg ccc cct cag ggg     1794
Glu Ala Gly Ala Val Ala Pro Tyr Gly Tyr Thr Arg Pro Pro Gln Gly
    475                 480                 485

ctg gcg ggc cag gaa agc gac ttc acc gca cct gat gtg tgg tac cct     1842
Leu Ala Gly Gln Glu Ser Asp Phe Thr Ala Pro Asp Val Trp Tyr Pro
490                 495                 500                 505

ggc ggc atg gtg agc aga gtg ccc tat ccc agt ccc act tgt gtc aaa     1890
Gly Gly Met Val Ser Arg Val Pro Tyr Pro Ser Pro Thr Cys Val Lys
                510                 515                 520

agc gaa atg ggc ccc tgg atg gat agc tac tcc gga cct tac ggg gac     1938
Ser Glu Met Gly Pro Trp Met Asp Ser Tyr Ser Gly Pro Tyr Gly Asp
            525                 530                 535

atg cgt ttg gag act gcc agg gac cat gtt ttg ccc att gac tat tac     1986
Met Arg Leu Glu Thr Ala Arg Asp His Val Leu Pro Ile Asp Tyr Tyr
        540                 545                 550

ttt cca ccc cag aag acc tgc ctg atc tgt gga gat gaa gct tct ggg     2034
Phe Pro Pro Gln Lys Thr Cys Leu Ile Cys Gly Asp Glu Ala Ser Gly
    555                 560                 565

tgt cac tat gga gct ctc aca tgt gga agc tgc aag gtc ttc ttc aaa     2082
Cys His Tyr Gly Ala Leu Thr Cys Gly Ser Cys Lys Val Phe Phe Lys
570                 575                 580                 585

aga gcc gct gaa ggg aaa cag aag tac ctg tgc gcc agc aga aat gat     2130
Arg Ala Ala Glu Gly Lys Gln Lys Tyr Leu Cys Ala Ser Arg Asn Asp
                590                 595                 600

tgc act att gat aaa ttc cga agg aaa aat tgt cca tct tgt cgt ctt     2178
Cys Thr Ile Asp Lys Phe Arg Arg Lys Asn Cys Pro Ser Cys Arg Leu
            605                 610                 615

cgg aaa tgt tat gaa gca ggg atg act ctg gga gca gct gtt gtt gtt     2226
Arg Lys Cys Tyr Glu Ala Gly Met Thr Leu Gly Ala Ala Val Val Val
        620                 625                 630

tct gaa aga atc ttg agg gtg ttt gga gtc tca gaa tgg ctt cct taa     2274
Ser Glu Arg Ile Leu Arg Val Phe Gly Val Ser Glu Trp Leu Pro
    635                 640                 645

agactacctt cagactctca gctgctcatc cacaacagag atcagccctt ctttgtagat   2334

gattcattcc tggctgcatt tgaaaaccac atattgttaa ttgcttgacg aatttaaatc   2394

ccttgactac ttttcatttc aaaaaaaaaa aaaaaa                             2430


<210> SEQ ID NO 6
<211> LENGTH: 2427
<212> TYPE: DNA
<213> ORGANISM: Homo sapiens
<220> FEATURE:
<221> NAME/KEY: CDS
<222> LOCATION: (328)...(2271)

<400> SEQUENCE: 6

gacactgaat ttggaaggtg gaggattttg tttttttctt ttaagatctg ggcatctttt     60

gaatctaccc ttcaagtatt aagagacaga ctgtgagcct agcagggcag atcttgtcca    120

ccgtgtgtct tcttctgcac gagactttga ggctgtcaga gcgctttttg cgtggttgct    180

cccgcaagtt tccttctctg gagcttcccg caggtgggca gctagctgca gcgactaccg    240

catcatcaca gcctgttgaa ctcttctgag caagagaagg ggaggcgggg taagggaagt    300

aggtggaaga ttcagccaag ctcaagg atg gaa gtg cag tta ggg ctg gga agg    354
                              Met Glu Val Gln Leu Gly Leu Gly Arg
                               1               5

gtc tac cct cgg ccg ccg tcc aag acc tac cga gga gct ttc cag aat      402
```

```
Val Tyr Pro Arg Pro Pro Ser Lys Thr Tyr Arg Gly Ala Phe Gln Asn
 10                  15                  20                  25

ctg ttc cag agc gtg cgc gaa gtg atc cag aac ccg ggc ccc agg cac      450
Leu Phe Gln Ser Val Arg Glu Val Ile Gln Asn Pro Gly Pro Arg His
                 30                  35                  40

cca gag gcc gcg agc gca gca cct ccc ggc gcc agt ttg ctg ctg cag      498
Pro Glu Ala Ala Ser Ala Ala Pro Pro Gly Ala Ser Leu Leu Leu Gln
             45                  50                  55

cag cag cag cag cag cag cag cag cag cag cag cag cag cag cag cag      546
Gln Gln Gln Gln Gln Gln Gln Gln Gln Gln Gln Gln Gln Gln Gln Gln
         60                  65                  70

cag cag cag cag cag cag cag cag cag cag caa gag act agc ccc agg      594
Gln Gln Gln Gln Gln Gln Gln Gln Gln Gln Glu Thr Ser Pro Arg
     75                  80                  85

cag cag cag cag cag cag ggt gag gat ggt tct ccc caa gcc cat cgt      642
Gln Gln Gln Gln Gln Gln Gly Glu Asp Gly Ser Pro Gln Ala His Arg
 90                  95                 100                 105

aga ggc ccc aca ggc tac ctg gtc ctg gat gag gaa cag caa cct tca      690
Arg Gly Pro Thr Gly Tyr Leu Val Leu Asp Glu Glu Gln Gln Pro Ser
                110                 115                 120

cag ccg cag tcg gcc ctg gag tgc cac ccc gag aga ggt tgc gtc cca      738
Gln Pro Gln Ser Ala Leu Glu Cys His Pro Glu Arg Gly Cys Val Pro
            125                 130                 135

gag cct gga gcc gcc gtg gcc gcc agc aag ggg ctg ccg cag cag ctg      786
Glu Pro Gly Ala Ala Val Ala Ala Ser Lys Gly Leu Pro Gln Gln Leu
        140                 145                 150

cca gca cct ccg gac gag gat gac tca gct gcc cca tcc acg ttg tcc      834
Pro Ala Pro Pro Asp Glu Asp Asp Ser Ala Ala Pro Ser Thr Leu Ser
    155                 160                 165

ctg ctg ggc ccc act ttc ccc ggc tta agc agc tgc tcc gct gac ctt      882
Leu Leu Gly Pro Thr Phe Pro Gly Leu Ser Ser Cys Ser Ala Asp Leu
170                 175                 180                 185

aaa gac atc ctg agc gag gcc agc acc atg caa ctc ctt cag caa cag      930
Lys Asp Ile Leu Ser Glu Ala Ser Thr Met Gln Leu Leu Gln Gln Gln
                190                 195                 200

cag cag gaa gca gta tcc gaa ggc agc agc agc ggg aga gcg agg gag      978
Gln Gln Glu Ala Val Ser Glu Gly Ser Ser Ser Gly Arg Ala Arg Glu
            205                 210                 215

gcc tcg ggg gct ccc act tcc tcc aag gac aat tac tta ggg ggc act     1026
Ala Ser Gly Ala Pro Thr Ser Ser Lys Asp Asn Tyr Leu Gly Gly Thr
        220                 225                 230

tcg acc att tct gac aac gcc aag gag ttg tgt aag gca gtg tcg gtg     1074
Ser Thr Ile Ser Asp Asn Ala Lys Glu Leu Cys Lys Ala Val Ser Val
    235                 240                 245

tcc atg ggc ctg ggt gtg gag gcg ttg gag cat ctg agt cca ggg gaa     1122
Ser Met Gly Leu Gly Val Glu Ala Leu Glu His Leu Ser Pro Gly Glu
250                 255                 260                 265

cag ctt cgg ggg gat tgc atg tac gcc cca ctt ttg gga gtt cca ccc     1170
Gln Leu Arg Gly Asp Cys Met Tyr Ala Pro Leu Leu Gly Val Pro Pro
                270                 275                 280

gct gtg cgt ccc act cct tgt gcc cca ttg gcc gaa tgc aaa ggt tct     1218
Ala Val Arg Pro Thr Pro Cys Ala Pro Leu Ala Glu Cys Lys Gly Ser
            285                 290                 295

ctg cta gac gac agc gca ggc aag agc act gaa gat act gct gag tat     1266
Leu Leu Asp Asp Ser Ala Gly Lys Ser Thr Glu Asp Thr Ala Glu Tyr
        300                 305                 310

tcc cct ttc aag gga ggt tac acc aaa ggg cta gaa ggc gag agc cta     1314
Ser Pro Phe Lys Gly Gly Tyr Thr Lys Gly Leu Glu Gly Glu Ser Leu
    315                 320                 325
```

```
ggc tgc tct ggc agc gct gca gca ggg agc tcc ggg aca ctt gaa ctg     1362
Gly Cys Ser Gly Ser Ala Ala Ala Gly Ser Ser Gly Thr Leu Glu Leu
330                 335                 340                 345

ccg tct acc ctg tct ctc tac aag tcc gga gca ctg gac gag gca gct     1410
Pro Ser Thr Leu Ser Leu Tyr Lys Ser Gly Ala Leu Asp Glu Ala Ala
                350                 355                 360

gcg tac cag agt cgc gac tac tac aac ttt cca ctg gct ctg gcc gga     1458
Ala Tyr Gln Ser Arg Asp Tyr Tyr Asn Phe Pro Leu Ala Leu Ala Gly
            365                 370                 375

ccg ccg ccc cct ccg ccg cct ccc cat ccc cac gct cgc atc aag ctg     1506
Pro Pro Pro Pro Pro Pro Pro Pro His Pro His Ala Arg Ile Lys Leu
        380                 385                 390

gag aac ccg ctg gac tac ggc agc gcc tgg gcg gct gcg gcg gcg cag     1554
Glu Asn Pro Leu Asp Tyr Gly Ser Ala Trp Ala Ala Ala Ala Ala Gln
    395                 400                 405

tgc cgc tat ggg gac ctg gcg agc ctg cat ggc gcg ggt gca gcg gga     1602
Cys Arg Tyr Gly Asp Leu Ala Ser Leu His Gly Ala Gly Ala Ala Gly
410                 415                 420                 425

ccc ggt tct ggg tca ccc tca gcc gcc gct tcc tca tcc tgg cac act     1650
Pro Gly Ser Gly Ser Pro Ser Ala Ala Ala Ser Ser Ser Trp His Thr
                430                 435                 440

ctc ttc aca gcc gaa gaa ggc cag ttg tat gga ccg tgt ggt ggt ggt     1698
Leu Phe Thr Ala Glu Glu Gly Gln Leu Tyr Gly Pro Cys Gly Gly Gly
            445                 450                 455

ggg ggt ggt ggc ggc ggc ggc ggc ggc ggc ggc ggc ggc ggc ggc ggc     1746
Gly Gly Gly Gly Gly Gly Gly Gly Gly Gly Gly Gly Gly Gly Gly Gly
        460                 465                 470

gag gcg gga gct gta gcc ccc tac ggc tac act cgg ccc cct cag ggg     1794
Glu Ala Gly Ala Val Ala Pro Tyr Gly Tyr Thr Arg Pro Pro Gln Gly
    475                 480                 485

ctg gcg ggc cag gaa agc gac ttc acc gca cct gat gtg tgg tac cct     1842
Leu Ala Gly Gln Glu Ser Asp Phe Thr Ala Pro Asp Val Trp Tyr Pro
490                 495                 500                 505

ggc ggc atg gtg agc aga gtg ccc tat ccc agt ccc act tgt gtc aaa     1890
Gly Gly Met Val Ser Arg Val Pro Tyr Pro Ser Pro Thr Cys Val Lys
                510                 515                 520

agc gaa atg ggc ccc tgg atg gat agc tac tcc gga cct tac ggg gac     1938
Ser Glu Met Gly Pro Trp Met Asp Ser Tyr Ser Gly Pro Tyr Gly Asp
            525                 530                 535

atg cgt ttg gag act gcc agg gac cat gtt ttg ccc att gac tat tac     1986
Met Arg Leu Glu Thr Ala Arg Asp His Val Leu Pro Ile Asp Tyr Tyr
        540                 545                 550

ttt cca ccc cag aag acc tgc ctg atc tgt gga gat gaa gct tct ggg     2034
Phe Pro Pro Gln Lys Thr Cys Leu Ile Cys Gly Asp Glu Ala Ser Gly
    555                 560                 565

tgt cac tat gga gct ctc aca tgt gga agc tgc aag gtc ttc ttc aaa     2082
Cys His Tyr Gly Ala Leu Thr Cys Gly Ser Cys Lys Val Phe Phe Lys
570                 575                 580                 585

aga gcc gct gaa ggg aaa cag aag tac ctg tgc gcc agc aga aat gat     2130
Arg Ala Ala Glu Gly Lys Gln Lys Tyr Leu Cys Ala Ser Arg Asn Asp
                590                 595                 600

tgc act att gat aaa ttc cga agg aaa aat tgt cca tct tgt cgt ctt     2178
Cys Thr Ile Asp Lys Phe Arg Arg Lys Asn Cys Pro Ser Cys Arg Leu
            605                 610                 615

cgg aaa tgt tat gaa gca ggg att ctg gga gca gct gtt gtt gtt tct     2226
Arg Lys Cys Tyr Glu Ala Gly Ile Leu Gly Ala Ala Val Val Val Ser
        620                 625                 630

gaa aga atc ttg agg gtg ttt gga gtc tca gaa tgg ctt cct taa         2271
Glu Arg Ile Leu Arg Val Phe Gly Val Ser Glu Trp Leu Pro
    635                 640                 645
```

```
agactacctt cagactctca gctgctcatc cacaacagag atcagccctt ctttgtagat   2331

gattcattcc tggctgcatt tgaaaaccac atattgttaa ttgcttgacg aatttaaatc   2391

ccttgactac ttttcatttc aaaaaaaaaa aaaaaa                             2427


<210> SEQ ID NO 7
<211> LENGTH: 4039
<212> TYPE: DNA
<213> ORGANISM: Homo sapiens
<220> FEATURE:
<221> NAME/KEY: CDS
<222> LOCATION: (328)...(2376)

<400> SEQUENCE: 7

gacactgaat ttggaaggtg gaggattttg tttttttctt ttaagatctg ggcatctttt     60

gaatctaccc ttcaagtatt aagagacaga ctgtgagcct agcagggcag atcttgtcca    120

ccgtgtgtct tcttctgcac gagactttga ggctgtcaga gcgctttttg cgtggttgct    180

cccgcaagtt tccttctctg gagcttcccg caggtgggca gctagctgca gcgactaccg    240

catcatcaca gcctgttgaa ctcttctgag caagagaagg ggaggcgggg taagggaagt    300

aggtggaaga ttcagccaag ctcaagg atg gaa gtg cag tta ggg ctg gga agg    354
                              Met Glu Val Gln Leu Gly Leu Gly Arg
                               1               5

gtc tac cct cgg ccg ccg tcc aag acc tac cga gga gct ttc cag aat      402
Val Tyr Pro Arg Pro Pro Ser Lys Thr Tyr Arg Gly Ala Phe Gln Asn
 10                  15                  20                  25

ctg ttc cag agc gtg cgc gaa gtg atc cag aac ccg ggc ccc agg cac      450
Leu Phe Gln Ser Val Arg Glu Val Ile Gln Asn Pro Gly Pro Arg His
                 30                  35                  40

cca gag gcc gcg agc gca gca cct ccc ggc gcc agt ttg ctg ctg cag      498
Pro Glu Ala Ala Ser Ala Ala Pro Pro Gly Ala Ser Leu Leu Leu Gln
             45                  50                  55

cag cag cag cag cag cag cag cag cag cag cag cag cag cag cag cag      546
Gln Gln Gln Gln Gln Gln Gln Gln Gln Gln Gln Gln Gln Gln Gln Gln
         60                  65                  70

cag cag cag cag cag cag cag cag cag cag cag caa gag act agc ccc      594
Gln Gln Gln Gln Gln Gln Gln Gln Gln Gln Gln Glu Thr Ser Pro
     75                  80                  85

agg cag cag cag cag cag cag ggt gag gat ggt tct ccc caa gcc cat      642
Arg Gln Gln Gln Gln Gln Gln Gly Glu Asp Gly Ser Pro Gln Ala His
 90                  95                 100                 105

cgt aga ggc ccc aca ggc tac ctg gtc ctg gat gag gaa cag caa cct      690
Arg Arg Gly Pro Thr Gly Tyr Leu Val Leu Asp Glu Glu Gln Gln Pro
                110                 115                 120

tca cag ccg cag tcg gcc ctg gag tgc cac ccc gag aga ggt tgc gtc      738
Ser Gln Pro Gln Ser Ala Leu Glu Cys His Pro Glu Arg Gly Cys Val
            125                 130                 135

cca gag cct gga gcc gcc gtg gcc gcc agc aag ggg ctg ccg cag cag      786
Pro Glu Pro Gly Ala Ala Val Ala Ala Ser Lys Gly Leu Pro Gln Gln
        140                 145                 150

ctg cca gca cct ccg gac gag gat gac tca gct gcc cca tcc acg ttg      834
Leu Pro Ala Pro Pro Asp Glu Asp Asp Ser Ala Ala Pro Ser Thr Leu
    155                 160                 165

tcc ctg ctg ggc ccc act ttc ccc ggc tta agc agc tgc tcc gct gac      882
Ser Leu Leu Gly Pro Thr Phe Pro Gly Leu Ser Ser Cys Ser Ala Asp
170                 175                 180                 185

ctt aaa gac atc ctg agc gag gcc agc acc atg caa ctc ctt cag caa      930
Leu Lys Asp Ile Leu Ser Glu Ala Ser Thr Met Gln Leu Leu Gln Gln
                190                 195                 200
```

```
cag cag cag gaa gca gta tcc gaa ggc agc agc agc ggg aga gcg agg      978
Gln Gln Gln Glu Ala Val Ser Glu Gly Ser Ser Ser Gly Arg Ala Arg
            205                 210                 215

gag gcc tcg ggg gct ccc act tcc tcc aag gac aat tac tta ggg ggc     1026
Glu Ala Ser Gly Ala Pro Thr Ser Ser Lys Asp Asn Tyr Leu Gly Gly
        220                 225                 230

act tcg acc att tct gac aac gcc aag gag ttg tgt aag gca gtg tcg     1074
Thr Ser Thr Ile Ser Asp Asn Ala Lys Glu Leu Cys Lys Ala Val Ser
    235                 240                 245

gtg tcc atg ggc ctg ggt gtg gag gcg ttg gag cat ctg agt cca ggg     1122
Val Ser Met Gly Leu Gly Val Glu Ala Leu Glu His Leu Ser Pro Gly
250                 255                 260                 265

gaa cag ctt cgg ggg gat tgc atg tac gcc cca ctt ttg gga gtt cca     1170
Glu Gln Leu Arg Gly Asp Cys Met Tyr Ala Pro Leu Leu Gly Val Pro
                270                 275                 280

ccc gct gtg cgt ccc act cct tgt gcc cca ttg gcc gaa tgc aaa ggt     1218
Pro Ala Val Arg Pro Thr Pro Cys Ala Pro Leu Ala Glu Cys Lys Gly
            285                 290                 295

tct ctg cta gac gac agc gca ggc aag agc act gaa gat act gct gag     1266
Ser Leu Leu Asp Asp Ser Ala Gly Lys Ser Thr Glu Asp Thr Ala Glu
        300                 305                 310

tat tcc cct ttc aag gga ggt tac acc aaa ggg cta gaa ggc gag agc     1314
Tyr Ser Pro Phe Lys Gly Gly Tyr Thr Lys Gly Leu Glu Gly Glu Ser
    315                 320                 325

cta ggc tgc tct ggc agc gct gca gca ggg agc tcc ggg aca ctt gaa     1362
Leu Gly Cys Ser Gly Ser Ala Ala Ala Gly Ser Ser Gly Thr Leu Glu
330                 335                 340                 345

ctg ccg tct acc ctg tct ctc tac aag tcc gga gca ctg gac gag gca     1410
Leu Pro Ser Thr Leu Ser Leu Tyr Lys Ser Gly Ala Leu Asp Glu Ala
                350                 355                 360

gct gcg tac cag agt cgc gac tac tac aac ttt cca ctg gct ctg gcc     1458
Ala Ala Tyr Gln Ser Arg Asp Tyr Tyr Asn Phe Pro Leu Ala Leu Ala
            365                 370                 375

gga ccg ccg ccc cct ccg ccg cct ccc cat ccc cac gct cgc atc aag     1506
Gly Pro Pro Pro Pro Pro Pro Pro Pro His Pro His Ala Arg Ile Lys
        380                 385                 390

ctg gag aac ccg ctg gac tac ggc agc gcc tgg gcg gct gcg gcg gcg     1554
Leu Glu Asn Pro Leu Asp Tyr Gly Ser Ala Trp Ala Ala Ala Ala Ala
    395                 400                 405

cag tgc cgc tat ggg gac ctg gcg agc ctg cat ggc gcg ggt gca gcg     1602
Gln Cys Arg Tyr Gly Asp Leu Ala Ser Leu His Gly Ala Gly Ala Ala
410                 415                 420                 425

gga ccc ggt tct ggg tca ccc tca gcc gcc gct tcc tca tcc tgg cac     1650
Gly Pro Gly Ser Gly Ser Pro Ser Ala Ala Ala Ser Ser Ser Trp His
                430                 435                 440

act ctc ttc aca gcc gaa gaa ggc cag ttg tat gga ccg tgt ggt ggt     1698
Thr Leu Phe Thr Ala Glu Glu Gly Gln Leu Tyr Gly Pro Cys Gly Gly
            445                 450                 455

ggt ggg ggt ggt ggc ggc ggc ggc ggc ggc ggc ggc ggc ggc ggc ggc     1746
Gly Gly Gly Gly Gly Gly Gly Gly Gly Gly Gly Gly Gly Gly Gly Gly
        460                 465                 470

ggc gag gcg gga gct gta gcc ccc tac ggc tac act cgg ccc cct cag     1794
Gly Glu Ala Gly Ala Val Ala Pro Tyr Gly Tyr Thr Arg Pro Pro Gln
    475                 480                 485

ggg ctg gcg ggc cag gaa agc gac ttc acc gca cct gat gtg tgg tac     1842
Gly Leu Ala Gly Gln Glu Ser Asp Phe Thr Ala Pro Asp Val Trp Tyr
490                 495                 500                 505

cct ggc ggc atg gtg agc aga gtg ccc tat ccc agt ccc act tgt gtc     1890
Pro Gly Gly Met Val Ser Arg Val Pro Tyr Pro Ser Pro Thr Cys Val
```

```
                510                 515                 520

aaa agc gaa atg ggc ccc tgg atg gat agc tac tcc gga cct tac ggg     1938
Lys Ser Glu Met Gly Pro Trp Met Asp Ser Tyr Ser Gly Pro Tyr Gly
            525                 530                 535

gac atg cgt ttg gag act gcc agg gac cat gtt ttg ccc att gac tat     1986
Asp Met Arg Leu Glu Thr Ala Arg Asp His Val Leu Pro Ile Asp Tyr
        540                 545                 550

tac ttt cca ccc cag aag acc tgc ctg atc tgt gga gat gaa gct tct     2034
Tyr Phe Pro Pro Gln Lys Thr Cys Leu Ile Cys Gly Asp Glu Ala Ser
    555                 560                 565

ggg tgt cac tat gga gct ctc aca tgt gga agc tgc aag gtc ttc ttc     2082
Gly Cys His Tyr Gly Ala Leu Thr Cys Gly Ser Cys Lys Val Phe Phe
570                 575                 580                 585

aaa aga gcc gct gaa ggg aaa cag aag tac ctg tgc gcc agc aga aat     2130
Lys Arg Ala Ala Glu Gly Lys Gln Lys Tyr Leu Cys Ala Ser Arg Asn
                590                 595                 600

gat tgc act att gat aaa ttc cga agg aaa aat tgt cca tct tgt cgt     2178
Asp Cys Thr Ile Asp Lys Phe Arg Arg Lys Asn Cys Pro Ser Cys Arg
            605                 610                 615

ctt cgg aaa tgt tat gaa gca ggg atg act ctg gga gga ttt ttc aga     2226
Leu Arg Lys Cys Tyr Glu Ala Gly Met Thr Leu Gly Gly Phe Phe Arg
        620                 625                 630

atg aac aaa tta aaa gaa tca tca gac act aac ccc aag cca tac tgc     2274
Met Asn Lys Leu Lys Glu Ser Ser Asp Thr Asn Pro Lys Pro Tyr Cys
    635                 640                 645

atg gca gca cca atg gga ctg aca gaa aac aac aga aat agg aag aaa     2322
Met Ala Ala Pro Met Gly Leu Thr Glu Asn Asn Arg Asn Arg Lys Lys
650                 655                 660                 665

tcc tac aga gaa aca aac ttg aaa gct gtc tca tgg cct ttg aat cat     2370
Ser Tyr Arg Glu Thr Asn Leu Lys Ala Val Ser Trp Pro Leu Asn His
                670                 675                 680

act taa gttttatgat ggaaggatac gactatgaag aaagacacag agcaacatca      2426
Thr

gacagtcaag aatttcagag ccagctggca tgcagtggac ctcatgccag cccattttat   2486

gactatttag ggaaacagaa gtacctgtgc gccagcagaa atgattgcac tattgataaa   2546

ttccgaagga aaaattgtcc atcttgtcgt cttcggaaat gttatgaagc agggatgact   2606

ctgggagaaa aattccgggt tggcaattgc aagcatctca aaatgaccag accctgaaga   2666

aaggctgact tgcctcattc aaaatgaggg ctctagaggg ctctagtgga tagtctggag   2726

aaacctggcg tctgaggctt aggagcttag gtttttgctc ctcaacacag actttgacgt   2786

tggggttggg ggctactctc ttgattgctg actccctcca gcgggaccaa tagtgttttc   2846

ctacctcaca gggatgttgt gaggacgggc tgtagaagta atagtggtta ccactcatgt   2906

agttgtgagt atcatgatta ttgtttcctg taatgtggct tggcattggc aaagtgcttt   2966

ttgattgttc ttgatcacat atgatggggg ccaggcactg actcaggcgg atgcagtgaa   3026

gctctggctc agtcgcttgc ttttcgtggt gtgctgccag gaagaaactt tgctgatggg   3086

actcaaggtg tcaccttgga caagaagcaa ctgtgtctgt ctgaggttcc tgtggccatc   3146

tttatttgtg tattaggcaa ttcgtatttc ccccttaggt tctagccttc tggatcccag   3206

ccagtgacct agatcttagc ctcaggccct gtcactgagc tgaaggtagt agctgatcca   3266

cagaagttca gtaaacaagg accagatttc tgcttctcca ggagaagaag ccagccaacc   3326

cctctcttca aacacactga gagactacag tccgactttc cctcttacat ctagccttac   3386

tgtagccaca ctccttgatt gctctctcac atcacatgct tctcttcatc agttgtaagc   3446
```

```
ctctcattct tctcccaagc cagactcaaa tattgtattg atgtcaaaga agaatcactt   3506

agagtttgga atatcttgtt ctctctctgc tccatagctt ccatattgac accagtttct   3566

ttctagtgga gaagtggagt ctgtgaagcc agggaaacac acatgtgaga gtcagaagga   3626

ctctccctga cttgcctggg gcctgtcttt cccaccttct ccagtctgtc taaacacaca   3686

cacacacaca cacacacaca cacacacaca cacacacgct ctctctctct ctcccccccc   3746

aacacacaca cactctctct ctcacacaca cacacataca cacacacttc tttctctttc   3806

ccctgactca gcaacattct ggagaaaagc caaggaagga cttcaggagg ggagtttccc   3866

ccttctcagg gcagaatttt aatctccaga ccaacaagaa gttccctaat gtggattgaa   3926

aggctaatga ggtttatttt taactacttt ctatttgttt gaatgttgca tatttctact   3986

agtgaaattt tcccttaata aagccattaa tacacccaaa aaaaaaaaaa aaa          4039


<210> SEQ ID NO 8
<211> LENGTH: 3922
<212> TYPE: DNA
<213> ORGANISM: Homo sapiens
<220> FEATURE:
<221> NAME/KEY: CDS
<222> LOCATION: (328)...(2259)

<400> SEQUENCE: 8

gacactgaat ttggaaggtg gaggattttg tttttttctt ttaagatctg ggcatctttt     60

gaatctaccc ttcaagtatt aagagacaga ctgtgagcct agcagggcag atcttgtcca    120

ccgtgtgtct tcttctgcac gagactttga ggctgtcaga gcgctttttg cgtggttgct    180

cccgcaagtt tccttctctg gagcttcccg caggtgggca gctagctgca gcgactaccg    240

catcatcaca gcctgttgaa ctcttctgag caagagaagg ggaggcgggg taagggaagt    300

aggtggaaga ttcagccaag ctcaagg atg gaa gtg cag tta ggg ctg gga agg    354
                              Met Glu Val Gln Leu Gly Leu Gly Arg
                               1               5

gtc tac cct cgg ccg ccg tcc aag acc tac cga gga gct ttc cag aat      402
Val Tyr Pro Arg Pro Pro Ser Lys Thr Tyr Arg Gly Ala Phe Gln Asn
 10                  15                  20                  25

ctg ttc cag agc gtg cgc gaa gtg atc cag aac ccg ggc ccc agg cac      450
Leu Phe Gln Ser Val Arg Glu Val Ile Gln Asn Pro Gly Pro Arg His
                 30                  35                  40

cca gag gcc gcg agc gca gca cct ccc ggc gcc agt ttg ctg ctg cag      498
Pro Glu Ala Ala Ser Ala Ala Pro Pro Gly Ala Ser Leu Leu Leu Gln
             45                  50                  55

cag cag cag cag cag cag cag cag cag cag cag cag cag cag cag cag      546
Gln Gln Gln Gln Gln Gln Gln Gln Gln Gln Gln Gln Gln Gln Gln Gln
         60                  65                  70

cag cag cag cag cag cag cag cag cag cag cag caa gag act agc ccc      594
Gln Gln Gln Gln Gln Gln Gln Gln Gln Gln Gln Glu Thr Ser Pro
     75                  80                  85

agg cag cag cag cag cag cag ggt gag gat ggt tct ccc caa gcc cat      642
Arg Gln Gln Gln Gln Gln Gln Gly Glu Asp Gly Ser Pro Gln Ala His
 90                  95                 100                 105

cgt aga ggc ccc aca ggc tac ctg gtc ctg gat gag gaa cag caa cct      690
Arg Arg Gly Pro Thr Gly Tyr Leu Val Leu Asp Glu Glu Gln Gln Pro
                110                 115                 120

tca cag ccg cag tcg gcc ctg gag tgc cac ccc gag aga ggt tgc gtc      738
Ser Gln Pro Gln Ser Ala Leu Glu Cys His Pro Glu Arg Gly Cys Val
            125                 130                 135

cca gag cct gga gcc gcc gtg gcc gcc agc aag ggg ctg ccg cag cag      786
Pro Glu Pro Gly Ala Ala Val Ala Ala Ser Lys Gly Leu Pro Gln Gln
```

```
        140                 145                 150

ctg cca gca cct ccg gac gag gat gac tca gct gcc cca tcc acg ttg      834
Leu Pro Ala Pro Pro Asp Glu Asp Asp Ser Ala Ala Pro Ser Thr Leu
    155                 160                 165

tcc ctg ctg ggc ccc act ttc ccc ggc tta agc agc tgc tcc gct gac      882
Ser Leu Leu Gly Pro Thr Phe Pro Gly Leu Ser Ser Cys Ser Ala Asp
170                 175                 180                 185

ctt aaa gac atc ctg agc gag gcc agc acc atg caa ctc ctt cag caa      930
Leu Lys Asp Ile Leu Ser Glu Ala Ser Thr Met Gln Leu Leu Gln Gln
                190                 195                 200

cag cag cag gaa gca gta tcc gaa ggc agc agc agc ggg aga gcg agg      978
Gln Gln Gln Glu Ala Val Ser Glu Gly Ser Ser Ser Gly Arg Ala Arg
            205                 210                 215

gag gcc tcg ggg gct ccc act tcc tcc aag gac aat tac tta ggg ggc     1026
Glu Ala Ser Gly Ala Pro Thr Ser Ser Lys Asp Asn Tyr Leu Gly Gly
        220                 225                 230

act tcg acc att tct gac aac gcc aag gag ttg tgt aag gca gtg tcg     1074
Thr Ser Thr Ile Ser Asp Asn Ala Lys Glu Leu Cys Lys Ala Val Ser
    235                 240                 245

gtg tcc atg ggc ctg ggt gtg gag gcg ttg gag cat ctg agt cca ggg     1122
Val Ser Met Gly Leu Gly Val Glu Ala Leu Glu His Leu Ser Pro Gly
250                 255                 260                 265

gaa cag ctt cgg ggg gat tgc atg tac gcc cca ctt ttg gga gtt cca     1170
Glu Gln Leu Arg Gly Asp Cys Met Tyr Ala Pro Leu Leu Gly Val Pro
                270                 275                 280

ccc gct gtg cgt ccc act cct tgt gcc cca ttg gcc gaa tgc aaa ggt     1218
Pro Ala Val Arg Pro Thr Pro Cys Ala Pro Leu Ala Glu Cys Lys Gly
            285                 290                 295

tct ctg cta gac gac agc gca ggc aag agc act gaa gat act gct gag     1266
Ser Leu Leu Asp Asp Ser Ala Gly Lys Ser Thr Glu Asp Thr Ala Glu
        300                 305                 310

tat tcc cct ttc aag gga ggt tac acc aaa ggg cta gaa ggc gag agc     1314
Tyr Ser Pro Phe Lys Gly Gly Tyr Thr Lys Gly Leu Glu Gly Glu Ser
    315                 320                 325

cta ggc tgc tct ggc agc gct gca gca ggg agc tcc ggg aca ctt gaa     1362
Leu Gly Cys Ser Gly Ser Ala Ala Ala Gly Ser Ser Gly Thr Leu Glu
330                 335                 340                 345

ctg ccg tct acc ctg tct ctc tac aag tcc gga gca ctg gac gag gca     1410
Leu Pro Ser Thr Leu Ser Leu Tyr Lys Ser Gly Ala Leu Asp Glu Ala
                350                 355                 360

gct gcg tac cag agt cgc gac tac tac aac ttt cca ctg gct ctg gcc     1458
Ala Ala Tyr Gln Ser Arg Asp Tyr Tyr Asn Phe Pro Leu Ala Leu Ala
            365                 370                 375

gga ccg ccg ccc cct ccg ccg cct ccc cat ccc cac gct cgc atc aag     1506
Gly Pro Pro Pro Pro Pro Pro Pro Pro His Pro His Ala Arg Ile Lys
        380                 385                 390

ctg gag aac ccg ctg gac tac ggc agc gcc tgg gcg gct gcg gcg gcg     1554
Leu Glu Asn Pro Leu Asp Tyr Gly Ser Ala Trp Ala Ala Ala Ala Ala
    395                 400                 405

cag tgc cgc tat ggg gac ctg gcg agc ctg cat ggc gcg ggt gca gcg     1602
Gln Cys Arg Tyr Gly Asp Leu Ala Ser Leu His Gly Ala Gly Ala Ala
410                 415                 420                 425

gga ccc ggt tct ggg tca ccc tca gcc gcc gct tcc tca tcc tgg cac     1650
Gly Pro Gly Ser Gly Ser Pro Ser Ala Ala Ala Ser Ser Ser Trp His
                430                 435                 440

act ctc ttc aca gcc gaa gaa ggc cag ttg tat gga ccg tgt ggt ggt     1698
Thr Leu Phe Thr Ala Glu Glu Gly Gln Leu Tyr Gly Pro Cys Gly Gly
            445                 450                 455

ggt ggg ggt ggt ggc ggc ggc ggc ggc ggc ggc ggc ggc ggc ggc ggc     1746
```

```
Gly Gly Gly Gly Gly Gly Gly Gly Gly Gly Gly Gly Gly Gly Gly
        460                 465                 470

ggc gag gcg gga gct gta gcc ccc tac ggc tac act cgg ccc cct cag     1794
Gly Glu Ala Gly Ala Val Ala Pro Tyr Gly Tyr Thr Arg Pro Pro Gln
    475                 480                 485

ggg ctg gcg ggc cag gaa agc gac ttc acc gca cct gat gtg tgg tac     1842
Gly Leu Ala Gly Gln Glu Ser Asp Phe Thr Ala Pro Asp Val Trp Tyr
490                 495                 500                 505

cct ggc ggc atg gtg agc aga gtg ccc tat ccc agt ccc act tgt gtc     1890
Pro Gly Gly Met Val Ser Arg Val Pro Tyr Pro Ser Pro Thr Cys Val
                510                 515                 520

aaa agc gaa atg ggc ccc tgg atg gat agc tac tcc gga cct tac ggg     1938
Lys Ser Glu Met Gly Pro Trp Met Asp Ser Tyr Ser Gly Pro Tyr Gly
            525                 530                 535

gac atg cgt ttg gag act gcc agg gac cat gtt ttg ccc att gac tat     1986
Asp Met Arg Leu Glu Thr Ala Arg Asp His Val Leu Pro Ile Asp Tyr
        540                 545                 550

tac ttt cca ccc cag aag acc tgc ctg atc tgt gga gac gaa gct tct     2034
Tyr Phe Pro Pro Gln Lys Thr Cys Leu Ile Cys Gly Asp Glu Ala Ser
    555                 560                 565

ggg tgt cac tat gga gct ctc aca tgt gga agc tgc aag gtc ttc ttc     2082
Gly Cys His Tyr Gly Ala Leu Thr Cys Gly Ser Cys Lys Val Phe Phe
570                 575                 580                 585

aaa aga gcc gct gaa gga ttt ttc aga atg aac aaa tta aaa gaa tca     2130
Lys Arg Ala Ala Glu Gly Phe Phe Arg Met Asn Lys Leu Lys Glu Ser
                590                 595                 600

tca gac act aac ccc aag cca tac tgc atg gca gca cca atg gga ctg     2178
Ser Asp Thr Asn Pro Lys Pro Tyr Cys Met Ala Ala Pro Met Gly Leu
            605                 610                 615

aca gaa aac aac aga aat agg aag aaa tcc tac aga gaa aca aac ttg     2226
Thr Glu Asn Asn Arg Asn Arg Lys Lys Ser Tyr Arg Glu Thr Asn Leu
        620                 625                 630

aaa gct gtc tca tgg cct ttg aat cat act taa gttttatgat ggaaggatac   2279
Lys Ala Val Ser Trp Pro Leu Asn His Thr
    635                 640

gactatgaag aaagacacag agcaacatca gacagtcaag aatttcagag ccagctggca   2339

tgcagtggac ctcatgccag cccattttat gactatttag ggagacagaa gtacctgtgc   2399

gccagcagaa atgattgcac tattgataaa ttccgaagga aaaattgtcc atcttgtcgt   2459

cttcggaaat gttatgaagc aggggtgact ctgggagaaa aattccgggt tggcaattgc   2519

aagcatctca aaatgaccag accctgaaga aaggctgact tgcctcattc aaaatgaggg   2579

ctctagaggg ctctagtgga tagtctggag aaacctggcg tctgaggctt aggagcttag   2639

gtttttgctc ctcaacacag actttgacgt tggggttggg ggctactctc ttgattgctg   2699

actccctcca gcgggaccaa tagtgttttc ctacctcaca gggatgttgt gaggacgggc   2759

tgtagaagta atagtggtta ccactcatgt agttgtgagt atcatgatta ttgtttcctg   2819

taatgtggct tggcattggc aaagtgcttt ttgattgttc ttgatcacat atgatggggg   2879

ccaggcactg actcaggcgg atgcagtgaa gctctggctc agtcgcttgc ttttcgtggt   2939

gtgctgccag gaagaaactt tgctgatggg actcaaggtg tcaccttgga caagaagcaa   2999

ctgtgtctgt ctgaggttcc tgtggccatc tttatttgtg tattaggcaa ttcgtatttc   3059

ccccttaggt tctagccttc tggatcccag ccagtgacct agatcttagc ctcaggccct   3119

gtcactgagc tgaaggtagt agctgatcca cagaagttca gtaaacaagg accagatttc   3179

tgcttctcca ggagaagaag ccagccaacc cctctcttca aacacactga gagactacag   3239
```

```
tccgactttc cctcttacat ctagccttac tgtagccaca ctccttgatt gctctctcac   3299

atcacatgct tctcttcatc agttgtaagc ctctcattct tctcccaagc cagactcaaa   3359

tattgtattg atgtcaaaga agaatcactt agagtttgga atatcttgtt ctctctctgc   3419

tccatagctt ccatattgac accagtttct ttctagtgga gaagtggagt ctgtgaagcc   3479

agggaaacac acatgtgaga gtcagaagga ctctccctga cttgcctggg gcctgtcttt   3539

cccaccttct ccagtctgtc taaacacaca cacacacaca cacacacaca cacacacaca   3599

cacacacgct ctctctctct ctcccccccc aacacacaca cactctctct ctcacacaca   3659

cacacataca cacacacttc tttctctttc ccctgactca gcaacattct ggagaaaagc   3719

caaggaagga cttcaggagg ggagtttccc ccttctcagg gcagaatttt aatctccaga   3779

ccaacaagaa gttccctaat gtggattgaa aggctaatga ggtttatttt taactacttt   3839

ctatttgttt gaatgttgca tatttctact agtgaaattt tcccttaata aagccattaa   3899

tacacccaaa aaaaaaaaaa aaa                                           3922
```

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9

```
tccttcacca atgtcaactc c                                              21
```

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10

```
gagccatcca aactcttgag a                                              21
```

<210> SEQ ID NO 11
<211> LENGTH: 22
<212> TYPE: DNA
<213> ORGANISM: Artificial Sequence
<220> FEATURE:
<223> OTHER INFORMATION: Probe

<400> SEQUENCE: 11

```
agtaccgcat gcacaagtcc cg                                             22
```

<210> SEQ ID NO 12
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 12

```
gcgctctgac agcctc                                                    16
```

<210> SEQ ID NO 13
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 13 cacctgcggg aagctc 16

<210> SEQ ID NO 14
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 14 ggctgtgatg atgcgg 16

<210> SEQ ID NO 15
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 15 cttcgcgcac gctctg 16

<210> SEQ ID NO 16
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 16 atggtgctgg cctcgc 16

<210> SEQ ID NO 17
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 17 ggtcgaagtg cccccct 16

<210> SEQ ID NO 18
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 18 gacaccgaca ctgcct 16

<210> SEQ ID NO 19
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 19 cccgaagctg ttcccc 16

<210> SEQ ID NO 20

<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 20 cttgcctgcg ctgtcg 16

<210> SEQ ID NO 21
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 21 gttgtagtag tcgcga 16

<210> SEQ ID NO 22
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 22 aagttgtagt agtcgc 16

<210> SEQ ID NO 23
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 23 gcgctgccgt agtcca 16

<210> SEQ ID NO 24
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 24 aggatgagga agcggc 16

<210> SEQ ID NO 25
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 25 gctcccgcct cgccgc 16

<210> SEQ ID NO 26
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 26 cgctttcctg gcccgc 16

<210> SEQ ID NO 27
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 27 gccgccaggg taccac 16

<210> SEQ ID NO 28
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 28 ccaaacgcat gtcccc 16

<210> SEQ ID NO 29
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 29 agcttcatct ccacag 16

<210> SEQ ID NO 30
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 30 tcccttcagc ggctct 16

<210> SEQ ID NO 31
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 31 tttctgctgg cgcaca 16

<210> SEQ ID NO 32
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 32 gttcattcga agttca 16

<210> SEQ ID NO 33
<211> LENGTH: 16
<212> TYPE: DNA

<213> ORGANISM: Artificial Sequence
<220> FEATURE:
<223> OTHER INFORMATION: Synthetic Oligonucleotide

<400> SEQUENCE: 33 gaggatcatc acagat 16

<210> SEQ ID NO 34
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 34 ctaaacttcc cgtggc 16

<210> SEQ ID NO 35
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 35 ttgatttaat ggttgc 16

<210> SEQ ID NO 36
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 36 gttgatttaa tggttg 16

<210> SEQ ID NO 37
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 37 atggttgatt taatgg 16

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 38 tggttgattt aatggttgca 20

<210> SEQ ID NO 39
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 39 tgatttaatg gttgca 16

<210> SEQ ID NO 40
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 40 ggttgattta atggtt 16

<210> SEQ ID NO 41
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 41 tggttgattt aatggt 16

<210> SEQ ID NO 42
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 42 agttgtagta gtcgcg 16

<210> SEQ ID NO 43
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 43 gatttaatgg ttgcaa 16

<210> SEQ ID NO 44
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 44 acagcactgg agcggc 16

<210> SEQ ID NO 45
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 45 aacttcaccg aagagg 16

<210> SEQ ID NO 46
<211> LENGTH: 16
<212> TYPE: DNA
<213> ORGANISM: Artificial Sequence
<220> FEATURE:

<223> OTHER INFORMATION: Synthetic Oligonucleotide

<400> SEQUENCE: 46 agtctttagc agcttt 16

<210> SEQ ID NO 47
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 47 gcttcctccg agtctt 16

<210> SEQ ID NO 48
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 48 ccttgcttcc tccgag 16

<210> SEQ ID NO 49
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 49 gcactttcct tgcttc 16

<210> SEQ ID NO 50
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 50 tcagtcctac caggca 16

<210> SEQ ID NO 51
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 51 gactgaggca gctgcg 16

<210> SEQ ID NO 52
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 52 ccgactgagg cagctg 16

<210> SEQ ID NO 53
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 53 gctagctcgc ccgctc 16

<210> SEQ ID NO 54
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 54 cagctagctc gcccgc 16

<210> SEQ ID NO 55
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 55 gcaatgtgca gctagc 16

<210> SEQ ID NO 56
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 56 gtcgcctggc tcctaa 16

<210> SEQ ID NO 57
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 57 ctggctccgc actcgg 16

<210> SEQ ID NO 58
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 58 atctctggct ccgcac 16

<210> SEQ ID NO 59
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 59 tgatctctgg ctccgc 16

<210> SEQ ID NO 60
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 60 agtgtccact gaagta 16

<210> SEQ ID NO 61
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 61 aggctcacag tctgtc 16

<210> SEQ ID NO 62
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 62 gacacacggt ggacaa 16

<210> SEQ ID NO 63
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 63 agaagacaca cggtgg 16

<210> SEQ ID NO 64
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 64 cgctctgaca gcctca 16

<210> SEQ ID NO 65
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 65 gtcgctgcag ctagct 16

<210> SEQ ID NO 66
<211> LENGTH: 16

<212> TYPE: DNA
<213> ORGANISM: Artificial Sequence
<220> FEATURE:
<223> OTHER INFORMATION: Synthetic Oligonucleotide

<400> SEQUENCE: 66 ggtagtcgct gcagct 16

<210> SEQ ID NO 67
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 67 gcggtagtcg ctgcag 16

<210> SEQ ID NO 68
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 68 atgcggtagt cgctgc 16

<210> SEQ ID NO 69
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 69 gtgatgatgc ggtagt 16

<210> SEQ ID NO 70
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 70 ctgtgatgat gcggta 16

<210> SEQ ID NO 71
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 71 gaagagttca acaggc 16

<210> SEQ ID NO 72
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 72 gcttggctga atcttc 16

<210> SEQ ID NO 73
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 73 ccttgagctt ggctga 16

<210> SEQ ID NO 74
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 74 atccttgagc ttggct 16

<210> SEQ ID NO 75
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 75 tccatccttg agcttg 16

<210> SEQ ID NO 76
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 76 gtaggtcttg gacggc 16

<210> SEQ ID NO 77
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 77 gattctggaa agctcc 16

<210> SEQ ID NO 78
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 78 gctctggaac agattc 16

<210> SEQ ID NO 79
<211> LENGTH: 16
<212> TYPE: DNA
<213> ORGANISM: Artificial Sequence <220> FEATURE:
<223> OTHER INFORMATION: Synthetic Oligonucleotide

<400> SEQUENCE: 79 cgcgcacgct ctggaa 16

<210> SEQ ID NO 80
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 80 tcacttcgcg cacgct 16

<210> SEQ ID NO 81
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 81 tggatcactt cgcgca 16

<210> SEQ ID NO 82
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 82 gttctggatc acttcg 16

<210> SEQ ID NO 83
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 83 cgctcgcggc ctctgg 16

<210> SEQ ID NO 84
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 84 tgcgctcgcg gcctct 16

<210> SEQ ID NO 85
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 85 gctgcgctcg cggcct 16

<210> SEQ ID NO 86
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 86 aggtgctgcg ctcgcg 16

<210> SEQ ID NO 87
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 87 gctgttcctc atccag 16

<210> SEQ ID NO 88
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 88 tgctgcggca gcccct 16

<210> SEQ ID NO 89
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 89 ggtgctggcc tcgctc 16

<210> SEQ ID NO 90
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 90 tgcatggtgc tggcct 16

<210> SEQ ID NO 91
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 91 gttgcatggt gctggc 16

<210> SEQ ID NO 92
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 92 tgctgttgct gaagga 16

<210> SEQ ID NO 93
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 93 ggatactgct tcctgc 16

<210> SEQ ID NO 94
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 94 tcggatactg cttcct 16

<210> SEQ ID NO 95
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 95 tgccttcgga tactgc 16

<210> SEQ ID NO 96
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 96 ctcgctctcc cgctgc 16

<210> SEQ ID NO 97
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 97 tgtccttgga ggaagt 16

<210> SEQ ID NO 98
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 98 tggtcgaagt gccccc 16

<210> SEQ ID NO 99

<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 99 cagaaatggt cgaagt 16

<210> SEQ ID NO 100
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 100 tgttcccctg gactca 16

<210> SEQ ID NO 101
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 101 agctgttccc ctggac 16

<210> SEQ ID NO 102
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 102 gaagctgttc ccctgg 16

<210> SEQ ID NO 103
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 103 ccgaagctgt tcccct 16

<210> SEQ ID NO 104
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 104 gtacatgcaa tccccc 16

<210> SEQ ID NO 105
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 105 acagcgggtg gaactc 16

<210> SEQ ID NO 106
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 106 ggacgcacag cgggtg 16

<210> SEQ ID NO 107
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 107 gtgggacgca cagcgg 16

<210> SEQ ID NO 108
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 108 tgcattcggc caatgg 16

<210> SEQ ID NO 109
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 109 cctttgcatt cggcca 16

<210> SEQ ID NO 110
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 110 aacctttgca ttcggc 16

<210> SEQ ID NO 111
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 111 gctcttgcct gcgctg 16

<210> SEQ ID NO 112
<211> LENGTH: 16
<212> TYPE: DNA

<213> ORGANISM: Artificial Sequence
<220> FEATURE:
<223> OTHER INFORMATION: Synthetic Oligonucleotide

<400> SEQUENCE: 112 cagtgctctt gcctgc 16

<210> SEQ ID NO 113
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 113 ttcagtgctc ttgcct 16

<210> SEQ ID NO 114
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 114 tcttcagtgc tcttgc 16

<210> SEQ ID NO 115
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 115 actcagcagt atcttc 16

<210> SEQ ID NO 116
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 116 atactcagca gtatct 16

<210> SEQ ID NO 117
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 117 tttggtgtaa cctccc 16

<210> SEQ ID NO 118
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 118 cctttggtgt aacctc 16

<210> SEQ ID NO 119
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 119 ctaggctctc gccttc 16

<210> SEQ ID NO 120
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 120 cagcctaggc tctcgc 16

<210> SEQ ID NO 121
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 121 agcagcctag gctctc 16

<210> SEQ ID NO 122
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 122 ctgccagagc agccta 16

<210> SEQ ID NO 123
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 123 tcgcgactct ggtacg 16

<210> SEQ ID NO 124
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 124 agtcgcgact ctggta 16

<210> SEQ ID NO 125
<211> LENGTH: 16
<212> TYPE: DNA
<213> ORGANISM: Artificial Sequence
<220> FEATURE:

<223> OTHER INFORMATION: Synthetic Oligonucleotide

<400> SEQUENCE: 125 gtagtcgcga ctctgg 16

<210> SEQ ID NO 126
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 126 tagtagtcgc gactct 16

<210> SEQ ID NO 127
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 127 tctccagctt gatgcg 16

<210> SEQ ID NO 128
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 128 cagcgggttc tccagc 16

<210> SEQ ID NO 129
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 129 ccttcttcgg ctgtga 16

<210> SEQ ID NO 130
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 130 ggtccataca actggc 16

<210> SEQ ID NO 131
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 131 acacatcagg tgcggt 16

<210> SEQ ID NO 132
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 132 cgccagggta ccacac 16

<210> SEQ ID NO 133
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 133 catgccgcca gggtac 16

<210> SEQ ID NO 134
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 134 accatgccgc cagggt 16

<210> SEQ ID NO 135
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 135 ctgctcacca tgccgc 16

<210> SEQ ID NO 136
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 136 acacaagtgg gactgg 16

<210> SEQ ID NO 137
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 137 cccttcagcg gctctt 16

<210> SEQ ID NO 138
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 138 cagagtcatc cctgct 16

<210> SEQ ID NO 139
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 139 caccctcaag attctt 16

<210> SEQ ID NO 140
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 140 aaggtagtct ttaagg 16

<210> SEQ ID NO 141
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 141 gttttcaaat gcagcc 16

<210> SEQ ID NO 142
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 142 gccatgagac agcttt 16

<210> SEQ ID NO 143
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 143 attcttgact gtctga 16

<210> SEQ ID NO 144
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 144 gcatgccagc tggctc 16

<210> SEQ ID NO 145
<211> LENGTH: 16

<212> TYPE: DNA
<213> ORGANISM: Artificial Sequence
<220> FEATURE:
<223> OTHER INFORMATION: Synthetic Oligonucleotide

<400> SEQUENCE: 145 cgcgcaggta ggagcc 16

<210> SEQ ID NO 146
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 146 tctaaacatg acggtt 16

<210> SEQ ID NO 147
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 147 atgcaattgc ctgcca 16

<210> SEQ ID NO 148
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 148 atgggagtaa cttttg 16

<210> SEQ ID NO 149
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 149 catattattg tgctgc 16

<210> SEQ ID NO 150
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 150 gtcaatatca aagcac 16

<210> SEQ ID NO 151
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 151 gagttgtgat ttcagg 16

<210> SEQ ID NO 152
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 152 ttgatggaat gctgat 16

<210> SEQ ID NO 153
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 153 ggttaacttt ctctga 16

<210> SEQ ID NO 154
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 154 tggattgtaa attacg 16

<210> SEQ ID NO 155
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 155 gaacattatt aggcta 16

<210> SEQ ID NO 156
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 156 tcaatctaga taccat 16

<210> SEQ ID NO 157
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 157 cacatcagaa ggagta 16

<210> SEQ ID NO 158
<211> LENGTH: 16
<212> TYPE: DNA
<213> ORGANISM: Artificial Sequence <220> FEATURE:
<223> OTHER INFORMATION: Synthetic Oligonucleotide

<400> SEQUENCE: 158 gagtgttaat gaagac 16

<210> SEQ ID NO 159
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 159 ctgattagct atgacc 16

<210> SEQ ID NO 160
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 160 atgagtcctc agaatc 16

<210> SEQ ID NO 161
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 161 gtagattcta gctttg 16

<210> SEQ ID NO 162
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 162 acaggctctg actagg 16

<210> SEQ ID NO 163
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 163 tgtgtgaccc ttggac 16

<210> SEQ ID NO 164
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 164 aagtatgagc atggtt 16

<210> SEQ ID NO 165
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 165 ggattctcta cacaca 16

<210> SEQ ID NO 166
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 166 ccatttgtgc caaacc 16

<210> SEQ ID NO 167
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 167 aggttaggga gtaggc 16

<210> SEQ ID NO 168
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 168 tagggtttgg tcagaa 16

<210> SEQ ID NO 169
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 169 ccttatggat gctgct 16

<210> SEQ ID NO 170
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 170 gttatcttac tctccc 16

<210> SEQ ID NO 171
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 171 gattgtgtat agctgc 16

<210> SEQ ID NO 172
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 172 ggttatggtt ctgtct 16

<210> SEQ ID NO 173
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 173 cttcattgca ggtctg 16

<210> SEQ ID NO 174
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 174 tagccaactt tcttta 16

<210> SEQ ID NO 175
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 175 cattgtacta tgccag 16

<210> SEQ ID NO 176
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 176 tttggtaaca ttaggc 16

<210> SEQ ID NO 177
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 177 atggttgtcc tgtaca 16

<210> SEQ ID NO 178

<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 178 accaagtttc ttcagc 16

<210> SEQ ID NO 179
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 179 tcttatgttt ccgaaccgtt 20

<210> SEQ ID NO 180
<211> LENGTH: 21
<212> TYPE: DNA
<213> ORGANISM: Artificial Sequence
<220> FEATURE:
<223> OTHER INFORMATION: Primer

<400> SEQUENCE: 180 gcccctggat ggatagctac t 21

<210> SEQ ID NO 181
<211> LENGTH: 21
<212> TYPE: DNA
<213> ORGANISM: Artificial Sequence
<220> FEATURE:
<223> OTHER INFORMATION: Primer

<400> SEQUENCE: 181 ccacagatca ggcaggtctt c 21

<210> SEQ ID NO 182
<211> LENGTH: 24
<212> TYPE: DNA
<213> ORGANISM: Artificial Sequence
<220> FEATURE:
<223> OTHER INFORMATION: Probe

<400> SEQUENCE: 182 actgccaggg accatgtttt gccc 24

<210> SEQ ID NO 183
<211> LENGTH: 18
<212> TYPE: DNA
<213> ORGANISM: Artificial Sequence
<220> FEATURE:
<223> OTHER INFORMATION: Primer

<400> SEQUENCE: 183 cttgcgcccc aggagtct 18

<210> SEQ ID NO 184
<211> LENGTH: 27
<212> TYPE: DNA
<213> ORGANISM: Artificial Sequence
<220> FEATURE:
<223> OTHER INFORMATION: Primer

<400> SEQUENCE: 184 ctcagagtaa gctctagcac acatgtc 27

<210> SEQ ID NO 185
<211> LENGTH: 28
<212> TYPE: DNA
<213> ORGANISM: Artificial Sequence
<220> FEATURE:
<223> OTHER INFORMATION: Probe

<400> SEQUENCE: 185 agtgtgtgag cctccatctc ctgtccaa 28

<210> SEQ ID NO 186
<211> LENGTH: 19
<212> TYPE: DNA
<213> ORGANISM: Artificial Sequence
<220> FEATURE:
<223> OTHER INFORMATION: Primer

<400> SEQUENCE: 186 gccaaggagg gagggtctt 19

<210> SEQ ID NO 187
<211> LENGTH: 21
<212> TYPE: DNA
<213> ORGANISM: Artificial Sequence
<220> FEATURE:
<223> OTHER INFORMATION: Primer

<400> SEQUENCE: 187 ccccccatag tgaatcagct t 21

<210> SEQ ID NO 188
<211> LENGTH: 28
<212> TYPE: DNA
<213> ORGANISM: Artificial Sequence
<220> FEATURE:
<223> OTHER INFORMATION: Probe

<400> SEQUENCE: 188 atgaagtaag gagagggact ggaccccc 28

<210> SEQ ID NO 189
<211> LENGTH: 174000
<212> TYPE: DNA
<213> ORGANISM: Macaca mulatta
<220> FEATURE:
<221> NAME/KEY: misc_feature
<222> LOCATION: (1)...(174000)
<223> OTHER INFORMATION: n = A,T,C or G

<400> SEQUENCE: 189 aagttgtggt gggattaaat gttgcaatga gtattcaaat aaggttgaag tatctatgca 60 ttctacttac atatggttga ggtatattca aggaagcctg tagccattaa aatctcaggg 120 aacaattttt cacctcctca ggtgaaaggg tcttcaggcc tttgtgttct ggaaggttca 180 tttatagcca tttcccaaat aacattgaga cggatgagtc tagagtctag ctcaaatggc 240 aatgggctgg aagactagtt tagtttttac taatgtggaa catagaacaa aattatgtcc 300 ttgtttcagc ctgctcatct gtgaagtaga gcctatcata tccagtctcc cttgccttta 360 ggtttgagtt accttctttg gtcaaggtaa gtaaatgcct atgatgtttt gctgtgcaca 420 agataaagct acaacaaagc tacaacctgt cttttctctg tagaagacgg caaaaagcaa 480

-continued

```
aagagaccca ggcaaaaatc tcggaatgac ttttgaaaca gacagcctcc ctagaatcag    540
aagtcaaagg aatttaaaac atagggaggc ccagggtctc tactgacata aaagaaagct    600
gttttcgtta taggtttact tttacatttt ctctctcttt ccattcccac ctgcctctcc    660
acctttacac agggcttatg ggacctcctc cacaaaagag cagttgcaat aacccacatc    720
atcctccacg cctggctgtc catcaagagg cgaaaagcag ccctatatag gttctatcct    780
tggatagttc cggttggaaa gtttaaaata tgcaaaggca acttggaaaa gcaagcggct    840
gcatacaaca caaacctttg caaagctctg cacaaaattg agggcctatg cgtacatggc    900
aagtgttttt agtgtttgcg tgtttacctg cttgtctggg tggttttgcc tttgcaagtc    960
tggatgagaa atgcatggtt aaaggcaatt ccagacagga agaaaggcag agaagagggt   1020
agaaatgacc tctgattctt ggggctgagg gttcctagag caaatggcac aatgccagga   1080
ggcccgatct atccctatga cggaatctaa ggtttcagct agtatctgct ggcttggtca   1140
tggcttgctc ctcagtttgt aggagactct cccgtctgca cgctcttatc agtcctgaaa   1200
agaacccctg gcagccatta ggagcaggta ctcctatcgt ccttttcctc cctcctcctc   1260
tacaccccgt tggtttttta gattgggctt tggaaccaaa tttggtgagt gctggcctcc   1320
aggaaatctg gatctctggc gcttaaagct tggtttagca aagcaggagc tattcaggaa   1380
gcaggggtcc tccagggcta cagctagcct ctcctgccct cgcccacgct gcgccagcac   1440
ttgtttctcc aaagccacta ggcaggcgtt agcgcgcgat gaggggaggg gagaaaaaga   1500
aaggggaggg gagggaaaag gaggtgggaa ggcaaggagg ccggcccggc gggggcggga   1560
cccgactcgc aaactgttgc atttgctctc cacctcccag cgccccctcc gagatcccgg   1620
ggagccagct tgctgggaga gcgggacggt ccggagcaag cccagaggca gaggaggcga   1680
cagagggaaa aacggccgag ctagccgctc cagtgctgta caggagccga agggacgcac   1740
cacgacagcc ccagcccggc tccagcgaca gccaacgcct tttgcagcgc ggcgacttcg   1800
aagccgccgc cccggagctg ccctttcctc ttcggtgaag tttttaaaag ctgctaaaga   1860
ctcggaggaa gcaaggaaag tgcctggtag gactgacggc tgcctttgtc ctcctcctct   1920
ccaccccgcc tccccccacc ctgctccccc ccccgccccg cgtcttctct cccgcagctg   1980
cctcagtcgg ctactctccg ccaacccccc ttactgcccc tctccccacc ctccctcccc   2040
cgtcggccca gcgctgccag cccgagtttg cagagaggta actccctttg gctgcgagcg   2100
ggcgagctag ctgcacattg caaagaaggc tcttaggagc caggcgactg gggagcggct   2160
tcagcactgc agccacgacc tgcctggtta ggctgcacgc ggagagaacc ctccgtttcc   2220
ccccactctc tctctacttc ctcctgcttt ccccaccccg agtgcggagc cagagatcaa   2280
aagatgaaaa gacagtcagg gcttcagtag ccaaaaaata aaacaaacaa aaacaaaaca   2340
aaacaaaaaa acgaaataaa agaaaaagat aataactcag ttcttatttg cacctacttc   2400
agtggacact gaatttggaa ggtggaggat tttgtttttt cttttaagat tcgggcatct   2460
tttgaatcta cccttcaagt gttaagagac agactgtgag cctagcaggg cagatcttgt   2520
ccaccgtgtg tcttcttctg caggagactt tgaggctgtc agagcgcttt ttgcgtggtt   2580
gctcccgcaa gtttccttct ctggagcttc ccgcaggtgg gcagctagct gcagcgacta   2640
ccgcatcatc acagcctgtt gaactcttct gagcaagaga aggggaggcg gggtaaggga   2700
agtaggtgga agattcagcc aagctcaagg atggaggtgc agttagggct ggggagggtc   2760
taccctcggc cgccgtccaa gacctaccga ggagctttcc agaatctgtt ccagagcgtg   2820
cgcgaagtga tccagaaccc gggccccagg cacccagagg ccgcgagcgc agcacctccc   2880
```

```
ggcgccagtt tgcagcagca gcagcagcag cagcaagaaa ctagcccccg gcaacagcag   2940
cagcagcagc agggtgagga tggttctccc caagcccatc gtagaggccc cacaggctac   3000
ctggtcctgg atgaggaaca gcagccttca cagcctcagt cagccccgga gtgccacccc   3060
gagagaggtt gcgtcccaga gcctggagcc gccgtggccg ccggcaaggg gctgccgcag   3120
cagctgccag cacctccgga cgaggatgac tcagctgccc catccacgtt gtctctgctg   3180
ggccccactt tccccggctt aagcagctgc tccgccgacc ttaaagacat cctgagcgag   3240
gccagcacca tgcaactcct tcagcaacag cagcaggaag cagtatccga aggcagcagc   3300
agcgggagag cgagggaggc ctcgggggct cccacttcct ccaaggacaa ttacttaggg   3360
ggcacttcga ccatttctga cagcgccaag gagctgtgta aggcagtgtc ggtgtccatg   3420
ggcttgggtg tggaggcgtt ggagcatctg agtccagggg aacagcttcg gggggattgc   3480
atgtacgccc cagttttggg agttccaccc gctgtgcgtc ccactccgtg tgccccattg   3540
gccgaatgca aaggttctct gctagacgac agcgcaggca agagcactga agatactgct   3600
gagtattccc ctttcaaggg aggttacacc aaagggctag aaggcgagag cctaggctgc   3660
tctggcagcg ctgcagcagg gagctccggg acacttgaac tgccgtccac cctgtctctc   3720
tacaagtccg gagcactgga cgaggcagct gcgtaccaga gtcgcgacta ctacaacttt   3780
ccactggctc tggccgggcc gccgccccct ccaccgcctc cccatcccca cgctcgcatc   3840
aagctggaga acccgctgga ctatggcagc gcctgggcgg ctgcggcggc gcagtgccgc   3900
tatggggacc tggcgagcct gcatggcgcg ggtgcagcgg gacccggctc tgggtcaccc   3960
tcagcggccg cttcctcatc ctggcacact ctcttcacag ccgaagaagg ccagttgtat   4020
ggaccgtgtg gtggtggggg cggcggcggt ggcggcggcg gcggcggcgc aggcgaggcg   4080
ggagctgtag ccccctacgg ctacactcgg ccacctcagg ggctggcggg ccaggaaggc   4140
gacttcaccg cacctgatgt gtggtaccct ggcggcatgg tgagcagagt gccctatccc   4200
agtcccactt gtgtcaaaag cgagatgggc ccctggatgg atagctactc cggaccttac   4260
ggggacatgc ggtaagtttc tccttccaga aatgtcgcct ttcggcccag ggcacagagt   4320
cgctctgcat tctggggtgt ctagtggctc ctacctgcgc gaacactcag actgcccctg   4380
ggagagctca gcagggtaaa cctagagctc tccccgtgga ctcccggcct gccagaggtt   4440
taacctgagc tctcctaatt tctgctgcgt gtcctgggtg ctgattcctg ccctcccaga   4500
ttcttcaact cccccaacgg ccccaaattc tcgctacctc ctggtacccg agtcccaaac   4560
ttaaatccta ttgtacgggc caccttcaga gacaaagctc ataagccctc cactcttcct   4620
tttctcctgt cctcgaagtc tgagaacctc aatcagaaat ttgggcaatt tcttctcttc   4680
gggtctgtta ggacttccct ttcagcctgt gcagattaga gtcaaaaaga ctggcccaag   4740
agcttctcag cggatctcct ccaaagaggt aaaatgaaat tctcggttag ggaaagaaag   4800
tggtctctgg gtgctgaggt ctgctatgtg aaggagtgaa cttctttccc ggaagcaact   4860
ggggacttgc tccagggctg gaggtcagta gagataatct gaaccgtcat gtttagagta   4920
ggcagagggg caactttctt ggtaaagact ccacaggatt tgcattcaca gtttctcaac   4980
gttggttgac tatgttgaaa gtagttgctt gggtcggttt tctcttataa agtgtttatt   5040
ttctctgtgg attttaacag atccacaacc ccctacttca ggtttgcatc agatctataa   5100
agaggagaat attcttttaa tgtacaattt aattaggctt cagtctgact tacaaaagtg   5160
ttggaaaaca tatttttgtg aaacatttcc tgctatttca gtgtgcccca aaatctccac   5220
```

```
tggggaggga ggagtgaggt ttttcttatt atattccttc atttttagga catgttggca   5280
ttttagaata catgctgtta gctctaacaa attgagtaag aactcttagt gacctatgag   5340
ccataatctt accccagagt tttaattagc atatgagaaa agtggcaggc aattgcatcg   5400
tgcttattaa aaattattcc tcaccgcaat tgttgagctt cttggagacc atgctgaaga   5460
ttttctcccc cagcaaatta agatattagt ttatctagtg agggaggaca tactgaattg   5520
gggaattcac tcctcaggta gaccaggtgc tgatgtccct gtggacttat gtcttattct   5580
ttgtttctat ggctgttttc ttttatctgt gacttctccg aaatttcttt gttagcctta   5640
acatcttcgt ttggggactt aaatccagca atttgccttc tttcactgat gctttccttg   5700
ttacaaggta gagatagcac gctattagtg aagaaagaaa gaggagggta ggatttcata   5760
ttattttgtg ggctgttgaa gaaacagctt cttaccaggc tttacattcc attaggtttt   5820
taatgtttgg cttacaagat tttgaaaggg ttcatttgat atcgtcaaag tattttccag   5880
ttaatttaga ctctttattt ttgtaatggg tttatcctat gggacaaaaa aagtattctt   5940
cattttataa gaataaattt tcttggcagg gttaattttt tttctaagcc tgtcactaga   6000
cggtggagcc cttcttctac tgtaaacttt tcttgtggga aaatgtctaa ggtgcatttt   6060
gacctgccat gatactaaac ccagactctg gaaccttcca tcttctgcat gcctccccca   6120
caacttactt acttagcagg gaaaaaactg atggttccac atatttctta aaaaatgtgt   6180
gccttcaaag gcaaaaccaa aatttttagg gaataactat agagagcaaa agttactccc   6240
atcaggtaga caatgagctt ggtgatttta tttcaggtct taatgaaaaa agcttcttta   6300
tgaggaagat tatcatatct tggtgcctcc ttgacagtct gcttaaatta atgacataaa   6360
ctaatgagaa tttagcagtt cctgcagaaa gtacaagatt ttttttctg gtttttgatt   6420
gctgcactga ttatgaggag tctagttaaa aggaaaactg gtgttcctgt ctcgtaagtt   6480
gacgaagact ttccatttct aggatagaga aaatccttaa gtcagtttat tgaaaattaa   6540
tcaatttaat cagaatgcaa tcaattccaa tccaaaagtt gatattttct tactttctct   6600
ttttttcccc tcactttgta ggggtgcaat ttggtgaaag gcaagagatt tcttaagcca   6660
aatcaagagt gtcttccctt tctgtattgc atgcattatg tgccattttt tagctaaaaa   6720
tctcaaaatt gtgcaggctt ccagtgacct gttgggttcc tctcttttcc attcatgtgt   6780
gtgtttatgc acattagtta attttgtgaa gggatttttt taaaccttag taacatctgc   6840
actcactctg tgttcttaca catttacaat gtttctgctg agaggatggg agatgcaaag   6900
gtggtctctt ttacttaatt tagcatgtga tttaaacaga aggaaaaata aaaagtgatg   6960
ggacttgtgt gcaaccctga tgatattttg tggagttgtc tgtcttctct ctgagatcaa   7020
acaggactac aactttgtta attgaccact ggctcccttg gcagaggtag ggcttcttag   7080
attccagcag gcagcacaat aatatgacaa aaatttattc ttgggagttg ggttctaaga   7140
gagtctgcat gccagaatta gagtttgggg tttagagaaa ttatccagat gcaaaaagaa   7200
cattttaatt tttctcttgg taatttgttc tggtctccat agtaggtagt actttagcag   7260
tgctttgata ttgacaagtc ttgttccctt tttctattag attttacaaa ataaggcatt   7320
ttattaattc ctctttcctt ctcctctctc ctctcagtta ccaagcattt ttatgactat   7380
cttacaaggg acagtttgtc ttgtaaagca gaattttcct ttgaaaccaa gacagactat   7440
ttctccccat aggcttcaag aaccaatatt ttggcaagaa gcatcttttc cttgtggtca   7500
gcaaataggt agtgagttct gtctggattc caacaatcaa cacctgagga ccaaatagcc   7560
acactgggtg gcaccccatc tggaagtata cacaggatgt agccctcttt cttgtccaca   7620
```

gctcaagtca gccaaagatt aacactggtg agagatattt tcgaagaagt ttgcaggctt 7680
ccaattgcag ggtcgttttg gggtgctttc ttgcctgtgc taattttatc tcatcaggct 7740
tccattcttt gagctgtaaa ctttgaaata atatattaga ttcgctggta cgtttaattt 7800
tctttgtcaa gtgtttttca ttccaatagt aatttttcat ctggtgtaca tatatgcatt 7860
taaaacaaaa aattctttgg tctcctttcg cgtacatgca ctgtggcttg tacgtgtgca 7920
agccacttgg tgggattatg tgaattgggg ttagaaatgt ggacaatttt attatgatta 7980
tttttaatgg tgatatcaag atcaccagtt tcattcagaa ccttgcataa gcagggagca 8040
gaatgtggac tgggtgtggc aaagcaaggg cttattttat agccaaacct gaaatcacaa 8100
ctctgaaata taaaaaaaaa agcaaacaaa aaaatcaagt tttgtgagct tggtcagaga 8160
aggaaaagaa aatctctccc cacccccccac ctccaccatt ttctctttgt ctgcagcttc 8220
ctcaagtgct gcctgtcccc gattttcttt tattccactc ctttcatgtt tttgacattg 8280
aaatacagac tcttctttcc acttctcagg gcatttttct cattacacct gtggcatgct 8340
cctaaataat ttcttaaaaa aaaaaaatct gtaaagtagc cgattagatc aaccccagca 8400
tctctccctt aagacctaga tgacatgagg ggattgcaaa atgaatagct gggtttttt 8460
taccttgagg ttaaagcctg gttcaacagt tgctgaggga gttaactaga tggcttgagg 8520
acttggcaat ttcataaagt attttgtctt atgctgtcgc tgtctctgtc tctgtcttga 8580
tctctgtctc tctctgtgta ctgtaatgtt ggccaccttc tctcagaacc tgagagagag 8640
ctctgagacc cttcccaggt cggttcggtt cagacctcgg tagcctggtc acaagcagta 8700
cctaatatgc atatgtgggt gcatgctgta agtgtcctgc tgggctaatc tgcttaagct 8760
acataaaaat taatcatatg aaaacaaaga aagatattaa agaaattatt ctacctccga 8820
cttctcatat cagcattcca tcaagttctg ggatgttaaa ttcagagaaa gttaacctca 8880
tcttaaacac aaagttgact tttaaacaaa attgcttata aagttccgta cagttaccag 8940
cattggttgc cctttgtcat acggaagaga attatgaaat ctcatattta catagcattc 9000
ttaaaaaaaa aaaaaagaca cagtgttttc cagtttattc actgcattca tgttagtttg 9060
agtaggccag gaggggtgct tagtgattac ccttttgcta ggtaaagaag tagaaagata 9120
gattttctat gatgtttgtt taccatgtag gggaatctct ttagagcaac actcccaggc 9180
tttttcttct tgaaatttcc cacctgacaa atactttaga ttgttactcc taaggacttc 9240
tctcagtagc tgctacatag agacgatagt ctatgaatta ttgcttgcac actcatgggt 9300
gatgccacac gctctctctc ctggcagttc ttgctgccaa cctgcaggcc acaccaggac 9360
tgaaggcagc tcatctagat aagtttatag cattaaagtg ctgggtcact tgagaatgtt 9420
gtcaatttag gttacttagt acctaagtgt tatttttaa ataatagctt tattgagacg 9480
taatttacaa tccatacaat tcactcttct aaagtgtaca gttccatgct tttcagtata 9540
ttcagagttg tgcaaccatt attgcaatca attttagaac attttaatca cccccaaagg 9600
aaacgctatg cacctttttg ttcaatgcct tatgttccct cagtccttag caaccaataa 9660
tctacttcta tctatggatg tgcttattct aatattttgt atgaatgaaa tcatgtaata 9720
tgtggtcttt tgtgactagc ttctttcaca cagaatatgt tttcaaggtc atccatgctg 9780
aagcacgtat cagtacttcg ctatttttta tagcctaata atgttccact gtatgactat 9840
acaacatttt atctatccgt ttatcaggag atgagcatta gggttgtttc cacctttga 9900
ctattatgaa taatactgct gtgaacattc atgtacaagt ttattgtgga catattcagt 9960

```
ccacatattg tggacatttt caattctttt ggatacatac ataggattga aatctctgag  10020
tcatatggta cctctatgtt tatcctttga agaactgtca aactgttttc gaaagtgtct  10080
gcactgtttt acaatcccat cagcaacgta tgaggggtcc atttcttcca catccttgca  10140
aacacttgta attctctttt ttattacagc tatattagtg ggtgtgaagt ggtacctcat  10200
tgtggttttt atttctattt ccctaataac gaataatgtt cagtatctat tcatgttctt  10260
attggccatt tgtatatctt ctttttgag aaatatctat ttggattctt tgcccatttt  10320
ttagttgggt tttttattat tgagttttaa gagttttaaa aaatatattc tggatgcatg  10380
tcctttaata gattgtgatt tgtggatatt ttttcacatt ctgtgggttg tctttttac  10440
tttccttttt tttctttttg tgttcttaat ggtatctaga ttgaagcaca aaaaaagttt  10500
ttaagtttga tgaagtccaa ttcatctgtt tttttttttc tgttttggcg tatgattttg  10560
gcatcatatc taagaaggct ttgcctaatc caagattaca aagatttaca catatgtttc  10620
cttctaagag ttttatagtt ttcgctgttt acacttaggt ctttcatcag ttttgatgta  10680
atgtttatat atgattgagg taggggtccg acttcattct tttacacata gatactcatt  10740
tcttacaata ttcttgttga atttttcctc acttaactgt cttggcaccc tttgtgtaaa  10800
atcagttgac tgtaaatgtg agggtttatt tgtggactct caactgtatt cagttgatct  10860
atatgtttat tcctatgcca gtaccacatt atcttgatta ttgtaggttt ttagtgagtt  10920
ttgaaattag gaattttgtg ctctttgact ttggtcttgt ttttcaaggt tgttttggct  10980
cttgtgggtc ccttgagttt tcatatgaat tgggataagt ttgtcaattt ctacaaagaa  11040
gtcagctggg attctcacag gaactatatt acatctgtaa atcaatttgg ggagcattgc  11100
catctcaaca acgttaagtt ttttcatcca taaatatgag atgtcttccc atttatttag  11160
atcttccttt tgtcaacaat tttttattgt tttcagatga taagttttgc agttcttttt  11220
aaaatttagt cttaagtgat ttatttttg atactattat aaattgaact gttttgttga  11280
ttttcttttc agattattca ctgccaatgt atgaaaacat aattgttttg tgtattgatc  11340
ttgcatcctg caaccttgct gaaaatacct gagttttgaa tacttctggg acttatgggg  11400
aagagggctt ctgctgtttc actgaacgtt aaagcttatt tcatttcatc ctgtatgaag  11460
gctgcataca agccttctgt atgaagggga cactgttgtc atttttactc agctataaat  11520
ttgaactggt aatcccatcc cctttcagga tgaataggag agtgttttta aatgttcatc  11580
tctttagaga acagcgggaa agaagcctaa taaggtttgg gtcgtttata atccctttt  11640
cagaatttgg atttgggaac tattagcaag ggagtgagta ataataataa tttctacata  11700
gaaaactaac atgtagaggt gacaaatgaa atcactagct atatttggct tatgtttagg  11760
tttttataag cagctaaaat cataattttg tgtttttatc tcttgtcctt tggacagagt  11820
aaattccaat actccttctg atgtgcattt ctagatgggg aaaggattcc tttactctca  11880
tataatttaa gcttcttttt agagatgtac tccatagcca tgaagcaaag ataaaattca  11940
tctatgtaga gattgaactt tgtcttcatt aacactctag gctaaaggtc atagctaatc  12000
agctacaact gtcatgtcct gataattgtg agttaactgc aggccaccca gcaaaaggtt  12060
tagttataat ctgatagctg tctgtagaga ttaccctaat aaagggaatt ttttaaaaaa  12120
gaatctggca ggggatagta gctcactcct gtaatcccag cactttggga ggccgaggtg  12180
ggcggatcat ctgaggtcag gagttcaaga ccagcctggc caacatggtg aaaccccatg  12240
tctactaaaa atacaaaaat tatccaggcg ttttggtggg cacccataat cccagctact  12300
tgggaggctg aggcaggagg atcacttgag cctaggaggc agatgttgca gcgagccgag  12360
```

```
atcatgccac tgcactccag gatccgtcaa aaaaaaaaaa aaaaaaaaaa aaaaaaaaaa  12420
aaaagactct atcaatcaac cacttttcat taagcacctg ctatgtgtcc agcatgtact  12480
aggaagagat aagataaaag gggacacaat tcagacagaa tcttcttgag gtaattgctt  12540
acaaggagct tatagccact gaaaacaaaa acaaacaaaa acaaataacc aaaacccaaa  12600
cagaaatgca gcaccatcat gccataatgc ctgtatgaga tcctggattg tacggtgtgg  12660
atctttttaa atgtagatat ttaaaaaaaa aaaaaaagag agagagagag agagaaatga  12720
atcaatagag gctgaagtgg tcaacaatgt tacctgtggc tgcttttaat cctttgtggc  12780
agtaagtagg agcatgtcta aactcaagca atagattaaa gatcctgatg tatattttaa  12840
ataacagaag ttggtacctc tggaaagaat taactggagg catgggttga aatctatttc  12900
tgcttattaa atagtgcacc ccagtcaagt tagttgccaa tttttttca gtttctttgg  12960
ctatatcatc gcacttgttg ggtacatgtt tttgatgtat ttatctgaac aagtccgcaa  13020
taatatgagt aataaattag aatagaaggt gattaatagc tctgaatttg atataagatg  13080
cccagtgtgg tggtcagatc aagagttgtt tttcggccgg gcgcggtggc tcaagcctgt  13140
aatcccagca ctttgggagg ccgaggcggg tggatcacga ggtcaggaga tcgagaccat  13200
cctggctaac atggtgaaac cccgtctcta ctaaaaatac aaaaaactag ccgggcgtgg  13260
tggcgggcgc ctgtagtccc agctactcgg aggctgaggc gggagaatgg cgtgaacccg  13320
ggaggcggag cttgcagtga gccgagatcg cgccactgca ctccagcctg ggcgacacag  13380
cgagactccg tctcaaaaaa aaaaaaaaaa gagttgtttt tctgccttct aagtttccat  13440
tgatcctgat ggattgcaca aatagaacaa ttcggggagt atgggggcac atgacgatct  13500
tataagagct ttgctgtaat agacaacgta acattctgaa acggcctacc acctaacatg  13560
ggctctggtt ctctgcaggt tgagtgagtt ccttgcttgt ggaactgtag tcccgctatc  13620
tggccgctag ggggactgca agtgccccgt ggcaggattt ccctgggaat ggtgagcctc  13680
cattgacggt ttcaacacac agccaaggcc ctatcgcagg ataacttcaa ccagaactgc  13740
ttagcaccag acaataaata agctactatg gtacttactg tttcatttgg gatgttcttt  13800
ctcgaagtgt caagcatttt aaagtaatat tttgactttt taatacctct ctttgcatat  13860
ggagcaggac acagcaaata tattcaagta gcactgtcca gtttatagag aagtttcata  13920
ttccattatt gcatttcatt cttgtttcta ccctgtacaa gtaactagag tttggagtat  13980
tataatagta ttcatactat tacaatactt ttattcccat tataaaaatt atgctaagag  14040
tggttaagtt acatgtttac aatcaaacag catcaaagtg acagatctgg gatttcagtc  14100
tcattctttc ttctccagat catgtgttcc ctgcttttat ctcacagctc tttttacctt  14160
atagatagga aacatgagag tcagagaggc aaaagaacca caagtggtgt caatactaga  14220
aatttatgaa gttcttaagg cttctaggtt tgttacccat ccaccagact gatggatttg  14280
gttgtgtgag agttctgggt gtcaataacc ttgccattct actttacaga ctgcatacat  14340
tcaataaatg cctattaagc atctactatg tgccaaattc tgtactaggc accaatgatg  14400
tagcagcgaa cagaacacac aaaaatatct gaatggagct gacagtttaa tgagaggaga  14460
catgtagtat acatctgagc atgaatagtg tcatgcagaa taacttcaga gtatagggta  14520
tagagattca tggtgagagg gaatatttta tatctgctgg ccagggaaaa ccttactgga  14580
aaggtaaatt ttgagcagtg acctgaagga aattaggaaa tgagctgcta tttggacatc  14640
tggagttaga atattccagg cccagggaac cacaggcaca aagggcctga ggcaggagag  14700
```

```
catgcttgct ttgatggagg acaaaaaggc tcatatggct ggtttaaata agtgaaggat  14760
ggtagacaat gagatcagag ttaatgaggt tgcatggtag gtcttcttta agactttgga  14820
ttttactcct aagcagggtg tattggaagg ttttgagcaa agtaacatga cctgacttac  14880
actttaacag gctccctcct cttcataaca tctgtcactc tgatatatta tacgtttgtt  14940
tgtttactta ctgtatgtgt ggagaagaga ctgtgggagc aaggagggaa gcagggagac  15000
aaggccactg cagtgatctg ggtgagaggt aaccatgtct cagactaagg tagtattggt  15060
ggagaagata ggaagtggct gaattctaga tgagttttga tggtagagcc aacagcattt  15120
actgacaggt tggatattca ctgtgaaaaa aatagaggag atgaggatga ttgccaaatt  15180
tttggtctga gtaactggaa aaatgagatt gccatttact aaaattgtga agactgtatg  15240
tagagcaggt gcatgggcag gatagaaatc aagagtttga ttttttactt ataaagtttg  15300
agttatctga tgagcatcct gatggcttct cagttttcat tcagtgccct cagctttgct  15360
gttcttcaag aagattaaaa aggaccttag agatcaccta ggctgtaggt accctctccc  15420
ttctttcctt ttactttata gaggtctata gaagggtagg gacttatcca aggtaaaaca  15480
gtgagctggt gacagaacta gggcacaaac ccagttctct tcgattctga ttcagtagat  15540
ttttgtgtgt gtgtgtgtga ttctgaggac tcatttgggc aagagtgagt tttttgtttg  15600
tttgtttgtt tgcgcaaacc taaaaccagg tgattaaact aaatagtgac taaaactgga  15660
aaactataca aattggttgc tctccccaat caaactgaaa tattattatt aggtttttac  15720
tgaactacat accaaaatat ttttttcctg taaaaacaca gtaagtgggc ttttaaaggc  15780
aattgagctt ttatcaaagc tagaatctac agggcacctg gacaaaaatg gcctaaaatc  15840
ctaagaaatt agagttcatg gaacctggaa gaccatcttg tccagctagc tcattttatt  15900
ggtagagtgc ctgaggcacc gagatggaaa gggacttggc taagctcata cagcaagcta  15960
gtgcctgacc tagtcagagc ctgttctaag tattagttgt atgttgtttt cttgaaaaaa  16020
gtctatattg gaaaaatgaa aattctttgt tccatactga gaacaaagaa ttatatataa  16080
tcatatataa taataatgat agcacttact gaatgtttgc tgtgtaaact tccgcacctt  16140
gcatgaactg attcatttaa ttctcatgtc aactttagga agcaggccta gagacgttaa  16200
ataacttgtc caagggtcac acagctagga agtagcagaa cttgtgtgca ctcccaggaa  16260
gtctggcttc taaccacaag gttctaacta ctgtgcaata tcagcagctt ctcagattac  16320
tcttcacctt caccatccca aaagactggc gacataggtg acttcattat gcactgcccc  16380
tattatagtc cactgatcct caccaaatag ctgggtggcc tagaggttaa agtaggggca  16440
cagtgatgga aaggggtggt tagaagaggt tgataactta tgatagggat tggaaaacag  16500
aactctagga attattgaaa agggcctaga gatcccaagg aggttgatct cagactgcta  16560
caaaccaggg caattcgatg cctgcttaaa taggagagtt aagataagaa aaataaaatt  16620
gccagttttt acagtcaggc attgttttat ttcttttaca tgtattaatt cgtttaatcc  16680
tcaaaataat ccatgaggta gctacaatta tcatttctat gttatagatg aagaaacagg  16740
cacagagcaa ttaagtaacc tgcccaagat tagagaacaa gtaagtgaaa gtgccaatat  16800
tagaatctag gtgattcagc tccacaactt atgttatttt ccaatacatt tatggaacga  16860
ggtaattttc atataacaga aagtgtttaa agtgcaaaaa cattgtgcct gaacttcaaa  16920
cattgaacaa ctcatatcct taatatacac cagctgcttt taaggactct tagaagtaag  16980
gatacttacc taaagtcata tgttgaacaa gtagcagaac cggaacttga atttgagact  17040
ccagactgcc agacctcttt ccactctatc acttgggctc ccttctaacg ttgatttgtc  17100
```

tctctccatt cttcctccgt attgctctgc ccttcacctt ttaattacct gtctccatca 17160
acaagattgg acagagaatt gggggagtga gcagagtcca tttccttcca gagactggac 17220
aaaaggaaca aaatgttggg aaaaaagtca gcatgtggat tttgtgggat ttacactaaa 17280
taagaacgga cacttgccag gactgacaag atgctacctc aatccctcta ggccccaatg 17340
tgttatgcag gatcccataa gaagtcatga atgtagttgt cagataatct ttttgttact 17400
gtggaaatgg aagcaggata ctgcaaaaat ctgtctctcc aggttttctt ttaaagaagg 17460
tacagtcttg ctaaatgata actgtttgga catttatttg aaaatgggca gtgcaggaga 17520
gaaagaattt ttccaagctt gtcacattgg gccatctctc tgaagcattg tccaacctct 17580
aattagatga ggagactgca ttaaccaaga gttgagagta aagatggaaa cacttgatgt 17640
ttggtgtttg ggtgcagaaa ggattccaaa acatgttctg agtttcttta ctctgcccat 17700
ccctccttcc ctttcatctt tgtttaaaaa ccatggttag caaatgtgtg tagtctgttt 17760
gcaattgttc atctgaaaaa tttgtttgat cagccttttg aaaaaaagat caaaatagac 17820
tgagatattt tagtcaccaa ctatctaata atagaccaaa aatttaaacc atgctcatac 17880
tttcatatgg tatgtggttt gttttagacg ctttctgggc ttcgctgagg tgctagattg 17940
actcaaagta tggcaggtca gatgtggaat tgagtagggt ggactcttct ctatgcctcc 18000
agattcagaa ttccccatca gagatgatct catagtgttt ggaaaaacca agctgaaggc 18060
tttgggaatt agggtggtga agggatatgt tgtttcccaa agccttctca gtcattcctt 18120
ctcccccaat tcagattctt aacacctctt gccgggatta gtgcagtgat cccacatcct 18180
ttctctctag ctctctctgc tactctctaa ttcctattgt atttgtgcca ccagatcttt 18240
ccaaagttta gctccaaccg tttctgtata ctgctttaaa tgtctattag tctttaagct 18300
ccataagggc aggagtcctg tcttattttt tccctattct tcatgcttaa tacaaaggaa 18360
gctttgtatg attaaaattt cagcttctcg ccattggctt atgggtaagt ccaaattatt 18420
taaatctggt gttcaagtcc ttttatgatc tgcttatttt tccagcctga attcctggag 18480
ttcccttaca aaactcttaa aacccagcca aatggatcta gtcaccgtca ctttaaacca 18540
tcctcactct cttgtttttt gaacatgtta cttttattat tatccctttg accttgaagg 18600
ctatcccaat ttcaatacta tccattcttc tataacagtc ccctacaaaa tgaatattat 18660
caaccccca acccaaggag aagtgatcta tatgacacaa catggttgaa agaatgttgg 18720
tttcactact ttatctgtaa accaggggct agaaatctct agtttataag attttgtgga 18780
gaggggatca catgtgatta tggatgttag gctcgagtca agagtgcata agactttttg 18840
gatttatccc tttcttcttt ctccatcaat atggtactta gtcccttaag tactcgtggt 18900
acttgtgtta atgactgata gcatccttct aaatatactt ctaaacatct gtctcttttt 18960
agggcaaagg ttggatatat ctgcaaagat tctctttgga tataagatat ccacagcaca 19020
taacttaaca gtgttgtaca tagtagatat tccataagta tttctttatt aaatgattca 19080
gagtcaatag tagtaagtga ctgccgaaga caactgatag attgtaagtt ccattaacag 19140
aaatacagtt agccctccac atccataggt tccatatcca cagatttaag caacagcaga 19200
tggaaaatat attttagaga cacagtaaaa ataacaattc aacagtaaaa aaaaaagtta 19260
tgtaaaacaa ctatttacat aacacattgt attggctatt acaagtaatc tagatataaa 19320
tgaaatatat gggggatgtg tataggttaa atacaaatgt gacaccattt tatatgtttt 19380
aggtaaggaa catgaatatt tttggatttt ggtattcctg ggagtggggg aatggaacca 19440

-continued

```
agccccttca aataccaagg gactattata tgggatacag aataaaggaa ttgattgtct  19500
tgctctgtta aattctggtc agacacattt gcaatgtgtt gttcagcccc aatattcatg  19560
gagcatctcc ttttgtaaag catggaggag ctatgagaga gacatggagc agtgaacata  19620
actattgttt caatgaacct gaaggattat catggaataa agaagttaga tgtttttctg  19680
tagcacccca aagggcaaac gcaatgagga cagattacaa ttcagtaaaa gaaagagttt  19740
tttttttttt gtttggtttg ttttgttttt gggtttttt gggtttttt tgtttgtttg  19800
tttgtttttg tttttttttt tttagatgga gtcttcactc ttgttgccca ggctggagtg  19860
caatggcgca atcttggctt actgcaacct ctgcctccct ggttcaagtg attctcctgc  19920
ctcaccctct ggagtagctg ggattacagg tgcacaccac caatcctggg caattttttt  19980
tttttttttt ttttagtaga gatggggatt tcaccatgtt ggccaagctg gtctcaaact  20040
cctgactgca ggtgatccgc ctgcctcggc ctcccaaagt gttgggatta caggcgtgaa  20100
tcaacgagac cagcctgaaa gatattttct tagaagggct tctttcatcc ttcatcagaa  20160
gttgttaaca tggaccatat gagttttgtt tggtctatat ggggtgtgtg tgtgtgtttg  20220
tgtgtgtgtg tgtgtgtgtg tgtgtgtgtg tgtattgaat tacttgctaa cattttactt  20280
caaaattcag atttccaccg tagggaatga agatctgaca atacagaact ttcattctta  20340
catggtaatg accagctgca ggtgaaaagc agctgatcct ctggatgggc catgcacttt  20400
gcagtttgcc caggcaccag tgacccactt tattcattta agttacctgc ttgactcttc  20460
tagtcattcg agtatgtcat ccctgtcaga tcagagacct aagcaaatct tgagtccctt  20520
gcttactcca agggctttca ctcctcgtat aggaggggct aaagaaatgt acaagcagca  20580
ccacaatagg atcagacctg actttcaatt ctagcacagc catgtaacat agttggatga  20640
cctcaggtca gtaatataac ccctctgagc ctctagatct tcattatctg tagaacactc  20700
tccttacaga gttattgtaa gaatgaaata aaacaactag gataaagggc attacactta  20760
gtaggtgctg aaatattggt tcccttcttc ttattcatca caccatttct gtctgtctat  20820
tggctgaatt acataaatag taaattcaca ttcactgaag acatttaaga agagtctgga  20880
ccctttggga accatgtata ggacaaagat ttggactcat agattatttt tacagtcact  20940
ttctaacaat ttaaaagcct atggatgact ccaaaatgcc catttggatg atttgaggca  21000
tactttgtgt agttaaggat tttaaataca taacagagag actgaagggc ctttgggaaa  21060
caagctgggg taagagtcaa aatgtaatat gttgactgat gttcaggaat aggctttggc  21120
atctgataga ttttgttttc agtactgccc ctgggtctta ctagcttcca gttctgggcc  21180
acttcacctc tcttgagttt tagtttcttt atttctaaaa tgaagatact aatgcttcct  21240
ttgttgggtt tttgtgaaga taagtgagat aataaatgta aaacatgtag cccagggcct  21300
ggtgcatagt aaaagcttca taaattgtac ctattattat tagtagtagt agtagtccag  21360
acaaacagag cttgggaaaa tgctagactc tggctgacat acatggactt ttccccaggc  21420
cactgctgcc tggcttcccc ttccacaaag ctttgagtct ccaaaatgct ttggctggaa  21480
tgtaagcgtg aggtcattgc agataacagg ggagcatgat ttgcttcggt aatgcaagtt  21540
attaagttac ttccctcagc ccagctaaaa tctcttattg gttgatgttt gcttcaaagt  21600
gtgagactga gctagtttga ggagagaggg agagtaagaa gattcctctt cttggccaga  21660
ggtcatggtc ttccacaagg aacagaatga ctcaacgcaa attatgggac ctctttgagt  21720
ttggggcccc tacatttaaa ccagtcactc cattgcacaa attggtaccc ttcccccaac  21780
aaaattactg ggcaggaatt ttcttgactc cttccatggc ctggaatgat ctcccttctc  21840
```

```
atccttgtga tccacacagc tggcaaatgg caggcagcag aacaaaaaca agcctcttag  21900
catagagaga gagagaaaga gtcacagcag tactgaattt gcttgggaac ctaatgttaa  21960
caaaggatct tcctctcaac accccaaaca gattaaaaca tttttttta acagcaagtt  22020
gtgtctcaga gcagctcttt gcttgggtat atttaaagat ctgctgagtc atttaagagc  22080
aggctggcag atcgtaagag gcaaggacta taccccagtc tatgggggag taagttgaga  22140
ggtgaaatct gtttggcttt ctcccatgtg aaacaaacaa ggtgatccac ttccatctcc  22200
cacaactctg gagagcatct actaaggctt cttattctat caactttgaa ctcctcagag  22260
tataatagag taagggtgag agggaaggag cagttgtacc agtgtgtctg ctgtctgaaa  22320
ttgtaatgcc cctgcattgg tagctgagag tagcatggaa gtgtcaggtt gatgggttca  22380
tttcattctt ttcttttcag tttctggtca catgcattgt taccatggca tatgacagtt  22440
gctagaaagt gaaataattt tttctacttt attcttaatt gcacttctaa atttattaaa  22500
ggagaaatta gcagttagca actgttaact ataggtacac attggggttt ccttagagcc  22560
aattttcccc ctagttttca acttgtaaat ctgatagatt ttgtcctaaa agttggcaaa  22620
acctggagct tctctttggt cctggccttt ttgaaccctg ttccacagag cccaatcttc  22680
tttcttgttt gagacaacta tccttctctt tgcccactgc cattttcctt catctacttt  22740
tcccatctct agcacctcag actgtcttcc cacagtggca cagactccca ctccactttc  22800
actgtgccat cttcttgcta tcaaaaccat cctcacagac ccttactttg ctgaaaccac  22860
ttctaggaag ggaaatcaca gtggatccat gaaggatgct ttctggatga ctttaaaaga  22920
ttggtattaa gatattttat tagtggtggc aacactgact tactcaggca gccatgccca  22980
ggatctataa gaaatcagat aagctaaaag ttgcttgagc tggcaggaga cctagttctc  23040
tgttttcctt tccctcatgc attttgttta tcaatggttt tcagagggct tagaggctgg  23100
ctttgttata gttagttggt aagagaaatg gtggaggact ggaaaatggg agtggaacca  23160
ttgagcatgt tattacaatt cctaggatgt ataaatcgct tgaaagtcta ccaagtactt  23220
tcagacacat tatctttttt actcttcaaa atcaacttgg aggtaggcac aacagggatc  23280
aaatccttag ttcacagatg agtaaaacga gactggagga aattaaagga cattccaagg  23340
taactcagac aataagcaac agaactagga tttgattagt tttttggggg gtggggagga  23400
cagagtctca ctcaggctgg agtgcagtgg caaggtctcg tctcactgca acctctgcct  23460
cctgagttca agtgattctc atgcctcagc ctcctgagta gctgggatta cagacatacg  23520
ccacaatgcc tggcaaattt ttgtcttttt agtagagatg gggttttgtc atgttgccca  23580
ggctggtcct gaattcttgg tctcaagtga tccacccccca ttggccttcc aaagtgcgtg  23640
gaaccactgc tcccggcccc ggaccattaa tttttgatgg taggtccacg ttttttcaag  23700
ttcacagctc ggatttgcta tataatgaat gaatgagtat atatgtcatt tgggaacatt  23760
attccaactt tcggttgaag atttgtttta tcagttgtgg aactttttt catttttagc  23820
attatcagtt tagttaaatg aacatttcgt tcatgaattc actaattaat tattttattc  23880
atcaatacat ttcctgagta ccaaactttc tatcaaatgc tgtgctggat tctgaggcta  23940
caaaaagaaa tacgacacca tctcatgact ctaaaatatc acagactggg gactgacatc  24000
tcagtagtaa acatatgaat agcaacttat gaaatgccat tagaaaaatc tcaagttata  24060
ttcctcagtg agtatggcca tcctaaaaat gagaagtctt ttattttggg tacatgaaaa  24120
tgaagcgttg tgagaaattg cattttaatc taatcttgtc ttactaagaa cagaagtgaa  24180
```

atgtttcagc ctctgtgtgt gtatttgtgt gagtgaaggt tgagtgtgtg atgatggatg 24240
gggctgcgag attgctaagt aggatctatg gggggcctta gatggtcctg gtgagtccca 24300
actttctggt tatgtatttg ggtgcagtat gggagtgaca aagattgttg tttaagagtt 24360
gattttagat tttttccaag taaatagtca gcagacttgg agcatcatca ttccacttgc 24420
tttgaaaacc taccacttaa ggctccttct tgtcataggt taactctttc tggtcaagta 24480
ttactctttt tgagcatttg cctgtcagtg acaggtgcaa tgttagatgt tgtctctctg 24540
ttttcttgtt taatctttac tttgatccta ggtagctctt attagttcca ctttataggt 24600
aagaaactga atttcagaga ctttaatgac ttgttcaaga tcacatagta agtaacttgg 24660
tagtttggga cttgaatttt gattgttcaa tttttttcg tttcctggcc tcactgctgt 24720
tttcactatt ccacaccact tcagctttat ttttcacaga ggccgttaaa tgtaccctcc 24780
atcagccaaa gcctcttgcc tcccttcaac gtaactcttc tctagcgtgt tcctaataat 24840
cttctgaaaa ggttttacag cctttctggg tactgggacc cagagtctta atccaggctc 24900
ttaagtgcct tagttaactg taatatggat aatcaaagtc acagctaatt caggaaaaat 24960
gagtttggga tgtgaatttc ctgggcaaca tgtcatctct tttttactcc cttagcttca 25020
taaacttacc cacaatgttc cctgaggact aacagtaatg gagggtgatg aggaaaggct 25080
ttcctccctt cctggtttcc aagagtcctt tagccaaatg ccacacctcc tcctgtttcc 25140
ctagtctctg tgcagagatg gaggtgggag atagacatgg gttcttttca gccctgagtt 25200
catgccagag tttttttttt ccctctagct ggagtgaagt aggaagagag gttcaatgtc 25260
caccaagaag accatgagtg aagaagacta aagtacttga aagaacatca gacctatgcg 25320
taaaatacca gggtttgtgt ccagactttg tgggttacta tctgtataat tttgggcaag 25380
tcaacagttc tgagtcagag tttccttatc agcagattgg aagataaatt ctaattatat 25440
ggatgaaaca ttaagtctag aagtattttg taaattcaga aagggcttat agatttaaag 25500
tgtagctgtt ttatcacata ctaaatccta tacttcaggg ataaaacctt ctcctgtttt 25560
ttctaaaagc ctgtgcatgt gtggtgtaag ggatgggttt tgcccctgta ccagccactt 25620
agcaattgta gtaactgggg gctgagggca gtggcctgct tctgcactga gcaagtgtga 25680
aaagagggta atgcattcag gggtcagcag atgacaggca gagtagcccc tccaaatctc 25740
cctcccatac cgcaaagccc cttatttatt caaacttaac attggaaact catttcaagt 25800
aggtacgtct gtgtctgggc gtctattttc tttctttgta tatagcaggc atttgtcaac 25860
ttggtgaaaa gcattaccct tctttccatt tctgaggact aattgtgctt attcgctaga 25920
catgagttca aaacagtggg ttgaaagagg gcaagtttat gccaaagaat cagaagtagt 25980
cataatttag agagaattct agaggtcagt tccctttcgt gtggattggg caactgaaac 26040
ccagatagaa aagcggatta gaccaagttc acaagcacaa acacgttact ggcacattca 26100
gattggaagt tgagggcttc tgctcccagg tcagaactaa atgccctttc cagctagggc 26160
gttctttgat ctcagtgatt tggactcttt ctactacact ctggggacag tgggttctga 26220
gataccaact ccaattaaag taggaatatg taccagctcc tccccttggt ttttttctag 26280
aggcctggca ttcagaggca gtgtgatctc tatatgtaat attttcacac tattgttctt 26340
atttaaatca catttgaatt ttggcaatta acaaggcagt aattggcatc aggaaggtat 26400
gttagtttgc ttatctgccc catccccccct cttcccgacc cactgtgcat tgcagaatgt 26460
tttatcagct ctgatttgcc aagttgctct cttctccagt aggtgctgca agcagagagg 26520
gattcctcgg aggtcatctg ctccatcttc ttgcctatgc aaatgcctgc ctgaagctgc 26580

```
tggaggctgg ctttgtacca gactttgtac agggaaccag ggaaatgaat gcagagtgct  26640
cctgacattg cctatcactt tttcccatga tactctggct tcacacgtgg gaggttcttc  26700
agctgaaaac ttagaactca ttttctaggg tagtgagtgt tgtaaggttt ggactgtgac  26760
ctaatattat gcagccatga cattatctat taggcatcta gaccagcttg cttgaatatc  26820
ttagcatgtt gactaatttg gggcagacta cagtgtgggt ggaggattgt gtgtgtgtgt  26880
gtgtgtgtgt gtgtgtgtgt gtgtatgggg ttgagcaatt cattattatt aatatgcaaa  26940
aagcacttat ttcgctatga caaggttgcc tttttcatgc atattggcct acctgcaaga  27000
cccctagaga cagtaagcaa catacatggt gtcttccagt tttcagcctt tgtgcaagga  27060
acaactgtgg gtttttgcat gtgtgttgtg gtttgatgtt tgtgtgtgat tgtgtaccag  27120
ggtatgtgtg tctgttactg tgagttcact tctgagcagt tgtgacacac agagatccag  27180
aaacagtgtc ttactctgtg tgctctgcta gtgggaacgt gtcttctctt ttgtgctcgt  27240
atctctgtgt aatcaagtgt cttgctaagt cagtgtgcct ctgtctcttt ttaccagttc  27300
ttccgtcttt gtgtctctat gccttcttgc gtttctttcc cctgagtttg cacatgtctc  27360
tgtctatgtg gatatctctc actccaggcc actgtgtcac tgtgtctgta tttacagctg  27420
tttctttctg tcggtgtgtg gattctttct gtcggtgtgt ggatttctat gtctgttttc  27480
atcttaattt gtgtgtctaa gcaagaagac tgttttgggg tcactatttc cgtttatgtc  27540
atagccccga ttgtccccat ctccatgtct ctctgtgtgt atatgttcta atgtatctgc  27600
ctacttatct ttattcgtat ttctctgggc atatatccct ctcttgcagt tcttggcctt  27660
tgcagttttt ggcttatgtt tttgtatata tcgactagaa ttggcctcct tatgtttttt  27720
gtgcatgttt tagtttttg tatatatcca ctagaattga cctccttatc atttttgtgc  27780
atgtatgagt gagcatatcc aactctgtct ttgagaagca gaactgtcta tgtttgcagt  27840
caattgtgtt ggctgtccct gtgtttgtcc ctgtgtgtgc atttcattgt atgtgcaccc  27900
attcatgtat ctttctgctt ctgtatgacc atatacttct gtgtagctgt ctatgtatat  27960
tggcttctat ctgtgtctgt gttgttggct acatgtctgt gcatatgcac ccactgagtt  28020
cataaaaagc tcacctgctc tctaaggaat ctaccagatt gttttgtgaa ataactcaca  28080
tctcgttttt tacttgctta gttatcttct ggcttgccag atgctttggt acttaaaagt  28140
gtgttggtac gtaggggtgc ataatttatt catgtaggat gtcaaaagag tcagttaaaa  28200
attatacaca gtgtgtcttt attaacagga cagttgtgtg tagagaatcc ttgagaaatg  28260
agcggttaga tgataaatct tttcatatta atttcatgat ttgagtgaag taaatttgaa  28320
aggtacaggc tgcataagag ctatgtgctt tttaaaactc attgtattga tggtggagaa  28380
agcatttatt tgtactgcaa agtcttattt gtgatgttca ttactgggtt agaaggtgtt  28440
acttttctga ttttgtttgg ctttttgaag agttactaca aatgacatct tagagacaaa  28500
gagctctgaa ggtgacttag aacacatgga gtacagacaa aaaggagaat ggaaaataac  28560
agagagatgg gcatattcct catttgaatg gagtcagcca ggggctcagg atggggtgca  28620
caggaaatgg agaggtgacg gtcatagaga gaagcttagc aggaccagat ctttccttgt  28680
cctgggctgc tgtgaccata taaggaaggc agtaagggga ggggtaggga tgaggaagag  28740
accagctctc cctttctttc tgatggaagg ttaccacctc tatttaaaac ttctgttctt  28800
ttggttctct ttctttgttt gattatatta ttttctggtc ttgttctgcc atagcaagaa  28860
ggaaattcca catgtggctc actcatttat tatacttgtt tctttgcatg atattataga  28920
```

```
gagcttgtta agtgtcactg cgaacatcac acacactgat ccactgatat gggcagggtg  28980
gtctttatgc cagctctgct cccttcccag tgtatctgtg gtgcttaatg gggacaacca  29040
tgatttttct gatgtcagtc tgtgatgtca gttgtccagt gtgtatgcag actgcttaaa  29100
agtacataca gttcctttgt aattatggta gtccctgaga aggaagtgct cactaataaa  29160
agactaggtt cagtagaaac atgtaagttg tctaggtgtt ggaaattaat atagtactct  29220
gctaagggaa tatatatcta gaagttaact ggattatgct caataaaaag attacaaaag  29280
tttcataaat atttttaact aattctataa gattaggaga gggatatttc agatattcaa  29340
ataatttttt taattgacaa acaccttaga catattattt acatacaatt gacataataa  29400
ttaaatcatt atgtctgttt tatgataaaa caggatcttt tggcttagtt tgaattattg  29460
aatgtaaaat aatgaaaatt taaaaaaaac agaggaggaa tctatcctat tttataattc  29520
agaccgttga attgaatttt tcttttgttg tattgatttc aatgtagaga agtctgtggt  29580
gctggattcc agtcaaaaga taaacatttg tatgtgggct ctacattgca gccaatcttg  29640
ataatttcaa accttgattt tctcatctgt ataatggtaa taataaagac tgtctcagct  29700
accaaatgat tgcatatgac aaacctctca cttatgtaag ggaaaaaaga aaaagaagga  29760
caatggggtg gatttttcgt atagtaaaat ttattcagtt agggtaatat tctgagcttg  29820
tcttctgaag caaaccctgc aaactctggc cattctgttt tgtttaggaa agagttaatc  29880
agttctgatt ctgcgttttc tggggaagga ggctgagtat ggattgaaga ggagtcacta  29940
cttttctgag atgatatatc tgtgctaaaa attagtaatg ctttgcacat gcaacataca  30000
gtgttcaatt ttgttagtca acagatattt aagtggcagc tgttatgacc tcaggggtgt  30060
agtgacttcc ttatataatg tcctttaatt attgaaaaag aaatctacat cagaatatca  30120
ggtaaaatct tattacatca aatattataa caaagatact ttttatattc tctaaaaaaa  30180
gtggagatct cagatgttgg ttcatttatc aatataatat tggatttgaa aattccagta  30240
tacaaaggga aaaagacagc ttcttaaagt ttatagtgat tttctatgaa ctttcaattc  30300
aggatttttt ctgttttact ggtatgatag agctaaattt cgaattgtaa gtagtagatc  30360
attagactgc agggtaagcc ttgagattgc ttcttttcag gtaggaaact ctactgtgta  30420
tttggctagt tcaacatatc atgggtagtc aaaaatagtt acatatccaa gtcagcattt  30480
tttaagttgt tcagttgtgc ttaaagattg gtcctttcca ggaccaatcc agctttatca  30540
aaaagttatt atgtacatct aaagtgttct gacattttaa tgctcacagt agccgaatga  30600
tgtgagtagg aatctttgtc ttcattttat agatgaagag acacagagaa ataaactaac  30660
tgggccaggg tcctaccact agaatgtgac agatgacaat ttgagcccag catatagttg  30720
tttccctata atattcgttt tatgattgta tagatatctg ctgaccaacc ttaatctctg  30780
ctccctgaga ttaaccgttc tacaaagcag aaactggagg tcgttcaaat gaaaactcta  30840
cacttttaga gggccattaa caatgctcaa gttaaagaaa agcaatcaaa gacaactgaa  30900
atactggtac cttcagacag tacatatgga tttttttttt ttttttgta ttatacttta  30960
agttctaggg tacatgtgca caacatgcag gtttgttaca tatgccatgt tggtgtgctg  31020
cacccattaa ctcgtcattt acaataggta tgtctcctaa tgctatccct ccccccttccc  31080
cctgccccaa aacaggccct ggtgtgtcat gtttcccttc ctgtgtccaa gtgttctcat  31140
tgttcaattc ccacctgtga gtgagaacag gcggtgtttg gtttttttgt ccttgcgata  31200
ttttgctgag aatgatggtt tccagctgca tccatgtccc tacaaaggac atgaactcag  31260
cctttttat ggctgcatag tattccatgg tgtatatgtg ccacattttc ttaatccagt  31320
```

```
ctatcattga tgtacatttg ggttggttcc aagtcttggc tattgtgaat actgccgcag  31380
taaacatacg tgtgcatgtg tctttatagc agcatgattt ataatccttt gggtatatac  31440
ccagtaatgg gatggctggg tcaaacggga tttctagttc tagatccttg aggaattgcc  31500
acactatctt ccacaatggt tgaactagtt tacactctga ccaacagtgt aaaagtgttc  31560
ctatttctcc acatcctctc cagcacctgt tgtttcctga ctttttaatg attgccattc  31620
taactggtgt gagatggtat ctcattgtgg ttttgatttg catttctctg atggccagtg  31680
atgatgagca tgttttcatg tatctgttgg ctgcataaat gtcttatttt gagaagtgtc  31740
tgttcatatc ctttgcccat tttttgatgg ggttgtttgt ttttttcttg taaatttgtt  31800
tgagttcttt gtagattctt gatattagcc ctttgtcaga tgagcagatt gcaaaaattt  31860
tctcccattc tgtaggttgc ctgttcactc tgatggtagt ttcttttgct atacagaagc  31920
tctttagttt aattagatcc catttgccag ttttggcttt tgttaccatt gcttttggtg  31980
ttttagacat gaagtccttg cccatgccta tgtcctgaat ggtattgcct aggttttctt  32040
ctcgggtttt tatggtttta ggtcttacat ttaagtctct aatccatctt gaattaattt  32100
ttgtataagg tgtaaggaag ggatccagtt tcagctttct acatatggct agccagtttt  32160
cccagcacca tttattaaat aggaaatcct ttcccaattt cttgtttttg tcaggtttgt  32220
caaagatcgg atggttgtag atatgtggta ctgtttctga gggctctgtt ctgttccatt  32280
ggtctatatc tctgttttgg taccagtacc atgctgtttt ggttactgta gccttgtagt  32340
atagtttgaa gtcaggtagc acgatgcctc cagctttgtt cttttggctt aggattgtct  32400
tggcaatgcg ggctcttgtt tggttccata tgaactttaa agcaattttt tccaattctg  32460
tgaagaaact cattggtagc ttgatgggga tggcattgaa tctataaatt accttgggca  32520
gtatggccgt tctcattata ttgatacttc ctatccatga gcatggaatg ttcttgtttg  32580
tttgtgtcct cttttatttt gttgagcagt ggtttgtagt tctccttgaa gaggtccttc  32640
acatccattg taggttggat tcctaggtat tttattctct ttgaagcaat tgtgaatggg  32700
cgttcactca tgatttggct ctctgtttgt ctcttactgg tgtataagaa tgcttgtggg  32760
ttttgcacat tcattttgta tcctgagact ttgctgaagt ttcttatcag cttaaggaga  32820
ttttgggctg agacaatggg gttttctaaa tatacaatca tgtcatctgc aaacagggac  32880
aatttgactt catcttttcc taactgaata ccctttaatg aattatttaa ccttagataa  32940
tttggctttg agctagaaag gtagagaaag atggaggaac caattcttcc ctgggttggt  33000
acttatttat cttgctcttt tgaagtctag gtcaatcgtc ctatttgttc tgaatggccc  33060
attcatgttt atccatttag ggacagcagg tttggcacaa atggattggt tttctgaggt  33120
ctcatgtaga gggctgcact gactgacttc tgaaagtccc ctctaaccct tcaaatctcg  33180
ggatcatttg atctcaagcc ttcattcatg catacatttc tatttccttt ttgagtacca  33240
gcacaacact gcaggctgac ccactggatg gatagaatgg ggctcttgcc ctaccaccct  33300
ttggcaaaca atttgagggt ggcattgtca ctatctcatt gatatagggt ctcttgaggc  33360
ccagaatgac aaagtaattt tcccactctc acacagctag ttattgtcag agtaaatagc  33420
aattttgaat ttgtagaaca cgtggtttta cctctatcat ttctgtttat tatgaaaatt  33480
ttagaagtaa taattaatta gaagtagaaa tgatgattaa aataaatgcg taactactaa  33540
aaagtagttc attgcagcac cacctaaatt catctcacca ttctaccagt agtacacatt  33600
tcgccattgg gttaacattg ttttggatct tatagctgtt gaagaagaca aaattctttc  33660
```

```
cattctctag attatatttt ccccatttgt aaaacataat ggaagtgtat ggaaaatagg  33720
agttgataat ttttaaggcc cctgtcagca tattggcaca taggattctt gtaagtggtg  33780
gtttacttca cttcagctat ggaaggccta tgcgacacca cccatagagg atagtttgaa  33840
agaaactgct agtgactgcg tgtgtttcct tcctgacata tttgctagaa ggtgatgagt  33900
tccagctttt tttcagactt ggatctggct ttcattcccc ttctcctccc accctcttaa  33960
acaacagagg cagcaaccat ttatacactt tccagaagta agtaagactc tattccagaa  34020
acaccctatt tcaaaatgga aatatactca gtgccccaat gacccattgg gcgagtttga  34080
acgtgtgcat tctctgtgct ccccgtttta gcttaggcct actccctaac ctgtcatatg  34140
tcacccagcg atggagccta gggcaatgag tgccatcata tctgactttg tggcctctca  34200
gctttcaatg actagctttg tagcagaagt ttagcctctc atccccagac ctttggaagt  34260
agtgttgaga taaagagagg ttgaattgaa ggttgtgttt tctagatttc tttcaattgc  34320
tccttaggct ttagaagaca aattctccta aaagacaggt gctacaatta atccaagcaa  34380
agggaaagat gtcaatagag ctgccccttt tcgtagaggt gtggcaactg ctgggaagga  34440
agaaattagc tggaggccgt gtgatcacta ataaaactca aagcggtgtt tttttacttc  34500
tcaatatgag gttgaaacta taagcttaaa ttgctgactt tctggcagca ccaaacagta  34560
aggaaaccac aaagataaac ccaaataata gagccaattt tctttttttg tgggggtggg  34620
ggatgacttc taactggtga tatgaggaag gataagaaaa tgtttatttt aatctaaaaa  34680
aaatggatag cacatatgat ctttgctaag tgcactgaat gtatgtagag gagacaagtc  34740
tgctaaaggt atgagaattg ggccgagatt taacacattt tcaaagctcc atgaagaaac  34800
ctactgaaca gtgggagtgg agcaggttgg ggatagtgaa gtatttgtaa tttattttta  34860
aaaaggagag ggagagagag aaaaggaaaa actgggccac ccatcctttg aaaagaaacc  34920
ttgaaagagg tccaaatatc cttagaaatc cttgacttct taaaagtgat aagagtttgt  34980
tttttccccc tgacaattat agaggtcaga gagttttctt ttctattgca aaacattgag  35040
agtgtgtaga aataattgta ggtagcttag ccttggctgt agtcagaact tttgtactgt  35100
gactttagga tctgtataga attgtatgat atgaggatac accaaaaact ctatgggcta  35160
tcaaaatggg atagcattaa aagaaatagt gcttttgttt agaagaagaa atgaaatgct  35220
tgtgtccagg tgcttaaagg aaggcagtgc agactttcag aaactagact ttaagagcta  35280
tactcagata ctgagaaggt ctgatggctg aaggaggaac aatttaaaag aatagccatc  35340
tctcccttcc ctgtaaatta gacataaaag aatatcccat tcatctcaga aatgtaatac  35400
aacattttag cttgctagta actttacatg ctatttcctt tacctcttat atttgaggtg  35460
tctatttgga gtgggctgtg tttctagcta ttctgtttat ctggtttgtt tttgtttgca  35520
taggaaactg gtgtacattt tatttgggta aatatcacct caattttcaa ataaagcttt  35580
atttaagttt cacatgaaaa agacaaatga gacaaagaag agaataattg cattgtcaga  35640
attataagaa aaaaatcaaa taaacatatt tgaaatgtcc agaaaaccta gagttttatg  35700
tatattatac aggagagata ttctgtcatc tggttgccaa actatggagg gtgggagact  35760
tagaattttt gtccaaaagt attgcttcat tagaaagata catgggtgtg cttccacatc  35820
agcaacatga ctgcagaccg ggaagtcctc acggagagct ggaatatggg tattttggac  35880
tctctggtaa gatgcggctt ttacttcact tcctcagtgg tactactgta aattttcatt  35940
ttcctatgga ataccctatt tggttccatt gtatatagtt gacaactaga attcgttcgc  36000
tgttgcttga actcaactgt aacttcttgg cactatacat atcttctgat gcgcctgtgg  36060
```

aagagctacc ataatgactg tgtacatgga caaaaaaaaa aaaaagagag agagagagag 36120
aattaaatca tgagtttgtg ccttgggagc tacagtttaa acatttgctg gttttctcaa 36180
ttaatgaaaa atttatttga aaataacagc acagaaagga agaaagacag gccggcaagc 36240
atcctcctcc taatatactt atccactttt ggataccttg atctcagtct cagaggtcat 36300
atttttagta aaatggccac cagaagtaaa ggattttatt ttccagactt tggtgtttgg 36360
agctggtgtg ctgagagctg gtagagaaag cgctactcag gtagatgtac caaaggagga 36420
tggttgctgg tggatatggc agagtacctt ttatgtggtt atctcttcct tgtaactctt 36480
ggctgcataa ctcttatttt cttttctatt tttgttctct ctcttggaaa aaatttggtg 36540
gtaaattttc atatgagcca tattgtcttt ttaaatagtt ttattaatat aaaatgtaca 36600
taccataaag catacccatt taaactgtaa aattcaatgg gtctctctct ctctctctct 36660
ctctttttt tttgtatact cagagttgtg caacaattat caaaatcaat tttgaaacat 36720
tttcattgcc ccaaaaggaa accctctgcc cattagcagt tactccccat ttcccccacc 36780
cccagtcccc ttcaacccta ggcaaccaca aatctacttt ctgtctctat agatttagct 36840
gttctggaca tttcatgtaa acggaatcat gcagcatgtc acccttttgta tctggcttct 36900
ttcacttagc atgatgtttc caaggttcag ccgcattgta gcatctgcca atacttcatt 36960
ccttatttat gactgaataa tattccattg tattaatgta tcatatttgt tttttccaat 37020
catcagttga tggacacttg ggttgttttc atcctttgtt tttttcttgg ctattttaaa 37080
taatgctgct atgaatgttc atgtacaaat tttttaatga acatctgttt ttatttctcc 37140
ttggtataca cctaggagtg gaattgctgg gtaatatggt agcttaacat ttaacctttt 37200
gaggaactgc cagatttttc caaagcagca caatcatttt acattttgac cagaagtata 37260
tgggagtttt agtttctcca catcctcaac aacactcatt attgtcattg tccttttcag 37320
ctcttttgat aatagtaatc tcaatgggtg tgaattggga ccccattatg gttttaattt 37380
gcatttcctt gaagactaag gatattgatc atcttttcat gtgcttattg gccgtttgta 37440
tattttttga tcttttgctc atttccaaat tgtgttgtct tttcattatt gagttgtaag 37500
attttaaaat atattttgga tatgtttgtc attttaggga tgatacttca cagttacatg 37560
atgttttcta gcaagcattt gtgttgttct actggtgtta catatcttag ctgcattagc 37620
cacttcgttg ggtatgaatg ccagcagaat ctaaatgacc ttggcttcac tgctgagaat 37680
gcaacccaag aacagaaatt tgtcagaaat ttaacactta agcccccccac ttcccaaact 37740
catctgggac aaggagaatc tacatttaaa gttctatatt ttgtgttgct gtggtttttt 37800
tttttttttt tttttacttt agcttggttg ggtttaggat cttttctttt tgttttgcct 37860
taggcatacc taagcagagg caagggagga aagggatatg aaactgatag aaaagtgagt 37920
aagctttatt cagatcagca tattcatctt aatatggttc aattggctga agaaatatct 37980
caactaaaac tctggaatac tttgaagtac caataaaatg tacctaatgt acattttatt 38040
tatgtttggt ctctatgtac ttgtgtgtga aacaatgagc acaaataatt ccctcctttt 38100
ttttaagcaa tttatattgg tgatttaaaa ataaaataaa tgcaagtggg aagtcatgaa 38160
accccatgta aaacgaataa gagcatatat taaaatccca cagactttag tttcaaatag 38220
tggttttgct gtttcttagc tgtgtgtcac tgtgcaagtt actttgcttc tctgagtctt 38280
tatttcttta ttggtgatgt atgtaaaaac ccaccttctc gaattattgt gaggacaaaa 38340
tgaattaatt aacataaagt tcctggtgta taataagtgg tcatattttg tatttgagca 38400

```
cagggcaact gagtttttga aactgcacat taatgttgca gtcaaatccg gcatgaaatt  38460
agagagtgca tagacagagt gggctgggaa aatgaaagga ctttgaacat ttatattctg  38520
ctttatttag gcatcagtgc ttaataatta ttgatagttt cttctggtta tctgacattt  38580
tgaagagact attacctagc agaaatttct tgtaataata atctcttaca cttatatagt  38640
gttttgtgcc tttagaagta cttaatgctc tttatttcac tatccataaa tattctctga  38700
agcaagcata cagtcagtat caattccatt tttcagatga gactgcaaga catagagtta  38760
cttgtttcaa ttcacatagt aaagtgacag tttgaaccag agcccaggtc ttctctctga  38820
acatagctct ttttctcctt cattatatca ggcatagcgg caatgtatta ttttactagc  38880
tttttatctt gaatatcctt ttagtgacct gcctttggtg ttagtgtgcc tataacattg  38940
tcgttgaata tcttaataca tttagtggtc ttagcaagca gttttgtctt cagaaggaca  39000
ctgaaatctg tggaaaggac tgcagaagat tgggtgggca gatacctatc actttctggg  39060
ctggtagact ttctgttgaa gctatttgca aggctagttt gtattatcga aaagcactac  39120
ttcagaagag ggttgtgatg tcaaagtagg cactttgagt gaagaaaggg ctgtaagcat  39180
gggtggaaaa tgtggtagat gattgtcttg agttattttc tttaatgtca agcaggcagt  39240
ccttggaatg ctatttcaaa aagtgttgta taatgttgaa gacacagtta cagatttcca  39300
acacgaagct cataaatctg caattccctg tcctcctagg cacatgaagg aaaatttatg  39360
agcttcaggt ttctatgcag ctattaaagc atatttaatc tgctttgagc tcaagctccc  39420
tctcatttgc tctcttcgtt tgttcctctt acatgagcaa actgcctttc tttttcttta  39480
aaagtagtaa gtagatttgt tttcctccag gtgtcatgaa tgcaaacatt gtaatacctc  39540
atctgttagt tcagtctttt gcaaaacaaa atggcagcac ccaggaggtt gaaagagtta  39600
aattgtttcc ttctctgagt ggtaccataa gttgttagtc tgctactctt tctcccagtt  39660
ggcacatgac gctaacatcc aatcgctagt gatgtggcca ttttttgcct tattttggcc  39720
tttcctcagc caccagtcat cagttttcat gcatatttgt cagaccctgc ttcctcaact  39780
ccacagttct tagttcatct taagcaaatc gctgtctttt ctctaaagat cctcaaggaa  39840
aataaaaagc atctccaggg ggaatttact gcctcatagc cctgacagag atttctgacc  39900
aaaccctaac caaaaaattt cttccctcca tttgtctttt attgttttta caggggagat  39960
atgtaacata ataacaatta tattgtacat aataattact tttacaaata ataatatctg  40020
tcatcaaaaa tatacagagc tttggatttc cttagtatgg cacttcatta agttgtggtt  40080
taagaatagc tatgattatt acttttgtga taattacgtt ccataatatg gaaacttata  40140
aaattacctt taaaatgtta ctcttattct ggccacagga tggaaagatg ttcgctagtt  40200
actcatttat aacctgaatg tactttttac tgaatctaaa ggtatcatct ttgcttggca  40260
attcccatga cttgtctttc tgactcttca gatctcagct taaaagctca ctcttcaaag  40320
aagccttccc ctgaccactc tggttttgtc ttcttnnnnn nnnnnnnnnn nnnnnnnnnn  40380
nnnnnnnnnn nnnnnnnnnn nnnnnnnnnn nnnnnnnnnn nnnnnnnnnn nnnnnnnnnn  40440
nnnnnnnnnn nnnnnnnnnn nnnnnnnnnn nnnnngagtt tatattttaa ctcttagttg  40500
aataatctaa gccaagaatt atcaaccttg ggttgcacat gagaatcacc aatgaagctt  40560
taaaacagtg acaaggctat cccaatctat tcattaatta tctccaggtc taaactttag  40620
catgtatata catttttaaa agctcataag tgattcttat gtatagccag tgctatctgt  40680
ctcttctcct gttctttccc ctcctctcct tactcctttc tcatagtttt aagataagca  40740
tggccccaca acaagccttt aattcgcatg gcagtttcta gggtttatca tggaaaatga  40800
```

```
gccaaattgc cttcaagaag tttttacgta cctcttatat agagtgtgac attttatatg  40860
tacctcttat aaaatgtgag cttttaagag tcatatctta ttgcaagaaa tttcaatgtc  40920
gaaaaaagta ttgaatattt ataaagtcac aaatacaaac ttttatatga ttctcaaacc  40980
tgtgaagtta tgtcatgttc aggccttctt taaagcatgt ggctctcagc cctggtactg  41040
tccttaacca taaacctcat ctttgccctc tatagggaga ggattgtgat tataattact  41100
cattttaaat aatgtatatt agtaatgtac cttattcata tatttgttga gcacctccta  41160
tgtgccaacc actatgctag aaatttttta atattcttca aaatcttcaa gatattaaca  41220
tatccccatt ttacaaatga ggaaactgct ctcaaagagc ttagtttaca cagccagtaa  41280
gctgctaagc ctagattgga tggagggtgt gtgagaaaaa aagcagcatc cataaggttt  41340
tcattctcct accctgtatg atagaggtac tagaaattat taaagaaaca atagaatttt  41400
acaagacttt aggaagggag aatgtgaagg gtacagttcc cagttgctgg aatgagtact  41460
ggagtaccaa tacatggctt gccatggggt ttggactacc tatcttaact cctttgctcc  41520
tcccaatctt gatctcattt gtttgaaaga tcatctgccc aacataaaaa tgcatttcta  41580
attctgtaat ttaagtcagt ggcaagatca gattcagtta aagtttactt tcctgacaac  41640
tatttaggat gatatctatt ttgcaaaact ctagtgataa atgtatgcac acttacacat  41700
catacagcgt ctcttctgat tctgactaag atgtgatgga gctgtgcaga tgtgatgggc  41760
tctttggaag aaaggtttga tatactacta atctaaggac tgaattttct ctctcatctt  41820
tgtttttgtc ccttttgaat gatgatgaga gcagcagcac ataacattct tttgtgctaa  41880
cagtatctct gcatcacatt gatcaggaga attggccctg gaatggtatc ttctcagttg  41940
attttcagga aagattaggt gattattttc tccataggaa gaggatgttt gatgtgtctt  42000
ggctttggca aaaggaagct tgtcgactca actgtaagta gatagaattg cctttgactt  42060
catctgtttc agtcgttgtt catactcagg tcctccagaa ggcctttaag catttttatt  42120
gactttgtgg tctattacac aaaactaaag atactgattc tcagtcgtga gtctgcttca  42180
aaattgccta gagaatcaaa aataattgta ccagttcctg ttcctggaca ttgtgattca  42240
tttggtctgg tatgaaggcc aggaatctgt atttttaaaa ttcactcaag taatttttgt  42300
atatagctat agttatgaaa ttataacaat aatgaaataa taataatgaa taatgaaata  42360
ataatgaaaa tctgtggctg aacttgtcca ctcccctatc ccctgcaata cttccccaag  42420
gtggcattta agatgggcct agaaggttat ataagatttg aatattaaaa catggattga  42480
cagtgaggac tttttgagag gtgacaatgt gctagcagcc ctggcttgct cttggcacct  42540
cctcgacctt ggcgtccact ctggccacac ttgaggagcc cttcagccta ccgctgcact  42600
gtgggagccc ctctctgggc tggctgaggc cagagccagc tccctctgct tgcagggagg  42660
tgtggaggga gaggcatgcg tgggaaccgg ggcacggggc tcatgggcca gctcgagttc  42720
ctggtgggca caggctccac cggccctgca ctcggagcag ctgactggcg ccgtgggccc  42780
tgggcagtga ggggcttagc acccgggcca ataactgcgg agggtgcacc aggtccccca  42840
gcagtgctgg cacaccaatg ccacgcttga attcttgcag ggcctcagct gccttcccgc  42900
ggggcagggc tcaggacctg cagcccgcta tgcccaagcc atccccctgt gggatcctgt  42960
gtgtgccaag cctccccaac gggcaccatc ccctgctcca cagtgcctgg tcccatctac  43020
tgcccaaggg ctgaggagtg tgggcacgta gtgcgggact ggtgggcagc tccacccaca  43080
gccgcagtgc cagatccact aggtgaagcc agctgagctc ctgagtaggg tggggacttg  43140
```

```
gagaactttt atgtctagct ggaggattgt aaatgtacca atcagcactc tgtgtctagc  43200
tccgggttcg tggatgcacc aatcagcact ctgtatctag ctaatctggt ggggacttgg  43260
agaactttta tgtctagctg gagaattgta aatgcaccaa tcagcacttt gtgtctagct  43320
caagtttgta aatgcaccaa taagcactct gtgtctagct caaggtttgt aaatgcacca  43380
atcagtgctc tgtgtctagc taatctatgg gaacttggag aacttttgtg tctagctaaa  43440
ggattgtaaa tgcaccaatc agcactctgt gtctggctca aggtttgtaa atgcaccaat  43500
cagcaccctg tcaaaacaga ccaatcagtt ctctgtaaaa tggaccaatc agcaggatgt  43560
gggcagggtc agataaggta ataaaagcag gctgcctgag ccagcagctg caaccactct  43620
ggtccacttc cacacagtgg aaggtctgtt ctttggctct ttgcagtaaa tcttgctgcc  43680
gctcactctt tgggtccaca atgccttcat gagctgtaac actcaccgtg aagatctgca  43740
acctcactcc tgaaatcagt gagaccacga acccactggg agggatgaac aactccaaac  43800
gcgccacctt aagagctgta acactcactg caaaggtctg cagcttccct cctgaagcca  43860
gtgagaccac aaactcacca gaaggaagaa actctggaca tgtatgaaca tctgaaggaa  43920
caaactctgg agataccatc gttaagaact gtaacaccta ccacaagcgt ctgcagcttt  43980
attcttgaag tcagtgagac caagaaccca ccaattccgg acacgttttc acatggagat  44040
aatttggaag aaaaacttgt aaaaatgtga gaacattgag aacttttatt ttccaaggaa  44100
agaagtggca gcttcatttt tggtcattgc aaacagcagt gccatacatg aaaggaaagt  44160
ggtggtgctc atcaacttag aacacttgag actcttttct gcttataaag aaaaagtgtc  44220
aactgtaaag ttgatttatt tatgaaccat aggctactat gaaatctctg ttcacagcta  44280
gaggcctggg agagtaagat aactacttgt ttattccatg aagccactta ctgtttcttt  44340
tctattgcac atacctcaaa tgaagcattt caatagaaga accacattct attcacttgc  44400
ttcattttat tctgatttct gtaaaaactc aaaaattcct caagcagtgt ttctttgcaa  44460
ggcaacaatc ttcagttctg ttgcaaaggt caggagtgat agaatgaaaa tggtactaga  44520
ttcaacagaa ctttggtatt tgcatggcta taacattgcc atggggctgc aagacttgtg  44580
agagcttgat attttgcttg ttgatgaatg agtctgtgtt ggtgctggtg gagtgatttg  44640
agaggtagtt ttccactgtc aatcaagagg ttggttttga aagctgattg ccagtagtca  44700
ttctgctaac cactctggtt ctcctttaga tagagaccta ctcagattca agtctcatgt  44760
actttgtggc ataaacattg tacacaccag atgtattgaa caaccacaaa gaaaactatt  44820
aggactcaag tagtatgtca gagagtagtc actgatgatg tataattctc cacttccaag  44880
aagatgtaag cgcactgttg agtggctaca tcctacatat gttggccaga atttaggaat  44940
acacatgtgc tctatacatt ttgaggtact gcctgacccc tagagaatcc tggtgaagtt  45000
tttctggtgt cagtttggtc ttaatgttta ggaaatgccc acagacgact cctgctttct  45060
gcttactcat gtagtaaaca caaagcacag gactagtttg tcttctggat caaggagaaa  45120
tgagttagca gatataaaac aaatcagaaa ggaagtagtt ctcacatatt taaccataaa  45180
tagttgctgg atgttcatta actctatagc aatatttact acttattggg gatcctggaa  45240
agaaaatata ctgtccatgt ccactgttca ctgagggccc cccgccaccg agaaactccc  45300
tgtcttcatc actcactctc cacattcatt gacctagagg aacagttcat ggatgagtga  45360
gagcttgagc tatatcttaa aggatggagt tggatttcaa ggcaagaggt ataagagaaa  45420
attcagagac aatattgacc atggtctttg cgaagaaaag tactttggga gataaggttg  45480
aggaaaagta cgtttgaatc ttcatccaga ggtagcccct aaatatgttg actctgttga  45540
```

aagagtactt gacttggatt cagacagatc tgcatttgac tcctgttttg ccatttataa 45600
gaacttgagt aattattgtt tctgaataag agtttattta gccaagcact cagtaaatgc 45660
ttgaatgtga aaatttactg ccctgttttt ctattgtcag atggtcccct tccttggata 45720
actttgtaat cgttgataac cttttctcag gaatcagaag gtagaaggat tgggaaaata 45780
taagaaacaa aaaggcatat tcttattttt attttcatat tgtcttccaa ctctccaagg 45840
catcttcgtt tgcaaggctg acttatctaa tacttgttgg gtagagcagg tctttctttg 45900
gttttcccct gtttggggtt aaactctgag taacgttatt ttctaggtct cagccaactt 45960
tgaagcgcat gaactcacag tagcctcacg agggtcactt cagcagtgag aagttacctt 46020
tcccatataa aagtgtaaga gtcgatggcg gccaggcgca atggctcatg cctgtaatcc 46080
cagcatttta ggaggccgag acgggtggat catctgaggt caggagttca agaccagcct 46140
gaccaacatg gtgaaactct gtgtctacta aaaatactaa aattagttgg gcgtggtggc 46200
acacacctgt aatcccagct actcagaagg ctgagacagg agaattgctt gaacccggaa 46260
ggcagaagtt ggaggttgca gtgagccgag actgcaccac tgcactccag cctgggtgac 46320
agaatgagac tctgtcaaaa aataataata ataataagag ttgatagcaa aataactatc 46380
tgtagcgtaa acctcagtat tctttatcat tcagtatcaa cattattacc aaaaaaacga 46440
taagcaatag ggactgagtt tctgtggggt ggaaatgtga agtggatctt ggcatgatat 46500
aacttgtgat ttggcttcct ttataaacat tatcaactac ctcagctcta tcaatcactt 46560
ggcagtccat agtgaacatt ataactcaaa tgactagtcg agtctgttca ttgtccatgt 46620
aaaggcgtat acctgaagtg agaagtctga ggtaacttag caataagttt gcagtacagt 46680
gtttagtgaa gtctgaaaat tcaaggcttc gagtcatgcc agattgctcc ataaccatag 46740
cctatctctg tcacaagtaa gaaggtttaa aaatcacata ccattattgg tcacaatgtt 46800
tggagatggg gaagagtttg tggatggatc atggcagtgc atggacagtg attagcccac 46860
agcacagcca gtgagcactg ttgtacccaa agcacgtaaa tcaccacata tactatcaat 46920
atatttatgg atgacaacag acactatagt tttatgtcag tgctttctgc tgctgaaaac 46980
aaagttagtt aagggtacct tttgtatatt tgcaacatat ctccacacct gttcctttgt 47040
ctccttcttg caagttcttt ctttcagctg actatccgct gttcctacta tggctcccag 47100
tggcttttca agagggtgat tgtttttaa gagaagatcc ttgaaggaca gagaaagcct 47160
gaatcgttca aaataatgaa ttactcagga tgaaatttca ataatttgca agtttgtgga 47220
gacagatatt ttggggaagc ataattttct atgtacccct caaatcatgg ctggagatga 47280
cagcctcttc cacctccata taagaccatt tcatttcttt ctactttttt ctccctcctt 47340
ccccccaaaa cacaaacata cacatatcct gtgcttcagc cacccagaac ttcttactat 47400
gtcttttcaa ttctctgtgg ctttgcatgt tctgctcctt ctgcctagaa tgctcctttc 47460
cttttcttac ctggaaacac cccaattcaa atgtcacctt ccttatttat accaactttg 47520
tccataactc ctttatcaca cttcttcttg tgattagtct attcacttgt ctgctgttac 47580
acctgtatga gagatgaaaa ttccttcttc atctctggaa ctcacgccct tagcatatag 47640
tagacaatct gtaaatgttt gaaggttgag tgaattaatg aatgaccttc aacctttcag 47700
gcttccaatt ttctctctga aaaggacagc taaatgaaaa ctcataattt tagaagatga 47760
ggttagacgg ttggtaggtg catgcagaga ccaattatta tttaggcatt atagaagtgt 47820
atagttcttg tatgttgagt gcagtgtaag agtggcccca aatatagtta atgcccactc 47880

```
cagacccagt tattatagag ttggccccag ctgtattgct tctatttaag actgagataa  47940
gaaatgacac tttcctattt ttttacctta ttgaaagggt aggggctggc tgttatcaat  48000
ctcagttcac ttgttgattg cattggcttg ccaagtgaga atattagcac ccctgcacat  48060
ttctatagtt ctgccactta tgagatcctt ccttcccatt gtcatattta ataatcagga  48120
tagccctata aaatatgcat tcttatttcc cagatgagga tactaaggct caagtaggag  48180
aacttacttg tttagtaaga tcgtacaact aggaagtggg agaggcaaga gttgaaccca  48240
gatcttccta gctcccggta catcgctctg tctactgagt cacactggag cagccaggag  48300
gcaggaaaat catctgggga atgtggtgcc aacgtgtgat gtttgcctaa atgtgtgcat  48360
ccttgctgga agccagccat gattccatgc tgcataagta ttcattaatg ttcatttcat  48420
ttatttggct atccatatgc tttccagggc gaaggcaagc taggacaagg gcagacaagc  48480
agccttaaag tttgggtgct ttccttcaaa gctgggctgc ctgtttgaaa atcaaacatt  48540
tttggtgata gaagatggtt ccagtacaga ttttattcat tactgcatct acatggacag  48600
acattttcca aagcatagct gaaaatatgt gtaagtccca gaatatttcc tgatttagac  48660
acagactttg agcatgataa ccacatttag catgttagga aattctgtca gaatgcttct  48720
ggaaaggcta cctttccaga atgaaatgaa aaaaaaaaaa aaaaaaagga tggactttga  48780
aactgattag atttgggtta tactccctca cagtgtgacc ctggcaaatg atttaactta  48840
tccgagtttc acttttctta ttctttgaag tgaaatttta aaatgtcatc ttgcctgatt  48900
tttgtgagaa tgaaaatgag atcccacacc aggaatttag aagctactca gtaaatattg  48960
cttctctcct ttccccttcc cgagtcctgt cccccaagtc attcattagt tattcagagg  49020
catgcattct gaaatctgcc tactgctcca cgttgaaatg cactgctctt gcaaagactg  49080
attatctatt tttttgtctt ccaaggcccc ctgtgttcca ctccaccctc ccaattctgg  49140
gggcttccaa agtgggcagg tacagaatgt tctgtggagc atcggaggct gttactcaat  49200
atcctggcca gcactctcaa ctgctctttg cacatactcc atatgaaggc aaactccaga  49260
acttggagtc catgtttgtg tcatgcattg cactgcttct tttacccaaa tccatctcaa  49320
gggtgagtag accaagctca gacttgtctt tggagcagat ttctcaagct gcccatgtcc  49380
ccacactgct tgattaaaag gaggtgcttc aaactctttg gctttatata gactagaagc  49440
agaatgattg gtggtgcctc tgttctcaag gtatcccaaa gcactttgta aggaaatatg  49500
acaagcgctg aggccacgca ggctagtaca acagccgcca cccagcactt cacaattagt  49560
catgcccagc ctgggatcat caagcctgtt tttgttggaa gagcaagaga gggagggaat  49620
gctagctggc aatttccccc ggtacccttt atgaaagtgc ccttggctct tccaatttca  49680
cctgaataac cagctcaggc aaattttcct ctatcaaaaa gcagaacgtt atagtgacaa  49740
gctgatgcct ggctgatgcc ccaggacatt gaccaaatag gcttggcctc acaattggtt  49800
tttattcccc atatcctttc ttccctttg ttctttttct atgtttcttt cccccatcgc  49860
catctgcaga gtgtcctcag tcagaagtca gctgtggggt ggacagtttg tcatttaaaa  49920
tcatccctat tctgtctacc cttcttatcc ctcacataat tgcttttaga gcaaggacaa  49980
ttctggaagt gaaactacaa taacaccctg ggctcctttc cctctagtag tactcagcac  50040
acttgcaatt acatgttcaa atttgtcttt cttatttctg tttaggttca tgaaggcaag  50100
ggacatgcct gtgttgctta ctttctcttg gcaggcacat atagcaagtc ttcaaaaaat  50160
gcttgttaac tataaattaa gtgtttaaga agcccatcgt tagtatcttt gcccctgcct  50220
tatttgtaaa caaccggccc cttctatttg taagttacct tgttttgatt tccatatccc  50280
```

```
ccaaagcaaa ctttagctca tggccttaca gagtgtgtat attagtatgt taaaatgaaa  50340
tcaactctcc tcccccaagc cttctaattg acatgaattt gggagttgac ttgcattggc  50400
ctttgtcctg acagccaaca gagtcctctt ctggtgtatt cactgttggc ttccatgaag  50460
atgctatgga gaaagtttgc cattgacata cattttgagg gcagactcaa cctgagtaga  50520
ccggattgag ctttccccat ctgcctgcca gagatcacta cctgtgtgtt gctaaaaaga  50580
gaattatagg agtcctctca aggcagaaag acctaaaatt agacatggca gccatgcctt  50640
tggtgtgtat gggggtggga tacaggcagc cagtttcccc tctgttttct cccttgctta  50700
cacagccaag gagtggagcc aagcctcaaa gggaagagct gtatactgga gcatgccagt  50760
atacaggttc ctggccctgg ctgagttact attttatata ttccaataga gaagcataga  50820
agacttctag gttgccactg tcatttgaaa ttgggtattt ttaaaagaga aacttgaaga  50880
ctcaaagaaa gctttctttt gcctcccctt acagttgatt tttgagcttc ataaagctac  50940
ctagtccaaa gtacccacac tcttattatt tttgtctttc ctaccggttt tttttttttt  51000
tttttttttc atcttcccag gtgtttgatg atcactaaga gcttcaacat tgctcacctt  51060
gaccaggtat gaaaccaaga gttttgttta aggcataaaa gaatgtagga actcaaggat  51120
taggttgaga tggggaaggg ggatgaaggc ttctttttc ttgggttaaa cagaaatgac  51180
ttagatctca gagtgaaagc cttgaattgt cacatatatc actggcaaag actagttctt  51240
tgctatgata agaattgttc atcatctcgc ccctgaggat ttagggtcaa ggcctggcta  51300
cacctttga tgatctcagt catatgactt aacctcttta aagttaacct ttggtgagca  51360
ctgtgccccc tgcaacccca gtaaggccca acagggctct ccaaggaggc aaaattctga  51420
tgatacattt ctgtttagtg aaaatgggta gggaaaatta tgtcttagaa tcaattaacc  51480
aaacataaaa tcctccaagg ggcttggtag gatgcctagg gaagagcaac gagataaaaa  51540
ctccaggctg gaagggcatt gttgcagcac tgtcattctc cagtttctct tggagttgtc  51600
actaccctct cctttgttct cactgctgac atcatttgta aaataatttc ttcccataaa  51660
taaacaaaac gtacaatcct ctaaatgact aaagaacagt tatctagaag aacagtggaa  51720
agtattttct tcacctaagg gatgattctc tttacagagg tggagtaaag gatgtgcgag  51780
gaggcataat caagctaaga gatgcatgct gacttaaaag gcatgacatg tgtgaaacta  51840
agataatgtg ttcaagagtg atgctttgtt gatgcagaac ccactgaatt ccttactgtt  51900
atgtttgact gactatcagc ttattaataa agaaattgtg gtttgagtgt tcattgaaat  51960
tagccatgtt aggtttatgt ggggatgtga ggatctatgt ctaccaattg cagcttctga  52020
tgcagattgg aggcagaaat ctggcctgaa caataagtaa gagtgtcagc tctacagata  52080
tctcacatgc taagcaagca caatataggg caatccaggt ttacacaaag gattaatttg  52140
ggaacaatta tcctcatttt cactttctta aacgattttg aataaggtct tttaagtaag  52200
aagctccctg aatgcattta aaatatggtt tgattatgta catttaagat ttttctacct  52260
ttgtaggagt atctctgttg tataaaaaca caaaattccg gaacttttga aaggaagatg  52320
tgcctctctt catacatttg tcattcttga aagattgtaa aatgaagtga ctgcatatca  52380
tgtcgtgttc cctattgatt tcttttctca ttttaggaat attcccagaa taaaaaaaaa  52440
tttttttaa tctactaagc atgctaggta agactgaaga tgaatctatt taagttatgt  52500
caatatctat ttataaagat ttttgtgata ttctttttac tgtagaactt gaagcatatc  52560
ctaaagggaa tggttagcta tgtctgcaaa ctgtggcaat gacttactga gtaattgcta  52620
```

gcaactgatt tttggtgctt cttgttttga tagtatagca gtgcgagtag gttttagaaa 52680
agcaaaacta agaaaatcca gggaaatgcc atttgagaat ttctaacttt aaaaaacaaa 52740
taaaatagtg tcaagaaaaa atattatcca actaacccca aagtctacaa tgtaactctt 52800
ttattttgat aatgctgttc taactctatc tacttcagtc cattgccatc cagctggttt 52860
aggaatcaaa ttcccaatgt ttcatcactg ttaacattac tgttttactc ttcagtttag 52920
ttcttaaatg gcatagtgtc ttaaattccc tcagcctctt tcacgtttga tttctttgga 52980
aactttttac cttttcattg aagcccatat gatcttttct gaaacagacc cttatcttta 53040
ccttcttctt tggagtcttt ctcctacttg aatttctgaa cttcttaaaa tggccgcttt 53100
ggattggtgt aataaatttt cttttctttc tttctttcct tttttttttt tttttttttt 53160
tttttttgag aaggagtctt gctttgtcac caggctgcag cctgtagtgc tgtggagcaa 53220
tcttggctca ctgcaacctc cacttcccag gttcaagcga ttctcctgcc tcagcctccc 53280
aagtagctgg tactacagga gtgcagcacc atgcccagct aatgtttgta tttttagtag 53340
agttggggtt ttaccatgtt ggccaggatg gtctcgatct cttgacctca tgatctgcca 53400
ggctcgccct cccaaagtgc tgggattaca ggcgcgtgcc actatgcctg gccagtaata 53460
agttttctta agtgctttct taatgttctg atattttaaa aaagatctgg actattttgt 53520
catacaggca acagaatgtt aaaccatttc ataaagcaat gacaaatata catgattttt 53580
catcagttat aaatgctttt cctttataac attgaacatg tttttgcaac tgaaataagt 53640
gtgattttca tttttagaag gtacatgata aagttaaggc agtggttaat taattttttc 53700
agattaattt ttcagaaaag tgactgtttc tgtctgttca cttaacccca ggcatcaaac 53760
gactttaatc agaaagaact gaagagtaat ttggttattt tagtgccctt ttttgaggca 53820
aagtcttatt ctgtcaccca ggctggattg cagtagtgtg ctcatggttc actatagcct 53880
cgatctcctg ggttcaagtg atcctccaac ttcagtttcc cagataactg ggaccacagg 53940
tgggccccac actctctgct atttttttt ttttaatttt tcatagaaat ggggtctcac 54000
tatgttgcct tggctggtct caaaatccta ggttcaagca atccttccac ctcagcctcc 54060
taaattgctg tgattacagg cgtaagccac tacacttgcc ctattttaga gatttgtcaa 54120
gctttggaaa gagaaccatt tacaatataa taggtaaatt atggatattt gaggcagttt 54180
ttatcatagt atttgtagta aactacagcc cccccttttat aatatttgta tttaataaaa 54240
atgaaaatat tacttttatc ttgaacaaca aacataagtt ttaacaaagc aagcatattt 54300
agattagcac taataaccaa acgaaaacct ttataatgat agctgttttt aacatgatta 54360
caaaaaattc gctacacaaa tttttatcct aatcagtgtg aaaaacggaa aatattagct 54420
tatagggcca acttagtctt cagagtcctc ttcctaccta ctactgctaa taagccaatg 54480
aaaaactccc tgatgtgtgt ggtggctcag gcctgtaatc ccagcacttt gggaggccaa 54540
ggtgggtgga ttgcttgcac tcaggagttt aagaccaacc tgggcaacat ggtgaaactt 54600
tgtctctact aaaaatacaa aaaattagct aggtgttgtg gttcacacct gtagtctcag 54660
ctactcagga ggttgaggtg gggggatcgt ttgagcccag gtggtcgagg ttgcagtgag 54720
ccgagatcac aggactgcac tccagcctaa gctacaaagt gaaaccttgt caaaaagaaa 54780
gaaagagaga gagaaaaaga gagagagaaa gagagagagg caggcttctc cgctttttca 54840
gttcctgaat aattttccaa tctagaatgc aaaagattct gaaggaagac agttaccatt 54900
tcagattggc agaagttgtg actttaatct ggacttgaat atgttttaca tcaaagggtt 54960
gcctcaacag tgctcaaacc tgcctctctg aaaacatgct gagcgcaaag gttacttgaa 55020 gtcttagctt gagtacttaa gagaatgcta tggagggatt gttgaagaga gctgtgtcac 55080
agctaattct tctttagtaa ttaaaggttt agaaaactct tacactgcat attgacaaat 55140
ttagcaacaa aatgagcttg agaaaaaaat caaggcctgc tgtggaatct tttttttttt 55200
tctctaaaac aaacaaacaa acaaacgaaa ccttttaga aagattatgc aactgtatta 55260
tctgtaacta ctgcaatagt gtaaattctg atagtataat ttgcttttta aagctatctt 55320
tacttcagtg caacttagat taaatttatt ttaaatttaa acgatatttt tctctttgtt 55380
tattatttta tagtaagttt cccatagaat tcacaaaatt cattagaaag attttctttt 55440
ttttacttcc ttaggtcatt aagtttctga tttgtcagtg gatttcacag aaaccctgtc 55500
tttccaaaaa tatacaaaaa aaaaaaaaaa aaaaaaagcc aggtgtgatg gtgtgtgcct 55560
gtagtcccag ctactcagaa agccgagttg ggaggactgc ttgagcccag aagttgtggc 55620
tgcagtgagc tatggtcaca ccacttcact ccagcctggg caacaaagcg agaccccatc 55680
tccaataaat aaataaacaa ataagtaaaa agtttttcac cttgaaaagc ttataaacat 55740
atgaaacacc attagggtct ctgatatagt ttggatgtgt gtccccgccc aaatttggtt 55800
ttgaattgta atccccagtg ttggaggtgg ggcctgcggg gaagtaattg gatcatgagg 55860
gcagtttttt catgaatggt ttagcaccat ccccttggta ctgttgtcgt gatagtgagt 55920
aagttctcat gagatctggt tgtatagcac ctctcccctt gctctcttgt tcctgctttc 55980
accatgtgac atgcctgctc ccccttcacc ttctgccata attttaagtt gcctgaggcc 56040
tccccagaag ccgagcagat gccagcacca tgctttttgt acagcttgca taaccatgag 56100
ccaattaaac ctcattttta atataaatta cacagtctca ggtattcttt atagcaaggc 56160
aagaatggac ttacacagtc tcttttgtat cagggagaag gtctcctggg tgactccact 56220
tcttttcttg tttatgtatc cttccagatg atgtatttat ttcctttgtt tttcaattga 56280
tatttactct taaattaaac taatttatta ataaaaagca ttttaaagtc tcattttaga 56340
ttattttgac tatctgattt tttaaatgga gtaaaaaaaa tctaccttgg cctccatatg 56400
caatcaagca agaaacacat tttaagcata ttatttgcct tgtggattct gccttcctcg 56460
atgtgttcag tctgtatata ttcatttctc ccacactgta agaagctagt cagatgtata 56520
attggattat catgctacat gatcttagca cactcatttt aagcttacat agactagtga 56580
gcaccactca ttacatgtca tttctctaga gaaactagtt gggccgtggc tgcaggactc 56640
tcacttgaag agacacatgt ggtgatgttt tctcaggcag ttaagcaata aagtgtaccc 56700
tgatttgcac tgaaaataaa gattccttta aagggagcag ttctagttat ctctctcttt 56760
agataccata tgctaaacgt ttttctatgc actaaaacaa taactaggtt ttatactctg 56820
ccttacagcc tacttcacac ccatttcaca gggagaggaa cagagaggta agtgatttgc 56880
cccaacttac ataactagga agttatttac tcagtgtgga aacttgttca gacggtcatt 56940
tcattgaaat gtaggaagag tttctggcac ttctcttgag caggagtcaa aaacttcttt 57000
tttgcactag cccagatagt aaatatttta ggctttctgg gccatatggt ctctgtcaaa 57060
actcctctac tttgttgttg tagtgcataa gcagctatac acaatcctga aatgaatggg 57120
tgtggccgtg ttccagtaca accttacaga aaaggcaata ggctggattt ggctctgaga 57180
ctgtagtttg ctgacctcag ctcttgaact gagctcttta actgacctca gctctcgaac 57240
tatggtccaa gatcccgtgg tcctgtttgg tacctccatt tgccctcctt ttcactctct 57300
gggagcatag ctaagttcaa aattgaatta ggtacttgta gtaagagtac acttataatc 57360

```
ctgggatctt catgttgcca gatattaacc tcttgaagtt tatcaccaca gcctgggcac  57420
ttttctgatt tgctcacttc tagccccacg tttgggcccc ttcacaagca aacatgcaga  57480
ttttccagag agctgtatgc tactgaatgt agaaaatttg gctcatactg gcctatggac  57540
tatctgctca ctgccctgat aactattttc caagggagtg ggtgccctac ctttcctaca  57600
cagagttttt ttgctagtct cgccctaaaa attctaggta tcccttgctt ttaggataaa  57660
tatgtttcac taggaccagc cgaaaaatga aaaatagagt tatccaacta ccactttaaa  57720
actggacaag gatttttgtt gctgttgttg gagggggtgg taaacatcat tttggcagac  57780
caaatatact tttggtgtaa ggcagccttt tgcaaagaca gaacacttgg acaagatttt  57840
gaagtcctgg ttgcctttac tactgattta actacagtat ttgtggactt gggcaagtca  57900
cttcccttct gtgagcctca ggttattcat ctttgaaatg agtataatac ctgtgattat  57960
aattacttct ctggattctg cagagaactg aaggagataa tggatgtaaa agtactttag  58020
tgcccagcac tgctccttat gaaaatgagg aaataattga gatgagtgag ccattgagac  58080
aaccgtacaa aaagtgctga aaactcactg cttaaataag cacctcttac tgcttttgtg  58140
gcactttgta gcaatgtgtt tttattctga ttagaaagta atgtttggtt ttgtttggct  58200
ctttgctcag taaacccata ataaggatac ctatttgccc ttggaccatc agttcaaata  58260
ttattttact aatatggaat tatttggctc cagaagccac agttttctta gctgctcccc  58320
atccccactc tcacctcaaa tttttttttc actttatttt ttttttcttc tcagggaaag  58380
gtttgaggca aaaaaatgcc ttcttatgat ccaaaaccaa gcatggtggt gatttattca  58440
ccaagcgatt cctgagtacc tgtgtgatgg acatggtaga atctttgtcc tgatccatgc  58500
cttctgatat gcagccagta gccacttgtg gtaatggagc aacagaaaca tcactagttc  58560
aagtggaaat gtgagatgag aagtaggagg tggagagaac taaccagaag agggtaccca  58620
aataaaccag aaataggtat ttgttagaga aggggcctat tgagtgggtg gcagtggtat  58680
gtgtggcatt acttgctcct gtattctctg ctttttactt agttgtggct ttggtggtat  58740
agtctcagat ctctaagtta tgcaggtaat attgttatgt atcatgtttt ggcaatgtag  58800
actgaatact tgctcataag agtacaggac aatgaagata gtttggtttt atttactgca  58860
tggaaagtac aggatgttta gtaaacagat ccatggcata gtgagttcac cactaaaatc  58920
agactctgag aatgggtttg atttagatgg ctagtttaga atactggatt caggccactt  58980
gattaagaaa ggccattttg gctaattata agccaccaac attgtgtttt caatgttaaa  59040
gcttatattt gtcttccagt taccagaatg taagcttctt gaggaagaaa agaggagttt  59100
tcttaatctc tgaacctata cctgtctttc ttctgtgtct agcccagtgc ctggcaccaa  59160
acaggtgctc aatcaatgtt gattctatgc taccaacaaa aatgagttca tgatgtttac  59220
tattcgataa atgaatgcaa ttttagagtc aatttttact acttacacta catgtagatt  59280
ttctttttag agatttcaca atgctgattt ttttcaaaat aagcttgaag ctaagtgaca  59340
aagctgaatg atgatttgtt ttttattttt aattctaaac ttacaatttt ccatgtcatt  59400
gccagaaaaa tcattaaata aattatgata tactcatatg gaatactttg caaccattaa  59460
atcaaccatt aaatactatg caaccattaa atcagccatt aacgtattta atggctgatt  59520
taatggttgc atagtattta atggttgatt tgcacatttg catataccaa catattatat  59580
agttgagtga gaaaagttag tttcaaatga ctatgttaat atcccctgac tcttgcaaaa  59640
agaaaaccat acatttgaat gtacgtatac gcgtatgttt atacgtgcat agaaaaagct  59700
atgggggat atacctcaag ttgctaaaag tggctccacc tggagaggga catggaaagg  59760
```

agctggctaa aaactgaggt ttgttacgtt atacacccct gcacagtttg atttcttaaa 59820
agcgatgatt ataaattcct tttgttattt ataaaaatat tatttaaaac tttggtacta 59880
aaaacagagc tccatcaaca gatcaatgga taaagaaaat gtggtacgta tatacagtgg 59940
agtactattc ggccataaaa aatgagatcc tgtcattttt acaacaaaat ggatggaact 60000
ggaaattatt atattaagtg aaataaggca ggcacagaaa ggcagacatt gcatgttctc 60060
atttaatctg tggaatctaa aaatcaaaac aattgaactc atggatatag agagtagaat 60120
gatggtaacc aaaggctagg aaggatagtt ggtggggcag gggagggtga ggtgaggatg 60180
ttaaatgggc acaaaaaaat agaaagaatg ccattctaac tggtgtgaga tcaggaaaca 60240
acaggtgctg gagagaatgt ggagaaatag gaacactgtt tacactgttg gagggattgt 60300
aaactagttc aaccattatg gaaaacagta tggcaattcc tcaacgattt agaactagat 60360
gtaccatatg acccagccat cccattattg gggatatacc caaaggatta taagtcatgc 60420
tgctataaag acacatgcac acatatgttt attgtggcac tattcataat agcaaagact 60480
tggaatcaag ccaaatgtcc atcagtgaca gactggatta agaaaatgtg gcacatatac 60540
accatggaat actatgcagc cataaaaaag gatgagtttg tgtcctttgt agggacatgg 60600
atgcagctgg aaaccatcat tctcagcaaa ctatcactag aacagaaaac caaacaccgc 60660
atgttctcac tcataggtgg gaactgaaca atgagatcac ttggactcgg gaaggggaac 60720
atcatacact ggggcctatc acggggagag gggagagggg agggattgca ttgggagtta 60780
tacctgatgt aaatgacgag ttgatgggtg ctgacgagtt gatgggtgca gcacgccaac 60840
atgacacaag tatacatatg taacaaacct gcacgttatc cacatgtacc ctagaactta 60900
aagtataata ataaaaaaaa attaaaaaaa tagaaagaat gaataagacc tactatgtga 60960
taacacaata aggtgactat agttataatg atttaattgt acattttaaa ataactaaag 61020
gggtacaata ggattgattg taacacaaag aataaatgct tgagggatgt atacctcatt 61080
ctctataatg tgattagtac acattgcatg cttctatcaa aacatttcat ataccccata 61140
aatatataca cctattgtgt actcacaaaa atttaaaaaa aaactgtaca ttaaagaaaa 61200
acaaaaataa aaactgtagt tcaagttata aacaaaataa aagtaatttg gaggaaaact 61260
atcttcagtt atattggata tttgggggac atttttgtat gttagttagc aaaaatcact 61320
tgaaaaaaag gattcttcct tccatgattc aaaggagcat agcaaaaaat aaatgaaata 61380
aaataaaata ataaaaagag aaaaagaaaa ttattccata aattctactt acttatttct 61440
ggcaaacttg ttgacagcac atgtgacctt tttggtaaaa agacatattt ttatattttt 61500
agttaagttt caaatataaa ttgtttgtgt ttttaaaata aattaaatgg atgacttcag 61560
ccaggtcatc atgaaaacac atgagatatt gggttatgca atgactaaca gtgtgtacgt 61620
tttcttggta tttattcata aactggggaa taaaaatact ttttggctca tttactcccc 61680
aaataatttt atgtctccca aggagaattg taagttgttt gatagtaaat gctatgtatt 61740
ttgtatctta gtgtatgtat gggatttcag cgttagaaga gctcttaaat gccgtcttca 61800
tagtccaacc tgtcttctga tgcttgaaag ccccttgcaa taggaaatgc aaagtagaga 61860
gtagatactc aataatgtgg ttattgaatt atttagaaag aggcattttg agcccataat 61920
gtacaatagg tacttctaga tttattgttt tattctttgc agagctgcag aaaactaaga 61980
aaaaagttta tttcagattc atgtgtttat ttgattaatc tcttcataag tttcattttt 62040
cagctcctgt cagaaaatac agattcttat aaggttcacc tttacccata agaataatag 62100

```
tataaaaggg ttaatgtgaa atacaatcac ttcacagact gtttcaatta aataagagct  62160
cgtagataat tcagtccacc ccaccccatt ttacagatgt tgaaattgaa gcccccacca  62220
aaagtaaaag acttgctcaa agtcacacag caagtcagtg gtgagcctaa ttaggccccc  62280
tgccttccat tttggtgaga ttcctgtgct gatagtcata cccgtgtcaa atcctcttcg  62340
gcagttatgg cttgcccaca gtaatgtgtc ctgaaaaata tgacaataaa ttaagttgga  62400
gacagaacca taacctcttt ataaaaatgt tctggaaagt ttacatgaca gtacgtaata  62460
tataattaga aaggataatt cttatttcat atttatcttt ttgtttcaga ataataaact  62520
aagctatctc tactcagtcc attttaatac aaaaatattt ttaaccagat tgagttttta  62580
tgctttttag gaactttttg tctacctcac ttaattaaaa tactagctgc actaatcact  62640
tactgtggta ggcagaattc tagaatgacc ctgattacct tgtccttgta tgattccttc  62700
ctctttaagt aaggatagaa actgtgaata tgatatcact cccatgatta agctttgtta  62760
catggcgcag ttaactttaa gaaaggacca gtcacacaag ccatttgaaa gcagagagtt  62820
tgggattttt ttaactggtg acagaaagcc acgcagagat ttgaacattg agggtaattt  62880
gaatttgata tgccagtact aacttgaaga tagaggaggc tgcacagaaa gtggccttta  62940
ggaatgatcc ctggctgaca gccatctaga aaatgagggc ctcagaccta cggccataaa  63000
gaattctgtc aacgaacttg aacttggaag tggattcttt ctccagaact tccatataag  63060
agtccagcct gattgacact gtgattttgg ccttgtgcga ccctgagtag agaatccagt  63120
tgacttctga cttaaaaaaa aagtaagata ataaatgagt attgttttaa actgctaatt  63180
ttgtgataat ttgttacgca gcaataaaaa ctaatatatt taccatacaa gtcaaggcat  63240
ttatcctttc atgattcagt ttctttttac ctgacataat ggaattaatt tatactgttg  63300
tgaaattgta gttgagaaac acgacttcca aagtaataaa atacatgtat tattaatttt  63360
aatagtatta atagtaatga tactgattct ccgaggccta tacaaatcct ttgatacaca  63420
aatgaatagt aaaggaacat aagttgtctc taggtaggct ttcccacaat gcaattttac  63480
gatacagaag tcatatgcct attattctac tatggcagag aaaataagga gcctggaaaa  63540
ctgttcattt gcatcacata catcttaaga gctcactctg aacctggtac cttaataagc  63600
tctgtagaca gtataaagaa gaaaggaatc agacatggtg tctgacctca ggtgtctcat  63660
aatggagtag aagaggtaaa atatgggtca cactaactct actgctaaat aggaagtgct  63720
cgttgccttg agattgacaa aatttgataa gagttcagag gacattttct gtgaactggg  63780
ccttgaaaaa taggatatga gtaggagaag atgaagaagg aaggcattcc agctagagag  63840
aagagcacaa gcaaaagaat agataacctt gaaagtcatc atatgggata attcaagagt  63900
tcagtataat ggaagtataa gatgcataaa aataagtgta gtaggaaacg agtttgaaag  63960
tacagattgg ggtttgtcat agaaggcctt gaatttcagg ctgaggagtt ttaatattaa  64020
catttgtttt tgaacaaagg ggttaactga tcacatctgt gatttagaaa gaaaattcta  64080
gcaatagtgt agataagggt tgatggtaaa gtttggaggg tggtgaggca gagactggag  64140
acagggaggg catttaggat agaaagatga tgaagagatg atttagaaga gttgttttgg  64200
aaaaggagga gagagaaaat gttttagatg tgtcacagag ataaaatggg catggcatgg  64260
tgcaaggagg taaagcccaa tagctttgta aggtgctgag atagattgaa atcacagagt  64320
taagaagttt tagaatcagg attagtacca agacagcttg gctctagatc tcatacttaa  64380
ccattatggt ataatcctga gagggtgggt aacagcaata gtcagaggaa agaacccttt  64440
tatacatgat ggtacaggaa cagcactgtc ttccaacccc acagctgctc tttaacagaa  64500
```

ggtcagaaac tggggagaaa ttgtgtgtgt gtgtgtgtgt gtgtgtgtgt ctgtgtgtgt 64560
gtgtgtgtgc catttctgga actaaggatg ggaagtagat tagatgaggc cactgcagtg 64620
gagtctgcaa gttactagca ctcacccgtt ccaagaggcc ttaagggtgt tgacctgttc 64680
cctgggcatc accacattct acaaatttat gttcctctga gagaataggg tgattcaatt 64740
tcactgtgct tgaaggttac ttttggggtt catgtttgtt tgttctaact ctatgctaat 64800
gatctgccaa ctgtttgtca ctttctctaa cccttaggat gtctaaactg atctgttggg 64860
aaatgtgtag catttacagg atggtaggat ttgtaacatg cgatcacagg gctgtctata 64920
tagagtcctt gggaagggga gagaagagta tttctgttac aaatgcagat tcctagggcc 64980
ctcctcaaac ttactgaggt tcaaggattg atatttataa taagcacata tccattttca 65040
ataagcatga aagtttcata ccctctttta atgtttgaaa tcctcaaata aattagtcat 65100
tgatgccaga gtattacata attatggtac agaatgtgtt tctctgaatg acactttctc 65160
ccagagattc tgatatatat tcctctgcac tcaccctgtt tgataattac cagtatatgg 65220
accatttacc tgaagaataa gagtagggtt ttctactatt gttgaaaatg ttctcgactc 65280
ttaacaactt gtgtgtgact gtaacaagat cacacagggt aaacagtatt agcttattca 65340
accactggct gaagaaattt aggaaagtga acacattttt ctttacattt ctctttgttc 65400
tgtgagcctt ttatgctgga atagttttca ctgcaggctg ttattgtctg cccccagagg 65460
agggagttga cctagcgatg gtaactggag agtgtttttt gaaacctctt tcctaggttg 65520
gttgccaatg gcatctttgg aacagtgtcc ttcactttag tccctcaggg accagtgtga 65580
gaatgggaac tttatgatct ggagctggtt aagtgaagtc caaaaataat taggaaagtg 65640
tttccttccc tgggaatgag ttcagtagga atctcaatat attgtagagc acgaaggact 65700
cagcatcagg catttgcaaa ggattcttcc agttgcctgt gttacagagg acacagttgg 65760
aatttccttt tagtgttgag gggagatgtg tacatgattg tgagatgact cacccttttt 65820
gcttagatgg ttccactttc attgtggaca gactctttgg agggccagtt tggcatgcac 65880
gtgtgtgttc attccatcct ggagcattct ttatgagaaa gccatttgtt gagtggtttg 65940
ccattttgtt ttacagccac tctgtgggct atgaaatggt catctggccg ctttatttgt 66000
ccctaaaaaa gcagtttttt cctttcttat cttcaaggct gccaagcagc agaaagagta 66060
actcagggaa gccatgtgat agccttttat ctgtctgttc agaaactgat gatgtatcgg 66120
atttgataat tcatgaaatg tgaggtttac tggtttgcat ttgcctcaaa atgggcatgc 66180
aatattttgt caggtaacat aatagataat tggcattgct ttattgaagt gaattaattc 66240
aataagccta taagtgcctg acatgtgcca ggcactgtgc taggcattct gttaatagat 66300
gagacaaatc tctgtctttt aggtgttttt agtcaaccag gggagacaaa acacctttaa 66360
aaagacaaaa acacttttta aattgctatt ttaaaaaaaa ttcatagtgt acgtgaatat 66420
aaggtgctga atatgtgatt gattctgagg gaaaagagtg ataagggaaa attctcagag 66480
aaactcaagc tgagggaaga aaaggacccc agacagaggg actaggctag agctatgcta 66540
ctacattgca ttaaggggaa tggcacatac ttcactgttg cttcagcaga gagcaggcct 66600
gtgttaggtt acaaagggcc ttggatgaca tcctgtgggg ttttaaaatt ttatttaatt 66660
tttaattgac aaaatataat tatatatttc agtggggtac aatgtgatgt tatgatgtag 66720
gtatgcaatg tagaatgatt aaatcaagct aatttgcata tttatcactt cacatactta 66780
tggtttggtt acaacattta aaatttattc ttaacaattt tgaaatagac aacacattat 66840

```
tatcaactat agtcaccatg ttgtgcagat ttcaaaaact tctaacaaaa actttttgcc  66900
cttcgaagat attgaacttt gtcttatgaa catagtctta gaaggattta aaaaataatt  66960
tgctattcac tgagtacttc ttatgtacac tgtgcatgaa atgagtatta ctttttctaa  67020
tattagtttt cttgattgag gcttggcaat tattagtttg tatgcctgta gaaggattat  67080
aaacagaggt gtatcccagt aggatttgca ttttagaatg atgactgcga gtaaaataca  67140
gagaagtaaa accaaagata gtgggatcat tcaggagtct gtttcctaca ctgaacagta  67200
gttgagcaaa aaaaggatgg gcagaatgtg ttgcttctgg gtactgcaaa ttcatggcac  67260
ttgaatgaac aagtttaagc cttttattgg ctctttgtgc atatcttcaa catgtatgac  67320
tacaaagaga ccacacggtt ttgttgttgt tgttgttgtt gttgttgttg ttgttttatc  67380
tgaggtggag tttcactctt cttgcccagg ctggagtgca atggctcgaa tttggctcac  67440
tgcaacctcc gcctcctggg ttcaagcgat tctcctgcct aagcctcccg agtagctgga  67500
attagaatca tgtgccacca ctcccagcta attttgtatt tttagtagag acagggtttc  67560
catgttggtc gggctggtct tgaactccca acttcaggtg atcctcccgc ctcagcctcc  67620
caaagtactg ggattacagg tatgagccac cacggccggc ccacacggta tttttgaaag  67680
aacagtgagc ttggaattag aacactagtg tctgggccct ggtgctactg cataagtaat  67740
tatgaatcca tagccatctt gttgctcttc ttctctaagc cttggtttct ttagctataa  67800
aatggaaagt tgaaactttc tagctacttc tttgagttat gagtaacaag ttaggtaata  67860
cacttgaagg agaatgtgct atacaaatac tggttcttaa gacagctgtt gttaatgtac  67920
tgagtattat gcttacctca cagggttgtt gtgagcatca aatgggataa tggatttgaa  67980
agcattttgt ttaaagtgtg attcaaatgt taagaattag taaaaatagt aaaagagaac  68040
aattcattct ccatccagat gttccgtccc cacttatgtg ctcattcaga gttgtacaga  68100
aaaacctcca cgtaattttc acagactgga gttccacatg taacagaatc atatgggacc  68160
aaaaaagctc tctattgact tctttcctgc catattttgg ctctgggacc aacaagacac  68220
ctatttttca tgagctgcct gccaccaact ttgggctcac atctagttct gttgcccatg  68280
tgcatgctga atttgggccc atgtccccag atctaacatg aaactcaagt ttccttctgt  68340
tcaaactgtc caggcataat agtcttgaag tgtgatgccc aggagagctg tagatttttc  68400
actgtccaaa aatcaacatg aaaccagatg tatctgtaaa tctagtttca tgccactttg  68460
tagtcaatgg aaatacacta gcaggcagac aagaccagag tttactattt ccagcggaat  68520
taatagccac atggaaactt tgcctttggt atctgtgaga tggaagataa aggtgagaaa  68580
tcaaagcagt tcccacctca tcctctaaat tccaacataa agaggccttg aatatccttc  68640
tatcttattg tatatttcat taacagaagt atgttcctaa ttacttagtc attctatctc  68700
cattctcctt tgttttaact tcagtggtgc caggttaaga tgctctggct ttcagctttc  68760
atggagcatg gcatgttttt aaacttattt ttaaggacag gtatgttggg aagatcctag  68820
ttcctcatct ctttgctcct ggcaaggaaa tttagaattg cctaaagaaa agctgtattg  68880
gccaacataa taataaatca gtattagtga atctaaagcg tattggagaa ctttgtaaca  68940
tgagttgaaa ttcagacctg caatgaagtt tttttaaaag atttaaaatt gaaataataa  69000
aaaaaaagtt aaaaacaagt aaaacatatc agtagttaat cattctacca aaatttggtt  69060
ttacgtttgc atatttaacc atttttattt tctgtatttg tccatgaaca tgtgtttttg  69120
tatattgttt atattaaaca tggttttaat catggcttat ttcttttatg ttttacttct  69180
tttcctttga cataaaatat tgtattttta aaattttaac tgcttcttgg tataccattc  69240
```

caatataggt ggctacatag attgaagtta aaactaatta caatcagaga aaattaacaa 69300
ttcatccctt cagtctcatt agtcacaagt taaatactca atagccacat gtatctagtt 69360
gctaccgttt tgaatagaac agatataaga cattttcatc aacacagaaa attcagttgg 69420
aaagtattgc cctggagtaa atgtgccata ctgtactaaa tcatttttct cttgttggac 69480
atctaagtta tttcttattt ttttaatatt ttatataact tgacggtgaa tatacatacg 69540
tacatagcta tttgctttgc tgaattattt cttagaatca atttcaaaag tggagttatc 69600
aggtcaaaga gcctgagaag atttttgga acctgtagtg tattgccata gtcctttcac 69660
aaaagtttat gtcaacttaa agtacttcta gcagcaaatg attgtactaa tttcgctgca 69720
atctcaacaa cactggacat tataagtttt tattctaccc tattttccat taaaagataa 69780
cttatgcttg attgactttg cattttattt tattattaat aatgttgtgg tttccttttt 69840
ctgattttat ttttagttaa ggtatccttt aattttaacc tgatattttt ctctaaaaat 69900
tattctaaga aaagacaaag gtgatgtcaa atatatcctg agttttcatt ttttcttgca 69960
tggaatttgt atatttgcac ctttgcccat ttatattatg atttcttagt gtcttcccta 70020
tcaattttaa tgaagatttc atatatatca atttttccac aaatataatc tttttaaaaa 70080
tatatttttt ccacgatata attctaatgt attctccgaa atgttggaaa aacttaagta 70140
gtcatcaaag catttgaaga ttttttaaag gttgttttta taccagtctt aaatgttaat 70200
ttaagggtcg taaaaagagg tgaaaattaa atcatttttc agtaaggggt aagaccattt 70260
aactcttgga aaatacagga aacatgtaga tttctagagg ccaagaagga ggtagggatt 70320
aattattttg taactgcccc caaccttcta acctataatg aaagaaccac tgaaggccct 70380
taaatatttt taggcttaat tggctgtcct tgtacttagg gcacatctaa aaatcctgag 70440
gcaaccactt aagagaacat gcttttgtta attcacaggg agctgtccta agagtgtcca 70500
gaatcctctg tagtcttggg cctggtgctt gagagaccca aaggaaaggt caatggaatt 70560
gcagcttagt gttagagttt tcatggatca cactaattag ttaatgtcat aaaggtctct 70620
ctcctgttat gggaaaaagc agcaaatagg aacttctggt agggtgctta aagttggttt 70680
gatatttttc ttagtaattt taactaataa aagtaataca tgcttatggt agaatgataa 70740
acctgaacga aaaggtatga aaatgtagaa gttctcctac ttatgacctc acccttctt 70800
tgcactccca gtttcactcc tcagagggta accatagtga ctagtttctt gtgtttggtt 70860
cctgagattt tctgtgcata tatattgtta gatatatgca tattatattt tcaaaattcc 70920
tatcacatga caactactgt tctgtaactt aatttcttca cttaattaat agaccttata 70980
tatgcttttc catatcaata tatatagatc tatataagtt ttcctaaagg ttgcacaatt 71040
ttcaactgta tggctgtctt gtaatttact ttttgtttcg cctactaatg gatatttcat 71100
gttttcataa ctcttttgat attaaaagta gtgctgcaat taacatcctt gagaggcagt 71160
atatatggtg tttaaggtga atggctctgg agccagacta ctttggactg aatattgatg 71220
ccactaattc cttgctgtat gaccttaggc aagttgctta atttctttgc ctcagtgtcc 71280
ttgtgtgaaa aaatggaggc aataatggtc actatccagt agagttttta tgaggattta 71340
ataagttaat aatgcacatt aagaacttag ttatttttag attaagtagt gaaggactat 71400
ataattgtta gtataattgt ataccttttat tagcatactt ttgcatgtat agcaataaga 71460
caaattctta gatgtttaac agttggacat aaggagtgta cacattttca gtactggtag 71520
atgttacctt ttccctgcca aaaattgcaa atatttgata ttaactttta aaatcttagt 71580 aaatctgata agtataaata acaatttatg atcattttaa gttgcctttc ttaattttgt 71640
gtgaaaatga gtatcttttc acatgttttt tggccattta tgtttctttc catgtgaact 71700
aactgttctt ggccgttgcc tattttttgt tcctgttact atatggcttt tcatctgttt 71760
ctcgttgggt tatggagctc tttgtatata aaaggattta gcctcttgtt atatgtgtga 71820
caaatacttt ttccaattta tatttcaact ttgcttatgt tttcctattc atcagtctaa 71880
aattatgtag ttaaattcat cattgttttt tcttacggct ttggagtttg gagatcatgc 71940
ttcaaaggtc tttctaggtg gggttgattt aaatcaagta ctggaagtat ttttgccaaa 72000
aagactcatg aattatagat gttagagcta aaagggacct tagagatttg ctagttcaac 72060
ctccttttct tcataccttt ttaatttttc tctgcagatg aaaagaagtt tagtcccaaa 72120
gaaagaaagg actctaaagg ttctccagta agctaatggc aaaaatgtag actggaactt 72180
ctagctcctg atgggtattt cagtgatcat tcaatttaac cagatggttt cacaaaagga 72240
gctttctact aaaaaataaa atacatattt aagcaactca gataaatatt ttttatttat 72300
cagattaatt tttacttaga gattcatcag catatgtact atatatgtac aaatcaccta 72360
tgtgttttgg atatttagtt gaacaaatgt gcaaatattt taaccaaagg agcatatcta 72420
ttttcatttt actttcttaa tggttttagt tatgaatgtg aaatgtgtac ttaccttaac 72480
agaaattaag tagatttttg gtctgacata tatgagaact gaaaagcatt ggcttggctg 72540
ctaactgcat tctcatcttt ctttccctgc tttggcaaag tctgggatta aatctaatac 72600
cttttaaact gtttgggact tcagccagag tgacctgtct tgaattcaga actgtgcaga 72660
tcattcccca ttctaaggtc ctctcatggc tcctcattgc ctgtaggatg agatccaagt 72720
accttagcat agcttacgca ctgcagtcac ttgacctcta gcacctatgc agtcttccag 72780
tcttatttcc acattccttt gcacatgctg tttccccatg tggggcaact tttttcttgc 72840
ctgtctgcct gcctaagcca acttaaataa acatgatttc tgtaacttct gtgaagcctt 72900
ttccaatctc tccattccaa gacgaaggtg tttctatagg catgacttct ggaatggcag 72960
atcaaggatc tggtggaccc tctactcagt gaaacaacca tttaactggt aaaaatgatt 73020
taactggtaa aaatgatcaa tcaaccattt aaaatcttca gaaaatatcc taagggcaca 73080
tagcaaaaag agaaatgttt attcaagaaa agctattaag cctcagtaaa aacagcaaga 73140
gtctatggca tttgagtcat gacctgttcc tattccttcc cttagctcca ttctacaggc 73200
aagtgcaacc aagaagacgt aggcttcctc tctttcaaaa tcttactcca tagttataat 73260
ttcaccctac aatggggcag gccacaagca tctctttccc cccccacccc agccctatat 73320
tacagaagca ctgttctagg aaggcatagc tgagaggatt ggagattcct tcctcaccca 73380
ctttctacat atgagggctt tgccccaggg atggtaaacc aagaatacag gggtcctgct 73440
tgtgcctgcc tcagctcatc tataaggtaa aacttccaca ctaggaaagg ctaattaaga 73500
ggactaggga acataccatt atccccaggg tccacttgta gaacagggga gttattctgg 73560
gagaagcagg tcactgcccc acttgtggaa caggggagtc actctgggag aagcagatca 73620
ccgtccctgc tcccaattct attgcagtga cagaagttct gtcccaggga aaggcattag 73680
gatggagaac tctatagttc tccctgaggt gactgacttt atttggaaca gagcatgaag 73740
aagcttatgc ctaagggcac tgtcaaaaat aatgcagatc ttggtggtaa gcaattaaga 73800
gtggattggt agctccatga taactagtag caacaagcaa aacagcagac caacatggag 73860
gataccagag aaccagacaa aggaatcact aagaagcgcc cttgtggaac tacactcact 73920
gctgggtgtg tggaaagtta tgcatgtgtg ctttactgta ccctctcaaa agcaacctaa 73980 acaggatgtg gcgtaggctc taaagcattc ctcaagccac acatggatcc atcagtaaaa 74040
tatggagggc ttaaggttaa aaaggcttaa gtacaatgtc tggccctaca ttttctacat 74100
gttatgccac cctgaccaag gggcaactcc tacaaagcca ggcataataa taaaatcata 74160
tttgtctctt ttggaatgga tgactgtgcc taaaactgtg ccctttgaaa agcaactaga 74220
gagataattt ctgaagtgtt tgtccctacc tgaatgcggg caaaattcta aactccctga 74280
agtgtgaaag tgttttccaa gtcacatgca catccagtag tggtaaaggg taaaaatcta 74340
actgactaag agggcttcac agcaacatta accaaaaagt ggtttatgta atctttgcct 74400
acctcataat tccctaggca ttctatgcta ttctgtactc agaaggctta aaagtcaggt 74460
tagggaaagg aggcctttga ggttactgtg cagaggcagt gctgggaaag gaatgaagtt 74520
caataaattt aggccatcat ggtttaaaga atggattatg tagataggaa ggataaagga 74580
aacccagagt caagaaaagt aaagcttttc attggtgcta tgccaaccca tatctgagcc 74640
tgaggcaaaa ggaaaaatgt gctccccaat atacatttat acaaaatatc aactaatttt 74700
atttgttgaa ctgaatttaa aaagtcaaca aaaattaaaa ataaaaaaat cgtgactata 74760
ttcttaataa gtggtttatg taaacccaga gttgaccaat gggatgccag tctcaaccat 74820
aaaaacaaac aaataatgtg agtagcaaca ccagaagttt caaagtgtca gggaaaccag 74880
tttcacagaa gtggttcagc caagtcacta aacaaagaaa tgactaagca aaaaacaaaa 74940
tgagtctcag agagggtcag gtcaatatcc agagttgtta caatatagta actaaaatat 75000
tgttttgaac taaaaatttt gaggcatgca aagaatgagg aaagtgtaac tcatacatgg 75060
tattatatga aaaaatcaac aaaaaactat ccatgaggaa acaaggatgt tgaacttaac 75120
taggcaaaaa ctttaaaaat cagctattta aacatattca aagaactgaa ggaactatgt 75180
ctaaaatact aaaataaagc gtaataacaa tttctcatca agtagagaat gctaataaag 75240
agatagaagt tatagaaaaa gaagaaaatg gaaaatctgg agttgaaaag tataactgaa 75300
atgaaaaata cactagaaaa ggtcacaaga agatataact tggcagaaga aacaatcagc 75360
aatttagaac atagatcaat atagattatt catttttaaa gatagaagga aaaaaagaat 75420
gaaccaaact gaagattccc aaagaaatgt aggacatctt aaaggcacat cattaggaga 75480
agaaaagaag aaaaagaaaa gagcagaaag aatatttttt aaaaatggat aaaatcttcc 75540
caaatttaat gaaaaacatc aatctacaca tcaaagaaga tttttttta atttcaagga 75600
ggaaaatgta aagatattga tacttagata catcatagtc aaaatattgg agccaaatat 75660
aaagagaaaa ttttgaaatt agcaagagaa aaatgaaacg gaaccacaat aagattaaca 75720
actgattctc atcagaaata gcagagagca gaaggcagtg caatgccata ttctaaacat 75780
tgaaagaatg aaaaaactgt cagccaagaa tcatatattc aacaaaagta tctttaaagg 75840
taaaaatgaa atgaagacat tcctaggtaa acaaaggctg agaaaatttt ttgttagctg 75900
acatgccttg aaagaaatac taaaagcttc ctagacagta gcttgaatct gcatgaaaaa 75960
agcaattcca ataaagggaa atttgtaaat aataaaaagg tatcattata tattattttc 76020
cacttaactt acttaaaatc aatttcttaa agcactatct gtaaaaatgt attgttattt 76080
gataataaaa tgtaaaagag gggagtggga attaagctaa attggagtaa ggaaatggta 76140
tcatatggta aattgaattt acagaaagaa atgaaaaaaa ttaagtggca aatatgaaga 76200
ttaacaaaaa cttctataaa ttaattgtgt tctctttccc ttagcttctg taaaagacat 76260
aagactattc aaaatgacaa tagcttaaac gcattgtttt attggtaaca aatatagaca 76320 aattatgtac aacaattatt attatacaag gagagagaat ggagctatag aggattaaag 76380
tttttataac ctattggaac taagtcagta taaatctgat gtggattctg ttaatttaag 76440
atatatgtta gaagccccaa agtaatcact gagaaaatga tgcaaaaata cagttttaaa 76500
aagttaaaaa catagtttag cttatgtatg cctagtattc cattattttt ttttttatac 76560
tttaagttct ggggtacatg tgcagaacgt gcaggtttgt tacataagta tacaagtgcc 76620
atggtagttt gcagatccca tcaacacgtc atctacatta ggtatttctc ctaatgctat 76680
ccctcccaca gtcccccacc cccctcgaca ggccctagtg tgtgatattc ccctccctgt 76740
gtccatgtgt tctcattgtt caactcccac ttacgagtga gaacatgcgg tattccgttt 76800
tctgttctgt gttagtttgc tgagaatgat ggtttccagc ttcatccatg tccctgcaga 76860
ggacatgaac tcatcctttt ttatggctgc atagtattcc atggtgtata tgtgccacat 76920
tttctttctg cttgttccta ggagaaagtg gctgaagctt ccagagagaa gctgagagta 76980
gtttaattct ttttgccata aacacggcaa cccagttttc tgcaagctgt gttagtttgc 77040
tctctccttg gttcatccat tcatttattc atagcttcca taaatgttta acaaacatta 77100
attaggggcc aagccatgtg ctaggcgcag gggataaaac tgtggacaaa acaagcccca 77160
gctactctta aggaactgat agacaaatgg accagcaaac aggctggtcc tgttttgaag 77220
gcaaagtgcc tggtgctcct gatctcatga gcacaaagca tttagcctaa atctcatcct 77280
cctaaggcct cagaaacaag gccttatttt aataactgca agtcagtcat ttgaagacta 77340
aatcatagaa tcctagaaaa ctagtactgg gagcaaaaca aaagaatggg atgagcatga 77400
aacatatatt cagaagttgt ggtgtgtagg tgtataagcc aagctctttt cttcacttgc 77460
ttgctaagtc acttagcttt tctgcctttt tctttgctct gtctggaaat tgagttaatg 77520
aaatatatct acatgataga gatattgaga tgattaaata agatgctgct gtcacccagt 77580
atgcccttac ctgctgtact tagaagtatc tgtaattcat tttctaaact ttttgtatga 77640
gtgcttcatg catgcccacc accatggaag ctaccttaag acagtgaggg cctttgttta 77700
acttgtttgt actgtatcct cagtctaatg gtgtctggct tatagtaggc accgaataca 77760
attttattga cagaatggat tataatgaat gtgaaggcat ttttaaattt atgaagtgtt 77820
gtgcatattg ttgttaattt taagctgttc agttaaagaa cccctaatcc aactctcttg 77880
agttttatag atatcataga agatatatct tcccttgaca cagaagcttt ccttgaagct 77940
tcccttgact catctatttg cctcacagag tgattgtgca gatcccacaa gataaattta 78000
tgtgaatgtg ctttatgtgt ttgaagcgct ccacaaatac gggttttata agttgagaaa 78060
atagagtcag ggagaaaggt gactgatcca aggtcatgca gcgagttagt atcagaattt 78120
atgatggaat ttcaggctcc caatttccag tccagtatac taaggcagat tccagagaag 78180
aaacagtgga gagcaggcac tgacgaggga cgaagaaaag caggctccgt ctggctgcaa 78240
cttgtctctt catggcaaag agaaactagg acagtactat gccagagacc acatgataac 78300
tttgcagaat ggaaagagct tgtttaccaa attgaacact ttatctgtgt ttatctaaca 78360
atgacagttc caccagctcc ttaccagctc tcttttgcct agtttaacaa tataccaact 78420
atgacacatt ttccttctca gtttttattc tagattacat tttgttcaac ttcatcttaa 78480
tgtgtagtat agaaagagta aggtaagagt ataacaagtg gttattttcc atttctactg 78540
aggacagaga aataatctaa gggatttgta ttagatatga agaagttcat ggccgggaca 78600
tgagagatac tgtgatagaa tggatattgt taagtctttg gtagtttttg aggggaaaaa 78660
agagaaattt tttatttgtc tgataatagt ttagcaatgt cttaatttag gattcaaaag 78720

```
ttgttcaggg tccatcttgg ccttcaaatt aagatgcctg ttgagagata acgttgttgt  78780
tttcaaactc cattctgtga cttaagaatg agagaaggag gaagaaaaga ggagaaaatt  78840
ggagggaaaa gtgcccaggc agtgtcaagg ctagacactg gaaatttatc aatgaaagcc  78900
acatggtgga tgggaatcag atatgtgcat caattatttg tgttctaatc catagagaag  78960
taccgtataa tgcaccaaga tatgagatgc tttgaaagaa gaccatataa gtggagatgt  79020
gttcctattc tatctaggga tagagtcaga aagggcttca ttgaataagt ggcagcctct  79080
tgggctgaga cctgagttat gagatgatgt ggcaaaggag acagatgatt gggggcaagg  79140
tggggtcatt gaagttggag gcagtgacaa tataagcaaa gctacagggg catgaaacag  79200
caaggttaga ttagggaatt gcaacagggt ggtactgctg gaaggtcaca tggaaaagat  79260
tatgagagta ttgagataag aagctagaaa taagctttga atgccatcct agtgctttga  79320
atttgtatcc tgcaagccaa gtggttttca cttggtcatt taataaaatt gcagattctc  79380
aggtctcacc tgtaacttca gattcagaag agtctgtgct aactgaaggt ggaatcagtt  79440
tccatattgc taattagctc ctcagaggat tctaatatat cagtgagtta caaccactgc  79500
tgtaagccat aggtagttat tgaaagctgc tagggagagg agccacagaa gcagatgttt  79560
tagataggat ccctctgggg ttctgtgtaa tttatggact ggactggaga ggatcagaca  79620
ggaaacagaa agacttgaat aaggcagttg cagttagttt ggaggcaaag attctctctc  79680
tctctctctc tctctctctc tctctctctc tctctgtgtg tgtgtgtgtg tgtgtgtgtg  79740
tgtgtgtaat tgtaggaact atttaggcag taaaattaac agatattagt cactgattga  79800
ctgattggat ggcagtgata ggtggggtgc attgagggaa ttgtattaca ttaagtccag  79860
gatgactcat ggttttctaa gttgagtcat tggggattgc cagccaatgt gagaaactat  79920
atcgtctaat agttgatctt ggagttagac ttgaattaaa atcttgaagc catcaattgc  79980
tgtatgtggt cttgggcaga acacttaagg tttctagacc tcagctcttt cttctataaa  80040
ataaggataa taatgcatac ctcatgcatt tgttgtaaag actaaatgag gttaaattat  80100
gtagagtgta gtatagtaac tagcacatac agtggcccag taaacgtcag ctgttattat  80160
tgtgctatat gttgtgatgt gtactggagt gagatggggt aggggatttt ttagtctctg  80220
acaatgactc ctctccccat gatcaaaatc agaaaatcag tctcttatgt gctgagaaga  80280
gagacacttc tcccaagtgt ttaaggctaa taccttgcct tgttttgcct tgggccagac  80340
ctcactacac atctgtttaa gagataaggg taagctctgt tcttggtgag tatctcagtg  80400
gggctgtttt tctagttctt gtagtttctt tgggccaaca tgaaatgtct aaccttggct  80460
tcttggttgt ggattctcgt caacatttca ctgctaccca agttgtgtct gctcacatga  80520
tgctatcttc cttcttttgg gtttccgaag ccctcagaca cttggctgaa cactttttc  80580
acatttctta agctatatca tctgtgtttt ccctgccaca gacaaagtca caaaaggact  80640
ttaagatagg gtctttttcc ccccagggtt tttatacatt ttgagtaagg gcaagtggta  80700
aatgctgctt ttctgcctta accagtagtg tctgacagag gaggcagcat gatgattgca  80760
gagctcactg aactgaaagt cagatgcctt acccacctgg actctagtac caaggggaag  80820
atggagtggg atggggaaaa tggggataaa ttatcattta ttttgagtgt gccaggccct  80880
ttcccatgta ttgtctgatg catttgtcac aattctcttt gggtttgaaa tgtgattttc  80940
ttcattttat agataaggaa acttatggga agggagatta ggttcatctc gtgcccaact  81000
ttacatggct agtgatcaat aatagtgaga ttcaaactca ggtttctctg ttccaaaacc  81060
```

```
tttgcttttt catcttttga cactgtaact tattagaaga tgtctttgac tctgagtctc  81120
atttgcctca actgtaaaat ggagctctgt aacccttgct ctgtatgaca gtaaatctcc  81180
tgagaccaga tttatgatag gggacaagga tatttgtatc tttgggcccc taatgtattg  81240
aaagtgcctc tcagtgcctg gcacagagaa gggcactcaa taaatattta ctaatcattt  81300
tccagaaaga gggtagctcc ataatgagcg agattcattt tgatggctgc tgtagtgttt  81360
aatgttttta ccacctgtta aaatgatttt ggagtataga tggataactg atgatggttg  81420
ttatatagat tttttcatag gttgcctgtt ccaaattcta tgccctggaa gaagctaaat  81480
atccagaatt tgacaggaaa tattattcta caacagatcc ctggcataag aacagtaaca  81540
cctctgttct attctcagac ttgcctctga ataactgttt ctcctggtca attctctgtc  81600
tctatctggg attgaaactt ccccctggac aatgagggag ttgaactagt ttagtggggt  81660
tcagccttga gtggccatta caattatttg gggattgttg aaaaaaattg gatgcccaga  81720
tttttgtcgt tgttgttgtt gtttgttttt taattatact ttaagttctg ggatacatat  81780
gcagaatgtg caggttggct acataggtat acacgtgcca tggtggtttg ctgcacccat  81840
caacccgtca tctatattag gtatttctcc tgatgctatc cctccctagc cccctagccc  81900
cagacaggcc atagtgtgtg atgttcccct ccctgagtct atctgttctc attgttcaac  81960
tcccacttat gagtgagaac atgtggtgtt tggttttctg ttcctgtgtt agtttgctga  82020
gaatgatggt ttccagcttc atctgtgttc ctgcaaagga catgaactca tccttttata  82080
tggttgccta atatttcatg gtgtattgaa ctgcttaccc cagttcaatc aaataagaat  82140
acagaatgtt gagaggagca tcagtatttt aagaaggcca cctagtgagt tcaatgtgca  82200
accaaggatg agaaacactg aactagatga ttggtaaggg ccatccaact ttgatagtcg  82260
acaagagaca atgctataga gtatggtgga cagagcatgg gctttagagt tagccaggca  82320
tgcattcaga ccctggctct gttacttact agttgtgtga tcttgaagaa atcaaaatgg  82380
agatacactt tgtccctggc agtaatagtt gtggggatta agcacctttg ccagtgctta  82440
ggacataata aacccccagt aaatagcttc tttagtatca gaagttcaga tggaagatgt  82500
gagaaaaata ttggttcagt aagatttaac atgtagatta aaatcaagta tttaaaaaaa  82560
ttttcctgtt tctttagcaa tggattccag aaacataatg tggaaatagc tctgagtcct  82620
aagatttgat gacattgcag aaagaaatct ggctagttgt cccatggctg attggctatg  82680
atggctaaga agccattgga aaaaaaaatt ggctcacaga agacagcaga tgtggcttgg  82740
gaaatgcaag gacatgactc taataaggat ttgtcccatt tatgagagtg attccaggag  82800
aaaaggacag atttgtattg tcagtgggat atgctgttaa aaaacacttt tgctaccacc  82860
actccagctg tcttggcatg tttgttggtg atgtaagcta cagaaaatgg aaatcaccaa  82920
aagggctata gcagcctgat gcatagtgac aagtaattgt tctattcatg gttatgtgtt  82980
gtacagagca cttgctgcat gtcaggtttg aggtttgagt atgcattagg gccatggata  83040
cccccatctt ctctctaagt agatttcaaa gtaaatattt gatgagtatg taaaatattt  83100
agtttggtca gtcataggac tgagaacgtg gtgggggtta cctcctagta tctgcaggca  83160
aaaaaacttt tttcttccta tagcaattgc catctcagcc ccttttgcag cgtttctctt  83220
gctacacttt gcattaacca tctgtgcact tgtcttagcc tcaaacaggc catgaaagct  83280
ccttgaggat aggggctatg tctttttcat ctttatatat gcatcattta gcagagctgc  83340
tcctttataa tgtactaatt actgaatgaa gggatccata gatgaataaa tgaatgcaaa  83400
gtaggagtga cctctcttct gtctttcttc atgatgggga ttagtgtgtg tgtataaggg  83460
```

aataatcgtg tcacataaaa tataacctta cttagaaggc aagacttcca gaatggtgga 83520
atgagaacca acccccgccc ccataaattc acccttttcat gaaagcaatg aaaacactag 83580
gaaacgttgt gaaaattaac ttttccagaa ctctgggaag gaaacaaagg tttccaacaa 83640
tctgagaaga atgtattcaa gaaaaacttc ggtaagttct ctgatcacag tggaaataat 83700
aaacaattag taatagaagg atatttggga aattcaccat ttgtagaaca taaacagtgg 83760
atcaaagaag aaatcataag ggaaatgaga aaatactttg agattaatga aaatgaaaat 83820
acattatacc gaaacttaca ggatacagcc aagctaaagc agtacttaaa gggtaattta 83880
taactgtgaa tgcctacatc aacaaagaca aatgatctca aatcaagaac ctaactttcc 83940
accttaggaa actaggaaag gaacagcaaa ctacaaagaa agaaggaaga aagattaata 84000
aagactagaa gggaaataaa tgaaatatag aatagaaaaa cactagaatc aatgaaatta 84060
aaaattgttt ctttgaagag atcaacaaaa ttgaaaaaac tttagtcaga ttgaataaga 84120
aaaaaaagag agaagattca aattatcaaa atgagcagtg aaactggggc catcactacg 84180
taccttaaaa agaattctca aaggattaaa aggaaatacc attgcattag tttattctca 84240
tacagctata aaaacaacta cctgagactg ggtgtttatg aagaaaagcg ctttaattga 84300
ctcatagttc cacaggctgt acaggaggca tggatggtga agcctcaaga aacttacaat 84360
caggtggaag gctaaggggc atgaaagaca tgtcttcaca caatggcagg agagagagag 84420
agagcaaagg gggaagtgcc acaaactttt aaaccatcag atcttatgac aactcactca 84480
ctacaatgag aacagcaagg agaaaatctg cccacgtgat ccagttacct cctacgaggt 84540
cccttcccca acactggaaa ttacaattca acgtgagatt tgggtgggga cacagagcaa 84600
aaccatatca accatactgt atgccaaaaa cttagatgat ctagatgaaa tggacaaata 84660
ctcagagaaa cacaaactat ctgaagtgtc tgaagtgacc agtgaagaaa cagaaaatct 84720
gagtagtcct gtaacaagtc ttgtaacaaa actggattaa taattaagaa acttcccaca 84780
aataaaaacc caggttcaga tgtcttcact ggtgaatatt atcaaatatt taaggaaaat 84840
ttaatccttc acaaattctt tcaaaaattg gaagaggctg gaacccttcc cttcccaact 84900
aattctgcac agtcagcatt accctgatgc caaaaccaaa gatatgacac aaaaataaaa 84960
ctgcaggcta atatcacatt tgaatataga taactttcta aaaatcttaa caaaatgcta 85020
gcaaactgaa ttcaacaaca aataaaaagg tttataaagg gtgaccaggt aggatttatc 85080
tctgcaatgt aaattaatat tcaaaaagct aagaatagga ggaaactttc ttaactttgt 85140
aatggacatc tctgaaaaac acacagctaa catcatactt agtagtgaaa gactgaaatt 85200
tttccttgta agatcaggaa caagacaagg atgactgctg tcaccatttc aatttaccat 85260
tgtattgtag gtttattgta ggctcaagtc aagcaaaaaa aaaaaaaaaa gtaaaagaca 85320
cccatattgg aaaggaagag gtgaaattat ctatattcac agatgacatg atcttataca 85380
aagaaaaccc ctaaagaatc catgacaaac tattaaaatg agtaaacgag ttcagcaagg 85440
tttcagaata caagattaat gtgcaaaaat caattgtatt tctgtgcact agcaatgaac 85500
aatctgaaaa tgaaattaag agaacagttc actcacaata tcatcaaaat accagaatac 85560
ttaaaaataa atttaacaaa agaagtgtaa gacttgtatg ctacaaaccg taaaacactg 85620
tggaaagtaa ttaaaaatct aaataaatag aaaaacattc cttgttcatg tgccagagga 85680
ctcaatattg tcaagatgga aatactcccc aaaggttgaa ggaaatccct gtcaaaatcc 85740
tggctgtttt cttagcagaa aatgaaaatc tgaccctaaa attaatattt aaatacatag 85800

```
aatctaggat agccaaaata atattgagaa agaaaaacaa agtcagtgta cccacgcttc  85860
ctgattccaa accttactac aaagcagtgg taatcaagag cgtatggtat tggcatacgt  85920
acaaacagat caataaatgg aatactattg agaatccaaa aattaactct tacatttaag  85980
ggcaattgat cttcaaaagt gttgttaaga caatttaatg aggaaagaat agtcttttca  86040
ataaattgta ctggaaaaat tggatatcca catgaaaata aaagatgttg gaccacttca  86100
aacctgcaaa aaaaaaaaaa aatgatctaa tggtgtatca tggatctaaa tgctatagag  86160
ctaagatgat aaatctcaga agaaaatatc agagtaaatc tttatgacct tgaagtaggc  86220
aatgtttttt tggctgtaac accagaagca caagtagtaa gagaaaaaaa aaatggactt  86280
catcagattt gaaatttttg tgctgcaaat gatgccatca agaaagtgaa aatctcaccc  86340
acagaatgag agaaagtatt tgcaaatcat atatctgata agggtattga atttagaata  86400
tataaagaac tcttgcaact caatataaaa agacaaccca attttaaaat gggcaaagta  86460
tttgaatata aatttcttga tagaagatat acaaatttaa aactgctcaa cttcattagt  86520
cattagggaa atgcagatca aaaccaaatt gagataccgg tttacaccta ttaggatggc  86580
tatagtgaaa aagaacaaat aacaagtatt ggctttaatg tggaggaacc ttatacattg  86640
gtggtaaaat gtaaagtcgt gcagcccttt ggaaaacagt ctgaaagtct ttaaaaattt  86700
actatttgtt atttggtttt tcttcacttt taatttaggt tcagaggtac atatgcaggt  86760
ttgctatata gctaaattat gtgtcacagg ggtttagtgt acacattatt tcatcaccca  86820
ggtaataagc atggtaccca ataggtagtt tttggatctt caccctcctc ctaacctcca  86880
ccatcaagta ggccctggtg cctcttgctc tcttctttgt gttcatatgt actcaatatt  86940
tagcttccac ttatcagtga gaatatgcgg tatttggttt tctgttcctg ctttagtttg  87000
cttaggatat tggcctccag attcatccac gttgctgcaa aggacatgat ctcattcttt  87060
ttgcatagtg tactatggtg tacatgtatc aaaaatgtta ctgtttgacc tagtaattct  87120
attccaatat aactactcaa gagaaatgaa aacatgtcca cacaaaaact tgtacacaaa  87180
tgttcattgc agcattattt ataatagcca aagagtggaa gacaaatgtc ttccaaatgt  87240
gggctccaaa tgtccaccaa ctgataaatg gaaaaacaaa atgtggtata tccacgccat  87300
ggtttatctg tcaataataa gaaatgaagt aatgatacat gctacaatga accttgaaaa  87360
tattatgcta ggtgagagaa gcaactcaca aaagaccaca ctgtatgatt ttatttatat  87420
taaatgtcca taaaagaaaa atatttagag atagaaagga aattagtgtt tccagggtct  87480
gggaggagat ggtataagca atggctgcta atgggtacag gatttctttt tggggtgata  87540
taattgctct aaaattagtt tgaggtaata gatgtgaata tgctaaaatg ggtgaatttt  87600
ataatatgtg aaatataact cagtaagccc attaaaaaca acctaattaa attaaaagca  87660
agctataaca gaaatattat atagccttgg cagtttagaa tagtgggaaa atatggagtt  87720
ggggcaggga aatagtcgca agtataattc tggttttgtc actactagtg tatggacttg  87780
gatgagtcat ttcctttctc taagtctcag tttgcatata tgcaaaatag aggtaatgat  87840
acctacctca gtggtagctt ttcaaaacct tgttctccct catctctcct ctacaacttt  87900
ctcgtaagat tattacagta ataaccattt attaagcact gtgtcagcaa tggtgtggga  87960
ccacaacttc actgaatcct cattgcaatc ttgtggggtc tgtatttctt tgcctgtttt  88020
acatgtaaag aaattgacgt caaaagagtt gttcaaggtc attctgttag caagtggcag  88080
agatggacat gaaaactaga tgttctacct atatgtcttt ccacttcaac taaagaattt  88140
attaaagaga attaaaaagc tatgaactac ttttaatagt aaacattgct gtcctcgtga  88200
```

```
atgaacacac actaaatttc aaatctcacg atggcaggga ataaagatgc tacctgtctt  88260
aagccattac ttcaccaact tctccaccaa aatattcctt gtaaccacaa ataagtaagt  88320
acaatagatc tataaggaga gaataattga gaactctctg attttatctt aaaagtcatg  88380
tagggatgtc atgttccaca atgtaattaa taaaatatat tttgttacta aacataagga  88440
aaaattttat gttcaacata aagatgtttg gtggttgcct caacctcttt tagtttgaaa  88500
agtaggtatg tatgagaaag atacgtgttt acatgtctac ccttgccctc tctgtctctt  88560
cccctctctc tctctctctc cctccctccc cacccccctct gccctacacc ccccaacccc  88620
cacatgtatt tacctttctc taaaagctct gcataaccaa gaaaaatggt ctttttttatt  88680
tttaggatgt tagatatttc attttcttat ggtaagacaa aagattaagg caaccaagac  88740
ttacaatgta tctaccgtgt ggcaggcacg gaggcaaggg cttttacatg tgttatttaa  88800
tgtaattgta attctcacaa aagccgtcta gagttgaaaa tatttccagc tctaattgag  88860
gcaaatggag cacagagagc cttaattatt tcacccaaag ttcagtggta gaggcaggat  88920
tccaacccag gtctggtggg ctccaaagcc ttgttggttt gccattcctc tcgctaacaa  88980
atgaaactgg tctgtgactt ttgcatttca ccccacttcc acagtcactg gtgggactta  89040
tttaaattaa tcagatcctt caaagtatcc ccaagtcctc ctttaaaaag aaagttaggg  89100
ggcaggggga ggagcagagg agaggagata aaaaggaaag gagtcagaga gagagagaga  89160
gagagagaga gagagagaga gagagagaga cctggtggtc tcagctgggt gccaaggttt  89220
cctaagccca agttccccat ggttgagcct gcattagcag gccgacagct tctagtaatt  89280
cacttttatt taattaatag tgaaactgtt gaagaattgc aagtggtgtt ctagttcaga  89340
aaccttccat tctatggggc attgcttttg cctcagactc ataaaaccaa atgccctgcc  89400
tcaggataat aagtgaacat gtaacccacg agaggtaaga aaaaacacaa tgtcacgtgc  89460
aaattctgca cttgttctca aagcaaacct ctcctgtgtt tgcaattagg atgttatcta  89520
ggagcatatt caaaactttt gaggttttta ttttagtttt tcttttatta tgtgctgttt  89580
tagtaatatc aaagaataca tgtaatatat gttatatggc ataacaataa aattaatgtt  89640
tatgagccct gattaaagaa tcaacaacat taacatcatc attgcaacaa ccctattaga  89700
atggaagctc tgtgaaggca aggatttttt tctgttttgt tcactgctat atccccagga  89760
cctagaggag tgtcagccac ataataggag cttagtcaat atttttttaaa taagagcata  89820
aatctactta tatcctcttt cctcttatca tcactcccag cctcccctca gaggtagcca  89880
ctatcctatt ttagggtttt aatattccct tgcattttgt taacttttca catgtgtatt  89940
cccaaataat atattgtttg cttttgcttc tttttgaact ttatataatg gaatcatatt  90000
gtatgtatcc aattgtgagt tatgactttt acgcaacatt agtatttgag attcaactat  90060
gtgtagctcg attccattcc ttttcattgc tgaattgtat tttattggat atgtgtgcca  90120
taaattattt ttctcctgtc agttgatgtt tatcttttat gcttttataa acaaaacggc  90180
tatgactgtt cctgcatgtg cctcctggta catatgtgcc caactttctc taggatataa  90240
gcctcagagg gggactgcac ttggaatttt catttccaga gcccaaagtt tagctcatga  90300
gtcagagctg caatgtgccc tttgtccaca ctaggtcagg atcagtggga gtgctaccca  90360
aaatattttc ctagtggggg aatcagggag aggcagagac tgacctagtg aggccaggag  90420
ttactatctc aggtctctag tcaaaatggg ttgcaattag taaaagttca gattctgaat  90480
ccccttcatt atttatcttc ttcttcctcc tttacagtta tttttgttca aggtgcactt  90540
```

```
tattaaactc atacctaaca aacaaaactc taatgaatat tttgtctttc attgattgta  90600
aattcaatta gattctttga aaaaatttta actgtatttt cactttagca tggatgaaaa  90660
tttcgatttc tttaaaaaac atttttaata ataacacaat aaggtctacc ctcataacaa  90720
aatttaaggg cacaacacca tattgttaac tataggcaca atgttgtaca gcagatgtct  90780
agaatttttt tcttcatgct taactgaaac tttatagcca ttgaacggca acagtccatt  90840
tctatttctt aaaagtcctt tacaaaatga gctttctaca tgtttccatt ttgtttatct  90900
gataattttt tttcgttttt tattatactt taagttctgg gatacatgtg cagaatgtgc  90960
aggtttgtta cataggtata cacgtgccag ggtggcttgc cacacccatc aacccgtcat  91020
ctacattaga tattactcct aaagctattc cctccgcttg cccctcaccc atcactggcc  91080
ccagtgtgtg atgttccctg tcctgtgtcc aagtgttctc attgttcaac tcccacttat  91140
gagtgagaac atgtagtgtt tggttttctt ttcttgtgtc agtttgctga gaatgatggt  91200
ttccagcttc atccatgccc ctgcaaagga catgaactca tctttttata tggctgcata  91260
gtattccatg gtgtatatgt gccacatttt ctttatccag tctatcattg atgggcattt  91320
gggttggttc caagtctttg ctattgtgaa tagtgcctct gtaaacatac gtgtgcatgt  91380
gtctttatag caccatgatt tataatcctt tgggtatata cccagtattg ggatggctag  91440
gtcaaatggt atttctagtt ctagatcctt gaggaattgc cacactgtct tccacaatgg  91500
ttgaactaag ttacaacccc accaacaatg taaaagcatt cctatttctc cacatcctct  91560
ccagcatctg ttgtattctg actttttaat gatcatgatt ctaactggca tgtgatagtc  91620
tctcattatg gttttgattt gcatttctct aatgaccagt gttgatgacc tttttttat  91680
atgtttgttg gttgcataaa tgtcttcttt tgagaagtgc ctgttaattt ccttcaccca  91740
ctttttgatg gggttgtttt tttcttgtaa atttgtttaa gttccttgta cattctggat  91800
attagccttt tgtcagatgg atacattgca aaaattttct ctcattctgt aggttttctg  91860
ttcactctga tgataattta ttttgccgtg cagaagctct ttagtttaat tagattccat  91920
ttgtcaattt tggcttttgt tgccgttgct tttggtgttt tagtcatgaa gtctttgacc  91980
atacttatgt cttgaatagt attacctagg ttttcttcta gggatttaat ggttttaggt  92040
cttacgttta agactcatct tgatttaatt tttgtataag gtgtaaggaa ggggtccagg  92100
ttcagttttc tgcatatggc tagccagttt tcccaacacc atttattaaa gagggaatcc  92160
tttccccatt gcttgctttt gtcaggtttg tcaaagatca gatggttgta gatgtgtggt  92220
gttatttatg agacctctgt tctgttccat tggtctgtat atctgttttg gtaccagtat  92280
catgctgttt tggttactgt agccttgtag tatagtttga agtcaggtag cgtgatgcct  92340
ccagttttgc tctttttgct tagaattgtc ttggctatgg gggctcttta ttggttccat  92400
atgaaattta aagtagtttt ttctaattct gtgaggaaag tcattggtag cttgatggga  92460
ttagcattga atctgtaaat tactttgggc agtatggcca ttttcatgat aatgattctt  92520
cctagccttc agcatggaat ggttttccag ttatttttgt cctctcttat ttacttgagc  92580
agtggtttgc aattctccat gaagaggtcc ttcacatccc ttgtaagttg tattcctaca  92640
tattttattc tgtttgtagc aattgtgaat gggagttcac tcatgatttg gttctctgtt  92700
tgtctgttat tggtgtatag gaatgcttgt gattttcaca cactgatttt gtatcctgag  92760
actttgctga agttgctgat aagcttaagg tgattttgga ctgagacgat ggggttttct  92820
gaatatacag tcatgtcatc tgcaaacaga gacaatttga cttcctgttt tcctatttga  92880
ataccccttta ttgatttctc ttgcctgatt gccctggctg gaacttccaa tgctatgttg  92940
```

aataggagtg gtgagagacg gcatccttgt cttgtgctgg ttttcaaagg gaatgcttcc 93000
agtttttgcc cattcagtat gatattgggt ctgagtttgt cataaatagc tcttattttg 93060
agatatattt cattaatacc tagtttattg agagttttag catgaagggg tgttgaattt 93120
tgtcaaaggc cttttctgca tctattgaga taatcatatg gtttttgtca ttggttctgt 93180
tgatgtgatg gattatgttt actgatttgc gtatgttgaa ccagccttgc attccaggga 93240
tgaaacccac ttgatcatgg tggataagct ttttgatgtg ctgctggatt cggtttgcca 93300
gtattttatt gaggattttc gcattgatgt tcatcagggt tattgtcctg acattttctt 93360
tttttgttgt gtctctgcca ggttttggtg tcaggatgat gctggcccat aaaatgagtt 93420
agggaggatt ccttcttttt ctattgattg gaatagtttc agaaggaata gtaccagctc 93480
ctctttgtac ctctggtaga attcggctgt gaatccatct ggtcctggac attttctggt 93540
tggtaggcta ttaattactg cctcaatttc agaacttgtt attggtctat tcagggattt 93600
ggaggtctat ttaggcttgg gagggtatat gtgttcagga atttttctat ttcttctaga 93660
ttttctattt tatgtgcccc agaggtgttt atagtattct ctgatggtaa tttatatttc 93720
tatgggatga gtggtgatat actctttatc atttttttatt gcatctatga ttcttctctc 93780
tcttcttttt tattagtctg gctagtggtc tatctacaaa atagatagac tgtttatctg 93840
atatttattt tgtaattatc taataataat catcattatc atcagcatca tcattgtcat 93900
ctcctttacc catacataca tttgtgtctt tcaaataata atcccatctt tgaagtacat 93960
cctcatctgt agcagtcttc actctgcttt cttatatcat ttactatctt attttataat 94020
tatttacttc ccgtctttct tctctaacag atagtatttt tttagggcca aggaaatatc 94080
tcgatcacca ctatatcccc agcatctacc cctgtgcctg gtccataggg ctagatgcta 94140
agagttgagt tgaaccaatc tacctaatct taaccttcag tagcacaaca tggtttgtca 94200
gtggttaaga atctacactt tggagtcaga ctcacccagg atggaatcct ggcattacca 94260
cttattatta atagatacat gaccttgaac aagttcactt aattgttctt agcatcagtt 94320
tcctcttctg tgatataggg atgatacaga gctacctggt aggttgttgg aataattaaa 94380
tgagatgata tgtatgaaat ggcctggcac atagagtgcc taaatacacg ttgttctgat 94440
tttatttgga ctgtttgtgt tagtaacaga aatcaaaaag gtggagaaag gagaaaggta 94500
cttgggaaaa ttttctattt cttctccatg tttcattcaa gactgaggaa gggggcacag 94560
tttttaccca aggaaacgac atttttagcc aaaggaatta tgatcttagc atttagctga 94620
attgtatatt ggaagtaagc tccttccttg tggaacttat ggccttgcta gccttggttt 94680
gttggaagtg ctcttgctgg ctttctagtt agggtaggga aaggaaggct tgtggggagt 94740
gaagataggc catgatatca agccactgag tgtgcaaatc agtagaactt ttcgattgct 94800
ttctgttgta cttgggactt gaataaaggc tgatatttgt gtcttgctgg taaagtgctt 94860
gtaaagtgag tgaaagtttt ctttgttctt gtcctgccag agctgttcac ttggggctga 94920
ggggaggata acctttcatg tttttatttt tttttattct gatgactgtg ctgagcattt 94980
gaacgaaatg gccattggtg gaaagtaaag gtgaatggtg agaagacaat aggataatgg 95040
aaactgtgat ggacttggag tcaaattctt ctgaacttct cctctccaag tcttacttct 95100
ttcatctgta caatgaatat taaaatgaga aaataagctt gtcttcacag agttattgtt 95160
aggtgttgaa atcacccgac acagcaaaca ggctcccatt agggctcatt ttccttcatt 95220
ccttagtaag gaagaagtac ttataaaata cagcagttgt gctcttgtga atgatagcat 95280

```
gggcagttgt catctctctg aggcagatta acccagaatg ccacttgagt tttgtttaat  95340
gcttaggcat aagacatagg aaagacaaaa gttgaccttt gggtagtaag aacaatgttc  95400
cattttgttc aaacttgaat ttttttacta taggagactg agaattaacc ttccatgaag  95460
gttttaggat ttgctttctg actcttctct ttcatatcca cctgaaagag cttgggcaca  95520
gatgttcttg gagaaaggta gttaaacaag gtgacttctg aagctccatc cttgcccaaa  95580
gaacttatga gtcccttagt ggccaagtat tttgatggta gtagcctaaa agatgtccag  95640
gatcaccgtg catcattttt tcaacagaag cctcaggcat agggattatg cttggtactt  95700
tatgttgtgg aatggaatcc ggcagatgtc catgtgatct agagaaacac ctaaggaaag  95760
tgaagaaatg ggggaaaaaa taacaagact tgtatgataa tactaatcac tatccttgtg  95820
tatttattcc aaggacattt tctccattat ctgatttata ttaccactca cagcagcagc  95880
tcaataggat gggagatatt atccctattt tatagatgag atttgaggct cgaggagcta  95940
aaacaagaaa catcaaattc ctttgatatt tggtctgatt ttgttatagt tctccctttg  96000
gatgaggtaa agtcacaaaa ctgggttcat atcatttaat tagtctgaaa atgttgcctg  96060
aacaccacct taagttagat atcttaacct caggtttcct actttcattg ctgcctctta  96120
tagacataga ctatgagatt ggctaatccc agagaacttc cctaatccct tggcaagatc  96180
caaaaaggct cagtcacacc ctactaccac catctttagg agaagtctca gaaaattcag  96240
cttcacacta actcacttga gcatcaaata atagtagttt atgcatgcag gttaatcctg  96300
aagacctcag acttcacttg cctatttctg ccattctatg acatgtgttg cattggtttt  96360
ttgtgtcttt ccagtttgga gactgccagg gaccatgttt tgccaattga ctattacttt  96420
ccaccccaga agacctgcct gatctgtgga gatgaagctt ctgggtgtca ctatggagct  96480
ctcacatgtg gaagctgcaa ggtcttcttc aaaagagccg ctgaaggtaa agggacatgc  96540
acatgcactt ctgtttccct ttctccttta ccttccagag agagacacta acctttcagg  96600
gcccaggatt ttatcatctc agaaacagag tcattggcaa ggccctatca aataacttag  96660
gagcctaagg aagcaaattt ttgcacttgc tagttccctg gtttcagcag ccttgtttgt  96720
acaggcaatg taggcagtga aggtggtccc agctggggct tggggctcag tgggtcctag  96780
aaatgaagga aaaattaatg atttgaaaag atttaatttc ctcccttctt gttttctact  96840
ctgctggcta gtaaaggaaa aatttgtcct tattagagag gttagaagtg gagaaacccc  96900
aactgagtcc ccagcctgtt ccttgggatg aatatgagac tgtttcttag caaaggcttc  96960
ctggcctcgg ccccagaaag agagtgttct cactcttcag cagactatca gtctctgcac  97020
ctgctccctc ctgttgctgc ctccttggga cctgtctttg cgttaatagt tcctaggtag  97080
gtaagaactc agagtgaaga aacacattta ttctcctctc cagagacctg acctcaaagc  97140
ctgtccatta gtccctaacc ttaatctaag gtagcatctt atatctggct aaattggttc  97200
aagccctagc tccttagttt tatttagctt agaacaactc atgtctgctc aacccctaaa  97260
ggtgctcagc ctacattctg cagtagaaac tcccattttc aggcctctta tatatgataa  97320
tgtctcttcc tctaaccacc cagggcttaa gcttcctgct tatccacttc actctccacc  97380
ctgtatcgag ggctttcttc tcaaaaggac attgatgagg agcccctaga gagagatttt  97440
gtgctctggg accagacccg ttgttaaacg ccagtattca cctctgcccc gactttcccc  97500
aaagaggtac ttcccgccaa ggcctttctc tttcctctca ctggctggaa gtgttgagtt  97560
ccatgtcaga accagaatag agaacctttc cttctataag ggctataaac cttgagaaca  97620
gtcttaaaga taggtatgta ggccacacca ttcaccacaa atgtactgat actcatcaga  97680
```

```
ggatggaaga agcaccagag agtttgaagc atctagagaa aaggtagaaa gagaatgccc  97740
tttaactgac ctcctcgatg atagtcaatc acaatgatga gtgttgattc atcattttgg  97800
ctgggtggca gaaatatcta taaaacagaa gctgccgtgt tgtttacttc cagtcctcgg  97860
ggcccacaag aaggcagcta tcatttggta ttactaaaaa catgccccat gttcagctca  97920
taccccccaaa tgacccactg ctactgttta tgctgggcta gcatgaagcc cagggcccta  97980
gtgtctaggt ctggtcagtg aggcctagag cagagcctaa agagcctgag agcagtgcct  98040
tcctttcttc agagtactca tgaaaggatg gctgtcagaa aaggaagtga ggaggggctc  98100
cagagacttc agaccacccc aacttcccca atgagaccct ggcacttccc cataacctct  98160
cactcagcgg gccctgtcta tagagcagaa aatgaaacag agcagtcatc tagaggtagt  98220
gtatcagcaa gcccaggcac cacagtaata gcaaccatat cagatgggaa aggagttcaa  98280
gtgaacaaac aagcaaattc aatagtcaga taggttagat tatacttgat gctgtttctg  98340
ggttttacaa atctgggtta ccaaattgtt attttcagaa aacagaggaa atgctctatc  98400
acattgtgaa agggaagatt ttactgtcgt atcatatatc ctacatggga gctttctgca  98460
gaagttagag ctgaaggagg gagacaggca gaagggcagc tggcagggct gcctgggagg  98520
agctctgcta taaggtggat cctgtgccat ttgagaacag ggaagaaagc aatgaagttg  98580
tggggaggga atcactcaac tcacagaaca tacagaaatc cagcaaggtt tcaaaatgct  98640
ctacacccta gagtctctta agttagggaa actctctgag ctcatggggc caaatgctct  98700
tgcctgcttg aaatatgaaa aatcaacaat ggattccttg caaaaccagg aaaagggaac  98760
cttctgagcc ccttggttat tttgaaatac ggaccataaa tttcagtcct gagccctttg  98820
aaggtaggag aaggtggttt agaaaacaca gacacagaca catacacaca cacccccaa  98880
aataaagcaa aaaaaaaaat actggtgttt tctttctccc cacatctgta aagttgttgg  98940
attgatttta ctgccatcgt tatccctatt tgaaggcagg gggctgtctt attacccaaa  99000
gaggacattt attgatttga ttatcttttt ccatttttac agtgcatcat ctttttcacc  99060
catatggcct ttctggaggt ggttctcaat ctggcttgtt gaagcatcaa attacacctg  99120
tcttagagag agtagaaaca caaatctttc tcttcctcat ttacttgttg tagtcagtta  99180
actcagactg tgtattcaga ctcttgatta tcacttaatt catagtttca gaaatctctg  99240
gaatgggcac aagtacagga cttaaaagcc tggaatctca gacagaaata tatttctagc  99300
tttgatggtt tataacacat gggactttta ggctgtcatt gatgcagggc tcagcacaga  99360
gtcagttgta atctggccag gttttgttgt tgaggaagag tgggaagggg gagtcctaca  99420
ttttctcctt gtcagtaata ttggagaatt ggggtgagag tgaagctggg cagggaaagg  99480
tctgcataga aaaaagggtc tggcgagaaa aaatcatgct actaagccat gagggtaaaa  99540
tgaccaagtt atggttgaca gaaacttggt catagtgtgt gggggggaggg tagggggtga  99600
gggcagagag aaagttggtc taagtctgtg ttgggggaca gtgcttggtg ggatgaactc  99660
tgggttagaa acaggcatgt agggaaatag ttggtttatg gtgtgggtag gatgaatggg  99720
gcggtgaaag ggaaggcatt ttgaatgcta agagaccagg aagtcaaagc aaagcaatac  99780
ccataaacag aggtaagggc tcagagaggt tttagttgta tagtcttggg taagaaattt  99840
cccctttga acctcagttt tccttgactg taaaacaacg gacttgaact agatatttca  99900
aaatgtgctt ccaacttaga cattttgtga tcgttctaca aattacaaac ataatcatca  99960
tcatttcagc aaactcacgt gtatttatac ctgcatatgt ttttggtctt gctttcctag 100020
```

aagatgacta atccaagatc ctaatcaatt aaagaagcaa tcttcagatg gggatagagc 100080 cagctgagag agtgtactat gtatggagtg ggttaaaact caggactctg agatttttac 100140 cttgtgatca ttgctgggta acttcctttc ttttctattt ctcatctgga aaatcaggat 100200 atgaatcccc atctctacct cattatgttt caaagagggt taattaatcc atcatgtgca 100260 ttatgtgctc aagaatttac tatttttcag atattttcta gtaaaacgtt ggagattata 100320 tgtccatttg ttttgtacac atggagtgct gtttggtaca catcataaaa ttgaaactgt 100380 agtttacatt ctgaactcaa agaattacac catcctcact gatgtttaca ataggtccca 100440 atttagtttc tttggcaaat tttatgtaag tatggctttg attctctctc tcaccccagg 100500 tttttgttag ggaagaaatg caagtgaacc ctcattgaac tctttctgtc ctttaaatcc 100560 attctttccc acctcaactc atgtggaatt gaatgttacc tctagtttgg agtctagcag 100620 agagtttttg gtgcatatca gtgtcccctt cactccctga ctttttgagt aacatttccc 100680 agaggcaaat taactctgct aagaggatct gcttgcagct tcaacagagc cttcatcagg 100740 tatctttggc caaggagttg actgatcctg actttgcgag tcctagagat cttttcacaa 100800 aactcctctc atgtttctgt ctctggtttt cttaaaagtc gcagacagac tttagattta 100860 ggggttggtt aactttttgt aaagggccat gtagtaaata ttttaggctt tgtagatcat 100920 atggtctctg tgtcaactac tcagctctgc ctttgcagga tgaaagcagc catggataat 100980 acttgaacta atgggagtag ctgtgttcca ataaaacttt atgggcactg aaatttgaat 101040 ttcacttaat tttcacatat catttaatat tatttttctt tttaaccatt taaaaattta 101100 gaaatcattc ttatctcgtt gggcctcaca aaaacagatg gtagagtaga tttggtttat 101160 gggctgcagt ttgttgacct ctgctttaga taatcacttc tgtacttata aatctgcaaa 101220 ggttttatgt tttcccatct cttggtattt tagtagctct ctagattatc taatttaaaa 101280 atttttctc agtaggccaa agtttgcaca tcttgttagc acagaatgcc tggcctagtg 101340 gcttcttggc cctgagcctt ttactaaaca ggagaaaaac taaatgtcta gaaatgctag 101400 aagaggatac tattttgttt taatgatcta gtagatcact cctccttgca atacccagag 101460 gagaaactga aaatatttca agcattttct agacttctgt gttgtaaatg tgtggataac 101520 tatgaactat acatgaaagc acttttctgg atgacacata tattccagat ggcaaaaagg 101580 aagcactttg gggactctct ggtaccaagt atcatggaaa aattgtgtgt ctcatagaaa 101640 gtagatccca ggaagccagc tgagttgtgg atctgccata tattacctca tgattctgtc 101700 ttcgcacact cactggctta attctgggcc tccccataac acgactagac cacaggcttg 101760 cagaagaaat aatttagctc tgtaactcat tgcagttggt gcccacccaa gtctctgtca 101820 gtgcccaatt cgggagccat gccaagaatt tgccattgct gcttcgtagt ggccctgtgc 101880 ctgcttattt atagcctgtg cattttatga aacagagatt aataagaagt tgccatagta 101940 cttgcaccat tatgtaaata tctgcaatgc ttacatagcc tttgtcactt gcaagatctt 102000 ttgagtccac tgccttctgc taccatgcct taccaatttc ctagtccctt attattattt 102060 tttaatttat tatatttaac ttttgtgata catgttcaga atgtgcaggt ttcttatata 102120 ggtatacacg tgctgtggtg gtgtgctgaa accaacaacc cgtcatctgc attagttatt 102180 tattctaatg ctatccctcc cctagcccag tgtgtgatgt tcccctccct gtgtccatgt 102240 tttctcattg ttcaactccc acttatgagt gagaacatgc agtgtttggt tttctgttcc 102300 tgtgtttgtt ttctgagaat gatggtttcc agcttcatct atgtccctgg aaaggacatg 102360 aactcatcct ttttgatggc tgtatagtat tccatggtgt atatgtgcca catttctttt 102420 atccagtcta tcattgatgg gcatttcggt tgattccaag tctgtgctat tgtgaatagt 102480
gctgcaataa acatacgtat gcatgtatct ttatagaaga atgatttata atcctttggg 102540
tgtataccca gtaatgggat tgctgggtca aatgatattt caggttctag atccttaagg 102600
aatctccaca ctgtctttca taatggttga actaatttac acccccacca ccaatgtaaa 102660
agcattccta tttcttcaca tcctctccat catctgttgt ttcctgactt cttaatgatc 102720
accattctaa ctggcatgac atggtatctc attgtggttt tgatttgcat ttctctaatg 102780
accagtgatg atgagctttt tttcatatgt ttgctggccg cataaatgtc ttcttttgag 102840
aagtgcctgt tcatatcctt cacccatttt ctgatgtggt tgtttttttc ttgtaaatat 102900
gtttaagttc cttgtagatt ctggatatta gccctttgtc agatggatgg attgcaaaaa 102960
tttctctcat tctgtagctt ggttgttcac tctgatgcta gtttcttttg ctatgtagaa 103020
gctctttagt ttaattagat ttcatttgtc atttttggct tttgttgcca ttacttttgg 103080
tattttagtc atgaagactt tgcccattca ctattgctac aaagagaaca aaatacctag 103140
gaatacaact tacaagggat gtgaaggacc tcttcgagga gaactacaaa ccactgctca 103200
aggcaataag agaggacaca aacaaatgga aaaacattcc atgctcatgg ataggaagaa 103260
tcaatatcgt gacaattgcc atactgccca aagtaaatta tagattcggt gctatcccca 103320
ttaagctacc attgactttc ttcacagaat tagaaaatac tactttaagt ttcatatgga 103380
accaaaaaga gcccatatac cctagacaat tctaagcaaa aagaataaag ctagaggtat 103440
caagttacct gacttcaaac tacagtacaa ggctacagta acccttatca attttgtatt 103500
gcctgtccat tttctgcagc cagaagcttc ttcagtcctt taagggaatt tctgggtgac 103560
tatcaaactc tggtagttca tttttgcagt tgactgctat tgtgaggata agtgtcagac 103620
tcactctctc ttcagagata gaaattatgt attaattatc tggattctag acccacagca 103680
aggagcaaac tgctcctcaa aataactgaa ttcttcgaga agtcatcatt gtaaaacaat 103740
atcttcagtt atagtagcca tgtgtgcatg cttctggaaa ctgtttttca gattttcatc 103800
ttccttccct gtctcttcat agcaaggcag ctgctttcag ccttgtacag atgctagtga 103860
gctttgtacc tacaaacctg agaaaattga actgagattt ggaggtgaat gactcttgat 103920
aaagggaaca aggtttagaa ttatcagtcc ctttgctccc aggctgtgtt gtgactactt 103980
aggcactcca gtgaaatcac tattcctcct atctagacta atgcctgtcc ctgcagagca 104040
cctcatgaga acaggcctgg tagtaatatc ctcatgcatt cagtcagtaa atatttacgg 104100
agtgcttact acatgtagga tattgggctg acatactcaa ggtacagggc ttgcttccag 104160
gaggttatag tttattaatc ataaaagtgg catttttttt gagacggagt cttgctctgc 104220
ctgtcgccca gactggagtg cagtggcatg atctcggctc actgcaagct ccgcctccca 104280
ggttcatgcg attctcctgc ctcaccctcc cgaacagctg ggactacagg ggtgcaccac 104340
cacacctagc tatttttttct tttatatata tatatatata tatatatata tatatatata 104400
tatatttttt tttttttttt tttttcagta gagacagagt ttcaccatat aggccaggct 104460
ggtctcgaac tcttgacttc gtgatccacc cacctcagcg tcccaaagtg ctgagattac 104520
aggtgtgaaa atgtgacaat ctttaaagct cttcagtgga tgaaaggcca ccctatctac 104580
tgtccatttg aactttgcaa ctatcttggt acagagtgag aagttattct cttggttttc 104640
catatgagta aactgaggct ttgccagttc atcagcaggt aataaataat gtatctggaa 104700
tttgaaccca ggtcttctgg ggtcaaaggc agcattcact ctgttccatc acagcagctc 104760 ctcaaataag ccaacataga aaccaagtac tatgcctagg caacaagaaa ggcagcaatg 104820 aagagcaaca gcagagtgaa atatgagaga aggaagttaa gaaagatgtt aagtactgtg 104880 gggagtaacc aagaaaccac caagtatcgc taacatcaca gggagcttgt cttcctaaga 104940 aaactccaag cacttaaaac agctggtagt tcatcagcaa ctctctttat tagatgtatg 105000 agggacatgt gggccatagt ccttctacca acttatatgc ttcaggggga agttctgatt 105060 ctgatgagac ccagcatggt cgcttttaat tcactgttgt cacacaacta tagaacagga 105120 agcacaactt aacacctgtg ctcatgagaa ttttgctcct tatgaccaag ctaaagaaag 105180 agcttagaca ggatgtgagg atataaatgt agattcatgg ttccttggct ctttggtttg 105240 agccttctca gcagagcatg ccacagagtg ttttccatgg ggccagtagc aagagaaatc 105300 catttccctc ctcctcgatg tcagaaaaca gagaatattg tctttcagga tagaattaaa 105360 aagtcataga ggcagcaact tgttttccta tattagggtt ttaaaattct gtttttcctt 105420 cctctcctga gtcacatcat tgtgtggatg gaccttgatt tcactgtggt atctggatgt 105480 gggccctgaa ggccatggac ttctaacagt tccttaagtt acagaagcac attcctatag 105540 gtcacaagct catttactta caggatggtt gattcagtca caggttattt catgaaaata 105600 cttaaaagat ttgcagtgtt caaaactgca ggatctttaa acactaaaac ttgaaggaag 105660 ggaatttgga aatcaaaaaa tctggtcaaa ccgtttcatg gaaaagtaaa gtgaggctca 105720 gagagaggaa attactttcc tgggtttcta tagcatataa atggcagaag tgagagcctc 105780 cctgccattt atagttttct gcctgagaga ccctcctgct tcacagctaa ttagcagagt 105840 tacagaggtc attaccttgc aattctcaag aattatgtga ggcagtatag taagcattta 105900 tggcccttgg ttcccagaag gagcttagtc cctgatagtc ctctctgcct ttgctgccat 105960 tgtgtgagac catcttctgt aactgtatgt cttccccccct agtaagttaa tgagtaataa 106020 aggtattccg tagtgagagg actctgtaag agaattcttg gtgtaaggat tgttgcaagg 106080 ttgttttgtg tgtatgtgca tgtataaact tttttaggga gtgtattcat agcttttaca 106140 tggatctcag aggctctgta acagaaaatt acagaatact ggtcttgtct ttggtaagga 106200 ttttatagac ccataaggga gtattctgac tacagtgata tccaacatgg ctatttaatg 106260 cctggcattt tccccacata acatacgttt attcaacagt cagtgcctac tgtgtacatg 106320 agacctatac caggcactgg gataagagac atgaaataac agctaaaact gtttattgag 106380 cagtcaatat gcattagatg ctttgtaggc attttcttat tcaatctgta taccctcaat 106440 ttacaaatga gggaaccgag acacaaaaga gttgagtgat ttgcccaaag tcatacaaat 106500 agtcagtggc tatgtggtga atagttacca acatgaaaga gtgagattac tgctgtacta 106560 aaagtaggca cataattccc tgagcagata gtatgagaga atgatttatt ttacctggaa 106620 agtttaggaa ggcttcacag aggagttaag ggttgatctg gatcttgagg gatggataag 106680 aatttgccag atacaaaaag gtagaaagag aacttcagga ggagggaaca ggttgagcaa 106740 agacaaggtg atatgaaagc gggaggcttg tttggggagc attatggaat ctcgaagtca 106800 ttgtggggaa tctcatcaga tgcagcaagc tgcttgacag gccttcaatt ggctctttgt 106860 accttgctcc ctccccatgc tgagctgtcc atagctgcct taggctggtg tctgggattt 106920 tcggaaggtt actatccagg tagtgtaaca agatgcagtg taagagcacc agatcggggc 106980 tctggctctg ctactgactt aacacctggc attaagcatg tctagttccc tctttgtaca 107040 ttaaaatctc cattggagca gtaacatggt tgtattaaat gatcttgaag attttaaaaa 107100 taaatatata acaatataaa tcgttaacaa taattttagt agtaaatctc taaaatttta 107160 cagataatcc agattcatcc attggccaat ggttcacttt gtatgcataa ttttttggga 107220
aacaggcaga ccgaatttca atccttagtt gtaagactta atacatatgt gacctcaagc 107280
aaattatatt gaatgcctct ataaggataa taatatctta cagaactatt gtaagaacta 107340
aatgatgtgt aataaagctc ctggtactca gtcagttttg gatccttttc ctagagtgag 107400
tcttggtcat aggcacgcat atacttgcag gggtccctga gtaggcagaa agaacaaatg 107460
agagatggta tctgtggtat tccccaggta aaggaggcct tgggttggtg taagatttca 107520
cttcacttta gagttactta attagggacc agaaaggcca tcgcatctgt atgagaatat 107580
aacaaaggtc aatttcttcc tctttacttt ttacgctgtg agtaacattc cccagccagc 107640
ccagccggca cgtgttcttt gcctctcctg acttccagac tttggtcttg aaggtgtcag 107700
agctctctgt gtatctttgc ccccaacagg ataagtctga cctccccagc aaattcaact 107760
cctaagccac tgtccaggag aagagctagc aaggtcataa attattctcc atattttcca 107820
gccattggtt tcccttgtcc agccagaggt gtgtcttaaa gtatgctgag gctagattca 107880
atagaaacct gagccagcac ctgtgtaact aatttttaaa actccctttc ctgaagctgg 107940
atgaatattt tttaaaacta agctggatta tcttttatct agcatgccgt ttcctacatt 108000
cctagtgcta tggacctctt ggaggaatgt agtttggtta tagtggtatt gtcttgcttg 108060
tctgttgtgg gggaggagga catttctttc aaaaacaagg taatacttcg gtctggacta 108120
tgactatttt gtttaaaatg aaactatggc actgtactgg tactcattct gcttcctata 108180
ggttagcttt acatccctct gtcttcaccc actctacagt tctgatcctt ttaaaaagca 108240
gccaaccaaa accagcaagt acatactgct tatctctgac ttctacctga atcaacttca 108300
gatcttgtcc aaagctccat ctgaagagag ggggataaca ccctgccaag agccctcagg 108360
gcccatcagt aagtagacat cctgtccttg aggtctctta actctgctca gcttcagaat 108420
acagaagggg ttggttcttc atttgtgttg tttataacta aaagcctcct acttcccgct 108480
ttttttgcat agcttcttct gccatcccac ctgtgtagcc tcttcaactc ccctaaaact 108540
cctctgtagc ccgtgtcact tggaaagagt tttctttgtc tcttttgcaa cttgacaatg 108600
actagccagc aagtttaagt tcaaattatt gttccatggg aacagagata gatataggaa 108660
acaaaaaaag ggatatggag gtatggagta atttcccacc tacctagtga gcactactga 108720
gatattcaaa tgctctctac tcaagaattc tattgatata aacgtaaaaa acttgatctt 108780
aggtctaata tccattagta gtgtgacctt gggaaaacga taccactccc aaaggcttag 108840
tttttttaac tataaaatag gaataatgat gaccaccccc agaggattca taaggataac 108900
atgagataag gcaacttgaa atttcctagc atggcgatag acttttgaaa ataaaatgaa 108960
ccaaacactg ataacagtac ttcctagtgc acaaatgaga aatcagtccc tcatcaaatt 109020
acagcacatt tccaatgctc cgattatgtc actgtagaaa tgctaatgtg gattaaataa 109080
tttgtctgtt gctatttata tggataattt gatagtaatt atttttggac atggatagtt 109140
ttgaagcctt acagatgagt ccatccccaa gtacccaaaa ttaaagaaag ttggctagag 109200
tgatggcaag gtggcagcac agagctccct gggttctggg ccctgtcccc tagctaggga 109260
gaactccagg ctataagcat ttgtattctc atagtccaat ggcagggaaa agggttgaag 109320
gtgagtactt ttcactcatt tatttttca acaagcatgt atggtgtcag gccttgtatg 109380
catccacaga caaatgtgag ctagccctga cctcaaggag atttcagttg cagctttagc 109440
actgcaaaga gtatctacct gcggcagata caatgtgatg ggacatggcg gagaaaaaat 109500

```
ctataaacag agcctcccca tccccaggca tggaaacaat cctaacccag gctggcatag 109560
tacaatgggc ctgtctctat cagcaggttt ggaagcttta acaacaacaa aaaaaacaat 109620
aataatgatg atgataatca tagtgcctaa tgttaccaaa cattttccgt gtgttaagta 109680
ctatactaag tgcatactta atcctcacag caactctata aggtagtaga tactcttact 109740
actaccctga ttttacaaat atggaaactg aggcacagaa gactgagaga acaggaatac 109800
acctaattca cctcagttca acaaacacca agcatctgtt ttatgtcagg cctcgtgctg 109860
ggtgccaggg agagagaaat gagtaaagca tagtttcagt ccagtgggag caaatgacag 109920
cacacagtgg acacatatat tgcagccctt ctgctttatg ctaagaactc attgtcagtg 109980
atgaatcaaa cacagtcctt ctctcaaaga tcttcaagct tagtaggaga tatctgtgtg 110040
aaaacaaaaa ttaaagactg ctgtgataag tgtcataaga gataagtgga aaatgagaga 110100
gagatcactg tagcagttga ttggtttaaa tcaaagcccc ccaaaaaaca gtgttattga 110160
gaattataga acaactaatt gatttaaatc aaagcccaaa cagaacagtg tttgctaatt 110220
ttatttcagg ttggttgata gattttcatt ttttattcca tcccgacaat ggaagattag 110280
tgcttgtttc ccacccaagg ataccaggat atttcaggga ctgtattaca atatagttaa 110340
attattcctt tatctcaaag cacacccaca ctttctccta tcctttcctt tactcaggct 110400
atctcttctg cctcaggtgc tttttctcca catttccata ttcttaagtc ctaccttcct 110460
tcaaggcctc actcgaatgc ctcctcctcc atgaagcatc caccccatcg aaaggtacct 110520
cgccatctcc tgtactccca catcacttca tgggtgtctc tctgtggttc ttaccacttc 110580
ctgctttatc tttcagtaat gcacttacag ttctctttcc tccactagac agagctcttc 110640
agacaaagat tcacttggct gaaaccatga ttttacttta aacacattga aaacctctac 110700
cggaatgcat tgtgtctggt gggcttcaac cttaattctt aagtatgtga aaatacatta 110760
cctatctgga ggtttacact ttctgctaat gactttattt ttaagtccac caccctaaca 110820
caacaaatgc ttaaaacatg tcttcatttc ctttaggtct ggccctcatg catgcatata 110880
atttatagag tcactgtttt gctcggttgt cctcatgcct ctatattatt ggaggtttag 110940
attgtttcca cacacttagg ttgtattcat gtacattttt ttttcttttt aaatttccct 111000
agcatccatt cccaccattg gaaattcagg gtcaaaacag gggttgggaa ttggagcatg 111060
tgtatcacag ataaccaatc atgtgttatg acttaagaat ttatgaaagg gccctctacc 111120
tgaagatatc ttgctactga tgctgtctca cagtgtctga aactcccatc atatgtggaa 111180
ttgttttgga agattttgcc tcctggggca cattcagcca taatcaggaa atagtattga 111240
gcattagact gtcagtatgt ccattagcaa gactgtggaa gaatggaatc accaatatta 111300
tattttatag gggatacaga attcaagaga agttctgaag agaaaatgct tatctagaat 111360
aggaaggctt agatacagca tgaaagctgc aggctttgag gagccagagg tcaaatgaaa 111420
gcactgagta tttgtttata tgaaagaaca gaaagggaaa agagaagcag aggaagggat 111480
agtagagaga aatgaataag ttttatccat ttaacttgga attgtgtttg gctatgggca 111540
caacagaagc agtgagatca ctttatttta ttttattctt catagacagg gtcttgctat 111600
gttgcgcagg ctggagtgtg cagctcttca caggtgtgat catagtgtac tacaccctcg 111660
aactcctgaa ctcaagcaat cctccaacct cagcctcctg agtagctggg acaagtgcac 111720
accaccacac ccaatgagat cacttaaaaa ctagggagag atgtgtgagt tctgggcaac 111780
cagtagttag aaaaccagga ggggtttgga aatcagaaaa ccagcagagg caggaaaact 111840
cagggcagca tggcagattt agtatataca agtaggttca caccagtcat cagacagaat 111900
```

tgtaactgct gatgtggagt agaggctagc tttgtctgct gtgtgatacc caaaccttta 111960
agaatagtag gtgtatacgg ggaattggag ggagataggt ggctgtattt actaattggt 112020
tgatttcact gagatggttt gggtattgtg gcttccagat gctcatattt tctttttgg 112080
gtagagactc caacatcatt acagaactat aaattacata tggaaaagaa aggcctccta 112140
tgttagaata gaaaatagaa tgctgtgggg ttgagggaca gagggtctgt ctaggaagtc 112200
agatagcatt ttcccgttct gtccctcaga gttccttgtc cccattgaga ctcaatttct 112260
cttactttgg tttctagtgt taccacccac tgttcttttc catctcaacc ctgagtataa 112320
gtacagatca cattccttgg gttcttagaa cataatagaa atgaactctc attcatcaaa 112380
atgcccatta gtaaatactg agggagaaca aactagaaat ccagtataga aagtaaaaat 112440
aggattatat tccttgcaat ctcagaaaaa acaatgaaga gctttcttcg ggcattagac 112500
accttcccat aaggtggctg actctctttt agtcatgtca acttgaccaa atcttcactt 112560
ggtagcactt ctttcttgtt cattaaccca tctgctatgc tcctatgggg tcctagagaa 112620
atgccgctca tgtacacgca tatccaataa cacaaagatc actctcgact ggcaagccct 112680
tttatgatgc tgtgagcatt tgataccctt gttgctagta atatcagtga gtgacctgac 112740
ccatatttgg aacagaatat gatcagtata ttgcctcaaa gaggccctca ctgttctaaa 112800
aaatataatt ccagagtttg ctgactcaca ccgtggaata tgtgcaaaaa tgaatcctgc 112860
agataagcct ttctctgact agtttcagaa tttttttctg ggtaatttta aaattatttt 112920
tttatttttg taggtacaaa gtaggtgcat atatgtatga ggtacctgag gcattttgat 112980
acaagtatac agtgtgtaat aatcaccagc gtcaatgggg tatcccttac cacaagtatt 113040
tatcctttct ttgtgataca aacaatccaa ttatattctt ttagttattt taagatggac 113100
aatgttattg ttgactgcag tcaccttgtt gagctatcaa atactagatc tcattcattc 113160
taactatatt tttgtaccca gtagccatcc cacttcctcc cctcccacta ccctttccag 113220
cctctgataa ccatcattcc actctctatg tctatgagct caattgtttt aagttttagc 113280
tcccacaaat atgtgagaaa atgccaagtt tgtctttctg tgcctggctt atttcacgta 113340
atataatgtc ttctagtgcc atccatgtta ttgcaaatga caggatctct ttctttttta 113400
tggctgaata gtactttatt gtacgtatgt accacatttt cttcatccat ttgcctgttg 113460
atggacaaga gttgcttcca aatattggct attgtgaata gtgctgcaat aaatgtggga 113520
atgcagatat ctcttcaata tgctgatttt ctttctttag ggtgtatacc cagcagtggg 113580
attgctgggt catatgatag ctctattttt agtattttgt ggaacctcaa atctattctc 113640
cataatggtt ttactgactt acatatccac caacagtgta tgaggatact cttttctcca 113700
catcctcacc agcattcatt acttcctgtt ctttggatga aagccatttt aaccgtggtg 113760
aaatgagatc ccattgttgt tttgatgtgc acttctctga tgatcagtga ggttgaggac 113820
cttgtcatat atctgtttgt catttgtatg ttttattttg agagatatct acccagatct 113880
tttgcccatt ttgtaatcag attgttatat atttttttcc tatagagtta cttgagctcc 113940
ttatataccc tagttattaa tacttggtca gatgggtagt ttgcaaatag tttctctcat 114000
tctgtgcatt gtctcttcac tttgttgact gaatcctttg ctgtgcagaa gctttttaac 114060
ttgatgtgac ctcatttgtc catttttagt tgcctgtgct ggtatggtat tatccaagaa 114120
atttttggcc agattaatgt tttggagagt ttccccaatg ttttcttgaa gtcgtttcat 114180
ggattgatgt cttagattta agtctttaat atgttttgat tattatattt gtatttgctg 114240 agagataggg ctctagtttc cttctgcata tggatatcca gtttttccag caccatcttt 114300 tgaagagact atccattctt taatatacat ccttggtacc tttgttgaaa ataagttcac 114360 tgtagatgta tggacttgtt tctgggttct ctgttctgtt tcattcgtct atgtgtttgc 114420 tttcatatga ataccatgtt gttttggtta caatagctct gtattataat ttgaagtcag 114480 ataatgtgat tcttccagtt ttgcttggtt ctttttcctc aagatagctt tgcctatcct 114540 gggtctcttg tggttctata tacattttag gattattttt tctatttatg tgaagaatgt 114600 cattgatatt ttgatataaa ttgcattgaa tctgtagata gcttcaggta gtgtggacat 114660 tttaacaata tcaattcttg aaattcacga gcatggaata tcattctatt atttggatgt 114720 cttcaatttc ttatatatgt attatatata tattagtttt cattgtagag atatttaatt 114780 tatttaacta aatttattgc taggtatttt attttatttt tacctattgt caatgggatt 114840 gttgtcttga tttctttttt agattgttca ctgttggcat acagaaaagc tactgatttt 114900 tatatgttga ttttgtatcc tgcaacttta ctgaatttgt ttatcagttc taataggctt 114960 ttggtgcagt ctttaggttt ttccaaatat aagatcatat cgtctgcaaa caagaataat 115020 ttgacttctt tcttttcaat ttggatgccc ttcatttctt tctcttgtct gattgctcta 115080 gctaggactt ccagtactct gttgaataac agtggggaaa gttaacatcc ttgttttgtt 115140 tcagatctta tagccaatgc cttcagtttt tccaaattta gtatgatgct agctatgggt 115200 ctgtcatata tggcttttgt tatgctgaag tatgctccct agtttttga aagtttttgt 115260 cttttaagga agataaaaat tgaatgttat caaatgcttt tcatgtaaca attgaaatga 115320 tcaagtgctt tttgtccttc attctgttga tatgatatat cacattgatt gacttagatg 115380 tattttgagc catccttgca gcccttggta aatcccactt agtcatggtg aatgaacttt 115440 ttaatgtgtt gttgaattca gtttgctagt attttcttga ggatttttgc atcaatgttt 115500 atcagggata ttggcctata gttttccttt ttgtgtgtgt atattttgga ttttgttatc 115560 aggttaatac tggccttgta gattgagttt ggaatgattc tctcctctat tttttgaaat 115620 actttgaata ggattgatgt tactttttct taaaatgttt ggtaaaattc tgcactgaag 115680 ccactgggtc ctggactttt tactgctgag aagacttttt gttacagctt caatcttatt 115740 atttgttatt ggtctgttca agttttagat ttttttcgtg gttcaatctt cccaagttgt 115800 ctgtttctcg aaatttatca atttattcta ggttttccaa tgtattgtca tatagttgct 115860 catagtagcc tctaatgatc ccttgaattt ttgcagtaac cattgtaata tttccttttt 115920 ttaaatctct gattttattt gagcattctc tttttttctt agtctagcta aatatttgtc 115980 aatgttgttt cttcatccac aaaaccaact tttcgtttca ctgatgtttt ttgtattttt 116040 tccttttaat tttatttatt tctactctga tctttatcat ttcatttatt ccagttattt 116100 gagtttggtt tgctcttgct tttctagttc tttaatatgc attgttaggt tatttatttg 116160 aactttttga tgtaggtgca tattgctata aactttcgtt ataatattgc ttttgctgga 116220 tcccataggt tttagtatgc tgtttagtat gttttcaatt tggtacattt caataaattt 116280 ttaaattttc ttctttattt attgacatag tcattccaga gtatactgtt taatttccat 116340 gtggttggta tagtttccaa aattcctcgt gtttttgatt tctagtttta ttctattgtg 116400 gtcagagaat aagcttgata tgattgcaat ttttaatact tttttaaaaa cttgttttgt 116460 ggcctaagat atgatctgtc attgagaatg atctatatgc tgaggaaaga atgtatattc 116520 tgcagccatt ggataaaatg gtctttaaat atctattatg tccatttaag acataatgca 116580 ggccaggcgc ggtggctcaa gcctgtaatc ccagcacttt gggaggccga gacgggcgga 116640 tcacgaggtc aagagatcga gaccatcctg gccgacacgg tgaaaccccg tctctactaa 116700
aaaatacaga aaactagccg ggcgaggtgg cgggcgcctg tagtcccagc tactcgggag 116760
gctgaggcag gagaatggcg taaacccggg aggcggagct tgcagtgagc cgagatccgg 116820
ccactgcact ccagcctggg cgacagagcg agactccgtc tcaaaaaaaa aaaaaaaaag 116880
acataatgcg gattaaggcc aatgtttcat tgttcatttt tctgtctgga taatcttttc 116940
aatgctgaaa gtggggtgtt aaaatctcca aatgttattg tattgggatc tttctcttct 117000
ttcaactctg ataatatttg ctttagatat ctgggtgctc cagtgttggg tgcatatata 117060
cttaaaattg ttgtatcctc ctgatgaatt gaccctttta tcattatata atgaccttct 117120
ttttctcttt gtgtagtgtt ggtcttgaaa tctattttgt ctgatattag tatagctgct 117180
aatttttttg gtttccattt gcatgaaata tctttttcat tcctttattt tcaatcaatg 117240
tgtttcttta tatttaatag gtgaaatatg tttcttgtaa ataaaaatta ttattttaac 117300
atattttaaa aataatactt tttaaataat aacagttatt attatttttt aaattttcat 117360
tagttttggg agcccaggtg gattttgatt acatgagtga gttctttagt agtggatttt 117420
gagattttag tggagcagtc acctgagaag tgtacattac ccaacatgta gttgtatgta 117480
tattatatat acagtatata tataaagcat atatacacac tatatatagt atatatgtac 117540
atatagtata aatatatata gtatatatgc tttatatata gtgtatatat gctttataat 117600
tgtatatata tgctttatat atgttgtgta tatctagtat atattgtata tatagtatat 117660
ataatatata atgctttatg tattgtattt atatattgta taatatataa agcatatata 117720
gtatatatac tatatataaa gcatatattt tgtatatata ttatatatgt tgtgtatata 117780
tattatatat ataattaaat tctgggatac atgtgcagaa cttgcagttt tcttacatag 117840
gtatacatgt gccatggtgg tttgctgcac ccatcaacct gccatataca ttaggtattt 117900
ctcctaatgc tatccctccc ctagccccac cctactccct gacaggcccc agtgtgtgat 117960
gtccccctcc ctgtgtccat gtgatctcat tgttcaactg ccacttatga gtgagaatat 118020
gcggtgtttg gttttctgtt cttgtgttca ctgagaatga tggtttccag cttcatccat 118080
gtccctgcaa aggacatgaa ctcatccttt tttatggcta catagtattc catggtgtat 118140
aggtgccaca ttttctatat ccagtctatc actgatgggc atttcggttg gttccaagtc 118200
catgctattg tgaatagtgc tgcaataaac atatgcgtgc atttgtcttt atagaagaat 118260
ggtttataat cctttgggta tatacccagt aatgggattg ctgagtcaaa tggtatttct 118320
ggttctagat ccttaaggaa ttgccacact gtcttccaca atggttgaac taatttatgc 118380
tcccaccaac aatgtaaaaa cgttcctatt tcttcaaatc ctcactaaca tctgttattt 118440
cctgactttt taatgatcac cattctaact ggcatgagat ggtatgtcat tgtggttttg 118500
ctttgcattt ctctaatgac cagtgatgat gagctttttt tcatgtgtgt tggcagcata 118560
aatgtcaaga agtgtctgtt catattcttc acccactttt ggatggggtt gtttggtttt 118620
ttttttcttg taaatttgtt taagttcctt gtagattctg gatattaccc ctttgtcaga 118680
tggatagatt gcaaaaattt tctcccattc tgtaggttgc ctcttcattc tgctgatagt 118740
ttcttctgct gtgcagaagc tttttagttt aattagatcc catttgtcaa ttttggcttt 118800
tgttgccatt gcttttggtg ttttagtcat gaagtctttg cccatgccca tgtcctgaat 118860
ggtattgcct tggttttctt ctatggtttt tatggtttta ggtcttgcat ttaagtcttt 118920
aatccatctt gagttaattt ttgtataaca tgtaaggaag gggtccagtt tcagttctct 118980 gcgtgaggtt agccagtttt cccaacacca tttattaaat agagaatcct ttccccattg 119040
cttgtttttg tcaagtttgt caaagatcag gtggttgtag atgtgtggtg ttatttctga 119100
ggcctctcct gtgttccact tgtctatata tctgttttgg taccagtacc atgtggtttt 119160
gggtaatgta cccttgtagt atggtttgaa gtcaggtagc gtgatgcctt cggctttggt 119220
ctttttgttt aggattgtct tgactatatg agctcttttt tggttccata tgaaatttga 119280
aaagtaaaca gtacaataag atgtaaatag aaacaacaaa gtgataacaa gcagagagat 119340
gaattagaaa aaaatatttt ttttctaatt ctgtgaagaa agtcaatgat agcttattgg 119400
ggatagcatt gaatctataa gttgctttgg gcagtgtggc cattttcatg ataatgattc 119460
ttcctatcca tgagtatgga atgtttttcc atttgtttgt gtcctctctt atttccttga 119520
gcaatggttt gtagttctcc ttaaagaggt atttcacatc cttgtgaatt gtattcctag 119580
gtattttatt ctctttgtag caattgtgaa tggcggttca ttcatgattt gattctctgt 119640
ctgttattgc tgtataggaa tgcttgtgat ttttgcaaat tgattttgta tactgagatt 119700
ttgataaagt tgcttatcag ctttaaggat atttttgggt gaggtgatgg ggttttctaa 119760
atatatggtc atgtcatctg caaacggaga caatttgact tcctctcttc ctatttgaat 119820
acctttattt ctttctcttg cttgattgcc ctcactgtaa ctttcaatac tatgttgaat 119880
aggattggtg aaagagagct tccttgtctt gcactggttt tcaaagggaa tgcttcagct 119940
tttgcccatt cagtatgacc aatatgtagt cttttattcc tcaccttctc tcaaccccta 120000
ccccaacgga gtcctcaagt cctttacatc actgtgtgtt attgcatcct catagcttag 120060
ctcccactta taaatgagaa aatgcagtat ttggttttct attctttgct tacttaatta 120120
gaataatggc ctccagctcc atccaggtgt cttgtttttc attcattcag ccagtctaca 120180
tgttttgctt ggagagtttc gtccatttag attcagtgtt atgactgata actaaggact 120240
tactcctgcc atttggttgt tttctggttg ttctgtggtc ttctcttcct tttttccttc 120300
cttcctgtct gccttttagt gaaagtgatt ttctctggtg gtgtatttta ttttattttc 120360
ttccttttta tttttatttt ttgtgtgtgt atttgttgta cgttattgat ttgaggttac 120420
cgtgaggctt gcgcataata ttttctaact cattatttta aactgatgac aacttaacac 120480
tctattgtgt aaaaaatcat ggaaagagaa aactaataaa aactgtacat tttaacttta 120540
tcgctctgct tgttatcact ttgtcatttc tatttacatc ttactgtact gtttatgtct 120600
tgaaaagtag tttcagttat tatttttat tggtccatct catagtcttt ctactcaaga 120660
tatgagtagt tcacatacca caattacagt gttacaatat tctgtgtttt tctctgtact 120720
tttaattacc agtgagtttt gtattttcag ataatttgtt attgctcact aacattctat 120780
tctttcagat taaagaggtc cctttagcat tacttatagg aaaagtctgg tgttaatgaa 120840
ttccttcagc ttttgtttgt ctgtgaaagt ctttattttt ccttcatgtt tcataggtat 120900
tttcactgga tattctattc tattctaagg taaaaggttt ttttgtttgt ttgtttgttt 120960
gttttcttca gccctttagg tatgtcatgc cactctctcc tgacctataa ggctaccact 121020
gaaaagtctg ctgccagaca tatatgagct ccattttatg ttacttgttt cttttctctt 121080
gttactttta ggatcctttc tttatccttg gacctttggg agtttgatta ttaaatgcct 121140
tgaggtggtc ttttttggat taaatcttct tggtgttctg taactttctt gtacttggat 121200
gttaatatct ttctctaggt ttgggaagtt ctctgttatt atccctttga ataaactttc 121260
taccaagatg tctctctctc tctctccctc tctctctcat tcttaaggcc aataactctt 121320
agatttgccc ttttgaggct attttctaga tctcgtaggt gtgcttcatt gtttgttatt 121380

```
ctttttgtc tcttctgact acattttcaa atagcctgtt ttaaaactca ctaattcttt 121440
cttctgcctg atcaattatg ttgttaagag actctgaggc attcttcagt gtgtcagttg 121500
catttttcag caccagaatg tctgcttatt tttcttaatt atttccatct ctttgttaaa 121560
tatatctgac agaattttga attctttctg tgttatcttt aatttccttg aatttcctca 121620
acacatctat tttgaattat ctgtctgaaa ggtcacatat ctctattttt ccaggatggt 121680
tatctggtgc tttatttagt tcattttgtg aggtcatgtt ttcctggatg gtgttaatgc 121740
cagatgtttt tcagtgtctg agcattcaaa agttaggtgt ttattgtagt cttcacagtc 121800
tgggcttgtt catacctgcc cttcttggga gactttccaa gtattccaag ggatttggat 121860
tctgtgatct tagtctttgg tcactacagc catatctgct ttatggagca tcccatgctc 121920
agtaatgctg tggctctttc agactcatag agttactgcc tgcatgctct tgggtaagag 121980
ccaggaaaat tccctggatt accaagcaga gactcttgtt ctcttccctt acttcccccc 122040
aaacagagta tctgtcgcat tctctttttc tctctttctc tctctctctc tctctctctc 122100
gctcattctc tgccgacctg cctggatctg gggtagggat gacataatca catttgtagt 122160
caccaccaat gggactgtgc taggtcagac ccaaagccag cacagcactg agtctcgccc 122220
aaagcccaca gagaccactc cctgggtact gtccgtgctt gctcaaggcc caagggctgt 122280
acaagctggt gaggccagcc tgtcttatgt ccttcccttc agggtgatga gttcttcaag 122340
caggtcaagg gatggtgtcc aggagccaag gcctcgagct gtgactgagc tggcacccaa 122400
tccataagac aacgattttt tccacacttt ccttcctttt tctcaagcaa aggagtctct 122460
ccctgtggcc accaccaccc ccatgttcat ggcaagtatt gtctggctac caccaatctt 122520
cactcaaggc ccaagcgttc tttagtcaac ttaaggtgaa tgctaccagg gctgggtctc 122580
taccttcagg gaagtgggct cctctctggc ccagggcagg tccagaaata ccatccaaga 122640
gccaaggcct gaaatcaggt tccccaagag cccatttggt gctctacccc cactgtggca 122700
gaaccagtac ccaagctgca agacaaagtc ctctttactc ttccttctcc tttacagaga 122760
ctctccctat agccaccaca gctaggaata tgctgggtca ctcttgaagc aagaacagct 122820
ctgagtctca ctcaaaactc ctggcaagtg ctgcctggct accacactga ttattcaggg 122880
cccaagggct ctttagtcag caggagttgc atcctgccag tactggttcc ttcccttcaa 122940
ggcagccgat taccttctgg cccagtgtgt atctagaaat atcgtttggg agctagggcc 123000
tggcatggtg acctcaggac tctgcctggt gccctttttct actgtggctg atgtagtgtc 123060
caaattgtaa gacaaagtcc tctgtactct cccctctccc atctttaagc agaaggaaag 123120
agtccaccct ggagttggga catgcattgc ctgagattgg aggaggggtg gcacaagcac 123180
tctcttggtc acctcagctg gtgtttcact aggtcacatg ttccccaagt ccactggctc 123240
tgagcccagc acaacaccag gagttgacca agaattgcaa ttcttgtggt ttagactgcc 123300
tttcaagttt atttgggact gcagaccact ttagcccaca gtgacagggc ttgccagaat 123360
ttagtttctg actgctgaga tgggcaattt gcctctgatt aggacggatc taagtgctcc 123420
ttctgtgggc actggctgag ttctgctcca tgttgctttc tgctgtgaca gggcaacatt 123480
gagtgccaat gcaagtccca caatcactgt aatcttcctc tcccaagcct actctgaaca 123540
ccatgtggtt gctgctggga gattggcgag ggatgttgta ggcaattcaa gaatgtcttt 123600
cctacccttt tcagtgcttc tttccttagt atgatgttaa aaccagttac tgtgattgct 123660
catctgattt ttggttctta ggaaggtgct ttttgtgtgg atcactgttc aatttgttgt 123720
```

gcctgcaggc aggggtgggg gacaattgct ggaggcttct ctttagccat cttgctccac 123780 ctcttcccta gtattagaaa tttcaaagca gttaggatga gggtagaagg aaagggtgct 123840 tggaatcaga aaatccatgt cttagctttg agccttagga aattcatttg acccttgtaa 123900 gcctctgttg cttcatctgt aaaagagaaa taatatagtg actgaaaata tcaaaggtga 123960 taatgctgtt gaaagcacta tagaaaatga tgaaatatca catgagtatt attttctagt 124020 ttctaggagt ctccttacca ttgtacagga caaccatgtc tatttttaaa taaattatta 124080 tttgcctctg agcacccctg caaagagttg cctataggag aaacagctta acttgcaaat 124140 cactccactg ttttctttgt gtacagttta ttaatacata aggcacatgt cctccagtct 124200 gtagtaacat tggaatgatt acctctttgg agtacctacc agagcttctc aaagtgaatt 124260 ttgtatatca ccaccaaaaa tagtctgttg cagagataac ctccaaattc aatgacaata 124320 tttccaatca cttttgcatg atacagaaat agacaaatat ataattttgg ttatacagat 124380 aattattgtc tcccaacaag tgattagtag tcagaaaatg gccaagaaat accatggggt 124440 gtgccttccc ataacaactt atctttgggt tttagttgca aggttactaa aagcctgtgt 124500 agggttcatg gcaaaagtaa aacttgctcc aagagcaagc ccttgtttca ttgtctaatg 124560 ttcttaatcc ccagcagaca tgatttggat ctggcatttg gcaacaggac agtttccaaa 124620 gttgctgtat gcaacttgag gaagagaggt gatattattg gaatgaattt atttgttgta 124680 agttataaat atatgggctt ttccaatccc atcaccctta aaaatttttc tgcagtaagg 124740 gtgtctctct tgtctttaat atgcttgctt tgagttcatg gatgaacatt cttgcttggc 124800 tgacatgtgg actctctgaa attgttctaa ggtctttttc tttgtttttt tcttgattcc 124860 caagctgcca agggtagtac tggtagtggt gggcagacaa ggaggtgata gcaagctgaa 124920 ctttgtcctc tggcttccct tgacccattg cattcattat ctaagggact ccaagtcagc 124980 attccacaga atggccttac caaactcact gagactgaaa gagaaccaag attccaaaca 125040 gccaatatga aaggaaagag agagagactt agggtttgca gaatgggata ctctgttgat 125100 tatttttatt ccatacagat actaatattc tttaggaaaa cattaaaatc acatgatctt 125160 ccaggacctg ggctgcttct ttaagaagca tgttacagag agctctcttg gccaacaaca 125220 tattgaaaga taaattaatc aatcattcat tcaaataagg tatattcaga attgaggtat 125280 attgtagcca gacagtgaga ctataaaaat gaatgcacct tacccttgtc tcttgcacaa 125340 tctaatgagg gagataacca ctcttccaat ttatagtgac ctataacatt tcatacgctg 125400 ctgaatatct ttacatgata atgacacaat agaaagattg caaaatagac agaggctggg 125460 ggaagaagga ttgagtgtga atatagcctc tcataaatcg agggggaatg gtctgcatct 125520 cctgatcatg cagaggtaat aaatacagaa atgatttcaa actaacaaac caaatgtgca 125580 gaaaatactg agaatatagt gggcaggata cctgagtttt agttctatct ctgttattga 125640 ctcattgtgt aatctgggtc aggtctgttc tgctctctgg atctcaccct ttcctatctg 125700 taaaatgaga ttattgaatt agacgatatc tatagaggtt ctcgcctatt ctgacattca 125760 aggagttttt ctttaagtaa taatatatgt gatctgtata gtgctttaca cttgacatga 125820 tatttttgca tctattatct catgtgagaa aatcactgga ctgctggact gggaatgagg 125880 acacctggat tcttgtccct attttgacac tgattcatgg tgtgaccttt aagcaaattc 125940 tctgagtttc agtttctcaa tctgtaaaat agggaggtat gaggattgga ctaaatcagt 126000 aggtctctaa aatgttccac aaagccctgg ggttggggac tcctacagag tttcactaag 126060 gcaaaccaca aggctaggcc tgcatagaag aggagaaaaa gagtgacctg gcaagagaag 126120 ttccaagttt cctatgccaa ccccaggcag attaggttta attttatctg ttttataaac 126180
agagcttcta tgtaatgttt tattggtaaa aagactttac tataaaaaac tcaactagtt 126240
tgatttttta aaattgcaca tttaagtgag atcatacagt cagtatttgt ctttctgtgg 126300
ctggcttatt tcacttagca taatgtcctc cagcatcatc tatgttgctg caaatgacac 126360
actcttcttt tcattaaagg cgatatagca ttccattgtg tatgcacacc acattttctg 126420
ttttgtaact ttcattttag gttcaggggt tcatgagcat gtttgataca taggtaaact 126480
gcatgtcaga gaggtttctt gtacagatta tttcatcacc caggtaataa gcatggtagc 126540
atagtaccta atggattttt tttttctgat cctctccctt ctcccaccct ccaacctcag 126600
gtaagccctg gtgtctgttg ttcccctctt tgtgtccatt acaccagatt ttctttatcc 126660
acttatccat ccatggacac ttagtttgct tccatatgtt ggctattgtg aataatgacg 126720
aaaaaagtca aactcataga agcagagagt agaatggtgg ttaccaggga ctgggaggca 126780
gttcagtgag ctaggaaaag agagctaata aaagggtaca atgtgtgagt tatatagaag 126840
gaataagtta tattgatcta ttgcccagca tcgtgaccat agttaaaaat aatgtattat 126900
atgtcttagt attgctaaaa gagtagattt taaatattct aaccacaaaa aattataagt 126960
aggtgaggtg atggatatgt taatttactt gatttaatct ttctacaatg catacatata 127020
tcaaaatatc ccactgtatc ccataaatat atactattat tatttgtcaa ttaaaaaatt 127080
taaaaacttg atttagatga gctctaaggc cttaagtatt aaaatattat taaagtgata 127140
tgtaaccaag tatattgctt ggtaacttca tttttgttgt tgttttaaca aaccaatata 127200
ttgtgaatat acttccaagt gaaaagaaaa aaagacatta cagtcatcat taattactgc 127260
aaaatattcc tttgcatgaa tatggaataa ttcatttaat cattccctta atgttagaca 127320
ttcaaatgtt tccaactttt tctgtttaaa taatgctaca ataaacttct attttgtgct 127380
tattgtatta ttttcttata acacatccct agaagtggaa tttctagaag tttatagaca 127440
tttccaattt ttttccaaat atgtgggaaa atttctctct aaagtattta tgttcctacc 127500
agaaatacct ctttaccaac acacagtgtt taatctgtac caatctggct tgagaaaatg 127560
atatttactt tgtatttctg tgatttctag ctaaattaaa taatcttcac atgcttattg 127620
gtcattttta tttctttgaa ttgcctcttc ctgtctgttg cccatttttc tattgtgctg 127680
tttattttta tatatcaaat atattgacca ttgattttac atacttgatg ctaataatta 127740
gtnnnnnnnn nnnnnnnnnn nnnnnnnnnn nnnnnnnnnn nnnnnnnnnn nnnnnnnnnn 127800
nnnnnnnnnn nnnnnnnnnn nnnnnnnnnn nnnnnnnnnn nnnnnnnnnn nnnnnnnnnn 127860
nnnnnnnnnn nnnnnnnnnn nnnnnnnnnn nnnnnntttt gattttaact agtaatttaa 127920
ctttattttc ttctccaaat gattcactag ttgttctgac attatttagt gaataattca 127980
tccttttttc actgaattgg aatggcatat tccatatact gtgtctggtt ttggcttttc 128040
tgttctcttc cactgatcaa cctaagctgg agccagtatc aaactgttat aatcattatg 128100
gctttagata ctttaaatgt acagcaggga atgtcttatt actcttattt ttcacaaata 128160
tcttgacact gtctcatgtt ttattccttc gataaatttt gggattcatt tgtgatgatt 128220
ttgtctgagt tgttttaaat ttttagattt cactggggaa gaactgaaat ccttgaaata 128280
ctgcttctta ttagccagga atatggtaca actttgcatt taattcaggt ctttccttaa 128340
ataccacaat gaagtttttt gttttgttca tataggtcct gcattaacac tgtttatata 128400
aagtgtaaga aagactatag tcctcaggct tctctatagg ttaacaatga agatgatgac 128460 tcaacctttt ctttatttgc ataatgtgat gccactaata gtgggcaact tccctgtctt 128520 acctcctctg ttccaaacag gatttttttgg aatgaacaag ttaaaagaat cgtaatcaga 128580 cactaacccc aagccatact gcatggcagc accaacggga ctgacagaaa acaacagaaa 128640 taggaaggaa gcctgcagaa aaacaaactt gaaagctgtc tcatggcctt tgttcctgct 128700 ggagctttga gtcatactta agttttatga tggaagaata ggagtgtgaa gaaagataca 128760 gagcaccatc agacagtcaa gaatttcaga gccagctggc atgcagtgga cctcatgcca 128820 gcccattttg ttactattta ggtagtcaag gatttaagat tcttctaata agacagtttt 128880 tatgcattta aatgagtgac ttctttgcag ctctagcgtg tggccttacc tacttcaaca 128940 tgagaagatt tttgtatttt gtcactcatt tcacaatgac ttatagtgag cccttcatta 129000 tacactgtgg atacaacttt gctgttggaa attaacagtg tcaaaaaact gggtataatg 129060 tttgtagtat ctgaggaggg agagctgcct aggaagttgt attccctgtg ttaatttttc 129120 agtctcttag gttatagaag accttctaga accaccttac agcaggccta gatctcattt 129180 acacacttct tctgtcactt gaatacagag aagggatcca caaggtcata tacttcctag 129240 acaaagagca aagatttcta ccacactcag aagactttgt cttcagactg taatcaccca 129300 caccatattt cctttggatc cagtttccag atttttgtgc tggcactaac accaacttgc 129360 tgtggcttgg ggcatgtaat ttcaatattt tgtgcccatt ttcttaactg aagagtcagg 129420 catcacactg ggcattttaa gattctttac agcccaatga ttctgtgttt ctaattaggc 129480 ccaatgggtt agagctataa ggaaacagtg agtttcctgg aaggaaagga cacataacac 129540 agtccagaga taaaacgggc tgcattcaag aaaagattgg gcaatacttt gcagggatgc 129600 tacagagaca attcaagcct tgtatggagg aatggatgtg atacaaccaa aaagtcttta 129660 aaaattcttt ccaactaatc tgggattcat aaccttatgg actgtgattt gcagcaaacc 129720 aaggatgtga tgccaggcag aacaatatct ctgatcaaca tcaatgcaag gttcctcaac 129780 aaaagactag tattgtttct ggaatgcaag gatggttcaa catatgcaaa tcaataatat 129840 taacagaatg aaggacaaaa actatatgat catctcaata gatgcagaaa aataatttga 129900 caaaattcaa catcatttta tgatgaaatc tttcaagaaa ttgggtatta gaaggaatgt 129960 ttctcaacac aataaaggcc atatcagaca agcccacagc taacattata ttcaatgacc 130020 aggaatgaga taaggatgct cactctcatc acttctattt aacatagtac tggaagtcct 130080 agccaatttc atattaatga gtctcatttt cttcatcata gaatgaagta tgtaataatc 130140 cctattatac ttactttgca caattattat tattttatta ttattttgag acagggtctc 130200 actctgtcac ccaggctgga gtgcagtacc acaatcacag cttacttaaa ccacgacctc 130260 ccaggcacaa aggatccagc ccctcagcct cctgagtagc tgggacttca ggtgcacacc 130320 accatgccta actaattttc tttttttcat ttttttatag agacggagtc tcactatgtt 130380 acccaggctg gtctcaaact cctgtgctca agcaatcttt ccaccttggt ctcccaaagt 130440 gctggtatta caggagtgag ccactgcacc tggccttgca gattattatt aaactttgta 130500 aactaatcaa atgagagtga ttattgttac tgttaagaac tctaatagcc tcattcatat 130560 atttggagaa attgaataaa taggaaagaa ataatagcag accaatgatt ttaccttggc 130620 tctatcatca tttggggaag tgataattca gataggagaa gtgacttgta agcagtcttg 130680 agagattacc tgttccatcc cctatatttg tccttaaacc aaattgtaca gataaataag 130740 gtcttatttt taggacttac agaaaaaaag attcctttca tatccatctt tggaatcctc 130800 agccacttct gtcactatta aatgtcattt taaacgttaa attcatcatt ctgctttgaa 130860 ggaacacatg tgtcatgtgt acctatttgt atgttttggt gtgttttatg ctttatatga 130920
tcacccacat atgcacagat aattagtgtg caggtgttgt attccctgtg ttaattattc 130980
agtcacacac tctcacacac ctatgcactc acacatacat gaatacacac atgttcatta 131040
gaatgtttat gcttatgttg catgtgactg gcaacatcag tgcctttcta aggcaatatt 131100
aaccactttg agttttggga gagctttaga aaacaaagac aagagactaa atgattctag 131160
atgtaagaga caatgttgca ataagttact atcctaaaaa gacagaatac aaggacaaga 131220
gattattatt ttggataatt tcttgcttac cagtaatact taagtccttt acattaaaaa 131280
aaaaaaaaca actctaaata tattacagaa gacatccaga tgtccttcaa gattcttaga 131340
gttggaaaag attttaatga ctttccagtc caatctattt catgtaatca gtgggatcag 131400
agaggcaaaa ggacttgtcc aaggtcatat agtgagttag tgataaggct gaacaaggat 131460
tcagatgttg gggcttccag cccactgatc tgtctctcat ctgggacttg tatatttttg 131520
ttcattagag attttcctct gtaacctcaa tatccaatgc agggccttgc acataataga 131580
ttaccagtaa atgttaaatt aatatgtcat ggctttggtt ttactgggct ttgcacttac 131640
tcctgagtaa attgtaaata atatctatgt tttaggtctc cttgttttag accaagatgt 131700
acccagagaa aaggtatgaa ctatgctaag aaaattatct gagtcccaaa ttgaaaaaaa 131760
aaaaaaaaaa tcatgctttt ccactatgac ctctctcatt cacagagtga ttctctttca 131820
aaagggcaat gtagaaccat tctggcattc tgggagccat attccattgg ctgtgcaatc 131880
atttattggc aaactggggt ccaggaaagt attttcctgg ggaagatgag atttctcaaa 131940
gaagtcatgc actttctaac ctaagcttat ttcagtaatc agtgtagcaa actggtcttg 132000
aggattgcag cagtaccaat actgtgggag tgtaccagtt ctagaacagc tacagcattg 132060
gaattgaacg cactagaatt ggatacagga cctgtttttg aggagctaac acccaaaggc 132120
tgaaagcact cgtagcactg tcctttctgt gcacatatcg tagtcctcag tttgcagcag 132180
aaaaaaaagc tgttagcaaa ttatgtgctc tgtttatgca aataaaatcc tgtggtatac 132240
tagaaagagc accggcctag aggccttagt tttctcatat gttaaaaaac cctaacacag 132300
gcctggttca tagtaggcac ccaataaata ctagagtttt tcctttgggg gcctctgatt 132360
cagtgtgctt cttcaggtaa ttcacttccc tggaactcct ccttgtaatg agagttgttc 132420
tgttgtgatt tttaacagtt ccttcaagcc aagcattttg gaatcctttc ataaagggag 132480
aaaggaagga aaggagaaag gaaaattaaa ggaaaaaaaa ggaaataaaa agttaaaaag 132540
gaggaaagga aaaagaatcc tttactacaa taaatctaat ctcatgctct tgcaagtagc 132600
actttaagta aaagaagttc tttgctgacc tggttactac tgaacctact acataaaata 132660
gcctactgta acacatgcat ttctgtgcct aatcttcacc ttttagcctt agtaaatgta 132720
gaggaatgct gatgtatagt taaatttatg tttttagttg ctttttttt ctactctcaa 132780
atgtcaatca ctctttagtt tctctttctt tttccgaccg caagtattct tcctctgcct 132840
aaagaagctt ccctaaaatc ccagtctatc cagtaaatca aagcacagca ataaatttga 132900
ggaaacaata ccagagacaa aaaggagtga ggggatgcag aagctcaagc tggagcagga 132960
ttgtaagcat gagaagttct gcgtgcttca gagcagcgaa ggatgtattt ttgcttattc 133020
ctgctggtga ctctttgtct atgcatccat ctgctgcaat tgcatgttta gtcagtcaat 133080
ccacgtttgt tgagagactg ctgtgtgcca ggattgtgct agcataaagg agcgaagtat 133140
tgagcaaaat atgtttgagc agctgtaatt ctgaggatct ctaggtctga gcatgtgtat 133200 gtgtatgcac ttctgtgtat ctgtgacaac tccaggtgtg catgacagtg atctttgtta 133260 ctctgttggc ttcatcaaac ttccttttag ttgctgtgat tcactacata gagtgggctt 133320 tatctctgat ttttataacc tgcatgacta ggggtatgat caccagaaat ctaaaaacag 133380 ttagaaatcc catggagtta tcttttatag aagttttcct gtactaatat tatgaaaaat 133440 aagcatcttg ttaacttgag tgtaattcta tgcatgatta caggtgtcaa taggaagaaa 133500 cattgactga gttcagatct cttctacgcc atgctaaagg ggtgacaagt tccacaatgg 133560 atcattttct catgggcatt tctggctttt ggtaaaagta gggcatctta ttttaaaaac 133620 cagtgagtag tcctaataat ggagatatca tcaggatctg aattgttcat ccctaaaaaa 133680 aaacaaaaaa aacaaaaaaa caaaaacaaa acaaaaaaaa aaaaaccaat ggaaatcaaa 133740 taatatagtg ccaaattaaa ctgctttaat atttaggttc tgtaggatca aattgtttgg 133800 tgccatactc tgtccacttt tctgtccact tttctcatgt gataggatat aattttatat 133860 cttttctgtt ctagaaatac ccaaagaaag agactctgga aactcattaa caggtctgtc 133920 cactcttgta tttgttatcc cagggaaaca gaagtacctg tgtgccagca gaaatgattg 133980 cactattgat aaattccgaa ggaaaaattg tccatcttgc cgtcttcgga aatgttatga 134040 agcagggatg actctgggag gtaagatact tttctttctc ttcttcctcc tccttcctgt 134100 ctccccttt cctccctcat tttctagtct ctctttaaac cagattttct tctttgatgc 134160 ttccaagggg accagccatg ctccagacac aggcggaccc tttcatagcc aacgtggcca 134220 tcagccagct ggtgcctttt tttttttaat ccttaactat accaatcccc attctggggc 134280 tcagcattag agcaggaggt gtgaagcagg gataaggagc caacagaggg tgagtgagga 134340 tgcatgtgac tgggcagggt ccccagggga cttaatggta ctgacctgat gttgttcaat 134400 ggtagctagg atgagagaac taagaaatcc agaacagtca caggtgcagg atgacccagg 134460 cataggtaca ggatgaccca ggcacagtct gaccctgaac acctgggaat atccctcagc 134520 taactgctgc ctatgttgta gggccagcca cctggaatga gaagctgctt ctctttggag 134580 cctgtgacta ggctgacaaa cagtgccaat ttcctatcct atctctccca aagatgaaca 134640 ggtgttttaa tcatttcctt ttctttgcaa agctattgat catttccaaa agcatttttt 134700 tttcagtagg acagtaacat tacagaagga agatacagct ctttcaaggg tgttcctcta 134760 tcataaggct ctctgtccca tgaacctgtc tgccatgagt gttgtcatca ttccagaaag 134820 gcttgacatc agttgattga catttatatt ttccctctcc aaactccccc atctctccat 134880 gtttacatct gcccaatgcc agggtcatca ctgcagcctg ctgcttccaa aaatatgtgt 134940 ctttccttag aaaaacaaga tcattaatct acttcaattt ggaaatggaa tttgaagaaa 135000 ggcaagccta tttctgagtg cctgcaactg tagcctcata tccgattatt cattattagc 135060 ctggaaaacc caagtgccta gaatccaacc ctttccccta tcctcttaag gctaatttag 135120 accagttgtc tatcactggc tttctgtgag ttgttcaata ccttgtctgc ctatgtgcac 135180 atctatagac aacaactagt gctcttatcc tggaacaggg ccatgtgtga atctatatgt 135240 agataactat atccttccca tcctcacagg gcagtggtat tatttaaaca gaacaaagta 135300 cctcaaatga attgacccag gctggatgag agacaatttc aaaagaatca tctcaagtag 135360 catccagtac tcccaaacat cacaggtaga tattctgtga gtggctttcc aagcatccct 135420 atcaaatgag aatcagatat ctgagaaaac tcaaccttgt tttggtttgc ttagtgtacc 135480 ccaaagaaat ccaacaattg aggtctacag tggagaagaa gtaggactgg ggtcagggag 135540 tacagaggca aaggcaggaa gggtgacaaa gtgattgaca agagaaaatg ttctccatat 135600 gaatgttgca gccccatgtt gagggttctt atacactcag ctttcaatta tttagccttc 135660
tgcgaattat gtatagtata agagatagag actctcaggt agggaacctc ttggctggtc 135720
atctggcaat atgaattgca agtccacttt gatgcaggta aagtttaatg gtaacaaaag 135780
tcctcataat atttggatac aaatcttaac attaattcca tgtctcagcc aacattctcc 135840
attataaatc aggctgtgat atgattacag tgacccactt ttgaaaagga gcctgtgtat 135900
aacagataat ttcactatac tatatagtac tcagatgcag gtttgtaaat taatttattg 135960
gtgagaatgg ttcagtacat tttcaaattg atttattagt agagtactca aatttgagtg 136020
ggcttggtga acacaatgaa gacaagctga gaagtgttgt gactggcctt catttcagtt 136080
gcaggcccat gatattttga gcatcttcca tgtacaaggc accatgctag tcattagagc 136140
ttgaggctgg caaacttcag gaaatgttca caagatacca gcattcttga tgttgtgtaa 136200
atggccttgc ctttagagtc aggcagatct agtttaaagg ctcagctcct ttatttaatg 136260
tgtgcccctc tgagcttcaa gatcttcgtc tgtgatttag aaataccatc ctcatagaat 136320
tataatgaag atcagatgac atgatgaatg tgaacatcct tgataaatag caaaatgcta 136380
gacaaatgtg ggggcttaat atgtcattga ggtcactagt aatttagctg gaaaggctgt 136440
aacacagcac ttcccgatgg cttttaccct aagtaacttg gtatgccata taatatgtaa 136500
cagatccaac aggcagagca tcgccagaaa acagtcttga ttacctcaaa ccaaaaagtt 136560
ccaccaggat cctgttcaga agctaatttt agtaattaag ggaatcatat gctatgttca 136620
agtaccatgc cagtaaaaac ccaattgtgt accttcttaa atcactgctt gaagagcaaa 136680
tctttccact ttggtgaatg aacttatctc cacattccct gccctactga cacaactccc 136740
tcccacgttt attgttaact tacacattca atgcacagca cacctttact caaacaacgg 136800
aaaagaaagt gtcaatacaa agtggccctt gtctattcct taaggagtag acttccattt 136860
tcatgagatg tggatttagc atagacatat tgattacctt gaagaagaat tcatataatt 136920
ttatcttctg attctcatca ctcaaatcaa aattatataa tatatcccaa aatgacaact 136980
agaaatgtgg ccttgggcaa gtcccttctc ttctctgatg cttggttttc ccatcataga 137040
attggaattg tgggcttcac caaggacctt tctggtgcta acattttgtg attctgtgta 137100
aaaagccacg cagaaaggat tgtttttcag ccctttctta gattgtctgt tccctgctcc 137160
cagaagtata gataatgaga cttgagtgct ttgatacatc gtaattgtat ctacctccat 137220
tcatacctac ttaagatatc tgtctaaaag tagactagac agattattga gagagtggag 137280
ggcagaaggg ctgtctctgt atcttaaaga agctggcact tttcagctga tggctgcttg 137340
gtcttgaggc ctcaagatct ctaatctggc tttctctata gtgtttcatt cactgtttgg 137400
tgatggaatc tcttcagctc agagatactt aatagatata gctttttatt tcctgcttcc 137460
aggcctacct acctgttcct tgctttttt tttttttttt tttttttat actagttgct 137520
gttgtttctg aaagaatctt gagggtggtt ggagtctcag aatggcttcc ttaaagacta 137580
ccttcaggct ctcagctgct catccacaac aaagataagc ctttatttgt agatgattca 137640
ttcctggctg catttgaaaa ccacatattg ctaattgctt gaagaattta aatcccttga 137700
ctacttttca tttcagaaaa cccttacaaa aaaagtccaa atgaggacct tccctccagt 137760
gaattagctg tggctttctc acagtccata gttaggatta atgtaaagcc atctctcatt 137820
tttctggaca cttcccaagg atacactcct tgtttccaaa atggaatgag aaagaaagaa 137880
gtgcccttcc tgccatcttc tcccatgacc cttttctcct tcccactttc cctcctattc 137940

```
ctcctcaaac atgatttatt tctgtgtttt gcaactcttg agttctcatc atttagtaaa 138000
tggtgttggc ccctattgat tccttcctgt cctggaccat ggagagtagt aggcctttca 138060
gaaatttcag gtagcagcca aaccctggaa gaagagaagg aacacggagt cctagaccat 138120
gtgagaacct gaggtgtgca gcatttcctt cacagattcg tctagcatat ttgagaagta 138180
tctttcccac taggagactg aactctgcat ctgagaaaaa aaaaaactta acatatctac 138240
aggttttgac aacctctatg aattacctag ttgagaggat ggctcaagga gcctatggcc 138300
atggtctgat gtcattatgg acactatgaa catccttgag gtttccattg ttgaagacag 138360
ccctgatgcc agctgtctca tcattcccca tgttcaagag catcccagca tcgctacctc 138420
aggatcccat gtcctgaatg caacagagtg atttcgctgc tgaattacta ttcatggcac 138480
ggctcttcac agcatttatt catccatgtc catccgtcct tccagccagc caagaagctc 138540
atgctttcat cttttcatcc tgagtaccaa ctatgtgcca gacactctgc taggcatttt 138600
ggggaagcag aactgaataa gatatcattc ctttcctgaa aaatttaagc aagaggagaa 138660
aggtagtgat aaggaatata ccttagccat aaaggaaaaa taataaatca cttagaagaa 138720
gttgagtgag atggaaggaa aaggacatcc aaagcaaagg gtacagtttg aataaaggca 138780
gagagacatg aacaaaatgc attgagggtt tgaggaacag caattggttt aacatggcca 138840
gagctgggga aatggtaaag gcaagctgaa agcacattga aagcaaactt cgttactata 138900
ctaggtagtt tagacttcaa agagttgaaa atctatgacc atgggacagg tatgatgaca 138960
tattattttg tttattttct tttttttttt tttttttttt tgagacggag tctcgctctg 139020
tcgcccaggc tggagtgcag tggccggatc tcagctcact gcaagctctg cctcccgggt 139080
ttacgccatt ctcttgcctc agcctcccga gtagctggga ctacaggcgc ctgccacctc 139140
gcccggctaa tttttttttt tgtatttttt agtagagacg gggtttcact gtgttagcca 139200
ggatggtctc aatctcccga cctcgtgatc cgcccgtctc ggcctcccaa agtgctggga 139260
ttacaggctt gagccaccgc gccgggcctt taatttgttt attttcatgt ttctttaaag 139320
aaaactggca gcagcacaaa tgttttgttg atgagggctt aaattttaga aagtgagaca 139380
attttagaaa ggccagctag agagaaattt ttagcatcaa gttttgctaa acacctagaa 139440
tttattcctg gagctagtta cctccatttg ggttgttacc tgcaagtact gaccacgtat 139500
atgaagaaat actggtttag accaaggcaa ttggctgtat aagaggccta ccctcatacc 139560
aaaagccagt ttccttggtc taggccagtg tttaccagta tgtgttctga gaaaactagt 139620
tccatgacat gttccatgaa aaatacgatt tctattctca aataagtgag agaaacttgc 139680
atattatggt cctgctcagg aagatttaca gtccttatta gcatatcgca ggtcctggtg 139740
aatactgcaa taaagtaacc tgaggagctt tgtaactcag gattcccaaa gttgattcaa 139800
ccacagaacc tcatttattc acataacacc tgttatccta caaaaccact gttctctaga 139860
atacactttc gaaaacttgg gtatagataa aaactctatc ctataggcag agaatacctc 139920
tagctcaggt catcattttg cagatgtgtg tgtcattaag aatcaatcca taatgcatta 139980
atgatcaaaa gcagaccatc cttaccacat ggtgcataag attatgctat tagctactaa 140040
agccactgaa gttaatcatg ttgggtctgt aatattgttg ttatgcacaa aggataggct 140100
gcaaaagtgt cctaggccaa agcatggcta ttgcccaagt tatctaatgt ctgcaggtac 140160
atattcctga cctaaggatt gtgctaaaga agttatttct aagaaatata gtgacttcca 140220
gcatcatgca gaatgatcat ttaatatttt gaatatctag acattttgct gtagaattta 140280
atagtccttt tatacactgt ctgaccaaca ttttgacatt tactcagaat cccatcacag 140340
```

tgctaccaca taacctcatt actaaagtag gaggcctaga aatcacagat ttgtagaaac 140400
catccaatga ttgaatcccc tctacctcct gttcagcagg cagcagagtg tcataaataa 140460
ttaacaatgt ggaactcagt tactgggatt tcttccattc tcctttggct ctctagacta 140520
gattctaaag accctcaggc tggtaatgca agtggtaagt ctcatttctg agaaatgctg 140580
cttcctacac acagttctct gatacctgag tgctttgact gatctgcata actgaggcat 140640
gcaccaagga gcagaattac tctataaatt ttggcatcaa tatgtacaac gtgtgactca 140700
gcactttgaa actctgggga tttttttgtt cggttggttt ttgttttaag aggtcctgtg 140760
gtatagtgga aatcgtatgg tagactcaga tacagagagg ccttgtttct agtcttggtt 140820
ctgtcactta ctatcttgat gaccttgggc aaatgactag aactctctga gcctcagttt 140880
ctccaaccac actgtaggaa taataaaatc ttgtttacgg catttttgta aatacgtaga 140940
gaaactggta cacagtaggc acacagtaaa tgtcaccata cccttcagtc cttcttttgt 141000
ggatgaaaaa tggtctttct ttgtgctccc agtaaccact ggggtctgtt ctctctctct 141060
gctggacagt gtggcttctg gttcttgttt ctttgttctt tggtctctaa attacccttg 141120
aaacaaccct tgaaatttcc actcgatgac ctaaattgtc atccctaagt tggttacatg 141180
catatttggt gacactttgg aggggaaaag ctttatgtct ctctaactgt agttcttaag 141240
ggaatttgca tatggaaaaa caagagactc catctcttaa ttcctccaaa ccaaattatc 141300
tgggatagta catatatgtt gtactctgtc tcttagcatt tgctcttaga gaaatatggt 141360
tagagagaag taattttttc taatcataaa aattaatgat actgcatatc tgatacttga 141420
atgagtacct ccttgtaaaa tttctactta aatccttgag tttttaaagt gtaatagcaa 141480
tagaaagatt ttattattgt ttacttttgc tatgagtgct ccaaaatccc tcagtagctc 141540
ttgagagagc aagatgatgt cataggcaat attttccaaa ggtagtaggc agaaaactaa 141600
gtacacagca cacaataggc catatataca aaggcaagta ttttacaaat atagtaattc 141660
aagaaaaaag tttcattttc actggtaacc tgactgtttg tttaaaaaca ttttattatt 141720
tattatttaa aaagagtgtc acttgttaca gattgtggga tgtgttcctt aagatcacaa 141780
aaatgtaaaa tattttcttt ttatattgaa cacatacata gacaactaac ctgagcaagc 141840
tgctttttag agacatttgc acatcttttg ggatcacgtt gttaagaagt agaactaagg 141900
gaaaaagaca cagccaccca gaaaccggta gagctttcag ttcatctgtt attaatattt 141960
ccatgacaca gatatctagg aagtaaacag aaaatagcat cgctatcctg cgtcaccttt 142020
tttggaatca ggttccattc ttctcagtcc agttcatcct tctgatactt ttaagatctc 142080
aaccaagaca tagaaatatc atattttccc ttgcttaata ccccatggaa ccaatgcccc 142140
tgtggctgaa gtaaaaatta attgttgagg gacatttcag ccctctagca gtcaacaatt 142200
aaaaacatgt aagcaccgag cacctgcaga aaacttgcac tggcatttgg atctaagaag 142260
aaaatctgca tcttaaacaa catgaaaagt cgccagccca agcttgtgca gtgaagtgtc 142320
atgctggcca caatgaaacc gaaagagact gatgactctc ctcagggtgg aaaacgaggc 142380
atggaagctt tgattagtga gctgttaggc acacagacat taatttcaaa gcattctcat 142440
ctccagtctg agtaataatt cttgtagtat tatgcaattg tttggctgct gcaagaaatt 142500
cagcagactc caacaagtag tctttcttgg tctctgagtg actgtaactt aaattctacc 142560
tcccttctct tctcctacat cttcccactc cccacccgac ctcaccccac acacacacac 142620
aattcttgta cactgtgttc agagagatgc acacacacat atatatgtat atatatagta 142680 tatttgtcaa taaagcagaa aagaagaaag aactccaatt aacaattttc catttcccca 142740 tctcacctct gtcttacaag tagataggaa aagagaaaac cccagtaaaa aatggcaacc 142800 acccgcctcc ccaactttac atgctgcttc ctatgttaga ggacttggct taggcatctg 142860 attgtggagc ctgctagata caagcccata tttagactgc tacattcaac aatgtctctc 142920 tttcatatta gaaaaattcc gggttggcaa ttacaagcat ctcaaaatga ccagaacctg 142980 aagaaaggct gacttgcctc gttcaaaatg agggctctgc tctagtggat agtccggaga 143040 aacctggagt ctgaggctta ggagcttagg tttttgctcc tcaacacaga ctttgacgtt 143100 ggggttgggg gctactctct tggttgctga ctccttccaa cgggaccaat agtgttttcc 143160 tacctcacag ggatgttgtg aggacgggct atagaagtaa tagtggttac cattcatgta 143220 gttatgagta tcatgattat tgtttcctgt aatgcggctt ggcattggca aagtgctttt 143280 tgattgttct tgatcatata tgatggtggc caggcactga ctcaggcaga tgcagtgaag 143340 ctctggctca gtcacttgct tttcgtggta tgttgctggg aagaaacttt gctgatggga 143400 ctcaaggtgt caccttggac aagaaacaac tgtgtctgtc tgaggttcct gtggccatct 143460 ttttttgttt attaggcaat tcgtatttcc cccttcggtt ctagccttcc agatccctgc 143520 caaggaccta gatcttagcc tcaggcccca tcactgagct gaaggtagta gctgatccac 143580 agaagttcag taaacaagga ccagatttct gcttctcccg gagaagaagc cagccaaccc 143640 ctctcttcaa acacactggg atactagagt cagactttcc ctcttacatc tagccttact 143700 gtagccacac tccctgattg ctctttcaca tcacatgctt ctcttcgtca gttgtgaggc 143760 cctctcattc ttctcccaag ccagactcaa acattatatt gatgtcaaag aagaatcact 143820 tagagtttgg aataccttgt tctctctctg ctccatagct tccatattga aaccagtttc 143880 tttctcgtgg agaagtggag tctgtgaagc cagagacagg cacatacgag agtcagaagc 143940 actctccctg acttgcctgg ggcctgtctt tcccaccttc ttctccagtt tgtctaaact 144000 ctctctctct ctctctctct ctctctctct ctctctcttt ctctcccccc cctacacaca 144060 cacacacaca cacacacaca cactttttc tctttcccct gactcagcaa cattctggag 144120 aaaagccaag gaaggacttc aggaggggag tttctccttt ctcagggcag aattttaatc 144180 tccagaccaa caagaaattc cctaatgtgg attgaaaggc taatgaggtt tatttttaac 144240 tgctttctat ttgtttgaat gttgcatatt tctgctagtg aaattttccc ttaataaagc 144300 cattaataca ccaatcgtat tttcttattt acaacagact gagagaatta atgctgttaa 144360 cattggacct tttttctttt tttctgtttt cctttttttt ttttttcctt tttttctctc 144420 ttgtttgctt tccaggtcat gctgacctgt tcagcttgga ctgtttcaca tttgttttta 144480 atgtcagttt aaatgtaatt gtaaaagcat gtatgctcta aattcatgta gttacttttt 144540 tcagtggaaa agcctggtat tcgaaagcat ttccaggctc cgcaatttca tatgagcagg 144600 ttttcggtaa aatcttttgt ccctcactca ggatggtatc tggacagtga gcccctttct 144660 tctggctcag tagtcagaga gaggagactt ggagacagtt tctgccggat cctgtgcttt 144720 ggcaaggatg tgcagcattg catatcattc tatcattaat tacgtttact cctccatgaa 144780 ctaaaaacca ttagactaaa tagtccaaca taaaccttga aagataaaat ttgatattct 144840 ttcgcctggc catttctctg acccagaatt ggggctggga ggggaatgga gacttggggg 144900 agagaatcaa ggaggcttct tgcctggggg aatttggcat gcacttatta atcccatttg 144960 gttgtactcc ctactaatcc ctcactccat acctgccaag gattggcttt gctccctgct 145020 tctcatcccg gtcctagttc ttcctcaacc atctccattt cccaccactg atccttctct 145080 ccagtaagat gctattcaac ctgatgaaat ataaagagta gcaccaccct ggaagtcagg 145140
ataccttagt tttagctcct gctctaccat tatctaactg tgtgaacttg ggtatgagtt 145200
aacctttgcc ctttaatctg aacagtcttt aagaattggt ttataggaga aaggaaggga 145260
tagacaagat ccaaggcctt tgaacccttt tttggaaatg aatccttttc ttcaaacaaa 145320
atttgactca gagtcccaaa tataggtaca gaataaaatg ctgctgttct tgtttgaaag 145380
gtggtggggt gcttggagcc acatgctcag gcccactttg ccacctctca ggaaccctcg 145440
aaaaaactta taggactctt ggggctctac cattgtacta gactgatgtc tggggagtct 145500
tctaactcca attttctctt ctgttacatt tcagtccttg tgaaaactct atatgtttca 145560
tcagttcact ttttcagaaa gttcacctgc ttggggtaaa gggcatgcag tggagaatgt 145620
ggggctcagt aactagcaat agtaaaaaac atcattggct ggcttacata atttactctg 145680
ttctaagcat cttaaacaca tactcatctg aaaaatcaca acaaccttgt gaggtagatc 145740
ctgttattat cttaggattc tgaaacctgc cagcttgact ctcaaccttt gacttgagac 145800
cagtcgccca agatggaaag ttatactttt cacagtttac caccgtaagc agtttttcag 145860
agtgacttct agctagagat ccattcttag aaaaagtcag aacctgccca ttagcatgca 145920
ctatcaccgg gcgcagagta ccttcactgg gttcatccca tttcctccta aaaatagtcc 145980
tatgcagtag tcaagtcata tcatcaccat tatataggtg agaaagctga ggtgtaggag 146040
aaatcaagag atctgttcaa ggttacacat cccataagac tctgaatacc accatcaaga 146100
ataataagcc ttttatgtga aaagcatttt agaacttcag tgtcattatt gcattctgcc 146160
tcctggagtt cagtgcactt tttcaccatg ctttaatctt ggagtcctgg tggtacagaa 146220
tctgccttct actctcaggc aacaccatag tgtctttatc cctcataaca aacatatgat 146280
ttaagtaatg atattatccc cattttacaa attagttaac tgagataccg agaggctaag 146340
tcttgcccaa agtcacaaag ctagtcagcg atagagccgg agttacaaat gaggcagcct 146400
gactccagaa tatttgctct taactactac tctttataca tatgtaagga aactaaaagc 146460
caaagaggga aagacgtccc tgaggtccca cattgagttc cccgactcat ccagtattct 146520
tctgaccttc taatcctaaa gttatacagt aagatccctt gactctaatc ctcgtagatg 146580
gaaagatggc tggcatgatt taagctacag gccacaaact ggctttcccg gagccagaaa 146640
tcacctgcag aattctgttt gtccagcaca gtgtttgttt agaaaattga catagactgc 146700
ccctaggcag ggcatcaatc actgtcactg tccccagccc tccctattta tgtttgccaa 146760
gctttttttt ttttttctca tttatgtgtc tgcctgactt gtgaaggtat ttgagtttat 146820
gacttttaga tttaagcatt ggaatatata agcactgcac atacacacat actcacatgc 146880
attcacaaaa gtatagccta gtctagcttc acaaagaatt tgtagcccta caccaaacac 146940
acctttatgt ttacttaaca tttagaatta gatttaagat ctgaatttag tttcacaggc 147000
attcaagtgt ggaagaatct cggttattat tttttgtttc atactgtttc actcttgctt 147060
tccctgctgt gtctggaccc ctgtcagtcc tgctttctgc cattctccat gcctgagtta 147120
gggcccctgc aagccactca ctcattaatc tttaggaata gatggagagt ggaaaccagt 147180
ttggagggtt caccatgtgc caggcatcct ctcatttagt tctcataagt gtcctaagag 147240
acaggtggca gcacattcgt tttataaatg aggaaactaa atcttagaga agctcaacaa 147300
agacctcaaa gtcattaagg tactaattaa cggagctggg atttgaatgc aagattgtcg 147360
gactccagag cctattcttt tgccctatac cacagttcct tacaaggaag atgtattcgt 147420

```
tttctattac tgcataacac attgccacaa atttagcagc ttcaaacatt tatcagctca 147480
gttttgtaag tcagaagtct ggcacagcat ggctagattc tcagttcagg gtctctgaag 147540
gatgaaggtg tttaccagga tgcattctaa tctgaagctc agggttctct tccaaactca 147600
tgtaattatt gcaggattca gttatttgtg gttgtaggac taaggttccc acttcctttc 147660
tggctaccag ccaagggcca ttcttagctc ctggaggctg ccctctttcc ttttcatgtg 147720
gaccccaaca ccttcaaagc cagcaacaga gactcttcct tgtgttgaat gtttctcact 147780
ctacggatgt ctttccagga gaatcccagt cctgtgaggg ctcacctgac gaggtcaggt 147840
acatcaagaa taaccacact tcaaattcaa ctgaattagc accttaatta catctgccta 147900
gtttttttcaa cagcacctag gttagtgctt gactgaatga ctggaaggaa ggatgtgtat 147960
gctcaggcct cagaatcttg ggggccatct tagaagtcag cctaccacag acgttgattg 148020
ctttcatgtg tcaaatttca tagtgagaca gggagaacag aaatatcctt gaccttagat 148080
agagcgattc aaactttcta agactttgga aacttcacat cactttcacc tttcccttga 148140
tcatggttga gaaggcctat gtcttggagt ggcaaggagt gagactggaa cagtacctaa 148200
aggttaagga gactaaagaa gttacagatt ggtcacatct gctcctccct aggaatgagc 148260
catggaacct gatttgaatt tttttttct ctggtgctat agagatagct cccacagggg 148320
tctaatgccc caaggctgaa aagttcgttc cccataggat ccaggcatga tatcagacca 148380
ggtgttacaa tctcctaaag aggaggtatg gacaggaaag ccccttgcca atgacccttt 148440
cttgtcactg ctctgactca agactaatag ggcagagata gtgagcaact cacatactac 148500
taaaactatc cacttatact gcccccttc tccttgcttt atcactccat ttaagtaagc 148560
cagtgagtct ctgccttgac acagtggcaa gctgatctgt atcttatatg gaagaattag 148620
atttgactct ggggctcagg tgcagagggc aggaggggca taggggtggc cctcatggaa 148680
gaaaacaagt ccttggatac tgagtaacag ctgagactag caagccttat tgtccaggat 148740
tccaagtcgt ctagcaacat ccttgcctct gctgcagaga gaacagagga tcccccggca 148800
gaatgaatgg agtctgattt caattacgtt cagtnnnnnn nnnnnnnnnn nnnnnnnnnn 148860
nnnnnnnnnn nnnnnnnnnn nnnnnnnnnn nnnnnnnnnn nnnnnnnnnn nnnnnnnnnn 148920
nnnnnnnnnn nnnnnnnnnn nnnnnnnnnn nnnnnnnnnn nnnnnnnnnn nnnnnnnnnn 148980
nnnnnnnnnn nnnnnnnnnn nnnnnnnnnn nnnnnnnnnn nnnnnnnnnn nnnnnnnnnn 149040
nnnnnnnnnn nnnnnnnnnn nnnnnnnnnn nnnnnnnnnn nnnnnnnnnn ngggtcctgg 149100
aggcaagtgg gaatgcagct tctcttcctt aagcagatgc catataggcc tggggaggag 149160
aatgtgagaa taccagccaa gttctcattg gcactatacg gagaaagggg aattatttca 149220
tcttgatgga ttctccccac agtctctgca catattgatc ttacttgtaa tgagtttgtt 149280
cagattcacg agtcatcatc ccagggagat ctgagtcatt ggtgggaaag tcgaggtgac 149340
agattatatc tcgctgatct cactgtcacc aattgctctg tgtgtccctc cacctttttga 149400
aaaagcccat ggaatcattt gtgtataatt aatttggatt tatttcttat ttatcaatag 149460
ctttagtggg gtattgtaaa tgggaaagct accccagaga acagtgtaca ttcacagtat 149520
tattcaatag aactttctga gatgatgaaa atcttctata tcttatgttg tccagtataa 149580
tacagccgct aactacatgt agcttttgaa cactgaacat gtggctagtg agactgaggg 149640
attctatttt taatttttta atgttgtaat taatttaatt ttttaaaagt tttgctttct 149700
attttatagc ttaataatta aactaaactt acatagccca catgtggcta gttggccact 149760
atactggaca gtacaagtct agaaagatct cagagagaca catgctgaga tacagcagga 149820
```

ataggttagt cagaaagaga gccaatgtaa catagggaat tctggattgg gaattagagc 149880
cctggctcta atctcagctc tgccactagg tgaccttgcc ctctctggct tcagtctccc 149940
catctttaac ttgaaaggtt aaactaacta acgtcaaaag tcccaaaatc gtggctatgg 150000
actgaattca atttgggata cataagtttc aggaattttt ttaaaaatct attaatgcct 150060
tctaggtgtg tgtatgcacg cttacaggca tgtacccatg cacaagcatg ggacggcagt 150120
aaggcattca ttccagttca ccagtgtact aaccattcac acatacacac acacacacac 150180
acacagacac atacacacac acgcatgcat acacacccta ctgtattgcc tatgtagacc 150240
ctgaaggtct ttgaatctgt caccattgga taagataatt tctaacgacc cttcccgttt 150300
tgtcctgctg aaaatcttta agccactata gtgtccccaa tctatttcaa tttgggcaga 150360
tgactggagt attctcatag cttcctgtct cttcccctct gaatttgata ctagttatga 150420
agtttggcgt caaggatgaa gaagggaggc agggaggata taaccccagc cccactcctt 150480
aactccgctt ttggattaga agtagcgttc agggcttcag attccttggg gaggaagtag 150540
agataatatg ggctttgtaa tcagaagatg gggttcagat gattgggttc tcactttttc 150600
gatagctgtg ttacctcagt ttattcattt gtaaaatagg gataagaaat atctttaacc 150660
tcctaagatc atgtggaatt aagtgatgta acgtgatgaa gcgaggcatg cagaaggccc 150720
tgaaaaaata atagttaccc ttaagggaac taaatggtct ggcaacttgt gagctcaaag 150780
ctagaaaggc ccggtgatgg ggaagatggg gtctttctgc aggaactaca gcaggggagc 150840
agaacctgta agccaccagt ctgtggagct gtgtccaaga actcatgttt gcaacaagtt 150900
caccaaatta caagatactg tggggtccag gcctctaact caagaagatg gtcttggccc 150960
agatcatacc ttgcagcctg tgcctttggt gggatgtgag tgttggcagt ggctatgcat 151020
atctccttat tactggctgt gcccaagccc tgcagaaatg attgttggac aaggtcatct 151080
tgcactcagg gttggttttc caggcttcct tgttattttc cccttagttc ttctgtgctc 151140
ctcttgcaac accaacccca ccatttccct cttccctacc ttagttgttg gtccaaacat 151200
gtaatccatt cttgcagtga tttattgagt gataccgtaa ctggagtttg cattgaagga 151260
cttatttttc taattagaac taaaagtcag ttccaggctg ggtgtagtgg ctcacgcctg 151320
taatcccagc actttgggag gccgagatgg aaggattgct taaggccagg agtttgagtc 151380
cagcctgggc aacatagtga gatcccatct ctacaaaaaa acatgttagc caggagtggt 151440
agtgtacacc tctggtccca gctacttggg agactgagga gggagaattg cttgagccca 151500
ggaagttgag gctacagtga gcttttatca tgccactgcc ctccagcttg ggtgacagag 151560
ggagatcctc cctcaaaaaa taaataaaaa ctacaaaaaa aaatgtcact tccaggttgt 151620
atctttttc acaggggcca gacacagatg aggagtaggt tttgttgtat ttatccattt 151680
aaattgagca atcagcttct ctctttggtt tataccttc ttatttatta ttattatttt 151740
aaaaggatta gagataaagt gctttatggt ctttctcagt gcaactgctt atgctagacc 151800
tcagaattat gacctcttca attatttata tttccgtctt tataaatact ggaaaaaata 151860
gtacaaagta aacatcggga tgcctaagga cctctaaatt gtgtgtgagc acctggggaa 151920
gatggttctt aaggtttgag ttttggatta ttgtggttgt cttaaataat gttatttcta 151980
tcattccttc caatggctgt ctcctagcat ggttcccatt ttacagactg atggtagagg 152040
cagaaagatt ctctcacttc tttgatagta ttgaggattt cagcctttca ccgctcctct 152100
ccccttttgct aaaaaagaaa aaaatcaata tgtatgttat agtgtatgtt caactatgag 152160 caactatgtg tattcaatga gaaatggaat accataaaat taccatagtt gaaccaaaat 152220
gataggatag aattcgatag tctgaggatg gaagggaact tcaaggccac tttaaaaaac 152280
cccattccta tataatgctt gaattcttaa ccactgtgca tctagtattt gatcatttcc 152340
agtgatatgt gtgcctggca acttttccat ctcccagcgc tttaactatc aaaatgtatg 152400
tatgtgtgtg tgtgcatgta tgtgtgtgtg tttagagaca gagagagaca gaaagagaaa 152460
gagagattaa aatccaagtc actgttcttt ctgggaccca aaaaacaagt ctagtcattc 152520
tccatttcta gtctctttcc ctagcaatcg gctagacatg ctagacatag acacatgtac 152580
atcactcctt tgatttacag cattcagtat ttgtctatca cttataagat aaaacccata 152640
cttacttttt atttttattt ttttagagac agtgttttac tatgtcaccc aggctagagc 152700
atcagtggca caatcatagc tcactgcagc ctagaactgc tgggctcaag caatccttcc 152760
acctctgcct cctgagtagc agagactaca gatgtgcacc accagacctg gctaatttag 152820
ttttttacta attttgtgga gatggtgtag tgtcttgcta tgttgctcag gctgatattg 152880
aggtcctggc ctcaagcact cctcccatct cagccttcca aaatgctggg attacaggta 152940
tgaaccacct tactcagcca gatttcttaa tatgatatac atgctccttt aaaatcaagc 153000
accatctttg ctttcaaccc cattattaac cactttccca tatacgcaac atatgcttca 153060
gtcatactag tctctggttg ttccccaaac actcctcagt gcttttgttt atgccctttc 153120
tgcccacctt tgcctggtga aatcctcatc aatcttcaaa ttctaggtca aatactatct 153180
ttcatataaa gcattttcta aacccacctg tgtaaaaaga ttagtggttt cctattttgt 153240
tgatgcctcc attgcagcat tttccagtct gactttttct agaattgact gtggcaaggc 153300
taccagcctg ggccagggcc tgtgtctttt ctgtcaccca gaagcaaagg tctaacaatg 153360
gatatctgct gaatgaatga atgaaaatga atcattaata tagtagtaaa tgagttaatt 153420
aaaggttcca ggtatgaata ctgaagcctg cattgaggca gagctgaatc caagactatg 153480
ttaggttggt ctggcacaag aatcagagtt ttcctctgca agctatgaaa aatttgggtt 153540
tagcacggat ttgggatgac gaattataca ttcaaccagt gttgaatgag cacttgtcct 153600
taaggagttt agagtctgtg accagggaga atgatgattt tcttagctcg ggcagttttt 153660
ctaacaaggt agttgcattg tgtgtttttg aacactgatg ataaattcaa gtttctcttc 153720
ctgccccata gcccggaagc tgaagaaact tggtaatctg aaactacagg aggaaggaga 153780
ggcttccagc accaccagcc ccactgagga gacagcccag aagctgacag tgtcacacat 153840
tgaaggctat gaatgtcagc ccatctttct gaatgtcctg gaggccattg agccaggtgt 153900
ggtgtgtgct ggacatgaca acaaccagcc cgactccttc gcagccttgc tctctagcct 153960
caatgaactg ggagagagac agcttgtaca tgtggtcaag tgggccaagg ccttgcctgg 154020
taaggaaaag ggaagtggga gcatgagata agggggatca tatttagtga acgctcctat 154080
gggccagcca ccacgtctgg tgcttttctg cccattaact caggtagtct tcgtcgtaac 154140
cctatgggag agggattgtt ataaatctca ctttaaacat acagggattg agactcagaa 154200
agcaaagaga aagataatat tataaggtgt cctatgtggc ccacattgat gcacagcagt 154260
catgctttca catttaactc acagaaatgg tcagcaaaat ttcccttaat cacaaaatca 154320
catagacata tccatatatg ccttaggata ctcttctata tttgcacaca caggctcacc 154380
ccaaagataa tctccagcct gactgacatt ctgtcttcag tgtcaccttt aggaactata 154440
tcatgggaac tctcataata tgatatggta gaaagaacat gaggttggga atcagaacac 154500
ttcagatcta cttttagttc tgctagtaac ttattgtgtg attccttccc cttctgggtc 154560 tcagtttctc tatctgtata atgtataagg catggtttgt accaaattga tggttttcaa 154620
attttgcttc gagaaatgct ttgtgcactt taaactacct aaggaatcat aataggagga 154680
aagattaggt gatagtgaaa gaattatcaa ctgttggtct aacagaagtt ggataacaga 154740
agttccccag tgatggggaa ctcacttctt tcttatgtca tctgttgctt aaacaagtct 154800
ggttattaaa atattacagc ttaaggaatt cttagagatc ctctatccaa tgattcacaa 154860
actttcattt aacagccaag tgctttattt ctcaaaagaa ttgtacacag atatgagtgg 154920
agctagttta tttaaagcca gagtctgtgg cttgggcctc accagttcag cctctttctc 154980
tctatcccag ggaagccccc aggtcactct tgcaaaatct tagggctccg aggaacacag 155040
tttgaaaacc agtgaagtat atgctcttta aaggttctcc taatcttgca attatgattt 155100
aaagactctt ttggaataat aacaactaaa ccttctcttg tggagtcaaa gattaaccgg 155160
cctttcaata ataactgcca ttcaggtaga aatgtatagt gaacagagca attttgtata 155220
tattacctga attgattctt ataggaatcc tataaaatga gattctttct cctgttttac 155280
agaccaaata gggaagctgt gagaataatg tgattgacct atagttacat agtcagaaaa 155340
tagcaggacc agaacttgag cccaggttct ctcctgattc caaatcctcc ctttattcca 155400
ctccacctgt aggctgcagc accactgcag ttctgtaact ctgggcttta cagtgagggg 155460
ccaaggcttc actgaaggcc acttgggtca tactgtgggc ttgctgcatt tgaagacatt 155520
gcatgttggc tgtcaagtct tagatttgta tttccaactc acaggttagg cctggtcaca 155580
gccctaacca tctcttgcac cttctcagct tgggaagctg aggttgacta ggcaataaga 155640
tcactgggaa ggaaacccaa ggactctgat tggatatgtt ctgtgccaaa gcagagggtt 155700
cacacagaga ggaaaaatat aaaaaagaaa aaggagaaag ctgctttaat tcttatcact 155760
ttttcatctg gatattttga tatcatgtgt ttgacaaaga ttcaaagttt aatcttccca 155820
agcagtttcc aaacacttat ctcattttat aagttacaga gctttttcat atatatgatc 155880
ccagttaatc ctcacaacaa ttctatgaat catagagact attatttcca tttcacatgc 155940
caaggctcaa agaggataac taacttgctc catttggtca cttaacacat ggaaccagaa 156000
cttgacctag accttcaggt ttctaaattg gttatcttga caataaccta gtgcaaaact 156060
ctatagcaga atttgtatga cttgggatca ctggggcttt ccttggccca gccaccagga 156120
tggaaagtcc cctcccctta cattaacaaa tctgcaaacc aatatcagtt caccatctag 156180
cttgccagac taagtgatct ctgactccga atcttttaaa agaatagctt caaaagaaag 156240
ccaattacca cattcataag aactgttctt catattatct ataattacct acaagttcaa 156300
gtaattcact aattcaatag attgagttct tgacctgtaa aatgaactgt gctaggcctc 156360
taataagata aattttgttg taagttttct acgacagtaa tgatgtatgg aaattgccta 156420
gtagagtacc tggcacatta ataaatgata actattaatt tagagtgggt gagtagactg 156480
ggtgtgcaca gtatatttag aatctaattt atctggtttg gaatcctagc tatggactat 156540
ttctgtgacc ttgagtaaat cacatgtctt ctctgtgctt ctgtgtcctc atttgtaaga 156600
tgatagaata atcgctacct ttcaaattgt cgtcaacaaa gagattatgt ataaagagca 156660
cctagtaagg tagcctgaaa catagtaaat gctctgtaaa tggtggttta ttattatgag 156720
acttgagtgc taagccactg ctttaatgaa actcaatttt agctaccact tgccttgcct 156780
gctcatgcat ggaccacaag gtgaaattgt cttctctgaa gaccttggca ggcagatgca 156840
ctacagcagc aaagatttcc aaactggcct ttctttgagc ctattctccc agaccagaca 156900

```
tgagactaca agtttctgct gcacatgaaa aaaatatgat gtcagttgga ttctagtgag 156960
aaaacagagt gtctaataaa ctgcttctgc tccctagcct gtttaatgtg tttcaaaacc 157020
tgagaatgac tcctctctgt ttctccagaa cagcctaaca caatggcaaa tgggcattga 157080
gtgaatgcat acttaaggaa atctgtaggg ctgcggctac tctttcctca agtaatccct 157140
tgatagtcat gcaggctact tcagagattg ggcattagag aacagagtca ggtattataa 157200
tcagattaga ctctagggag attagccagc catattgctg atatgtgcac agttactggg 157260
cttccgtgct aagcagctct cattaagcac agttaattaa tattatggcc aacttaagct 157320
ttccctttc tctcctgttt gttagttcgg cagcatttta gggagaaaaa aataagcatc 157380
agtatggaca atttgcttca tacctgtacg atttaattct catccttcca tgggccttca 157440
cattcacaca ctccactaga agaccaaggt tcaccagcca aagacttttc ttgctcccca 157500
ctgcctccta cccaagatat tcagggttca acctcccagg cctcttctct aagagatccc 157560
tggttgctac atgcctagac cctgcttctt atttcctact gagaagggtc agtccaaggc 157620
attctgtgct acagaagggt tccagacagg aactactctg ggatctgagg ctccagccag 157680
tctgtcagtg tgtcattacg gtgaaggtgg gaagcacagg cctgggagct aagactgcca 157740
agatgaggta ctctagaatc cctgatatct ggaaggctta ggatctaaag gaaaagaaca 157800
gtgaaatggg gctatatgag tggacaggga ccaaccaagc agaacaatgt atctggataa 157860
tgtagacttc agacctgatc ctatggctga caaaagttgg tgaccttggt ggttcctgag 157920
ctgtaacctt cagcagtgga gtagaaaaaa cactggagaa cagaatcaga acacctgggt 157980
tctagtatta gttcagccac atataaacca tatgaccttg ggcaagtcaa tttatttctc 158040
tggccctcat gttccttgtt ggtaaaataa gtgtcacatc acctaacctc tgggattatt 158100
gtgagagtta aattaggtca tcaacaggaa agtgagaagt ttggtctaca tttggggaag 158160
cattcctaat gaggtatgat gacaaaattt cagataattc tggatttgtt agtgagaaga 158220
gagagtgttg gtagggatga gctctgaggt gatgccttta taactttaag catccaactg 158280
tttcagaacc tccaggagaa catggccatg tctgtactac ctgtgtgtta ttgtagaggt 158340
agcatctggg agcctctgct ctctgagctt aagggaggta atttggagat catttaattc 158400
tcattttata aaaggaaaac aaattgagga tctttaggcc atttgtttag gtttcttaag 158460
tgcccactca aatacgtgga ctgtactaag tactagggag gtaaacttga atatgaagat 158520
atggtccctg tcttcaagaa gctctaagtc ttgtggggga gacagacatg tatgtacata 158580
gatttcaatg ctgtgtaatg agtgctataa ctgtgtgagg ctacacaagg agcaatgaga 158640
atgtaaaata agaatcttta agccttcttc ttggatgagt tggaaaagcc ttcacagaag 158700
aggtagcctt tgagtgaaga cttgaaagat gagtaggtgt ttaaccggat gaaagacctg 158760
agaaggagga atgcattcta ggcaaaagca actgcctgtg cagagataac agagatatag 158820
aggcatgtga gagggcaagt ggcaacagat cagtctaggc agcaggtcat aaagggcctg 158880
ttcatatata atgatggcag taagatgggg atggcagtaa ggtgggaaac tagtagggcc 158940
aggctaccta ttgagtagaa aagaatggag aggaactgcc aggcagaaag tgggatggac 159000
gcaagaaagg gaacatgaaa gtggtcaaca ggaggcagtg gctgtcaaga catctctcca 159060
tacactgtac actgtatgta atatccgtct cccagggttg ttagaagggt caaaccagct 159120
catagctgga aaagagcttt gtgaagtgaa aactgtttat gtgggagaaa tgatgttatc 159180
ctgcatcttc ggaaaggtag agtgatcaag agcacagacc ttggaatctg actgctttgc 159240
tttggaactt ggtctaccaa ttactagctg tatgatcttg gacaagttcc ttaatctctc 159300
```

tctgactcac ttgtactggt tcacagaatg gagataataa tagtacctac tttactaatt 159360
gttgtgaata ttaaatgaga taatataagt aaagtgctta gaaaagagtt aaatgtgccc 159420
cataaataca tacaactatc atatacccaa aatatttttt aagtttttt aaaaaagcaa 159480
tccaatggaa atcaaaagaa aaaaagtttg ctcgtatatg cagtcaataa gtgttagatt 159540
atttttctct tacaactgac aatgcccttt ttttctccat catcatctca tttgagcagc 159600
tcagtgatgt agggaggaca acgaatatta tcctcaccat atagtttgtg cttttcccca 159660
ccacccctca gtggccagtc tggatggtcc ctggggatcc ttaggggatg tccaaatgcc 159720
agagcatctc tacccagcag gggctcagac ttagctcagc ccgtcagtac ccagattgac 159780
cactgcctct gcctcttctt ctccaggctt ccgcaactta cacgtggacg accagatggc 159840
tgtcattcag tactcctgga tggggctcat ggtgtttgcc atgggctggc gatccttcac 159900
caatgtcaac tccaggatgc tctactttgc ccctgatctg gttttcaatg agtaagtgct 159960
cctggggccc agacctcact aaaatacagc agcttggcca gacccagttg gtggtgatgg 160020
tgatggagtg acagtgaagc ttacctcatt tgacctgcag gtgtggcatt ggatgcccca 160080
gccagccaac tcggtatgag gcagctttgc cctggctttc agccaactgg taggagctga 160140
ggaggatggt gctgagacta ccccttcac acccaagaac caatcctggt cgtgtttctg 160200
gtctccttta cagcttatct cagaaccaca tggaaagatt cctccccttc actttgagca 160260
acatataaaa gaggcagaaa gactctggct ttaagggctg aagtttcttg ggttctgttg 160320
ctaccaccaa aggctactgc tagtcaccac ttgctgagca attagtttgt gccaagaata 160380
tgctagatac tttctaaatc ctatctcatt gagtcctcat ggtgacctga cctccccttt 160440
ttatagataa ctctattttt tttatggacg gggaaagtca ggctcagcaa agtaaagtga 160500
ctcacccaaa gtcacagagc tagtgcctgt tggagagaag attcaaatgt atttccgtgt 160560
gaatcccagc tcttctgcgt catggtggta actgatgggg aggagtacct ctaccactct 160620
ctgtctgtgt gaccttggta ctgccatttt ctttctctta aacagcttta attaatacct 160680
gccctgccac tagctctata taacatcatg aatttggcca gtggctcaga ttttggaatt 160740
acatttttct ccactaaaat ctcagttcta ttattttctt aatcagcatc tttgggaaag 160800
acccttaact tttctgaccc ccaatttctt catcaattaa tgataataga accttcataa 160860
gtaatttctt atgataacta aatgggaact gacagatgtg gaatgtctgg cccatagtgg 160920
gcaagaagaa aaaaaaaaaa gtccctttct gatccaccat tccctaagag tgatattttt 160980
ttccccccaa gatggagttt ggcgctgcca cccaggctgg agggtggtgg tgcaatgatc 161040
tcggcccact gcaacctcca cctctctggt tcaagcaatt ctcctgcctc agcttcccga 161100
gtagctgggc ttatagatgc cagccagcaa tgtccagcta atttttgtat ttttggtaga 161160
gatgggattt caccatgtta gccaggctgg tcttgaactc ctgacctcat tatctgccca 161220
cctcagccag gcatgataat cttttctatg tctgctgtat gaggtccctc gatggcataa 161280
tgaatggagc tggccagaga aatcttccca aggaccttga gctagtctcc ccacagagaa 161340
tccttccagt caggacagga attgaccttc ccccctcttc agccctctaa cccagaagag 161400
tcttaaaata aaatctacag gccagtggtt ccttccagta cagcactgca atgtgaggga 161460
gagtgagcgt ccccagctgc cctctcccaa ccctgccagc ctggtagcca gaagctaaga 161520
ataaccacta ggcttttggc acaaactgct ttgtggtttt cagacctcca aaaagttgcc 161580
tatgatgcca tcttctgggg caggccttga aaagcccccct aactgttcat ctcccatcct 161640 caaacccctg ctgcccttaa gcaattgaat caactccatg agcacctgct ctaccttccc 161700 cagagctctg agacctttgg agctttgaaa agtgataatt ggctgttctc taaatcctca 161760 tttccttttc tacctctgag taagcatgtg gcatcccacc tcagcttcct ggtccagtct 161820 tgttcagctt ataaaaaggc ctccccacag ggtcagaggc ctagacccat caaatcccag 161880 ggctcctgaa acaataggac ccctattcct cctgtaggaa gccactatgt tagaactctc 161940 agggtgtcta caaacatcta gataagtgtt tctcaacatg gattattttg acatattggg 162000 aaaaataatt ttgtcaatat gtagaatatg gttgacatac ctggcaccag cctactttat 162060 accaaagagg attccagtca ttctgacagc ccaaactgct cccacgcatt tctaacaccc 162120 actgaagaag cagtactctc cagttgagag tgactaattg ctgccagcct ccctaaggtg 162180 ctaatgggga gcctcagacc caaagaggga gataagaact tgttcaaagt aggtcaaccc 162240 atttgctgat ctcttcaaca ccaaactcta ttatcagccc tgtttttcc tttccttctg 162300 tctttgtaga gatcacatgt tgtgaggata atgagcctga actttagctg tgtgaccttg 162360 ggcaaattac tgaacttcta tatgcctcaa attttatctg gagactgctg aagagtatta 162420 taatagcacc tttctacatg tcatttatgg aacacctgct atgtgtcagg cactgtgctt 162480 agtgttttcc aatcttcatt tctcatctta ttttctctct tgcactccca ccaaccctgc 162540 tctcctccta aattccattc ctgcctcatt tttataccct ccattctcct ctctcttcct 162600 tcctttaact gtctccctag tatttttcc ctttttcccc ctttcttgtc cccttcccct 162660 atgaatttcc tccctttcct ttccccttct ctttcctcca ttccccactt tttctgcccc 162720 gaggcctgca gcaatgttaa aggaatcctc attccagcat tgtgatttca atggtaaaaa 162780 aagattgcag cactgtcatc aacagaggtg ggaaagtaca ttggagactg gagcagggcc 162840 agacctcagg gtcagccaat cttactaaaa aattctctat agtgaaagag cttggagcaa 162900 cactgttctg ctcaattgat ttgtgatacc atctaaacac ttcctctttc cagttgggct 162960 tcagcctgag ttgaataatt ctacaccatc tgccccttc tctctttctc caggacagcc 163020 aagatctctc tgagatagga tgctgagttt ccacccagac aataccaggc cttctcatcc 163080 tgtggagtag gctagtggct tggaaaccaa aatgtcaaac catagccttt aggctccatc 163140 tgggaggtct ttgtcctcac cacttaagtg ggtgtcagat ttccttccct ttctgcacat 163200 gctgcacaat caatttctgt cttacacaca cacacacaca cacacacaca cacacacaca 163260 caatttttga agtgctgaaa actagaaagc ctactagcat gaggatgctg tgtcttctct 163320 tagaggtatg ccatggtcag ccatggaacc aagagggtgc tcttccttga aaagttggcc 163380 aagcattggc cacctccccg tataatttat aggtgataat gtggtgatct gttcagaagt 163440 aactataata aatgcagctc acatatgtct acagtttcca aactgtggta aggagcagcc 163500 agcatatgag ggaatgggct ccccttcagc aggggacatt taaattagac attcaaaaac 163560 actccctggc agatttaaca ttgaaactca ttttgaaaga acaatgtgga atctccttca 163620 ctggaagttt ttgaagaaat attaaatttc tagtattcca ggccagaggc aaaggggtca 163680 acaggatgac caaacacttc gggtcacttg caaatcctgg tgtcctgatg ttaagagctg 163740 actactgggg cttctcctaa aaatccttca tgttgagctg cctgggaggc aggttcttgt 163800 tctggctgta gatgggatat tagaactgta gtcagggaga ccatgtgcct gccccattgt 163860 gttcatttgg ttaggctttc ttgtccccga ctcagaaaac agaaggggca cagagacctg 163920 gaaattccat gtgctaaccc atatcctggc cagggaagat agtagtaatc aggatgtcag 163980 gattttggaa aagagagaga taaaaaaaaa acaaaaaaac aaaaaaaaaa acagaccaac 164040 aaacaaacaa aaacctcatc ctgatccctg aagcaccagc aggagaaaca gcaagctctt 164100
cttggagaac ctggggagga agggcaatca gagacattcc ctctgggctt attgcaagcc 164160
tcccctcatt ccttttcct ctatgtatct ccttcccagg taccgcatgc acaaatcccg 164220
gatgtacagc cagtgtgtcc gaatgaggca cctctctcaa gagtttggat ggctccaaat 164280
cacccccag gaattcctgt gcatgaaagc gctgctactc ttcagcatta gtaagtgcct 164340
agaggtgcag ggaatgcccc tgagggcaca gagactcaga gaggaccact tttgacatta 164400
aaacgttatt agggagaagc cagctccttg acatttccct tcttcatttc ccctccccat 164460
ccccactgta ctctccctca gtatcattct tctaacaaga aacaatttca tgactagaag 164520
ccaatgtatt tgctagaagt cagcttccat cagattcccc acctatccct agtctatctt 164580
tgggacaagg ccttttgac tggttatagc aggtctgtga atttctccac agcttctgct 164640
atagaaacaa acatgggcca ccttgtattc cttgcagggc agtaaagcag gaggcatttc 164700
ctcctggaaa gatttcctct tctgccaaca ggaggaggtc tatgtaagca actcaggtag 164760
gatttatttg gcagccaagg aacttttctt taatatcttt tctaacaaga gccctttctt 164820
agcctctgtt gagggagaaa ggcaaaattt gatattcaaa gctatgtgtt ttagttgtct 164880
aaatcagggt ttgactgtaa atgacataaa agcttaggtc ctaaaaaatg agtatatgag 164940
aagagtagaa aaagaaaaga ttcaggaaat ttgatttact tgactccctt cagattggat 165000
ccagctatcc tttcccctga gatctccctg acagactgaa gtccccaagc ccacagactt 165060
caactaacag gaagccaagt agatggttcc ctgtgggggt gggggtcaag tttgtggtca 165120
gaaaacttgg tgctttgtct aatgttcctt cgtgggcatg cttcccctcc ccattctgtc 165180
ttcatcccac atcagttcca gtggatgggc tgaaaaatca aaaattcttt gatgaacttc 165240
gaatgaacta catcaaggaa ctcgatcgta tcattgcatg caaaagaaaa aatcccacat 165300
cctgctcaag gcgtttctac cagctcacca agctcctgga ctccgtgcag cctgtaagca 165360
aacgatggag ggtgctttat cagggagaac agcctgatag agccaatgat aatatgcttc 165420
tctagggtct ggcaccacct gttgggaggt gcttccattc ccctctggct ttgagtgtgg 165480
tccaggaaga aaatgtggtg aagaaaggaa cacgggtcac agtgtcccag ctggatattg 165540
tgaaaggggt ggaggagttg agaacagagc agttgggact cagggaaggg acttacagca 165600
gatgaattct ctaggcagac aaaacagacc tggatgtttc tcccctcttc tttgagtcat 165660
gttcatgtga gtttgtgtgt gtgtgtgcgc gcgcgtgtgt gtgtgtgtgt gtgtgtgaca 165720
gagagagaga ggagagaggg agagagagag agagagagag agatggagtg cagaggctgg 165780
ggtgagagca caagctggag aagtcttgag tcagaaagct tacaatggta taagacatcg 165840
cttgggagcc ctcagtgact cnnnnnnnnn nnnnnnnnnn nctctctctc tctctctctc 165900
tctctctctc tcactcacac acacacacac acacacacac acacacacac acacacacac 165960
gacctcatgg gggaggacca aggaaggaca gggaaggggg aggaaacaaa agactgaaag 166020
accaaaaatc aaaggttagg gaagagtcta gcagagccca cctccttgtc aaccctgttt 166080
ttctctctct tattgttccc tacagattgc gagagagctg catcagttca cttttgacct 166140
gctaatcaag tcacacatgg tgagcgtgga ctttccggaa atgatggcag agatcatctc 166200
tgtgcaagtg cccaagatcc tttctgggaa agtcaagccc atctatttcc acacccagtg 166260
aagcattgga aatccctatt tcctcacccc agctcatgcc ccctttcaga tgtcttctgc 166320
ctgttataac tctgcactac tcctctgcag tgccttgggg aatttcctct attgatgtac 166380 agtctgtcat gaacatgttc ctgagttcta tttgctgggc tttttttttc tctttctctc 166440 ctttcgtttt cttcttccct ccctatctaa tcctcccatg gcaacttcag actttgctcc 166500 ccattgtgac tcctatctgt gttttgaatg gtgttgtatg cctttaaatc tgtgatgatc 166560 ctcatgtggc ccagtatcaa gttgtgcttg tttacagcac tactctctgc cagccacaca 166620 aacgtttact tatcttatgc cacgggaagt ttagagagct aagattatct ggggaaatca 166680 aaacaaaagc aagcaaaaaa aaaaaaaaag gcaaaaacaa aacgaaaaat aagccaaaaa 166740 accttgctag tgtttttcc tcaaaaataa ataaataaat aaataattac acacatacaa 166800 acaaatatat agaaatcccc aaagaggcca atagtgacta gaaggtgaaa attgcaggcc 166860 cctgggaagt tactgatttt ttcatctcct ccctccatgg gagactttat tttctgccaa 166920 tggctgttgc cattagaggg cagagtgacc ccagagctga gttgggcagg gggctggaca 166980 gagagagagg agaggacaag gagggcagat ggaacatcag tacctgccca cagccttggc 167040 ccctgggggc tagactgctc aactgtagag caattcatta tactgaaaat gtgcttgttg 167100 ttgaaaattt gtctgcatgt taatgcctca cccccaaacc cttttctttc tcactctctg 167160 cctccaacct caaattgact ttcaatagtt tttctaagac ctttgaactg aatgttctct 167220 ttagccaaaa cttggtgact tccacagaaa agtcagacca ctgagaagaa ggggagcaga 167280 gatttaaccc tttgtaaggc cccatttgga tccaggtctg ctttctcatg tgtgagtcag 167340 agaggagctg gagccagagg agaagaaagt gatagcttga ctgttctcct gcttaggaca 167400 ctgactgaat agttaaactt tcactgccac tacattttcc ccacctttaa aagacctgaa 167460 tgaagttttc tgccaaactc cgtgaagcca caagcacctt atgtcctcca ttcagtgttt 167520 tgtaggcccg aacttcatca cactgcattt cagccatggt ggtcaagcct gtttgcttct 167580 tttgggcatg ttcacagatt ctctgctaag agctccccc atcaagaagg ttagcaggcc 167640 aacagctctg acatctatct gtagatgcca gtagtcacaa agatttctta ccaactgtca 167700 gatcgctgga gcccttagac aaactggaaa gaaggcatca aagggatcag acaaactggg 167760 tgtcttgtcc ttgtccccca gagatgacac ccttccagca agtggagaag ttctcacttc 167820 cttctttaga gcagctaaag gggctgccca gatcagggtt gaagagaaaa ctcaattacc 167880 agggtgggaa gaatgaaggc actagaacca gaaaccctgc aaatgctctt cttgccaccc 167940 agcatatcca cctgcagaag tcatgagaag agagaaggaa caaagaggag actttgacta 168000 ctgaattaaa atcttcagcg gcaaagccta aagtcagatg aacaccatct ggtgagttca 168060 ctcatcatcc tcctctgctg ctgattctgg gctctgacat tgcccatact cactcagatt 168120 ccccaccttt gttgctgcct cttagtcaga gggaggccaa accattgaga ctttctatag 168180 aaccatggtt tcttccggaa aggtctggtt ggtgtggctc caatacattg ccacccatga 168240 actcaaggtg tgccctggga cactggtttc atctagtctt ttggcacgcc tgtgttctgt 168300 tgacttcatt ctccaacccc aagtgcaagg caaaatgtcc acctactttc tcatcttggc 168360 cactgcctcc ttacttagct cttaatctca tctgttgaac tcaagaaatc aagggccagt 168420 catcaagctg cccattttaa ttggttcact ctgtttgttg agaggatagt ttctgagtga 168480 catgatatga tccacaaggg tttccttccc tgatttctgc attgatatta atagccaaac 168540 gaacttgcaa aacagcttct ttaaataaca agggagaggg gaacctaaga tgagtaatat 168600 gccaatccaa gactgctgga caaaactaaa gctaacaggt tccctttctg ggatgggata 168660 gacacattct ggttttcttt attactacac catctggctc atgtacagga tcacttttag 168720 ctgttttaaa cagaaaaaaa ttccaccact cttttcagtt acactaggtt acattttaat 168780 aggtccttta catctgtttt ggaatgattt tcatcttttg tgatacatgg attgaattat 168840
atcattctca tatctctcct tgtaaatact agaagctctc ctttacattt ctctatcaaa 168900
tgtttcatct ttatgggttt cccagttgtg actcttgtct ctatgaatat atgtttttca 168960
tttgcaaaag ccaaaaatca gtgaaacagc agtgtaatta aaagcaacaa ctggattact 169020
ccaaatttcc aaatgacaag actagggaaa aatagcctac acaaggcttt aggccttctc 169080
tttctgtgct tggatttgag tgaacaaagg aggttttagc ttggctctgt tctcccatgg 169140
atgaaaggag gaggattatt tttttttct tttggccatt gatgttctag ccaatgtaat 169200
tgacagaagt ctcattttgc atgcactctg ctctacaaac agagttggta tggttggtat 169260
actgtactca cctgtgaagg actggccact cagacccact taactggcga gctagaagat 169320
gaggatcact caccggaaaa gtcacgagga ccatctccaa acaagttggc agtgcttgat 169380
gtggatgaag agtgaggaag agaaaaagaa ggagcaccag ggaaaagacc tcgtctgtgc 169440
caggcagcag actgctgcca ggatcacgaa ctctgtagtc aaagaaaaga gtcgtgtggc 169500
ggtttcagct ctcgttcatt gggcagctcg cctgggccca gcctctgtgt tgacatggga 169560
gttgttggat tctttgtttc atagcttttt ctatgccaca ggcaatgttg ttgttcttgg 169620
aaagtttatt atttttttta attcccttac tctgagaaag ggatattttg aaggactgtc 169680
atatatcttt gaaaaaagaa aatctgtaat acatatattt ttatgtatgt tcactggcac 169740
taaaaaaata tagagagctt cattctgtcc tttgggtagt tgctgaggta attgtccagg 169800
ttgaaaaaca atgtgctgat gctagagtcc ctctctgtcc atactctact tccaaatgga 169860
tataggcata cataataagt tttattcgac ttgtacttta agagaaaata tgtccaccat 169920
ccacatgata ctgacacaaa tgagctaaca ttgagcttca agtagcttct aagtgttcat 169980
ttcactaggc acagcacaga tgtggccttt cccccttct ctcccttgat atctggcagg 170040
gcataaaggc ccaggccact tcctctgccc cttcccagcc ctgcaccaaa gctgcatttc 170100
aggagactct ctcgagacag tccagtaact accggagcat ggcccctgca tagccctgga 170160
aaaataagag gctggctgtc tacgaatcat cttgtgccag ttgcccaggt gagagggcac 170220
tgggccaagg gagtggtttt catgtttgac ccactacaag gggtcatggg aatcaggaat 170280
gccaaagtac cagatcaaat ccaaaactta aagtcaaaat aagccattca gcatgttcag 170340
tttcttggaa aaggaagttt ctacccctga tgcctttgta ggcagatctg ttctcaccat 170400
taatcttttt gaaaatcttt taaagcagtt tttaaaaaga aagatgaaag catcacatta 170460
tgtaaccaaa gattacattg tatctgctaa gataccaaaa ttcacaaggg cagggaggga 170520
gcaagcatta gtgcctcttt gataagctgt ccaaagacag actaaaggac tttgctggtg 170580
actgacttat aagagttttg tggggttttt tttccctaat aatatacatg tttggaagag 170640
ttgaaaataa ttttgggaaa atgggtttat gggtccttca ctaagtgatt ttataagtag 170700
aactggcttt ccttttcttt agtagttgct gagcaaattc ttgaagctcc atcattgcat 170760
ggttggaaat ggagctattc ttagccactg tgtttgctag tgcccatgtt agcttatctg 170820
aagatgtgaa acccttgctg ataaggaatc atttaaagta ctagattttg cactagaggg 170880
acagcaggca gaaatcctta tttctgccca ctttggatgg cacaagaagt tatctgcagt 170940
tgaaggcaga aagttgaaat atattgtaaa tgaatatttg tattcatgtt tcaaaattga 171000
aatatatata tatatatttt atatatatat atatacacac acacacatat atagtgtgtg 171060
tgtgtgtgtg tgcgcgcgcg cgcgcgtgtg tgtgttctga tagctttacc tttctctgga 171120 tctttatact tggttccaga tcacacctga tgccatgtac ttgtgagaga ggatgcagtt 171180
atgttatgga agctctctca gaacagacaa gacatgtaga ttaatcagat aactgaaagt 171240
tttctcccct attgggtctg acccacaggt cctgtgaagg agcagagggg taaaaagagt 171300
agaggacatg atacattgta ctttactagt tcaagacaga tgaatgtgga aagtgtaaaa 171360
actcaatgga actgattgag atttaccaca gggaaggccc aaacttgggg ccaaaagcct 171420
actcaagtga ttgaccagtg gcgccctaat gggacctgag ctattgggag aagagaactg 171480
ttctttggtc ttcaccatcc ttgtgagaga aggacagttt cctgcattgg aacctggagc 171540
aagcgctcca tctttcacac aaattccctc acctgagatt gaggtgctcc tgttaatggg 171600
tgtctgtgtg ctgtaattct ggttttggat atgttctgta aagattttga caaatgaaaa 171660
tatgttttta tctgttaaaa cttgtcagag tactagaagt tgtatctctg taggtgcagg 171720
tccatttctg cccacgggta gggtgttttt ctttgactaa gagattgaca ccgggatctg 171780
ttgcccaggg cctcccaact caaccatttc taggtgaagg cagaaaaatc cacattagtc 171840
actcctcttc agacatttca gctgagataa caaatcattt ggaatttctt cacccataga 171900
aagagtggta gatatttgaa tttagtaggt ggagttttat agaaaaaaca gcttttgcct 171960
cagttttgat ttatcctcat ttgatttggc cagaacgtag gtaatatgca tcgattggct 172020
tctgattcca attcagtata gcagggtgct gggtttttc ttttccccac ccgtctctta 172080
gcctagggaa ttaaataaga agccttagaa tgggtggccc ttgtgacctg aaacacttcc 172140
tacataagct acttaacaag attgtcatgt agctgcagat tcctttgccc accaaagact 172200
agaacacacg catatccata aaccaaagga aagacaactc tgaaatgctg tttctctggt 172260
ggttccctct ctggctgttg cttcacagta tgggaacctg tactctgcat aggtgacagg 172320
ccagatttgc attctcttac aaccttagcc cttggtgtta actgtcctac agtgaagtgc 172380
ctgtggagtt gtcctatccc agaagccact tggatgctga gagcagccac catcagaacg 172440
acccacgcga aaaaaaaaaa attaaaaagt cccctcacaa cccagtgaca cctttctgct 172500
ttcctctaga ctggaacatt gattagggag tgcctcagac atgacattct tgtgctgtcc 172560
ttggaattaa tctgacagca ggagggcgca gactatgtaa acagagataa gaattaattt 172620
tcaaagttga aggggaaaaa aagaaagaaa aaagaagaga gagagaaaga aagcatcgta 172680
caaagatttt cttaaaaaaa acaattttgc ttgaaatttc tttagatggg gctcagttgt 172740
cacagtggca cttggcctcc actgggcagc aggaccagct ccaagcgcta gtgttctgtt 172800
ctctttttgt aatcttggaa tcttttgttg ctctaaatac aattaaaaat ggtagaaact 172860
tgtttgttgg actaaatgtg tgactttggg tctgtctctg cctctgcttt cagaaatgtc 172920
atccattgtg taaaatattg gcttgctggt ctgccagcta aaacttggcc acatcccctg 172980
ttgtggctgc aggatcgagt tattgttaac aaagagaccc aagaaaagct gctaatgtcc 173040
tcttatcatt gttgttaatt tgttaaaaca taaagaaatc taaaatttca gatgaatgtc 173100
atcagagttc ttttaattag ctctttttat tggctgtttt tattgaagtc aagagttggt 173160
atcatgccca gttgtgtttt atgctatttt gattttcata tatttttaaa agtctttgca 173220
caaggcttac aaatttgccc tgtggtggcc ttagcataag ctgacctggg accaccaaaa 173280
taacaaggaa tttgggctag aaagcacaga tggacactgg cggcccatca caacttctct 173340
tgaaaaacac caaacttgtc agctggggaa aagccacaca aagcccagtt gcctactttc 173400
acaaccttat ccatgtggga gcataaaatg gtggcatcac tgcccagttc taaccaagct 173460
tcagttaaag aatgggtacc ttcacatcct cactattttt caggggcctt accatcctca 173520 accacccaag taaaatctaa atcagccttc ttttgggttc ttcagttcaa gtaaggcctc 173580 ttcttgtggc ctctcagtgt gaatacttac gaggttccag attgaatttt tgggcctgag 173640 atacaaggca tcaatgaggt gtgacaaaac atgtcaacga ataataagaa aattctctat 173700 tcttccatat cctcccctgt aataagggtt gtcagaatgc cttctttctc ggctgagttg 173760 aagattcagt gagaacatat gtgacacagc tggtgggcta ttaagctctg gctttgctcc 173820 ctgttaaaat gccagaaccc ttgagaggga tcccacattc agccatgttt atcattgacc 173880 accttagaat ggatggattt ctcagatttt tcctgagatc agtgcttgat ggagaggaga 173940 ggagaacaat agattcttgg gatgtgtgct ttgcatgtgt ttaagtaaga gacagagagt 174000

<210> SEQ ID NO 190
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 190 gcgtttgctc ttcttcttgc gtttttt 27

<210> SEQ ID NO 191
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 191 tctggaacag attctg 16

<210> SEQ ID NO 192
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 192 gcttcatctc cacaga 16

<210> SEQ ID NO 193
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 193 ggctactacg ccgtca 16

<210> SEQ ID NO 194
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 194 gagaaccatc ctcacc 16

<210> SEQ ID NO 195

<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 195 ggaccaggta gcctgt 16

<210> SEQ ID NO 196
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 196 cccctggact cagatg 16

<210> SEQ ID NO 197
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 197 gcacaaggag tgggac 16

<210> SEQ ID NO 198
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 198 gctgtgaaga gagtgt 16

<210> SEQ ID NO 199
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 199 tttgacacaa gtggga 16

<210> SEQ ID NO 200
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 200 gtgacaccca gaagct 16

<210> SEQ ID NO 201
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 201 catccctgct tcataa 16

<210> SEQ ID NO 202
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 202 tggggagaac catcctcacc ctgc 24

<210> SEQ ID NO 203
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 203 tccaggacca ggtagcctgt gggg 24

<210> SEQ ID NO 204
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 204 tgttcccctg gactcagatg ctcc 24

<210> SEQ ID NO 205
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 205 tggggcacaa ggagtgggac gcac 24

<210> SEQ ID NO 206
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 206 ttcggctgtg aagagagtgt gcca 24

<210> SEQ ID NO 207
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 207 cgcttttgac acaagtggga ctgg 24

<210> SEQ ID NO 208
<211> LENGTH: 24
<212> TYPE: DNA

<213> ORGANISM: Artificial Sequence
<220> FEATURE:
<223> OTHER INFORMATION: Synthetic oligonucleotide

<400> SEQUENCE: 208 catagtgaca cccagaagct tcat 24

<210> SEQ ID NO 209
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 209 gagtcatccc tgcttcataa catt 24

<210> SEQ ID NO 210
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 210 ctgtgaagag agtg 14

<210> SEQ ID NO 211
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 211 tgtgaagaga gt 12

<210> SEQ ID NO 212
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 212 ttgacacaag tggg 14

<210> SEQ ID NO 213
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 213 tgacacaagt gg 12

<210> SEQ ID NO 214
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 214 tgacacccag aagc 14

```
<210> SEQ ID NO 215
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 215

gacacccaga ag                                                    12
```

What is claimed:

1. A single-stranded modified oligonucleotide consisting of 12 to 30 linked nucleosides having a nucleobase sequence comprising an at least [12] *11* contiguous nucleobase portion of SEQ ID NO: 12 or 175, wherein the modified oligonucleotide is at least 90% complementary to SEQ ID NO: 1 and comprises:

a gap segment consisting of linked deoxynucleosides;

a 5' wing segment consisting of linked nucleosides;

a 3' wing segment consisting of linked nucleosides;

wherein the gap segment is positioned between the 5' wing segment and the 3' wing segment and wherein each nucleoside of each wing segment comprises a modified sugar.

2. The single-stranded modified oligonucleotide of claim 1, wherein each internucleoside linkage is a phosphorothioate linkage.

3. The single-stranded modified oligonucleotide of claim 1, wherein the modified sugar comprises a 2'-O-methoxyethyl sugar.

4. The single-stranded modified oligonucleotide of claim 1, wherein the modified sugar comprises a bicyclic sugar.

5. The single-stranded modified oligonucleotide of claim 4, wherein the bicyclic sugar comprises a group selected from: [4'-CH(CH3)-O-2'] *4'-CH($CH_3$)—O-2'*, [4'-CH2-O-2'] *4'-$CH_2$—O-2'*, and [4'-(CH2)2-O-2'] *4'-($CH_2$)$_2$—O-2'*.

6. The single-stranded modified oligonucleotide of claim 1, wherein each cytosine is a 5-methylcytosine.

7. The single-stranded modified oligonucleotide of claim 1, wherein the modified oligonucleotide is 100% complementary to SEQ ID NO: 1.

8. The single-stranded modified oligonucleotide of claim 1, wherein the modified oligonucleotide comprises:

a gap segment consisting of linked deoxynucleosides;

a 5' wing segment consisting of linked nucleosides;

a 3' wing segment consisting of linked nucleosides;

wherein the gap segment is positioned between the 5' wing segment and the 3' wing segment, each nucleoside of each wing segment comprises a modified sugar, wherein each internucleoside linkage is a phosphorothioate linkage, and wherein each cytosine is a 5-methylcytosine.

9. The single-stranded modified oligonucleotide of claim 8, wherein the modified sugar comprises a 2'-O-methoxyethyl sugar.

10. The single-stranded modified oligonucleotide of claim 8, wherein the modified sugar comprises a bicyclic sugar.

11. The single-stranded modified oligonucleotide of claim 10, wherein the bicyclic sugar comprises a group selected from: [4'-CH(CH3)-O-2'] *4'-CH($CH_3$)—O-2'*, [4'-CH2-O-2'] *4'-$CH_2$—O-2'*, and [4'-(CH2)2-O-2'] *4'-($CH_2$)$_2$—O-2'*.

12. A single-stranded modified oligonucleotide consisting of 16 to 30 linked nucleosides having a nucleobase sequence comprising the nucleobase sequence of any one of SEQ ID NOs: 12, 13, 35, 39, 43, 124, 150, 155, 169, or 175, wherein the modified oligonucleotide comprises:

a gap segment consisting of linked deoxynucleosides;

a 5' wing segment consisting of linked nucleosides;

a 3' wing segment consisting of linked nucleosides;

wherein the gap segment is positioned between the 5' wing segment and the 3' wing segment and wherein each nucleoside of each wing segment comprises a modified sugar.

13. The single-stranded modified oligonucleotide of claim 12, wherein each internucleoside linkage is a phosphorothioate linkage.

14. The single-stranded modified oligonucleotide of claim 12, wherein the modified sugar comprises a 2'-O-methoxyethyl sugar.

15. The single-stranded modified oligonucleotide of claim 12, wherein the modified sugar comprises a bicyclic sugar.

16. The single-stranded modified oligonucleotide of claim 15, wherein the bicyclic sugar comprises a group selected from: [4'-CH(CH3)-O-2'] *4'-CH($CH_3$)—O-2'*, [4'-CH2-O-2'] *4'-$CH_2$—O-2'*, and [4'-(CH2)2-O-2'] *4'-($CH_2$)$_2$—O-2'*.

17. The single-stranded modified oligonucleotide of claim 12, wherein each cytosine is a 5-methylcytosine.

18. The single-stranded modified oligonucleotide of claim 12, wherein the modified oligonucleotide is 100% complementary to SEQ ID NO: 1.

19. The single-stranded modified oligonucleotide of claim 12, wherein the modified oligonucleotide comprises:

a gap segment consisting of linked deoxynucleosides;

a 5' wing segment consisting of linked nucleosides;

a 3' wing segment consisting of linked nucleosides;

wherein the gap segment is positioned between the 5' wing segment and the 3' wing segment, each nucleoside of each wing segment comprises a modified sugar, wherein each internucleoside linkage is a phosphorothioate linkage, and wherein each cytosine is a 5-methylcytosine.

20. The single-stranded modified oligonucleotide of claim 12, wherein the modified oligonucleotide consists of 16 linked nucleosides having a nucleobase sequence consisting of the nucleobase sequence of any one of SEQ ID NOs: 12, 13, 35, 39, 43, 124, 150, 155, 169, or 175.

21. The single-stranded modified oligonucleotide of claim 20, wherein each internucleoside linkage is a phosphorothioate linkage.

22. The single-stranded modified oligonucleotide of claim 20, wherein the modified sugar comprises a 2'-O-methoxyethyl sugar.

23. The single-stranded modified oligonucleotide of claim 20, wherein the modified sugar comprises a bicyclic sugar.

24. The single-stranded modified oligonucleotide of claim 23, wherein the bicyclic sugar comprises a group selected from: [4'-CH(CH3)-O-2'] *4'-CH($CH_3$)—O-2'*, [4'-CH2-O-2'] *4'-$CH_2$—O-2'*, and [4'-(CH2)2-O-2'] *4'-($CH_2$)$_2$—O-2'*.

25. The single-stranded modified oligonucleotide of claim 20, wherein each cytosine is a 5-methylcytosine.

26. The single-stranded modified oligonucleotide of claim 20, wherein the modified oligonucleotide has a nucleobase sequence consisting of the nucleobase sequence of any one of SEQ ID NOs: 43, 124, 150, 155, 169, or 175, and wherein the modified oligonucleotide comprises:

a gap segment consisting of ten linked deoxynucleosides;

a 5' wing segment consisting of 3 linked nucleosides; and a 3' wing segment consisting of 3 linked nucleosides;

wherein the gap segment is positioned between the 5' wing segment and the 3' wing segment; wherein each nucleoside of each wing segment comprises a constrained ethyl nucleoside; wherein each internucleoside linkage of the modified oligonucleotide is a phosphorothioate linkage; and wherein each cytosine of the modified oligonucleotide is a 5-methylcytosine.

27. A method of treating cancer in a subject comprising administering to the subject the compound of claim 26, thereby treating cancer in the subject.

28. The method of claim 27, wherein the cancer is prostate cancer, breast cancer, ovarian cancer, gastric cancer, or bladder cancer.

29. The method of claim 27, wherein the cancer is castrate-resistant prostate cancer.

30. The method of claim 29, wherein the castrate-resistant prostate cancer is resistant to an anti-androgenic agent selected from: MDV3100, ARN-059, ODM-201, abiraterone, TOK001, TAK700, and VT464.

*31. A compound comprising a single-stranded modified oligonucleotide consisting of 16 linked nucleosides, wherein the modified oligonucleotide has a nucleobase sequence consisting of the sequence of SEQ ID NO: 35, and is a pharmaceutically acceptable salt selected from the group consisting of sodium and potassium salts, wherein the modified oligonucleotide comprises:*

*a gap segment consisting of 9 linked deoxynucleosides;*

*a 5' wing segment consisting of three linked nucleosides; and*

*a 3' wing segment consisting of four linked nucleosides;*

*wherein the gap segment is positioned between the 5' wing segment and the 3' wing segment; wherein the sugars of the three linked nucleosides of the 5' wing segment are each a constrained ethyl (cEt) sugar; wherein the sugars of the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; wherein each internucleoside linkage is a phosphorothioate linkage; and wherein each cytosine is a 5-methylcytosine.*

*32. A compound comprising a single-stranded modified oligonucleotide consisting of 16 linked nucleosides, wherein the modified oligonucleotide has a nucleobase sequence consisting of the sequence of SEQ ID NO: 39 and is a pharmaceutically acceptable salt selected from the group consisting of sodium and potassium salts, wherein the modified oligonucleotide comprises:*

*a gap segment consisting of 7 linked deoxynucleosides;*

*a 5' wing segment consisting of four linked nucleosides; and*

*a 3' wing segment consisting of five linked nucleosides;*

*wherein the gap segment is positioned between the 5' wing segment and the 3' wing segment; wherein the sugars of the four linked nucleosides of the 5' wing segment are a 2'-O-methoxyethyl sugar, a constrained ethyl (cEt) sugar, a constrained ethyl (cEt) sugar, and a constrained ethyl (cEt) sugar in the 5' to 3' direction; wherein the sugars of the five linked nucleosides of the 3' wing segment are a constrained ethyl (cEt) sugar, a constrained ethyl (cEt) sugar, a constrained ethyl (cEt) sugar, a 2'-O-methoxyethyl sugar, and a 2'-O-methoxyethyl sugar in the 5' to 3' direction; wherein each internucleoside linkage is a phosphorothioate linkage; and wherein each cytosine is a 5-methylcytosine.*

*33. A composition comprising the compound of claim 31 or claim 32, or a pharmaceutically acceptable salt thereof, and a pharmaceutically acceptable diluent or carrier.*

*34. A combination comprising the compound of claim 31 or claim 32, or a pharmaceutically acceptable salt thereof, and an anti-androgenic agent selected from: MDV3100, ARN-059, ODM-201, abiraterone, TOK001, TAK700 and VT464.*

*35. The combination of claim 34, wherein the anti-androgenic agent is MDV3100.*

*36. A method of treating cancer comprising administering to a subject having cancer a compound or salt of claim 31 or claim 32, thereby treating cancer in the subject.*

*37. The method of claim 36, wherein the cancer is prostate cancer, breast cancer, ovarian cancer, gastric cancer or bladder cancer.*

*38. The method of claim 36, wherein the cancer is castrate-resistant prostate cancer.*

*39. The method of claim 38, wherein the castrate-resistant prostate cancer is resistant to an anti-androgenic agent selected from: MDV3100, ARN-059, ODM-201, abiraterone, TOK001, TAK700 and VT464.*

*40. A method of treating prostate cancer in a patient in need thereof, comprising administering to the patient a compound or salt of claim 31 or claim 32 and an anti-androgenic agent.*

*41. The method of claim 40, wherein the anti-androgenic agent is selected from: MDV3100, ARN-059, ODM-201, abiraterone, TOK001, TAK700 and VT464.*

*42. The method of claim 40, wherein the compound and the anti-androgenic agent synergize in combination to inhibit the growth or proliferation of the prostate cancer cell.*

*43. The method of claim 40, wherein the patient is administered an amount of the compound and an amount of anti-androgenic agent that are each or both less in combination than the amount of either the compound or anti-androgenic agent alone effective in inhibiting the growth or proliferation of said prostate cancer cell.*

*44. A method of inhibiting growth or proliferation of an androgen receptor (AR)-positive breast cancer cell comprising contacting the breast cancer cell with a compound or salt of claim 31 or claim 32 wherein the growth or proliferation of the breast cancer cell is inhibited.*

*45. A method of treating prostate cancer in a patient in need thereof, comprising administering to the patient a composition of claim 33 and an anti-androgenic agent.*

*46. The method of claim 45, wherein the anti-androgenic agent is selected from: MDV3100, ARN-059, ODM-201, abiraterone, TOK001, TAK700 and VT464.*

*47. The method of claim 41, wherein the anti-androgenic agent is MDV3100.*

*48. The method of claim 47, wherein the compound and the anti-androgenic agent synergize in combination to inhibit the growth or proliferation of the prostate cancer cell.*

*49. The method of claim 46, wherein the anti-androgenic agent is MDV3100.*

*50. The method of claim 49, wherein the compound and the anti-androgenic agent synergize in combination to inhibit the growth or proliferation of the prostate cancer cell.*

* * * * *